United States Patent [19]

Paoletti et al.

[11] Patent Number: 5,494,807
[45] Date of Patent: Feb. 27, 1996

[54] NYVAC VACCINIA VIRUS RECOMBINANTS COMPRISING HETEROLOGOUS INSERTS

[75] Inventors: Enzo Paoletti, Delmar; Marion E. Perkus, Altamont; Jill Taylor, Albany; James Tartaglia, Schenectady; Elizabeth K. Norton, Latham, all of N.Y.; Michel Riviere, Ecully; Charles de Taisne, Lyons, both of France; Keith J. Limbach, Troy, N.Y.; Gerard P. Johnson, Waterford, N.Y.; Steven E. Pincus, East Greenbush, N.Y.; William I. Cox, Troy, N.Y.; Jean-Christophe F. Audonnet, Albany, N.Y.; Russell R. Gettig, Averill Park, N.Y.

[73] Assignee: Virogenetics Corporation, Troy, N.Y.

[21] Appl. No.: 105,483

[22] Filed: Aug. 12, 1993

Related U.S. Application Data

[63] Continuation of Ser. No. 847,951, Mar. 6, 1992, abandoned, which is a continuation-in-part of Ser. No. 713,967, Jun. 11, 1991, abandoned, which is a continuation-in-part of Ser. No. 666,056, Mar. 7, 1991, abandoned.

[51] Int. Cl.$^6$ .................. A61K 39/285; A61K 39/295; C12N 7/01; C12N 15/63

[52] U.S. Cl. .................. 435/69.3; 424/199.1; 424/204.1; 424/205.1; 424/218.1; 424/224.1; 424/227.1; 424/229.1; 424/230.1; 424/231.1; 424/232.1; 424/239.1; 435/172.3; 435/320.1; 530/350; 530/826; 514/2

[58] Field of Search .................. 424/199.1, 204.1, 424/205.1, 206.1–233.1; 530/826, 350; 435/69.3, 235.1, 172.3, 320.1, 252.3; 514/2

[56] References Cited

U.S. PATENT DOCUMENTS

| | | | |
|---|---|---|---|
| 5,093,258 | 3/1992 | Cohen | 435/235.1 |
| 5,155,020 | 10/1992 | Paoletti | 435/69.1 |
| 5,174,993 | 12/1992 | Paoletti | 424/89 |
| 5,180,675 | 1/1993 | Drilliea | 435/235.11 |
| 5,364,773 | 11/1994 | Paslette et al. | 435/69.1 |

FOREIGN PATENT DOCUMENTS

| | | | |
|---|---|---|---|
| 8903429 | 4/1989 | WIPO | C12P 21/50 |
| WO-A-90/10693 | 9/1990 | WIPO | |
| 9010693 | 9/1990 | WIPO | C12N 7/01 |
| WO-A-90/12101 | 10/1990 | WIPO | |
| 9012101 | 10/1990 | WIPO | C12N 15/86 |

OTHER PUBLICATIONS

Hu. S–L et al. Proc. Natl. Acad. Sci. USA 86: 7213–7217, 1989.
Britt, W. et al. J. Vinl. 64(3): 1079–1085, 1990.
Pensiero M. N. et al. J. Virol. 62(3): 696–702, 1988.
Finkelstein, A. et al. (89) Trends in Biotech 7:273–277.
Lerner, R. A. et al. (83) in: The Biology of Immunologil Disease; Dixon F. S. and D. W. Fisher, eds; New York, NY, pp. 331–338.
Schlesinger, J. J. et al. Biotechnology 20:289–307, 1992.
Thomas, I. et al. J. Gen. Virol. 71:37–42, 1990.
Watanabe, et al. Vaccine 7:499–502, 1989.
Hahn, Y. S. et al. Arch. Virol. 115:251–265.
Marchioli, L. L. et al. J. virol. 61(12):3977–82.
Khanng, R. et al. Immunology 74:504–510, 1991.
Rooney, J. F. et al. J. Virol. 62(5):1530–34, 1988.
Guo, P. et al. J Virol. 63(10):4189–98, 1989.
Adamowicz, Ph., F. Tron, R. Vinas, M. N. Mevelec, I. Diaz, A. M. Courouce, M. C. Mazert, D. Lagarde and M. Girard, In Viral Hepatitis and Liver Disease, pp. 1087–1090 (1988).
Alexander, D. J. In Diseases of Poultry, 9th edition, eds. B. W. Calnek, H. J. Barnes, C. W. Beard, W. M. Reid and H. W. Yoder, Jr., (Iowa State University Press, Ames, Iowa, USA) pp. 496–519 (1991).
Alkhatib, G. and D. Briedis, Virology 150, 479–490 (1986).
Alkhatib, G., C. Richardson, and S–H. Shen, Virology 175, 262–270 (1990).
Allen, P. and Rapp, F., J. Infect. Dis. 145, 413–421 (1982).
Alp, N. J., T. D. Allport, J. Van Zanken, B. Rodgers, J. G. P. Sissons, and L. K. Borysiewicz, J. Virol. 65, 4812–4820.
Altenburger, W., C–P. Suter and J. Altenburger, Archives Virol. 105, 15–27 (1989).
Arikawa, J., Schmaljohn, A. L., Dalrymple, J. M., and Schmaljohn, C. S., J. Gen. Virology 70, 615–624 (1989).
Asada, H., Tamura, M., Kondo, K., Dohi, Y, Yamanishi, K., J. Gen Virology 69, 2179–2188 (1988).
Asada, H. M., Tamura, K., Kondo, Y., Okano, Y., Takahashi, Y., Dohi, T., Nagai, T., Kurata, T., and Yamanishi, K., J. Gen. Virology 68, 1961–1969 (1987).
Avery, R. J., and J. Niven., Infect. and Immun. 26, 795–801 (1979).
Baer. R., Bankie, A. T., Biggin. M. D., Deiniger. P. L., Farrel. P. J., Gibson. T. J., Hatfull. G., Hudsson. G. S., Satchwell. S. C., Seguin. C., Tuffnell. P. S., Barrell. B. G., Nature 310, 207–211 (1984).
Balachandran, N., Bacchetti, S. and Rawls, W., Infec. Immun. 37, 1132–1137 (1982).
Baxby D., Paoletti E., Vaccine 9, 8–9 (1992).
Beard, C. W., Avian Diseases 23, 327–334 (1979).

(List continued on next page.)

Primary Examiner—Hazel F. Sidberry
Assistant Examiner—Michael S. Tuscan
Attorney, Agent, or Firm—Curtis, Morris & Safford

[57] ABSTRACT

What is described is a modified vector, such as a recombinant poxvirus, particularly recombinant vaccinia virus, having enhanced safety. The modified recombinant virus has nonessential virus-encoded genetic functions inactivated therein so that virus has attenuated virulence. In one embodiment, the genetic functions are inactivated by deleting an open reading frame encoding a virulence factor. In another embodiment, the genetic functions are inactivated by insertional inactivation of an open reading frame encoding a virulence factor. What is also described is a vaccine containing the modified recombinant virus having nonessential virus-encoded genetic functions inactivated therein so that the vaccine has an increased level of safety compared to known recombinant virus vaccines.

22 Claims, 46 Drawing Sheets

OTHER PUBLICATIONS

Beard, C. W., and R. P. Hanson, In Disease of Poultry, 8th edition, ed. M. S. Hofstad, (Iowa State University Press, Ames, Iowa) pp. 452–470 (1984).

Beattie, E., Tartaglia, J., and Paoletti, E., Virology 183, 419–422 (1991).

Behbehani, A. M., Microbiological Reviews 47, 455–509 (1983).

Ben– Porat, T. and A. S. Kaplan, Virology 41, 265–273 (1970).

Ben–Porat, T. and A. S. Kaplan, In The Herpesviruses, vol. 3, ed. B. Roizman, (Plenum Publishing Corp., New York) pp. 105–173 (1985).

Ben–Porat, T., J. DeMarchi, J. Pendrys, R. A. Veach, and A. S. Kaplan, J. Virol. 57, 191–196 (1986).

Ben–Porat, T., F. J. Rixon, and M. L. Blankenship, Virology 95, 285–294 (1979).

Ben–Porat, T. In Organization and replication of viral DNA, ed. A. S. Kaplan, (CRC Press, Inc., Boca Raton, Florida) pp. 147–172 (1982).

Bergoin, M., and Dales, S., In Comparative Virology, eds. K. Maramorosch and E. Kurstak, (Academic Press, NY) pp. 169–205 (1971).

Berns, K. I., In: Fields Virology, eds. B. N. Fields and D. M. Knipe, (Raven Press, New York) pp. 1743–1763 (1990).

Bertholet, C., Drillien, R., and Wittek, R., Proc. Natl. Acad. Wolinsky, J. S., and Waxham, M. N., In: Virology, eds. Fields, B. N., and Knipe, D. M., (Raven Press), pp. 989–1011 (1990).

Wunner, W. H., B. Dietzschold, P. J. Curtis and T. J. Wiktor, J. Gen. Virol. 64, 1649–1656 (1983).

Wunsch, M., Schultz, A. S., Koch, W., Friedrich, R., and Hunsmann, G., EMBO J. 2, 2239–2246 (1983).

Yamagishi A., J. Vet. Med. 820, 14–18 (1989).

Yamanishi, K., Dantas, J. R., Jr., Takahashi, M., Yamanouchi, T., Damae, K., Takahoashi, Y., Tanishita, O., J. Virology 52, 231–237 (1984).

Yasuda, A., Kimura–Kuroda, J., Ogimoto, M., Miyamoto, M., Sata, T., Sato, T., Takamura, C., Kurata, T., Kojima, A., and Yasui, K., J. Virol. 64, 2788–2795 (1990).

Yelverton, E., S. Norton, J. F. Obijeski and D. V. Goeddel, Science 219, 614–620 (1983).

Yoshida I., Takagi M., Inokuma E., Goda H., Ono K., Takaku K., and Oku J., Biken J. 24, 47–67 (1981).

Yoshinaka, Y., Katch, I., Copeland, T. D. and Oroszlan, S. J. Virol. 55, 870–873 (1985).

Yuen, L., and Moss, B., Proc. Natl. Acad. Sci. USA 84, 6417–6421 (1987).

Zagury, D., Bernard, J., Cheynier, R., Desportes, I., Leonard, R., Fouchard, I., Reveil, B. Ittele, D., Lurhuma, Z., Mbayo, K., Wane, J., Salaun, J.–J., Goussard, B., Dechazal, L., Burny, A., Nara, P. and Gallo, R. C., Nature 332, 728–731 (1988).

Zanetti, A. R., E. Tanzi, L. Romano, P. Vigano, A. Cargnel, S. Hojvat and A. J. Zuckerman, J. Med. Virol. 32, 219–224 (1990).

Zarling, J. M., Morton, W., Moran, P. A., McClure, J., Kosowski, S. G. and Hu, S.–L., Nature 323, 344– 346 (1986).

Zhang, X.–K., Takashima, I., and Hashimoto, N., Arch. Virol. 105, 235–246 (1989).

Zhou, J., L. Crawford, L. McLean, X. Sun. M. Stanley, N. Almond and G. L. Smith, J. Gen Virol. 71, 2185–2190 (1990).

Zingernagel, R. M., Sato, T., Althage, A., and Kamisaku, H., Eur. J. Immunol. 14, 14–23 (1984).

Zweig, M., Showalter, S., Bladen, S., Heilman, C. and Hampar, B., J. Virol. 47, 185–192 (1983).

Asada, H. M., Tamura, K., Kondo, Y., Okano, Y., Takahashi, Y., Dohi, T., Nagai, T., Kurata, T., and Yamanishi, K., J. Gen. Virology 68, 1961–1969 (1987).

Jahn, G., B–C. Scholl, B. Troupe, and B. Fleckenstein. J. Gen Virol. 68, 1327–1337 (1987).

Jarrett, O., Hardy, Jr., W. D., Golder, M. C., and Hay, D., Int. J. Cancer 21, 334–337 (1978).

Thomson, G. R., Spooner, P. R., and Powell, D. G, Vet. Res. 100, 465–468 (1977).

Pedersen and Ott, *Feline Practice,* Evaluation of a Commercial Feline Leukemia Virus Vaccine for Immunogenicity, vol. 15, No. 6, 7–20, Nov.–Dec. 1985.

Tabor, S. and C. C. Richardson, Proc. Natl. Acad. Sci. USA 84, 4767–4771 (1987).

Tartaglia, J., Pincus, S., and Paoletti, E., Crit. Rev. Immunol. 10, 13–30 (1990a).

Tartaglia, J., M. E. Perkus, J. Taylor, E. K. Norton, J. C. Audonnet, W. I. Cox, S. W. Davis, J. VanderHoeven, B. Meignier, M. Riviere, B. Languet, and E. Paoletti, Virology 188, 217–232 (1992).

Tartaglia, J. and Paoletti, E., *In* Immunochemistry of viruses, 11, eds. van Regenmortel, M.H.V. and Neurath, A. R., (Elsevier Science Publishers B.V., Amsterdam) p. 125 (1990b).

Taylor, J., Weinberg, R., Tartaglia, J., Richardson, C., Alkhatib, G., Briedis, D., Appel. M., Norton, E., and Poaletti, E., Virology 187, 321–328 (1992).

Taylor, J., Weinberg, R., Kawaoka, Y., Webster, R. G, and Paoletti, E., Vaccine 6, 504–508 (1988a).

Taylor, J., C. Trimarchi, R. Weinberg, B. Languet, F. Guillemin, P. Desmettre and E. Paoletti, Vaccine 9, 190–193 (1991b).

Taylor, J., S. Pincus, J. Tartaglia, C. Richardson, G. Alkhatib, D. Briedis, M. Appel, E. Morton and E. Paoletti, J. Virology 65 in press Aug. (1991c).

Taylor, J., Edbauer, C., Rey–Senelonge, A., Bouquet, J.–F., Norton, E., Goebel, S., Desmettre, P., and Paoletti, E. *J. Virol.* 64, 1441–1450 (1990).

Taylor, J., R. Weinberg, B. Lanquet, P. Desmettre, and E. Paoletti, Vaccine 6, 497–503 (1988b).

Taylor, G., E. J. Stott, G. Wertz and A. Ball, J. Gen. Virol. 72, 125–130 (1991a).

Taylor et al., Vaccine 6, 466–467 (1988c).

Thomson, G. R., Spooner, P. R., and Powell, D. G., Vet. Res. 100, 465–468 (1977).

Thornton, G. B., D. Milich, F. Chisari, K. Mitamura, S. B. Kent, R. Neurath, R. Purcell and J. Gerin, *In* Vaccines 87, (Cold Spring Harbor Laboratory, Cold Spring Harbor, New York) (1987).

Tomley, F., Vaccine 9, 4–5 (1991).

Toyoda, T., T. Sakaguchi, K. Imai, N. M. Inocencio, B. Gotoh, M. Hamaguchi, and Y. Nagai, Virology 158, 242–247 (1987).

Tsubaki S., Masu S., Obata Y., and Shimada F., Kitasato Arch. Exp. Med., 23, 71–77 (1950).

Tsuchiya N. Karaki T, Kuroda A., Karoji Y., and Sasaki O., Virus, 20, 290–300 (1970).

Turner, P. C. and Moyer, R. W., *In* Poxvirus, eds. R. W. Moyer and P. C. Turner, (Springer Velag, WY.) pp. 125–152 (1990).

Ueda, Y., S. Morikawa and Y. Matsuura, Virology 177,

588–594 (1990).
Valenzuela, P., A. Medina, W. J. Rutter, G. Ammerer and B. D. Hall, Nature 298, 347–350 (1982).
Valenzuela, P., D. Coit, M. A. Medina–Selby, C. H. Kuo, G. V. Nest, R. L. Burke, P. Bull, M. S. Urdea and P. V.Graves, Bio/Technology 3, 323–326 (1985).
Valenzuela, P., P. Gray, M. Quiroga, J. Zaldivar, H. M. Goodman and W. J. Rutter, Nature 280, 815– 819 (1979).
Varma M. G., Pudney M., and Leeke C. J., Trans. R. Soc. Trop. Med. Hyg., 68, 374–382 (1974).
Vialard, J., M. Lalumiere, T. Vernet, . Briedis, G. Alkhatib, d. Henning, D. Levin, and C. Richardson, J. Virol. 64, 37–50 (1990).
Vos, J. C. and Stunnerberg, H. G., EMBO J. 7, 3487–3492 (1988).
Wachsman, M., Aurelian, L., Smith, C., Lipinskas, B., Perkus, M. and Paoletti, E., J. Infect. Dis. 155, 1188–1197 (1987).
Waddell, G. H., Teigland, M. B., and Sigel, M. M., JAVMA 143, 587–590 (1963).
Walker, B. D., Flexner, C., Birch–Limberger, K., Fisher, L. Paradis, T. J., Aldovini, A., Young, R., Moss, B, and Schooley, R. T., Proc. Natl. Acad. Sci. 86, 9514–9519 (1989).
Walker, B. D., Flexner, C., Paradis, T. J., Fuller, T. C., Hirsch, M. S., Schooley, R. T. and Moss, B., Science 240, 64–66 (1988).
Walker, B. D., Chakrabarti, S., Moss, B., Paradi, T. J., Flynn, T., Durno, A. G., Blumberg, R. S., Kaplan, J. C., Hirsch, M. S., and Schooley, R. T., Nature 328, 345–348 (1987).
Wathen, M. W. and Wathen, L. M. K., Virol. 51, 57–62 (1984).
Watson, R., Gene 26, 307–312 (1983).
Watson, C. J., and Jackson, J. F., In: DNA Cloning, vol. I., ed., Glover, D. M., (IRL Press, Washington, D.C.), pp. 79–88 (1985).
Waxham, M. N., Aronowski, J., Server, A. C., Walinsky, J. S., Smith, J. A., and Goodman, H. M., Virology 164, 318–325 (1988).
Waxham, M. N., Server, A. C., Goodman, H. M., and Walinsky, J. S., Virology 159, 381–388 (1987).
Weibel, R. E., In: Vaccines, eds. Plotkin, S. A., and Mortimer, E. A., (W. B. Saunders), pp. 223–234 (1988).
Weir, J., Bennett, M., Allen, E., Elkins, K., Martin, S. and Rouse, B., J. Gen Virol. 70, 2587–2594 (1989).
Weir, J. P. and B. Moss, J. Virol. 46, 530–537 (1983).
Weiss, R. A., Clapham, P. R., Cheingsong–Popov, R., Dalgleish, G., Carne, C. A. Weller, I. V., and Tedder, R. S., Nature 316, 69–72 (1985).
Wengler, G., and Wengler, G., J. Virol. 63, 2521–2526 (1989a).
Wengler, G., and Wengler, G., J. Gen, Virol. 70, 987–992 (1989b).
Weston, K., and B. G. Barrell, J. Mol. Biol. 192, 177–208 (1986).
WHO Meeting, Geneva, Jun. 19–22, Vaccine 8, 425–437 (1990).
Wiktor T. J., Macfarlan R. I., Reagan K. J. et al., Proc. Natl. Acad. Sci. USA, 81, 7194–7198 (1984).
Wiktor, T. J., S. A. Plotkin and H. Koprowski, In Vaccines, eds. Plotkin, S. A. and E. A. Mortimer (W. B. Saunders, Philadelphia), 474–491 (1988).
Wiktor, T. J., E. Gyorgy, H. D. Schlumberger, F. Sokol and H. Koprowski, J. Immunol. 110, 269–276 (1973).
Wiktor, T. J., R. I. Macfarlan, K. J. Reagan, B. Dietzschold, P. J. Curits, W. H. Wunner, M. P. Kieny, R. Lathe, J. P. Lecocq, M. Mackett, B. Moss and H. Koprowski, Proc. Natl. Acad. Sci. USA 81, 7194–7198 (1984).
Wiktor, T. J., Dev. Biol. Stand 40, 255–264 (1977).
Wild F., Giraudon P., Spenner D., et al., Vaccine 8, 441–442 (1990).
Wild, T. F., E. Malvoisin, and R. Buckland, J. Gen, Virol. 72, 439–447 (1991b).
Winkler, G., Randolph, V. B., Cleaves, G., R., Ryan, T. E., and Stollar, V., Virol 162, 187–196 (1988).
Wittmann, G. and Rziha, H.–J. Aujeszky's disease (pseudo-rabies) in pigs, In Herpesvirus Diseases of Cattle, Horses and Pigs, ed Wittmann, G., (Kluwer Academic Publishers), 230–325 (1989).
Wolff, L. H., Mathes, L. E., and Osone, R. G., J. Immunol. Meth. 26, 151–156 (1979).
Riviere Y., Tanneau–Salvadori, F., Regnault, A., Lopez, O., Sansonetti, P., Guy, B., Kieny, M.–P., Fournel, J.–J. and Montagnier, L., J. Virol. 63, 2270–2277 (1989).
Robbins, A. K., Dorney, D. J., Wathen, M. W., Whealy, M. E., Gold, C., Watson, R. J., Holland, L. E., Weed, S. D., Levine, M., Glorieso, J. C., and Enquist, L. W., J. Virol. 61, 2691–2701 (1987).
Robbins, A. K., J. H. Weis, L. W. Enquist, and R. J. Watson, J. Mol. Appl. Genet. 2, 485–496 (1984).
Robbins, A. K., R. J. Watson, M. E. Whealy, W. W. Hays, and L. W. Enquist, J. Virol. 58, 339–347 (1986a).
Rodriquez et al., Proc. Natl. Acad. Sci. USA 86, 1287–1291 (1989).
Roizman, B. and Sears, A., In Virology, eds. Fields, B. and Knipe, D., (Raven Press, Ltd.) pp. 1795– 1841 (1990).
Rojko, J. L., and Olsen, R. G. (1984) Vet. Imm. Immunopath. 6, 107–165 (1984).
Rojko, J. L., Hoover, E. A.Quackenbush, S. L., and Olsen, R. G., Nature 298, 385–388 (1982).
Romanos, M. A., Makoff, A. J., Fairweather, N. F., Beesley, K. M., Slater, D. E., Rayment, F. B., Payne, M. M., and Clare, J. J. *Nucleic Acids Res.* 19, 1461–1467 (1991).
Rooney F. F., Wohlenberg C., Cramer E. J. et al., J. Virol. 62, 1530–1534 (1988).
Rosenthal K., Smiley, S., South, S. and Johnson, D., J. Virol. 61, 2438–2447 (1987).
Rubenstein, A. S. and A. S. Kaplan, Virology 66, 385–392 (1975).
Ruegg, C. L., Monell, C. R., and Strand, M., J. Virol. 63, 3250–3256 (1989a).
Russell, P. H., and Jarrett, O., Int. J. Cancer 21, 768–778 (1978).
Russell, M., S. Kidd, and M. R. Kelley, Gene 45, 333–338 (1986).
Saiki, R. K., Gelfand, D. H., Stoffel, S. Scharf, S. J., Higuihi, R., Horn, G. T., Mullis, K. B., Erlich, H. A., Science 239, 487–491 (1988).
Saliki, J. T., Mizak, B., Flore, H. P., Gettig, R. R., Burand, J. P., Carmichael, L. E., Wood, H. A., and Parrish, C. R., J. Gen. Virol. 73, 369–374 (1992).
Sanchez–Pescador, R., Power, M. D. Barr, P. J., Steimer, K. S., Stempien, M. M. Brown–Shimer, S. L. Gee, W., Renard, A., Randolph, A., Levy, J. A., Dina, D., and Luciw, P. A., Science 227, 484– 492 (1985).
Sanger, F., Nickeln, S. Coulson, A. R., Proc. Natl. Acad. Sci. 74, 5463–5467 (1977).
Sarma, P. S., and Log, T., Virology 54:160–169 (1973).
Sazawa H., Sugimori T., Morimoto T., Miura Y. and Watanabe M., Natl. Inst. Anim. Health Q. 9, 74–82 (1969).

Scheid, A., L. A. Caliguiri, R. W. compans, and P. W. Choppin, Virology 50, 640–652 (1972).
Scheid, A., and P. W. Choppin, Virology 57, 475–490 (1974).
Scherer W. F., Moyer J. T., Izumi T., Gresser I., and McCown J., Am. J. Trop. Med. Hyg. 8, 698–706 (1959).
Schlesinger, J. J., Brandriss, M. W., and Walsh, E. E., J. Immunol. 135, 2805–2809 (1985).
Schlesinger, J. J., Brandriss, M. W., Cropp, C. B., and Monath, T. P., J. Virol. 60, 1153–1155 (1986).
Schlicht, H–J. and H. Schaller, J. Virol. 63, 5399–5404 (1989).
Schmaljohn, C. S., Jennings, G. B., Hay, J., Dalrymple, J. M., Virology 155, 633–643 (1986).
Schmaljohn, C. S., and Dalrymple, J. M., Virology 131, 482–491 (1983).
Schmaljohn, C. S., Sugiyama, K., Schmaljohn, A. L., and Bishop, D. H. L., J. Gen. Virology 69, 777–786 (1988).
Schmaljohn, C. S., Chu, Y. K., Schmaljohn, A. L., and Dalrymple, J. M., Virology 64, 3162–3170 (1990).
Schmidt, D. M., Sidhu, N. K., Cianciolo, G. J., and Snyderman, R. (1987) Proc. Natl. Acad. Sci. USA 84, 7290–7294.
Schmitt, J. F. C. and H. G. Stunnenberg, J. Virol. 62, 1889–1897 (1988).
Sebring, R. W., Chu, H.–J., Chavez, L. G., Sandblom, D. S., Hustead, D. R., Dale, B., Wolf, D., Acree, W. M., JAVMA 199, 1413–1418 (1991).
Seligmann, E. B., *In* Laboratory Techniques in Rabies, eds. M. M. Kaplan and H. Koprowski, (World Health Organization, Geneva) pp. 279–285 (1973).
Shafferman, A., Lennox, J., Grosfeld, H., Sadoff, J., Redfield, R. R., and Burke, D. S, AIDS Research and Human Retroviruses 5, 33–39 (1989).
Shapira, S. K., Chou, J., Richard, F. V. and Casadaban, M. J., Gene 25, 71–82 (1983).
Shibley, G. P., Tanner, J. E., and Hanna, S. A., JAVMA 199, 1402–1405 (1991).
Shida, H., Hinuma, Y., Hatanaka, M., Morita, M., Kidokoro, M. Suzuki, K., Maruyzam, T., Takahashi–Nishimaki, F., Sugimoto, M., Kitamura, R., Miyazawa, T., and Hayami, M., J. Virol. 62, 4474–4480 (1988).
Shida, H., Virology 150, 451–462 (1986).
Shida, H., T. Tochikura, T. Sato, T. Konno, k. Hirayoshi, M. Seki, Y. Ito, M. Hatanaka, Y. Hinuma, M. Sugimoto, F. Takahashi–Nishimaki, T. Maruyama, K. Miki, K. Suzuki, M. Morita, H. Sashiyama and M. Hayami, EMBO 6, 3379–3384 (1987).
Shioda, T. and H. Shibuta, Virology 175, 139–148 (1990).
Slabaugh, M. B. and N. A. Roseman, Proc. Natl. Acad. Sci. USA 86, 4152–4155 (1989).
Slabaugh, M., N. Roseman, R. Davis and C. Mathews, J. Virol. 62, 519–527 (1988).
Smith J. S. and Yager P. A. A rapid tissue culture test for determining rabies neutralization antibody. In: Laboratory Techniques on Rabies. Eds. M. M. Kaplan and H. Koprowski, 354–357.
Smith, G. L., M. Mackett and B. Moss, Nature 302, 490–495 (1983).
Smith, G. L. and Y. Sang Chan, J. Gen. Virol. 72, 511–518 (1991).
Smith, J. S., P. A. Yager and G. M. Baer, *In* Laboratory Techniques in Rabies, eds. M. M. Kaplan and H. Koprowski (WHO Geneva) pp. 354–357 (1973).
Spar, P., *In* Herpesviruses, vol. 3, ed. Roizman, B. (Plenum, NY) pp. 315–356 (1984).
Spehner, D., R. Drillien, and J. P. Lecocq, J. Virol. 64, 527–533 (1990).
Spehner, D., Gillard, S., Drillien, R., and Kirn, A., J. Virol. 62, 1297–1304 (1988).
Stahl, S. J. and K. Murray, Proc. Natl. Acad. Sci. USA 86, 6283–6287 (1989).
Stanberry, L. R., S. Kit and M. G. Myers, J. Virol. 55, 322–328 (1985).
Starcich et al., Cell 45, 637–648 (1986).
Stevely, W. S., J. Virol. 22, 232–234 (1977).
Stewart, M. A., Warnock, M., Wheeler, A., Wiklie, N., Mullins,J. I., Oniono, D. E., and Neil, J. C., J. Virol. 58, 825–834 (1986).
Stuve, L., Brown–Shimer, S., Pachl, C., Najarian, R., Dina, D. and Burke, R., J. Virol. 61, 326–335 (1987).
Norrby, E., and Y. Gollmar, Infect. and Immun. 11, 231–239 (1975).
Norrby, E., and M. N. Oxman, *In* Fields Virology, 2nd Edition, eds. B. N. Fields and D. M. Knipe, (Raven Press, NY) pp. 1013–1044 (1990).
Norrby, E., S. N. Chen, T. Togashi, H. Shesberadaran, and K. P. Johnson, Archives of Virology 71, 1– 11 (1982).
Nunberg, J. H., Williams, M. E., and Innis, M. A., J. Virol., 49, 629–632 (1984b).
Nunberg, J. H., Rodgers, J., Gilbert, and Snead, R. M., Proc. Natl. Acad. Sci. USA 81, 3675–3679 (1984a).
Oakes, J., Davis, W., Taylor, J. and Weppner, W., Infect. Immun. 29, 642–649 (1980).
Oakes, J. and Rosemond–Hornbeak, H., Infect. Immun. 21, 489–495 (1978).
Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).
Oie, M., Shida, H., and Ichihashi, Y., Virology 176, 494–504 (1990).
Ono, Y., H. Onda, R. Sasada, K. Igarashi, Y. Sugino and K. Nishioka, Nuc. Acids Res. 11, 1747–1757 (1983).
Osterhaus, A., Weijer, K., and UytdeHaag, F., Vaccine 7, 137–140 (1989).
Ou, J–H. and W. J. Rutter, J. Virol. 61, 782–786 (1987).
Oya A., Jpn. J. Med. Sci. Biol., Suppl. 20, 26–30 (1967).
Pachl, C., W. S. Probert, K. M. Hermsen, F. R. Masiarz, L. Rasmussen, T. C. Merigan, and R. R. Spaete, Virology 169, 418–426 (1989).
Paez, E., S. Dallo and M. Esteban, Proc. Natl. Acad. Sci. USA 82, 3365–3369 (1985).
Palumbo, G. J., D. J. Pickup, T. N. Fredrickson, L. J. McIntyre and R. M. L. Buller, Virology 172, 262–273 (1989).
Pande, H., K. Campo, B. tanamuchi, and J. A. Zaia, Virology 182, 220–228 (1991).
Panicali, D. and E. Paoletti, Proc. Natl. Acad. Sci. USA 79, 4927–4931 (1982).
Panicali, D., Grezlecki, A., and Huang, C., Gene 47, 193–199 (1986).
Panicali, D., Davis, S. W., Mercer, S. R., and Paoletti, E., J. Virol. 37, 1000– 1010 (1981).
Paoletti, E., B. Lipinskas, C. Samsonoff, S. Mercer and D. Panicali, Proc. Natl. Acad. Sci. USA 81, 193–197 (1984).
Parker, R. F., Bronson, L. H., and Green, R. H., J. Exp. Med. 74, 263–281 (1941).
Parrish, C. R., Aquadro, C. F., and Carmichael, L. E., Virology 166, 293–307 (1988).
Parrish, C. R., Aquadro, C. F., Strassheim, M. L., Evermann, J. F., Sgro, J–Y., and Mohammed, H. O., J. Virology 65, 6544–6552.
Parrish, C. R., Adv. Virus Res. 38, 403–450 (1990).
Patel, D. D., Ray, C. A., Drucker, R. P., and Pickup, D. J., Proc. Natl. Acad. Sci. USA 85, 9431– 9435 (1988).
Patel, D. D. and Pickup, D. J., EMBO 6, 3787–3794 (1987).
Pedersen, N. C., and Johnson, L. JAVMA 199, 1453–1455 (1991).
Pedersen, N. C., Johnson, L., and Oh, R. L., Feline Pract. 15, 7–20 (1985).
Perkus M. E., Piccini A., Lipinskas B. R., et al., Science 229, 981–984 (1985).
Perkus, M. E., Limbach, K., and Paoletti, E., J. Virol. 63, 3829–3836 (1989).
Perkus, M. E., D. Panicali, S. Mercer and E. Paoletti, Virology 152, 285–297 (1986).
Perkus, M. E., S. J. Goebel, S. W. Davis, G. P. Johnson, E. K. Norton and E. Paoletti, Virology 180, 406– 410 (1991).
Perkus, M. E., Goebel, S. J., Davis, S. W., Johnson, G. P., Limbach, K., Norton, E. K. and Paoletti, E., Virology 179, 276–286 (1990).
Petrovskis, E. A., Timmins, J. G., Armentrout, M. A., Marchioli, C. C., Yancey, Jr., R. J., Post, L. E., J. Virol. 59, 216–223 (1986b).
Petrovskis, E. A., J. G. Timmins, and L. E. Post, J. Virol. 60, 185–193 (1986a).
Piccini, A., M. E. Perkus, and E. Paoletti, Methods, in Enzymology 153, 545–563 (1987).
Pickup, D. J., B. S. Ink, B. L. Parsons, W. Hu and W. K. Joklik, Proc. Natl. Acad. Sci. USA 81, 6817–6821 (1984).
Pickup, D. J., B. S. Ink, W. Hu, C. A. Ray and W. K. Joklik, Proc. Natl. Acad. Sci. USA 83, 7698– 7702 (1986).
Plata, F., Autran, B., Martins, L. P., Wain–Hobson, S., Raphael, M., Mayaud, C., Denis, M., Guillon, J.–M., Debre, P., Nature 328, 348–351 (1987).
Plotkin, S. A., S. E. Starr, H. M. Friedman, E. Gonczol, and R. E. Weibel, J. Inf. Dis. 159, 860– 865 (1989b).
Plotkin, S. A., H. M. Friedman, S. E. Starr, and E. Gonczol, *In* Contemporary Issues in Infectious Diseases, vol. 8, eds. Root et al. (Churchill Livingstone, New York) pp. 65–92 (1989a).
Pontisso, P, M–A. Petit, M. J. Bankowski and M. E. Peeples, J. Virol. 63, 1981–1988 (1989).
Portetelle, D., Limbach, K., Burny, A., Mammerickx, M., Desmetttre, P., Riviere, M., Zavada, J. and Paoletti, E. Vaccine 9, 194–200 (1991).
Powell, K. and Watson, D. J., Gen. Virol. 29, 167–178 (1975).
Pratt, D. and S. subramani, Nuc. Acids Res. 11, 8817–8823 (1983).
Prevec, L., J. B. Campbell, B. S. Christie, L. Belbek, and F. L. Graham, J. Infect. Dis. 161, 27–30 (1990).
Rasmussen, L., M. Nelson, M. Neff, and T. C. Merigan, Jr., Virology 163, 308–318 (1988).
Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, S. R. Jr., Pearson, M. L., Lautenberger, J. A., Papas, T. S., Ghrayeb, J., Chang, N. T., Gallo, R. C., and Wong–Staal, F., Nature 313, 277 (1985).
Rautmann, G., Kieny, M. P., Brandely, R., Dott, K., Girard, M., Montagnier, L., and Lecocq, J.–P., AIDS Research and Human Retroviruses 5, 147–157 (1989).
Rea, T. J., J. G. Timmins, G. W. Long, and L. E. Post, J. Virol. 54, 21–29 (1985).

Reed, L. J. and Muench, H., Am. J. Hyg. 27, 493–497 (1938).
Rice, C. M., Strauss, E. G., and Strauss, J. H., *In* The Togaviridae and Flaviviridae, eds. S. Schlesinger and M. J. Schlesigner, (Plenum Press, New York/London) pp. 279–326 (1986).
Rice, C. M., Lenches, E. M., Eddy, S. R., Shin, S. J., Sheets, R. L., and Strauss, J. H., Science 229, 726–733 (1985).
Richardson, C., D. Hull, P. Greer, K. Hasel, A. Berkovich, G. Englund, W. Bellini, B. Rima, and R. Lazzarini, Virology 155, 508–523 (1986).
Richardson, C. D., A. Berkovich, S. Rozenblatt, and W. Bellini, J. Virol. 54, 186–193 (1985).
Rickinson, A. B., Rowe, M., Hart, I. J., Yao, Q. Y., Henderson, L. E., Rabin, H., and Epstein, M. A., Cell. Immunol. 87, 646–658 (1984). Pasteur, eds. Koprowski, H. and Plotkin, S. A., (Alan R. Liss, New York), 259–271 (1985).
Lecocq, J. P., M. Zukowski and R. Lathe, *In* Methods in Virology, eds. Maramorosch, K. and Koprowski, H., (Academic Press, New York) vol. VII, 124–172 (1984).
Liu, Y–N. C., A. Klaus, B. Kari, M. F. Stinski, J. Exhkardt, and R. C. Gehrz, J. Virol. 65, 1644–1648 (1991).
Lukacs, N., Theil, H.,–J., Mettenleiter, T. C., and Rziha, H.,–J., J. Virol. 53, 166– 172 (1985).
Lutz, H., Pedersen, N. C., and Higgens, J., Cancer Res. 40, 3642–3651 (1980).
Macfarlan, R. I., B. Dietzschold, and H. Koprowski, J. Mol Immunol. 23, 733–741 (1986).
Mackett M., Smith G. L., Moss B., Proc. Natl. Acad. Sci. 79, 7415–7419 (1982).
Makoff, A. J., Ballantine, S. P., Smallwood, A. E., and Fairweather, N. F. *Bio/Technology* 7, 1043–1046 (1989).
Mandecki, W., Proc. Natl. Acad. Sci. USA 83, 7177–7182 (1986).
Maniatis, T., Fritsch, E. F., and Sambrook, J. *In* Molecular cloning: a laboratory manual, (Cold Spring Harbor Laboratory, Cold Spring Harbor, NY) (1982).
Marsden, H., Buckmaster, A., Palfreyman, J., Hope, R. and Minson, A., J. Virol. 50, 547– 554 (1984).
Marsden, H., Stow, N., Preston, V., Timbury, M. and Wilkie, N., J. Virol. 28, 624– 642 (1978).
Marshall, G. S., G. P. Rabalais, G. G. Stuart, and S. L. Waldeyer, J. Infect. Dis. 165, 381–384 (1992).
Mason P. W., Virology 169, 354–364 (1989).
Mason P. W., Dalrymple J. M., Gentry M. K., McCown J. M., Hoke C. H., Burke D. S., Fournier M. J. and Mason T. L., J. Gen. Virol. 70, 2037–2049 (1989).
Mason, P. W., Pincus, S., Fournier, M. J., Mason, T. L., Shope, R. E., and Paoletti, E., Virol. 180, 294–305 (1991).
Mason, P. W., McAda, P. C., Dalrymple, J. M., Fournier, M. J., and Mason, T. L., Virlogy 158, 361– 372 (187a).
Mason, P. W., McAda, P. W., Mason, T. L., and Fournier, M. J., Virol. 161, 262–267 (1987b).
Mathes, L. E., Olsen, R. D., Hebebrand, L. C., Hoover, E. A., and Schaller, J. P., Nature 274, 687–691 (1978).
Matthews, R. E. F., Intervirology 17, 104–105 (1982a).
Matthews, R. E. F., Intervirology 17, 42–44 (1982b).
Mazzara, G. P., Destree, A. T., Williams, H. W., Sue. J. M., Belanger, L. M. and Panicali, D., Vaccines 87, 419–424 (1987).
McAda, P. C., Mason, P. W., Schmaljohn, C. S., Dalrymple, J. M., Mason, T. L. and Fournier, M. J. Virology 158, 348–360 (1987).
McGinnes, L. W., and T. G. Morrison, Virus Research 5, 343–356 (1986).

McLachlan, A., D. R. Milich, A. K. Raney, M. G. Riggs, J. L. Hughes, J. Sorge and F. V. Chisari, J. Virol. 61, 683–692 (1987).

McLaughlin–Taylor, E., Willey, D., Cantin, E., Eberle, R., Moss, B. and Openshaw H., J. Gen. Virol. 69, 1731–1734 (1988).

McGeoch, D., Moss, H., McNab, D. and Frame, M., J. Gen. Virol. 68, 19–38 (1987).

Meignier, B., Jourdier, T., Norrild, B., Pereira, L. and Roizman, B., J. Infect. Dis. 155, 921–930 (1987).

Merz, D. C., A. Scheid, and P. Choppin, J. Exper. Med. 151, 275–288 (1980).

Messing, J., vol. 101, eds. R. Wu, L. Grossman, and K. Moldave, (Academic Press, New York) pp. 20–78 (1983).

Mettenleiter, T. C., N. Lukacs, H.-J. Thiel, C. Schreurs, and H.-J. Rziha, Virology 152, 66–75 (1986).

Mettenleiter, T. C., N. Lukacs, and H.-J. Rziha, J. Virol. 53, 52–57 (1985).

Meulemans, G., C. Letellier, M. Gonze, M. C. Carlier, and A. Bunny, Avian Pathol. 17, 821–827 (1988).

Michel, F., Hoffenbach, A., Langlade–Demoyen, P., Guy, B., Lecocq, J.-P., Wain–Hobson, S., Kieny, M.-P. and Plata, F., Eur. J. Immunology 18, 1917 (1988).

Milich, D. R. and A. McLachlan, *In* Viral Hepatitis and Liver Disease, pp. 645–649 (1988).

Milich, D. R., A. McLachlan, A. Moriarty and G. B. Thornton, J. Immun. 138, 4457–4465 (1987a).

Milich, D. R., A. McLachlan, G. B. Thornton and J. L. Hughes, Nature 329, 547–549 (1987b).

Milich, D. R., G. B. Thornton, A. R. Neurath, S. B. Kent, M-L. Michel, P. Tiollais and F. V. Chisari, Science 228, 1195–1199 (1985).

Milich, D. R., A. McLachlan, F. V. Chisari, S. B. H. Kent and G. B. Thornton, J. Immun. 137, 315–322 (1986).

Miller, G., *In* Virology, Second Edition, eds. B. N. Fields, D. M. Knipe et al., (Raven Press) (1990).

Monath, T. P., *In The Togaviridae and Flaviviridae, eds. S. Schlesinger and M. J. Schlesinger, (Plenum Press, New York/London) pp. 375–440 (1986).*

Morgan, A. J., M. Mackett, S. Finerty, J. R. Arrand, F. T. Scullion and M. A. Epstein, J. Med. Virol. 25, 189–195 (1988).

Morgan, J. R. and B. E. Roberts, J. Virol. 51, 283–297 (1984).

Moss B., Smith G. L., Gerin, J. L. et al., Nature 311, 67–69 (1984).

Moss, B., E. Winters, and J. A. Cooper, J. Virol. 40, 387–395 (1981).

Moss et al., Science 252, 1662–1667 (1991).

Mullins, J. I., and Hoover, E. A., *In:* Retrovirus Biology and Human Disease, (eds. Gallo, R. C., Wong– Staal, F.) Marcel Dekker, Inc., New York, pp. 87–116 (1990).

Murphy, B. R., and R. G. Webster, In: Virology, eds. Fields, B. N., Knope, D. M. et al., Raven Press, NY, 1091–1151 (1990).

Murphy–Corb, M., Martin, L. N., Davison–Fairburn, B., Montelaro, R. C., Miller, M., West, M., Ohkawa, S., Baskin, G. B., Zhang, J.-Y., Putney, S. D., Allison, A. C. and Eppstein, D. A., Science 246, 1293– 1297 (1989).

Murray, K., S. A. Bruce, A. Hinnen, P. Wingfield, P. M. C. A. van Erd, A. de Reus and H. Schellekens, EMBO 3, 645–650 (1984).

Nagai, Y., H. D. Klenk, and R. Rott, Virology 72, 494–508 (1976).

Nagai, Y., T. Yoshida, M. Hamaguchi, H., Naruse, M. Iinuma, K. Maeno, and T. Matsumoto, Microbiol. Immunol. 24, 173–177 (1980).

Neurath, A. R.,S. B. H. Kent and N. Strick, Science 224, 392–395 (1984).

Neurath, A. R., S. B. H. Kent, N. Strick and K. Parker, Cell 46, 429–436 (1986).

Neurath, A. R., B. A. Jameson and T. Huima, Microbiological Sciences 4, 45–51 (1987).

Neurath, A. R. and S. B. H. Kent, Adv. Vir. Res. 34, 65–142 (1988).

Neurath, A. R., N. Strick and M. Girard, Mol. Immun. 26, 53–62 (1989).

Nixon, D. F., Townsend, A. R. M., Elvin, J. G., Rizza, C. R., Gallwey, J. and McMichael, A. J., Nature 326, 484–487 (1988).

Hu, S. L., Kosowski S. G., Dallyrmple J. M., Nature 320, 537–540 (1986).

Hu, S.-L., Travis, B. M., Garrigues, J., Zarling, J. M., Eichberg, J. W. and Alpers, C. E., *In* Vaccine 90, eds. Chanock, R. M., Lerner, R. A., Brown, F., and Ginsberg, H., (Cold Spring Harbor Press, Cold Spring Harbor, New York) pp. 231– 236 (1990).

Hu, et al., Proc. Natl. Acad. Sci. USA 86, 7213–7217 (1989).

Huang, C. H., Advances in Virus Research 27, 71–101 (1982).

Hunt, L. A., D. W., Brown, H. L. Robinson, C. W. Naeve, and R. G. Webster, J. Virol. 62, 3014–3019 (1988).

Ichihashi, Y. and Dales, S., Virology 46, 533–543 (1971).

Igarashi A., J. Gen. Virol. 40, 531–544 (1978).

Inoue Y. K., Bull. WHO 30, 181–185 (1964).

Itamura, S., H. Iinuma, H. Shida, Y. Morikawa, K. Nerome and A. Oya, J. Gen. Virol. 71, 2859–2865 (1990).

Itoh, Y., E. Takai, H. Ohnuma, K. Kitajima, F. Tsuda, A. Machida, S. Mishiro, T. Nakamura, Y. Miyakawa and M. Mayumi, Proc. Natl. Acad. Sci. USA 83, 9174–9178 (1986).

Jacobson, J. G., D. A. Leib, D. J. Goldstein, C. L. Bogard, P. A. Schaffer, S. K. Weller and D. M. Coen, Virology 173, 276–283 (1989).

Jamieson, A. T., G. A. Gentry and J. H. Subak–Sharpe, J. Gen. Virol. 24, 465–480 (1974).

Jarrett, O., and Russell, P. H., Int. J. Cancer 27, 466–472 (1978).

Jarrett, O., Laird, H. M., and Hay, D., J. Gen. Virol. 20, 169–175 (1973).

Javeherian, K., Langlois, A. J., McDanal, C., Ross, K. L., Eckler, L. I., Jellib, C. L., Profy, A. T., Rusche, J. R., Bolognesi, D. P., Putney, S. D., and Mathews, T. J., Proc. Natl. Acad. Sci. USA 86, 6768–6772 (1989).

Jilg, W., C. Delhoune, F. Deinhardt, A. J. Roumeliotou–Karayannis, G. J. Papaevangelous, I. K. Mushahwar and L. R. Overby, J. Med. Virol. 13, 171–178 (1984).

Jin, H. and Elliot, R. m., J. Virology 65, 4182–4189 (1991).

Joklik, W. K., Pickup, D. J., Patel, D. D., and Moody, M. D., Vaccine 6, 123–128 (1988).

Karacostas, V., Nagashima, K., Gonda, M. A., and Moss, B., Proc. Natl. Adad. Sci, USA 86, 8964–8968 (1989).

Kari, B., N. Lussenhop, R. Goertz, M. Wabuke–Bunoti, R. Radeke, and R. Gehrz, J. Virol. 60, 345–352 (1986).

Kato, S., M. Takahashi, S. Kameyama and J. Kamahora, Biken's 2, 353–363 (1959).

Kaufman, B. M., Summers, P. L., Dubois, D. R., and Eckels, K. H., Am. J Trop. Med. Hyg. 36, 427–434 (1987).

Kaufman, B. M., Summers, P. L., Dubois, D. R., Cohen, W. H., Gentry, M. I., Timchak, R. L., Burke, D. S. and Eckels, K. H., Am. J. Trop. Med. Hyg. 41, 576–580 (1989).

Kawaoka, Y., Bean, W. J., Webster, R. G., Virology 169, 283–292 (1989).

Keegan, K. and Collett, M. S., J. Virology 58, 263–270 (1986).

Kensil, C. R., Barrett, M. S., Kushner, B. S., Beltz, G., Storey, J., Patel, U., Recchia, J., Aubert, A., and Marciaini, D., JAVMA 199, 1402–1405 (1991).

Kieff, E., and Liebowitz, D., *In* Virology, Second Edition, eds. B. N. Fields, D. M. Knipe et al., (Raven Press) (1990).

Kieny, M. P., Lathe, R., Drillien, R., Spehner, D., Skory, S., Schmitt, D., Wiktor, T., Koprowski, H., and Lecocq, J. P., Nature (London) 312, 163–166 (1984).

Killington, R. A., J. Yeo, R. W. Honess, D. H. Watson, B. E. Duncan, I. W. Halliburton, and J. Mumford, J. gen. Virol. 37, 297–310 (1977).

Kimura-Kuroda, J., and Yasui, K., Immunol. 141, 3606–3610 (1988).

Kingsbury, D. W., *In* Virology, Second Edition, eds. B. N. Fields, D. M. Knipe et al., (Raven Press, Ltd. New York) pp. 1075–1089 (1990).

Kingsbury, D. W., M. A. Bratt, P. W. Choppin, R. P. Hanson, T. Hosaka, Y. ter Meulen, E. Morrby, W. Plowright, R. Rott and W. H. Wunner, Intervirology 10, 137–152 (1978).

Kingsford, L., Ishizawa, L. D., and Hill, D. W., Virology 129, 443–455 (1983).

Klasse, P. J., Pipkorn, R., and Blomberg, J., Proc. Natl. Acad. Sci. USA 85, 5225–5229 (1988).

Kleitmann W., Schottle A., Kleitmann B., et al., *In* Cell Culture Rabies Vaccines and Their Protective Effect in Man., ed. Kuwert/Wiktor/Koprowski, (International Green Cross–Geneva) pp. 330–337 (1981).

Knauf, V. C., and Nester, E. W., Plasmid 8, 45–54 (1982).

Kodama K., Sasaki N., and Kanda Inoue Y., J. Immunol. 100, 194–200 (1967).

Kodama, T., Wooley, D. P., Naidu, Y. M., Kestler III, H. W., Daniel, M. D., Li, Y. and Derosiers, R. C. J. Virol. 63, 4709–4714 (1989).

Koff, W. C. and Fauci, A. S., AIDS 1, 5125–5129 (1989).

Konishi, E., Pincus, S., Fonseca, B. A. L., Shope, R. E., Paoletti, E., and Mason, P. W., Virology 185, 401–410 (1991).

Konno J., Endo K., Agatsuma H., and Ishida N. Cyclic, Am. J. Epidemiol. 84, 292–300 (1966).

Kost, T. A., E. V. Jones, K. M. Smith, A. P. Reed, A. L. Brown, and T. J. Miller, Virology 171, 365–376 (1989).

Kotwal, G. J. and Moss, B., Nature (Lond.) 335, 176–178 (1988).

Kotwal, G. J. and Moss, B., J. Virol. 63, 600–606 (1989b).

Kotwal, G. J. and Moss, B, Virology 167, 524–537 (1988b).

Kotwal, G. J., S. N. Isaacs, R. McKenzie, M. M. Frank and B. Moss, Science 250, 827–830 (1990).

Kotwal, G. J., A. W. Hugin and B. Moss, Virology 171, 579–587 (1989a).

Koup, R. A., Sullivan, J. L., Levine, P. H., Brettler, D., Mahr, A., Mazzara, G., McKenzie, S., and Panicali, D. Blood 73, 1909–1919 (1989).

Kunkel, T. A., Proc. Natl. Acad. Sci. USA 82, 488–492 (1985).

Kunkel, T. A., Roberts, J. D., and Zakour, R. A., Method in Enzym. 154, 367–382 (1987).

Kuroda, K., C. Hauser, R. Rott, H.–D. Klenk, and W. Doerfler, EMBO 5, 1359–1365 (1986).

Kuroki, K., R. Russnak and D. Ganem, Mol. Cell. Biol. 9, 4459–4466 (1989).

Kuwert E. K., Barsenbach C., Werner J., et al., *In* Cell Culture Rabies Vaccines and Their Protection Effect in Man, eds. Kuwert/Wiktor/Koprowski (International Green Cross–Geneva) pp. 160–167 (1981).

Laemmli, U. K., Nature (London) 227, 680–685 (1970).

Lai, A. C.–K. and B. G.–T. Pogo, Virus Res. 12, 239–250 (1989).

Lane, J. M., Ruben, F. L., Neff, J. M., and Millar, J. D., New Eng. J. Med. 281, 1201–1208 (1969).

Lathe, R., M. P. Kieny, D. Schmitt, P. Curtis and J. P. Lecocq, J. Mol. Appl. Gen. 2, 331–342 (1984).

Le, L., R. Brasseur, C. Wemers, G. Meulemans, and A. Burny, Virus Genes 1, 333–350 (1988).

Lecocq, J. P., M. P. Kieny, Y. Lemoine, R. Drillien, T. Wiktor, H. Koprowski and R. Lathe, *In* World's Debt to Bouquet, P. Desmettre, and E. Paoletti, Virology 179, 901–904 (1990).

Eisel, U., Jarausch, W., Goretzki, K., Henschen, A., Engels, J., Weller, U., Hudel, M., Habermann, E., and Niemann, H. EMBO J. 5, 2495–2502 (1986).

Elder, J. H., McGee, J. S., Munson, M., Houghton, R. A., Kloetzer, W., Bittle, J. L., and Grant, C. K., J. Virol. 61, 8–15 (1987).

Elder, J. H., and Mullins, J. V., J. Virol. 46, 871–880 (1983).

Engelke, D. R., Hoener, P. A., and Collins, F. S., Proc. Natl. Acad. Sci. USA 85, 544–548 (1988).

Espion, D., S. de Henau, C. Letellier, C.–D. Wemers, R. Brasseur, J. F. Young, M. Gross, M. Rosenberg, G. Meulemans and A. Burny. Arch. Virol. 95, 79–95 (1987).

Esposito, J. J., K. Brechling, G. Baer and B. Moss, Virus Genes 1, 7–21 (1987).

Esposito, J. J., J. C. Knight, J. H. Schaddock, F. J. Novembre and G. Baer, Virology 165, 313–316 (1988).

Etlinger H. M., Altenburger W., Vaccine 1991, 9, 470–471.

Fairwather, N. F., and Lyness, V. A. *Nucleic Acids Res.* 14, 7809–7812 (1986).

Falgout, B., Chanock, R. and Lai, C.–J, J. Virology 63, 1852–1860 (1989).

Falkner, F. G. and B. Moss, J. Virol. 64, 3108–3111 (1990).

Fenner, F., Virology 5, 502–529 (1958).

Flexner, C., Hugen, A., and Moss, B., Nature 330, 259–262 (1987).

Franchini, G., Gurgo, C., Guo, H.–G., Gallo, R. C., Collati, E., Fargnoli, K. A., Hall, L. F., Wong–Staal, F., and Reitz, Jr., M. S., Nature (London) 328, 539–543 (1987).

Franchini, G., Fargnoli, K. A., Giomnini, F., Jagodzinski, L., DeRossi, A., Bosch, M., Biberfield, G., Fenyo, E. M., Albert, J., Gallo, R. C., and Wong–Staal, F., Proc. Natl. Acad. Sci. USA 86, 2433–2437 (1989).

Fujisaki Y., Sugimori T., Morimoto T., Muira Y., Kawakani Y. and Nakano K., Natl. Inst. Anim. Health Q. 15, 55–60 (1975b).

Funahashi, S., T. Sato and H. Shida, J. Gen. Virol. 69, 35–47 (1988).

Galibert, F., E. Mandart, F, Fitoussi, P. Tiollais and P. Charnay, Nature 281, 646–650 (1979).

Garten, W., Kohama, T., and H–D. Klenk. J. Gen. Virol. 51, 207–211 (1980).

Ghendon, Y. Z., and Chernos, V. I., Acta Virol. 8, 359–368 (1964).

Giavedoni, L., Jones, L., Mebus, C., and Yilma, T. A., Proc. Natl. Acad. Sci. USA 88, 8011–8015 (1991).

Gibson, C. A., Schlesinger, J. J., and Barrett, A. D. T., Vaccine 6, 7–9 (1988).

Gillard, S., Spehner, D., Drillien, R., and Kirn, A., Proc.

Natl. Acad. Sci. USA 83, 5573–5577 (1986).

Glosser, J. W., Environmental assessment and preliminary finding of NO significant impact. Verterinary biologics authorized field trial of an experimental biologic: The Wistar Institute of Anatomy and Biology proposed field trial of a live experimental vaccinia vectored rabies vaccine. United States Department of Agriculture, Animal, and Plant Health Inspection Services (1989).

Goebel S. J., Johnson G. P., Perkus M. E., Davis S. W., Winslow J. P. and E. Paoletti, Virology 179, 247–266 (1990).

Goebel, S. J., G. P. Johnson, M. E. Perkus, S. W. Davis, J. P. Winslow and E. Paoletti, Virology 179, 517–563 (1990b).

Goldstein, D. J. and S. K. Weller, Virology 166, 41–51 (1988).

Gonczol, E., Furlini, G., Ianacone, J, and Plotkin, S. A., J. Virol. 14, 37–41 (1986).

Gonzolez–Scarano, F., Shope, R. E., Calisher, C. H., and Nathanson, N, Virology, 120, 42–53 (1982).

Gould, E. A., Buckley, A., Barrett, A. D. T., and Cammack, N., J. Gen. Virol. 67, 591–595 (1986).

Graves, M. C., J. M. Silver, and P. W. Choppin, Virology 86, 254–263 (1978).

Gretch, D. R., B. Kari, L. Rasmussen, R. C. Gehrz, and M. F. Stinski, J. Virol. 62, 875–881 (1988).

Gubler, U., and Hoffman, B. J., Gene 25, 263–269 (1983).

Guilhot, S., Hampe, A., D'Auriol, L., and Galibert, F. Virology 161, 252–258 (1987).

Guo, P., Goebel, S., Perkus, M. E., Taylor, J., Norton, E., Allen, G., Languet, B., Desmettre, P., and Paoletti, E., J. Virol. 64, 2399–2406 (1990).

Guo, P., Goebel, S., Davis, S., Perkus, M. E., Languet, B., Desmettre, P., Allen, G., and Paoletti, E., J. Virol. 63, 4189–4198 (1989).

Guo, H–G., diMarzo Veronese, F., Tschachler, E., Pal, R., Kalyanaraman, V. S., Gallo, R. C., and Reitz, Jr., M. S., Virology 174, 217–224 (1990).

Gupta, R. K., Misra, C. N., Gupta, V. K., and Saxena, S. N., Vaccine 9, 865–867 (1991).

Gurgo, C., Guo, H.–G., Franchini, G., Aldovini, A., Collalti, E., Farrell, K., Wong–Staal, F., Gallo, R. C., and Reitz, M. S., Jr., Virology 164, 531 (1988).

Haffar, O., Garrigues, J., Travis, B., Moran, P., Zarling, J., and Hu, S.–L. J. Virol. 64, 2653–2659 (1990).

Halpern, J. L., Habing, W. H., Neale, E. A., and Stibitz, S. Infect. Immun. 58, 1004–1009 (1990).

Hampl, H., Ben–Porat, T., Ehrlicher, L., Habermehl, K.,–O., and Kaplan, A. S., J. Virol. 52, 583–590 (1984).

Hardy, Jr., W. D., Hess, P. W., MacEven, E. G., McClelland, A. J., Zuckerman, E. E., Essex, M., Cotter, S. M., and Jarrett, O., Cancer Res. 36 582–588 (1976).

Hardy, Jr., W. D., Adv. Viral Oncology 5, 1–34 (1985).

Heermann, K. H., U. Goldmann, W. Schwartz, T. Seyffarth, H. Baumgarten and W. H. Gerlich, J. Virol. 52, 396–402 (1984).

Henchal, E. A., Henchal, L. S., and Schlesinger, J. J., J. Gen. Virol. 69, 2101–2107 (1988).

Hinshaw, V. S., R. G. Webster, W. J. Bean, G. Sriram, Comp. Immunol. Microbiol. Infect. Dis. 3, 155–164 (1981).

Hinshaw, V. S., Naeve, C. W., Webster, R. G., Douglas, A., Dkehel, J. J., and Bryans, J. T., Bull. World Health Organization 61, 153–158 (1983).

Homma, M., and M. Ohuchi, J. Virol. 12, 1457–1465 (1973).

Hoshikawa, N., Kojima, A., Yasuda, A., Takayashiki, E., Masuko, S., Chiba, J., Sata, T., and Kurata, T., J. Gen. Virol. 72, 2509–2517 (1991).

Hosmalin, A., Nara, P. L., Zweig, M., Lerche, N. W., Cease, K. B., Gard, E. A., Markham, P. D., Putney, S. D., Daniel, M. D., Desrosiers, R. C., and Berzofsky, J. A. J. Immunol. 146, 1667–1673 (1991).

Hruby, D. E., R. A. Maki, D. B. Miller and L. A. Ball, Proc. Natl. Acad. Sci. USA 80, 3411–3415 (1983).

Hruby, D. E. and L. A. Ball, J. Virol. 43, 403–409 (1982).

Hu, S.–L. Travis, B. M., Garrigues, J., Zarling, J. M., Sridhar, P., Dykers, T.,Eichberg, J. W., and Alpers, C. Virology 179, 321–329 (1990).

Hu, S.–L., Fultz, P., McClure, H., Eichberg, J., Thomas, E., Zarling, J., Singhal, M., Kosowski, S., Swenson, R., Anderson, D. and Todaro, G., Nature 328, 721–723 (1987). Sci. USA 82, 2096–2100 (1985).

Bishop, D. H. L., In: Bunyaviridae and Their Replication in Virology: 2nd Edition, pp. 1155–1173 (1990).

Borysiewicz, L. K., J. K. Hickling, S. Graham, J. Sinclair, M. P. Crange, G. L. Smith, and J. G. Sissons, J. Exp. Med. 168, 919–931 (1988).

Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).

Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).

Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300 (1990c).

Boursnell, M. E. G., I. J. Foulds, J. I. Campbell and M. M. Binns, J. Gen. Virol. 69, 2995–3003 (1988).

Brandt, W. E., J Infect Dis. 157, 1105–1111 (1988).

Brochier B., Kieny M. P., Costy F., et al., Nature, 354 520–522 (1991).

Bryson, Y., Dillon, M., Lovett, M., Acuna, G., Taylor, S., Cherry, J., Johnson, B., Wiesmeier, E., Growdon, W., Creagh–Kirk, T. and Keeney, R., N. Engl. J. Med. 308, 916–921 (1983).

Bucher, D., Popplo, S., Baer, M., Mikhail, A., Gong, Y–F., Whitaker, C., Paoletti, E., and Judd, A., J. Virol. 63, 3622–3633 (1989).

Buller, R. M. L., and Palumbo, G. J., Microbiol. Rev. 55, 80–122 (1991).

Buller, R. M. L., Chakrabarti, S., Cooper, J. a., Twardzik, D. R., and Moss, B., J. Virol. 62, 866–874 (1988).

Buller, R. M. L., G. L. Smith, Cremer, K., Notkins, A. L., and Moss, B., Nature 317, 813–815 (1985).

Bunn, T. O., In: Rabies, eds. Campbell, J. B. and Charlton K. M. (Kluwer Academy Press, Boston) pp. 474–491 (1988).

Cantin, E., Eberle, R., Baldrick, J., Moss, B., Willey, D., Notkins, A. and Openshaw, H., Proc. Natl. Acad. Sci. USA, 84, 5908–5912 (1987).

Chakrabarti, S., Brechling, K., and Moss, B., Mol. Cell. Biol. 5, 3403–3409 (1985).

Chakrabarti, S., Robert–Guroff, M., Wong–Staal, F., Gallo, R. C., and Moss, B. Nature 320, 535–537 (1986).

Chambers, T. M., Y. Kawaoka, and R. G. Webster, Virology 167, 414–421 (1988).

Chambers, P., N. S. Millar, and P. T. Emmerson, J. Gen. Virol. 67, 2685–2694 (1986).

Chambers, T. J., Hahn, C. S., Galler, R., and Rice, C. M., Ann. Rev. Microbiol. 44, 649–688 (1990).
Chan, W., Immunol. 49, 343–352 (1983).
Charles, I. G., Rodgers, B. C., Makoff, A. J., Chatfield, S. N., Slater, D. E., and Fairweather, N. F., Infect. Immun. 59, 1627–1632 (1991).
Chen, C., R. W. Coupans, and P. W. Choppin, J. Gen. Virol. 11, 53–58 (1971).
Cheng, K–C, G. L. Smith and B. Moss, J. Virol. 60, 337–344 (1986).
Child, S. J., Palumbo, G. J., Buller, R. M. L., and Hruby, D. E. Virology 174, 625–629 (1990).
Chirgwin, J. M., Przybyla, A. E., MacDonald, R. J., and Rutter, W. J., Biochemisrty 18, 5294–5299 (1979).Chisari, F. V., P. Filippi, A. McLachlan, D. R. Milich, M. Riggs, S. Lee, R. R. Palmiter, C. A. Pinkert and R. L. Brinster, J. Virol. 60, 880–887 (1986).
Cianciolo, G. J., Copeland, T. D., Oroszlan, S., and Snyderman, R. Science 230, 453–455 (1985).
Clark, N., Kushner, B. S., Barrett, M. S., Kensil, C. R., Salsbury, D., and Cotter, S., JAVMA 199, 1433–1442 (1991).
Clarke, B. E., S. E. Newton, A. R. Carroll, M. J. Francis, G. Appleyard, A. D. Syred, P. E. Highfield, D. J. Rowlands and F. Brown, Nature 330, 381–384 (1987).
Clarke D. H., and Casals J. Am., J. Trop. Med. Hyg. 7, 561–573 (1958).
Clewell, D. B., J. Bacteriol 110, 667–676 (1972).
Clewell, D. B. and D. R. Helinski, Proc. Natl. Acad. Sci. USA 62, 1159–1166 (1969).
Colinas, R. J., R. C. Condit and E. Paoletti, Virus Research 18, 49–70 (1990).
Collett, M. S., Keegan, K., Hu, S.–L, Sridhar, P., Purchio, A. F., Ennis, W. H., and Dalrymple, J. M., *In:* The Biology of Negative Strand Viruses, pp. 321–329 (1987).
Collins P. L., Purcell R. H., London W. T. et al., Vaccine 8, 154–168 (1990).
Cooney E. L., Corrier A. C., Greenberg P. D., et al., Lancet 337, 567–572 (1991).
Cox, J. H., B. Dietzschold, and L. G. Schneider, Infect. Immun. 16, 754–759 (1977).
Dales, S., Ann. Rev. Microbiol. 44, 173–192 (1990).
Daniels, R. S., Skehel, J. J., and Wiley, D. C., J. Gen. Virol. 66, 457–464 (1985).
Dantas, J. R., Fr., Okuno, Y., Asada, H., Tamura, M., Takahashi, M., Tanishita, O., Takahashi, Y. Kurata, T., and Yamanishi, K., Virology 151, 379–384 (1986).
Davis, W., Taylor, J. and Oakes, J., J. Infect. Dis. 140, 534–540 (1979).
De, B. K., M. W. Shaw, P. A. Rota, M. W. Harmon, J. J. Esposito, R. Rott, N. J. Cox and A. P. Kendal, Vaccine 6, 257–261 (1988).
Delpeyroux, F., N. Peillon, B. Blondel, R. Crainic and R. E. Streeck, J. Virol., 62, 1836–1839 (1988).
DeNoronaha, F., Schafer, W., and Essex, M., Virology 85, 617–621 (1978).
Derosiers, R. C., M. S. Wyand, T. Kodama, T. J. Ringler, L. O. Arthur, P. K. Sehgal, N. L. Letvin, N. W. King and M. D. Daniel, Proc. Natl. Acad. Sci. USA 86, 6353–6357 (1989).
Diallo, A., Vet. Micro. 23, 155–163 (1990).
Douglas, J., Critchlow, C., Benedetti, J., Mertz, G., Connor, J., Hintz, M., Fahnlander, A., Remington, M., Winter, C. and Corey, L., N. Engl. J. Med. 310, 1551–1556 (1984).
Dowbenko, D. and Lasky, L., J. Virol. 52, 154–163 (1984).
Dowling, P. C., B. M. Blumberg, J. Menonna, J. E. Adamus, P. Cook, J. C. Crowley, D. Kolakofsky, and S. D. Cook, J. Gen. Virol. 67, 1987–1992 (1986).
Dreyfuss, G., Adam, S. A. and Choi, Y. D., Mol. Cell. Biol. 4, 415–423 (1984).
Drillien, R., F. Koehren and A. Kirn, Virology 111, 488–499 (1981).
Drillien, R., D. Spehner, A., Kirn, P. Giraudon, R. Buckland, F. Wild, and J. P. Lecocq, Proc. Natl. Acad. Sci. USA 85, 1252–1256 (1988).
Easterday, B. C. and V. S. Hinshaw, *In* Diseases of Poultry, Ninth edition eds. B. W. Calnek, H. J. Barnes, et al., (Iowa State University Press, Ames, Iowa) pp. 531–551 (1991).
Eble, B. E., V. R. Lingappa and D. Ganem, Mol. Cell. Biol. 6, 1454–1463 (1986).
Edbauer, C., R. Weinberg, J. Taylor, A. Rey–Senelonge, J. F.

```
            10        20        30        40        50        60
TTCTTTATTCTATACTTAAAAAGTGAAAATAAATACAAAGGTTCTTGAGGGTTGTGTTAA 70        80        90       100       110       120
ATTGAAAGCGAGAAATAATCATAAATTATTTCATTATCGCGATATCCGTTAAGTTTGTAT 130       140       150       160       170       180
GCTAATGCAGTGGAATTCTACTACTTTTCACCAAACTTTACAAGATCCTAGAGTAAGAGG
     M  Q  W  N  S  T  T  F  H  Q  T  L  Q  D  P  R  V  R  G
     S2
           190       200       210       220       230       240
ATTATATTTTCCTGCTGGAGGATCTTCTTCTGGAGCTGTAAATCCTGTACCTACTACTGC
  L  Y  F  P  A  G  G  S  S  S  G  A  V  N  P  V  P  T  T  A>

250       260       270       280       290       300
TTCTCCTTTATCTTCTATTTTTAGTAGAATTGGAGATCCTGCTTTAAATATGGAAAATAT
  S  P  L  S  S  I  F  S  R  I  G  D  P  A  L  N  M  E  N  I
                                                     S
           310       320       330       340       350       360
TACTTCTGGATTTTTAGGACCTTTATTAGTATTACAAGCTGGATTCTTTCTATTAACTAG
  T  S  G  F  L  G  P  L  L  V  L  Q  A  G  F  F  L  L  T  R>

370       380       390       400       410       420
AATTTTAACTATTCCTCAATCTCTAGATTCTTGGTGGACTTCTTTAAATTTTTTAGGAGG
  I  L  T  I  P  Q  S  L  D  S  W  W  T  S  L  N  F  L  G  G 430       440       450       460       470       480
AACTACTGTTTGTTTAGGACAAAATTCTCAATCTCCTACTTCTAATCACTCTCCTACTTC
  T  T  V  C  L  G  Q  N  S  Q  S  P  T  S  N  H  S  P  T  S>
```

FIG. 9A

```
        490       500       510       520       530       540
TTGTCCTCCTACTTGTCCTGGATATCGTTGGATGTGTTTAAGAAGATTTATTATTTTCTT
  C  P  P  T  C  P  G  Y  R  W  M  C  L  R  R  F  I  I  F  L 550       560       570       580       590       600
ATTTATTTTATTATTGTGTTTAATTTTCTTATTAGTATTATTAGATTATCAAGGAATGTT
  F  I  L  L  L  C  L  I  F  L  L  V  L  L  D  Y  Q  G  M  L>

610       620       630       640       650       660
ACCTGTTTGTCCTTTAATTCCTGGATCCTCTACTACTTCTACTGGACCTTGTAGAACTTG
  P  V  C  P  L  I  P  G  S  S  T  T  S  T  G  P  C  R  T  C 670       680       690       700       710       720
TATGACTACTGCTCAAGGAACTTCTATGTATCCTTCTTGTTGTACTAAACCTTCTGA
  M  T  T  A  Q  G  T  S  M  Y  P  S  C  C  C  T  K  P  S  D>

730       740       750       760       770       780
CGGAAATTGTACTTGTATTCCTATTCCTTCTTCTTGGGCTTTTGGAAAATTCTTGTGGGA
  G  N  C  T  C  I  P  I  P  S  S  W  A  F  G  K  F  L  W  E 790       800       810       820       830       840
GTGGGCTTCTGCTAGATTTTCTTGGTTATCTTTATTAGTACCTTTTGTACAGTGGTTTGT
  W  A  S  A  R  F  S  W  L  S  L  L  V  P  F  V  Q  W  F  V>

850       860       870       880       890       900
AGGATTATCTCCTACTGTTTGGTTATCTGTAATTTGGATGATGTGGTATTGGGGACCTTC
  G  L  S  P  T  V  W  L  S  V  I  W  M  M  W  Y  W  G  P  S 910       920       930       940       950       960
TTTATATTCTATTTTATCTCCTTTTTTACCTTTATTACCTATTTCTTTTGTTTGTGGGT
  L  Y  S  I  L  S  P  F  L  P  L  L  P  I  F  F  C  L  W  V>

970
ATATATTTAA
  Y  I  *
```

FIG. 9B

```
          10        20        30        40        50        60
GTAGACTGTTTATACAAGATTGAAAATATATTTCTTTTTATTGAGTGGTGGTAGTTACGG 70        80        90       100       110       120
ATATCTAATATTAATATTAGACTATCTCTATCGTCACACAACAAAATCGATTGCCATGGG
                                                          M   G>
                                                          S1

130       140       150       160       170       180
GCAGAATCTTTCCACCAGCAATCCTCTGGGATTCTTTCCCGACCACCAGTTGGATCCAGC
  Q  N  L  S  T  S  N  P  L  G  F  F  P  D  H  Q  L  D  P  A 190       200       210       220       230       240
CTTCAGAGCAAACAACGCAAATCCAGATTGGGACTTCAATCCCAACAAGGACACCTGGCC
  F  R  A  N  N  A  N  P  D  W  D  F  N  P  N  K  D  T  W  P>

250       260       270       280       290       300
AGACGCCAACAAGGTAGGAGCTGGAGCATTCGGGCTGGGTTTCACCCCACCGCACGGAGG
  D  A  N  K  V  G  A  G  A  F  G  L  G  F  T  P  P  H  G  G 310       320       330       340       350       360
CCTTTTGGGGTGGAGCCCTCAGGCTCAGGGCATACTACAAACTTTGCCAGCAAATCCGCC
  L  L  G  W  S  P  Q  A  Q  G  I  L  Q  T  L  P  A  N  P  P>

370       380       390       400       410       420
TCCTGCCTCCACCAATCGCCAGACAGGAAGGCAGCCTACCCCGCTGTCTCCACCTTTGAG
  P  A  S  T  N  R  Q  T  G  R  Q  P  T  P  L  S  P  P  L  R 430       440       450       460       470       480
AAACACTCATCCTCAGGCCATGCAGTGGAATTCCACAACCTTTCACCAAACTCTGCAAGA
  N  T  H  P  Q  A  M  Q  W  N  S  T  T  F  H  Q  T  L  Q  D>
                    S2

490       500       510       520       530       540
TCCAGAGTGAGAGGCCTGTATTTCCCTGCTGGTGGCTCCAGTTCAGGAGCAGTAAACCC
  P  R  V  R  G  L  Y  F  P  A  G  G  S  S  S  G  A  V  N  P 550       560       570       580       590       600
TGTTCCGACTACTGCCTCTCCCTTATCGTCAATCTTCTCGAGGATTGGGGACCCTGCGCT
  V  P  T  T  A  S  P  L  S  S  I  F  S  R  I  G  D  P  A  L>

610       620       630       640       650       660
GAACATGGAGAACATCACATCAGGATTCCTAGGACCCCTTCTCGTGTTACAGGCGGGGTT
  N  M  E  N  I  T  S  G  F  L  G  P  L  L  V  L  Q  A  G  F
    S
```

FIG. 11A

```
         670       680       690       700       710       720
CTTCTTGTTGACAAGAATCCTCACAATACCGCAGAGTCTAGACTCGTGGTGGACTTCTCT
 F  L  L  T  R  I  L  T  I  P  Q  S  L  D  S  W  W  T  S  L >

730       740       750       760       770       780
CAATTTTCTAGGGGGAACTACCGTGTGTCTTGGCCAAAATTCGCAGTCCCCAACCTCCAA
 N  F  L  G  G  T  T  V  C  L  G  Q  N  S  Q  S  P  T  S  N 790       800       810       820       830       840
TCACTCACCAACCTCCTGTCCTCCAACTTGTCCTGGTTATCGCTGGATGTGTCTGCGGCG
 H  S  P  T  S  C  P  P  T  C  P  G  Y  R  W  M  C  L  R  R >

850       860       870       880       890       900
TTTTATCATCTTCCTCTTCATCCTGCTGCTATGCCTCATCTTCTTGTTGGTTCTTCTGGA
 F  I  I  F  L  F  I  L  L  L  C  L  I  F  L  L  V  L  L  D 910       920       930       940       950       960
CTATCAAGGTATGTTGCCCGTTTGTCCTCTAATTCCAGGATCCTCAACCACCAGCACGGG
 Y  Q  G  M  L  P  V  C  P  L  I  P  G  S  S  T  T  S  T  G >

970       980       990      1000      1010      1020
ACCATGCCGAACCTGCATGACTACTGCTCAAGGAACCTCTATGTATCCCTCCTGTTGCTG
 P  C  R  T  C  M  T  T  A  Q  G  T  S  M  Y  P  S  C  C  C 1030      1040      1050      1060      1070      1080
TACCAAACCTTCGGACGGAAATTGCACCTGTATTCCCATCCCATCATCCTGGGCTTTCGG
 T  K  P  S  D  G  N  C  T  C  I  P  I  P  S  S  W  A  F  G >

1090      1100      1110      1120      1130      1140
AAAATTCCTATGGGAGTGGGCCTCAGCCCGTTTCTCCTGGCTCAGTTTACTAGTGCCATT
 K  F  L  W  E  W  A  S  A  R  F  S  W  L  S  L  L  V  P  F 1150      1160      1170      1180      1190      1200
TGTTCAGTGGTTCGTAGGGCTTTCCCCCACTGTTTGGCTTTCAGTTATATGGATGATGTG
 V  Q  W  F  V  G  L  S  P  T  V  W  L  S  V  I  W  M  M  W >

1210      1220      1230      1240      1250      1260
GTATTGGGGGCCAAGTCTGTACAGCATCTTGAGTCCCTTTTTACCGCTGTTACCAATTTT
 Y  W  G  P  S  L  Y  S  I  L  S  P  F  L  P  L  L  P  I  F 1270      1280
CTTTTGTCTTTGGGTATACATTTAA
 F  C  L  W  V  Y  I  * >
```

FIG. 11B

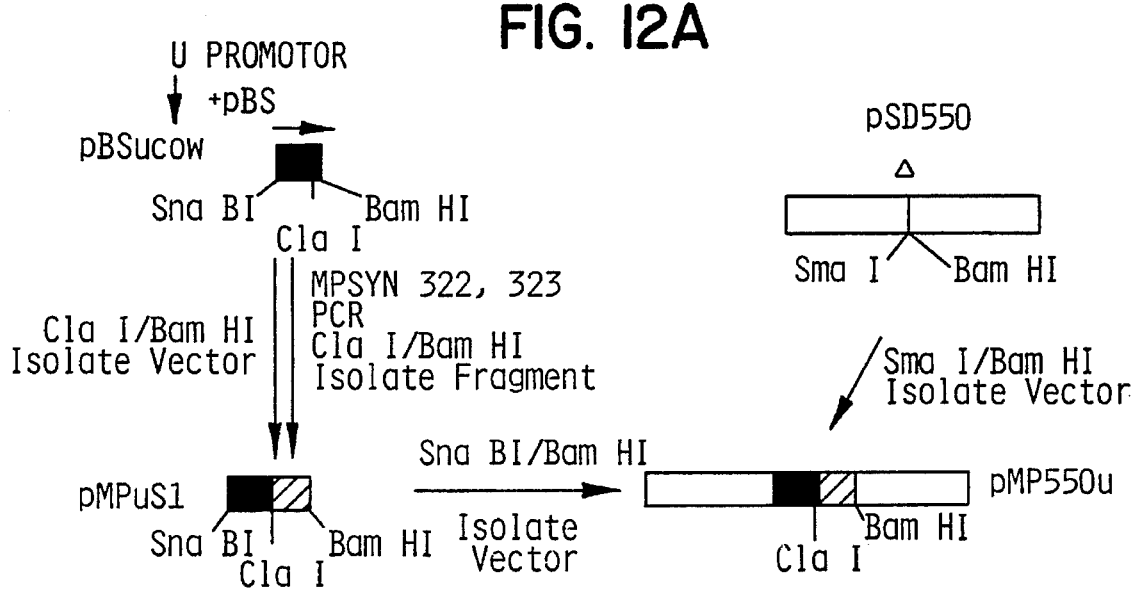
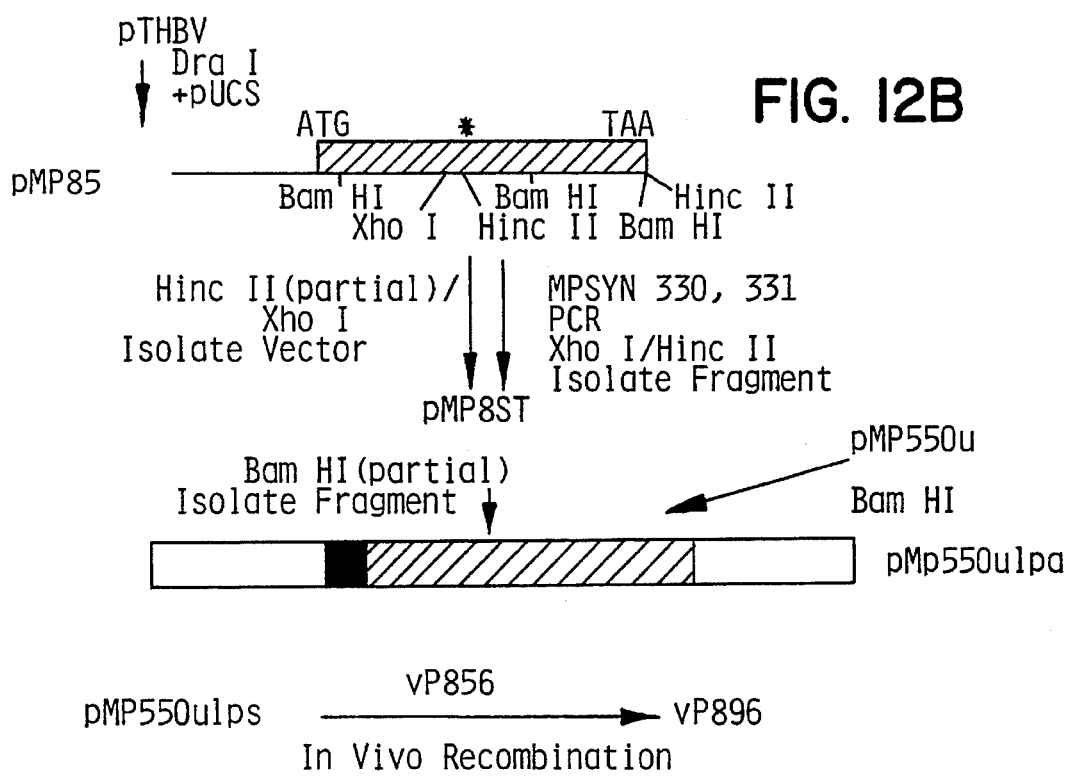

```
         10        20        30        40        50        60
TACATCATGCAGTGGTTAAACAAAAACATTTTTATTCTCAAATGAGATAAAGTGAAAATA 70        80        90       100       110       120
TATATCATTATATTACAAAGTACAATTATTTAGGTTTAATCATGGGAACGAACCTATCTG
                                         M  G  T  N  L  S
                                         S1

130       140       150       160       170       180
TTCCCAACCCACTTGGATTTTTTCCTGATCATCAGTTAGACCCTGCTTTCGGAGCCAACT
 V  P  N  P  L  G  F  F  P  D  H  Q  L  D  P  A  F  G  A  N 190       200       210       220       230       240
CAAACAATCCTGACTGGGATTTTAACCCCGTCAAAGACGATTGGCCTGCAGCCAACCAAG
 S  N  N  P  D  W  D  F  N  P  V  K  D  D  W  P  A  A  N  Q 250       260       270       280       290       300
TAGGTGTGGGAGCTTTCGGACCAAGGCTCACTCCTCCACACGGCGGTATATTAGGTTGGT
 V  G  V  G  A  F  G  P  R  L  T  P  P  H  G  G  I  L  G  W 310       320       330       340       350       360
CTCCACAAGCTCAAGGCATATTGACCACAGTGTCAACAATTCCTCCACCAGCCTCTACTA
 S  P  Q  A  Q  G  I  L  T  T  V  S  T  I  P  P  P  A  S  T 370       380       390       400       410       420
ATCGGCAGTCTGGTAGACAGCCAACTCCCATCTCTCCTCCTCTAAGAGACAGTCACCCAC
 N  R  Q  S  G  R  Q  P  T  P  I  S  P  P  L  R  D  S  H  P 430       440       450       460       470       480
AAGCTATGCAGTGGAATTCAACTGCTTTTCACCAGACACTTCAAGACCCTAGAGTCAGGG
 Q  A  M  Q  W  N  S  T  A  F  H  Q  T  L  Q  D  P  R  V  R
    S2

490       500       510       520       530       540
GTCTATATCTTCCTGCAGGTGGATCTAGTTCTGGAACTGTAAACCCAGCTCCGAATATTG
 G  L  Y  L  P  A  G  G  S  S  S  G  T  V  N  P  A  P  N  I 550       560       570       580       590       600
CCAGTCACATCTCGTCTATCTCCGCGAGGACTGGAGACCCAGTGACGAACATGGACATCG
 A  S  H  I  S  S  I  S  A  R  T  G  D  P  V  T  N  M  D  I
                                                      core
```

FIG. 13A

```
         610          620         630         640          650          660
ACCCTTATAAAGAATTTGGAGCTACTGTGGAGTTACTCTCGTTTTTGCCTTCTGACTTCT
 D  P  Y  K  E  F  G  A  T  V  E  L  L  S  F  L  P  D  S  F 670          680         690         700          710          720
TTCCTTCAGTACGAGATCTTCTAGATACCGCCTCAGCTCTGTATCGGGAAGCCTTAGAGT
 F  P  S  V  R  D  L  L  D  T  A  S  A  L  Y  R  E  A  L  E 730          740         750         760          770          780
CTCCTGAGCATTGTTCACCTCACCATACTGCACTCAGGCAAGCAATTCTTTGCTGGGGGG
 S  P  E  H  C  S  P  H  H  T  A  L  R  Q  A  I  L  C  W  G 790          800         810         820          830          840
AACTAATGACTCTAGCTACCTGGGTGGGTGTTAATTTGGAAGATCCAGCATCTAGAGACC
 E  L  M  T  L  A  T  W  V  G  V  N  L  E  D  P  A  S  R  D 850          860         870         880          890          900
TAGTAGTCAGTTATGTCAACACTAATATGGGCCTAAAGTTCAGGCAACTCTTGTGGTTTC
 L  V  V  S  Y  V  N  T  N  M  G  L  K  F  R  Q  L  L  W  F 910          920         930         940          950          960
ACATTTCTTGTCTCACTTTTGGAAGAGAAACCGTTATAGAGTATTTGGTGTCTTTCGGAG
 H  I  S  C  L  T  F  G  R  E  T  V  I  E  Y  L  V  S  F  G 970          980         990        1000          1010         1020
TGTGGATTCGCACTCCTCCAGCTTATAGACCACCAAATGCCCCTATCCTATCAACACTTC
 V  W  I  R  T  P  P  A  Y  R  P  P  N  A  P  I  L  S  T  L 1030          1040        1050        1060          1070         1080
CGGAAACTACTGTTGTTAGACGACGAGGCAGGTCCCCTAGAAGAAGAACTCCCTCGCCTC
 P  E  T  T  V  V  R  R  R  G  R  S  P  R  R  R  T  P  S  P 1090          1100        1110        1120          1130         1140
GCAGACGAAGGTCTCAATCGCCGCGTCGCAGAAGATCTCAATCTCGGGAATCTCAATGTTAG
 R  R  R  R  S  Q  S  P  R  R  R  R  S  Q  S  R  E  S  Q  C  *
```

FIG. 13B

```
           10        20        30        40        50        60
CAAAATTGAAAATATATAATTACAATATAAAATGGGGCAGAATCTTTCCACCAGCAATCC
                                M G Q N L S T S N P
                                S1

70        80        90       100       110       120
TCTGGGATTCTTTCCCGACCACCAGTTGGATCCAGCCTTCAGAGCAAACAACGCAAATCC
 L G F F P D N Q L D P A F R A N N A N P>

130       140       150       160       170       180
AGATTGGGACTTCAATCCCAACAAGGACACCTGGCCAGACGCCAACAAGGTAGGAGCTGG
 D W D F N P N K D T W P D A N K V G A G 190       200       210       220       230       240
AGCATTCGGGCTGGGTTTCACCCCACCGCACGGAGGCCTTTTGGGGTGGAGCCCTCAGGC
 A F G L G F T P P N G G L L G W S P Q A>

250       260       270       280       290       300
TCAGGGCATACTACAAACTTTGCCAGCAAATCCGCCTCCTGCCTCCACCAATCGCCAGAC
 Q S I L Q T L P A N P P P A S T N R Q T 310       320       330       340       350       360
AGGAAGGCAGCCTACCCCGCTGTCTCCACCTTTGAGAACACTCATCCTCAGGCCATGCA
 G R Q P T P L S P P L R N T H P Q A M Q>
                                         S2

370       380       390       400       410       420
GTGGAATTCCACAACCTTTCACCAAACTCTGCAAGATCCCAGAGTGAGAGGCCTGTATTT
 W N S T T F N Q T L Q D P R V R G L Y F 430       440       450       460       470       480
CCCTGCTGGTGGCTCCAGTTCAGGAGCAGTAAACCCTGTTCCGACTACTGCCTCTCCCTT
 P A G G S S S G A V N P V P T T A S P L>

490       500       510       520       530       540
ATCGTCAATCTTCTCGAGGATTGGGGACCCTGCGCTGAACATGGAGAACATCACATCAGG
 S S I F S R I G D P A L N M E N I T S G
                                  S 550       560       570       580       590       600
ATTCCTAGGACCCCTTCTCGTGTTACAGGCGGGGTTCTTCTTGTTGACAAGAATCCTCAC
 F L G P L L V L Q A G F F L L T R I L T>

610       620       630       640       650       660
AATACCGCAGAGTCTAGACTCGTGGTGGACTTCTCTCAATTTTCTAGGGGGAACTACCGT
 I P Q S L D S W W T S L N F L G G T T V 670       680       690       700       710       720
GTGTCTTGGCCAAAATTCGCAGTCCCCAACCTCCAATCACTCACCAACCTCCTGTCCTCC
 C L G Q N S Q S P T S N H S P T S C P P>
```

FIG. 15A

```
       730       740       750       760       770       780
AACTTGTCCTGGTTATCGCTGGATGTGTCTGCGGCGTTTTATCATCTTCCTCTTCATCCT
   T  C  P  G  Y  R  W  M  C  L  R  R  F  I  I  F  L  F  I  L 790       800       810       820       830       840
GCTGCTATGCCTCATCTTCTTGTTGGTTCTTCTGGACTATCAAGGTATGTTGCCCGTTTG
   L  L  C  L  I  F  L  L  V  L  L  D  Y  Q  G  M  L  P  V  C>

850       860       870       880       890       900
TCCTCTAATTCCAGGATCCTCAACCACCAGCACGGGACCATGCCGAACCTGCATGACTAC
   P  L  I  P  G  S  S  T  T  S  T  G  P  C  R  T  C  M  T  T 910       920       930       940       950       960
TGCTCAAGGAACCTCTATGTATCCCTCCTGTTGCTGTACCAAACCTTCGGACGGAAATTG
   A  Q  G  T  S  M  Y  P  S  C  C  C  T  K  P  S  D  G  N  C>

970       980       990      1000      1010      1020
CACCTGTATTCCCATCCCATCATCCTGGGCTTTCGGAAAATTCCTATGGGAGTGGGCCTC
   T  C  I  P  I  P  S  S  W  A  F  G  K  F  L  W  E  W  A  S 1030      1040      1050      1060      1070      1080
AGCCCGTTTCTCCTGGCTCAGTTTACTAGTGCCATTTGTTCAGTGGTTCGTAGGGCTTTC
   A  R  F  S  W  L  S  L  L  V  P  F  V  Q  W  F  V  G  L  S>

1090      1100      1110      1120      1130      1140
CCCCACTGTTTGGCTTTCAGTTATATGGATGATGTGGTATTGGGGGCCAAGTCTGTACAG
   P  T  V  W  L  S  V  I  W  M  M  W  Y  W  G  P  S  L  Y  S 1150      1160      1170      1180      1190      1200
CATCTTGAGTCCCTTTTTACCGCTGTTACCAATTTTCTTTTGTCTTTGGGTATACATTTAA
   I  L  S  P  F  L  P  L  L  P  I  F  F  C  L  W  V  Y  I  *>
```

FIG. 15B

```
   1 TGAATGTTAA ATGTTATACT TTGGATGAAG CTATAAATAT GCATTGGAAA AATAATCCAT
  61 TTAAAGAAAG GATTCAAATA CTACAAAACC TAAGCGATAA TATGTTAACT AAGCTTATTC
 121 TTAACGACGC TTTAAATATA CACAAATAAA CATAATTTTT GTATAACCTA ACAAATAACT
 181 AAAACATAAA AATAATAAAA GGAAATGTAA TATCGTAATT ATTTTACTCA GGAATGGGGT
 241 TAAATATTTA TATCACGTGT ATATCTATAC TGTTATCGTA TACTCTTTAC AATTACTATT
 301 ACGAATATGC AAGAGATAAT AAGATTACGT ATTTAAGAGA ATCTTGTCAT GATAATTGGG
 361 TACGACATAG TGATAAATGC TATTTCGCAT CGTTACATAA AGTCAGTTGG AAAGATGGAT
 421 TTGACAGATG TAACTTAATA GGTGCAAAAA TGTTAAATAA CAGCATTCTA TCGGAAGATA
 481 GGATACCAGT TATATTATAC AAAAATCACT GGTTGGATAA AACAGATTCT GCAATATTCG
 541 TAAAAGATGA AGATTACTGC GAATTTGTAA ACTATGACAA TAAAAAGCCA TTTATCTCAA
 601 CGACATCGTG TAATTCTTCC ATGTTTTATG TATGTGTTTC AGATATTATG AGATTACTAT
 661 AAACTTTTTG TATACTTATA TTCCGTAAAC TATATTAATC ATGAAGAAAA TGAAAAAGTA
 721 TAGAAGCTGT TCACGAGCGG TTGTTGAAAA CAACAAAATT ATACATTCAA GATGGCTTAC
 781 ATATACGTCT GTGAGGCTAT CATGGATAAT GACAATGCAT CTCTAAATAG GTTTTTGGAC
 841 AATGGATTCG ACCCTAACAC GGAATATGGT ACTCTACAAT CTCCTCTTGA AATGGCTGTA
 901 ATGTTCAAGA ATACCGAGGC TATAAAAATC TTGATGAGGT ATGGAGCTAA ACCTGTAGTT
 961 ACTGAATGCA CAACTTCTTG TCTGCATGAT GCGGTGTTGA GAGACGACTA CAAAATAGTG
1021 AAAGATCTGT TGAAGAATAA CTATGTAAAC AATTTCTTTT ACAGCGGAGG CTTTACTCCT
1081 TTGTGTTTGG CAGCTTACCT TAACAAAGTT AATTTGGTTA AACTTCTATT GGCTCATTCG
1141 GCGGATGTAG ATATTTCAAA CACGGATCGG TTAACTCCTC TACATATAGC CGTATCAAAT
1201 AAAAATTTAA CAATGGTTAA ACTTCTATTG AACAAAGGTG CTGATACTGA CTTGCTGGAT
1261 AACATGGGAC GTACTCCTTT AATGATCGCT GTACAATCTG GAAATATTGA AATATGTAGC
1321 ACACTACTTA AAAAAAATAA AATGTCCAGA ACTGGGAAAA ATTGATCTTG CCAGCTGTAA
1381 TTCATGGTAG AAAAGAAGTG CTCAGGCTAC TTTTCAACAA AGGAGCAGAT GTAAACTACA
1441 TCTTTGAAAG AAATGGAAAA TCATATACTG TTTTGGAATT GATTAAAGAA AGTTACTCTG
1501 AGACACAAAA GAGGTAGCTG AAGTGGTACT CTCAAAATGC AGAACGATGA CTGCGAAGCA
1561 AGAAGTAGAG AAATAACACT TTATGACTTT CTTAGTTGTA GAAAAGATAG AGATATAATG
1621 ATGGTCATAA ATAACTCTGA TATTGCAAGT AAATGCAATA ATAAGTTAGA TTTATTTAAA
1681 AGGATAGTTA AAAATAGAAA AAAAGAGTTA ATTTGTAGGG TTAAAATAAT ACATAAGATC
1741 TTAAAATTTA TAAATACGCA TAATAATAAA AATAGATTAT ACTTATTACC TTCAGAGATA
1801 AAATTTAAGA TATTTACTTA TTTAACTTAT AAAGATCTAA AATGCATAAT TTCTAAATAA
1861 TGAAAAAAAA GTACATCATG AGCAACGCGT TAGTATATTT TACAATGGAG ATTAACGCTC
1921 TATACCGTTC TATGTTTATT GATTCAGATG ATGTTTTAGA AAAGAAAGTT ATTGAATATG
1981 AAAACTTTAA TGAAGATGAA GATGACGACG ATGATTATTG TTGTAAATCT GTTTTAGATG
2041 AAGAAGATGA CGCGCTAAAG TATACTATGG TTACAAAGTA TAAGTCTATA CTACTAATGG
2101 CGACTTGTGC AAGAAGGTAT AGTATAGTGA AAATGTTGTT AGATTATGAT TATGAAAAAC
2161 CAAATAAATC AGATCCATAT CTAAAGGTAT CTCCTTTGCA CATAATTTCA TCTATTCCTA
2221 GTTTAGAATA CTTTTCATTA TATTTGTTTA CAGCTGAAGA CGAAAAAAAT ATATCGATAA
2281 TAGAAGATTA TGTTAACTCT GCTAATAAGA TGAAATTGAA TGAGTCTGTG ATAATAGCTA
2341 TAATCAGAGA AGTTCTAAAA GGAAATAAAA ATCTAACTGA TCAGGATATA AAAACATTGG
2401 CTGATGAAAT CAACAAGGAG GAACTGAATA TAGCTAAACT ATTGTTAGAT AGAGGGGCCA
2461 AAGTAAATTA CAAGGATGTT TACGGTTCTT CAGCTCTCCA TAGAGCTGCT ATTGGTAGGA
2521 AACAGGATAT GATAAAGCTG TTAATCGATC ATGGAGCTGA TGTAAACTCT TTAACTATTG
2581 CTAAAGATAA TCTTATTAAA AAAAAATAAT ATCACGTTTA GTAATATTAA AATATATTAA
2641 TAACTCTATT ACTAATAACT CCAGTGGATA TGAACATAAT ACGAAGTTTA TACATTCTCA
2701 TCAAAATCTT ATTGACATCA AGTTAGATTG TGAAAATGAG ATTATGAAAT TAAGGAATAC
2761 AAAAAATAGGA TGTAAGAACT TACTAGAATG TTTTATCAAT AATGATATGA ATACAGTATC
2821 TAGGGCTATA AACAATGAAA CGATTAAAAA TTATAAAAAT CATTTCCCTA TATATAATAC
2881 GCTCATAGAA AAATTCATTT CTGAAAGTAT ACTAAGACAC GAATTATTGG ATGGAGTTAT
2941 AAATTCTTTT CAAGGATTCA ATAATAAATT GCCTTACGAG ATTCAGTACA TTATACTGGA
3001 GAATTCTAAT AACCATGAAC TAAAAAAAT TTTAGATAAT ATACATTAAA AAGGTAAATA
3061 GATCATCTGT TATTATAAGC AAAGATGCTT GTTGCCAATA ATATACAACA GGTATTTGTT
3121 TTTATTTTTA ACTACATATT TGATGTTCAT TCTCTTTATA TAGTATACAC AGAAAATTCA
3181 TAATCCACTT AGAATTTCTA GTTATCTAG
```

FIG. 16

```
              10         20         30         40         50         60
   1 GATATCTGTG GTCTATATAT ACTACACCCT ACCGATATTA ACCAACGAGT TTCTCACAAG
  61 AAAACTTGTT TAGTAGATAG AGATTCTTTG ATTGTGTTTA AAAGAAGTAC CAGTAAAAAG
 121 TGTGGCATAT GCATAGAAGA AATAAACAAA AAACATATTT CCGAACAGTA TTTTGGAATT
 181 CTCCCAAGTT GTAAACATAT TTTTTGCCTA TCATGTATAA GACGTTGGGC AGATACTACC
 241 AGAAATACAG ATACTGAAAA TACGTGTCCT GAATGTAGAA TAGTTTTTCC TTTCATAATA
 301 CCCAGTAGGT ATTGGATAGA TAATAAATAT GATAAAAAAA TATTATATAA TAGATATAAG
 361 AAAATGATTT TTACAAAAAT AACCTATAAG AACAATAAAA ATATAATTAC ATTTACGGAA
 421 AATAGCTGGT TTTAGTTTAC CAACTTAGAG TAATTATCAT ATTGAATCTA TATTGTTTTT
 481 TAGTTATATA AAAACATGAT TAGCCCCCAA TCGGATGAAA ATATAAAAGA TGTTGAGAAT
 541 TTCGAATACA ACAAAAGAG GAATCGTACG TTGTCCATAT CCAAACATAT AAATAAAAAT
 601 TCAAAAGTAG TATTATACTG GATGTTTAGA GATCAACGTG TACAAGATAA TTGGGCTTTA
 661 ATTTACGCAC AACGATGTAC GTTAAAACTC AAAATACCTC TAAGAATATG CTTTTGTGTC
 721 GTGCCAAAAT TTCACACTAC TACTTCTAGA CACTTTATGT TTTTTAATAT CCGGTCTTAA
 781 AGAAGTCGCG GAAGAATGTA AAAGACTATG TATAGGGTTT TCATTGATAT ATGGCGTACC
 841 AAAAGTAATA ATTCCGTGTA TAGTAAAAAA ATACAGAGTC GGAGTAATCA TAACGGATTT
 901 CTTTCCATTA CGTGTTCCCG AAAGATTAAT GAAACAGACT GTAATATCTC TTCCAGATAA
 961 CATACCTTTT ATACAAGTAG ACGCTCATAA TATAGTACCT TGTTGGGAAG CTTCTGATAA
1021 AGAAGAATAC GGTGCACGAA CTTTAAGAAA AAAGATATTT GATAAATTAT ATGAATATAT
1081 GACAGAATTT CCTGTTGTTC GTAAACATCC ATACGGTCCA TTTTCTATAT CTATTGCAAA
1141 ACCCAAAAAT ATATCATTAG ACAAGACGGT ATTACCCGTA AAATGGGCAA CGCCTGGAAC
1201 AAAAGCTGGA ATAATTGTTT TAAAAGAATT TATAAAAAAC AGATTACCGT CATACGACGC
1261 GGATCATAAC AATCCTACGT GTGACGCTTT GAGTAACTTA TCTCCGTGGC TACATTTTGG
1321 TCATGTATCC GCACAACGTG TTGCCTTAGA AGTATTAAAA TGTATACGAG AAAGCAAAAA
1381 AAACGTTGAA ACGTTTATAG ATGAAATAAT TGTAAGAAGA GAACTATCGG ATAATTTTTG
1441 TTACTATAAC AAACATTATG ATAGTATCCA GTCTACTCAT TCATGGGTTA GAAAAACATT
1501 AGAAGATCAC ATTAATGATC CTAGAAAGTA TATATATTCC ATTAAACAAC TCGAAAAAGC
1561 GGAAACTCAT GATCCTCTAT GGAACGCGTC ACAAATGCAG ATGGTGAGAG AAGGAAAAAT
1621 GCATAGTTTT TTACGAATGT ATTGGGCTAA GAAGATACTT GAATGGACTA GAACACCTGA
1681 AGACGCTTTG AGTTATAGTA TCTATTTGAA CAACAGTAC GAACTAGACG GCACGGATCC
1741 TAACGGATAC GTAGGTTGTA TGTGGTCTAT TTGCGGATTA CACGATAGG CGTGGAAAGC
1801 AAGACCGATA TTTGGAAAGA TAAGATATAT GAATTATGAG AGTTCTAAGA AGAAATTTGA
1861 TGTTGCTGTA TTTATACAGA AATACAATTA AGATAAATAA TATACAGCAT TGTAACCATC
1921 GTCATCCGTT ATACGGGGAA TAATATTACC ATACAGTATT ATTAAATTTT CTTACGAAGA
1981 ATATAGATCG GTATTTATCG TTAGTTTATT TTACATTTAT TAATTAAACA TGTCTACTAT
2041 TACCTGTTAT GGAAATGACA AATTTAGTTA TATAATTTAT GATAAAATTA AGATAATAAT
2101 AATGAAATCA ATAATTATG TAAATGCTAC TAGATTATGT GAATTACGAG GAAGAAAGTT
2161 TACGAACTGG AAAAAATTAA GTGAATCTAA AATATTAGTC GATAATGTAA AAAAAATAAA
2221 TGATAAAACT AACCAGTTAA AAACGGATAT GATTATATAC GTTAAGGATA TTGATCATAA
2281 AGGAAGAGAT ACTTGCGGTT ACTATGTACA CCAAGATCTG GTATCTTCTA TATCAAATTG
2341 GATATCTCCG TTATTCGCCG TTAAGGTAAA TAAAATTATT AACTATTATA TATGTAATGA
2401 ATATGATATA CGACTTAGCG AAATGGAATC TGATATGACA GAAGTAATAG ATGTAGTTGA
2461 TAAATTAGTA GGAGGATACA ATGATGAAAT AGCAGAAATA ATATATTTGT TTAATAAATT
2521 TATAGAAAAA TATATTGCTA ACATATCGTT ATCAACTGAA TTATCTAGTA TATTAAATAA
2581 TTTTATAAAT TTTATAAATT TAATAAAAA ATACAATAAC GACATAAAGA TATTTAATCT
2641 TTAATTCTTG ATCTGAAAAA CACATCTATA AAACTAGATA AAAAGTTATT CGATAAAGAT
2701 AATAATGAAT CGAACGATGA AAAATTGGAA ACAGAAGTTG ATAAGCTAAT TTTTTTCATC
2761 TAAATAGTAT TATTTTATTG AAGTACGAAG TTTTACGTTA GATAAATAAT AAAGGTCGAT
2821 TTTTACTTTG TTAAATATCA AATATGTCAT TATCTGATAA AGATACAAAA ACACACGGTG
2881 ATTATCAACC ATCTAACGAA CAGATATTAC AAAAAATACG TCGGACTATG GAAAACGAAG
2941 CTGATAGCCT CAATAGAAGA AGCATTAAAG AAATTGTTGT AGATGTTATG AAGAATTGGG
3001 ATCATCCTCA ACGAAGAAAT AGATAAAGTT CTAAACTGGA AAAATGATAC ATTAAACGAT
3061 TTAGATCATC TAAATACAGA TGATAATATT AAGGAAATCA TACAATGTCT GATTAGAGAA
3121 TTTGCGTTTA AAAAGATCAA TTCTATTATG TATAGTTATG CTATGGTAAA ACTCAATTCA
3181 GATAACGAAC ATTGAAAGAT AAAATTAAGG ATTATTTTAT AGAAACTATT CTTAAAGACA
3241 AACGTGGTTA TAAACAAAAG CCATTACCCG GATTGGAAAC TAAAATACTA GATAGTATTA
3301 TAAGATTTTA AAAACATAAA ATTAATAGGT TTTTATAGAT TGACTTATTA TATACAATAT
3361 GGATAAAAGA TATATATCAA CTAGAAAGTT GAATGACGGA TTCTTAATTT TATATTATGA
3421 TTCAATAGAA ATTATTGTCA TGTCGTGTAA TCATTTTATA AATATATCAG CGTTACTAGC
3481 TAAGAAAAAC AAGGACTTTA ATGAATGGCT AAAGATAGAA TCATTTAGAG AAATAATAGA
3541 TACTTTAGAT AAAATTAATT ACGATCTAGG ACAACGATAT TGTGAAGAAC TTACGGCGCA
3601 TCACATTCCA GTGTAATTAT TGAGGTCAAA GCTAGTAACT TAATAGATGA CAGGACAGCT
3661 G
```

FIG. 21

```
   1 TGTCTGGACT AACTGATTTC ATGGAACAAT TTTCATCAAA AATATCAGTT ATACCTAGTT
  61 CTACAAAGAC AGAACTTTGA TGTTATGTTT GTGTTTGTAT AGAAAATTTT GGGATACTAA
 121 CTGATATTTC TGAATATTTC TGAATATTTC ATGTTACTTA CTTACTCCTA TCTTAGACGA
 181 TAATAAAATT CGAGGCGTAA TATGTTTTTC CAAATATTTG AAATTCTTAT ACGTATCGGC
 241 GAAGAAAAGT AACATACTAT AAGTGTTATG CAAGTAAGGT ATGTTAATGA TATTGGATTT
 301 AATTTCATTG ACAATACATA TGTCCAAACA TTCCACTCGT AATTATGTAC GGAACGACTT
 361 TAGTTAAATA CTTAGTCACA AAAAACTTAT GACTGTCATT ATCTGAAAAC GGTGATTCCC
 421 ATAAATCAGA ATACTTAATA TTAAATAGAA TGCTCGCTTC TGGAGGTTTC CGGATACTAG
 481 ATAACATATC TTCTGTATTA TAGTTTAATT CACTCATTTT ATTACATAAT ACAGTAACAT
 541 CTCCCGAAAC CAATGATGTT ATATTAGATT TACTTACATA CTTCTTGTAA CTATCATGAA
 601 TACGTTTGTT GATGTCTATA AAGAAGATGG ATGTATATTC TGTTCTAGAT AGCAAGTTCT
 661 TTAAGTTATT CTTTGTCTGT ATTACTATCA TCGTCTTCAT CATCGTCTAA AGGTAGCATT
 721 ATATAATAAA TCTAATAGTT GATTTCTCGA TCTATCAGTA CTCGCTTTCA ATAACATTTT
 781 TACTATAAGC ATAATAGAAG GCGGTGATAT CACTATATTT TTATCGGGTA TTCTTTTAGT
 841 AATTAGTTAG TTCGTAGAAT TTCGTAGAGA TAAAAGCCAA TTTGTTGTTG ATACTGCTTA
 901 CGTTACTCAT GTTTCTTGTT TCTGTTAATT AACAGGTATA CCCTTACAAT AAGTTTAATT
 961 AACTTTTAGG TTTTTGTGAA GAACTTTTAG CTTCTAGTTC CCTTATCCAT AATTGGGTCT
1021 TAGATCTAGA TTCTTCCCAT GTATAAAGGG GGACATACCC AAAATCTTTA AATGCTTTGT
1081 CCGTTTCTAT AGTAAATGTC GTACATTCCT TAATCAAAGT ATAAGGATTT AGTAAAGGCG
1141 TGTAAGAACA AATAGGTGAT AGTAATACTC TTAAACCTTT ATTAATATTA GCGATAAACC
1201 TTAAACACCA TAAAGGAAGA CATGTATTCC GTAGATCCAT CCCTAATTGA TTAAAGAAAT
1261 GCATGTTAAA ATCATGATAA TGTTCAGTAG GAGAGGTATC GTAACAGTAA TACACGTTAT
1321 TGCAGAGAGG ACTATGTTGA CCATTTTCTA TCATATTTCT TGCTGCTAAA ATATGCATCC
1381 AAGCTACGTT TCCTGCATAG ACTCTGCTAT GAAATACTTT ATCATCCGCA TATTTATACA
1441 TTTTCCTGCT TTTATACGAT CTTCTGTATA AAGTTTCTAG TACTGGACAG TATTCTCCGA
1501 AAACACGTAA TGGGCGTAGC GACAAGTGCA TAATCTAAGT CCTATATTAG ACATAGTACC
1561 GTTAGCTTCT AGTATATATT TCTCAGATAA CTTGTTTACT AAGAGGATAA GCCTCTTTAT
1621 GGTTAGATTG ATAATACGTA TTCTCGTTTC CTCTTATCAT CGCATCTCCG GAGAAAGTTA
1681 GGACCTACCG CAGAATAACT ACTCGTATAT ACTAAGACTC TTACGCCGTT ATACAGACAA
1741 GAATCTACTA CGTTCTTCGT TCCGTTGATA TTAACGTCCA TTATAGAGTC GTTAGTAAAC
1801 TTACCCGCTA CATCATTTAT CGAAGCAATA TGAATGACCA CATCTGCTGA TCTAAGCGCT
1861 TCGTCCAAAG TACTTTTATT TCTAACATCT CCAATCACGG GAACTATCTT TATTATATTA
1921 CATTTTTCTA CAAGATCTAG TAACCATTGG TCGATTCTAA TATCGTAAAC ACGAACTTCT
1981 TTTTAAAGAG GATTCGAACA AGATAAGATT ATTTATAATG TGTCTACCTA AAAATCCACA
2041 CCCTCCGGTT ACCACGTATA CTAGTGTACG CATTTTGAGT ATTAACTATA TAAGACCAAA
2101 ATTATATTTT CATTTTCTGT TATATTATAC TATATAATAA AAACAAATAA ATATACGAAT
2161 ATTATAAGAA ATTTAGAACA CGTTATTAAA GTATTGCCTT TTTTATTAAC GGCGTGTTCT
2221 TGTAATTGCC GTTTAGAATA GTCTTTATTT ACTTTAGATA ACTCTTCTAT CATAACCGTC
2281 TCCTTATTCC AATCTTCTTC AGAAGTACAT GAGTACTTAC CGAAGTTTAT CATCATAGAG
2341 ATTATATATG AAGAAA
```

FIG. 22

```
   1 AGCAAAAGCA GGGGATACAT AATGAACACT CAAATTCTAA TATTAGCCAC TTCGGCATTC
  61 TTCTATGTAC GTGCAGATAA AATCTGCCTA GGACATCATG CTGTGTCTAA TGGAACCAAA
 121 GTAGACACCC TTACTGAAAA AGGAATAGAA GTTGTCAATG CAACAGAAAC AGTTGAACAA
 181 ACAAACATCC CTAAGATCTG CTCAAAAGGA AAACAGACTA TTGACCTTGG TCAATGTGGA
 241 TTACTAGGGA CCGTTATTGG TCCTCCCCAA TGTGACCAAT TTCTTGAATT CTCTGCTAAT
 301 TTAATAGTTG AAAGAAGGGA AGGTAATGAC ATTTGTTATC CAGGCAAATT TGACAATGAA
 361 GAAACATTGA GAAAAATACT CAGAAAATCC GGAGGAATTA AAAAGGAGAA TATGGGATTC
 421 ACATATACCG GAGTGAGAAC CAATGGAGAG ACTAGCGCAT GTAGAAGGTC AAGATCTTCC
 481 TTTTATGCAG AGATGAAATG GCTTCTATCC AGCACAGACA ATGGGATATT TCCACAAATG
 541 ACAAAGTCCT ACAAGAACAC TAAGAAGGTA CCAGCTCTGA TAATCTGGGG AATCCACCAC
 601 TCAGGATCAA CTACTGAACA GACTAGATTA TATGGAAGTG GGAATAAATC GATAACAGTT
 661 TGGAGCTCCA AATACCAACA ATCTTTTGTC CCAAATCCTG GACCAAGGCC GCAAATCAAT
 721 GGACAATCAG GAAGAATTGA CTTTGACTGG CTGATGGTAG ATCCCAATGA TACTGTGACT
 781 TTCAGTTTTA ATGGGGCCTT TATAGCACCT GACCGCGCCA GTTTTCTAAG AGGTAAATCT
 841 CTAGGAATTC AAAGTGACGC ACAGCTTGAC AATAATTGTG AAGGTGAATG CTATCATATT
 901 GGAGGTACTA TAATTAGCAA CTTGCCCTTT CAAAACATTA ATAGTAGGGC AATCGGAAAA
 961 TGCCCCAGAT ACGTGAAGCA GAAGAGCTTA ATGCTAGCAA CAGGAATGAA AAATGTTCCT
1021 GAAGCTCCTG CACATAAACA ACTAACTCAT CACATGCGCA AAAAAAGAGG TTTATTTGGT
1081 GCAATAGCAG GATTCATTGA AAATGGGTGG GAAGGATTAA TAGACGGATG GTATGGATAT
1141 AAGCATCAGA ATGCACAAGG AGAAGGGACT GCTGCAGACT ACAAAAGTAC ACAATCTGCT
1201 ATCAACCAAA TAACCGGGAA ATTGAACAGA CTAATAGAAA AAACAACCA GCAATTCGAA
1261 CTAATAGATA ATGAGTTCAA TGAAATAGAA AAACAAATTG GCAATGTTAT TAACTGGACT
1321 AGAGATTCTA TCATCGAAGT ATGGTCATAT AATGCAGAAT TCCTCGTAGC AGTGGAGAAT
1381 CAACACACTA TTGATTTAAC TGACTCAGAA ATGAACAAAC TATATGAAAA GGTAAGAAGA
1441 CAACTGAGAG AAAATGCTGA GGAAGATGGT AATGGCTGTT TTGAAATATT CCACCAATGT
1501 GACAATGATT GCATGGCCAG CATTAGAAAC AATACATATG ATCATAAAAA ATACAGAAAG
1561 GAGGCAATAC AAAACAGAAT TCAGATTGAT GCAGTAAAGT TGAGCAGCGG TTACAAAATA
1621 ATACTTTGGT TTAGCTTCGG GGCATCATGT TTCTTATTTC TTGCCATTGC AATGGTTCTT
1681 GCTTTCATAT GCATAAAAAA TGGAAACATG CGGTGCACTA TTTGTATATA AGTTTGAAAA
1741 AACACCCTTG TTTTCTACT
```

FIG. 23

```
   1 AGCAAAAGCA GGGGATATTT CTGTCAATCA TGAAGACAAC CATTATTTTG ATACTACTGA
  61 CCCATTGGGT CTACAGTCAA AACCCAACCA GTGGCAACAA CACAGCCACA CTATGTCTGG
 121 GACACCATGC AGTAGCAAAT GGAACATTGG TAAAAACAAT AACTGACGAC CAAATTGAGG
 181 TGACAAATGC TACTGAATTA GTTCAGAGCA CTTCAATAGG GAAAATATGC AACAACCCAT
 241 ATAGGGTTCT AGATGGAAGA AACTGCACAT TAATAGATGC AATGCTAGGA GATCCCCACT
 301 GTGATGTTTT TCAGTATGAG AATTGGGACC TCTTCATAGA AAGAAGCAGC GCTTTCAGCA
 361 ATTGCTACCC ATATGACATC CCTGACTATG CATCGCTCCG GTCTATTGTG GCATCTTCAG
 421 GAACATTAGA ATTCACAGCA GAGGGATTCA CATGGACAGG TGTCACTCAA AACGGAAGAA
 481 GTGGCGCCTG CAGAAGGGGA TCAGCCGATA GTTTCTTTAG CCGACTGAAT TGGCTAACAG
 541 AATCTGGAAA TTCTTACCCC ACATTGAATG TAACAATGCC TAACAATAAC AATTTCGATA
 601 AACTATACAT CTGGGGGATC CATCACCCGA GCACAAACAA TGAGCAGACA AAATTGTATG
 661 TCCAAGAATT AGGGCGAGTA ACAGTCTCAA CAAAAAGAAG TCAACAAACA ATAATCCCCA
 721 ACATCGGATC TAGACCGGGG GTCAGGGGTC AATCAGGCAG GATAAGCATA TATTGGACCA
 781 TTGTGAAACC TGGAGATATC CTAATGATAA ACAGTAATGG CAACTTAGTT GCACCGCGGG
 841 GATATTTCAA AATGCGAACA GGAAAAAGCT CTATAATGAG ATCAGATGCA CCCATAGACA
 901 CTTGTGTGTC CGAGTGTATT ACACCAAATG GAAGCATCCC CAACGACAAA CCATTTCAAA
 961 ATGTGAACAA AGTTACATAT GGAAAATGCC CCAAGTATAT CAAGCAGAAT ACTTTGAAGC
1021 TGGCCACTGG GATGAGGAAT GTACCAGAAA AGCAAATCAG AGGAATCTTT GGAGCAATAG
1081 CGGGATTCAT AGAAAATGGC TGGGAGGGAA TGGTTGATGG GTGGTATGGA TTCCGATATC
1141 AGAATTCGGA AGGAACAGGA CAAGCTGCAG ATCTAAAGAG CACTCAAGCA GCCATCGACC
1201 AGATCAATGG AAAATTGAAC AGAGTGATTG AGAGGACCAA TGAGAAATTC CATCAAATAG
1261 AGAAGGAATT CTCAGAAGTA GAAGGGAGAA TCCAGGACTT GGAGAAGTAT GTAGAAGACA
1321 CCAAAATAGA CCTATGGTCC TACAATGCAG AGTTACTGGT GGCTCTAGAA AATCAACATA
1381 CGATTGACTT AACAGATGCA GAGATGAATA AATTATTCGA GAAGACTAGG CGCCAGTTAA
1441 GAGAAAACGC GGAAGACATG GGGGGTGGAT GTTTCAAGAT TTATCACAAA TGTGATAATG
1501 CATGCATTGG ATCAATAAGA AATGGGACAT ATGACCATTA CATATACAGA GATGAAGCAT
1561 TAAACAACCG ATTTCAAATT AAAGGTGTTG AGTTGAAATC AGGCTACAAA GATTGGATAC
1621 TGTGGATTTC ATTCGCCATA TCATGCTTCT TAATTTGCGT TGTTCTATTG GGTTTCATTA
1681 TGTGGGCTTG CCAAAAAGGC AACATCAGAT GCAACATTTG CATTTGAGTA AACTGATAGT
1741 TAAAAACACC CTTGTTTCTA CT
```

FIG. 24

```
   1 AGCAAAAGCA GGGGATATTT CTGTCAATCA TGAAGACAAC CATTATTTTG ATACTACTGA
  61 CCCATTGGGT CTACAGTCAA AACCCAACCA GTGGCAACAA CACAGCCACA TTATGTCTGG
 121 GACACCATGC AGTAGCAAAT GGAACATTGG TAAAAACAAT AACTGATGAC CAAATTGAGG
 181 TGACAAATGC TACTGAATTA GTTCAGAGCA TTTCAATAGG GAAAATATGC AACAATCCAT
 241 ATAGGGTTCT AGATGGAAGA AATTGCACAT TAATAGATGC AATGCTAGGA GACCCCCACT
 301 GTGATGTTTT TCNGTATGAG AATTGGGACC TCTTCATAGA AAGAAGCAGC GCTTTCAGCA
 361 ATTGCTACCC ATATGACATC CCTGACTATG CATCGCTCCG GTCCATTGTA GCATCCTCAG
 421 GAACATTAGA ATTCACAGCA GAGGGATTCA CATGGACAGG TGTCACTCAA AACGGAAGAA
 481 GTGGAGCCTG CAAAAGGGGA TCAGCCGATA GTTTCTTTAG CCGACTGAAT TGGCTAACAA
 541 AATCTGGAAA TTCTTACCCC ATATTGAATG TGACAATGCC TAACAATAAA AATTTCGATA
 601 AACTATACAT CTGGGGGATT CATCACCCGA GCTCAAACAA AGAGCAGACA AAATTGTATA
 661 TCCAAGAATC AGGACGAGTA ACAGTCTCAA CAGAAAGAAG TCAACAAACA GTAATCCCTA
 721 ACATCGGATC TAGACCGTGG GTCAGGGGTC AATCAGGCAG GATAAGCATA TACTGGACCA
 781 TTGTAAAACC TGGAGATATT CTAACGATAA ACAGTAATGG CAACTTAGTT GCACCGCGGG
 841 GATATTTTAA ATTGAGAACA GGGAAAAGCT CTGTAATGAG ATCAGATGCA CCCATAGACA
 901 CTTGTGTGTC TGAATGTATT ACACCAAATG GAAGCATCCC CAACGACAAA CCATTTCAAA
 961 ATGTGAACAA AGTTACATAT GGAAAATGCC CCAAGTATAT CAGGCAAAAC ACTTTAAAGC
1021 TGGCCACCGG GATGAGGAAT GTACCAGAAA AGCAAATCAG AGGAATCTTT GGAGCAATAG
1081 CGGGATTCAT AGAAAACGGC TGGGAAGGAA TGGTTGATGG GTGGTATGGA TTCCGATATC
1141 AAAACTCGGA AGGAACAGGA CAAGCTGCAG ATCTAAAGAG CACTCAAGCA GCCATCGACC
1201 AGATCAATGG AAAATTAAAC AGAGTGATTG AAAGGACCAA TGAGAAATTC CATCAAATAG
1261 AGAAGGAATT CTCAGAAGTA GAAGGGAGAA TCCAGGATTT GGAGAAGTAT GTAGAAGACA
1321 CCAAAATAGA CCTATGGTCC TACAATGCAG AATTGCTGGT GGCTCTAGAA AATCAACATA
1381 CAATTGACTT AACAGATGCA GAAATGAATA AATTATTCGA GAAGACTAGG CGCCAGTTAA
1441 GAGAAAACGC GGAAGACATG GGAGGTGGAT GTTTCAAGAT TTACCACAAA TGTGATAATG
1501 CATGCATTGG ATCAATAAGA AATGGGACAT ATGACCATTA CATATACAGA GATGAAGCAT
1561 TAAACAACCG ATTTCAAATC AAAGGTGTTG AGTTGAAATC AGGCTACAAA GATTGGATAC
1621 TGTGGATTTC ATTCGCCATA TCATGCTTCT TAATTTGCGT TGTTCTATTG GGTTTCATTA
1681 TGTGGGCTTG CCAAAAAGGC AACATCAGAT GCAACATTTG CATTTGAGTA AACTGATAGT
1741 TAAAAACACC CTTGTTTCTA CT
```

FIG. 25

```
   1 CCCCAGCTCA GACGATCTGT CAAGATGGAA GGTCCAACGC ACCCAAAACC CTCTAAAGAT
  61 AAGACTTTCT CGTGGGACCT AATGATTCTG GTGGGGGTCT TACTAAGACT GGACGTGGGA
 121 ATGGCCAATC CTAGTCCGCA CCAAATATAT AATGTAACTT GGACAATAAC CAACCTTGTA
 181 ACTGGAACAA AGGCTAATGC CACCTCCATG TTGGGAACCC TGACAGACGC CTTCCCTACC
 241 ATGTATTTTG ACTTATGTGA TATAATAGGA AATACATGGA ACCCTTCAGA TCAAGAACCA
 301 TTCCCAGGGT ATGGATGTGA TCAGCCTATG AGGAGGTGGC GACAGAGAAA CACACCCTTT
 361 TATGTCTGTC CAGGACATGC CAACCGGAAG CAATGTGGGG GGCCACAGGA TGGGTTCTGC
 421 GCTGTATGGG GTTGCGAGAC CACCGGGGAA ACCTATTGGA GACCCACCTC CTCATGGGAC
 481 TACATCACAG TAAAAAAAGG GGTTACTCAG GGAATATATC AATGTAGTGG AGGTGGTTGG
 541 TGTGGGCCCT GTTACGATAA AGCTGTTCAC TCCTCGACAA CGGGAGCTAG TGAAGGGGGC
 601 CGGTGCAACC CCTTGATCTT GCAATTTACC CAAAAGGGAA GACAAACATC TTGGGATGGA
 661 CCTAAGTCAT GGGGGCTACG ACTATACCGT TCAGGATATG ACCCTATAGC CCTGTTCTCG
 721 GTATCCCGGC AAGTAATGAC CATTACGCCG CCTCAGGCCA TGGGACCAAA TCTAGTCCTG
 781 CCTGATCAAA AACCCCCATC CAGGCAATCT CAAATAGAGT CCCGAGTAAC ACCTCACCAT
 841 TCCCAAGGCA ACGGAGGCAC CCCAGGTGTA ACTCTTGTTA ATGCCTCCAT TGCCCCTCTA
 901 CGTACCCCTG TCACCCCCGC AAGTCCCAAA CGTATAGGGA CCGGAAATAG GTTAATAAAT
 961 TTAGTGCAAG GGACATACCT AGCCTTAAAT GCCACCGACC CCAACAAAAC TAAAGACTGT
1021 TGGCTCTGCC TGGTTTCTCG ACCACCTTAT TACGAAGGGA TTGCAATCTT AGGTAACTAC
1081 AGCAACCAAA CAAACCCCTC CCCATCCTGC CTATCTACTC CGCAACATAA GCTAACTATA
1141 TCTGAGGTGT CAGGGCAAGG ACTGTGCATA GGGACTGTTC CTAAGACCCA CCAGGCTTTG
1201 TGCAATAAGA CACAACAGGG ACATACAGGG GCTCACTATC TAGCCGCCCC CAATGGCACC
1261 TATTGGGCCT GTAACACTGG ACTCACCCCA TGCATTTCCA TGGCAGTGCT CAATTGGACC
1321 TCTGATTTTT GTGTCTTAAT CGAATTATGG CCCAGAGTGA CCTACCATCA ACCCGAATAC
1381 ATTTACACAC ATTTCGACAA AGCTGTCAGG TTCCGAAGAG AACCAATATC ACTAACCGTT
1441 GCCCTTATAA TGGGAGGACT CACTGTAGGG GGCATAGCCG CGGGGGTCGG AACAGGGACT
1501 AAAGCCCTCC TTGAAACAGC CCAGTTCAGA CAACTACAAA TGGCTATGCA CGCAGACATC
1561 CAGGCCCTAG AAGAGTCAAT TAGTGCCTTA GAAAAATCCC TGACCTCCCT CTCCGAGGTA
1621 GTCTTACAAA ATAGACGGGG CCTAGATATT CTGTTCTTAC AAAAGGGAGG GCTCTGTGCC
1681 GCCTTAAAGG AAGAATGCTG CTTCTATGCA GATCACACCG GACTCGTCAG AGACAATATG
1741 GCTAAATTAA GAGAAAGACT GAAACAGCGA CAACAACTGT TTGACTCCCA ACAGGGATGG
1801 TTTGAAGGAT GGTTCAACAA GTCCCCCTGG TTTACAACCC TAATTTCCTC CATTATAGGC
1861 CCCTTACTAA TCCTACTCCT AATTCTCCTC TTCGGCCCAT GCATCCTTAA CCGATTAGTG
1921 CAATTCGTAA AAGACAGAAT ATCTGTGGTA CAAGCCTTAA TTTTAACCCA ACAGTACCAA
1981 CAGATACAGC AATATGATCC GGACCGACCA TGATTTCCAA TTAAATGTAT GATTCCATTT
2041 AGTCCCTAGA AGAAGGGGGG AATGAAAGAC CCCCCCCACC CCAAAACTTA GCCAGCTACT
2101 GCAGTGATGC CATTTCACAA GACATGGAAA ATTACCCAAG CATGTTCCCG TGAGATATAA
2161 GGAAGTTAGA AGCTAAAACA GGATATCTGT GGTTAGACAC CTAGGCCCCG GCTTGAGGCC
2221 AAGAACAGTT AAGCCCCGGA TATAGCTGAA ACAGCAGAAG TTTCAAGGCC ACTGCCAGCA
2281 GTCTCCAGGC TCCCCAGTTG ACCAGAGTTC GACCTTCCGC CTCATTTAAA CTAACCAATC
2341 CCCACGCCTC TCGCTTCTGT ACGCGCGCTT TTTGCTATAA AACGAGCCAT CAGCCCACCA
2401 CCAGGCGCGC AAGTCTTTGC AGAGACTTGA CGCCCCGGGC CCACGCCTCT CGCTTCTGTA
2461 CGCGCGCTTT TTGCTATAAA ACGAGCCATC AGCCCACCA
```

FIG. 26

```
   1 CTGCAGTGGT GTCATTTCAC AAGGCATGGA AAATTACTCA AGTATGTTCC CATGAGATAT
  61 AAGGAAGTTA GAGGCTAAAA CAGGATATCT GTGGTTAAGC ACCTGGGCCC CGGCTTGAGG
 121 CCAAGAACAG TTAAACCCCG GATATAGCTG AAACAGCAGA AGTTTCAAGG CCGCTGCCAG
 181 CAGTCTCCAG GCTCCCCAGT TGACCAGAGT TCGACCTTCC GCCTCATTTA AACTAACCAA
 241 TGCCCACGCC TCTCGCTTCT GTGCGCGCGC TTTCTGCTAT AAAACGAGCC ATCAGCCCCC
 301 AACGGCGCGC AAGTCTTTGC TGAGACTTGA CCGCCCCGGG TACCCGTGTA CGAATAAACC
 361 TCTTGCTGAT TGCATCTGAC TGTGGTCTCG GTGTTCCGTG GGCACGGGGT CTCATCGCCG
 421 AGGAAGACCT AGTTCGGGGG TCTTTCATTT AGGGGCTCGT CCGGGATAGA GACCCCCAAC
 481 CCCCGGGACC ACCGACCCAC CACCATCAGG AGGTAAGCTG GCCGGCGACC ATACCTGTTG
 541 TCCTTGTATA AGTGTCTCTG TCAATTGATC TGATTTTGGC GGTGGGATCG AAGGAGCTGA
 601 CGAGCTCGTA CTTCGCCCCC GCAACCCTGG AAGACATTCC ACGGGTGTCT GATGTCTGGA
 661 GCCTCTAGTG GGACAGCCAT TGGGGCTCAT CTGTTTGGGG TCTCACCTGA ATACAGGGTG
 721 TTGATCGGAG ACGAGGGAGC CGGACCTCA AGGTCTCTTT CTGAGGTTTC ATTTTCGGTT
 781 TGGTACCAAA GACGCGCGGC ACGTCTTGTC ATTTTTTGTC TGGTTGCGTC TTTTCTTGTC
 841 CCTTGTCTAA CCTTTTTAAT TGCAGAAACC GTCATGGGCC AAACTATAAC TACCCCCTTA
 901 AGCCTCACCC TTGATCACTG GTCTGAAGTC CGGGCACGAG CCCATAATCA AGGTGTCGAG
 961 GTCCGGAAAA AGAAATGGAT TACCTTATGT GAGGCCGAAT GGGTGATGAT GAATGTGGGC
1021 TGGCCCCGAG AAGGAACTTT TTCTCTTGAT AGCATTTCCC AGGTTGAAAA GAAGATCTTC
1081 GCCCCGGGAC CATATGGACA CCCCGACCAA GTTCCTTACA TTACTACATG GAGATCCTTA
1141 GCCACAGACC CCCCTTCGTG GGTTCGTCCG TTCCTACCCC CTCCCAAACC TCCCACACCC
1201 CTCCCTCAAC CTCTTTCGCC GCAGCCCTCC GCCCCTCTTA CCTCTTCCCT CTACCCCGTT
1261 CTCCCCAAGC CAGACCCCCC CAAACCGCCT GTGTTACCGC CTGATCCTTC TTCCCCTTTA
1321 ATTGATCTCT TAACAGAAGA GCCACCTCCC TATCCGGGGG GTCACGGGCC ACCGCCATCA
1381 GGTCCTAGGA CCCCAACCGC TTCCCCGATT GCAAGCCGGC TAAGGGAACG ACGAGAAAAC
1441 CCTGCTGAAG AATCGCAAGC CCTCCCCTTG AGGGAAGGCC CCAACAACCG ACCCCAGTAT
1501 TGGCCATTCT CAGCTTCAGA CTTGTATAAC TGGAAGTCGC ATAACCCCCC TTTCTCCCAA
1561 GATCCAGTGG CCCTAACTAA CCTAATTGAG TCCATTTTAG TGACGCATCA ACCAACCTGG
1621 GACGACTGCC AGCAGCTCTT GCAGGCACTC CTGACAGGCG AAGAAAGGCA AAGGGTCCTT
1681 CTTGAGGCCC GAAAGCAGGT TCCAGGCGAG GACGGACGGC CAACCCAACT ACCCAATGTC
1741 ATTGACGAGA CTTTCCCCTT GACCCGTCCC AACTGGGATT TTGCTACGCC GGCAGGTAGG
1801 GAGCACCTAC GCCTTTATCG CCAGTTGCTA TTAGCGGGTC TCCGCGGGGC TGCAAGACGC
1861 CCCACTAATT TGGCACAGGT AAAGCAGGTT GTACAAGGGA AAGAGGAAAC GCCAGCAGCA
1921 TTTTTAGAAA GATTAAAAGA GGCTTATAGA ATGTACACTC CCTATGACCC TGAGGACCCA
1981 GGGCAAGCGG CTAGTGTTAT CCTATCCTTT ATATACCAGT CTAGCCCAGA TATAAGAAAT
2041 AAGTTACAAA GGCTAGAAGG CCTACAAGGG TTCACCCTAT CTGATCTGCT AAAAGAGGCA
2101 GAAAAGATAT ACAACAAAAG GGAGACCCCA GAGGAAGGG AAGAAAGATT ATGGCAGCGA
2161 CAGGAAGAAA GAGATAAAAA GCGCCACAAG GAGATGACTA AAGTTCTGGC CACAGTAGTT
2221 GCTCAGAATA GAGATAAGGA TAGAGAAGAA AGTAAACTGG GGGATCAAAG GAAAATACCT
2281 CTGGGGAAAG ACCAGTGTGC CTATTGCAAG GAAAAGGGGC ATTGGGTTCG CGATTGCCCC
2341 AAACGACCCA GGAAGAAACC CGCCAACTCC ACTCTCCTCA ACTTAGGAGA TTAGGAGAGT
2401 CAGGGCCAGG ACCCCCCCCC CTGAGCCCAG GATAACCTTA AAAATAGGGG GGCAACCGGT
2461 GACTTTTCTG GTGGACACGG GAGCCCAGCA CTCAGTACTG ACTCGACCAG ATGGACCTCT
2521 CAGTGACCGC ACAGCCCTGG TGCAAGGAGC CACGGGAAGC AAAAACTACC GGTGGACCAC
2581 CGACAGGAGG GTACAACTGG CAACCGGTAA GGTGACTCAT TCTTTTTTAT ATGTACCTGA
2641 ATGTCCCTAC CCGTTATTAG GGAGAGACCT ATTAACTAAA CTTAAGGCCC AAATCCATTT
2701 TACCGGAGAA GGGGCTAATG TTGTTGGGCC CAGGGGTTTA CCCCTACAAG TCCTTACTTT
2761 ACAATTAGAA GAGGAGTATC GGCTATTTGA GCCAGAAAGT ACACAAAAAC AGGAGATGGA
2821 CACTTGGCTT AAAAACTTTC CCCAGGCGTG GGCAGAAACA GGAGGTATGG GAATGGCTCA
2881 TTGTCAAGCC CCCGTTCTCA TTCAACTTAA GGCTACTGCC ACTCCAATCT CCATCCGACA
2941 GTATCCTATG CCCCATGAAG CGTACCAGGG AATTAAGCCT CATATAAGAA GAATGCTAGA
3001 TCAAGGCATC CTCAAGCCCT GCCAGTCCCC ATGGAATACA CCCTTATTAC CTGTTAAGAA
3061 GCCAGGGACC GAGGATTACA GACCAGTGCA GGACTTAAGA GAAGTAAACA AAAGAGTAGA
3121 AGACATCCAT CCTACTGTGC CAAATCCATA TAACCTCCTT AGCACCCTCC CGCCGTCTCA
3181 CCCTTGGTAC ACTGTCCTAG ATTTAAAGGA CGCTTTTTTC TGCCTGCGAC TACACTCTGA
3241 GAGTCAGTTA CTTTTTGCAT TTGAATGGAG AGATCCAGAA ATAGGCCCAA CAGGGCAACT
3301 AACCTGGACA CGCCTTCCTC AGGGGTTCAA GAATAGCCCC ACCCTATTTG ATGAGGCCCT
3361 GCACTCAGAC CTGGCCGATT TCAGGGTAAG GTACCCGGCT CTAGTCCTCC TACAATATGT
3421 AGATGACCTC TTGCTGGCTG CGGCAACCAG CAGTGAATGC CTGGAAGGGA CTAAGGCACT
3481 CCTTGAGACT TTGGGCAATA AGGGGTACCG AGCCTCTGGA AAGAAGGCCC AAATTTGCCT
3541 GCAAGAAGTC ACATACCTGG GGTACTCTTT AAAAGATGGC CAAGGTGGC TTACCAAAGC
3601 TCGGAAAGAA GCCATCCTAT CCATCCCTGT GCCTAAAAAC CCACGACAAG TGAGAGAGTT
3661 CCTTGGAACT GCAG
```

FIG. 27

```
   1 ATGATGACAC GTCTACATTT TTGGTGGTGT GGAATCTTTG CGGTCCTGAA ATATCTGGTA
  61 TGTACTTCAA GCCTTACGAC CACGCCAAAA ACAACTACGG TTTATGTGAA GGGATTTAAT
 121 ATACCTCCAC TACGCTACAA TTATACTCAA GCCAGAATCG TGCCAAAAAT TCCCCAGGCG
 181 ATGGATCCGA AGATAACAGC TGAAGTACGT TATGTAACAT CAATGGATTC ATGTGGGATG
 241 GTGGCATTGA TATCAGAGCC GGATATAGAC GCTACTATTC GAACCATACA ACTATCTCAA
 301 AAAAAAACAT ATAACGCGAC TATAAGTTGG TTTAAGGTAA CCCAGGGTTG TGAATACCCT
 361 ATGTTTCTTA TGGATATGAG ACTTTGTGAT CCTAAACGGG AATTTGGAAT ATGTGCTTTA
 421 CGGTCGCCTT CATATTGGTT GGAACCTTTA ACAAAGTATA TGTTCCTAAC AGACGATGAA
 481 CTGGGTTTGA TTATGATGGC CCCGGCCCAA TTTAATCAAG GACAATATCG AAGAGTTATA
 541 ACCATCGATG GTTCCATGTT TTATACAGAT TTTATGGTAC AACTATCTCC AACGCCATGT
 601 TGGTTCGCAA AACCCGATAG ATACGAAGAG ATTCTACATG AATGGTGTCG AAATGTTAAA
 661 ACTATTGGCC TTGATGGAGC TCGTGATTAC CACTATTATT GGGTACCCTA TAACCCACAA
 721 CCTCACCATA AAGCCGTACT CTTATATTGG TATCGGACTC ATGGCCGAGA ACCCCCAGTA
 781 AGATTCCAAG AGGCCATTCG ATATGATCGT CCCGCCTACA CGTCTGGGAG TGAGGATTCG
 841 AAACGGTCCA ACGACTCTAG AGGAGAATCG AGTGGACCCA ATTGGATAGA CATTGAAAAT
 901 TACACTCCTA AAAATAATGT GCCTATTATA ATATCTGACG ATGACGTTCC TACAGCCCCT
 961 CCCAAGGGCA TGAATAATCA GTCAGTAGTG ATACCCGCAA TCGTACTAAG TTGTCTTATA
1021 ATAGCACTGA TTCTAGGAGT GATATATTAT ATTTTGAGGG TAAAGAGGTC TCGATCAACT
1081 GCATATCAAC AACTTCCTAT AATACATACA ACTCACCATC CTTAA
```

FIG. 28

```
   1 GAGCTCGAAA ATAGAATTGA TCAGTAATCA TGAAGGCTTT TTTAGTTACT TGCTTAAGCT
  61 TTGCAGTCTT TTCATCTTCT GTATGTGTGA ATATCAACAT CTTGCAGCAA ATTGGATATA
 121 TCAAGCAACA AGTCAGGCAA CTAAGCTATT ACTCACAAAG TTCAAGCTCC TACATAGTGG
 181 TCAAGCTTTT ACCGAATATC CAACCCATTG ATAACAGCTG TGAATTTAAG AGTGTAACTC
 241 AATACAATAA GACCTTGAGT AATTTGCTTC TTCCAATTGC AGAAAACATA AACAATATTG
 301 CATCGCCCTC ATCTGGGTCA AGACGGCATA AAAGGTTTGC TGGTATTGCT ATTGGCATTG
 361 CTGCGCTCGG TGTTGCGACC GCAGCACAAG TAACTGCCGC TGTCTCATTA GTTCAAGCAC
 421 AGACAAATGC ACGTGCAATA GCGGCGATGA AAAATTCAAT ACAAGCAACT AATCGAGCAG
 481 TCTTCGAAGT GAAGGAAGGC ACTCAACAGT TAGCTATAGC GGTACAAGCA ATACAAGACC
 541 ACATCAATAC TATTATGAAC ACCCAATTGA ACAATATGTC TTGTCAGATC CTTGATAACC
 601 AGCTTGCAAC TTTCCTAGGA TTATACCTAA CAGAATTAAC AACAGTGTTT CAGCCACAAT
 661 TAATTAATCC GGCATTGTCA CCGATTAGTA TACAAGCCTT GAGGTCTTTG CTTGGAAGTA
 721 TGACGCCTGC AGTGGTCCAA GCAACATTAT CTACTTCAAT CTCTACTGCT GAAATACTAA
 781 GTGCCGGTCT AATGGAGGGT CAGATTGTTT CTGTTCTGCT AGATGAGATG CAGATGATAG
 841 TTAAGATAAA TATTCCAACT ATTGTCACAC AATCAAATGC ATTGGTGATT GACTTCTACT
 901 CAATTTCGAG CTTTATTAAT AATCAGGAAT CCATAATCCA ATTGCCAGAC AGAATCTTGG
 961 AGATCGGGAA TGAACAATGG AGCTATCCAG CTAAAAATTG TAAGTTGACA AGACACCACA
1021 TATTCTGCCA ATACAATGAG GCAGAGAGGC TGAGCCTAGA ATCAAAACTA TGCCTTGCAG
1081 GTAATATAAG TGCCTGTGTG TTCTCACCCA TAGCAGGGAG TTATATGAGG CGATTTACGG
1141 CACTGGATGG AACAATTGTT GCAAACTGTC GAAGTCTAAC GTGTCTATGC AAGAATCCAT
1201 CTTATCCTAT ATACCAACCT GACCATCATG CAGTCACGAC CATTGATCTA ACCGCATGTC
1261 AAACATTGTC CCTAGACGGA TTGGATTTCA GCATTGTCTC TCTAAGCAAC ATCACTTACG
1321 CTGAGAACCT TACCATTTCA TTGTCTCAGA CAATCAATAC TCAACCCATT GACATATCAA
1381 CTGAACTGAG TAAGGTTAAT GCATCCCTCC AAAATGCCGT TAAGTACATA AAGGAGAGCA
1441 ACCATCAGCT CCAATCTGTG AGTGTAAACT CCAAAATCGG AGCTATAATT GTAGCAGCCT
1501 TAGTTTTGAG CATTCTGTCA ATTATCATTT CGCTATTGTT TTGCTGCTGG GCTTACATTG
1561 CAACTAAAGA AATCAGAAGA ATCAACTTCA AAACAAATCA TATCAATACA ATATCAAGTA
1621 GTGTCGATGA TCTCATTAGG TACTAATCCT AACATTGTGA TTCATCCTGC ATTCAGAAAG
1681 GTACC
```

FIG. 29

```
   1 GAGCTCCAAT ACAACACAGA ACCCCAGCTG CCATCACAAC TGTTCTCTGG CCGCTCGAAA
  61 GATGGAGCCC TCAAAACTCT TCACAATGTC AGACAATGCC ACCTTTGCAC CTGGACCTTT
 121 TATCAATGCG GCAGACAAGA AGACGTTCCG AACCTGCTTC CGAATATTGG TACTGTCTGT
 181 ACAAGCTGTT ACCCTTATAT TAGTTATTGT CACTTTAGGT GAGCTTGTGA GGATGATCAA
 241 TGATCAAGGC TTGAGCAATC AGTTGTCTTC AATTGCAGAC AAGATAAGAG AGTCAGCTAC
 301 TATGATTGCA TCTGCTGTGG GAGTAATGAA TCAAGTTATT CACGGAGTAA CGGTATCCTT
 361 ACCCCTACAA ATTGAGGGAA ACCAAAATCA ATTGTTATCC ACACTTGCCA CAATCTGTAC
 421 AGGCAAAAAA CAAGTCTCAA ACTGCTCTAC AAACATCCCC TTAGTTAATG ACCTTAGGTT
 481 TATAAATGGG ATCAATAAAT TCATCATTGA AGATTATGCA ACTCATGATT TCTCTATCGG
 541 CCATCCACTC AACATGCCTA GCTTTATCCC AACTGCAACT TCACCCAATG GTTGCACAAG
 601 AATTCCATCC TTTTCTCTAG GTAAGACACA CTGGTGCTAC ACACATAATG TAATTAATGC
 661 CAACTGCAAG GATCATACTT CGTCTAACCA ATATATTTCC ATGGGGATAC TCGTTCAGAC
 721 CGCGTCAGGG TATCCTATGT TCAAAACCTT AAAAATCCAA TATCTCAGTG ATGGCCTTAA
 781 TCGGAAAAGC TGCTCAATTG CAACAGTCCC TGATGGATGC GCAATGTACT GTTACGTCTC
 841 AACTCAACTT GAAACCGACG ACTATGCGGG GTCCAGCCCA CCTACCCAGA AACTTACCCT
 901 GTTATTCTAT AATGATACCG TCACAGAAAG GACAATATCT CCAACTGGTC TTGAAGGGAA
 961 TTGGGCTACT TTGGTTCCAG GAGTGGGGAG TGGAATATAT TTCGAGAATA AATTGATTTT
1021 TCCTGCATAT GGGGGTGTCT TGCCCAATAG TACACTCGGA GTTAAATCAG CAAGAGAATT
1081 TTTCCGGCCT GTTAATCCAT ATAATCCATG TTCAGGACCA CAACAAGATT TAGATCAGCG
1141 TGCTTTGAGA TCATACTTCC CAAGTTACTT CTCTAATCGA AGAGTACAGA GTGCATTTCT
1201 TGTCTGTGCC TGGAATCAGA TCCTAGTTAC AAATTGCGAG CTAGTTGTCC CCTCAAACAA
1261 TCAGACACTG ATGGGTGCAG AAGGAAGAGT TTTATTGATC AATAATCGAC TATTATATTA
1321 TCAGAGAAGT ACCAGCTGGT GGCCGTATGA ACTCCTCTAT GAGATATCAT TCACATTTAC
1381 AAACTCTGGT CAATCATCTG TGAATATGTC CTGGATACCT ATATATTCAT TCACTCGTCC
1441 TGGTTCAGGC AACTGCAGTG GTGAAAATGT GTGCCCAACT GCTTGTGTGT CAGGGGTTTA
1501 TCTTGATCCC TGGCCATTAA CTCCATATAG CCACCAATCA GGCATTAACC GAAATTTCTA
1561 TTTCACAGGC GCACTATTAA ATTCAAGCAC AACTAGAGTA AATCCTACCC TTTATGTCTC
1621 TGCCCTTAAT AATCTTAAAG TACTAGCCCC ATATGGTAAT CAGGGACTGT TTGCCTCGTA
1681 CACCACAACC ACCTGCTTTC AAGATACCGG TGATGCTAGT GTGTATTGTG TTTATATTAT
1741 GGAACTAGCA TCGAATATCG TTGGAGAATT CCAAATTCTA CCTGTGCTAA CCAGATTGAC
1801 CATCACTTGA GTAATAGTGA ATGCGGTACC
```

FIG. 30

FIG. 36 v908 AND vP555 — piM | E | NS1 | NS2A v923 AND vP829 — piM | E

↑ SIGNAL-PEPTIDASE CLEAVAGE SLIES
■ N-TERMINAL SIGNAL PEPTIDES

SEQUENCE LISTING ( 1 ) GENERAL INFORMATION:

( i i i ) NUMBER OF SEQUENCES: 462

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TAATTAACTA GCTACCCGGG    20

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATTCCCGGG TAGCTAGTTA ATTACATG    28

(2) INFORMATION FOR SEQ ID NO:3:

(i) SEQUENCE CHARACTERISTICS:
       (A) LENGTH: 73 base pairs
       (B) TYPE: nucleic acid
       (C) STRANDEDNESS: single
       (D) TOPOLOGY: linear (xi) SEQUENCE DESCRIPTION: SEQ ID NO:3:

AGCTTCCCGG GTAAGTAATA CGTCAAGGAG AAAACGAAAC GATCTGTAGT TAGCGGCCGC        60

CTAATTAACT AAT        73

(2) INFORMATION FOR SEQ ID NO:4:

(i) SEQUENCE CHARACTERISTICS:
       (A) LENGTH: 69 base pairs
       (B) TYPE: nucleic acid
       (C) STRANDEDNESS: single
       (D) TOPOLOGY: linear (xi) SEQUENCE DESCRIPTION: SEQ ID NO:4:

ATTAGTTAAT TAGGCGGCCG CTAACTACAG ATCGTTTCGT TTTCTCCTTG ACGTATTACT        60

TACCCGGGA        69

(2) INFORMATION FOR SEQ ID NO:5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:5:

TTAGTTAATT AGGCGGCCGC        20

(2) INFORMATION FOR SEQ ID NO:6:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (xi) SEQUENCE DESCRIPTION: SEQ ID NO:6:

CGATTACTAT GAAGGATCCG TT        22

(2) INFORMATION FOR SEQ ID NO:7:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:7:

AACGGATCCT TCATAGTAAT        20

(2) INFORMATION FOR SEQ ID NO:8:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (xi) SEQUENCE DESCRIPTION: SEQ ID NO:8:

```
CGATTACTAG ATCTGAGCTC CCCGGGCTCG AGGGATCCGT T                              41
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AACGGATCCC TCGAGCCCGG GGAGCTCAGA TCTAGTAAT                                 39
```

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GATCCGAATT CTAGCT                                                         16
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGCTAGAATT CG                                                             12
```

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TATGAGTAAC TTAACTCTTT TGTTAATTAA AAGTATATTC AAAAAATAAG TTATATAAAT          60

AGATCTGAAT TCGTT                                                          75
```

( 2 ) INFORMATION FOR SEQ ID NO:13:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
AACGAATTCA GATCTATTTA TATAACTTAT TTTTGAATA TACTTTTAAT TAACAAAAGA           60

GTTAAGTTAC TCA                                                            73
```

( 2 ) INFORMATION FOR SEQ ID NO:14:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAAATGGGCG TGGATTGTTA ACTTTATATA ACTTATTTTT TGAATATAC 49

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ACACGAATGA TTTTCTAAAG TATTTGGAAA GTTTTATAGG TAGTTGATAG AACAAAATAC 60

ATAATTT 67

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TCTATCAACT ACCTATAAAA CTTTCCAAAT ACTTTAGAAA ATCATTCGTG T 51

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TGTAAAAATA AATCACTTTT TATACTAAGA TCTCCCGGGC TGCAGC 46

( 2 ) INFORMATION FOR SEQ ID NO:18:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGCCGCTGCA GCCCGGGAGA TCTTAGTATA AAAGTGATT TATTTTTACA AAATTATGTA 60

TTTTGT 66

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TTTCTGTATA TTTGCACCAA TTTAGATCTT ACTCAAAATA TGTAACAATA 50

( 2 ) INFORMATION FOR SEQ ID NO:20:

( i ) SEQUENCE CHARACTERISTICS:
        ( A ) LENGTH: 44 base pairs
        ( B ) TYPE: nucleic acid ( C ) STRANDEDNESS: single
            ( D ) TOPOLOGY: linear ( x i ) SEQUENCE DESCRIPTION: SEQ ID NO:20:

TGTCATTTAA CACTATACTC ATATTAATAA AAATAATATT TATT          44

( 2 ) INFORMATION FOR SEQ ID NO:21:

( i ) SEQUENCE CHARACTERISTICS:
            ( A ) LENGTH: 72 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:21:

GATCCTGAGT ACTTTGTAAT ATAATGATAT ATATTTTCAC TTTATCTCAT TTGAGAATAA          60

AAAGATCTTA GG          72

( 2 ) INFORMATION FOR SEQ ID NO:22:

( i ) SEQUENCE CHARACTERISTICS:
            ( A ) LENGTH: 72 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:22:

AATTCCTAAG ATCTTTTTAT TCTCAAATGA GATAAAGTGA AATATATAT CATTATATTA          60

CAAAGTACTC AG          72

( 2 ) INFORMATION FOR SEQ ID NO:23:

( i ) SEQUENCE CHARACTERISTICS:
            ( A ) LENGTH: 72 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:23:

GATCCAGATC TCCCGGGAAA AAAATTATTT AACTTTTCAT TAATAGGGAT TTGACGTATG          60

TAGCGTACTA GG          72

( 2 ) INFORMATION FOR SEQ ID NO:24:

( i ) SEQUENCE CHARACTERISTICS:
            ( A ) LENGTH: 72 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:24:

AATTCCTAGT ACGCATCATA CGTCAAATCC CTATTAATGA AAAGTTAAAT AATTTTTTC          60

CCGGGAGATC TG          72

( 2 ) INFORMATION FOR SEQ ID NO:25:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:25:

GGGAGATCTC TCGAGCTGCA GGGCGCCGGA TCCTTTTTCT          40

( 2 ) INFORMATION FOR SEQ ID NO:26:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

AGAAAAAGGA TCCGGCGCCC TGCAGCTCGA GAGATCTCCC        40

( 2 ) INFORMATION FOR SEQ ID NO:27:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CGATATCCGT TAAGTTTGTA TCGTAATGGG CTCCAGATCT TCTACCAGGA TCCCGGTAC        59

( 2 ) INFORMATION FOR SEQ ID NO:28:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

CGGGATCCTG GTAGAAGATC TGGAGCCCAT TACGATACAA ACTTAACGGA TATCG        55

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AATTCGAGCT CCCCGGG        17

( 2 ) INFORMATION FOR SEQ ID NO:30:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCCGGGGAGC TCG        13

( 2 ) INFORMATION FOR SEQ ID NO:31:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CTTTTTATAA AAAGTTAACT ACGTAG        26

( 2 ) INFORMATION FOR SEQ ID NO:32:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

GATCCTACGT AGTTAACTTT TTATAAAAAG AGCT 34

( 2 ) INFORMATION FOR SEQ ID NO:33:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:33:

CTTAACTCAG CTGACTATCC 20

( 2 ) INFORMATION FOR SEQ ID NO:34:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:34:

TACGTAGTTA ACTTTTTATA AAAATCATAT TTTTGTAGTG GCTC 44

( 2 ) INFORMATION FOR SEQ ID NO:35:

( i ) SEQUENCE CHARACTERISTICS:
  ( A ) LENGTH: 67 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:35:

AATTCAGGAT CGTTCCTTTA CTAGTTGAGA TTCTCAAGGA TGATGGGATT TAATTTTTAT 60

AAGCTTG 67

( 2 ) INFORMATION FOR SEQ ID NO:36:

( i ) SEQUENCE CHARACTERISTICS:
  ( A ) LENGTH: 67 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:36:

AATTCAAGCT TATAAAATT AAATCCCATC ATCCTTGAGA ATCTCAACTA GTAAAGGAAC 60

GATCCTG 67

( 2 ) INFORMATION FOR SEQ ID NO:37:

( i ) SEQUENCE CHARACTERISTICS:
  ( A ) LENGTH: 68 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:37:

CTAGACACTT TATGTTTTTT AATATCCGGT CTTAAAAGCT TCCCGGGGAT CCTTATACGG 60

GGAATAAT                                                                                                        68

( 2 ) INFORMATION FOR SEQ ID NO:38:

( i ) SEQUENCE CHARACTERISTICS:
            ( A ) LENGTH: 65 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:38:

ATTATTCCCC GTATAAGGAT CCCCCGGGAA GCTTTTAAGA CCGGATATTA AAAAACATAA          60

AGTGT                                                                     65

( 2 ) INFORMATION FOR SEQ ID NO:39:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( x i ) SEQUENCE DESCRIPTION: SEQ ID NO:39:

Arg  Arg  Gln  Arg  Arg
   1                      5

( 2 ) INFORMATION FOR SEQ ID NO:40:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:40:

GACTATCCTA CTTCCCTTGG GATGGGGGTT ATCTTTGTA                                 39

( 2 ) INFORMATION FOR SEQ ID NO:41:

( i ) SEQUENCE CHARACTERISTICS:
            ( A ) LENGTH: 44 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:41:

TATCCGTTAA GTTTGTATCG TAATGGGTCT CAAGGTGAAC GTCT                           44

( 2 ) INFORMATION FOR SEQ ID NO:42:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:42:

GATCCATTCC ATGGTTG                                                        17

( 2 ) INFORMATION FOR SEQ ID NO:43:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:43:

( 2 ) INFORMATION FOR SEQ ID NO:44:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
AGCTTGATAT CCGTTAAGTT TGTATCGTAA TGCCCGCTGG TGGCGGTCTT TGGCGCGGGC    60
C                                                                   61
```

( 2 ) INFORMATION FOR SEQ ID NO:45:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
CGCGCCAAAG ACCGCCAACC AGCGGGATTA CGATACAAAC TTAACGGATA TCA           53
```

( 2 ) INFORMATION FOR SEQ ID NO:46:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

```
CCCAGATCTC CTTG                                                     14
```

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
GTACGGGTCT AGAGGAACCT AG                                            22
```

( 2 ) INFORMATION FOR SEQ ID NO:48:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
GGCACTACCA GCGCCTCGAG AGCGAGGACC CCGACGCCCT GTAGAATTTT TATCGGCCGA    60
```

( 2 ) INFORMATION FOR SEQ ID NO:49:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TAGCAACCAT GGAATG    16

AGCTTCGGCC GATAAAAATT CTACAGGGCG TCGGGGTCCT CGCTCTCGAG GCGTAGTGCC        60

( 2 ) INFORMATION FOR SEQ ID NO:50:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AGCTTCTGCA GCCATGGCGA TCGG        24

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

AATTCCGATC GCCATGGCTG CAGA        24

( 2 ) INFORMATION FOR SEQ ID NO:52:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

GCGAGCGAGG CCATGCATCG TGCGAATGGC CCC        33

( 2 ) INFORMATION FOR SEQ ID NO:53:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

GGGGGGACGC GCGGGTCTAG AAGGCCCCGC CTGGCGG        37

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

ATCATCGGAT CCGGTGGTTT GCCATTCCG        29

( 2 ) INFORMATION FOR SEQ ID NO:55:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GATTAAACCT AAATAATTG        19

( 2 ) INFORMATION FOR SEQ ID NO:56:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GGGCTGAAGC TTGCGGCCGC TCATTAGACA AGCGAATGAG GGAC        44

( 2 ) INFORMATION FOR SEQ ID NO:57:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

AGATCTCCCG GGCTCGAGTA ATTAATTAAT TTTTATTACA CCAGAAAGAC GGCTTGAGAT        60

C        61

( 2 ) INFORMATION FOR SEQ ID NO:58:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

TAATTACTGA GCCCGGGAGA TATAATTTAA TTTAATTTAT ATAACTCATT TTTTCCCC        58

( 2 ) INFORMATION FOR SEQ ID NO:59:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

TATCTCGAAT TCCCGCGGCT TTAAATGGAC GGAACTCTTT TCCC        44

( 2 ) INFORMATION FOR SEQ ID NO:60:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

TAAAGTCAAT AAATTTTTAT TGCGGCCGCT ACCGAGCTCG AATTCG        46

( 2 ) INFORMATION FOR SEQ ID NO:61:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

GCTTGCATGC CTGCAGATAT CCGTTAAGTT TGTATCGTAA TGGAGGCAGC CTTGC        55

( 2 ) INFORMATION FOR SEQ ID NO:62:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

```
CCCTACGCCG AGTCATTACG ATACAAACTT AACGGATATC AGAGTCGTAC GTAGG          55
```

( 2 ) INFORMATION FOR SEQ ID NO:63:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

```
CTGGAAACAC TTGGGAATTC AAGCTTCATA AAAGGGTTA TAGAAGAGTC C               51
```

( 2 ) INFORMATION FOR SEQ ID NO:64:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
ACACAGAGCA ACTGCAGATC TCCCGATTTC CCCTCT                               36
```

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

```
GGGCAAAGCC ACAAATATG CAGGATTTCT GCG                                   33
```

( 2 ) INFORMATION FOR SEQ ID NO:66:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

```
GCCAGGGTTT TCCCAGATCT GATAAAACG ACGGCCAGTG                            40
```

( 2 ) INFORMATION FOR SEQ ID NO:67:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

```
GGGTCAAAAT TGAAAATATA TAATTACAAT ATAAATGCA GTTGCTCTGT GTT             53
```

( 2 ) INFORMATION FOR SEQ ID NO:68:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:68:

ATGGATCCTT CAGAGACAG                                 19

( 2 ) INFORMATION FOR SEQ ID NO:69:

( i ) SEQUENCE CHARACTERISTICS:
    ( A ) LENGTH: 7 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:69:

CTAATAG                                         7

( 2 ) INFORMATION FOR SEQ ID NO:70:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:70:

GATCCTATTA GAGCT                                  15

( 2 ) INFORMATION FOR SEQ ID NO:71:

( i ) SEQUENCE CHARACTERISTICS:
    ( A ) LENGTH: 74 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:71:

ATCCGTTAAG TTTGTATCGT AATGCGCGGG GGGGGCTTGA TTTGCGCGCT GGTCGTGGGG     60

GCGCTGGTGG CCGC                                  74

( 2 ) INFORMATION FOR SEQ ID NO:72:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:72:

GGCCACCAGC GCCCCACGA CCAGCGCGCA AATCAAGCCC CCCCGCGCA TTACGATACA     60

AACTTAACGG AT                                   72

( 2 ) INFORMATION FOR SEQ ID NO:73:

( i ) SEQUENCE CHARACTERISTICS:
    ( A ) LENGTH: 59 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:73:

ATCCGTTAAG TTTGTATCGT AATGGCCCTT GGACGGGTGG GCCTAGCCGT GGGCCTGTG     59

( 2 ) INFORMATION FOR SEQ ID NO:74:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:74:

| | | | | | |
|---|---|---|---|---|---|
| AGGCCCACGG | CTAGGCCCAC | CCGTCCAAGG | GCCATTACGA | TACAAACTTA | ACGGAT | 56 |

( 2 ) INFORMATION FOR SEQ ID NO:75:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

ATCCGTTAAG TTTGTATCGT AATGGGGCGT TTGACCTCCG G      41

( 2 ) INFORMATION FOR SEQ ID NO:76:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:76:

CGCCGGAGGT CAAACGCCCC ATTACGATAC AAACTTAACG GAT      43

( 2 ) INFORMATION FOR SEQ ID NO:77:

( i ) SEQUENCE CHARACTERISTICS:
    ( A ) LENGTH: 146 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:77:

GGCAGTACCC TGGCGGCGCT GGTCATCGGC GGTATTGCGT TTTGGGTACG CCGCCGGCGC    60

TCAGTGGCCC CCAAGCGCCT ACGTCTCCCC CACATCCGGG ATGACGACGC GCCCCCTCG    120

CACCAGCCAT TGTTTTACTA GCTGCA    146

( 2 ) INFORMATION FOR SEQ ID NO:78:

( i ) SEQUENCE CHARACTERISTICS:
    ( A ) LENGTH: 142 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:78:

GCTAGTAAAA CAATGGCTGG TGCGAGGGGG GCGCGTCGTC ATCCCGGATG TGGGGGAGAC    60

GTAGGCGCTT GGGGGCCACT GAGCGCCGGC GGCGTACCCA AAACGCAATA CCGCCGATGA    120

CCAGCGCCGC CAGGGTACTG CC    142

( 2 ) INFORMATION FOR SEQ ID NO:79:

( i ) SEQUENCE CHARACTERISTICS:
    ( A ) LENGTH: 10 base pairs
    ( B ) TYPE: nucleic acid ( C ) STRANDEDNESS: single
( D ) TOPOLOGY: linear ( x i ) SEQUENCE DESCRIPTION: SEQ ID NO:79:

TCGATCTAGA 10

( 2 ) INFORMATION FOR SEQ ID NO:80:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( x i ) SEQUENCE DESCRIPTION: SEQ ID NO:80:

AGCTTCTAGA 10

( 2 ) INFORMATION FOR SEQ ID NO:81:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:81:

CTCGCGATAT CCGTTAAGTT TGTATCGTAA TGCAGTGG 38

( 2 ) INFORMATION FOR SEQ ID NO:82:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:82:

AATTCCACTG CATTACGATA CAAACTTAAC GGATATCGCG AGGTAC 46

( 2 ) INFORMATION FOR SEQ ID NO:83:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:83:

CCCAGATCTA TCGATTGCCA TGGGGCAGA 29

( 2 ) INFORMATION FOR SEQ ID NO:84:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:84:

TCTGAAGGCT GGATCCAACT 20

( 2 ) INFORMATION FOR SEQ ID NO:85:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:85:

CAATCTTCTC GAGGATT 17

( 2 ) INFORMATION FOR SEQ ID NO:86:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:86:

AACAAGAAGA ACCCCGCC 18

( 2 ) INFORMATION FOR SEQ ID NO:87:

( i ) SEQUENCE CHARACTERISTICS:
    ( A ) LENGTH: 1142 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:87:

| | | | | | |
|---|---|---|---|---|---|
| TACATCATGC | AGTGGTTAAA | CAAAAACATT | TTTATTCTCA | AATGAGATAA | AGTGAAAATA | 60 |
| TATATCATTA | TATTACAAAG | TACAATTATT | TAGGTTTAAT | CATGGGAACG | AACCTATCTG | 120 |
| TTCCCAACCC | ACTTGGATTT | TTTCCTGATC | ATCAGTTAGA | CCCTGCTTTC | GGAGCCAACT | 180 |
| CAAACAATCC | TGACTGGGAT | TTTAACCCCG | TCAAAGACGA | TTGGCCTGCA | GCCAACCAAG | 240 |
| TAGGTGTGGG | AGCTTTCGGA | CCAAGGCTCA | CTCCTCCACA | CGGCGGTATA | TTAGGTTGGT | 300 |
| CTCCACAAGC | TCAAGGCATA | TTGACCACAG | TGTCAACAAT | TCCTCCACCA | GCCTCTACTA | 360 |
| ATCGGCAGTC | TGGTAGACAG | CCAACTCCCA | TCTCTCCTCC | TCTAAGAGAC | AGTCACCCAC | 420 |
| AAGCTATGCA | GTGGAATTCA | ACTGCTTTTC | ACCAGACACT | TCAAGACCCT | AGAGTCAGGG | 480 |
| GTCTATATCT | TCCTGCAGGT | GGATCTAGTT | CTGGAACTGT | AAACCCAGCT | CCGAATATTG | 540 |
| CCAGTCACAT | CTCGTCTATC | TCCGCGAGGA | CTGGAGACCC | AGTGACGAAC | ATGGACATCG | 600 |
| ACCCTTATAA | AGAATTTGGA | GCTACTGTGG | AGTTACTCTC | GTTTTTGCCT | TCTGACTTCT | 660 |
| TTCCTTCAGT | ACGAGATCTT | CTAGATACCG | CCTCAGCTCT | GTATCGGGAA | GCCTTAGAGT | 720 |
| CTCCTGAGCA | TTGTTCACCT | CACCATACTG | CACTCAGGCA | AGCAATTCTT | TGCTGGGGGG | 780 |
| AACTAATGAC | TCTAGCTACC | TGGGTGGGTG | TTAATTTGGA | AGATCCAGCA | TCTAGAGACC | 840 |
| TAGTAGTCAG | TTATGTCAAC | ACTAATATGG | GCCTAAAGTT | CAGGCAACTC | TTGTGGTTTC | 900 |
| ACATTTCTTG | TCTCACTTTT | GGAAGAGAAA | CCGTTATAGA | GTATTTGGTG | TCTTTCGGAG | 960 |
| TGTGGATTCG | CACTCCTCCA | GCTTATAGAC | CACCAAATGC | CCCTATCCTA | TCAACACTTC | 1020 |
| CGGAAACTAC | TGTTGTTAGA | CGACGAGGCA | GGTCCCCTAG | AAGAAGAACT | CCCTCGCCTC | 1080 |
| GCAGACGAAG | GTCTCAATCG | CCGCGTCGCA | GAAGATCTCA | ATCTCGGGAA | TCTCAATGTT | 1140 |
| AG | | | | | | 1142 |

( 2 ) INFORMATION FOR SEQ ID NO:88:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:88:

GATCTCAATC TCGGGAATCT CAATGTTAGA TAACTAATTT TTATCCCGGG T    51

( 2 ) INFORMATION FOR SEQ ID NO:89:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

AATTACCCGG GATAAAAATT AGTTATCTAA CATTGAGATT CCCGAGATTG A    51

( 2 ) INFORMATION FOR SEQ ID NO:90:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

AGCTTGTACA ATTATTTAGG TTTAATCATG GGAACGAACC TATCTGTT    48

( 2 ) INFORMATION FOR SEQ ID NO:91:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:91:

CCCAACCCAC TTGGATTTTT TCCTGATCAT CAGTTAGACC CTGCTTTC    48

( 2 ) INFORMATION FOR SEQ ID NO:92:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:92:

GGAGCCAACT CAAACAATCC TGACTGGGAT TTTAACCCCG TCAAAGACGA TTGGCCTGCA    60

( 2 ) INFORMATION FOR SEQ ID NO:93:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

GCCAACCAAG TAGGTGTGGG AGCTTTCGGA CCAAGGCTCA CTCCTCCACA CGGCGGT    57

( 2 ) INFORMATION FOR SEQ ID NO:94:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

ATATTAGGTT GGTCTCCACA AGCTCAAGGC ATATTGACCA CAGTGTCAAC CCG    53

(2) INFORMATION FOR SEQ ID NO:95:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:95:

AGCTTGTCAA CAATTCCTCC ACCAGCCTCT ACTAATCGGC AGTCTGGT     48

(2) INFORMATION FOR SEQ ID NO:96:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:96:

AGACAGCCAA CTCCCATCTC TCCTCCTCTA AGAGACAGTC ACCCACAAGC TATGCAGTGG     60

(2) INFORMATION FOR SEQ ID NO:97:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:97:

AGCTTGGGAA TTCAACTGCT TTTCACCAGA CACTTCAAGA CCCTAGAGTC AGGGGTCTAT     60

ATCTTCCTGC A     71

(2) INFORMATION FOR SEQ ID NO:98:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:98:

GGTGGATCTA GTTCTGGAAC TGTAAACCCA GCTCCGAATA TTGCCAGTCA CATCTC     56

(2) INFORMATION FOR SEQ ID NO:99:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:99:

GTCTATCTCC GCGAGGACTG GAGACCCAGT GACGAACATG GACAT     45

(2) INFORMATION FOR SEQ ID NO:100:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:100:

CCCCCCAAGC TTCCCGGGCT ACATCATGCA GTGGTTAAAC     40

( 2 ) INFORMATION FOR SEQ ID NO:101:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

ACTTTGTAAT ATAATGAT      18

( 2 ) INFORMATION FOR SEQ ID NO:102:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

AATTCAGATC TCAAAATTGA AAATATATAA TTACAATATA AAATGGGGC      49

( 2 ) INFORMATION FOR SEQ ID NO:103:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

TTCTGCCCCA TTTTATATTG TAATTATATA TTTTCAATTT TGAGATCTG      49

( 2 ) INFORMATION FOR SEQ ID NO:104:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

AGAATCTTTC CACCAGCAAT CCTCTGGGAT TCTTTCCCGA CCACCAGTTG      50

( 2 ) INFORMATION FOR SEQ ID NO:105:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

GATCCAACTG GTGGTCGGGA AAGAATCCCA GAGGATTGCT GGTGGAAAGA      50

( 2 ) INFORMATION FOR SEQ ID NO:106:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

GCTTCCCGGG AATTCTAGCT AGCTAGTTT      29

( 2 ) INFORMATION FOR SEQ ID NO:107:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:107:

ACTCTCAAAA GCTTCCCGGG AATTCTAGCT AGCTAGTTTT TATAAA 46

( 2 ) INFORMATION FOR SEQ ID NO:108:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:108:

GATCTTTATA AAAACTAGCT AGCTAGAATT CCCGGGAAGC TTTTGAGAGT 50

( 2 ) INFORMATION FOR SEQ ID NO:109:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:109:

CTGAAATTAT TTCATTATCG CGATATCCGT TAAGTTTGTA TCGTAATGGT TCCTCAGGCT 60

CTCCTGTTTG T 71

( 2 ) INFORMATION FOR SEQ ID NO:110:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:110:

CATTACGATA CAAACTTAAC GGATATCGCG ATAATGAAAT AATTTCAG 48

( 2 ) INFORMATION FOR SEQ ID NO:111:

( i ) SEQUENCE CHARACTERISTICS:
    ( A ) LENGTH: 73 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:111:

ACCCCTTCTG GTTTTTCCGT TGTGTTTTGG GAAATTCCCT ATTTACACGA TCCCAGACAA 60

GCTTAGATCT CAG 73

( 2 ) INFORMATION FOR SEQ ID NO:112:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:112:

CTGAGATCTA AGCTTGTCTG GGATCGTGTA AATAGGGAAT TTCCAAAAC A 51

( 2 ) INFORMATION FOR SEQ ID NO:113:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

| | | | | |
|---|---|---|---|---|
| CAACGGAAAA | ACCAGAAGGG | GTACAAACAG | GAGAGCCTGA | GGAAC | 45 |

( 2 ) INFORMATION FOR SEQ ID NO:114:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

TCGAGCCCGG GATGACTAAA AAACCAGGAG GGCC      34

( 2 ) INFORMATION FOR SEQ ID NO:115:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

CTCCTGGTTT TTTAGTCATC CCGGGC      26

( 2 ) INFORMATION FOR SEQ ID NO:116:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

CTTGATTTTT ATTGACGGCC GA      22

( 2 ) INFORMATION FOR SEQ ID NO:117:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

AGCTTCGGCC GTCAATAAAA ATCAAGCATG      30

( 2 ) INFORMATION FOR SEQ ID NO:118:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

GGGATGGGCG TTAACGCACG AGACCGATCA ATTGCTTTGG CCTTCTTAGC CACAGGAGGT      60

GTGCTCGTGT TCTTAGCGAC CAATGTGCAT G      91

( 2 ) INFORMATION FOR SEQ ID NO:119:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:119:

```
CACATTGGTC GCTAAGAACA CGAGCACACC TCCTGTGGCT AAGAAGGCCA AAGCAATTGA      60

TCGGTCTCGT GCGTTAACGC CCATCCC                                         87
```

( 2 ) INFORMATION FOR SEQ ID NO:120:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

```
AGCTTCTTTA TTCTATACTT AAAAAGTGAA AATAAATACA AAGGTTCTTG AGGGTTGTGT      60

TAAATTGAAA GCGAGAAATA ATCATAAATT ATTTCATTAT CGCGATATCC GTTAAGTTTG     120

TATCGTAC                                                              128
```

( 2 ) INFORMATION FOR SEQ ID NO:121:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

```
TCGAGTACGA TACAAACTTA ACGGATATCG CGATAATGAA ATAATTTATG ATTATTTCTC      60

GCTTTCAATT TAACACAACC CTCAAGAACC TTTGTATTTA TTTTCACTTT TTAAGTATAG     120

AATAAAGA                                                              128
```

( 2 ) INFORMATION FOR SEQ ID NO:122:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:122:

```
TTCTTCTTCT TGT                                                         13
```

( 2 ) INFORMATION FOR SEQ ID NO:123:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:123:

```
AGCTTCTCGA GCATCGATTA CTATGTCTGG TCGTAAAGCT CAGGGAAAAA CCCTGGGCGT      60

CAATATGGT                                                              69
```

( 2 ) INFORMATION FOR SEQ ID NO:124:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:124:

```
ACCATATTGA CGCCCAGGGT TTTTCCCTGA GCTTTACGAC CAGACATAGT AATCGATGCT      60
CGAGA                                                                  65
```

( 2 ) INFORMATION FOR SEQ ID NO:125:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:125:

```
CTAGATGATT TTTATCGGCC GA                                               22
```

( 2 ) INFORMATION FOR SEQ ID NO:126:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:126:

```
AGCTTCGGCC GATAAAAATC AT                                               22
```

( 2 ) INFORMATION FOR SEQ ID NO:127:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

```
AGCTTCCCGG GATGCTCCTC ATGCTGCTGC CCACAGCCCT GGCGTTCCAT CTGACCACCC      60
GAGT                                                                   64
```

( 2 ) INFORMATION FOR SEQ ID NO:128:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

```
CTAGACTCGG GTGGTCAGAT GGAACGCCAG GGCTGTGGGC AGCAGCATGA GGAGCATCCC      60
GGGA                                                                   64
```

( 2 ) INFORMATION FOR SEQ ID NO:129:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

```
AGCTGATATC CGTTAAGTTT GTATCGTAAT GAACAGGAGG AAAA                       44
```

( 2 ) INFORMATION FOR SEQ ID NO:130:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

GATCTTTTCC TCCTGTTCAT TACGATACAA ACTTAACGGA TATCA         45

( 2 ) INFORMATION FOR SEQ ID NO:131:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

TTCCCAAGCT TGTCGACGAT AAATATGGATC CTCATGAC         38

( 2 ) INFORMATION FOR SEQ ID NO:132:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

TTCCCAGATC TATGAGTATA GTGTTAAATG AC         32

( 2 ) INFORMATION FOR SEQ ID NO:133:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

GATCCTTGTT AACCCGATAT CCCGGG         26

( 2 ) INFORMATION FOR SEQ ID NO:134:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

AATTCCCGGG ATATCGGGTT AACAAG         26

( 2 ) INFORMATION FOR SEQ ID NO:135:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

TCGAGAATTC CCGGGTCAAA ATTGAAAATA TATAATTACA ATATAAAATA         50

5,494,807

291                                                                                                     292
-continued ( 2 ) INFORMATION FOR SEQ ID NO:136:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

GATCTATTTT ATATTGTAAT TATATATTTT CAATTTTGAC CCGGGAATTC          50

( 2 ) INFORMATION FOR SEQ ID NO:137:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

ATGGTAGAAA TTAATTGTAC          20

( 2 ) INFORMATION FOR SEQ ID NO:138:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

ATCATCGAAT TCAAGCTTAT TATTTGCTC TACTAATGTT AC          42

( 2 ) INFORMATION FOR SEQ ID NO:139:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

ATGAATGTGA CAGAAAATTT TAACATGTGG AAAAATGTAG AAATTAATTG TACAAGACCC          60

( 2 ) INFORMATION FOR SEQ ID NO:140:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

GGGTCTTGTA CAATTAATTT CTACATTTTT CCACATGTTA AAATTTCTG TCACATTCAT          60

( 2 ) INFORMATION FOR SEQ ID NO:141:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

AGTAATGTGA CAGAAAATTT TAAC          24

( 2 ) INFORMATION FOR SEQ ID NO:142:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:142:

AGGCAAGCTT TCAAAAAAT ATAAATGATT C                    31

( 2 ) INFORMATION FOR SEQ ID NO:143:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:143:

TTTATATTGT AATTATATAT TTTC                            24

( 2 ) INFORMATION FOR SEQ ID NO:144:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:144:

GTTTTAATTG TGGAGGGGAA TTCTTCTACT GTAATTC              37

( 2 ) INFORMATION FOR SEQ ID NO:145:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:145:

ATCATCTCTA GAATAAAAAT TATAGCAAAA TCCTTTC              37

( 2 ) INFORMATION FOR SEQ ID NO:146:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:146:

TGCTACTCCT AATGGTTC                                   18

( 2 ) INFORMATION FOR SEQ ID NO:147:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:147:

CATATGCTTT AGCATCTGAT G                               21

( 2 ) INFORMATION FOR SEQ ID NO:148:

( i ) SEQUENCE CHARACTERISTICS:
  ( A ) LENGTH: 21 base pairs ( B ) TYPE: nucleic acid
( C ) STRANDEDNESS: single
( D ) TOPOLOGY: linear ( x i ) SEQUENCE DESCRIPTION: SEQ ID NO:148:

ATGAAAGAGC AGAAGACAGT G    21

( 2 ) INFORMATION FOR SEQ ID NO:149:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:149:

ATCATCGGTA CCGATTCTTT ATTCTATAC    29

( 2 ) INFORMATION FOR SEQ ID NO:150:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:150:

TACGATACAA ACTTAACGG    19

( 2 ) INFORMATION FOR SEQ ID NO:151:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:151:

GAATTACAGT AGAAGAATTC CCCTCCACAA TTAAAAC    37

( 2 ) INFORMATION FOR SEQ ID NO:152:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:152:

CAATAGATAA TGATACTAC    19

( 2 ) INFORMATION FOR SEQ ID NO:153:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:153:

GTATTATATC AAGTTTATAT AATAATGCAT ATTC    34

( 2 ) INFORMATION FOR SEQ ID NO:154:

( i ) SEQUENCE CHARACTERISTICS:
( A ) LENGTH: 18 base pairs
( B ) TYPE: nucleic acid
( C ) STRANDEDNESS: single ( D ) TOPOLOGY: linear ( x i ) SEQUENCE DESCRIPTION: SEQ ID NO:154:

GTTGATGATC TGTAGTGC 18

( 2 ) INFORMATION FOR SEQ ID NO:155:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:155:

ATCATCTCTA GAATAAAAAT TATGGTTCAA TTTTTACTAC TTTTATATTA TATATTTC 58

( 2 ) INFORMATION FOR SEQ ID NO:156:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:156:

CAATAATCTT TAAGCAAATC CTC 23

( 2 ) INFORMATION FOR SEQ ID NO:157:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

AGAGGGGAAT TCTTCTACTG CAATACA 27

( 2 ) INFORMATION FOR SEQ ID NO:158:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:158:

```
Leu Gln Ala Arg Val Leu Ala Val Glu Arg Tyr Leu Arg Asp Gln Gln
 1               5                  10                  15
Leu
```

( 2 ) INFORMATION FOR SEQ ID NO:159:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

TTGGAAAGGC TTTTGGCATG CCACGCGTC 29

( 2 ) INFORMATION FOR SEQ ID NO:160:

( i ) SEQUENCE CHARACTERISTICS:
        ( A ) LENGTH: 42 base pairs
        ( B ) TYPE: nucleic acid ( C ) STRANDEDNESS: single
( D ) TOPOLOGY: linear ( x i ) SEQUENCE DESCRIPTION: SEQ ID NO:160:

ACAGTCTGGG GCATCAAGCA GCTAGGGATT TGGGGTTGCT CT  42

( 2 ) INFORMATION FOR SEQ ID NO:161:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:161:

CCGTTAAGTT TGTATCGTAA TGAAAGTGAA GGGGACCAGG  40

( 2 ) INFORMATION FOR SEQ ID NO:162:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:162:

ATGAGTGGTA AAATTCAGCT GCTTGTTGCC TTTCTGCTAA CTAGTGCTTG CTTA  54

( 2 ) INFORMATION FOR SEQ ID NO:163:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:163:

TAAGCAAGCA CTAGTTAGCA GAAAGGCAAC AAGCAGCTGA ATTTTACCAC TCAT  54

( 2 ) INFORMATION FOR SEQ ID NO:164:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:164:

ATCATCAAGC TTGATTCTTT ATTCTATAC  29

( 2 ) INFORMATION FOR SEQ ID NO:165:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:165:

CAGCTGAATT TTACCACTCA TTACGATACA AACTTAACG  39

( 2 ) INFORMATION FOR SEQ ID NO:166:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:166:

TAAGCAAGCA CTAGTTAG 18

( 2 ) INFORMATION FOR SEQ ID NO:167:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

CCGCCTCTTG ACCAGAC 17

( 2 ) INFORMATION FOR SEQ ID NO:168:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

ATCATCTCTA GAATAAAAAT TACAGGAGGG CAATTTCTG 39

( 2 ) INFORMATION FOR SEQ ID NO:169:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:169:

ATCATCTCTA GAATAAAAAT TATCTCTTAT GTCTCCCTGG 40

( 2 ) INFORMATION FOR SEQ ID NO:170:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:170:

AATTAACTTT ACAGCACC 18

( 2 ) INFORMATION FOR SEQ ID NO:171:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:171:

CGATATCCGT TAAGTTTGTA TCGTAATGGG ATGTCTTGGG AATC 44

( 2 ) INFORMATION FOR SEQ ID NO:172:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:172:

CAAGGCTTTA TTGAGGTCTC 20

( 2 ) INFORMATION FOR SEQ ID NO:173:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:173:

CCTGGCCTTG GCAGATAG 18

( 2 ) INFORMATION FOR SEQ ID NO:174:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:174:

ATCATCGAAT TCAAAAATAT TACAAAGAGC GTGAGCTCAA GTCCTTGCCT AATCCTCC 58

( 2 ) INFORMATION FOR SEQ ID NO:175:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:175:

CCCCCCAAGC TTTTTATTCT ATACTT 26

( 2 ) INFORMATION FOR SEQ ID NO:176:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:176:

CAAGGCTTTA TTGAGGTCTC 20

( 2 ) INFORMATION FOR SEQ ID NO:177:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:177:

CAGTTGGTAC CACTGGTATT TTATTTCAG 29

( 2 ) INFORMATION FOR SEQ ID NO:178:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:178:

TATCTGAATT CCTGCAGCCC GGGTTTTTAT AGCTAATTAG TCAAATGTGA GTTAATATTA 60

( 2 ) INFORMATION FOR SEQ ID NO:179:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:179:

```
TCGCTGAATT  CGATATCAAG  CTTATCGATT  TTTATGACTA  GTTAATCAAA  TAAAAAGCAT    60
ACAAGC                                                                    66
```

( 2 ) INFORMATION FOR SEQ ID NO:180:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:180:

```
TTATCGAGCT  CTGTAACATC  AGTATCTAAC                                        30
```

( 2 ) INFORMATION FOR SEQ ID NO:181:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:181:

```
TCGAGTGAGA  TAAAGTGAAA  ATATATATCA  TTATATTACA  AGTACAATTA  TTTAGGTTTA    60
ATCATGGGCG                                                                70
```

( 2 ) INFORMATION FOR SEQ ID NO:182:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

```
CCCATGATTA  AACCTAAATA  ATTGTACTTT  GTAATATAAT  GCTATATATT  TTCACTTTAT    60
CTCAC                                                                     65
```

( 2 ) INFORMATION FOR SEQ ID NO:183:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:183:

```
AATCAGAGAG  CAGGCT                                                        16
```

( 2 ) INFORMATION FOR SEQ ID NO:184:

( i ) SEQUENCE CHARACTERISTICS:
        ( A ) LENGTH: 23 base pairs
        ( B ) TYPE: nucleic acid

G                         61

(C) STRANDEDNESS: single
(D) TOPOLOGY: linear (xi) SEQUENCE DESCRIPTION: SEQ ID NO:184:

TTGGATCCCT ATGCCACCTC TCT  23

(2) INFORMATION FOR SEQ ID NO:185:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:185:

AGACCAACAG CACCATCTAG CGGCAGAGGA GGAAATTACT AATTTTTATT CTAGAG  56

(2) INFORMATION FOR SEQ ID NO:186:

(i) SEQUENCE CHARACTERISTICS:
(A) LENGTH: 58 base pairs
(B) TYPE: nucleic acid
(C) STRANDEDNESS: single
(D) TOPOLOGY: linear (xi) SEQUENCE DESCRIPTION: SEQ ID NO:186:

GATCCTCTAG AATAAAAATT AGTAATTTCC TCCTCTGCCG CTAGATGGTG CTGTTGGT  58

(2) INFORMATION FOR SEQ ID NO:187:

(i) SEQUENCE CHARACTERISTICS:
(A) LENGTH: 79 base pairs
(B) TYPE: nucleic acid
(C) STRANDEDNESS: single
(D) TOPOLOGY: linear (xi) SEQUENCE DESCRIPTION: SEQ ID NO:187:

TAGACAAAAT TGAAAATATA TAATTACAAT ATAAATGCC AGTACAACAA ATAGGTGGTA  60

ACTATGTCCA CCTGCCATT  79

(2) INFORMATION FOR SEQ ID NO:188:

(i) SEQUENCE CHARACTERISTICS:
(A) LENGTH: 80 base pairs
(B) TYPE: nucleic acid
(C) STRANDEDNESS: single
(D) TOPOLOGY: linear (xi) SEQUENCE DESCRIPTION: SEQ ID NO:188:

GCTTAATGGC AGGTGGACAT AGTTACCACC TATTTGTTGT ACTGGCATTT TATATTGTAA  60

TTATATATTT TCAATTTTGT  80

(2) INFORMATION FOR SEQ ID NO:189:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:189:

TGGATGTACA GACAAC  16

(2) INFORMATION FOR SEQ ID NO:190:

(i) SEQUENCE CHARACTERISTICS:

(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:190:

AAGGATCCGA ATTCTTACAT TAATCTAGCC TTC                    33

(2) INFORMATION FOR SEQ ID NO:191:

(i) SEQUENCE CHARACTERISTICS:
(A) LENGTH: 68 base pairs
(B) TYPE: nucleic acid
(C) STRANDEDNESS: single
(D) TOPOLOGY: linear (xi) SEQUENCE DESCRIPTION: SEQ ID NO:191:

CTAGACACTT TATGTTTTTT AATATCCGGT CTTAAAAGCT TCCCGGGGAT CCTTATACGG    60

GGAATAAT                                                            68

(2) INFORMATION FOR SEQ ID NO:192:

(i) SEQUENCE CHARACTERISTICS:
(A) LENGTH: 65 base pairs
(B) TYPE: nucleic acid
(C) STRANDEDNESS: single
(D) TOPOLOGY: linear (xi) SEQUENCE DESCRIPTION: SEQ ID NO:192:

ATTATTCCCC GTATAAGGAT CCCCGGGAA GCTTTTAAGA CCGGATATTA AAAACATAA      60

AGTGT                                                               65

(2) INFORMATION FOR SEQ ID NO:193:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:193:

TCATTATCGC GATATCCGTG TTAACTAGCT AGCTAATTTT TATTCCCGGG ATCCTTATCA    60

(2) INFORMATION FOR SEQ ID NO:194:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:194:

GTATAAGGAT CCCGGGAATA AAAATTAGCT AGCTAGTTAA CACGGATATC GCGATAATGA    60

(2) INFORMATION FOR SEQ ID NO:195:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:195:

GACAATCTAA GTCCTATATT AGAC                              24

(2) INFORMATION FOR SEQ ID NO:196:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:196:

GGATTTTTAG GTAGACAC                        18

( 2 ) INFORMATION FOR SEQ ID NO:197:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:197:

TCATCGTCTT CATCATCG                        18

( 2 ) INFORMATION FOR SEQ ID NO:198:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:198:

GTCTTAAACT TATTGTAAGG GTATACCTG            29

( 2 ) INFORMATION FOR SEQ ID NO:199:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:199:

AACGATTAGT TAGTTACTAA AAGCTTGCTG CAGCCCGGGT TTTTTATTAG TTTAGTTAGT    60
C                                                                   61

( 2 ) INFORMATION FOR SEQ ID NO:200:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:200:

GACTAACTAA CTAATAAAAA ACCCGGGCTG CAGCAAGCTT TTTGTAACTA ACTAATCGTT    60

( 2 ) INFORMATION FOR SEQ ID NO:201:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:201:

GCACGGAACA AAGCTTATCG CGATATCCGT TAAGTTTGTA TCGTAATGCT ATCAATCACG    60
ATTCTGTTCC TGCTCATAGC AGAGGGCTCA TCTCAGAAT                          99

( 2 ) INFORMATION FOR SEQ ID NO:202:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

```
ATTCTGAGAT GAGCCCTCTG CTATGAGCAG GAACAGAATC GTGATTGATA GCATTACGAT      60
ACAAACTTAA CGGATATCGC GATAAGCTTT GTTCCGTGC                             99
```

( 2 ) INFORMATION FOR SEQ ID NO:203:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

```
GAAAAATTTA AAGTCGACCT GTTTTGTTGA GTTGTTGCG TGGTAACCAA TGCAAATCTG        60
GTCACT                                                                  66
```

( 2 ) INFORMATION FOR SEQ ID NO:204:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

```
TCTAGCAAGA CTGACTATTG CAAAAGAAG CACTATTTCC TCCATTACGA TACAAACTTA        60
ACGGAT                                                                  66
```

( 2 ) INFORMATION FOR SEQ ID NO:205:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

```
ATCCGTTAAG TTTGTATCGT AATGGAGGAA ATAGTGCTTC TTTTTGCAAT AGTCAGTCTT      60
GCTAGAAGTG ACCAGATTTG CATTGGT                                          87
```

( 2 ) INFORMATION FOR SEQ ID NO:206:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

```
TACCACGCAA ACAACTCAAC AAAACAGGTC GACTTAAAT TTTTCTGCA                   49
```

( 2 ) INFORMATION FOR SEQ ID NO:207:

( i ) SEQUENCE CHARACTERISTICS:
        ( A ) LENGTH: 132 base pairs
        ( B ) TYPE: nucleic acid
        ( C ) STRANDEDNESS: single (D) TOPOLOGY: linear (xi) SEQUENCE DESCRIPTION: SEQ ID NO:207:

| | | | | | |
|---|---|---|---|---|---|
| GTACAGGTCG | ACAAGCTTCC | CGGGTATCGC | GATATCCGTT | AAGTTTGTAT | CGTAATGAAT | 60
| ACTCAAATTC | TAATACTCAC | TCTTGTGGCA | GCCATTCACA | CAAATGCAGA | CAAAATCTGC | 120
| CTTGGACATC | AT | | | | | 132

(2) INFORMATION FOR SEQ ID NO:208:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:208:

ATGATGTCCA AGGCAGATTT TGTCTGCATT TGTGTGAATG GCTGCCACAA GAGTGAGTAT 60
TAGAATTTGA GTATTCATTA CGATACAAAC TTAACGGATA TCGCGATACC CGGGAAGCTT 120
GTCGACCTGT AC 132

(2) INFORMATION FOR SEQ ID NO:209:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:209:

ATAACATGCG GTGCACCATT TGTATATAAG TTAACGAATT CCAAGTCAAG C 51

(2) INFORMATION FOR SEQ ID NO:210:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:210:

GCTTGACTTG GAATTCGTTA ACTTATATAC AAATGGTGCA CCGCATGTTA T 51

(2) INFORMATION FOR SEQ ID NO:211:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:211:

GATCAGAAAA ACTAGCTAGC TAGTACGTAG TTAACGTCGA CCTGCAGAAG CTTCTAGCTA 60
GCTAGTTTTT AT 72

(2) INFORMATION FOR SEQ ID NO:212:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:212:

AGCTATAAAA ACTAGCTAGC TAGAAGCTTC TGCAGGTCGA CGTTAACTAC GTACTAGCTA 60

GCTAGTTTTT CT                                                                                       72

( 2 ) INFORMATION FOR SEQ ID NO:213:

( i ) SEQUENCE CHARACTERISTICS:
        ( A ) LENGTH: 970 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

```
TTCTTTATTC  TATACTTAAA  AAGTGAAAAT  AAATACAAAG  GTTCTTGAGG  GTTGTGTTAA    60
ATTGAAAGCG  AGAAATAATC  ATAAATTATT  TCATTATCGC  GATATCCGTT  AAGTTTGTAT   120
CGTAATGCAG  TGGAATTCTA  CTACTTTTCA  CCAAACTTTA  CAAGATCCTA  GAGTAAGAGG   180
ATTATATTTT  CCTGCTGGAG  GATCTTCTTC  TGGAGCTGTA  AATCCTGTAC  CTACTACTGC   240
TTCTCCTTTA  TCTTCTATTT  TTAGTAGAAT  TGGAGATCCT  GCTTAAATA   TGGAAATAT    300
TACTTCTGGA  TTTTTAGGAC  CTTTATTAGT  ATTACAAGCT  GGATTCTTTC  TATTAACTAG   360
AATTTTAACT  ATTCCTCAAT  CTCTAGATTC  TTGGTGGACT  TCTTTAAATT  TTTTAGGAGG   420
AACTACTGTT  TGTTTAGGAC  AAAATTCTCA  ATCTCCTACT  TCTAATCACT  CTCCTACTTC   480
TTGTCCTCCT  ACTTGTCCTG  GATATCGTTG  GATGTGTTTA  AGAAGATTTA  TTATTTTCTT   540
ATTTATTTTA  TTATTGTGTT  TAATTTTCTT  ATTAGTATTA  TTAGATTATC  AAGGAATGTT   600
ACCTGTTTGT  CCTTTAATTC  CTGGATCCTC  TACTACTTCT  ACTGGACCTT  GTAGAACTTG   660
TATGACTACT  GCTCAAGGAA  CTTCTATGTA  TCCTTCTTGT  TGTTGTACTA  AACCTTCTGA   720
CGGAAATTGT  ACTTGTATTC  CTATTCCTTC  TTCTTGGGCT  TTTGGAAAAT  TCTTGTGGGA   780
GTGGGCTTCT  GCTAGATTTT  CTTGGTTATC  TTTATTAGTA  CCTTTTGTAC  AGTGGTTTGT   840
AGGATTATCT  CCTACTGTTT  GGTTATCTGT  AATTTGGATG  ATGTGGTATT  GGGGACCTTC   900
TTTATATTCT  ATTTTATCTC  CTTTTTTACC  TTTATTACCT  ATTTCTTTT   GTTTGTGGGT   960
ATATATTTAA                                                              970
```

( 2 ) INFORMATION FOR SEQ ID NO:214:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( x i ) SEQUENCE DESCRIPTION: SEQ ID NO:214:

```
Met  Gln  Trp  Asn  Ser  Thr  Thr  Phe  His  Gln  Thr  Leu  Gln  Asp  Pro  Arg
 1              5                        10                       15

Val  Arg  Gly  Leu  Tyr  Phe  Pro  Ala  Gly  Gly  Ser  Ser  Ser  Gly  Ala  Val
               20                       25                       30

Asn  Pro  Val  Pro  Thr  Thr  Ala  Ser  Pro  Leu  Ser  Ser  Ile  Phe  Ser  Arg
          35                       40                       45

Ile  Gly  Asp  Pro  Ala  Leu  Asn  Met  Glu  Asn  Ile  Thr  Ser  Gly  Phe  Leu
     50                       55                       60

Gly  Pro  Leu  Leu  Val  Leu  Gln  Ala  Gly  Phe  Phe  Leu  Leu  Thr  Arg  Ile
65                       70                       75                       80

Leu  Thr  Ile  Pro  Gln  Ser  Leu  Asp  Ser  Trp  Trp  Thr  Ser  Leu  Asn  Phe
                85                       90                       95

Leu  Gly  Gly  Thr  Thr  Val  Cys  Leu  Gly  Gln  Asn  Ser  Gln  Ser  Pro  Thr
               100                      105                      110
```

| | | | | | | | | | | | | | | | |
|---|---|---|---|---|---|---|---|---|---|---|---|---|---|---|---|
|Ser|Asn|His<br>115|Ser|Pro|Thr|Ser|Cys<br>120|Pro|Pro|Thr|Cys|Pro<br>125|Gly|Tyr|Arg|
|Trp|Met<br>130|Cys|Leu|Arg|Arg|Phe<br>135|Ile|Ile|Phe|Leu|Phe<br>140|Ile|Leu|Leu|Leu|
|Cys<br>145|Leu|Ile|Phe|Leu|Leu<br>150|Val|Leu|Leu|Asp|Tyr<br>155|Gln|Gly|Met|Leu|Pro<br>160|
|Val|Cys|Pro|Leu|Ile<br>165|Pro|Gly|Ser|Ser|Thr<br>170|Thr|Ser|Thr|Gly|Pro<br>175|Cys|
|Arg|Thr|Cys|Met<br>180|Thr|Thr|Ala|Gln|Gly<br>185|Thr|Ser|Met|Tyr|Pro<br>190|Ser|Cys|
|Cys|Cys|Thr<br>195|Lys|Pro|Ser|Asp|Gly|Asn<br>200|Cys|Thr|Cys|Ile<br>205|Pro|Ile|Pro|
|Ser|Ser<br>210|Trp|Ala|Phe|Gly|Lys<br>215|Phe|Leu|Trp|Glu|Trp<br>220|Ala|Ser|Ala|Arg|
|Phe<br>225|Ser|Trp|Leu|Ser|Leu<br>230|Leu|Val|Pro|Phe|Val<br>235|Gln|Trp|Phe|Val|Gly<br>240|
|Leu|Ser|Pro|Thr|Val<br>245|Trp|Leu|Ser|Val|Ile<br>250|Trp|Met|Met|Trp|Tyr<br>255|Trp|
|Gly|Pro|Ser|Leu<br>260|Tyr|Ser|Ile|Leu|Ser<br>265|Pro|Phe|Leu|Pro|Leu<br>270|Leu|Pro|
|Ile|Phe|Phe<br>275|Cys|Leu|Trp|Val|Tyr<br>280|Ile| | | | | | | |

( 2 ) INFORMATION FOR SEQ ID NO:215:

( i ) SEQUENCE CHARACTERISTICS:
( A ) LENGTH: 1285 base pairs
( B ) TYPE: nucleic acid
( C ) STRANDEDNESS: single
( D ) TOPOLOGY: linear ( x i ) SEQUENCE DESCRIPTION: SEQ ID NO:215:

```
GTAGACTGTT TATACAAGAT TGAAAATATA TTTCTTTTTA TTGAGTGGTG GTAGTTACGG        60
ATATCTAATA TTAATATTAG ACTATCTCTA TCGTCACACA ACAAAATCGA TTGCCATGGG       120
GCAGAATCTT TCCACCAGCA ATCCTCTGGG ATTCTTTCCC GACCACCAGT TGGATCCAGC       180
CTTCAGAGCA AACAACGCAA ATCCAGATTG GGACTTCAAT CCCAACAAGG ACACCTGGCC       240
AGACGCCAAC AAGGTAGGAG CTGGAGCATT CGGGCTGGGT TTCACCCCAC CGCACGGAGG       300
CCTTTTGGGG TGGAGCCCTC AGGCTCAGGG CATACTACAA ACTTTGCCAG CAAATCCGCC       360
TCCTGCCTCC ACCAATCGCC AGACAGGAAG GCAGCCTACC CCGCTGTCTC CACCTTTGAG       420
AAACACTCAT CCTCAGGCCA TGCAGTGGAA TTCACAACC  TTTCACCAAA CTCTGCAAGA       480
TCCCAGAGTG AGAGGCCTGT ATTTCCCTGC TGGTGGCTCC AGTTCAGGAG CAGTAAACCC       540
TGTTCCGACT ACTGCCTCTC CCTTATCGTC AATCTTCTCG AGGATTGGGG ACCCTGCGCT       600
GAACATGGAG AACATCACAT CAGGATTCCT AGGACCCCTT CTCGTGTTAC AGGCGGGGTT       660
CTTCTTGTTG ACAAGAATCC TCACAATACC GCAGAGTCTA GACTCGTGGT GGACTTCTCT       720
CAATTTTCTA GGGGGAACTA CCGTGTGTCT TGGCCAAAAT TCGCAGTCCC CAACCTCCAA       780
TCACTCACCA ACCTCCTGTC CTCCAACTTG TCCTGGTTAT CGCTGGATGT GTCTGCGGCG       840
TTTTATCATC TTCCTCTTCA TCCTGCTGCT ATGCCTCATC TTCTTGTTGG TTCTTCTGGA       900
CTATCAAGGT ATGTTGCCCG TTTGTCCTCT AATTCCAGGA TCCTCAACCA CCAGCACGGG       960
ACCATGCCGA ACCTGCATGA CTACTGCTCA AGGAACCTCT ATGTATCCCT CCTGTTGCTG      1020
TACCAAACCT TCGGACGGAA ATTGCACCTG TATTCCCATC CCATCATCCT GGGCTTTCGG      1080
```

```
AAAATTCCTA TGGGAGTGGG CCTCAGCCCG TTTCTCCTGG CTCAGTTTAC TAGTGCCATT      1140

TGTTCAGTGG TTCGTAGGGC TTTCCCCCAC TGTTTGGCTT TCAGTTATAT GGATGATGTG      1200

GTATTGGGGG CCAAGTCTGT ACAGCATCTT GAGTCCCTTT TTACCGCTGT TACCAATTTT      1260

CTTTTGTCTT TGGGTATACA TTTAA                                            1285
```

( 2 ) INFORMATION FOR SEQ ID NO:216:

( i ) SEQUENCE CHARACTERISTICS:
        ( A ) LENGTH: 389 amino acids
        ( B ) TYPE: amino acid
        ( C ) STRANDEDNESS: single
        ( D ) TOPOLOGY: linear ( x i ) SEQUENCE DESCRIPTION: SEQ ID NO:216:

```
Met Gly Gln Asn Leu Ser Thr Ser Asn Pro Leu Gly Phe Phe Pro Asp
 1               5                  10                  15

His Gln Leu Asp Pro Ala Phe Arg Ala Asn Asn Ala Asn Pro Asp Trp
             20                  25                  30

Asp Phe Asn Pro Asn Lys Asp Thr Trp Pro Asp Ala Asn Lys Val Gly
         35                  40                  45

Ala Gly Ala Phe Gly Leu Gly Phe Thr Pro Pro His Gly Gly Leu Leu
 50                  55                  60

Gly Trp Ser Pro Gln Ala Gln Gly Ile Leu Gln Thr Leu Pro Ala Asn
 65                  70                  75                  80

Pro Pro Pro Ala Ser Thr Asn Arg Gln Thr Gly Arg Gln Pro Thr Pro
                 85                  90                  95

Leu Ser Pro Pro Leu Arg Asn Thr His Pro Gln Ala Met Gln Trp Asn
                100                 105                 110

Ser Thr Thr Phe His Gln Thr Leu Gln Asp Pro Arg Val Arg Gly Leu
            115                 120                 125

Tyr Phe Pro Ala Gly Gly Ser Ser Ser Gly Ala Val Asn Pro Val Pro
        130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
        275                 280                 285

Thr Thr Ala Gln Gly Thr Ser Met Tyr Pro Ser Cys Cys Cys Thr Lys
        290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
```

|     |     |     |     |     | 325 |     |     |     |     | 330 |     |     |     |     | 335 |     |     |
| --- | --- | --- | --- | --- | --- | --- | --- | --- | --- | --- | --- | --- | --- | --- | --- | --- | --- |
| Ser | Leu | Leu | Val | Pro | Phe | Val | Gln | Trp | Phe | Val | Gly | Leu | Ser | Pro | Thr |     |     |
|     |     |     | 340 |     |     |     |     | 345 |     |     |     |     | 350 |     |     |     |     |
| Val | Trp | Leu | Ser | Val | Ile | Trp | Met | Met | Trp | Tyr | Trp | Gly | Pro | Ser | Leu |     |     |
|     |     | 355 |     |     |     |     | 360 |     |     |     |     | 365 |     |     |     |     |     |
| Tyr | Ser | Ile | Leu | Ser | Pro | Phe | Leu | Pro | Leu | Leu | Pro | Ile | Phe | Phe | Cys |     |     |
|     | 370 |     |     |     |     | 375 |     |     |     |     | 380 |     |     |     |     |     |     |
| Leu | Trp | Val | Tyr | Ile |     |     |     |     |     |     |     |     |     |     |     |     |     |
| 385 |     |     |     |     |     |     |     |     |     |     |     |     |     |     |     |     |     |

( 2 ) INFORMATION FOR SEQ ID NO:217:

( i ) SEQUENCE CHARACTERISTICS:
        ( A ) LENGTH: 346 amino acids
        ( B ) TYPE: amino acid
        ( C ) STRANDEDNESS: single
        ( D ) TOPOLOGY: linear ( x i ) SEQUENCE DESCRIPTION: SEQ ID NO:217:

| Met | Gly | Thr | Asn | Leu | Ser | Val | Pro | Asn | Pro | Leu | Gly | Phe | Phe | Pro | Asp |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| His | Gln | Leu | Asp | Pro | Ala | Phe | Gly | Ala | Asn | Ser | Asn | Asn | Pro | Asp | Trp |
|     |     |     | 20 |     |     |     |     | 25 |     |     |     |     | 30 |     |     |
| Asp | Phe | Asn | Pro | Val | Lys | Asp | Asp | Trp | Pro | Ala | Ala | Asn | Gln | Val | Gly |
|     |     | 35 |     |     |     |     | 40 |     |     |     |     | 45 |     |     |     |
| Val | Gly | Ala | Phe | Gly | Pro | Arg | Leu | Thr | Pro | Pro | His | Gly | Gly | Ile | Leu |
|     | 50 |     |     |     |     | 55 |     |     |     |     | 60 |     |     |     |     |
| Gly | Trp | Ser | Pro | Gln | Ala | Gln | Gly | Ile | Leu | Thr | Thr | Val | Ser | Thr | Ile |
| 65 |     |     |     |     | 70 |     |     |     |     | 75 |     |     |     |     | 80 |
| Pro | Pro | Pro | Ala | Ser | Thr | Asn | Arg | Gln | Ser | Gly | Arg | Gln | Pro | Thr | Pro |
|     |     |     |     | 85 |     |     |     |     | 90 |     |     |     |     | 95 |     |
| Ile | Ser | Pro | Pro | Leu | Arg | Asp | Ser | His | Pro | Gln | Ala | Met | Gln | Trp | Asn |
|     |     |     | 100 |     |     |     |     | 105 |     |     |     |     | 110 |     |     |
| Ser | Thr | Ala | Phe | His | Gln | Thr | Leu | Gln | Asp | Pro | Arg | Val | Arg | Gly | Leu |
|     |     |     | 115 |     |     |     |     | 120 |     |     |     |     | 125 |     |     |
| Tyr | Leu | Pro | Ala | Gly | Gly | Ser | Ser | Ser | Gly | Thr | Val | Asn | Pro | Ala | Pro |
|     | 130 |     |     |     |     | 135 |     |     |     |     | 140 |     |     |     |     |
| Asn | Ile | Ala | Ser | His | Ile | Ser | Ser | Ile | Ser | Ala | Arg | Thr | Gly | Asp | Pro |
| 145 |     |     |     |     | 150 |     |     |     |     | 155 |     |     |     |     | 160 |
| Val | Thr | Asn | Met | Asp | Ile | Asp | Pro | Tyr | Lys | Glu | Phe | Gly | Ala | Thr | Val |
|     |     |     |     | 165 |     |     |     |     | 170 |     |     |     |     | 175 |     |
| Glu | Leu | Leu | Ser | Phe | Leu | Pro | Ser | Asp | Phe | Phe | Pro | Ser | Val | Arg | Asp |
|     |     |     | 180 |     |     |     |     | 185 |     |     |     |     | 190 |     |     |
| Leu | Leu | Asp | Thr | Ala | Ser | Ala | Leu | Tyr | Arg | Glu | Ala | Leu | Glu | Ser | Pro |
|     |     | 195 |     |     |     |     | 200 |     |     |     |     | 205 |     |     |     |
| Glu | His | Cys | Ser | Pro | His | His | Thr | Ala | Leu | Arg | Gln | Ala | Ile | Leu | Cys |
|     | 210 |     |     |     |     | 215 |     |     |     |     | 220 |     |     |     |     |
| Trp | Gly | Glu | Leu | Met | Thr | Leu | Ala | Thr | Trp | Val | Gly | Val | Asn | Leu | Glu |
| 225 |     |     |     |     | 230 |     |     |     |     | 235 |     |     |     |     | 240 |
| Asp | Pro | Ala | Ser | Arg | Asp | Leu | Val | Val | Ser | Tyr | Val | Asn | Thr | Asn | Met |
|     |     |     |     | 245 |     |     |     |     | 250 |     |     |     |     | 255 |     |
| Gly | Leu | Lys | Phe | Arg | Gln | Leu | Leu | Trp | Phe | His | Ile | Ser | Cys | Leu | Thr |
|     |     |     | 260 |     |     |     |     | 265 |     |     |     |     | 270 |     |     |
| Phe | Gly | Arg | Glu | Thr | Val | Ile | Glu | Tyr | Leu | Val | Ser | Phe | Gly | Val | Trp |
|     |     | 275 |     |     |     |     | 280 |     |     |     |     | 285 |     |     |     |
| Ile | Arg | Thr | Pro | Pro | Ala | Tyr | Arg | Pro | Pro | Asn | Ala | Pro | Ile | Leu | Ser |

|             |     |     |     |     | 290 |     |     |     |     | 295 |     |     |     |     | 300 |     |     |     |     |
|---|---|---|---|---|---|---|---|---|---|---|---|---|---|---|---|---|---|---|---|

```
            290                    295                    300
    Thr Leu Pro Glu Thr Thr Val Val Arg Arg Arg Gly Arg Ser Pro Arg
    305                 310                 315                 320

Arg Arg Thr Pro Ser Pro Arg Arg Arg Ser Gln Ser Pro Arg Arg
                    325             330                 335

Arg Arg Ser Gln Ser Arg Glu Ser Gln Cys
                    340             345
```

( 2 ) INFORMATION FOR SEQ ID NO:218:

( i ) SEQUENCE CHARACTERISTICS:
        ( A ) LENGTH: 1201 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:218:

```
CAAAATTGAA  AATATATAAT  TACAATATAA  AATGGGGCAG  AATCTTTCCA  CCAGCAATCC    60
TCTGGGATTC  TTTCCCGACC  ACCAGTTGGA  TCCAGCCTTC  AGAGCAAACA  ACGCAAATCC   120
AGATTGGGAC  TTCAATCCCA  ACAAGGACAC  CTGGCCAGAC  GCCAACAAGG  TAGGAGCTGG   180
AGCATTCGGG  CTGGGTTTCA  CCCCACCGCA  CGGAGGCCTT  TTGGGGTGGA  GCCCTCAGGC   240
TCAGGGCATA  CTACAAACTT  TGCCAGCAAA  TCCGCCTCCT  GCCTCCACCA  ATCGCCAGAC   300
AGGAAGGCAG  CCTACCCCGC  TGTCTCCACC  TTTGAGAAAC  ACTCATCCTC  AGGCCATGCA   360
GTGGAATTCC  ACAACCTTTC  ACCAAACTCT  GCAAGATCCC  AGAGTGAGAG  GCCTGTATTT   420
CCCTGCTGGT  GGCTCCAGTT  CAGGAGCAGT  AAACCCTGTT  CCGACTACTG  CCTCTCCCTT   480
ATCGTCAATC  TTCTCGAGGA  TTGGGGACCC  TGCGCTGAAC  ATGGAGAACA  TCACATCAGG   540
ATTCCTAGGA  CCCCTTCTCG  TGTTACAGGC  GGGGTTCTTC  TTGTTGACAA  GAATCCTCAC   600
AATACCGCAG  AGTCTAGACT  CGTGGTGGAC  TTCTCTCAAT  TTTCTAGGGG  GAACTACCGT   660
GTGTCTTGGC  CAAAATTCGC  AGTCCCCAAC  CTCCAATCAC  TCACCAACCT  CCTGTCCTCC   720
AACTTGTCCT  GGTTATCGCT  GGATGTGTCT  GCGGCGTTTT  ATCATCTTCC  TCTTCATCCT   780
GCTGCTATGC  CTCATCTTCT  TGTTGGTTCT  TCTGGACTAT  CAAGGTATGT  TGCCCGTTTG   840
TCCTCTAATT  CCAGGATCCT  CAACCACCAG  CACGGGACCA  TGCCGAACCT  GCATGACTAC   900
TGCTCAAGGA  ACCTCTATGT  ATCCCTCCTG  TTGCTGTACC  AAACCTTCGG  ACGGAAATTG   960
CACCTGTATT  CCCATCCCAT  CATCCTGGGC  TTTCGGAAAA  TTCCTATGGG  AGTGGGCCTC  1020
AGCCCGTTTC  TCCTGGCTCA  GTTTACTAGT  GCCATTTGTT  CAGTGGTTCG  TAGGGCTTTC  1080
CCCCACTGTT  TGGCTTTCAG  TTATATGGAT  GATGTGGTAT  TGGGGGCCAA  GTCTGTACAG  1140
CATCTTGAGT  CCCTTTTTAC  CGCTGTTACC  AATTTTCTTT  TGTCTTTGGG  TATACATTTA  1200
A                                                                      1201
```

( 2 ) INFORMATION FOR SEQ ID NO:219:

( i ) SEQUENCE CHARACTERISTICS:
        ( A ) LENGTH: 389 amino acids
        ( B ) TYPE: amino acid
        ( C ) STRANDEDNESS: single
        ( D ) TOPOLOGY: linear ( x i ) SEQUENCE DESCRIPTION: SEQ ID NO:219:

```
    Met Gly Gln Asn Leu Ser Thr Ser Asn Pro Leu Gly Phe Phe Pro Asp
    1               5                   10                  15

His Gln Leu Asp Pro Ala Phe Arg Ala Asn Asn Ala Asn Pro Asp Trp
                    20                  25                  30
```

| | | | | | | | | | | | | | | |
|---|---|---|---|---|---|---|---|---|---|---|---|---|---|---|
|Asp|Phe|Asn 35|Pro|Asn|Lys|Asp|Thr 40|Trp|Pro|Asp|Ala|Asn 45|Lys|Val|Gly|
|Ala|Gly 50|Ala|Phe|Gly|Leu|Phe 55|Thr|Pro|Pro|His 60|Gly|Gly|Leu|Leu| |
|Gly 65|Trp|Ser|Pro|Gln|Ala 70|Gln|Gly|Ile|Leu|Gln 75|Thr|Leu|Pro|Ala|Asn 80|
|Pro|Pro|Pro|Ala|Ser 85|Thr|Asn|Arg|Gln|Thr 90|Gly|Arg|Gln|Pro|Thr 95|Pro|
|Leu|Ser|Pro|Pro 100|Leu|Arg|Asn|Thr|His 105|Pro|Gln|Ala|Met|Gln 110|Trp|Asn|
|Ser|Thr|Thr 115|Phe|His|Gln|Thr|Leu 120|Gln|Asp|Pro|Arg|Val 125|Arg|Gly|Leu|
|Tyr|Phe 130|Pro|Ala|Gly|Gly|Ser 135|Ser|Ser|Gly|Ala|Val 140|Asn|Pro|Val|Pro|
|Thr 145|Thr|Ala|Ser|Pro|Leu 150|Ser|Ser|Ile|Phe|Ser 155|Arg|Ile|Gly|Asp|Pro 160|
|Ala|Leu|Asn|Met|Glu 165|Asn|Ile|Thr|Ser|Gly 170|Phe|Leu|Gly|Pro|Leu 175|Leu|
|Val|Leu|Gln|Ala 180|Gly|Phe|Phe|Leu|Leu 185|Thr|Arg|Ile|Leu|Thr 190|Ile|Pro|
|Gln|Ser|Leu 195|Asp|Ser|Trp|Trp|Thr 200|Ser|Leu|Asn|Phe|Leu 205|Gly|Gly|Thr|
|Thr|Val 210|Cys|Leu|Gly|Gln|Asn 215|Ser|Gln|Ser|Pro|Thr 220|Ser|Asn|His|Ser|
|Pro 225|Thr|Ser|Cys|Pro|Pro 230|Thr|Cys|Pro|Gly|Tyr 235|Arg|Trp|Met|Cys|Leu 240|
|Arg|Arg|Phe|Ile|Ile 245|Phe|Leu|Phe|Ile|Leu 250|Leu|Leu|Cys|Leu|Ile 255|Phe|
|Leu|Leu|Val|Leu 260|Leu|Asp|Tyr|Gln|Gly 265|Met|Leu|Pro|Val|Cys 270|Pro|Leu|
|Ile|Pro|Gly 275|Ser|Ser|Thr|Thr|Ser 280|Thr|Gly|Pro|Cys|Arg 285|Thr|Cys|Met|
|Thr|Thr 290|Ala|Gln|Gly|Thr|Ser 295|Met|Tyr|Pro|Ser|Cys 300|Cys|Cys|Thr|Lys|
|Pro 305|Ser|Asp|Gly|Asn|Cys 310|Thr|Cys|Ile|Pro|Ile 315|Pro|Ser|Ser|Trp|Ala 320|
|Phe|Gly|Lys|Phe|Leu 325|Trp|Glu|Trp|Ala|Ser 330|Ala|Arg|Phe|Ser|Trp 335|Leu|
|Ser|Leu|Leu|Val 340|Pro|Phe|Val|Gln|Trp 345|Phe|Val|Gly|Leu|Ser 350|Pro|Thr|
|Val|Trp|Leu 355|Ser|Val|Ile|Trp|Met 360|Met|Trp|Tyr|Trp|Gly 365|Pro|Ser|Leu|
|Tyr|Ser 370|Ile|Leu|Ser|Pro|Phe 375|Leu|Pro|Leu|Leu|Pro 380|Ile|Phe|Phe|Cys|
|Leu 385|Trp|Val|Tyr|Ile| | | | | | | | | | | |

( 2 ) INFORMATION FOR SEQ ID NO:220:

( i ) SEQUENCE CHARACTERISTICS:
        ( A ) LENGTH: 3209 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:220:

| | | | | | |
|---|---|---|---|---|---|
|TGAATGTTAA|ATGTTATACT|TTGGATGAAG|CTATAAATAT|GCATTGGAAA|AATAATCCAT| 60
|TTAAAGAAAG|GATTCAAATA|CTACAAAACC|TAAGCGATAA|TATGTTAACT|AAGCTTATTC| 120
|TTAACGACGC|TTTAAATATA|CACAAATAAA|CATAATTTTT|GTATAACCTA|ACAAATAACT| 180
|AAAACATAAA|AATAATAAAA|GGAAATGTAA|TATCGTAATT|ATTTTACTCA|GGAATGGGGT| 240
|TAAATATTTA|TATCACGTGT|ATATCTATAC|TGTTATCGTA|TACTCTTTAC|AATTACTATT| 300
|ACGAATATGC|AAGAGATAAT|AAGATTACGT|ATTAAGAGA|ATCTTGTCAT|GATAATTGGG| 360
|TACGACATAG|TGATAAATGC|TATTTCGCAT|CGTTACATAA|AGTCAGTTGG|AAAGATGGAT| 420
|TTGACAGATG|TAACTTAATA|GGTGCAAAAA|TGTTAAATAA|CAGCATTCTA|TCGGAAGATA| 480
|GGATACCAGT|TATATTATAC|AAAAATCACT|GGTTGGATAA|AACAGATTCT|GCAATATTCG| 540
|TAAAAGATGA|AGATTACTGC|GAATTTGTAA|ACTATGACAA|TAAAAAGCCA|TTTATCTCAA| 600
|CGACATCGTG|TAATTCTTCC|ATGTTTTATG|TATGTGTTTC|AGATATTATG|AGATTACTAT| 660
|AAACTTTTTG|TATACTTATA|TTCCGTAAAC|TATATTAATC|ATGAAGAAAA|TGAAAAGTA| 720
|TAGAAGCTGT|TCACGAGCGG|TTGTTGAAAA|CAACAAATT|ATACATTCAA|GATGGCTTAC| 780
|ATATACGTCT|GTGAGGCTAT|CATGGATAAT|GACAATGCAT|CTCTAAATAG|GTTTTTGGAC| 840
|AATGGATTCG|ACCCTAACAC|GGAATATGGT|ACTCTACAAT|CTCCTCTTGA|AATGGCTGTA| 900
|ATGTTCAAGA|ATACCGAGGC|TATAAAAATC|TTGATGAGGT|ATGGAGCTAA|ACCTGTAGTT| 960
|ACTGAATGCA|CAACTTCTTG|TCTGCATGAT|GCGGTGTTGA|GAGACGACTA|CAAAATAGTG|1020
|AAAGATCTGT|TGAAGAATAA|CTATGTAAAC|AATGTTCTTT|ACAGCGGAGG|CTTTACTCCT|1080
|TTGTGTTTGG|CAGCTTACCT|TAACAAAGTT|AATTTGGTTA|AACTTCTATT|GGCTCATTCG|1140
|GCGGATGTAG|ATATTTCAAA|CACGGATCGG|TTAACTCCTC|TACATATAGC|CGTATCAAAT|1200
|AAAAATTTAA|CAATGGTTAA|ACTTCTATTG|AACAAAGGTG|CTGATACTGA|CTTGCTGGAT|1260
|AACATGGGAC|GTACTCCTTT|AATGATCGCT|GTACAATCTG|GAAATATTGA|AATATGTAGC|1320
|ACACTACTTA|AAAAAAATAA|AATGTCCAGA|ACTGGGAAAA|ATTGATCTTG|CCAGCTGTAA|1380
|TTCATGGTAG|AAAAGAAGTG|CTCAGGCTAC|TTTTCAACAA|AGGAGCAGAT|GTAAACTACA|1440
|TCTTTGAAAG|AAATGGAAAA|TCATATACTG|TTTTGGAATT|GATTAAAGAA|AGTTACTCTG|1500
|AGACACAAAA|GAGGTAGCTG|AAGTGGTACT|CTCAAAATGC|AGAACGATGA|CTGCGAAGCA|1560
|AGAAGTAGAG|AAATAACACT|TTATGACTTT|CTTAGTTGTA|GAAAAGATAG|AGATATAATG|1620
|ATGGTCATAA|ATAACTCTGA|TATTGCAAGT|AAATGCAATA|ATAAGTTAGA|TTTATTTAAA|1680
|AGGATAGTTA|AAAATAGAAA|AAAAGAGTTA|ATTTGTAGGG|TTAAAATAAT|ACATAAGATC|1740
|TTAAAATTTA|TAAATACGCA|TAATAATAAA|AATAGATTAT|ACTTATTACC|TTCAGAGATA|1800
|AAATTTAAGA|TATTTACTTA|TTTAACTTAT|AAAGATCTAA|AATGCATAAT|TTCTAAATAA|1860
|TGAAAAAAAA|GTACATCATG|AGCAACGCGT|TAGTATATTT|TACAATGGAG|ATTAACGCTC|1920
|TATACCGTTC|TATGTTTATT|GATTCAGATG|ATGTTTTAGA|AAAGAAAGTT|ATTGAATATG|1980
|AAAACTTTAA|TGAAGATGAA|GATGACGACG|ATGATTATTG|TTGTAAATCT|GTTTTAGATG|2040
|AAGAAGATGA|CGCGCTAAAG|TATACTATGG|TTACAAAGTA|TAAGTCTATA|CTACTAATGG|2100
|CGACTTGTGC|AAGAAGGTAT|AGTATAGTGA|AAATGTTGTT|AGATTATGAT|TATGAAAAAC|2160
|CAAATAAATC|AGATCCATAT|CTAAAGGTAT|CTCCTTTGCA|CATAATTTCA|TCTATTCCTA|2220
|GTTTAGAATA|CTTTTCATTA|TATTTGTTTA|CAGCTGAAGA|CGAAAAAAAT|ATATCGATAA|2280
|TAGAAGATTA|TGTTAACTCT|GCTAATAAGA|TGAAATTGAA|TGAGTCTGTG|ATAATAGCTA|2340
|TAATCAGAGA|AGTTCTAAAA|GGAAATAAAA|ATCTAACTGA|TCAGGATATA|AAACATTGG|2400

| CTGATGAAAT | CAACAAGGAG | GAACTGAATA | TAGCTAAACT | ATTGTTAGAT | AGAGGGGCCA | 2460 |
| AAGTAAATTA | CAAGGATGTT | TACGGTTCTT | CAGCTCTCCA | TAGAGCTGCT | ATTGGTAGGA | 2520 |
| AACAGGATAT | GATAAAGCTG | TTAATCGATC | ATGGAGCTGA | TGTAAACTCT | TTAACTATTG | 2580 |
| CTAAAGATAA | TCTTATTAAA | AAAAAATAAT | ATCACGTTTA | GTAATATTAA | AATATATTAA | 2640 |
| TAACTCTATT | ACTAATAACT | CCAGTGGATA | TGAACATAAT | ACGAAGTTTA | TACATTCTCA | 2700 |
| TCAAATCTT | ATTGACATCA | AGTTAGATTG | TGAAATGAG | ATTATGAAAT | TAAGGAATAC | 2760 |
| AAAAATAGGA | TGTAAGAACT | TACTAGAATG | TTTTATCAAT | AATGATATGA | ATACAGTATC | 2820 |
| TAGGGCTATA | AACAATGAAA | CGATTAAAAA | TTATAAAAAT | CATTTCCCTA | TATATAATAC | 2880 |
| GCTCATAGAA | AAATTCATTT | CTGAAAGTAT | ACTAAGACAC | GAATTATTGG | ATGGAGTTAT | 2940 |
| AAATTCTTTT | CAAGGATTCA | ATAATAAATT | GCCTTACGAG | ATTCAGTACA | TTATACTGGA | 3000 |
| GAATCTTAAT | AACCATGAAC | TAAAAAAAAT | TTTAGATAAT | ATACATTAAA | AAGGTAAATA | 3060 |
| GATCATCTGT | TATTATAAGC | AAAGATGCTT | GTTGCCAATA | ATATACAACA | GGTATTTGTT | 3120 |
| TTTATTTTTA | ACTACATATT | TGATGTTCAT | TCTCTTTATA | TAGTATACAC | AGAAAATTCA | 3180 |
| TAATCCACTT | AGAATTTCTA | GTTATCTAG |  |  |  | 3209 |

( 2 ) INFORMATION FOR SEQ ID NO:221:

( i ) SEQUENCE CHARACTERISTICS:
        ( A ) LENGTH: 3661 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:221:

| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAGAAGTAC | CAGTAAAAAG | 120 |
| TGTGGCATAT | GCATAGAAGA | AATAAACAAA | AAACATATTT | CCGAACAGTA | TTTTGGAATT | 180 |
| CTCCCAAGTT | GTAAACATAT | TTTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAAA | TATTATATAA | TAGATATAAG | 360 |
| AAAATGATTT | TTACAAAAAT | AACCTATAAG | AACAATAAAA | ATATAATTAC | ATTTACGGAA | 420 |
| AATAGCTGGT | TTTAGTTTAC | CAACTTAGAG | TAATTATCAT | ATTGAATCTA | TATTGTTTTT | 480 |
| TAGTTATATA | AAAACATGAT | TAGCCCCCAA | TCGGATGAAA | ATATAAAAGA | TGTTGAGAAT | 540 |
| TTCGAATACA | ACAAAAAGAG | GAATCGTACG | TTGTCCATAT | CCAAACATAT | AAATAAAAAT | 600 |
| TCAAAGTAG | TATTATACTG | GATGTTTAGA | GATCAACGTG | TACAAGATAA | TTGGGCTTTA | 660 |
| ATTTACGCAC | AACGATTAGC | GTTAAAACTC | AAAATACCTC | TAAGAATATG | CTTTTGTGTC | 720 |
| GTGCCAAAAT | TTCACACTAC | TACTTCTAGA | CACTTTATGT | TTTTAATAT | CCGGTCTTAA | 780 |
| AGAAGTCGCG | GAAGAATGTA | AAAGACTATG | TATAGGGTTT | TCATTGATAT | ATGGCGTACC | 840 |
| AAAAGTAATA | ATTCCGTGTA | TAGTAAAAAA | ATACAGAGTC | GGAGTAATCA | TAACGGATTT | 900 |
| CTTTCCATTA | CGTGTTCCCG | AAAGATTAAT | GAAACAGACT | GTAATATCTC | TTCCAGATAA | 960 |
| CATACCTTTT | ATACAAGTAG | ACGCTCATAA | TATAGTACCT | TGTTGGGAAG | CTTCTGATAA | 1020 |
| AGAAGAATAC | GGTGCACGAA | CTTTAAGAAA | AAAGATATTT | GATAAATTAT | ATGAATATAT | 1080 |
| GACAGAATTT | CCTGTTGTTC | GTAAACATCC | ATACGGTCCA | TTTTCTATAT | CTATTGCAAA | 1140 |
| ACCCAAAAAT | ATATCATTAG | ACAAGACGGT | ATTACCCGTA | AAATGGGCAA | CGCCTGGAAC | 1200 |

```
AAAAGCTGGA  ATAATTGTTT  TAAAAGAATT  TATAAAAAAC  AGATTACCGT  CATACGACGC  1260
GGATCATAAC  AATCCTACGT  GTGACGCTTT  GAGTAACTTA  TCTCCGTGGC  TACATTTTGG  1320
TCATGTATCC  GCACAACGTG  TTGCCTTAGA  AGTATTAAAA  TGTATACGAG  AAAGCAAAAA  1380
AAACGTTGAA  ACGTTTATAG  ATGAAATAAT  TGTAAGAAGA  GAACTATCGG  ATAATTTTG   1440
TTACTATAAC  AAACATTATG  ATAGTATCCA  GTCTACTCAT  TCATGGGTTA  GAAAAACATT  1500
AGAAGATCAC  ATTAATGATC  CTAGAAAGTA  TATATATTCC  ATTAAACAAC  TCGAAAAAGC  1560
GGAAACTCAT  GATCCTCTAT  GGAACGCGTC  ACAAATGCAG  ATGGTGAGAG  AAGGAAAAAT  1620
GCATAGTTTT  TTACGAATGT  ATTGGGCTAA  GAAGATACTT  GAATGGACTA  GAACACCTGA  1680
AGACGCTTTG  AGTTATAGTA  TCTATTTGAA  CAACAAGTAC  GAACTAGACG  GCACGGATCC  1740
TAACGGATAC  GTAGGTTGTA  TGTGGTCTAT  TTGCGGATTA  CACGATAGAG  CGTGGAAAGC  1800
AAGACCGATA  TTTGGAAAGA  TAAGATATAT  GAATTATGAG  AGTTCTAAGA  AGAAATTTGA  1860
TGTTGCTGTA  TTTATACAGA  AATACAATTA  AGATAAATAA  TATACAGCAT  TGTAACCATC  1920
GTCATCCGTT  ATACGGGGAA  TAATATTACC  ATACAGTATT  ATTAAATTTT  CTTACGAAGA  1980
ATATAGATCG  GTATTTATCG  TTAGTTTATT  TTACATTTAT  TAATTAAACA  TGTCTACTAT  2040
TACCTGTTAT  GGAAATGACA  AATTTAGTTA  TATAATTTAT  GATAAAATTA  AGATAATAAT  2100
AATGAAATCA  AATAATTATG  TAAATGCTAC  TAGATTATGT  GAATTACGAG  GAAGAAAGTT  2160
TACGAACTGG  AAAAAATTAA  GTGAATCTAA  AATATTAGTC  GATAATGTAA  AAAAAATAAA  2220
TGATAAAACT  AACCAGTTAA  AAACGGATAT  GATTATATAC  GTTAAGGATA  TTGATCATAA  2280
AGGAAGAGAT  ACTTGCGGTT  ACTATGTACA  CCAAGATCTG  GTATCTTCTA  TATCAAATTG  2340
GATATCTCCG  TTATTCGCCG  TTAAGGTAAA  TAAAATTATT  AACTATTATA  TATGTAATGA  2400
ATATGATATA  CGACTTAGCG  AAATGGAATC  TGATATGACA  GAAGTAATAG  ATGTAGTTGA  2460
TAAATTAGTA  GGAGGATACA  ATGATGAAAT  AGCAGAAATA  ATATATTTGT  TTAATAAATT  2520
TATAGAAAAA  TATATTGCTA  ACATATCGTT  ATCAACTGAA  TTATCTAGTA  TATTAAATAA  2580
TTTTATAAAT  TTTATAAATT  TTAATAAAAA  ATACAATAAC  GACATAAAGA  TATTTAATCT  2640
TTAATTCTTG  ATCTGAAAAA  CACATCTATA  AAACTAGATA  AAAGTTATT   CGATAAAGAT  2700
AATAATGAAT  CGAACGATGA  AAAATTGGAA  ACAGAAGTTG  ATAAGCTAAT  TTTTTTCATC  2760
TAAATAGTAT  TATTTTATTG  AAGTACGAAG  TTTTACGTTA  GATAAATAAT  AAAGGTCGAT  2820
TTTTACTTTG  TTAAATATCA  AATATGTCAT  TATCTGATAA  AGATACAAAA  ACACACGGTG  2880
ATTATCAACC  ATCTAACGAA  CAGATATTAC  AAAAAATACG  TCGGACTATG  GAAAACGAAG  2940
CTGATAGCCT  CAATAGAAGA  AGCATTAAAG  AAATTGTTGT  AGATGTTATG  AAGAATTGGG  3000
ATCATCCTCA  ACGAAGAAAT  AGATAAAGTT  CTAAACTGGA  AAAATGATAC  ATTAAACGAT  3060
TTAGATCATC  TAAATACAGA  TGATAATATT  AAGGAAATCA  TACAATGTCT  GATTAGAGAA  3120
TTTGCGTTTA  AAAAGATCAA  TTCTATTATG  TATAGTTATG  CTATGGTAAA  ACTCAATTCA  3180
GATAACGAAC  ATTGAAAGAT  AAAATTAAGG  ATTATTTTAT  AGAAACTATT  CTTAAAGACA  3240
AACGTGGTTA  TAAACAAAAG  CCATTACCCG  GATTGGAAAC  TAAAATACTA  GATAGTATTA  3300
TAAGATTTTA  AAAACATAAA  ATTAATAGGT  TTTTATAGAT  TGACTTATTA  TATACAATAT  3360
GGATAAAAGA  TATATATCAA  CTAGAAAGTT  GAATGACGGA  TTCTTAATTT  TATATTATGA  3420
TTCAATAGAA  ATTATTGTCA  TGTCGTGTAA  TCATTTTATA  AATATATCAG  CGTTACTAGC  3480
TAAGAAAAAC  AAGGACTTTA  ATGAATGGCT  AAAGATAGAA  TCATTTAGAG  AAATAATAGA  3540
TACTTTAGAT  AAAATTAATT  ACGATCTAGG  ACAACGATAT  TGTGAAGAAC  TTACGGCGCA  3600
```

-continued

| | | | | | |
|---|---|---|---|---|---|
| TCACATTCCA | GTGTAATTAT | TGAGGTCAAA | GCTAGTAACT | TAATAGATGA | CAGGACAGCT | 3660 |
| G | | | | | | 3661 |

( 2 ) INFORMATION FOR SEQ ID NO:222:

( i ) SEQUENCE CHARACTERISTICS:
        ( A ) LENGTH: 2356 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:222:

| | | | | | | |
|---|---|---|---|---|---|---|
| TGTCTGGACT | AACTGATTTC | ATGGAACAAT | TTTCATCAAA | AATATCAGTT | ATACCTAGTT | 60 |
| CTACAAAGAC | AGAACTTTGA | TGTTATGTTT | GTGTTTGTAT | AGAAAATTTT | GGGATACTAA | 120 |
| CTGATATTTC | TGAATATTTC | TGAATATTTC | ATGTTACTTA | CTTACTCCTA | TCTTAGACGA | 180 |
| TAATAAAATT | CGAGGCGTAA | TATGTTTTTC | CAAATATTTG | AAATTCTTAT | ACGTATCGGC | 240 |
| GAAGAAAAGT | AACATACTAT | AAGTGTTATG | CAAGTAAGGT | ATGTTAATGA | TATTGGATTT | 300 |
| AATTTCATTG | ACAATACATA | TGTCCAAACA | TTCCACTCGT | AATTATGTAC | GGAACGACTT | 360 |
| TAGTTAAATA | CTTAGTCACA | AAAAACTTAT | GACTGTCATT | ATCTGAAAAC | GGTGATTCCC | 420 |
| ATAAATCAGA | ATACTTAATA | TTAAATAGAA | TGCTCGCTTC | TGGAGGTTTC | CGGATACTAG | 480 |
| ATAACATATC | TTCTGTATTA | TAGTTTAATT | CACTCATTTT | ATTACATAAT | ACAGTAACAT | 540 |
| CTCCCGAAAC | CAATGATGTT | ATATTAGATT | TACTTACATA | CTTCTTGTAA | CTATCATGAA | 600 |
| TACGTTTGTT | ATGATCTATA | AAGAAGATGG | ATGTATATTC | TGTTCTAGAT | AGCAAGTTCT | 660 |
| TTAAGTTATT | CTTTGTCTGT | ATTACTATCA | TCGTCTTCAT | CATCGTCTAA | AGGTAGCATT | 720 |
| ATATAATAAA | TCTAATAGTT | GATTTCTCGA | TCTATCAGTA | CTCGCTTTCA | ATAACATTTT | 780 |
| TACTATAAGC | ATAATAGAAG | GCGGTGATAT | CACTATATTT | TATCGGGTA | TTCTTTTAGT | 840 |
| AATTAGTTAG | TTCGTAGAAT | TTCGTAGAGA | TAAAAGCCAA | TTTGTTGTTG | ATACTGCTTA | 900 |
| CGTTACTCAT | GTTTCTTGTT | TCTGTTAATT | AACAGGTATA | CCCTTACAAT | AAGTTTAATT | 960 |
| AACTTTTAGG | TTTTTGTGAA | GAACTTTTAG | CTTCTAGTTC | CCTTATCCAT | AATTGGGTCT | 1020 |
| TAGATCTAGA | TTCTTCCCAT | GTATAAAGGG | GGACATACCC | AAAATCTTTA | AATGCTTTGT | 1080 |
| CCGTTTCTAT | AGTAAATGTC | GTACATTCCT | TAATCAAAGT | ATAAGGATTT | AGTAAAGGCG | 1140 |
| TGTAAGAACA | AATAGGTGAT | AGTAATACTC | TTAAACCTTT | ATTAATATTA | GCGATAAACC | 1200 |
| TTAAACACCA | TAAAGGAAGA | CATGTATTCC | GTAGATCCAT | CCCTAATTGA | TTAAAGAAAT | 1260 |
| GCATGTTAAA | ATCATGATAA | TGTTCAGTAG | GAGAGGTATC | GTAACAGTAA | TACACGTTAT | 1320 |
| TGCAGAGAGG | ACTATGTTGA | CCATTTTCTA | TCATATTTCT | TGCTGCTAAA | ATATGCATCC | 1380 |
| AAGCTACGTT | TCCTGCATAG | ACTCTGCTAT | GAAATACTTT | ATCATCCGCA | TATTTATACA | 1440 |
| TTTTCCTGCT | TTTATACGAT | CTTCTGTATA | AAGTTTCTAG | TACTGGACAG | TATTCTCCGA | 1500 |
| AAACACCTAA | TGGGCGTAGC | GACAAGTGCA | TAATCTAAGT | CCTATATTAG | ACATAGTACC | 1560 |
| GTTAGCTTCT | AGTATATATT | TCTCAGATAA | CTTGTTTACT | AAGAGGATAA | GCCTCTTTAT | 1620 |
| GGTTAGATTG | ATAATACGTA | TTCTCGTTTC | CTCTTATCAT | CGCATCTCCG | GAGAAAGTTA | 1680 |
| GGACCTACCG | CAGAATAACT | ACTCGTATAT | ACTAAGACTC | TTACGCCGTT | ATACAGACAA | 1740 |
| GAATCTACTA | CGTTCTTCGT | TCCGTTGATA | TTAACGTCCA | TTATAGAGTC | GTTAGTAAAC | 1800 |
| TTACCCGCTA | CATCATTTAT | CGAAGCAATA | TGAATGACCA | CATCTGCTGA | TCTAAGCGCT | 1860 |
| TCGTCCAAAG | TACTTTTATT | TCTAACATCT | CCAATCACGG | GAACTATCTT | TATTATATTA | 1920 |
| CATTTTTCTA | CAAGATCTAG | TAACCATTGG | TCGATTCTAA | TATCGTAAAC | ACGAACTTCT | 1980 |

| | | | | | |
|---|---|---|---|---|---|
| TTTTAAAGAG | GATTCGAACA | AGATAAGATT | ATTTATAATG | TGTCTACCTA | AAAATCCACA | 2040
| CCCTCCGGTT | ACCACGTATA | CTAGTGTACG | CATTTTGAGT | ATTAACTATA | TAAGACCAAA | 2100
| ATTATATTTT | CATTTCTGT | TATATTATAC | TATATAATAA | AAACAAATAA | ATATACGAAT | 2160
| ATTATAAGAA | ATTTAGAACA | CGTTATTAAA | GTATTGCCTT | TTTTATTAAC | GGCGTGTTCT | 2220
| TGTAATTGCC | GTTAGAATA | GTCTTTATTT | ACTTAGATA | ACTCTTCTAT | CATAACCGTC | 2280
| TCCTTATTCC | AATCTTCTTC | AGAAGTACAT | GAGTACTTAC | CGAAGTTTAT | CATCATAGAG | 2340
| ATTATATATG | AAGAAA | | | | | 2356

( 2 ) INFORMATION FOR SEQ ID NO:223:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:223:

ATGTCCTCTG GTTGCCGTTC T                                            21

( 2 ) INFORMATION FOR SEQ ID NO:224:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:224:

GACGGTGGAT CCGGTAGGCG G                                            21

( 2 ) INFORMATION FOR SEQ ID NO:225:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:225:

TTTTTCTAGA CTGCAGCCCG GGACATCATG CAGTGGTTAA AC                42

( 2 ) INFORMATION FOR SEQ ID NO:226:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:226:

GATTAAACCT AAATAATTGT                                              20

( 2 ) INFORMATION FOR SEQ ID NO:227:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:227:

TATAGCTGCA TAATAGAG                                                  18

( 2 ) INFORMATION FOR SEQ ID NO:228:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:228:

```
AATTAAGCTT GATATCACAA AAACTAAAAA GTCAGACTTC TTG                    43
```

( 2 ) INFORMATION FOR SEQ ID NO:229:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:229:

```
ATCCGTTAAG TTTGTATCGT AATGTCTACC TTCAAGCTTA TGATGGATGG ACGTTTGGTT    60
TTTGC                                                                65
```

( 2 ) INFORMATION FOR SEQ ID NO:230:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:230:

```
CATGGCAAAA ACCAAACGTC CATCCATCAT AAGCTTGAAG GTAGACATTA CGATACAAAC    60
TTAAGCGAT                                                            69
```

( 2 ) INFORMATION FOR SEQ ID NO:231:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:231:

```
TGTGTGATGA GAGATCAG                                                  18
```

( 2 ) INFORMATION FOR SEQ ID NO:232:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:232:

```
AACTCGAGTT AACAAAAATT ACGGAAGCTG GGTATATTTA ACAT                     44
```

( 2 ) INFORMATION FOR SEQ ID NO:233:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:233:

```
CTCTATGACC TCATCCAC                                                         18
```

(2) INFORMATION FOR SEQ ID NO:234:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:234:

```
ATGTCTACCT TCAAGCTTAT G                                                     21
```

(2) INFORMATION FOR SEQ ID NO:235:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:235:

```
TTTATATTGT AATTATA                                                          17
```

(2) INFORMATION FOR SEQ ID NO:236:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:236:

```
TTTGGATCCG TTAACTCAAA AAAATAAATG                                            30
```

(2) INFORMATION FOR SEQ ID NO:237:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:237:

```
AGGCCAAGCT TGAAGAGGCT C                                                     21
```

(2) INFORMATION FOR SEQ ID NO:238:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:238:

```
AAAGGATCCG TTAACACAAA AATTAAACCA TTTTTTCATT                                 40
```

(2) INFORMATION FOR SEQ ID NO:239:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:239:

```
TCGAGCTTAA GTCTTATTAA TATGCAAGGG CCGACATTGG CCGTGCTGGG CGCGCTGCTC           60
```

GCCGTTGCGG TGAGCTTGCC TACACCCGCG CCGC    94

( 2 ) INFORMATION FOR SEQ ID NO:240:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:240:

GGCGCGGGTG TAGGCAAGCT CACCGCAACG GCGAGCAGCG CGCCAGCAC GGCCAATGTC    60

GGCCCTTGCA TATTAATAAG ACTTAAGC    88

( 2 ) INFORMATION FOR SEQ ID NO:241:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:241:

GGGTGACTGC A    11

( 2 ) INFORMATION FOR SEQ ID NO:242:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:242:

GTCACCC    7

( 2 ) INFORMATION FOR SEQ ID NO:243:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:243:

ATCCGTTAAG TTTGTATCGT AATGGCCGCT CGCGGCGGTG CTGAACGCGC CGC    53

( 2 ) INFORMATION FOR SEQ ID NO:244:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:244:

GGCGCGTTCA GCACCGCCGC GAGCGGCCAT TACGATACAA ACTTAACGGA T    51

( 2 ) INFORMATION FOR SEQ ID NO:245:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:245:

CCATGGTTTA ATGCA 15

( 2 ) INFORMATION FOR SEQ ID NO:246:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:246:

TTAAACCATG GTGCA 15

( 2 ) INFORMATION FOR SEQ ID NO:247:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:247:

CATGGTTTAA GATCTC 16

( 2 ) INFORMATION FOR SEQ ID NO:248:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:248:

CATGGAGATC TTAAAC 16

( 2 ) INFORMATION FOR SEQ ID NO:249:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:249:

GATCCTGAGA TAAAGTGAAA ATATATATCA TTATATTACA AAGTACAATT ATTTAGGTTT 60

AAT 63

( 2 ) INFORMATION FOR SEQ ID NO:250:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:250:

CATGATTAAA CCTAAATAAT TGTACTTTGT AATATAATGA TATATATTTT CACTTTATCT 60

CAG 63

( 2 ) INFORMATION FOR SEQ ID NO:251:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:251:

TCGAGCCCGG GTAATCCAAC CCGGTCTTAC TCGCGCTCGC GCCCTCGGCT CCGCGCCCTA    60

GG    62

( 2 ) INFORMATION FOR SEQ ID NO:252:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:252:

GTACCCTAGG GCGCGGAGCC GAGGGCGCGA GCGCGAGTAA GACCGGGTTG GATTACCCGG    60

GC    62

( 2 ) INFORMATION FOR SEQ ID NO:253:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:253:

AGCTTGATAT CCGTTAAGTT TGTATCGTAA TGGGCAAACT AGAGAAAGCC CTGT    54

( 2 ) INFORMATION FOR SEQ ID NO:254:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:254:

GGGCTTTCTC TAGTTTGCCC ATTACGATAC AAACTTAACG GATATCA    47

( 2 ) INFORMATION FOR SEQ ID NO:255:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:255:

TCGAGGATCC    10

( 2 ) INFORMATION FOR SEQ ID NO:256:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:256:

CGATTACTAT GGGCAAACTA GAGAAAGCCC TGT    33

( 2 ) INFORMATION FOR SEQ ID NO:257:

( i ) SEQUENCE CHARACTERISTICS:
        ( A ) LENGTH: 28 base pairs
        ( B ) TYPE: nucleic acid
        ( C ) STRANDEDNESS: single ( D ) TOPOLOGY: linear ( x i ) SEQUENCE DESCRIPTION: SEQ ID NO:257:

GGGCTTTCTC TAGTTTGCCC ATAGTAAT 28

( 2 ) INFORMATION FOR SEQ ID NO:258:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:258:

CGATTACTAT GGAGTTGATT ACAAATGAAC TTTTATACAA AACATACAAA CAAAACCCG 60

CTGGAGTGGA GGAACCAGTA TATAACCAAG CAGGTGACCC T 101

( 2 ) INFORMATION FOR SEQ ID NO:259:

( i ) SEQUENCE CHARACTERISTICS:
        ( A ) LENGTH: 103 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:259:

CTAGAGGGTC ACCTGCTTGG TTATATACTG GTTCCTCCAC TCCAGCGGGT TTTTGTTTGT 60

ATGTTTTGTA TAAAAGTTCA TTTGTAATCA ACTCCATAGT AAT 103

( 2 ) INFORMATION FOR SEQ ID NO:260:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:260:

TTTCGCGATA TCCGTTAAGT TTGTATCGTA ATGCTCCAG TTTGCAAACC C 51

( 2 ) INFORMATION FOR SEQ ID NO:261:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:261:

TCTCCACCTT TACACCACAC T 21

( 2 ) INFORMATION FOR SEQ ID NO:262:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

GCCTCATCGC TGCTGGATAT CCGTTAAGTT TGTATCGTAA TGGAATCCAG GATCTG 56

( 2 ) INFORMATION FOR SEQ ID NO:263:

( i ) SEQUENCE CHARACTERISTICS:
        ( A ) LENGTH: 37 base pairs (B) TYPE: nucleic acid
(C) STRANDEDNESS: single
(D) TOPOLOGY: linear (xi) SEQUENCE DESCRIPTION: SEQ ID NO:263:

GACAGATTGT GATTTTTATA AGCATCGTAA GCTGTCA    37

(2) INFORMATION FOR SEQ ID NO:264:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:264:

GGTCGACGGA TCCT    14

(2) INFORMATION FOR SEQ ID NO:265:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:265:

GATCAGGATC CGTCGACCTG CA    22

(2) INFORMATION FOR SEQ ID NO:266:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:266:

TCCGGTACCG CGGCCGCAGA TATTTGTTAG CTTCTGC    37

(2) INFORMATION FOR SEQ ID NO:267:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:267:

TCGCTCGAGT AGGATACCTA CCTACTACCT ACG    33

(2) INFORMATION FOR SEQ ID NO:268:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:268:

TCGCTCGAGC TTTCTTGACA ATAACATAG    29

(2) INFORMATION FOR SEQ ID NO:269:

(i) SEQUENCE CHARACTERISTICS:
(A) LENGTH: 30 base pairs
(B) TYPE: nucleic acid
(C) STRANDEDNESS: single ( D ) TOPOLOGY: linear ( x i ) SEQUENCE DESCRIPTION: SEQ ID NO:269:

TAGGAGCTCT TTATACTACT GGGTTACAAC  30

( 2 ) INFORMATION FOR SEQ ID NO:270:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:270:

TCGGGATCCG GGTTAATTAA TTAGTTATTA GACAAGGTG  39

( 2 ) INFORMATION FOR SEQ ID NO:271:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:271:

TAGGAATTCC TCGAGTACGA TACAAACTTA AGCGGATATC G  41

( 2 ) INFORMATION FOR SEQ ID NO:272:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:272:

AATTCCTCGA GGGATCC  17

( 2 ) INFORMATION FOR SEQ ID NO:273:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:273:

CGGGATCCCT CGAGG  15

( 2 ) INFORMATION FOR SEQ ID NO:274:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

TCGGGTACCT CGCGATATCC GTTAAGTTTG TATCGTAATG AGTGATGGAG CAGT  54

( 2 ) INFORMATION FOR SEQ ID NO:275:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

TAGGAATTCC TCGAGTTAAT ATAATTTTCT AGGTGC    36

( 2 ) INFORMATION FOR SEQ ID NO:276:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

ATCAGATCTG AGACATTGGG TTTCTATCCA TG    32

( 2 ) INFORMATION FOR SEQ ID NO:277:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:277:

TTAGTCTACA TGGTTTACAA TCAAAGAAGA ATGTTCCTG    39

( 2 ) INFORMATION FOR SEQ ID NO:278:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:278:

ATCATCCTGC AGAGCAAAAG CAGG    24

( 2 ) INFORMATION FOR SEQ ID NO:279:

( i ) SEQUENCE CHARACTERISTICS:
        ( A ) LENGTH: 1759 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:279:

AGCAAAAGCA GGGGATACAT AATGAACACT CAAATTCTAA TATTAGCCAC TTCGGCATTC    60
TTCTATGTAC GTGCAGATAA AATCTGCCTA GGACATCATG CTGTGTCTAA TGGAACCAAA    120
GTAGACACCC TTACTGAAAA AGGAATAGAA GTTGTCAATG CAACAGAAAC AGTTGAACAA    180
ACAAACATCC CTAAGATCTG CTCAAAAGGA AAACAGACTA TTGACCTTGG TCAATGTGGA    240
TTACTAGGGA CCGTTATTGG TCCTCCCCAA TGTGACCAAT TTCTTGAATT CTCTGCTAAT    300
TTAATAGTTG AAAGAAGGGA AGGTAATGAC ATTTGTTATC CAGGCAAATT TGACAATGAA    360
GAAACATTGA GAAAAATACT CAGAAAATCC GGAGGAATTA AAAGGAGAA TATGGGATTC    420
ACATATACCG GAGTGAGAAC CAATGGAGAG ACTAGCGCAT GTAGAAGGTC AAGATCTTCC    480
TTTTATGCAG AGATGAAATG GCTTCTATCC AGCACAGACA ATGGGATATT TCCACAAATG    540
ACAAAGTCCT ACAAGAACAC TAAGAAGGTA CCAGCTCTGA TAATCTGGGG AATCCACCAC    600
TCAGGATCAA CTACTGAACA GACTAGATTA TATGGAAGTG GAATAAATC GATAACAGTT    660
TGGAGCTCCA AATACCAACA ATCTTTTGTC CCAAATCCTG GACCAAGGCC GCAAATCAAT    720
GGACAATCAG GAAGAATTGA CTTTGACTGG CTGATGGTAG ATCCCAATGA TACTGTGACT    780

```
TTCAGTTTTA ATGGGGCCTT TATAGCACCT GACCGCGCCA GTTTTCTAAG AGGTAAATCT      840

CTAGGAATTC AAAGTGACGC ACAGCTTGAC AATAATTGTG AAGGTGAATG CTATCATATT      900

GGAGGTACTA TAATTAGCAA CTTGCCCTTT CAAAACATTA ATAGTAGGGC AATCGGAAAA      960

TGCCCCAGAT ACGTGAAGCA GAAGAGCTTA ATGCTAGCAA CAGGAATGAA AAATGTTCCT     1020

GAAGCTCCTG CACATAAACA ACTAACTCAT CACATGCGCA AAAAAGAGG TTTATTTGGT     1080

GCAATAGCAG GATTCATTGA AAATGGGTGG GAAGGATTAA TAGACGGATG GTATGGATAT     1140

AAGCATCAGA ATGCACAAGG AGAAGGGACT GCTGCAGACT ACAAAAGTAC ACAATCTGCT     1200

ATCAACCAAA TAACCGGGAA ATTGAACAGA CTAATAGAAA AAACCAACCA GCAATTCGAA     1260

CTAATAGATA ATGAGTTCAA TGAAATAGAA AAACAAATTG GCAATGTTAT TAACTGGACT     1320

AGAGATTCTA TCATCGAAGT ATGGTCATAT AATGCAGAAT TCCTCGTAGC AGTGGAGAAT     1380

CAACACACTA TTGATTTAAC TGACTCAGAA ATGAACAAAC TATATGAAAA GGTAAGAAGA     1440

CAACTGAGAG AAAATGCTGA GGAAGATGGT AATGGCTGTT TTGAAATATT CCACCAATGT     1500

GACAATGATT GCATGGCCAG CATTAGAAAC AATACATATG ATCATAAAAA ATACAGAAAG     1560

GAGGCAATAC AAAACAGAAT TCAGATTGAT GCAGTAAAGT TGAGCAGCGG TTACAAAATA     1620

ATACTTTGGT TTAGCTTCGG GGCATCATGT TTCTTATTTC TTGCCATTGC AATGGTTCTT     1680

GCTTTCATAT GCATAAAAAA TGGAAACATG CGGTGCACTA TTTGTATATA AGTTTGAAAA     1740

AACACCCTTG TTTTCTACT                                                   1759
```

(2) INFORMATION FOR SEQ ID NO:280:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:280:

```
GTTGGTTTTT TCTATTAG                                                      18
```

(2) INFORMATION FOR SEQ ID NO:281:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:281:

```
CGATATCCGT TAAGTTTGTA TCGTAATGAA GACTCAAATT CTAATATTAG CC                52
```

(2) INFORMATION FOR SEQ ID NO:282:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:282:

```
ATCATCGGAT CCATAAAAAT TATATACAAA TAGTGCACCG                              40
```

(2) INFORMATION FOR SEQ ID NO:283:

(i) SEQUENCE CHARACTERISTICS:
        (A) LENGTH: 25 base pairs
        (B) TYPE: nucleic acid
        (C) STRANDEDNESS: single ( D ) TOPOLOGY: linear ( x i ) SEQUENCE DESCRIPTION: SEQ ID NO:283:

ATCATCAAGC TTAGTAGAAA CAAGG 25

( 2 ) INFORMATION FOR SEQ ID NO:284:

( i ) SEQUENCE CHARACTERISTICS:
( A ) LENGTH: 1762 base pairs
( B ) TYPE: nucleic acid
( C ) STRANDEDNESS: single
( D ) TOPOLOGY: linear ( x i ) SEQUENCE DESCRIPTION: SEQ ID NO:284:

| | | | | | |
|---|---|---|---|---|---|
| AGCAAAAGCA | GGGGATATTT | CTGTCAATCA | TGAAGACAAC | CATTATTTTG | ATACTACTGA | 60 |
| CCCATTGGGT | CTACAGTCAA | AACCCAACCA | GTGGCAACAA | CACAGCCACA | CTATGTCTGG | 120 |
| GACACCATGC | AGTAGCAAAT | GGAACATTGG | TAAAAACAAT | AACTGACGAC | CAAATTGAGG | 180 |
| TGACAAATGC | TACTGAATTA | GTTCAGAGCA | CTTCAATAGG | GAAAATATGC | AACAACCCAT | 240 |
| ATAGGGTTCT | AGATGGAAGA | AACTGCACAT | TAATAGATGC | AATGCTAGGA | GATCCCCACT | 300 |
| GTGATGTTTT | TCAGTATGAG | AATTGGGACC | TCTTCATAGA | AGAAGCAGC | GCTTTCAGCA | 360 |
| ATTGCTACCC | ATATGACATC | CCTGACTATG | CATCGCTCCG | GTCTATTGTG | GCATCTTCAG | 420 |
| GAACATTAGA | ATTCACAGCA | GAGGGATTCA | CATGGACAGG | TGTCACTCAA | AACGGAAGAA | 480 |
| GTGGCGCCTG | CAGAAGGGGA | TCAGCCGATA | GTTTCTTTAG | CCGACTGAAT | TGGCTAACAG | 540 |
| AATCTGGAAA | TTCTTACCCC | ACATTGAATG | TAACAATGCC | TAACAATAAC | AATTTCGATA | 600 |
| AACTATACAT | CTGGGGGATC | CATCACCCGA | GCACAAACAA | TGAGCAGACA | AAATTGTATG | 660 |
| TCCAAGAATT | AGGGCGAGTA | ACAGTCTCAA | CAAAAAGAAG | TCAACAAACA | ATAATCCCCA | 720 |
| ACATCGGATC | TAGACCGGGG | GTCAGGGGTC | AATCAGGCAG | GATAAGCATA | TATTGGACCA | 780 |
| TTGTGAAACC | TGGAGATATC | CTAATGATAA | ACAGTAATGG | CAACTTAGTT | GCACCGCGGG | 840 |
| GATATTTCAA | AATGCGAACA | GGAAAAAGCT | CTATAATGAG | ATCAGATGCA | CCCATAGACA | 900 |
| CTTGTGTGTC | CGAGTGTATT | ACACCAAATG | GAAGCATCCC | CAACGACAAA | CCATTTCAAA | 960 |
| ATGTGAACAA | AGTTACATAT | GGAAAATGCC | CCAAGTATAT | CAAGCAGAAT | ACTTTGAAGC | 1020 |
| TGGCCACTGG | GATGAGGAAT | GTACCAGAAA | AGCAAATCAG | AGGAATCTTT | GGAGCAATAG | 1080 |
| CGGGATTCAT | AGAAAATGGC | TGGGAGGGAA | TGGTTGATGG | GTGGTATGGA | TTCCGATATC | 1140 |
| AGAATTCGGA | AGGAACAGGA | CAAGCTGCAG | ATCTAAAGAG | CACTCAAGCA | GCCATCGACC | 1200 |
| AGATCAATGG | AAAATTGAAC | AGAGTGATTG | AGAGGACCAA | TGAGAAATTC | CATCAAATAG | 1260 |
| AGAAGGAATT | CTCAGAAGTA | GAAGGGAGAA | TCCAGGACTT | GGAGAAGTAT | GTAGAAGACA | 1320 |
| CCAAAATAGA | CCTATGGTCC | TACAATGCAG | AGTTACTGGT | GGCTCTAGAA | AATCAACATA | 1380 |
| CGATTGACTT | AACAGATGCA | GAGATGAATA | AATTATTCGA | GAAGACTAGG | CGCCAGTTAA | 1440 |
| GAGAAAACGC | GGAAGACATG | GGGGGTGGAT | GTTTCAAGAT | TTATCACAAA | TGTGATAATG | 1500 |
| CATGCATTGG | ATCAATAAGA | AATGGGACAT | ATGACCATTA | CATATACAGA | GATGAAGCAT | 1560 |
| TAAACAACCG | ATTTCAAATT | AAAGGTGTTG | AGTTGAAATC | AGGCTACAAA | GATTGGATAC | 1620 |
| TGTGGATTTC | ATTCGCCATA | TCATGCTTCT | TAATTTGCGT | TGTTCTATTG | GGTTTCATTA | 1680 |
| TGTGGGCTTG | CCAAAAAGGC | AACATCAGAT | GCAACATTTG | CATTTGAGTA | AACTGATAGT | 1740 |
| TAAAAACACC | CTTGTTTCTA | CT | | | | 1762 |

( 2 ) INFORMATION FOR SEQ ID NO:285:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:285:

ATCATCACTA GTATAAAAAT CAAATGCAAA TGTTGCATCT GATGTTGCC 49

( 2 ) INFORMATION FOR SEQ ID NO:286:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:286:

ATCATCGGAT CCATCACCCG AGCACAAACA ATGAGCAG 38

( 2 ) INFORMATION FOR SEQ ID NO:287:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:287:

TTGACTTAAC AGATGCAG 18

( 2 ) INFORMATION FOR SEQ ID NO:288:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:288:

ATGAAGACAA CCATTATTTT G 21

( 2 ) INFORMATION FOR SEQ ID NO:289:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:289:

TGTTGAGACT GTTACTCG 18

( 2 ) INFORMATION FOR SEQ ID NO:290:

( i ) SEQUENCE CHARACTERISTICS:
        ( A ) LENGTH: 1125 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:290:

ATGATGACAC GTCTACATTT TTGGTGGTGT GGAATCTTTG CGGTCCTGAA ATATCTGGTA 60

TGTACTTCAA GCCTTACGAC CACGCCAAAA ACAACTACGG TTTATGTGAA GGGATTTAAT 120

ATACCTCCAC TACGCTACAA TTATACTCAA GCCAGAATCG TGCCAAAAAT TCCCCAGGCG 180

ATGGATCCGA AGATAACAGC TGAAGTACGT TATGTAACAT CAATGGATTC ATGTGGGATG 240

| | | | | | | |
|---|---|---|---|---|---|---|
|GTGGCATTGA|TATCAGAGCC|GGATATAGAC|GCTACTATTC|GAACCATACA|ACTATCTCAA|300|
|AAAAAAACAT|ATAACGCGAC|TATAAGTTGG|TTTAAGGTAA|CCCAGGGTTG|TGAATACCCT|360|
|ATGTTTCTTA|TGGATATGAG|ACTTTGTGAT|CCTAAACGGG|AATTTGGAAT|ATGTGCTTTA|420|
|CGGTCGCCTT|CATATTGGTT|GGAACCTTTA|ACAAGTATA|TGTTCCTAAC|AGACGATGAA|480|
|CTGGGTTTGA|TTATGATGGC|CCCGGCCCAA|TTTAATCAAG|GACAATATCG|AAGAGTTATA|540|
|ACCATCGATG|GTTCCATGTT|TTATACAGAT|TTTATGGTAC|AACTATCTCC|AACGCCATGT|600|
|TGGTTCGCAA|AACCCGATAG|ATACGAAGAG|ATTCTACATG|AATGGTGTCG|AAATGTTAAA|660|
|ACTATTGGCC|TTGATGGAGC|TCGTGATTAC|CACTATTATT|GGGTACCCTA|TAACCCACAA|720|
|CCTCACCATA|AAGCCGTACT|CTTATATTGG|TATCGGACTC|ATGGCCGAGA|ACCCCCAGTA|780|
|AGATTCCAAG|AGGCCATTCG|ATATGATCGT|CCCGCCATAC|CGTCTGGGAG|TGAGGATTCG|840|
|AAACGGTCCA|ACGACTCTAG|AGGAGAATCG|AGTGGACCCA|ATTGGATAGA|CATTGAAAAT|900|
|TACACTCCTA|AAAATAATGT|GCCTATTATA|ATATCTGACG|ATGACGTTCC|TACAGCCCCT|960|
|CCCAAGGGCA|TGAATAATCA|GTCAGTAGTG|ATACCCGCAA|TCGTACTAAG|TTGTCTTATA|1020|
|ATAGCACTGA|TTCTAGGAGT|GATATATTAT|ATTTTGAGGG|TAAAGAGGTC|TCGATCAACT|1080|
|GCATATCAAC|AACTTCCTAT|AATACATACA|ACTCACCATC|CTTAA| |1125|

( 2 ) INFORMATION FOR SEQ ID NO:291:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:291:

TACGATACAA ACTTAACGG                                    19

( 2 ) INFORMATION FOR SEQ ID NO:292:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:292:

GGTTGGGTTT TGACTGTAGA CCCAATGGGT CAGTAGTATC AAAATAATGG TTGTCTTCAT     60

TACGATACAA ACTTAACGG                                    79

( 2 ) INFORMATION FOR SEQ ID NO:293:

( i ) SEQUENCE CHARACTERISTICS:
    ( A ) LENGTH: 67 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:293:

CAATTTCGAT AAACTATACA TCTGGGGCAT CCATCACCCG AGCACAAACA ATGAGCAGAC     60

AAAATTG                                                  67

( 2 ) INFORMATION FOR SEQ ID NO:294:

( i ) SEQUENCE CHARACTERISTICS:
    ( A ) LENGTH: 35 base pairs
    ( B ) TYPE: nucleic acid ( C ) STRANDEDNESS: single
( D ) TOPOLOGY: linear ( x i ) SEQUENCE DESCRIPTION: SEQ ID NO:294:

ATCATCGAAT TCTGAATGTT AAATGTTATA CTTTG     35

( 2 ) INFORMATION FOR SEQ ID NO:295:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:295:

GGGGGTACCT TTGAGAGTAC CACTTCAG     28

( 2 ) INFORMATION FOR SEQ ID NO:296:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:296:

ATCATCCTGC AGGTATTCTA AACTAGGAAT AGATG     35

( 2 ) INFORMATION FOR SEQ ID NO:297:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:297:

ATCATCCTGC AGGTATTCTA AACTAGGAAT AGATG     35

( 2 ) INFORMATION FOR SEQ ID NO:298:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:298:

ATGAAGACAA CCATTATTTT G     21

( 2 ) INFORMATION FOR SEQ ID NO:299:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:299:

TCAAATGCAA ATGTTGCATC T     21

( 2 ) INFORMATION FOR SEQ ID NO:300:

( i ) SEQUENCE CHARACTERISTICS:
( A ) LENGTH: 1762 base pairs
( B ) TYPE: nucleic acid
( C ) STRANDEDNESS: single
( D ) TOPOLOGY: linear ( x i ) SEQUENCE DESCRIPTION: SEQ ID NO:300:

| | | | | | |
|---|---|---|---|---|---|
| AGCAAAAGCA | GGGGATATTT | CTGTCAATCA | TGAAGACAAC | CATTATTTTG | ATACTACTGA | 60
| CCCATTGGGT | CTACAGTCAA | AACCCAACCA | GTGGCAACAA | CACAGCCACA | TTATGTCTGG | 120
| GACACCATGC | AGTAGCAAAT | GGAACATTGG | TAAAAACAAT | AACTGATGAC | CAAATTGAGG | 180
| TGACAAATGC | TACTGAATTA | GTTCAGAGCA | TTTCAATAGG | GAAAATATGC | AACAATCCAT | 240
| ATAGGGTTCT | AGATGGAAGA | AATTGCACAT | TAATAGATGC | AATGCTAGGA | GACCCCACT | 300
| GTGATGTTTT | TCNGTATGAG | AATTGGGACC | TCTTCATAGA | AAGAAGCAGC | GCTTTCAGCA | 360
| ATTGCTACCC | ATATGACATC | CCTGACTATG | CATCGCTCCG | GTCCATTGTA | GCATCCTCAG | 420
| GAACATTAGA | ATTCACAGCA | GAGGGATTCA | CATGGACAGG | TGTCACTCAA | AACGGAAGAA | 480
| GTGGAGCCTG | CAAAAGGGGA | TCAGCCGATA | GTTTCTTTAG | CCGACTGAAT | TGGCTAACAA | 540
| AATCTGGAAA | TTCTTACCCC | ATATTGAATG | TGACAATGCC | TAACAATAAA | AATTTCGATA | 600
| AACTATACAT | CTGGGGGATT | CATCACCCGA | GCTCAAACAA | AGAGCAGACA | AAATTGTATA | 660
| TCCAAGAATC | AGGACGAGTA | ACAGTCTCAA | CAGAAAGAAG | TCAACAAACA | GTAATCCCTA | 720
| ACATCGGATC | TAGACCGTGG | GTCAGGGGTC | AATCAGGCAG | GATAAGCATA | TACTGGACCA | 780
| TTGTAAAACC | TGGAGATATT | CTAACGATAA | ACAGTAATGG | CAACTTAGTT | GCACCGCGGG | 840
| GATATTTTAA | ATTGAGAACA | GGGAAAAGCT | CTGTAATGAG | ATCAGATGCA | CCCATAGACA | 900
| CTTGTGTGTC | TGAATGTATT | ACACCAAATG | GAAGCATCCC | CAACGACAAA | CCATTTCAAA | 960
| ATGTGAACAA | AGTTACATAT | GGAAAATGCC | CCAAGTATAT | CAGGCAAAAC | ACTTTAAAGC | 1020
| TGGCCACCGG | GATGAGGAAT | GTACCAGAAA | AGCAAATCAG | AGGAATCTTT | GGAGCAATAG | 1080
| CGGGATTCAT | AGAAAACGGC | TGGGAAGGAA | TGGTTGATGG | GTGGTATGGA | TTCCGATATC | 1140
| AAAACTCGGA | AGGAACAGGA | CAAGCTGCAG | ATCTAAAGAG | CACTCAAGCA | GCCATCGACC | 1200
| AGATCAATGG | AAAATTAAAC | AGAGTGATTG | AAAGGACCAA | TGAGAAATTC | CATCAAATAG | 1260
| AGAAGGAATT | CTCAGAAGTA | GAAGGGAGAA | TCCAGGATTT | GGAGAAGTAT | GTAGAAGACA | 1320
| CCAAAATAGA | CCTATGGTCC | TACAATGCAG | AATTGCTGGT | GGCTCTAGAA | AATCAACATA | 1380
| CAATTGACTT | AACAGATGCA | GAAATGAATA | AATTATTCGA | GAAGACTAGG | CGCCAGTTAA | 1440
| GAGAAAACGC | GGAAGACATG | GGAGGTGGAT | GTTTCAAGAT | TTACCACAAA | TGTGATAATG | 1500
| CATGCATTGG | ATCAATAAGA | AATGGGACAT | ATGACCATTA | CATATACAGA | GATGAAGCAT | 1560
| TAAACAACCG | ATTTCAAATC | AAAGGTGTTG | AGTTGAAATC | AGGCTACAAA | GATTGGATAC | 1620
| TGTGGATTTC | ATTCGCCATA | TCATGCTTCT | TAATTTGCGT | TGTTCTATTG | GGTTTCATTA | 1680
| TGTGGGCTTG | CCAAAAAGGC | AACATCAGAT | GCAACATTTG | CATTTGAGTA | AACTGATAGT | 1740
| TAAAAACACC | CTTGTTTCTA | CT | | | | 1762

( 2 ) INFORMATION FOR SEQ ID NO:301:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:301:

| | | | |
|---|---|---|---|
| GTTTAATCAT | GAAGACAACC | ATTATTTTGA | TAC | 33

( 2 ) INFORMATION FOR SEQ ID NO:302:

( i ) SEQUENCE CHARACTERISTICS:

(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:302:

AGCAATTGCT GAAAGCGC 18

(2) INFORMATION FOR SEQ ID NO:303:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:303:

ATCATCGGAT CCCGGGACAT CATGCAGTGG TTAAAC 36

(2) INFORMATION FOR SEQ ID NO:304:

(i) SEQUENCE CHARACTERISTICS:
(A) LENGTH: 43 base pairs
(B) TYPE: nucleic acid
(C) STRANDEDNESS: single
(D) TOPOLOGY: linear (xi) SEQUENCE DESCRIPTION: SEQ ID NO:304:

CAAAATAATG GTTGTCTTCA TGATTAAACC TAAATAATTG TAC 43

(2) INFORMATION FOR SEQ ID NO:305:

(i) SEQUENCE CHARACTERISTICS:
(A) LENGTH: 69 base pairs
(B) TYPE: nucleic acid
(C) STRANDEDNESS: single
(D) TOPOLOGY: linear (xi) SEQUENCE DESCRIPTION: SEQ ID NO:305:

CCGGTTAATT AATTAGTTAT TAGACAAGGT GAAAACGAAA CTATTTGTAG CTTAATTAAT 60

TAGGTCACC 69

(2) INFORMATION FOR SEQ ID NO:306:

(i) SEQUENCE CHARACTERISTICS:
(A) LENGTH: 70 base pairs
(B) TYPE: nucleic acid
(C) STRANDEDNESS: single
(D) TOPOLOGY: linear (xi) SEQUENCE DESCRIPTION: SEQ ID NO:306:

CCGGGGTCGA CCTAATTAAT TAAGCTACAA ATAGTTTCGT TTTCACCTTG TCTAATAACT 60

AATTAATTAA 70

(2) INFORMATION FOR SEQ ID NO:307:

(i) SEQUENCE CHARACTERISTICS:
(A) LENGTH: 46 base pairs
(B) TYPE: nucleic acid
(C) STRANDEDNESS: single
(D) TOPOLOGY: linear (xi) SEQUENCE DESCRIPTION: SEQ ID NO:307:

AATAAATCAC TTTTTATACT AATTCTTTAT TCTATACTTA AAAAGT 46

(2) INFORMATION FOR SEQ ID NO:308:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (xi) SEQUENCE DESCRIPTION: SEQ ID NO:308:

| | | | | | |
|---|---|---|---|---|---|
| CGCTATAGGC | AATTCAAACA | TAGCATGGAA | GGTCCAAACG | CACCCA | 46 |

(2) INFORMATION FOR SEQ ID NO:309:

(i) SEQUENCE CHARACTERISTICS:
    (A) LENGTH: 111 base pairs
    (B) TYPE: nucleic acid
    (C) STRANDEDNESS: single
    (D) TOPOLOGY: linear (xi) SEQUENCE DESCRIPTION: SEQ ID NO:309:

| | | | | | |
|---|---|---|---|---|---|
| ACCTCCCTCT | CTGAGGTAGT | CTATGCAGAT | CACACCGGAC | TCGTCCGAGA | CAATATGGCT | 60 |
| AAATTAAGAG | AAAGACTAAA | ACAGCGGCAG | CAACTGTTTG | ACTCCCAACA | G | 111 |

(2) INFORMATION FOR SEQ ID NO:310:

(i) SEQUENCE CHARACTERISTICS:
    (A) LENGTH: 2499 base pairs
    (B) TYPE: nucleic acid
    (C) STRANDEDNESS: single
    (D) TOPOLOGY: linear (xi) SEQUENCE DESCRIPTION: SEQ ID NO:310:

| | | | | | |
|---|---|---|---|---|---|
| CCCCAGCTCA | GACGATCTGT | CAAGATGGAA | GGTCCAACGC | ACCCAAAACC | CTCTAAAGAT | 60 |
| AAGACTTTCT | CGTGGGACCT | AATGATTCTG | GTGGGGGTCT | TACTAAGACT | GGACGTGGGA | 120 |
| ATGGCCAATC | CTAGTCCGCA | CCAAATATAT | AATGTAACTT | GGACAATAAC | CAACCTTGTA | 180 |
| ACTGGAACAA | AGGCTAATGC | CACCTCCATG | TTGGGAACCC | TGACAGACGC | CTTCCCTACC | 240 |
| ATGTATTTTG | ACTTATGTGA | TATAATAGGA | AATACATGGA | ACCCTTCAGA | TCAAGAACCA | 300 |
| TTCCCAGGGT | ATGGATGTGA | TCAGCCTATG | AGGAGGTGGC | GACAGAGAAA | CACACCCTTT | 360 |
| TATGTCTGTC | CAGGACATGC | CAACCGGAAG | CAATGTGGGG | GGCCACAGGA | TGGGTTCTGC | 420 |
| GCTGTATGGG | GTTGCGAGAC | CACCGGGGAA | ACCTATTGGA | GACCCACCTC | CTCATGGGAC | 480 |
| TACATCACAG | TAAAAAAGG | GGTTACTCAG | GGAATATATC | AATGTAGTGG | AGGTGGTTGG | 540 |
| TGTGGGCCCT | GTTACGATAA | AGCTGTTCAC | TCCTCGACAA | CGGGAGCTAG | TGAAGGGGGC | 600 |
| CGGTGCAACC | CCTTGATCTT | GCAATTTACC | CAAAAGGGAA | GACAAACATC | TTGGGATGGA | 660 |
| CCTAAGTCAT | GGGGGCTACG | ACTATACCGT | TCAGGATATG | ACCCTATAGC | CCTGTTCTCG | 720 |
| GTATCCCGGC | AAGTAATGAC | CATTACGCCG | CCTCAGGCCA | TGGGACCAAA | TCTAGTCCTG | 780 |
| CCTGATCAAA | AACCCCCATC | CAGGCAATCT | CAAATAGAGT | CCCGAGTAAC | ACCTCACCAT | 840 |
| TCCCAAGGCA | ACGGAGGCAC | CCCAGGTGTA | ACTCTTGTTA | ATGCCTCCAT | TGCCCCTCTA | 900 |
| CGTACCCCTG | TCACCCCCGC | AAGTCCCAAA | CGTATAGGGA | CCGGAAATAG | GTTAATAAAT | 960 |
| TTAGTGCAAG | GGACATACCT | AGCCTTAAAT | GCCACCGACC | CAACAAAAAC | TAAAGACTGT | 1020 |
| TGGCTCTGCC | TGGTTTCTCG | ACCACCTTAT | TACGAAGGGA | TTGCAATCTT | AGGTAACTAC | 1080 |
| AGCAACCAAA | CAAACCCCTC | CCCATCCTGC | CTATCTACTC | CGCAACATAA | GCTAACTATA | 1140 |
| TCTGAGGTGT | CAGGGCAAGG | ACTGTGCATA | GGGACTGTTC | CTAAGACCCA | CCAGGCTTTG | 1200 |
| TGCAATAAGA | CACAACAGGG | ACATACAGGG | GCTCACTATC | TAGCCGCCCC | CAATGGCACC | 1260 |
| TATTGGGCCT | GTAACACTGG | ACTCACCCCA | TGCATTTCCA | TGGCAGTGCT | CAATTGGACC | 1320 |

```
TCTGATTTTT  GTGTCTTAAT  CGAATTATGG  CCCAGAGTGA  CCTACCATCA  ACCCGAATAC   1380

ATTTACACAC  ATTTCGACAA  AGCTGTCAGG  TTCCGAAGAG  AACCAATATC  ACTAACCGTT   1440

GCCCTTATAA  TGGGAGGACT  CACTGTAGGG  GGCATAGCCG  CGGGGGTCGG  AACAGGGACT   1500

AAAGCCCTCC  TTGAAACAGC  CCAGTTCAGA  CAACTACAAA  TGGCTATGCA  CGCAGACATC   1560

CAGGCCCTAG  AAGAGTCAAT  TAGTGCCTTA  GAAAATCCC   TGACCTCCCT  CTCCGAGGTA   1620

GTCTTACAAA  ATAGACGGGG  CCTAGATATT  CTGTTCTTAC  AAAAGGGAGG  GCTCTGTGCC   1680

GCCTTAAAGG  AAGAATGCTG  CTTCTATGCA  GATCACACCG  GACTCGTCAG  AGACAATATG   1740

GCTAAATTAA  GAGAAAGACT  GAAACAGCGA  CAACAACTGT  TTGACTCCCA  ACAGGGATGG   1800

TTTGAAGGAT  GGTTCAACAA  GTCCCCCTGG  TTTACAACCC  TAATTTCCTC  CATTATAGGC   1860

CCCTTACTAA  TCCTACTCCT  AATTCTCCTC  TTCGGCCCAT  GCATCCTTAA  CCGATTAGTG   1920

CAATTCGTAA  AAGACAGAAT  ATCTGTGGTA  CAAGCCTTAA  TTTTAACCCA  ACAGTACCAA   1980

CAGATACAGC  AATATGATCC  GGACCGACCA  TGATTTCCAA  TTAAATGTAT  GATTCCATTT   2040

AGTCCCTAGA  AGAAGGGGGG  AATGAAAGAC  CCCCCCACC   CCAAAACTTA  GCCAGCTACT   2100

GCAGTGATGC  CATTTCACAA  GACATGGAAA  ATTACCCAAG  CATGTTCCCG  TGAGATATAA   2160

GGAAGTTAGA  AGCTAAAACA  GGATATCTGT  GGTTAGACAC  CTAGGCCCCG  GCTTGAGGCC   2220

AAGAACAGTT  AAGCCCCGGA  TATAGCTGAA  ACAGCAGAAG  TTTCAAGGCC  ACTGCCAGCA   2280

GTCTCCAGGC  TCCCCAGTTG  ACCAGAGTTC  GACCTTCCGC  CTCATTTAAA  CTAACCAATC   2340

CCCACGCCTC  TCGCTTCTGT  ACGCGCGCTT  TTTGCTATAA  AACGAGCCAT  CAGCCCACCA   2400

CCAGGCGCGC  AAGTCTTTGC  AGAGACTTGA  CGCCCCGGGC  CCACGCCTCT  CGCTTCTGTA   2460

CGCGCGCTTT  TTGCTATAAA  ACGAGCCATC  AGCCCACCA                            2499
```

( 2 ) INFORMATION FOR SEQ ID NO:311:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:311:

```
GGGTGCGTTG  GACCTTCCAT  TACGATAGAA  ACTTAACGG                            39
```

( 2 ) INFORMATION FOR SEQ ID NO:312:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:312:

```
CCGTTAAGTT  TGTATCGTAA  TGGAAGGTCC  AAGCG                                35
```

( 2 ) INFORMATION FOR SEQ ID NO:313:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:313:

```
GGGTAAATTG  CAAGATCAAG  G                                                21
```

( 2 ) INFORMATION FOR SEQ ID NO:314:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:314:

```
CCCCATGCAT   TTCCATGGCA   GTGCTCAATT   GGACCTCTGA   TTTCTGTGTC   TTAATAG                 57
```

( 2 ) INFORMATION FOR SEQ ID NO:315:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:315:

```
ATCATCTCTA   GAATAAAAAT   CATGGTCGGT   CCGGATC                                           37
```

( 2 ) INFORMATION FOR SEQ ID NO:316:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:316:

```
CCGTTAAGTT   TGTATCGTAA   TGGAAAGTCC   AACGCAC                                           37
```

( 2 ) INFORMATION FOR SEQ ID NO:317:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:317:

```
CCATAATTCG   ATTAAGACAC   AGAATTCAGA   GGTCCAATTG   AGCACC                               46
```

( 2 ) INFORMATION FOR SEQ ID NO:318:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:318:

```
CAAGATGGGT   TTTGTGCG                                                                    18
```

( 2 ) INFORMATION FOR SEQ ID NO:319:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:319:

```
GGTGCTCAAT   TGGACCTCTG   AATTCTGTGT   CTTAATCGAA   TTATGG                               46
```

( 2 ) INFORMATION FOR SEQ ID NO:320:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:320:

ATCATCAAGC TTTCATGGTC GGTCCGG 27

( 2 ) INFORMATION FOR SEQ ID NO:321:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:321:

TAAGACTACT TCAGAAAG 18

( 2 ) INFORMATION FOR SEQ ID NO:322:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( x i ) SEQUENCE DESCRIPTION: SEQ ID NO:322:

GTCCTGTTGG GTATGAGTCT GCTGGAAATA AGAGGGTGGG GAAGAGAACA CTGGCCTATA 60

CCCCTGCCTT AACTTAG 77

( 2 ) INFORMATION FOR SEQ ID NO:323:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:323:

GCGGATCACA CCGGACTC 18

( 2 ) INFORMATION FOR SEQ ID NO:324:

( i ) SEQUENCE CHARACTERISTICS:
( A ) LENGTH: 3674 base pairs
( B ) TYPE: nucleic acid
( C ) STRANDEDNESS: single
( D ) TOPOLOGY: linear ( x i ) SEQUENCE DESCRIPTION: SEQ ID NO:324:

CTGCAGTGGT GTCATTTCAC AAGGCATGGA AAATTACTCA AGTATGTTCC CATGAGATAT 60

AAGGAAGTTA GAGGCTAAAA CAGGATATCT GTGGTTAAGC ACCTGGGCCC GGCTTGAGG 120

CCAAGAACAG TTAAACCCCG GATATAGCTG AAACAGCAGA AGTTTCAAGG CCGCTGCCAG 180

CAGTCTCCAG GCTCCCCAGT TGACCAGAGT TCGACCTTCC GCCTCATTTA AACTAACCAA 240

TGCCCACGCC TCTCGCTTCT GTGCGCGCGC TTTCTGCTAT AAAACGAGCC ATCAGCCCCC 300

AACGGCGCGC AAGTCTTTGC TGAGACTTGA CCGCCCCGGG TACCCGTGTA CGAATAAACC 360

TCTTGCTGAT TGCATCTGAC TGTGGTCTCG GTGTTCCGTG GGCACGGGGT CTCATCGCCG 420

AGGAAGACCT AGTTCGGGGG TCTTTCATTT AGGGGCTCGT CCGGGATAGA GACCCCCAAC 480

CCCCGGGACC ACCGACCCAC CACCATCAGG AGGTAAGCTG GCCGGCGACC ATACCTGTTG 540

| | | | | | |
|---|---|---|---|---|---|
| TCCTTGTATA | AGTGTCTCTG | TCAATTGATC | TGATTTTGGC | GGTGGGATCG | AAGGAGCTGA | 600 |
| CGAGCTCGTA | CTTCGCCCCC | GCAACCCTGG | AAGACATTCC | ACGGGTGTCT | GATGTCTGGA | 660 |
| GCCTCTAGTG | GGACAGCCAT | TGGGGCTCAT | CTGTTTGGGG | TCTCACCTGA | ATACAGGGTG | 720 |
| TTGATCGGAG | ACGAGGGAGC | CGGACCCTCA | AGGTCTCTTT | CTGAGGTTTC | ATTTTCGGTT | 780 |
| TGGTACCAAA | GACGCGCGGC | ACGTCTTGTC | ATTTTTGTC | TGGTTGCGTC | TTTTCTTGTC | 840 |
| CCTTGTCTAA | CCTTTTTAAT | TGCAGAAACC | GTCATGGGCC | AAACTATAAC | TACCCCCTTA | 900 |
| AGCCTCACCC | TTGATCACTG | GTCTGAAGTC | CGGGCACGAG | CCCATAATCA | AGGTGTCGAG | 960 |
| GTCCGGAAAA | AGAAATGGAT | TACCTTATGT | GAGGCCGAAT | GGGTGATGAT | GAATGTGGGC | 1020 |
| TGGCCCCGAG | AAGGAACTTT | TTCTCTTGAT | AGCATTTCCC | AGGTTGAAAA | GAAGATCTTC | 1080 |
| GCCCCGGGAC | CATATGGACA | CCCCGACCAA | GTTCCTTACA | TTACTACATG | GAGATCCTTA | 1140 |
| GCCACAGACC | CCCCTTCGTG | GGTTCGTCCG | TTCCTACCCC | CTCCCAAACC | TCCCACACCC | 1200 |
| CTCCCTCAAC | CTCTTTCGCC | GCAGCCCTCC | GCCCTCTTA | CCTCTTCCCT | CTACCCCGTT | 1260 |
| CTCCCCAAGC | CAGACCCCCC | CAAACCGCCT | GTGTTACCGC | CTGATCCTTC | TTCCCCTTTA | 1320 |
| ATTGATCTCT | TAACAGAAGA | GCCACCTCCC | TATCCGGGGG | GTCACGGGCC | ACCGCCATCA | 1380 |
| GGTCCTAGGA | CCCCAACCGC | TTCCCCGATT | GCAAGCCGGC | TAAGGGAACG | ACGAGAAAAC | 1440 |
| CCTGCTGAAG | AATCGCAAGC | CCTCCCCTTG | AGGGAAGGCC | CCAACAACCG | ACCCCAGTAT | 1500 |
| TGGCCATTCT | CAGCTTCAGA | CTTGTATAAC | TGGAAGTCGC | ATAACCCCCC | TTTCTCCCAA | 1560 |
| GATCCAGTGG | CCCTAACTAA | CCTAATTGAG | TCCATTTTAG | TGACGCATCA | ACCAACCTGG | 1620 |
| GACGACTGCC | AGCAGCTCTT | GCAGGCACTC | CTGACAGGCG | AAGAAAGGCA | AAGGGTCCTT | 1680 |
| CTTGAGGCCC | GAAAGCAGGT | TCCAGGCGAG | GACGGACGGC | CAACCCAACT | ACCCAATGTC | 1740 |
| ATTGACGAGA | CTTTCCCCTT | GACCCGTCCC | AACTGGGATT | TTGCTACGCC | GGCAGGTAGG | 1800 |
| GAGCACCTAC | GCCTTTATCG | CCAGTTGCTA | TTAGCGGGTC | TCCGCGGGGC | TGCAAGACGC | 1860 |
| CCCACTAATT | TGGCACAGGT | AAAGCAGGTT | GTACAAGGGA | AAGAGGAAAC | GCCAGCAGCA | 1920 |
| TTTTTAGAAA | GATTAAAAGA | GGCTTATAGA | ATGTACACTC | CCTATGACCC | TGAGGACCCA | 1980 |
| GGGCAAGCGG | CTAGTGTTAT | CCTATCCTTT | ATATACCAGT | CTAGCCCAGA | TATAAGAAAT | 2040 |
| AAGTTACAAA | GGCTAGAAGG | CCTACAAGGG | TTCACCCTAT | CTGATCTGCT | AAAAGAGGCA | 2100 |
| GAAAAGATAT | ACAACAAAAG | GGAGACCCCA | GAGGAAGGG | AAGAAAGATT | ATGGCAGCGA | 2160 |
| CAGGAAGAAA | GAGATAAAAA | GCGCCACAAG | GAGATGACTA | AAGTTCTGGC | CACAGTAGTT | 2220 |
| GCTCAGAATA | GAGATAAGGA | TAGAGAAGAA | AGTAAACTGG | GGGATCAAAG | GAAAATACCT | 2280 |
| CTGGGGAAAG | ACCAGTGTGC | CTATTGCAAG | GAAAAGGGGC | ATTGGGTTCG | CGATTGCCCC | 2340 |
| AAACGACCCA | GGAAGAAACC | CGCCAACTCC | ACTCTCCTCA | ACTTAGGAGA | TTAGGAGAGT | 2400 |
| CAGGGCCAGG | ACCCCCCCCC | CTGAGCCCAG | GATAACCTTA | AAAATAGGGG | GGCAACCGGT | 2460 |
| GACTTTTCTG | GTGGACACGG | GAGCCCAGCA | CTCAGTACTG | ACTCGACCAG | ATGGACCTCT | 2520 |
| CAGTGACCGC | ACAGCCCTGG | TGCAAGGAGC | ACGGGAAGC | AAAAACTACC | GGTGGACCAC | 2580 |
| CGACAGGAGG | GTACAACTGG | CAACCGGTAA | GGTGACTCAT | TCTTTTTAT | ATGTACCTGA | 2640 |
| ATGTCCCTAC | CCGTTATTAG | GGAGAGACCT | ATTAACTAAA | CTTAAGGCCC | AAATCCATTT | 2700 |
| TACCGGAGAA | GGGGCTAATG | TTGTTGGGCC | CAGGGGTTTA | CCCCTACAAG | TCCTTACTTT | 2760 |
| ACAATTAGAA | GAGGAGTATC | GGCTATTTGA | GCCAGAAAGT | ACACAAAAAC | AGGAGATGGA | 2820 |
| CACTTGGCTT | AAAAACTTTC | CCCAGGCGTG | GGCAGAAACA | GGAGGTATGG | GAATGGCTCA | 2880 |
| TTGTCAAGCC | CCCGTTCTCA | TTCAACTTAA | GGCTACTGCC | ACTCCAATCT | CCATCCGACA | 2940 |

```
GTATCCTATG  CCCCATGAAG  CGTACCAGGG  AATTAAGCCT  CATATAAGAA  GAATGCTAGA      3000

TCAAGGCATC  CTCAAGCCCT  GCCAGTCCCC  ATGGAATACA  CCCTTATTAC  CTGTTAAGAA      3060

GCCAGGGACC  GAGGATTACA  GACCAGTGCA  GGACTTAAGA  GAAGTAAACA  AAAGAGTAGA      3120

AGACATCCAT  CCTACTGTGC  CAAATCCATA  TAACCTCCTT  AGCACCCTCC  CGCCGTCTCA      3180

CCCTTGGTAC  ACTGTCCTAG  ATTTAAGGA   CGCTTTTTC   TGCCTGCGAC  TACACTCTGA      3240

GAGTCAGTTA  CTTTTTGCAT  TTGAATGGAG  AGATCCAGAA  ATAGGACTGT  CAGGGCAACT      3300

AACCTGGACA  CGCCTTCCTC  AGGGGTTCAA  GAATAGCCCC  ACCCTATTTG  ATGAGGCCCT      3360

GCACTCAGAC  CTGGCCGATT  TCAGGGTAAG  GTACCCGGCT  CTAGTCCTCC  TACAATATGT      3420

AGATGACCTC  TTGCTGGCTG  CGGCAACCAG  GACTGAATGC  CTGGAAGGGA  CTAAGGCACT      3480

CCTTGAGACT  TTGGGCAATA  AGGGTACCG   AGCCTCTGGA  AAGAAGGCCC  AAATTTGCCT      3540

GCAAGAAGTC  ACATACCTGG  GGTACTCTTT  AAAAGATGGC  CAAAGGTGGC  TTACCAAAGC      3600

TCGGAAAGAA  GCCATCCTAT  CCATCCCTGT  GCCTAAAAAC  CCACGACAAG  TGAGAGAGTT      3660

CCTTGGAACT  GCAG                                                            3674
```

( 2 ) INFORMATION FOR SEQ ID NO:325:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:325:

```
GATCTCCATG  TAGTAATG                                                          18
```

( 2 ) INFORMATION FOR SEQ ID NO:326:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:326:

```
CGATATCCGT  TAAGTTTGTA  TCGTAATGTC  TGGAGCCTCT  AGTG                         44
```

( 2 ) INFORMATION FOR SEQ ID NO:327:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:327:

```
CTAGCTAAGT  TAAGGCAGGG  GTATAGGCCA  GTGTTCTCTT  CCCCACCCTC  TTATTTCCAG       60

CAGACTCATA  CCCAACAG                                                         78
```

( 2 ) INFORMATION FOR SEQ ID NO:328:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:328:

```
AATTCAACCG  C                                                                11
```

( 2 ) INFORMATION FOR SEQ ID NO:329:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:329:

GATCTTTTGT TAACAAAAAC TAATCAGCTA TCGCGAATCG ATTCCCGGGG GATCCGGTAC     60

CC     62

( 2 ) INFORMATION FOR SEQ ID NO:330:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:330:

TCGAGGGTAC CGGATCCCCC GGGAATCGAT TCGCGATAGC TGATTAGTTT TTGTTAACAA     60

AA     62

( 2 ) INFORMATION FOR SEQ ID NO:331:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:331:

ATGATGACAC GTCTACATTT T     21

( 2 ) INFORMATION FOR SEQ ID NO:332:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:332:

TGTTACATAA CGTACTTCAG C     21

( 2 ) INFORMATION FOR SEQ ID NO:333:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:333:

AATTTTCTCG AGAAGCTTGT TAACAAAAAT CATTAAGGAT GGTAGATTGC ATG     53

( 2 ) INFORMATION FOR SEQ ID NO:334:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:334:

GAGGATTCGA AACGGTCC                                                                                      18

( 2 ) INFORMATION FOR SEQ ID NO:335:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:335:

ATGGGGATAT GGAAGTGG                                                                                      18

( 2 ) INFORMATION FOR SEQ ID NO:336:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

CATGTTCCTT TCAAGTCAAC                                                                                    20

( 2 ) INFORMATION FOR SEQ ID NO:337:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

ATCATGAGTC CAAGAGACAA AGGTTTCTTA TGCCCTGAG                                                               39

( 2 ) INFORMATION FOR SEQ ID NO:338:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

ATCATCGAAT TCATAAAAAC TATGATTTTT TATGCTTCCT TACGGGAC                                                     48

( 2 ) INFORMATION FOR SEQ ID NO:339:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

AGAAAAATCA GTTAGCTAAG ATCTCCCGGG CTCGAGGGTA CCGGATCCTG ATTAGTTAAT                                        60

TTTTGT                                                                                                   66

( 2 ) INFORMATION FOR SEQ ID NO:340:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

```
GATCACAAAA  ATTAACTAAT  CAGGATCCGG  TACCCTCGAG  CCCGGGAGAT  CTTAGCTAAC        60

TGATTTTTCT                                                                    70
```

( 2 ) INFORMATION FOR SEQ ID NO:341:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:341:

```
CAGTTGGTAC  CTATGTTAAG  GAGGACGA                                              28
```

( 2 ) INFORMATION FOR SEQ ID NO:342:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:342:

```
TATCTGAATT  CCTGCAGCCC  GGGTTTTTAT  AGCTAATTAG  TCATATGATA  TTATCTCTAT        60
```

( 2 ) INFORMATION FOR SEQ ID NO:343:

( i ) SEQUENCE CHARACTERISTICS:
    ( A ) LENGTH: 68 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:343:

```
TCGATGAATT  CGATATCAAG  CTTATCGATT  TTTATGATTA  ACTAGTCAAG  TGATTTATT         60

CAATTACG                                                                      68
```

( 2 ) INFORMATION FOR SEQ ID NO:344:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:344:

```
TTATCGAGCT  CATTTACATT  TCTAAACTC                                             29
```

( 2 ) INFORMATION FOR SEQ ID NO:345:

( i ) SEQUENCE CHARACTERISTICS:
    ( A ) LENGTH: 5 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:345:

```
GGTTG                                                                          5
```

( 2 ) INFORMATION FOR SEQ ID NO:346:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:346:

CCCTCTGTAA TTCCTCCATA GTTGCCATTA CGATACAAAC TTAACGG    47

( 2 ) INFORMATION FOR SEQ ID NO:347:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:347:

CCGTTAAGTT TGTATCGTAA TGGCAACTAT GGAGG    35

( 2 ) INFORMATION FOR SEQ ID NO:348:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:348:

GGACACGTAA AGATGTTTTG G    21

( 2 ) INFORMATION FOR SEQ ID NO:349:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:349:

GTCCTGCAGG ATGGAAAAGA ATGCCCCAAG C    31

( 2 ) INFORMATION FOR SEQ ID NO:350:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:350:

GGGGGAGGCA AACTACCAAG G    21

( 2 ) INFORMATION FOR SEQ ID NO:351:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:351:

ATCATCTCTA GAATAAAAAT TAGAGTTTCA AAGGC    35

( 2 ) INFORMATION FOR SEQ ID NO:352:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:352:

CGCCAGCATG CAGAAGCAGC 20

( 2 ) INFORMATION FOR SEQ ID NO:353:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:353:

GATCCCCGGG A 11

( 2 ) INFORMATION FOR SEQ ID NO:354:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:354:

GATCTCCCGG G 11

( 2 ) INFORMATION FOR SEQ ID NO:355:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:355:

ATCATCGCGA TATCCGTTAA GTTTGTATCG TAATGAAAAA TCTGGATTGT TGGG 54

( 2 ) INFORMATION FOR SEQ ID NO:356:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:356:

GTAATAGTTA TGAAAACCC 19

( 2 ) INFORMATION FOR SEQ ID NO:357:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:357:

GGGTTTTCAT AACTATTAC 19

( 2 ) INFORMATION FOR SEQ ID NO:358:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:358:

GGATGGACAA ATGATTAATT TTTATCTCGA GCCCGGGATG AT 42

( 2 ) INFORMATION FOR SEQ ID NO:359:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:359:

```
GTACGTGACT AATTAGCTAT AAAAGGATC CGGTACCCTC GAGTCTAGAA TCGATCCCGG      60
GTTTTTATGA CTAGTTAATC AC                                             82
```

( 2 ) INFORMATION FOR SEQ ID NO:360:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

```
GGCCGTGATT AACTAGTCAT AAAAACCCGG GATCGATTCT AGACTCGAGG GTACCGGATC      60
CTTTTTATAG CTAATTAGTC AC                                               82
```

( 2 ) INFORMATION FOR SEQ ID NO:361:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

```
TCGGGATCCG GGTTAATTAA TTAGTCATCA GGCAGGGCG                              39
```

( 2 ) INFORMATION FOR SEQ ID NO:362:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

```
TAGCTCGAGG GTACCTACGA TACAAACTTA ACGGATATCG                             40
```

( 2 ) INFORMATION FOR SEQ ID NO:363:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:363:

```
AATTGCGGCC GC                                                          12
```

( 2 ) INFORMATION FOR SEQ ID NO:364:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:364:

ACTACTAAGC TTCTTTATTC TATACTTAAA AAGTG  35

( 2 ) INFORMATION FOR SEQ ID NO:365:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:365:

TTAACGGATA TCGCGATAAT G  21

( 2 ) INFORMATION FOR SEQ ID NO:366:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:366:

TCTGAGCTCG AAAATAGAAT TGATCAG  27

( 2 ) INFORMATION FOR SEQ ID NO:367:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:367:

TCTGGTACCT TTCTGAATGC AGGATG  26

( 2 ) INFORMATION FOR SEQ ID NO:368:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:368:

TCTGAGCTCC AATACAACAC AGAACC  26

( 2 ) INFORMATION FOR SEQ ID NO:369:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:369:

TCTGGTACCG CATTCACTAT TACTCA  26

( 2 ) INFORMATION FOR SEQ ID NO:370:

( i ) SEQUENCE CHARACTERISTICS:
        ( A ) LENGTH: 1685 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:370:

GAGCTCGAAA ATAGAATTGA TCAGTAATCA TGAAGGCTTT TTTAGTTACT TGCTTAAGCT  60

| | | | | | | |
|---|---|---|---|---|---|---|
|TTGCAGTCTT|TTCATCTTCT|GTATGTGTGA|ATATCAACAT|CTTGCAGCAA|ATTGGATATA|120|
|TCAAGCAACA|AGTCAGGCAA|CTAAGCTATT|ACTCACAAAG|TTCAAGCTCC|TACATAGTGG|180|
|TCAAGCTTTT|ACCGAATATC|CAACCCATTG|ATAACAGCTG|TGAATTTAAG|AGTGTAACTC|240|
|AATACAATAA|GACCTTGAGT|AATTTGCTTC|TTCCAATTGC|AGAAAACATA|ACAATATTG|300|
|CATCGCCCTC|ATCTGGGTCA|AGACGGCATA|AAAGGTTTGC|TGGTATTGCT|ATTGGCATTG|360|
|CTGCGCTCGG|TGTTGCGACC|GCAGCACAAG|TAACTGCCGC|TGTCTCATTA|GTTCAAGCAC|420|
|AGACAAATGC|ACGTGCAATA|GCGGCGATGA|AAAATTCAAT|ACAAGCAACT|AATCGAGCAG|480|
|TCTTCGAAGT|GAAGGAAGGC|ACTCAACAGT|TAGCTATAGC|GGTACAAGCA|ATACAAGACC|540|
|ACATCAATAC|TATTATGAAC|ACCCAATTGA|ACAATATGTC|TTGTCAGATC|CTTGATAACC|600|
|AGCTTGCAAC|TTTCCTAGGA|TTATACCTAA|CAGAATTAAC|AACAGTGTTT|CAGCCACAAT|660|
|TAATTAATCC|GGCATTGTCA|CCGATTAGTA|TACAAGCCTT|GAGGTCTTTG|CTTGGAAGTA|720|
|TGACGCCTGC|AGTGGTCCAA|GCAACATTAT|CTACTTCAAT|CTCTACTGCT|GAAATACTAA|780|
|GTGCCGGTCT|AATGGAGGGT|CAGATTGTTT|CTGTTCTGCT|AGATGAGATG|CAGATGATAG|840|
|TTAAGATAAA|TATTCCAACT|ATTGTCACAC|AATCAAATGC|ATTGGTGATT|GACTTCTACT|900|
|CAATTTCGAG|CTTTATTAAT|AATCAGGAAT|CCATAATCCA|ATTGCCAGAC|AGAATCTTGG|960|
|AGATCGGGAA|TGAACAATGG|AGCTATCCAG|CTAAAAATTG|TAAGTTGACA|AGACACCACA|1020|
|TATTCTGCCA|ATACAATGAG|GCAGAGAGGC|TGAGCCTAGA|ATCAAAACTA|TGCCTTGCAG|1080|
|GTAATATAAG|TGCCTGTGTG|TTCTCACCCA|TAGCAGGGAG|TTATATGAGG|CGATTACGG|1140|
|CACTGGATGG|AACAATTGTT|GCAAACTGTC|GAAGTCTAAC|GTGTCTATGC|AAGAATCCAT|1200|
|CTTATCCTAT|ATACCAACCT|GACCATCATG|CAGTCACGAC|CATTGATCTA|ACCGCATGTC|1260|
|AAACATTGTC|CCTAGACGGA|TTGGATTTCA|GCATTGTCTC|TCTAAGCAAC|ATCACTTACG|1320|
|CTGAGAACCT|TACCATTTCA|TTGTCTCAGA|CAATCAATAC|TCAACCCATT|GACATATCAA|1380|
|CTGAACTGAG|TAAGGTTAAT|GCATCCCTCC|AAAATGCCGT|TAAGTACATA|AAGGAGAGCA|1440|
|ACCATCAGCT|CCAATCTGTG|AGTGTAAACT|CCAAAATCGG|AGCTATAATT|GTAGCAGCCT|1500|
|TAGTTTTGAG|CATTCTGTCA|ATTATCATTT|CGCTATTGTT|TTGCTGCTGG|GCTTACATTG|1560|
|CAACTAAAGA|AATCAGAAGA|ATCAACTTCA|AAACAAATCA|TATCAATACA|ATATCAAGTA|1620|
|GTGTCGATGA|TCTCATTAGG|TACTAATCCT|AACATTGTGA|TTCATCCTGC|ATTCAGAAAG|1680|
|GTACC| | | | | |1685|

(2) INFORMATION FOR SEQ ID NO:371:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (xi) SEQUENCE DESCRIPTION: SEQ ID NO:371:

| | | | | | | |
|---|---|---|---|---|---|---|
|GAGCTCCAAT|ACAACACAGA|ACCCCAGCTG|CCATCACAAC|TGTTCTCTGG|CCGCTCGAAA|60|
|GATGGAGCCC|TCAAAACTCT|TCACAATGTC|AGACAATGCC|ACCTTTGCAC|CTGGACCTTT|120|
|TATCAATGCG|GCAGACAAGA|AGACGTTCCG|AACCTGCTTC|CGAATATTGG|TACTGTCTGT|180|
|ACAAGCTGTT|ACCCTTATAT|TAGTTATTGT|CACTTTAGGT|GAGCTTGTGA|GGATGATCAA|240|
|TGATCAAGGC|TTGAGCAATC|AGTTGTCTTC|AATTGCAGAC|AAGATAAGAG|AGTCAGCTAC|300|
|TATGATTGCA|TCTGCTGTGG|GAGTAATGAA|TCAAGTTATT|CACGGAGTAA|CGGTATCCTT|360|

```
ACCCCTACAA ATTGAGGGAA ACCAAAATCA ATTGTTATCC ACACTTGCCA CAATCTGTAC      420
AGGCAAAAAA CAAGTCTCAA ACTGCTCTAC AAACATCCCC TTAGTTAATG ACCTTAGGTT      480
TATAAATGGG ATCAATAAAT TCATCATTGA AGATTATGCA ACTCATGATT TCTCTATCGG      540
CCATCCACTC AACATGCCTA GCTTTATCCC AACTGCAACT TCACCCAATG GTTGCACAAG      600
AATTCCATCC TTTTCTCTAG GTAAGACACA CTGGTGCTAC ACACATAATG TAATTAATGC      660
CAACTGCAAG GATCATACTT CGTCTAACCA ATATATTTCC ATGGGGATAC TCGTTCAGAC      720
CGCGTCAGGG TATCCTATGT TCAAAACCTT AAAAATCCAA TATCTCAGTG ATGGCCTTAA      780
TCGGAAAAGC TGCTCAATTG CAACAGTCCC TGATGGATGC GCAATGTACT GTTACGTCTC      840
AACTCAACTT GAAACCGACG ACTATGCGGG GTCCAGCCCA CCTACCCAGA AACTTACCCT      900
GTTATTCTAT AATGATACCG TCACAGAAAG GACAATATCT CCAACTGGTC TTGAAGGGAA      960
TTGGGCTACT TTGGTTCCAG GAGTGGGGAG TGGAATATAT TTCGAGAATA AATTGATTTT     1020
TCCTGCATAT GGGGGTGTCT TGCCCAATAG TACACTCGGA GTTAAATCAG CAAGAGAATT     1080
TTTCCGGCCT GTTAATCCAT ATAATCCATG TTCAGGACCA CAACAAGATT TAGATCAGCG     1140
TGCTTTGAGA TCATACTTCC CAAGTTACTT CTCTAATCGA AGAGTACAGA GTGCATTTCT     1200
TGTCTGTGCC TGGAATCAGA TCCTAGTTAC AAATTGCGAG CTAGTTGTCC CCTCAAACAA     1260
TCAGACACTG ATGGGTGCAG AAGGAAGAGT TTTATTGATC AATAATCGAC TATTATATTA     1320
TCAGAGAAGT ACCAGCTGGT GGCCGTATGA ACTCCTCTAT GAGATATCAT TCACATTTAC     1380
AAACTCTGGT CAATCATCTG TGAATATGTC CTGGATACCT ATATATTCAT TCACTCGTCC     1440
TGGTTCAGGC AACTGCAGTG GTGAAAATGT GTGCCCAACT GCTTGTGTGT CAGGGGTTTA     1500
TCTTGATCCC TGGCCATTAA CTCCATATAG CCACCAATCA GGCATTAACC GAAATTTCTA     1560
TTTCACAGGC GCACTATTAA ATTCAAGCAC AACTAGAGTA AATCCTACCC TTTATGTCTC     1620
TGCCCTTAAT AATCTTAAAG TACTAGCCCC ATATGGTAAT CAGGGACTGT TGCCTCGTA     1680
CACCACAACC ACCTGCTTTC AAGATACCGG TGATGCTAGT GTGTATTGTG TTTATATTAT     1740
GGAACTAGCA TCGAATATCG TTGGAGAATT CCAAATTCTA CCTGTGCTAA CCAGATTGAC     1800
CATCACTTGA GTAATAGTGA ATGCGGTACC                                      1830
```

( 2 ) INFORMATION FOR SEQ ID NO:372:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:372:

```
TTAGATATCC GGACCGCCCG GGCTGCAGAA T                                      31
```

( 2 ) INFORMATION FOR SEQ ID NO:373:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:373:

```
ATTCTGCAGC CCGGGCGGTC CGGATATCTA A                                      31
```

( 2 ) INFORMATION FOR SEQ ID NO:374:

( i ) SEQUENCE CHARACTERISTICS:

(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:374:

TATGAATTCC CATGGTTAAT TAATTAGTCA TC          32

(2) INFORMATION FOR SEQ ID NO:375:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:375:

TCTCCCGGGC GGATATCGCG ATAATG          26

(2) INFORMATION FOR SEQ ID NO:376:

(i) SEQUENCE CHARACTERISTICS:
(A) LENGTH: 95 base pairs
(B) TYPE: nucleic acid
(C) STRANDEDNESS: single
(D) TOPOLOGY: linear (xi) SEQUENCE DESCRIPTION: SEQ ID NO:376:

TAACCATGGT TTATTGGGAA GAATATGATA ATATTTGGG ATTTCAAAAT TGAAAATATA          60

TAATTACAAT ATAAAATGAA GGCTTTTTA GTTAC          95

(2) INFORMATION FOR SEQ ID NO:377:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:377:

CCACTGCAGG CGTCATAC          18

(2) INFORMATION FOR SEQ ID NO:378:

(i) SEQUENCE CHARACTERISTICS:
(A) LENGTH: 49 base pairs
(B) TYPE: nucleic acid
(C) STRANDEDNESS: single
(D) TOPOLOGY: linear (xi) SEQUENCE DESCRIPTION: SEQ ID NO:378:

TTATCGCGAT ATCCGTTAAG TTTGTATCGT AATGGAGCCC TCAAAACTC          49

(2) INFORMATION FOR SEQ ID NO:379:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:379:

AAACCTAAGG TCATTAAC          18

(2) INFORMATION FOR SEQ ID NO:380:

(i) SEQUENCE CHARACTERISTICS:

(A) LENGTH: 31 base pairs
        (B) TYPE: nucleic acid
        (C) STRANDEDNESS: single
        (D) TOPOLOGY: linear (x i) SEQUENCE DESCRIPTION: SEQ ID NO:380:

TTCCCGGGAG ATCTCTATGC CATTTCTCCA T                          31

(2) INFORMATION FOR SEQ ID NO:381:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (x i) SEQUENCE DESCRIPTION: SEQ ID NO:381:

GGATCCCCGG G                                                 11

(2) INFORMATION FOR SEQ ID NO:382:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (x i) SEQUENCE DESCRIPTION: SEQ ID NO:382:

CTTGATTTTT ATTGAT                                            16

(2) INFORMATION FOR SEQ ID NO:383:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:383:

CTAGATCAAT AAAAATCAAG CATG                                   24

(2) INFORMATION FOR SEQ ID NO:384:

(i) SEQUENCE CHARACTERISTICS:
        (A) LENGTH: 21 amino acids
        (B) TYPE: amino acid
        (C) STRANDEDNESS: single
        (D) TOPOLOGY: linear (x i) SEQUENCE DESCRIPTION: SEQ ID NO:384:

Cys Asn Thr Arg Lys Arg Ile Arg Ile Gln Arg Gly Pro Gly Arg Ala
    1               5                   10                  15

Phe Val Thr Gly Lys
                20

(2) INFORMATION FOR SEQ ID NO:385:

(i) SEQUENCE CHARACTERISTICS:
        (A) LENGTH: 20 amino acids
        (B) TYPE: amino acid
        (C) STRANDEDNESS: single
        (D) TOPOLOGY: linear (x i) SEQUENCE DESCRIPTION: SEQ ID NO:385:

Cys Asn Lys Arg Lys Arg Ile His Ile Gly Pro Gly Arg Ala Phe Tyr
    1               5                   10                  15

Thr Thr Lys Asn (2) INFORMATION FOR SEQ ID NO:386:

(i) SEQUENCE CHARACTERISTICS:
        (A) LENGTH: 20 amino acids
        (B) TYPE: amino acid
        (C) STRANDEDNESS: single
        (D) TOPOLOGY: linear (x i) SEQUENCE DESCRIPTION: SEQ ID NO:386:

```
Cys  Asn  Thr  Arg  Lys  Ser  Ile  Tyr  Ile  Gly  Pro  Gly  Arg  Ala  Phe  His
 1                   5                        10                       15
Thr  Thr  Gly  Arg
            20
```

(2) INFORMATION FOR SEQ ID NO:387:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:387:

GGGTTATTAA TGATCTGTAG        20

(2) INFORMATION FOR SEQ ID NO:388:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:388:

ATCATCGAGC TCTGTTCCTT GGGTTCTTAG        30

(2) INFORMATION FOR SEQ ID NO:389:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (x i) SEQUENCE DESCRIPTION: SEQ ID NO:389:

ATCATCTCTA GAATAAAAAT TATAGCAAAG CCCTTTCCAA GCC        43

(2) INFORMATION FOR SEQ ID NO:390:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (x i) SEQUENCE DESCRIPTION: SEQ ID NO:390:

ATCATCGAGC TCCTATCGCT GCTC        24

(2) INFORMATION FOR SEQ ID NO:391:

(i) SEQUENCE CHARACTERISTICS:
        (A) LENGTH: 55 base pairs
        (B) TYPE: nucleic acid
        (C) STRANDEDNESS: single
        (D) TOPOLOGY: linear ( x i ) SEQUENCE DESCRIPTION: SEQ ID NO:391:

AGCTTCTTTA TTCTATACTT AAAAAGTGAA AATAAATACA AAGGTTCTTG AGGGT    55

( 2 ) INFORMATION FOR SEQ ID NO:392:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

TGTGTTAAAT TGAAAGCGAG AAATAATCAT AAATTATTTC ATTATCGCGA TATCCGTTAA    60

GTTTGTATCG TAC    73

( 2 ) INFORMATION FOR SEQ ID NO:393:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

TCGAGTACGA TACAAACTTA ACGGATATCG CGATAATGAA ATAATTTATG ATTATT    56

( 2 ) INFORMATION FOR SEQ ID NO:394:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

TCTCGCTTTC AATTTAACAC AACCCTCAAG AACCTTTGTA TTTATTTTCA CTTTTTAAGT    60

ATAGAATAAA GA    72

( 2 ) INFORMATION FOR SEQ ID NO:395:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

AATACGACTC ACTATAG    17

( 2 ) INFORMATION FOR SEQ ID NO:396:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:396:

ATCATCTCTA GAATAAAAAT TATCTTTTTT CTCTCTGCAC CACTC    45

( 2 ) INFORMATION FOR SEQ ID NO:397:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( x i ) SEQUENCE DESCRIPTION: SEQ ID NO:397:

GAAATAATAA AACAATAATC 20

( 2 ) INFORMATION FOR SEQ ID NO:398:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:398:

GCTCCTATTC CCACTGCAGT TTTTCTCTC TGCAC 35

( 2 ) INFORMATION FOR SEQ ID NO:399:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:399:

GTGCAGAGAA AAAACTGCAG TGGGAATAGG AGC 33

( 2 ) INFORMATION FOR SEQ ID NO:400:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:400:

ATCATCTCTA GAATAAAAAT TACAAACTTG CCCATTTATC CAATTCC 47

( 2 ) INFORMATION FOR SEQ ID NO:401:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:401:

ATCATCTCTA GAATAAAAAT TACAAACTTG CCCATTTATC TAATTCC 47

( 2 ) INFORMATION FOR SEQ ID NO:402:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:402:

GCCTCCTACT ATCATTATGA ATAATCTTTT TCTCTCTG 38

( 2 ) INFORMATION FOR SEQ ID NO:403:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:403:

TTATTCATAA TGATAGTAGG AGGCTTGGTA GGTTTAAGAA TAGTTTTTGC TGTACTCTCT 60

GTAGTGAATA GAGTTAGGCA GGGATAA 87

( 2 ) INFORMATION FOR SEQ ID NO:404:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:404:

TTATCCCTGC CTAACTCTAT TCACTACAGA GAGTACAGCA AAAACTATTC TTAAACCTAC 60

CAAGCCTCCT ACTATCATTA TGAATAA 87

( 2 ) INFORMATION FOR SEQ ID NO:405:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:405:

ATCATCTCTA GAATAAAAAT TATCCCTGCC TAACTCTATT CAC 43

( 2 ) INFORMATION FOR SEQ ID NO:406:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:406:

GATCTTAATT AATTAGTCAT CAGGCAGGGC GAGAACGAGA CTATCTGCTC GTTAATTAAT 60

TAGGTCGACG 70

( 2 ) INFORMATION FOR SEQ ID NO:407:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:407:

GATCCGTCGA CCTAATTAAT TAACGAGCAC ATAGTCTCGT TCTCGCCCTG CCTGATGACT 60

AATTAATTAA 70

( 2 ) INFORMATION FOR SEQ ID NO:408:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:408:

TGTGGCAAAG AAGGGC 16

( 2 ) INFORMATION FOR SEQ ID NO:409:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:409:

TTGGATCCTT ATTGTGACGA GGGGTC                                                                                26

( 2 ) INFORMATION FOR SEQ ID NO:410:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:410:

GATCTTGAGA TAAAGTGAAA ATATATATCA TTATATTACA AAGTACAATT ATTTAGGTTT            60

AATCATGGGT GCGAGAGCGT CAGTATTAAG CGGGGGAGAA TTAGAT                           106

( 2 ) INFORMATION FOR SEQ ID NO:411:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:411:

CGATCTAATT CTCCCCCGCT TAATACTGAC GCTCTCGCAC CCATGATTAA ACCTAAATAA            60

TTGTACTTTG TAATATAATG ATATATATTT TCACTTTATC TCAA                            104

( 2 ) INFORMATION FOR SEQ ID NO:412:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:412:

CTGACACAGG ACACAGCAAT CAGGTCAGCC AAAATTACTA ATTTTATCT CGAGGTCGAC             60

AGGACCCG                                                                     68

( 2 ) INFORMATION FOR SEQ ID NO:413:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:413:

GATCCGGGTC CTGTCGACCT CGAGATAAAA ATTAGTAATT TTGGCTGACC TGATTGCTGT            60

GTCCTGTGTC AG                                                                72

( 2 ) INFORMATION FOR SEQ ID NO:414:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:414:

AAGAAAATTA TAGGAC 16

(2) INFORMATION FOR SEQ ID NO:415:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:415:

TTGGATCCCT AATCCTCATC CTGT 24

(2) INFORMATION FOR SEQ ID NO:416:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:416:

AAAGTCGACC CATATCACCT AGAAC 25

(2) INFORMATION FOR SEQ ID NO:417:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:417:

TTTGGATCCT TACAAAACTC TTGCCTTAT 29

(2) INFORMATION FOR SEQ ID NO:418:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:418:

TCGAGCAAAA TTGAAAATAT ATAATTACAA TATAAAATGC CTATAGTGCA GAACATCCAG 60

GGGCAAATGG TACATCAGGC CATATCACCT AGAACTTTAA ATGCA 105

(2) INFORMATION FOR SEQ ID NO:419:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (xi) SEQUENCE DESCRIPTION: SEQ ID NO:419:

TTTAAAGTTC TAGGTGATAT GGCCTGATGT ACCATTTGCC CCTGGATGTT CTGCACTATA 60

GGCATTTTAT ATTGTAATTA TATATTTTCA ATTTTGC 97

(2) INFORMATION FOR SEQ ID NO:420:

(i) SEQUENCE CHARACTERISTICS:
        (A) LENGTH: 43 base pairs
        (B) TYPE: nucleic acid
        (C) STRANDEDNESS: single
        (D) TOPOLOGY: linear ( x i ) SEQUENCE DESCRIPTION: SEQ ID NO:420:

GCCTCCTACT ATCATTATGA ATAAACTGAT GGGAGGGGCA TAC 43

( 2 ) INFORMATION FOR SEQ ID NO:421:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:421:

GGCCGCAAC 9

( 2 ) INFORMATION FOR SEQ ID NO:422:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:422:

TCGAGTTGC 9

( 2 ) INFORMATION FOR SEQ ID NO:423:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:423:

GGCCAAAC 8

( 2 ) INFORMATION FOR SEQ ID NO:424:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:424:

TCGAGTTT 8

( 2 ) INFORMATION FOR SEQ ID NO:425:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:425:

CCCCCCAAGC TTACATCATG CAGTGGTTAA AC 32

( 2 ) INFORMATION FOR SEQ ID NO:426:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:426:

GATTAAACCT AAATAATTGT 20

( 2 ) INFORMATION FOR SEQ ID NO:427:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:427:

ACAATTATTT AGGTTAACTG CA 22

( 2 ) INFORMATION FOR SEQ ID NO:428:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:428:

GTTAACCTAA ATAATTGT 18

( 2 ) INFORMATION FOR SEQ ID NO:429:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:429:

TAATCATGAA ACAAATTATT AATATGTGGC AAGAAGAGGA AAAGCTATGT ACGCTTGACT 60

AGTTAATCAC TCGAG 75

( 2 ) INFORMATION FOR SEQ ID NO:430:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:430:

GATCCTCGAG TGATTAACTA GTCAAGCGTA CATAGCTTTT CCTACTTCTT GCCACATATT 60

AATAATTTGT TTCATGATTA 80

( 2 ) INFORMATION FOR SEQ ID NO:431:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:431:

ATCCGTTAAG TTTGTATCGT AATGCACGAA GATATTATTT CTTTGTGGGA TCAATCTTTA 60

AAATGACTAG TTAATCAG 78

( 2 ) INFORMATION FOR SEQ ID NO:432:

( i ) SEQUENCE CHARACTERISTICS:
        ( A ) LENGTH: 82 base pairs
        ( B ) TYPE: nucleic acid ( C ) STRANDEDNESS: single
( D ) TOPOLOGY: linear ( x i ) SEQUENCE DESCRIPTION: SEQ ID NO:432:

GATCCTGATT AACTAGTCAT TTTAAAGATT GATCCCACAA AGAAATAATA TCTTCGTGCA      60

TTACGATACA AACTTAACGG AT      82

( 2 ) INFORMATION FOR SEQ ID NO:433:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:433:

AATTAATTAG CTGCAGCCCC GGGTCAAAAA AATATAAATG      40

( 2 ) INFORMATION FOR SEQ ID NO:434:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

CCTTGTACTA CTTCAATTAC TCTATCCATT TTATATTGTA ATTATATATT TTC      53

( 2 ) INFORMATION FOR SEQ ID NO:435:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:435:

TCAAAAAAT ATAAATGATT CACCATCTGA TAGAAAAAAA ATTTATTGGG AAGAATATGA      60

TAATATTTTG GGATTTCAAA ATTGAAAATA TATAATTACA ATATAAA      107

( 2 ) INFORMATION FOR SEQ ID NO:436:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:436:

ATGGATAGAG TAATTGAAGT AGTACAAGGA GCTTATAGAG CTATTAGATG ACTAGTTAAT      60

CACTCGAGGA TCC      73

( 2 ) INFORMATION FOR SEQ ID NO:437:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:437:

GGATCCTCGA GTGATTAACT AGTCATCTAA TAGCTCTATA AGCTCCTTGT ACTACTTCAA      60

TTACTCTATC CAT      73

( 2 ) INFORMATION FOR SEQ ID NO:438:

( i ) SEQUENCE CHARACTERISTICS:
          ( A ) LENGTH: 43 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:438:

```
ATCATCGGAT CCTCGAGTGA TTAAACTAGT CATCTAATAG CTC                      43
```

( 2 ) INFORMATION FOR SEQ ID NO:439:

( i ) SEQUENCE CHARACTERISTICS:
          ( A ) LENGTH: 84 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:439:

```
TTAATCAGGA TCCTTAATTA ATTAGTTATT AGACAAGGTG AAAACGAAAC TATTTGTAGC    60
TTAATTAATT AGCTGCAGCC CGGG                                           84
```

( 2 ) INFORMATION FOR SEQ ID NO:440:

( i ) SEQUENCE CHARACTERISTICS:
          ( A ) LENGTH: 84 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:440:

```
CCCGGGCTGC AGCTAATTAA TTAAGCTACA AATAGTTTCG TTTTCACCTT GTCTAATAAC    60
TAATTAATTA AGGATCCTGA TTAA                                           84
```

( 2 ) INFORMATION FOR SEQ ID NO:441:

( i ) SEQUENCE CHARACTERISTICS:
          ( A ) LENGTH: 34 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:441:

```
TTAATCAGGA TCCTTAATTA ATTAGTTATT AGAC                                34
```

( 2 ) INFORMATION FOR SEQ ID NO:442:

( i ) SEQUENCE CHARACTERISTICS:
          ( A ) LENGTH: 42 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:442:

```
ATCATCGGAT CCTCGAGTGA TTAACTAGTC ATCTAATAGC TC                       42
```

( 2 ) INFORMATION FOR SEQ ID NO:443:

( i ) SEQUENCE CHARACTERISTICS:
          ( A ) LENGTH: 51 amino acids
          ( B ) TYPE: amino acid
          ( C ) STRANDEDNESS: single
          ( D ) TOPOLOGY: linear ( x i ) SEQUENCE DESCRIPTION: SEQ ID NO:443:

```
    Met   Lys   Glu   Gln   Lys   Thr   Val   Ala   Met   Arg   Val   Lys   Glu   Lys   Tyr   Gln
    1                       5                       10                            15

His   Leu   Trp   Arg   Trp   Gly   Trp   Arg   Trp   Gly   Thr   Met   Leu   Leu   Gly   Met
                      20                            25                            30

Leu   Met   Ile   Cys   Ser   Ala   Thr   Glu   Lys   Leu   Trp   Val   Thr   Val   Tyr   Tyr
                35                            40                            45

Gly   Val   Pro
                50
```

( 2 ) INFORMATION FOR SEQ ID NO:444:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( x i ) SEQUENCE DESCRIPTION: SEQ ID NO:444:

```
    Pro   Phe   Arg   Lys   Gln   Ile   Ile   Asn   Met   Trp   Gln   Glu   Val   Gly   Lys   Ala
    1                       5                             10                            15

Met   Tyr   Ala   Pro   Pro   Phe   Arg   Lys   His   Glu   Asp   Ile   Ile   Ser   Leu   Trp
                      20                            25                            30

Asp   Gln   Ser   Leu   Lys   Pro   Pro   Phe   Arg   Lys   Asp   Arg   Val   Ile   Glu   Val
                35                            40                            45

Val   Gln   Gly   Ala   Tyr   Arg   Ala   Ile   Arg   Pro   Pro   Phe   Arg   Lys
          50                            55                            60
```

( 2 ) INFORMATION FOR SEQ ID NO:445:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( x i ) SEQUENCE DESCRIPTION: SEQ ID NO:445:

```
    Leu   Phe   Ile   Met   Ile   Val   Gly   Gly   Leu   Val   Gly   Leu   Arg   Ile   Val   Phe
    1                       5                             10                            15

Ala   Val   Leu   Ser   Val   Val   Asn   Arg   Val   Arg   Gln   Gly
                      20                            25
```

( 2 ) INFORMATION FOR SEQ ID NO:446:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:446:

CATATTAATT TGTTTTCTAA AAGGAGGTAC CCCATAATAG ACTGTG      46

( 2 ) INFORMATION FOR SEQ ID NO:447:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:447:

GCTCCTCCTT TTAGAAAACA CGAAGATATT ATTTCTTTGT GGGATCAATC TTTAAAACCT      60

CCTTTTAGAA AAGATAGAGT AATTGAAGTA GTAC      94

( 2 ) INFORMATION FOR SEQ ID NO:448:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:448:

```
GTACTACTTC AATTACTCTA TCTTTTCTAA AAGGAGGTTT TAAAGATTGA TCCCACAAAG    60

AAATAATATC TTCGTGTTTT CTAAAAGGAG GAGC                                94
```

( 2 ) INFORMATION FOR SEQ ID NO:449:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:449:

```
AAACAAATTA TTAATATGTG GCAAGAAGTA GGAAAAGCTA TGTACGCTCC TCCTTTTAGA    60

AAACACGAAG                                                           70
```

( 2 ) INFORMATION FOR SEQ ID NO:450:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:450:

```
ACTACTTCTA GATTATCTAA TAGCTCTATA AGCTCCTTGT ACTACTTCAA TTACTC        56
```

( 2 ) INFORMATION FOR SEQ ID NO:451:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:451:

```
TACTATCATT ATGAATAATT TTCTAAAAGG AGGTCTAATA GCTCTATAAG CTCCTTGTAC    60

TACTTCAATT ACTC                                                      74
```

( 2 ) INFORMATION FOR SEQ ID NO:452:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:452:

```
ATCATCGGAT CCAAGCTTAC ATCATGCAGT GG                                  32
```

( 2 ) INFORMATION FOR SEQ ID NO:453:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:453:

CGTTTTGACC ATTTGCCACC CATGATTAAA CCTAAATAAT TGTACTTTG  49

( 2 ) INFORMATION FOR SEQ ID NO:454:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:454:

AGTACAATTA TTTAGGTTTA ATCATGGGTG GCAAATGGTC AAAACG  46

( 2 ) INFORMATION FOR SEQ ID NO:455:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:455:

ATCATCGGAT CCTAACACTT CTCTCTCCGG  30

( 2 ) INFORMATION FOR SEQ ID NO:456:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:456:

ATCATCGGAT CCTAACACTT CTCTCTCCGG GTCATCCATC CATGCTGGCT CATAG  55

( 2 ) INFORMATION FOR SEQ ID NO:457:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:457:

AATTAACCCG GGATCCAAGC TTCTAGCTAG CTAATTTTTA TAGCGGCCGC TATAATCGTT  60

AACTTATTAG  70

( 2 ) INFORMATION FOR SEQ ID NO:458:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:458:

GCTAGAAATC TCTTAGTTTT TATAGTTG  28

( 2 ) INFORMATION FOR SEQ ID NO:459:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear (x i) SEQUENCE DESCRIPTION: SEQ ID NO:459:

GTTACATATG TACAGAATCT GATCATAG 28

(2) INFORMATION FOR SEQ ID NO:460:

(i) SEQUENCE CHARACTERISTICS:
  (A) LENGTH: 67 base pairs
  (B) TYPE: nucleic acid
  (C) STRANDEDNESS: single
  (D) TOPOLOGY: linear (x i) SEQUENCE DESCRIPTION: SEQ ID NO:460:

CTAGCTAGAA GCTTGGATCC CGGGTTAATT AATTAATAAA AAGCGGCCGC GTTAAAGTAG 60

AAAAATG 67

(2) INFORMATION FOR SEQ ID NO:461:

(i) SEQUENCE CHARACTERISTICS:
  (A) LENGTH: 67 base pairs
  (B) TYPE: nucleic acid
  (C) STRANDEDNESS: single
  (D) TOPOLOGY: linear (x i) SEQUENCE DESCRIPTION: SEQ ID NO:461:

CGCCCATGAT TAAACCTAAA TAATTGTACT TTGTAATATA ATGATATATA TTTTCACTTT 60

ATCTCAC 67

(2) INFORMATION FOR SEQ ID NO:462:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO:462:

ATGGCAGTTC ATTGCAT 17

NYVAC VACCINIA VIRUS RECOMBINANTS COMPRISING HETEROLOGOUS INSERTS

CROSS REFERENCE TO RELATED APPLICATIONS

This application is a continuation of application Ser. No. 07/847,951, filed Mar. 6, 1992 now abandoned, which is a continuation-in-part of application Ser. No. 07/713,967, filed Jun. 11, 1991 now abandoned, which in turn is a continuation-in-part of application Ser. No. 07/666,056, filed Mar. 7, 1991 now abandoned, both of which are hereby incorporated herein by reference. Reference is also made to copending U.S. applications Ser. Nos. 715,921, filed Jun. 14, 1991, 736,254, filed Jul. 26, 1991, 776,867, filed Oct. 22, 1991, and 820,077, filed Jan. 13, 1992, all of which are hereby incorporated herein by reference.

FIELD OF THE INVENTION

The present invention relates to a modified poxvirus and to methods of making and using the same. More in particular, the invention relates to improved vectors for the insertion and expression of foreign genes for use as safe immunization vehicles to protect against a variety of pathogens.

Several publications are referenced in this application. Full citation to these references is found at the end of the specification immediately preceding the claims or where the publication is mentioned; and each of these publications is hereby incorporated herein by reference. These publications relate to the art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. Nos. 4,769,330, 4,772,848, and 4,603,112, and in copending application Ser. No. 07/537,882, filed Jun. 14, 1990, the disclosures of which are incorporated herein by reference. In this regard reference is also made to copending U.S. application Ser. No. 537,890, filed Jun. 14, 1990, also incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmitt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982b) and there are no reports in the literature of the virus causing a productive infection in any non-avian species including man. This host restriction provides an inherent safety barrier to transmission of the virus to other species and makes use of FPV as a vaccine vector in poultry an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

The use of live attenuated vectored vaccines present a number of potential advantages. The vaccines are inexpensive to produce and a number of poultry pathogens can potentially be incorporated into one vector. The immunogen is presented to the immune system in an authentic manner such that both humoral and cell mediated responses can be invoked. Because the disease agent is not replicating, side effects of vaccination are minimal and the continual reintroduction of the disease agent into the environment is eliminated.

It can be appreciated that provision of a novel vaccine strains having enhanced safety would be a highly desirable advance over the current state of technology. For instance, so as to provide safer vaccines or safer products from the expression of a gene or genes by a virus.

OBJECTS OF THE INVENTION

It is therefore an object of this invention to provide modified recombinant viruses, which viruses have enhanced safety, and to provide a method of making such recombinant viruses.

It is an additional object of this invention to provide a recombinant poxvirus vaccine having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

STATEMENT OF THE INVENTION

In one aspect, the present invention relates to a modified recombinant virus having inactivated virus-encoded genetic functions so that the recombinant virus has attenuated virulence and enhanced safety. The functions can be nonessential, or associated with virulence. The virus is advantageously a poxvirus, particularly a vaccinia virus or an avipox virus, such as fowlpox virus and canarypox virus.

In another aspect, the present invention relates to a vaccine for inducing an immunological response in a host animal inoculated with the vaccine, said vaccine including a carrier and a modified recombinant virus having inactivated nonessential virus-encoded genetic functions so that the recombinant virus has attenuated virulence and enhanced safety. The virus used in the vaccine according to the present invention is advantageously a poxvirus, particularly a vaccinia virus or an avipox virus, such as fowlpox virus and canarypox virus.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein derived from a pathogen wherein the composition, when administered to a host, is capable of inducing an immunological response specific to the protein encoded by the pathogen.

In a further aspect, the present invention relates to a method for expressing a gene product in a cell cultured in vitro by introducing into the cell a modified recombinant virus having attenuated virulence and enhanced safety.

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b). In this respect, the open reading frame comprises a thymidine kinase gene, a hemorrhagic region, an A type inclusion body region, a hemagglutinin gene, a host range gene region or a large subunit, ribonucleotide reductase.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 9 (FIGS. 9A, 9B) shows the DNA sequence (SEQ ID NO:213) of the synthetic spsAg gene and modified synthetic vaccinia virus H6 early/late promoter with the predicted amino acid sequence (SEQ ID NO:214);

FIG. 11 (FIGS. 11A, 11B) shows the DNA sequence (SEQ ID NO:215) of the u promoter/lpsAg gene with the predicted amino acid sequence (SEQ ID NO:216);

FIG. 12 (FIGS. 12A, 12B) schematically shows a method for the construction of recombinant vaccinia virus vP896;

FIG. 13 (FIGS. 13A, 13B) shows the DNA sequence (SEQ ID NO:87) of the I3L promoter/S12/core gene with the predicted amino acid sequence (SEQ ID NO:217);

FIG. 15 (FIGS. 15A, 15B) shows the DNA sequence (SEQ ID NO:218) of the EPV 42 kDa promoter/lpsAg gene with the predicted amino acid sequence (SEQ ID NO:219);

FIG. 16 shows the DNA sequence (SEQ ID NO:220) of a canarypox PvuII fragment containing the C5 ORF.

FIG. 21 shows the nucleotide sequence (SEQ ID NO:221) of a 3661 base pair fragment of TROVAC DNA containing the F8 ORF;

FIG. 22 shows the DNA sequence (SEQ ID NO:222) of a base pair fragment of TROVAC DNA containing the F7 ORF;

FIG. 23 shows the nucleotide sequence of EIV HA (A1/Prague/56) (SEQ ID NO:279);

FIG. 24 shows the nucleotide sequence of EIV HA (A2/Fontainebleu/79) (SEQ ID NO:284);

FIG. 25 shows the nucleotide sequence of EIV HA (A2/Suffolk/89) (SEQ ID NO:300);

FIG. 26 shows the nucleotide sequence of FeLV-B Envelope Gene (SEQ ID NO:310);

FIG. 27 shows the nucleotide sequence of FeLV-A gag and partial pol genes (SEQ ID NO:324);

FIG. 28 shows the nucleotide sequence of the FHV-1 CO strain gD homolog gene (SEQ ID NO:290);

FIG. 29 shows the consensus F nucleotide sequence (mumps) represented by pURF3 (SEQ ID NO:370);

FIG. 30 shows the consensus HN nucleotide sequence (mumps) represented by pURHN5 (SEQ ID NO:371);

FIG. 36 shows JEV cDNA sequences contained in vP908, vP555, vP923 and vP829;

DETAILED DESCRIPTION OF THE INVENTION

Figure 1:
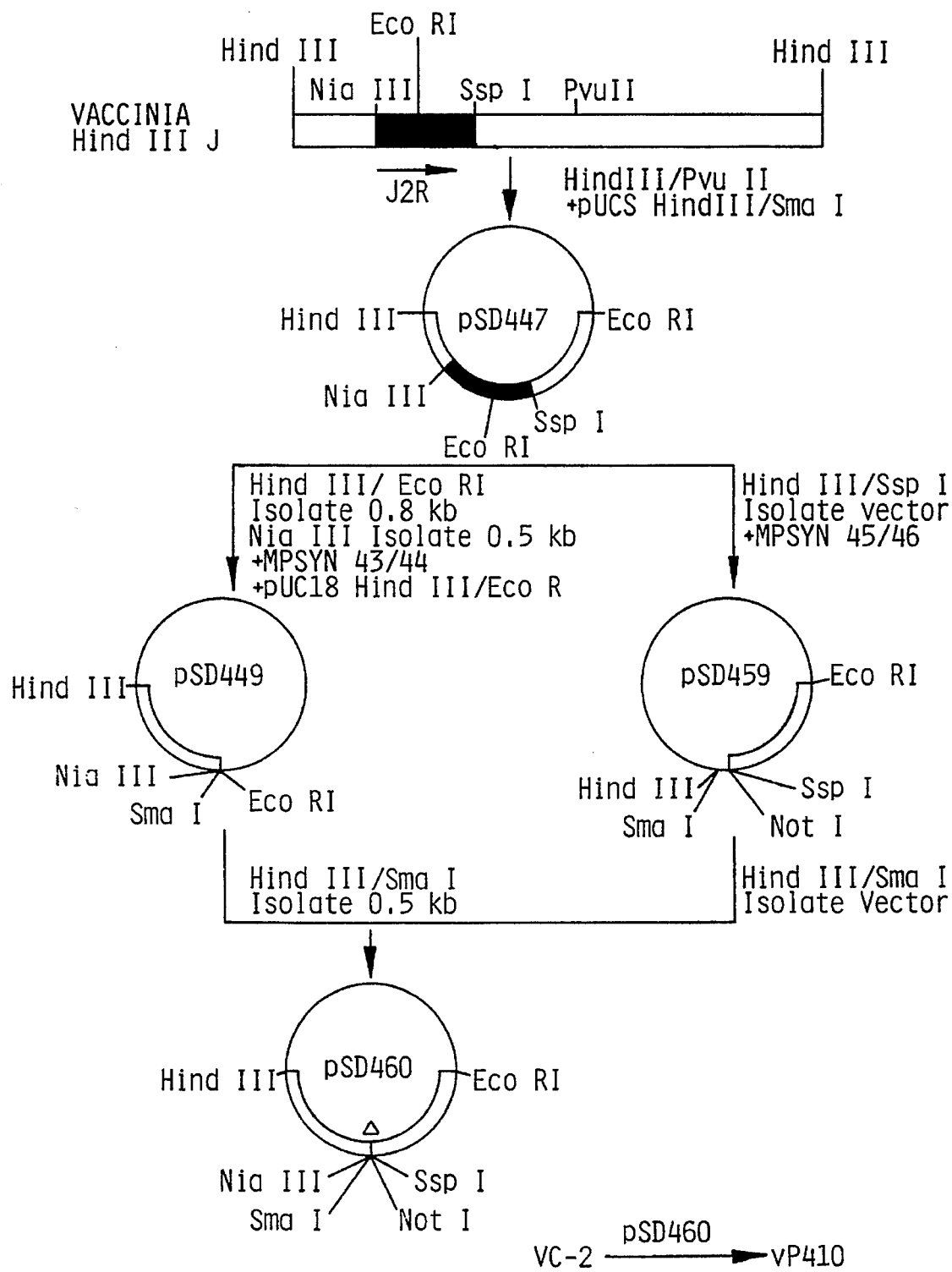
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and (6) large subunit, ribonucleotide reductase (I4L) vP866 (NYVAC).

DNA Cloning and Synthesis. Plasmids were constructed, screened and grown by standard procedures (Maniatis et al., 1982g; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Panicali et al., 1982; Perkus et al., 1989).

A better understanding of the present invention and of its many advantages will be had from the following examples, given by way of illustration.

EXAMPLE 1

CONSTRUCTION OF PLASMID pSD460 FOR DELETION OF THYMIDINE KINASE GENE (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated.

Annealed synthetic oligonucleotides MPSYN43/MPSYN44 (SEQ ID NO:1/SEQ ID NO:2)

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

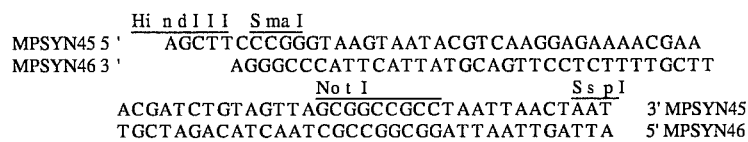

generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

EXAMPLE 2

CONSTRUCTION OF PLASMID pSD486 FOR DELETION OF HEMORRHAGIC REGION (B13R+B14R)

Figure 2:
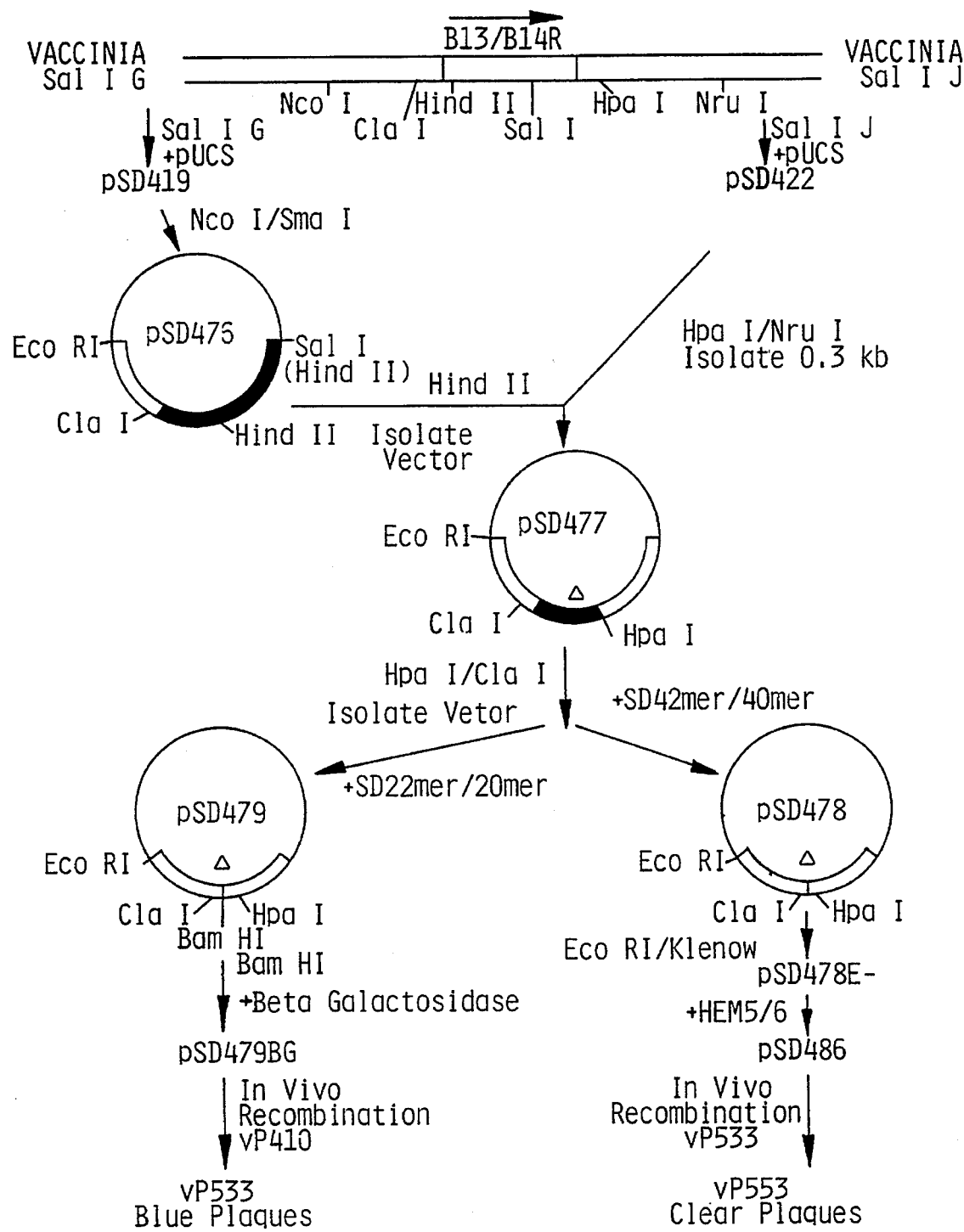
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

```
              ClaI              BamHI  HpaI
SD22mer 5' CGATTACTATGAAGGATCCGTT 3'
SD20mer 3'    TAATGATACTTCCTAGGCAA 5'
``` generating pSD479. pSD479 contains an initiation codon (underlined) followed by a BamHI site. To place *E. coli* Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
              ClaI        SacI         XhoI        HpaI
SD42mer 5' CGATTACTAGATCTGAGCTCCCCGGGCTCGAGGGATCCGTT 3'
SD40mer 3'    TAATGATCTAGACTCGAGGGGCCCGAGCTCCCTAGGCAA 5'
              BglII       SmaI         BamHI
``` generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6 (SEQ ID NO:10/SEQ ID NO:11)

```
         BamHI  EcoRI   HpaI
HEM5 5' GATCCGAATTCTAGCT    3'
HEM6 3'       GCTTAAGATCGA   5'
``` generating plasmid pSD486. pSD486 was used as donor plasmid for recombination with recombinant vaccinia virus vP533, generating vP553, which was isolated as a clear plaque in the presence of X-gal.

EXAMPLE 3

CONSTRUCTION OF PLASMID pMP494Δ FOR DELETION OF ATI REGION (A26L)

Figure 3:
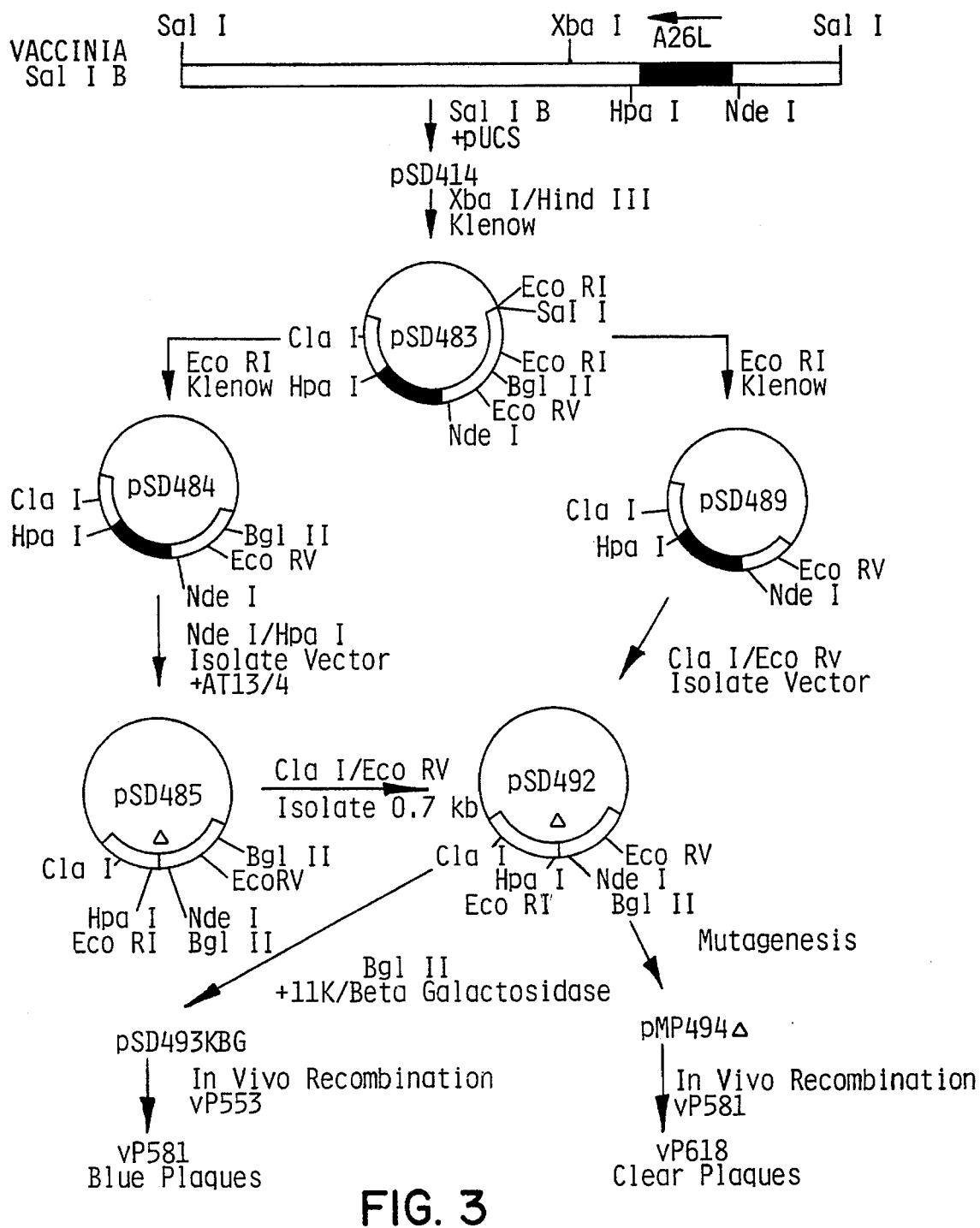
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
           NdeI
ATI3 5' TATGAGTAACTTAACTCTTTTGTTAATTAAAAGTATATTCAAAAAATAAGT
ATI4 3'     ACTCAATTGAATTGAGAAAACAATTAATTTTCATATAAGTTTTTATTCA
           BglII EcoRI  HpaI
        TATATAAATAGATCTGAATTCGTT    3' ATI3
        ATATATTTATCTAGACTTAAGCAA    5' ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the *E. coli* Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

13
EXAMPLE 4

CONSTRUCTION OF PLASMID pSD467 FOR DELETION OF HEMAGGLUTININ GENE (A56R)

Figure 4:
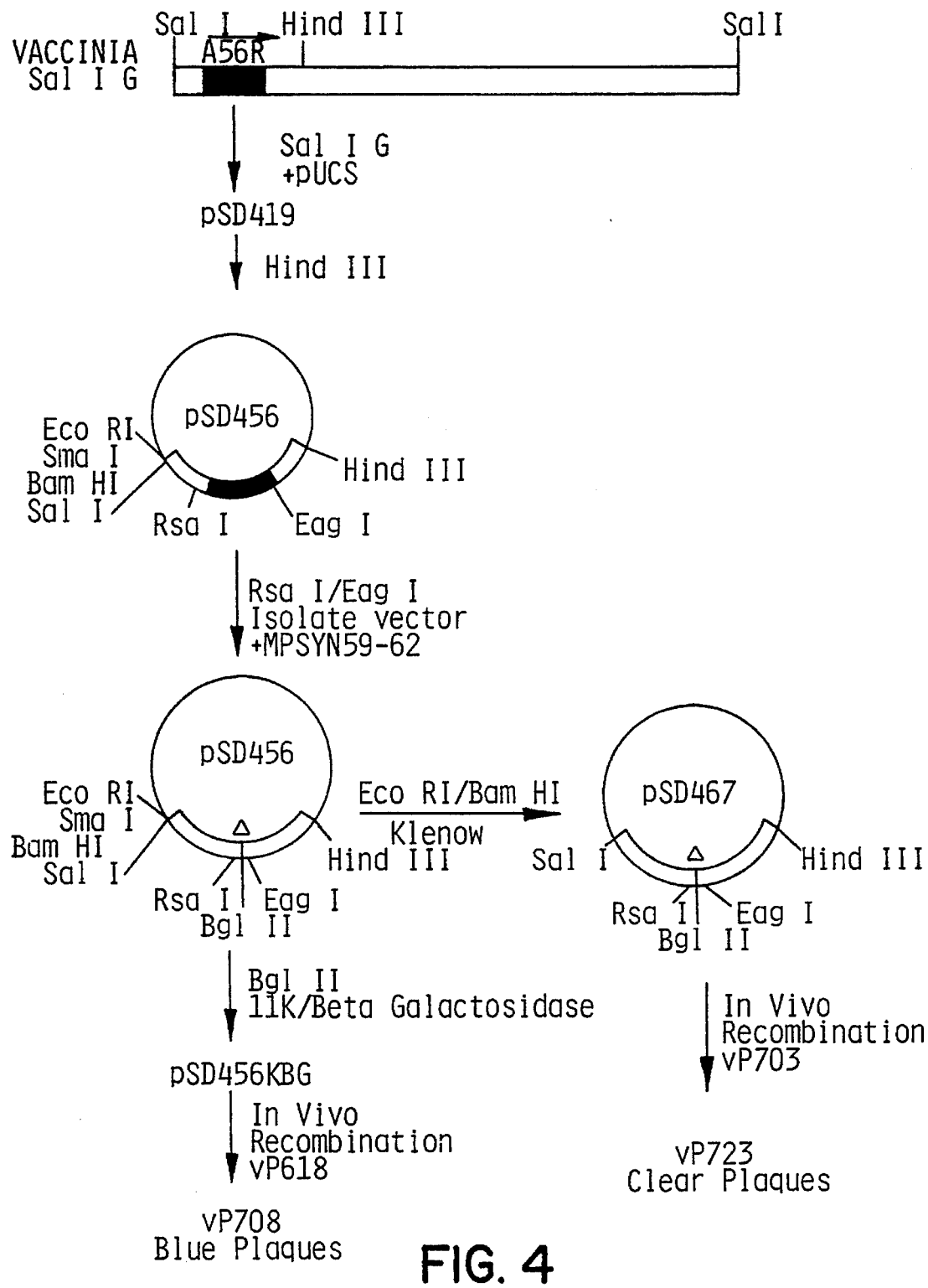
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN 61 (SEQ ID NO:18)

14
EXAMPLE 5

CONSTRUCTION OF PLASMID pMPCSK1Δ FOR DELETION OF OPEN READING FRAMES [C7L–K1L]

Figure 5:
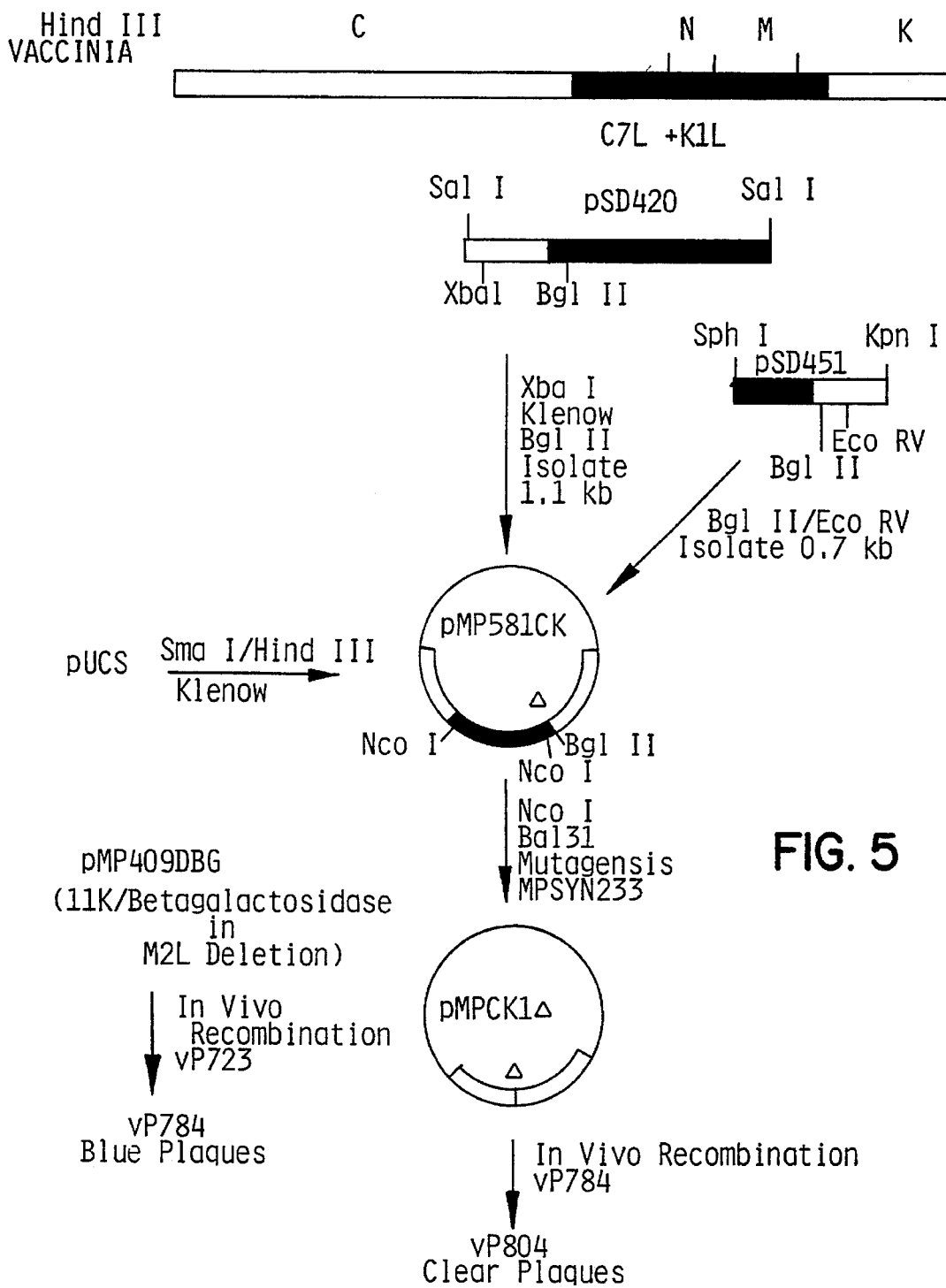
FIG. 5 schematically shows a method for the construction of plasmid pMPCSK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
              Rs a I
MPSYN59 5'    ACACGAATGATTTTCTAAAGTATTTGGAAAGTTTTATAGGT-
MPSYN62 3'    TGTGCTTACTAAAAGATTTCATAAACCTTTCAAAATATCCA-
MPSYN59       AGTTGATAGAACAAAATACATAATTT   3'
MPSYN62       TCAACTATCT   5'
MPSYN60 5'                            TGTAAAAATAAATCACTTTTTATA-
MPSYN61 3'    TGTTTTATGTATTAAAACATTTTTATTTAGTGAAAAATAT-
              Bg l I I  S ma I   Ps t I   Ea g I
MPSYN60       CTAAGATCTCCCGGGCTGCAGC
MPSYN61       GATTCTAGAGGGCCCGACGTCGCCGG   5'
``` reconstructing the DNA sequences upstream from the A56R ORF and replacing the A56R ORF with a polylinker region

```
                                                               Bg l I I
MPSYN82 (SEQ ID NO:19) 5' TTTCTGTATATTTGCACCAATTTAGATCTT-
                          ACTCAAAATATGTAACAATA   3'
``` as indicated above. The resulting plasmid is pSD466. The vaccinia deletion in pSD466 encompasses positions [161,185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

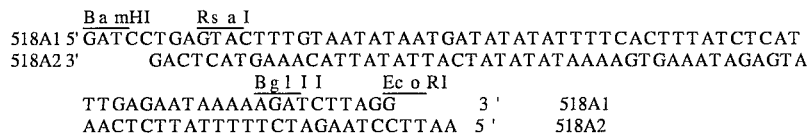

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTTAACACTATACTCATAT-TAATAAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

EXAMPLE 6

CONSTRUCTION OF PLASMID pSD548 FOR DELETION OF LARGE SUBUNIT, RIBONUCLEOTIDE REDUCTASE (I4L)

Figure 6:
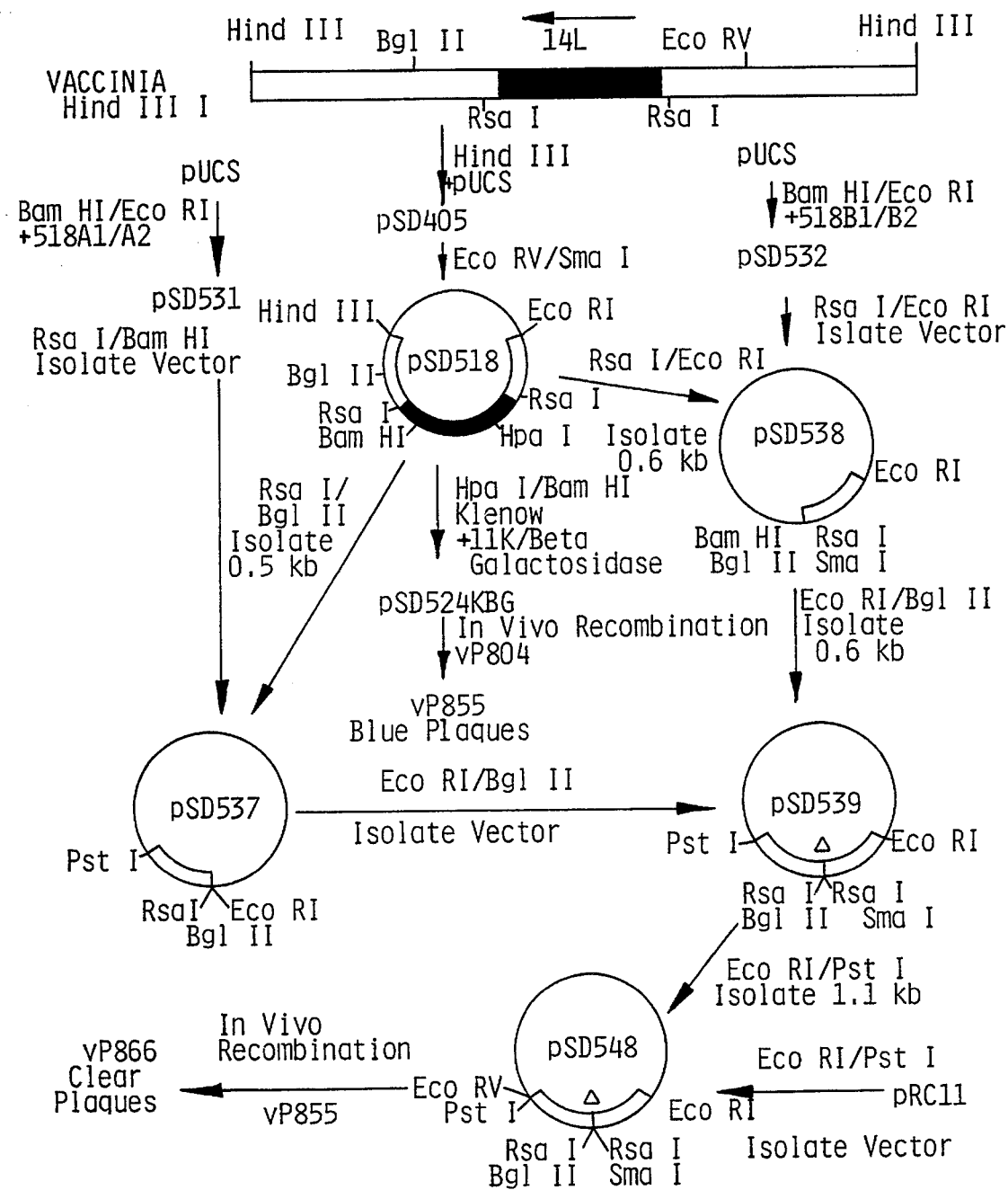
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

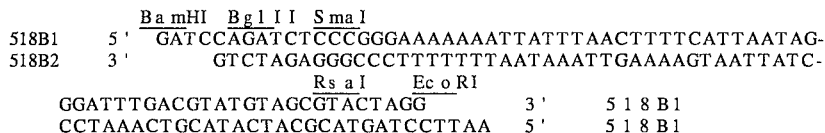

forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

forming plasmid pSD532. pSD532 was cut with RSaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

EXAMPLE 7

INSERTION OF A RABIES GLYCOPROTEIN G GENE INTO NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Figure 7:
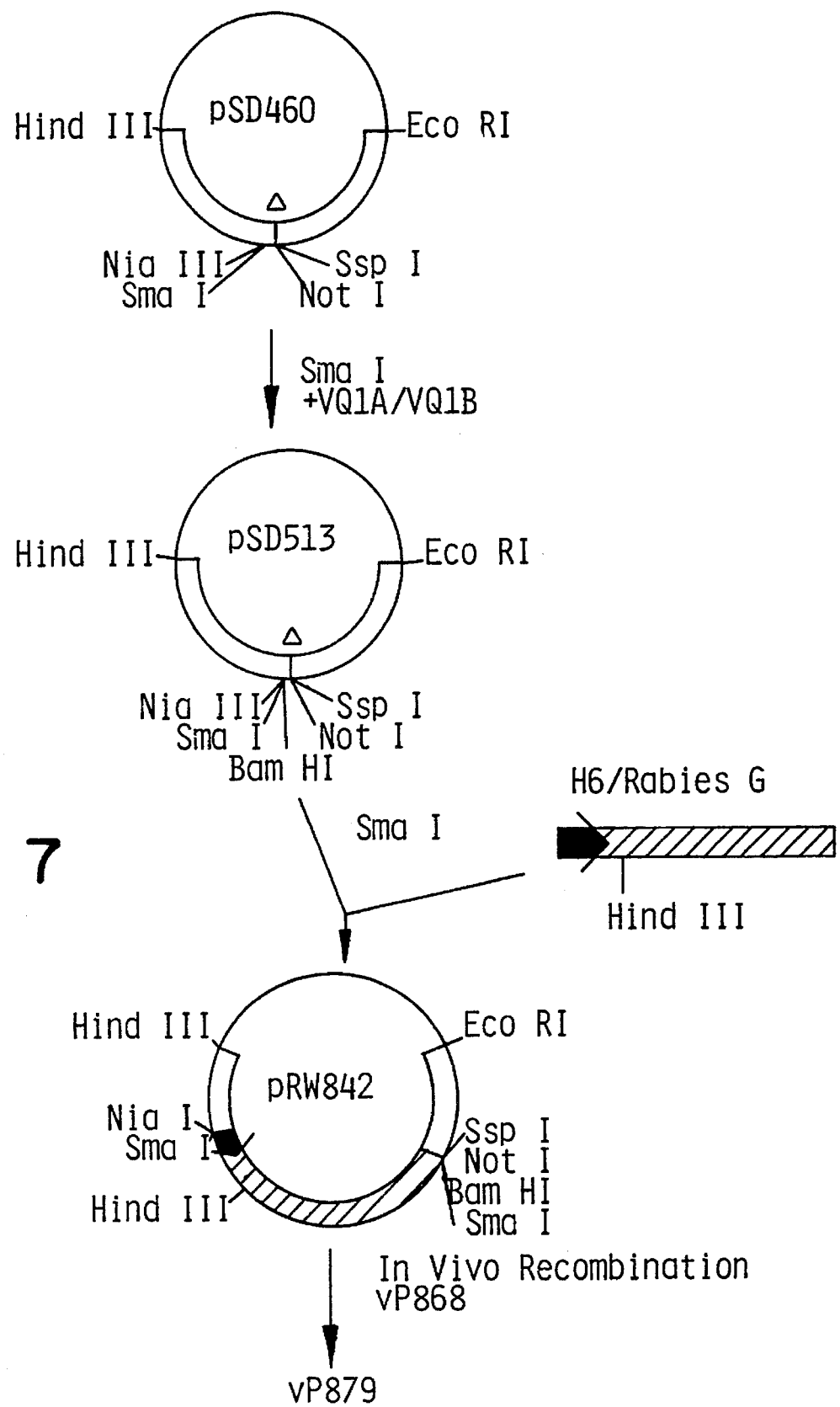
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
           SmaI  BglII  XhoI  PstI  NarI  BamHI
VQ1A  5'  GGGAGATCTCTCGAGCTGCAGGGCGCCGGATCCTTTTTCT  3'
VQ1B  3'  CCCTCTAGAGAGCTCGACGTCCCGCGGCCTAGGAAAAAGA  5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

EXAMPLE 8

CONSTRUCTION OF TROVAC-NDV EXPRESSING THE FUSION AND HEMAGGLUTININ-NEURAMINIDASE GLYCOPROTEINS OF NEWCASTLE DISEASE VIRUS

A fowlpox virus (FPV) vector expressing both F anti HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses. The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a Cassette for NDV-F. A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into pCE13 by digesting pCE13 with SalI, filling in the sticky ends with Klenow fragment of E. coli DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:27) and CE76 (SEQ ID NO:28) to generate pCE47.

CE75: CGATATCCGTTAAGTTTGTATCG-TAATGGGCTCCAGATCTTCTACCAG-GATCCCGGTAC

CE76: CGGGATCCTGGTAGAAGATCTGGAGC-CCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:29) and CE43 (SEQ ID NO:30) were then inserted to form pCE29.

CE42: AATTCGAGCTCCCCGGG
CE43: CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII - NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:31) and CE167 (SEQ ID NO:32) to generate pCE58.

CE166: CTTTTTATAAAAAGTTAACTACGTAG
CE167: GATCCTACGTAGTTAACTTTT-TATAAAAAGAGCT

A perfect 3' end for NDV-F was obtained by using the polymerase chain reaction (PCR) with pCE54 as template and oligonucleotides CE182 (SEQ ID NO:33) and CE183 (SEQ ID NO:34) as primers.

CE182: CTTAACTCAGCTGACTATCC
CE183: TACGTAGTTAACTTTTTATAAAAAT-CATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN. Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:35) and CE163 (SEQ ID NO:36) into the EcoRI site of pRW830 to form pCE59, the final cassette for NDV-HN.

Construction of Double Insertion Vector for NDV F and HN. The H6 promoted NDV-HN sequence was inserted into the H6 promoted NDV-F cassette by cloning a HindIII fragment from pCE59 that had been filled in with Klenow fragment of E. coli DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+. Plasmid pJCA021 was then digested with NdeI and BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV. Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

CE162:
AATTCAGGATCGTTCCTTTACTAGTTGAGATTCTCAAGGATGATGGGATTTAATTTTTAT
AAGCTTG

CE163:
AATTCAAGCTTATAAAAATTAAATCCCATCATCCTTGAGAATCTCAACTAGTAAAGGAAC
GATCCTG

Construction of FPV Insertion Vector. Plasmid pRW731-15 contains a 10 kb PvuII-PvuII fragment cloned from genomic DNA. The nucleotide sequence was determined on both strands for a 3660 bp PvuII-EcoRV fragment. The limits of an open reading frame designated here as F8 were determined. Plasmid pRW761 is a sub-clone of pRW731-15 containing a 2430 bp EcoRV-EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:37) and JCA018 (SEQ ID NO:38).

Immunofluorescence. Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation. Immunoprecipitation reactions were performed as described (Taylor et al., 1990) using a polyclonal anti-NDV serum obtained from SPAFAS Inc., Storrs, CN.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near

JCA017:5'
CTAGACACTTTATGTTTTTTAATATCCGGTCTTAAAAGCTTCCCGGGGATCCTTATACGG
GGAATAAT

JCA018:5'
ATTATTCCCCGTATAAGGATCCCCCGGGAAGCTTTTAAGACCGGATATTAAAAAACATAA
AGTGT

The plasmid resulting from this ligation was designated pJCA002.

the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO:39) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycolysated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant vFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

EXAMPLE 9

CONSTRUCTION OF NYVAC-MV RECOMBINANT EXPRESSINGMEASLES FUSION AND HEMAGGLUTININ GLYCOPROTEINS cDNA copies of the sequences encoding the HA and F proteins of measles virus MV (Edmonston strain) were inserted into NYVAC to create a double recombinant designated NYVAC-MV. The recombinant authentically expressed both measles glycoproteins on the surface of infected cells. Immunoprecipitation analysis demonstrated correct processing of both F and HA glycoproteins. The recombinant was also shown to induce syncytia formation.

Cells and Viruses. The rescuing virus used in the production of NYVAC-MV was the modified Copenhagen strain of vaccinia virus designated NYVAC. All viruses were grown and titered on Vero cell monolayers.

Plasmid Construction. Plasmid pSPM2LHA (Taylor et al., 1991c) contains the entire measles HA gene linked in a precise ATG to ATG configuration with the vaccinia virus H6 promoter which has been previously described (Taylor et al., 1988a,b; Guo et al., 1989; Perkus et al., 1989). A 1.8 kpb EcoRV/SmaI fragment containing the 3' most 24 bp of the H6 promoter fused in a precise ATG:ATG configuration with the HA gene lacking the 3' most 26 bp was isolated from pSPM2LHA. This fragment was used to replace the 1.8 kbp EcoRV/SmaI fragment of pSPMHHA11 (Taylor et al., 1991c) to generate pRW803. Plasmid pRW803 contains the en-tire H6 promoter linked precisely to the entire measles HA gene.

In the confirmation of previous constructs with the measles HA gene it was noted that the sequence for codon 18 (CCC) was deleted as compared to the published sequence (Alkhatib et al., 1986). The CCC sequence was replaced by oligonucleotide mutagenesis via the Kunkel method (Kunkel, 1985) using oligonucleotide RW117 (SEQ ID NO:40)

(5'GACTATCCTACTTCCCTTGGGATGGGGGTTATCTTTGTA-3').
PRO 18

Single stranded template was derived from plasmid pRW819 which contains the H6/HA cassette from pRW803 in pIBI25 (International Biotechnologies, Inc., New Haven, Conn.). The mutagenized plasmid containing the inserted (CCC) to encode for a proline residue at codon 18 was designated pRW820. The sequence between the HindIII and XbaI sites of pRW820 was confirmed by nucleotide sequence analysis. The HindIII site is situated at the 5' border of the H6 promoter while the XbaI site is located 230 bp downstream from the initiation codon of the HA gene. A 1.6 kbp XbaI/EcoRI fragment from pRW803, containing the HA coding sequences downstream from the XbaI (above) and including the termination codon, was used to replace the equivalent fragment of pRW820 resulting in the generation of pRW837. The mutagenized expression cassette contained within pRW837 was derived by digestion with HindIII and EcoRI, blunt-ended using the Klenow fragment of E. coli DNA polymerase in the presence of 2 mM dNTPs, and inserted into the SmaI site of pSD513 to yield pRW843. Plasmid pSD513 was derived from plasmid pSD460 by the addition of polylinker sequences. Plasmid pSD460 was derived to enable deletion of the thymidine kinase gene from vaccinia virus.

To insert the measles virus F gene into the HA insertion plasmid, manipulations were performed on pSPHMF7. Plasmid pSPHMF7 (Taylor et al., 1991c) contains the measles F gene juxtaposed 3' to the previously described vaccinia virus H6 promoter. In order to attain a perfect ATG for ATG configuration and remove intervening sequences between the 3' end of the promoter and the ATG of the measles F gene oligonucleotide directed mutagenesis was performed using oligonucleotide SPMAD (SEQ ID NO:41).
SPMAD: 5'-TATCCGTTAAGTTTGTATCG-TAATGGGTCTCAAGGTGAACGTCT-3'
The resultant plasmid was designated pSPMF75M20.

The plasmid pSPMF75M20 which contains the measles F gene now linked in a precise ATG for ATG configuration with the H6 promoter was digested with NruI and EagI. The resulting 1.7 kbp blunt ended fragment containing the 3' most 27 bp of the H6 promoter and the entire fusion gene was isolated and inserted into an intermediate plasmid pRW823 which had been digested with NruI and XbaI and blunt ended. The resultant plasmid pRW841 contains the H6 promoter linked to the measles F gene in the pIBI25 plasmid vector (International Biotechnologies, Inc., New Haven, Conn.). The H6/measles F cassette was excised from pRW841 by digestion with SmaI and the resulting 1.8 kb fragment was inserted into pRW843 (containing the measles HA gene). Plasmid pRW843 was first digested with NotI and blunt-ended witch Klenow fragment of E. coli DNA polymerase in the presence of 2 mM dNTPs. The resulting plasmid, pRW857, therefore contains the measles virus F and HA genes linked in a tail to tail configuration. Both genes are linked to the vaccinia virus H6 promoter.

Development of NYVAC-MV. Plasmid pRW857 was transfected into NYVAC infected Vero cells by using the calcium phosphate precipitation method previously described (Panicali et al., 1982; Piccini et al., 1987). Positive plaques were selected on the basis of in situ plaque hybridization to specific MV F and HA radiolabelled probes and subjected to 6 sequential rounds of plaque purification until a pure population was achieved. One representative plaque was then amplified and the resulting recombinant was designated NYVAC-MV (vP913).

Immunofluorescence. Indirect immunofluorescence was performed as previously described (Taylor et al., 1990). Mono-specific reagents used were sera generated by inoculation of rabbits with canarypox recombinants expressing either the measles F or HA genes.

Immunoprecipitation. Immunoprecipitation reactions were performed as previously described (Taylor et al., 1990) using a guinea-pig anti measles serum (Whittaker M. A. Bioproducts, Walkersville, Md.).

Cell Fusion Experiments. Vero cell monolayers in 60 mm dishes were inoculated at a multiplicity of 1 pfu per cell with parental or recombinant viruses. After 1 h absorption at 37° C. the inoculum was removed, the overlay medium replaced and the dishes inoculated overnight at 37° C. At 20 h post-infection, dishes were examined.

In order to determine that the expression products of both measles virus F and HA genes were presented on the infected cell surface, indirect immunofluorescence analysis was performed using mono-specific sera generated in rabbits against canarypox recombinants expressing either the measles F or HA genes. The results indicated that both F and HA gene products were expressed on the infected cell surface, as demonstrated by strong surface fluorescence with both mono-specific sera. No background staining was evident with either sera on cells inoculated with the parental NYVAC strain, nor was there cross-reactive staining when mono-specific sera were tested against vaccinia single recombinants expressing either the HA or F gene.

In order to demonstrate that the proteins expressed by NYVAC-MV were immunoreactive with measles virus specific sera and were authentically processed in the infected cell, immunoprecipitation analysis was performed. Vero cell monolayers were inoculated at a multiplicity of 10 pfu/cell of parental or recombinant viruses in the presence of $^{35}$S-methionine. Immunoprecipitation analysis revealed a HA glycoprotein of approximately 76 kDa and the cleaved fusion products $F_1$ and $F_2$ with molecular weights of 44 kDa and 23 kDa, respectively. No measles specific products were detected in uninfected Vero cells or Vero cells infected with the parental NYVAC virus.

A characteristic of MV cytopathology is the formation of syncytia which arise by fusion of infected cells with surrounding infected or uninfected cells followed by migration of the nuclei toward the center of the syncytium (Norrby et al., 1982). This has been shown to be an important method of viral spread, which for Paramyxoviruses, can occur in the presence of HA-specific virus neutralizing antibody (Merz et al., 1980). In order to determine that the MV proteins expressed in vaccinia virus were functionally active, Vero cell monolayers were inoculated with NYVAC and NYVAC-MV and observed for cytopathic effects. Strong cell fusing activity was evident in NYVAC-MV infected Vero cells at approximately 18 hours post infection. No cell fusing activity was evident in cells infected with parental NYVAC.

EXAMPLE 10

CONSTRUCTION OF NYVAC RECOMBINANTS EXPRESSING GLYCOPROTEINS OF PSEUDO-RABIES VIRUS

It has been demonstrated that vaccinia virus recombinants expressing the PRV gpII, gpIII, and gp50 glycoproteins either individually or in combination provide efficacious vaccine candidates, in that, they protect swine from a virulent challenge with live PRV. Considering the inability of the NYVAC vector to productively replicate in porcine cell cultures and the inherent safety of the vector due to the deletion of known potential virulence genes, NYVAC-based recombinants containing the PRV gpII, gpIII, and gp50 either alone or in various combinations have been generated. These recombinants were generated to provide efficacious vaccine candidates against PRV that were safe for swine and eliminated or severely limited transmission to the environment.

Viruses and Cells. Manipulations of NYVAC and molecular cloning were performed by standard techniques (Piccini et al., 1987; Maniatis et al., 1982). Cultivation Of NYVAC and NYVAC-based recombinants was as previously described (Piccini et al., 1987).

Cloning of the PRV gpII, gpIII, and gp50 Genes. The growth of PRV, extraction of PRV genomic DNA, and the identification of the PRV gpII, gpIII, and gp50 genes have been described.

Cloning and Expression of the Pseudorabies Virus (PRV) Genes into NYVAC (vP866). The NYVAC deletion mutant lacking a region encompassing the human and porcine host range genes (C7L and K1L), vP866, was the basic vector used to insert the PRV genes. This vector also lacks the vaccinia virus tk gene, hemagglutinin gene, hemorrhagic gene, ribonucleotide reductase (large subunit) gene, and A-type inclusion gene. Importantly, vP866 does not replicate efficiently, if at all, on human or pig kidney (LLC-PK1) cells. PRV genes gpII, gpIII, and gp50, which are homologous to the herpes simplex virus gB (Robbins et al., 1987), gC (Robbins et al., 1986b), and gD (Wathen and Wathen, 1984), respectively,, were inserted into vP866 as outlined below.

Insertion of the PRV gpII Gene into the Hemagglutinin Locus of vP866. The DNA sequence encoding the PRV gpII gene resides in the BamHI fragment 1 of the PRV genome (Mettenleiter et al., 1986).

The plasmid designated pPR9.25, containing the PRV BamHI fragment 1 inserted into the BamHI site of pBR322 was digested with NcoI. The resultant restriction fragments were fractionated on a 0.8% agarose gel and a 6.2 kb NcoI DNA fragment was purified using Geneclean (Bio101, Inc., LaJolla, Calif.) and subsequently inserted into the NcoI site of pBR328 (Boehringer Mannheim Biochemicals, Indianapolis, Ind.) treated with CiAP. The resulting plasmid, pPR2.15, was digested with SphI and fractionated on an agarose gel. The 2.7 kb and 1.8 kb fragments were purified and inserted into the SphI site of pUC18 to create pPR1 and pPR2, respectively.

The 1060 bp PRV SphI/NheI fragment from pPR1 was isolated from an agarose gel and inserted into the BamHI/SphI sites of pIBI25 with annealed oligonucleotides MRSYN1 (SEQ ID NO:42) (5'-GATCCATTCCATGGTTG-3') and MRSYN2 (SEQ ID NO:43) (5'-TAGCAACCATGGAATG-3') to generate pPR6. pPR6 was digested with HindIII and ApaI. The ApaI site is located 32 bp downstream from the ATG initiation codon of PRV gpII. This 3920 bp fragment was ligated to annealed oligonucleotides MRSYN3 (SEQ ID NO:44) (5'-AGCTTGATATCCGTTAAGTTTGTATCGTAATGCCCGCTGGTGGCGGTCTTTGGCGCGGGCC-3') and MRSYN4 (SEQ ID NO:45) (5'-CGCGCCAAAGACCGCCAACCAGCGGGATTACGATACAAACTTAACGGATATCA-3') to generate pPR9. These annealed oligonucleotides provide the DNA sequences specifying the vaccinia virus H6 promoter from the EcoRV site through the ATG, followed by the PRV gpII coding sequences. The plasmid pPR9 was digested with BamHI and NheI and treated with Calf Intestinal Alkaline Phosphatase (CiAP), and ligated to annealed oligonucleotides MRSYN7 (SEQ ID NO:46) (5'-CCCAGATCTCCTTG-3') and MRSYN8 (SEQ ID NO:47) (5'-GTACGGGTCTAGAGGAACCTAG-3') and a 1640 bp SphI/NheI fragment obtained from pPR1 generating plasmid pPR12.

The 1030 bp HindII/SphI fragment from pPR2 was isolated from an agarose gel and inserted into a HincII/SphI pUC18 vector. The resulting plasmid, pPR10, was digested with HindIII and NaeI and treated with CiAP. The NaeI site is located 44 bp upstream of the termination codon (TAG). Annealed oligonucleotides MRSYN9 (SEQ ID NO:48) (5'-GGCACTACCAGCGCCTCGAGAGCGAGGACCCCGACGCCCTGTAGAATTTTTATCGGCCGA-3') and MRSYN10 (SEQ ID NO:49) (5'-AGCTTCGGCCGATAAAAATTCTACAGGGCGTCGGGGTCCTCGCTCTCGAGGCGTAGTGCC-3') were ligated to the 3720 bp NaeI/HindIII fragment of pPR10 to yield plasmid pPR11. A 770 bp SphI/HincII fragment from pPR2 was purified from an agarose gel and inserted using the BamHI/SphI phosphorylated linker MRSYN7 (SEQ ID NO:46) and MRSYN8 (SEQ ID NO:47) into the BamHI/HincII sites of CiAP treated pPR11 to generate pPR13. Plasmid pPR12 digested with EcoRI and SphI was ligated using MRSYN19 (SEQ ID NO:50) (5'-AGCTTCTGCAGCCATGGCGATCGG-3') and MRSYN20 (SEQ ID NO:51) (5'-AATTCCGATCGCCATGGCTGCAGA-3') to a 990 bp HindIII/SphI fragment from pPR13 to yield plasmid pPR15. Plasmid, pPR15, was digested with HindIII/EcoRV to yield a 2780 bp fragment. This fragment was inserted into pTP15 (Guo et al., 1989) which was digested with XmaIII and EcoRV to generate pPR18. In pPR18, the PRVgpII is linked with the vaccinia virus H6 promoter in a HA deletion plasmid. pPR18 was used in in vitro recombination experiments with vP866 as the rescue virus to generate vP881.

Insertion of the PRV gpIII gene into the TK Locus of NYVAC. The sequences encoding the PRV gpIII gene map to the BamHI 2 and 9 fragments of the PRV genome (Robbins et al., 1986b). Plasmids pPR9.9 and pPR7.35 contain the PRV BamHI fragments 2 and 9, respectively, inserted into the BamHI site of pBR322. An SphI/BamHI fragment containing the 5' end of the PRV gpIII gene was isolated from pPR9.9. An NcoI/BamHI fragment containing the remainder of the gpIII gene was isolated from pPR7.35. The entire PRV gpIII gene was assembled by the ligation of these two fragments into pIBI25 to yield pPR17.

The PRV gpIII gene was manipulated to be expressed under the control of the early vaccinia virus hemorrhagic promoter, located in the HindIII B region (Goebel et al., 1990a,b). Using site-directed mutagenesis, an NsiI site was introduced by changing the sequence CGC (bases 192–194) in PRV gpIII to ATG and an XbaI site was introduced by changing the sequence GTCACGT to TTCTAGA (bases 1632–1638). To perform the mutagenesis reactions, single-stranded DNA was generated from plasmid pPR17 using the helper phage R408 (Stratagene, LaJolla, Calif.). The site-directed mutagenesis was done using MRSYN5 (SEQ ID NO:52) (5'-GCGAGCGAGGCCATGCATCGTGCGAATGGCCCC-3') and MRSYN6 (SEQ ID NO:53) (5'-GGGGGGACGCGCGGGTCTAGAAGGCCCCGCCTGGCGG-3') and selection on *E. coli* $dut^-$ $ung^-$ strain. CJ236 (International Biotechnologies, Inc., New Haven, Conn.). Mutagenesis was performed according to the protocols of Kunkel (1985). These mutations resulted in the generation of plasmid pPR28.

Plasmid pPR28 was digested with NsiI and XbaI and treated with Mung bean nuclease. A 1440 bp fragment was purified and inserted into a BglII/HpaI digested pSD478VC after treatment with Mung bean nuclease and calf-intestine alkaline phosphatase. The resultant plasmid was designated as pPR24.

The plasmid pPR24 was digested with SnaB1 and DraI to liberate a 1500 bp blunt-ended fragment containing the u promoter and PRV gpIII gene. This fragment was ligated into SmaI digested pSD513VC to yield pPRVIIIVCTK. In vitro recombination experiments were performed with pPRVIIIVCTK and vP866 as the rescue virus to generate vP883. In vP883, the vaccinia tk coding sequences are replaced by the PRV gpIII gene inserted in a right to left orientation, with respect to the genome, under the control of the 120 bp vaccinia u promoter element.

Insertion of the PRV gp50 Gene into the ATI Locus of NYVAC. DNA encoding the gene for the PRV glycoprotein gp50 is located on the BamHI fragment 7 of the PRV genome (Petrovskis et al., 1986a,b). Plasmid pPR7.1 contains the PRV BamHI fragment 7 inserted into the BamHI site of pBR322. A StuI/NdeI subfragment of pPR7.1 containing the entire gp50 gene was subcloned into pIBI25 to yield plasmid #856.

The coding sequences for PRV gp50 were placed under the control of the early/intermediate vaccinia promoter, I3L (Schmitt and Stunnenberg, 1988; Vos and Stunnenberg, 1988). This promoter element has been used previously to express foreign genes in vaccinia recombinants (Perkus et al., 1985; Bucher et al., 1989). DNA corresponding to promoter sequences upstream from the I3L open reading frame (Schmitt and Stunnenberg, 1988) was derived by PCR (Saiki et al., 1988) using synthetic oligonucleotides P50PPBAM (SEQ ID NO:54) (5'-ATCATCGGATCCG-GTGGTTTGCCATTCCG-3') and P50PPATG (SEQ ID NO:55) (5'-GATTAAACCTAAATAATTG-3') and pMPIVC, a subclone of the Copenhagen HindIII I region, as template. The resulting 126 bp fragment was digested with BamHI to generate a BamHI cohesive end at the 5' end of the promoter sequence. The 3' end remained blunt-ended.

The PRV gp50 coding region was excised from plasmid #856. Plasmid #856 was initially digested with NsiI, which cuts 7 bp upstream from the ATG and results in a 3' overhang. The 3' overhang was blunt-ended with T4 DNA polymerase in the presence of 2 mM dNTPs. The resulting DNA was partially digested with BglII, and a 1.3 kb blunt/BglII fragment containing the PRV gp50 gene was isolated.

The 126 bp I3L promoter fragment (BamHI/blunt) and the 1.3 kb gp50 gene containing fragment (blunt/BglII) were ligated into pBS-SK (Stratagene, La Jolla, Calif.) digested with BamHI. The resultant plasmid was designated as pBSPRV50I3. The expression cassette containing the I3L promoter linked to the PRV gp50 gene was excised by a BamHI/partial SmaI digestion. A 1.4 kb fragment containing the I3L promoter/PRV gp50 gene was isolated and blunt-ended using the Klenow fragment of the *E. coli* DNA polymerase in the presence of 2 mM dNTPs.

The 1.4 kb blunt-ended fragment containing the I3L promoter/PRV gp50 gene was inserted into the ATI insertion plasmid pSD541. Flanking arms for the ATI region were generated by PCR using subclones of the Copenhagen HindIII A region as template. Oligonucleotides MPSYN267 (SEQ ID NO:56) (5'-GGGCTGAAGCTTGCGGCCGCT-CATTAGACAAGCGAATGAGGGAC-3') and MPSYN268 (SEQ ID NO:57) (5'-AGATCTCCCGGGCTCGAGTAAT-TAATTAATTTTTATTACACCAGAAA-GACGGCTTGAGATC-3') were used to derive the 420 bp vaccinia arm to the right of the ATI deletion. Synthetic oligonucleotides MPSYN269 (SEQ ID NO:58) (5'-TAAT-TACTGAGCCCGGGAGATATAATTTAATT-TAATTTATATAACTCATTTTTTCCCC3') and MPSYN270 (SEQ ID NO:59) (5'-TATCTCGAATTC-CCGCGGCTTTAAATGGACGGAACTCTTTTCCC-3') were used to derive the 420 bp vaccinia arm to the left of the deletion. The left and right arms were fused together by PCR and are separated by a polylinker region specifying restriction sites for BglII, SmaI, and XhoI. The PCR-generated fragment was digested with HindIII and EcoRI to yield sticky ends, and ligated into pUC8 digested with HindIII and EcoRI to generate pSD541.

The pSD541 plasmid containing the I3L/PRV gp50 gene was designated as pATIgp50. This plasmid was used in in vitro recombination experiments to generate vP900. vP900 contains the PRV gp50 gene in place of the ATI gene.

Generation of Double and Triple PRV Recombinants in NYVAC. In vitro recombination experiments were performed to generate NYVAC-based recombinants containing multiple PRV genes. In vitro recombination experiments using the donor plasmid, pATIP50, were performed with vP881, vP883, and vP915 to generate vP912, vP916, and vP925, respectively (Table 1). Experiments were done with plasmid pPR18 and vP883 as rescue virus to yield vP915 (Table 1).

Immunoprecipitation from NYVAC/PRV Recombinant Infected Cells. Vero cells were infected at an m.o.i. of 10 pfu per cell with the individual recombinant viruses, with the NYVAC parent virus, or were mock infected. After a 1 hr absorption period, the inoculum was removed and infected cells were overlaid with methionine-free media containing $^{35}$S-methionine (20 uCi/ml). All samples were harvested at 8 hr post infection. For samples analyzed with the sheep anti-gpII sera, cells were harvested by centrifugation and were dissociated with RIPA buffer (1% NP-40, 1% Na-deoxycholate, 0.1% SDS, 0.01M methionine, 5 mM EDTA, 5 mM 2-mercapto-ethanol, 1 m/ml BSA, and 100 u/ml aprotinin). Samples analyzed with sheep anti-gpIII and a monoclonal specific for gp50 were lysed in 1× Buffer A (1% NP40, 10 mM Tris (pH7.4), 150 mM NaCl, 1 mM EDTA, 0.0% Na Azide, 0.2 mg/ml PMSF). All sera was preadsorbed with vP866 infected Vero cells and all lysates were preadsorbed with normal sera (sheep or mouse) and protein A-sepharose linked to the secondary antibody.

Lysates from the infected cells were analyzed for PRV gpII expression using a sheep anti-gpII serum. This primary antiserum was incubated with protein A-sepharose conjugated with rabbit anti-sheep IgG (Boehringer-Mannheim). After an overnight incubation at 4° C. samples were washed 4 times with 1×RIPA buffer, 2 times with LiCl-urea (0.2M LiCl, 2M urea, 10 mM Tris, ph 8.0). Precipitates were harvested by micro centrifugation. Precipitated protein was dissociated from the immune complexes by the addition of 2× Laemmli's buffer (125 mM Tris (pH 6.8), 4% (SDS), 20% glycerol, 10% 2 mercapto-ethanol) and boiling for 5 min. Proteins were fractionated on a 10% Dreyfuss gel system (Dreyfuss et al., 1984), fixed and treated with 1M Na-Salicylate for fluorography.

Lysates were analyzed for PRV gpIII expression using a sheep-anti gpIII sera. This primary antisera was incubated with Protein A-Sepharose conjugated with rabbit anti-sheep IgG (Boehringer-Mannhein). After an overnight incubation at 4° C., samples were washed 4 times with 1× Buffer A and 2 times with the LiCl-urea buffer. Precipitates were treated and analyzed by flurography as described above.

Lysates were analyzed for PRV gp50 expression using monoclonal antibody, 22M4 (provided by Rhone Merieux, Lyon, France). This primary antibody was incubated with Protein A-Sepharose conjugated with goat anti-mouse IgG and IgM (Boehringer-Mannheim). The precipitates were recovered and analyzed as described above for the PRV gpIII immunoprecipitations.

Expression of the PRV Glycoproteins in Cells Infected with the NYVAC/PRV Recombinants. The PRV gpII, gpIII, and gp50 products are typical glycoproteins associated with membranous structures in PRV infected cells. Anti-gpII, anti-gpIII and anti-gp50 specific monoclonal antibodies followed by fluorescein-conjugated goat anti-mouse IgG were used to analyze the PRV glycoprotein expression on the surface of recombinant infected Vero cells. Surface expression of neither gpII, gpIII, nor gp50 was detectable on the surface of mock infected cells or cells infected with the NYVAC (vP866) parent virus. PRV gpII expression was observed on the surface of vP881, vP912, vP915, and vP925 infected cells. PRV gpIII surface expression was observed in vP883, vP915, vP916, and vP925 infected cells. PRV gp50 surface expression was observed in vP900, vP912, vP916, and vP925 infected cells. In summary, the surface expression of the particular PRV glycoproteins was only detectable in cells infected with NYVAC/PRV recombinants containing the appropriate PRV gene(s).

Immunoprecipitation of PRV Glycoproteins from Cells Infected with the NYVAC/PRV Recombinants. The authenticity of the expressed PRV gpII, gpIII, and gp50 glycoproteins in Vero cells infected with the NYVAC/PRV recombinants was analyzed by immunoprecipitation. The PRV gpII gene product represents one of the major glycoproteins encoded in PRV-infected cells. The mature protein consists of a complex of glycoproteins linked by disulfide bonds (Hampl et al., 1984; Lukacs et al., 1985). Under reducing conditions, three species are resolved from this complex. These species (IIa–IIc) migrate with apparent size of 120 kDa, 74–67 kDa, and 58 kDa, respectively, on an SDS-polyacrylamide gel (Hampl et al., 1984).

In immunoprecipitation analyses using the anti-PRVgpII specific serum, no PRY-specific protein species were precipitated from mock infected cells or cells infected with the NYVAC (vP866) parent virus. PRV gpII was also not detectable in cells infected with the non-gpII containing NYVAC/PRV recombinants vP916, vP883, and vP900. It is evident that PRV gpII was expressed in all the NYVAC/PRV recombinants which harbor the PRV gpII gene. These are vP925, vP912, vP915 and vP881. Lysates from Vero cells infected with the PRV gpII containing recombinants all contained protein species consistent with the proper expression and processing of gpII to gpIIa (120 kDa), gpIIb (74–67 kDa), and gIIc (58 kDa). Two additional protein species of 45 kDa and 10 kDa were specifically precipitated with the anti-gpII serum. These protein species appear to emerge by an aberrant proteolytic processing of PRV gpII at late times in recombinant infected cells.

The PRV gpIII product is another major PRV glycoprotein. The gpIII exists as a monomer not complexed with other viral proteins that migrates with an apparent molecular weight of 92 kDa (Hampl et al., 1984; Robbins et al., 1986b). In immunoprecipitation analyses from NYVAC/PRV recombinant infected cells using antisera specific for gpIII, no anti-gpIII specific protein species were present in lysates from mock infected cells, nonrecombinant infected cells, or cells infected with NYVAC/PRV recombinants not containing gpIII (vP912, vP881, and vP900, respectively). Lysates from vP925, vP915, vP916, and vP883 infected cells all contained the 92 kDa PRV gpIII gene product.

The mature PRV gp50 gene product is approximately 50 to 60 kDa (Petrovskis et al., 1986a; Wathen et al., 1984), that most likely contains O-linked carbohydrate (Petrovskis et al., 1986b). In immunoprecipitations from lysates of cells infected with the NYVAC/PRV recombinants using antisera specific to the PRV gp50 gene product, gp50 was not present in lysates from mock infected cells, nonrecombinant infected cells, and cells infected with the recombinants not containing the gp50 gene (vP915, vP881, and vP883, respectively). Lysates from cells infected with recombinant NYVAC viruses containing the PRV gp50 gene (vP925, vP912, vP916, and vP900, respectively) all expressed a 50–60 kDa protein species which was specifically precipitated with the anti-PRV gp50 serum.

TABLE 1

NYVAC Recombinants Expressing PRV glycoproteins gpII, gpIII and gp50

| Recombinant | Parent | Donor Plasmid | PRV Glycoprotein |
|---|---|---|---|
| vP881 | vP866 | pPR18 | gpII |
| vP883 | vP866 | pPRVIIIVCTK | gpIII |
| vP900 | vP866 | pATIgp50 | gp50 |
| vP912 | vP881 | pATIgp50 | gpII, gp50 |
| vP915 | vP883 | pPR18 | gpII, gpIII |
| vP916 | vP883 | pATIgp50 | gpIII, gp50 |
| vP925 | vP915 | pATIgp50 | gpII, gpIII, gp50 |

EXAMPLE 11

CONSTRUCTION OF NYVAC RECOMBINANTS EXPRESSING THE gp340, gB and gH GENES OF EPSTEIN-BARR VIRUS A NYVAC donor plasmid containing the EBV gp340, gB, and gH genes was constructed. This donor plasmid was used to generate two recombinants: vP941 and vP944.

Restriction enzymes were obtained from Bethesda Research Laboratories, Inc. (Gaithersburg, Md.), New England BioLabs, Inc. (Beverly, Mass.) or Boehringer-Mannheim (Indianapolis, Ind.). T4 DNA ligase and DNA polymerase I Klenow fragment were obtained from New England BioLabs, Inc. Standard recombinant DNA techniques were used (Maniatis et al., 1982) with minor modifications for cloning, screening and plasmid purification. Nucleic acid sequences were confirmed using standard dideoxychain-termination reactions (Sanger, 1977) on alkaline-denatured double-stranded plasmid templates. M13mp18 phage, pIBI24 and pIBI25 plasmids were obtained from International Biotechnologies, Inc., Conn.

Cell Lines and Virus Strains. NYVAC was used as a rescue virus to generate recombinants. All vaccinia virus stocks were produced in Vero (ATCC CCL81) cells in Eagles MEM medium supplemented with 5–10% newborn calf serum (Flow Laboratories, Mclean, Va.).

Oligonucleotide-Directed Mutagenesis. The uracil-substituted single-stranded DNA template used for the mutagenesis reactions was from CJ236 transformed cells. The mutations were achieved by using the protocol of Kunkel et al. (1987). The various oligonucleotides were synthesized using standard chemistries (Biosearch 8700, San Rafael, Calif.; Applied Biosystems 380B, Foster City, Calif.)

Construction of Vaccinia Virus Recombinants. Procedures for transfection of recombinant donor plasmids into tissue culture cells infected with a rescuing vaccinia virus and identification of recombinants by in situ hybridization on nitrocellulose filters were as previously described (Panicali et al., 1982; Piccini et al., 1987).

Modifications and Expression in Vaccinia Recombinants of EBV Genes gp340, gB, and gH. The gp340 gene corresponds to the open reading frame BLLF1a of the complete EBV sequence (Baer et al., 1984). The gp220 gene derives from the gp340 mRNA by an internal splicing event (open reading frame BLLF1b). The gp340 and gp220 genes were isolated from cDNA clones (plasmids pMLPgp340 and pMLPgp220, respectively) provided by Dr. Perricaudet (Centre de Recherche sur le Cancer-IRSG, 7 rue Guy Mocquet, 94802 Villejuif, France).

The 2100 bp XmaI/ClaI fragment of pMLPgp220 was inserted into XmaI/ClaI M13 mp18, and the resulting plasmid was called mp18gp220. By in vitro mutagenesis using the oligonucleotides CM4 and CM5 the 5' and 3' extremities of gp220 gene were modified for expression under the control of the vaccinia H6 promoter. The plasmid containing the modified gp220 gene was called mp18gp220(4+5). The nucleotide composition of CM4 (SEQ ID NO:60) and CM5 (SEQ ID NO:61) were as follows:

CM4: TAAAGTCAATAAATTTTTATTGCGGCCGCTACCGAGCTCGAATTCG
              NotI

CM5: GCTTGCATGCCTGCA<u>GATAT</u>CCGTTAAGTTTGTATCGTAATGGAGGCAGCCTTGC
                    EcoRV                                  Met

The 2300 bp NarI/EcoRV fragment of mp18gp220(4+5) was cloned into the NarI/EcoRV plasmid SP131NotI. SP131NotI contains the complete H6 vaccinia promoter as previously defined (Taylor et al., 1988a, b). The resulting plasmid was called SP131gp220.

The 2360 bp ScaI/XhoI fragment of pMLPgp340 was cloned into the ScaI/XhoI SP131gp220 plasmid. The resulting plasmid was called SP131gp340.

The 2800 bp NotI/NotI fragment of SP131gp340 was cloned into the SmaI digested vaccinia donor plasmid pSD486. The resulting plasmid was called 486H6340.

The EBV gB gene corresponds to the open reading frame BALF4 of the complete EBV sequence (Baer et al., 1984). A 3500 bp EcoRI/XmnI fragment was isolated from the EBV BamHI A fragment and cloned into the HincII/EcoRI plasmid pIBI25. The resulting plasmid was called p25gB.

By in vitro mutagenesis, using the oligonucleotides EBVM5 (SEQ ID NO:62) and EBVM3 (SEQ ID NO:63), the EBV gB gene was adapted for expression under the control of the vaccinia H6 promoter. The nucleotide composition of EBVM5 (SEQ ID NO:62) and EBVM3 (SEQ ID NO:63) were as follows:
EBVM5: CCCTACGCCGAGTCATTACGATACAAACTTAACGGATATCAGAGTCGTACGTAGG
EBVM3: CTGGAAACACTTGGGAATTCAAGCTTCATAAAAAGGGTTATAGAAGAGTCC
The resulting plasmid was called p25gB(5+3).

The 2600 bp EcoRV/EcoRI fragment of p25gB(5+3) was cloned into the EcoRV/EcoRI Sp131 plasmid. The resulting plasmid was called SP131gB.

The EBV gH gene corresponds to the BXLF2 open reading frame of the complete EBV sequence (Baer et al., 1984). The complete BXLF2 open reading frame is contained in two BamHI EBV fragments: BamHI X and BamHI T. The complete BXLF2 open reading frame was reconstituted by cloning the 830 bp SmaI/BamHI fragment of EBV BamHI T fragment into the SmaI/BamHI pIBI24 plasmid; the resulting plasmid was called 24gH5. The 1850 bp BamHI/HindIII fragment of EBV BamHI X fragment was cloned into the BamHI/HindIII 24gH5 plasmid. The resulting plasmid was called 24gH.

By in vitro mutagenesis using the oligonucleotides HM5, HM4, and HM3 the EBV gH gene was modified to be expressed under the control of the vaccinia B13R hemorrhagic promoter (Goebel et al., 1990a,b). The oligonucleotide HM4 was used to modify a sequence corresponding to a vaccinia early transcription termination signal. The nucleotide compositions of HM5 (SEQ ID NO:64), HM4 (SEQ ID NO:65), and HM3 (SEQ ID NO:66) were as follows:
HM5: ACACAGAGCAACTGCAGATCTCCCGATTTCCCCTCT
HM4: GGGCAAAGCCACAAAATATGCAGGATTTCTGCG
HM3: GCCAGGGTTTTCCCAGATCTGATAAAAACGACGGCCAGTG
The resulting plasmid containing the modified gH was called 24gH(5+4+3).

The vaccinia hemorrhagic promoter does not appear to be a strong promoter when compared with other pox promoters. The EBV gH gene has been placed under the control of the 42 kDa entomopox promoter. This was achieved by using the polymerase chain reaction (PCR), specific oligonucleotides 42gH (SEQ ID NO:67) and BAMgH (SEQ ID NO:68) and the plasmid 24gH(5+4+3) as template.

42gH: GGGTCAAAATTGAAAATATATAATTACAATATAAAATGCAGTTGCTCTGTGTT
                                                                      Met

BAMgH: ATGGATCCTTCAGAGACAG (The first A residue corresponds to position 292 of the gH coding sequence)

The PCR reaction was processed in a Thermal Cycler (Perkin Elmer Cetus, Norwalk, Conn.) with 36 cycles at 94° C. for 1 minute, 42° C. for 1.5 minutes, and 72° C. for 3 minutes, and a final extension step at 72° C. for 5 minutes. The PCR product was purified, digested with BamHI and cloned into the 4550 bp SmaI/BamHI fragment of 24gH(5+4+3). The resulting plasmid was called 24BXLF2.42K.

Insertion of EBV gp340, gB, and gH Genes into the Vaccinia Donor Plasmid pSD542 and Isolation of vP941 and vP944. The vaccinia donor plasmid pSD542 is a derivative of pSD460 with an expanded polylinker region; it is used to recombine foreign genes into the vaccinia TK locus.

The 2820 bp BamHI/BglII fragment of 486H6340 plasmid was cloned into the BamHI/BglII pSD542 plasmid. The resulting plasmid was called 542.340.

The 2150 bp SmaI/BglII fragment of 24BXLF2.42K plasmid was cloned into the SmaI/BglII 542.340 plasmid. The resulting plasmid was called 542.340gH.

Figure 8:
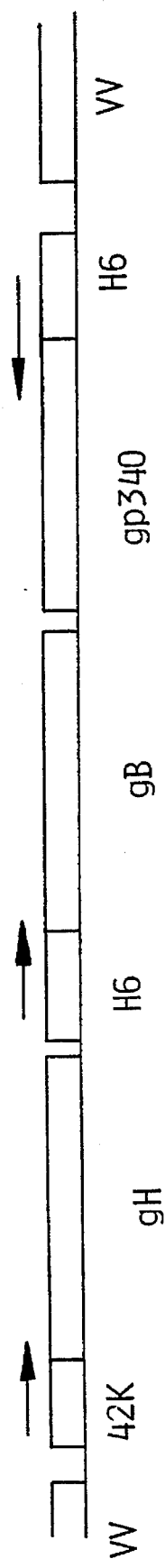
FIG. 8 is a map of the EBV coding regions inserted into EBV Triple.1 plasmid.

The 2700 bp HindIII/HindIII fragment of SP131gB plasmid was cloned into the BglII 542.340gH plasmid. The resulting plasmid was called EBV Triple.1. A map of the EBV coding regions inserted into EBV Triple.1 plasmid is presented in FIG. 8. The direction of transcription is indicated by the arrows in FIG. 8.

EBV Triple.1 plasmid was digested by NotI and transfected into Vero cells infected with NYVAC or vP919, a NYVAC based vaccinia recombinant containing three HBV genes. The corresponding recombinant vaccinia viruses vP944 and vP941 were isolated.

EXAMPLE 12

CONSTRUCTION OF NYVAC RECOMBINANTS EXPRESSING THE gB, gC and gD GENES OF HERPES SIMPLEX VIRUS TYPE 2

A recombinant vaccinia virus that expresses the HSV2 gB, gC and gD genes was constructed.

Cells and Viruses. HSV 2 (strain G) was propagated in VERO cells (ATCC CCL81) and purified by centrifugation on a sucrose gradient (Powell et al., 1975).

Vaccinia virus (Copenhagen) and recombinants derived therefrom were propagated in VERO cells (ATCC CCL81) as previously described (Panicali et al., 1982; Guo et al., 1989).

Isolation of the HSV2 gB Gene. A 12 kb BglII fragment, containing the HSV2 gB gene, was isolated from HSV2 genomic DNA and inserted into the BamHI site ofsite of pSD48 pUC19. The resulting plasmid was designated pJ4.

The gB gene was then cloned between vaccinia virus flanking arms. This was accomplished by cloning the 2,700 bp SstII-SacI (partial) fragment of pJ4 into the SstII-SacI fragment of pMP409DVC (Guo et al., 1989). This placed the gB gene between the vaccinia virus sequences flanking the M2L gene. The plasmid generated by this manipulation was designated pGB1.

An in-frame termination codon was then added to the 3'-end of the gB gene. This was accomplished by cloning the oligonucleotides, GBL3 (SEQ ID NO:69) 5'-CTAATAG-3' and GBL4 (SEQ ID NO:70) 5'-GATCCTATTAGAGCT-3', into the 6,300 bp BamHI-SacI (partial) fragment of pGB1. The plasmid generated by this manipulation was designated pGB2.

The vaccinia virus H6 promoter (Taylor et al., 1988a, b; Perkus et al., 1989) was then cloned upstream of the gB gene. This was accomplished by cloning the 370 bp BglII fragment of pBLVH14 (Portetelle et al., 1991), containing the H6 promoter, into the BglII site of pGB2. The plasmid generated by this manipulation was designated pGB3.

The initiation codon of the H6 promoter was then aligned with the initiation codon of the gB gene. This was accomplished by cloning the oligonucleotides, GBL1 (SEQ ID NO:71) 5'-ATCCGTTAAGTTTGTATCGTAAT-GCGCGGGGGGGGCTTGATTTGCGCGCTG-GTCGTGGGGGCGCTGGTGGCCGC-3' and GBL2 (SEQ ID NO:72) 5'-GGCCACCAGCGCCCCCACGAC-CAGCGCGCAAATCAAGCCCCCCCGCG-CATTACGATACAAACTTAACGGAT-3', into the 6,300 bp SstII-EcoRV (partial) fragment of pGB3. The plasmid generated by this manipulation was designated pGB5.

The H6-promoted gB gene was then cloned into a different vaccinia virus donor plasmid. This was accomplished by cloning the 2,800 bp BglII-BamHI fragment of pGB5, containing the H6-promoted gB gene, into the BglII site of pSD513VCVQ. (pSD513VCVQ is a subclone of the vaccinia virus HindIII J fragment in which the thymidine kinase (tk) gene is replaced by a polylinker region.) This placed the H6-promoted gB gene between the vaccinia virus sequences flanking the tk gene. The plasmid generated by this manipulation was designated pGB6.

Isolation of the HSV2 gC Gene. A 2,900 bp SalI fragment, containing the HSV2 gC gene, was isolated from HSV2 genomic DNA and inserted into the SalI site of pIBI25. The resulting plasmid was designated pGC3.

The gC gene was then cloned between vaccinia virus flanking arms. This was accomplished by cloning the 2,900 bp XhoI-BamHI fragment of pGC3 into the XhoI-BamHI site of pGC2. pGC2 was generated by cloning the 370 bp BglII fragment of pBLVH14 (Portetelle et al., 1991), containing the H6 promoter, into the BglII site of pSD486 (FIG. 2). This placed the gC gene between the vaccinia virus sequences flanking the u gene. The plasmid generated by this manipulation was designated pGC5.

The initiation codon of the H6 promoter was then aligned with the initiation codon of the gC gene. This was accomplished by cloning the oligonucleotides, GCL1 (SEQ ID NO:73) 5'-ATCCGTTAAGTTTGTATCGTAATGGC-CCTTGGACGGGTGGGCCTAGCCGTGGGCCTGTG3' and GCL2 (SEQ ID NO:74) 5'-AGGCCCACGGCTAGGC-CCACCCGTCCAAGGGCCATTACGATA-CAAACTTAACGGAT-3', into the 5,400 bp NruI-SfiI fragment of pGC5. The plasmid generated by this manipulation was designated pGC10.

Extraneous 3'-noncoding sequence was then eliminated from pGC10. This was accomplished by recircularizing the E. coli DNA polymerase I (Klenow fragment) filled-in 4,900 bp SalI-SmaI (partial) fragment of pGC10. The plasmid generated by this manipulation was designated pGC11.

Additional 3'-noncoding sequence was then eliminated from pGC11. This was accomplished by cloning the oligonucleotide, GCL3 5'-CTAGGGCC-3', into the 4,900 bp XbaI-ApaI (partial) fragment of pGC11. The plasmid generated by this manipulation was designated pGC12.

Isolation of the HSV2 gD Gene. A 7.5 kb XbaI fragment, containing the HSV2 gD gene, was isolated from HSV2 genomic DNA and inserted into the XbaI site of pIBI25. The resulting plasmid was designated pGD1.

The gD gene was then cloned downstream of the H6 promoter and between vaccinia virus flanking arms. This was accomplished by cloning the 1,500 bp DraI-PstI fragment of pGD1 into the 3,700 bp SmaI-PstI fragment of pTP15 (Guo et al., 1989). This placed the gD gene downstream of the H6 promoter and between the vaccinia virus sequences flanking the HA gene. The plasmid generated by this manipulation was designated pGD2.

The initiation codon of the H6 promoter was then aligned with the initiation codon of the gD gene. This was accomplished by cloning the oligonucleotides, GDL1 (SEQ ID NO:75) 5'-ATCCGTTAAGTTTGTATCG-TAATGGGGCGTTTGACCTCCGG-3' and GDL2 (SEQ ID NO:76) 5'-CGCCGGAGGTCAAACGCCCCATTAC-GATACAAACTTAACGGAT-3', into the 5,100 bp EcoRV-AhaII (partial) fragment of pGD2. The plasmid generated by this manipulation was designated pGD5.

Extraneous 3'-noncoding sequence was then eliminated. This was accomplished by cloning the oligonucleotides, GDL3 (SEQ ID NO:77) 5'-GGCAGTACCCTGGCG-GCGCTGGTCATCGGCGGTAT-TGCGTTTTGGGTACGCCGCCGGCGCT-CAGTGGCCCCCAAGCGCCTACGTCTCCCCCACATC-CGGGAT GACGACGCGCCCCCCTCGCACCAGCCAT-TGTTTTACTAGCTGCA- 3' and GDL4 (SEQ ID NO:78) 5'-GCTAGTAAAACAATGGCTGGTGC-GAGGGGGGCGCGTCGTCATCCCGGAT-GTGGGGGAGACGTAGGCGCTTGGGGGC-CACTGAGCGCC GGCGGCGTACCCAAAACGCAATACCGC-CGATGACCAGCGCCGCCAGGGTACTGCC-3', into the 4,800 bp NaeI-PstI fragment of pGD5. The plasmid generated by this manipulation was designated pGD7.

Additional sequence was then added upstream of the H6 promoter. This was accomplished by cloning the 150 bp BglII-EcoRV fragment of pGB6 (see above) into the 4,800 bp BglII-EcoRV fragment of pGD7. The plasmid generated by this manipulation was designated pGD8.

Construction of a Vaccinia Virus Donor Plasmid Containing the HSV2 gB, gC and gD Genes. A plasmid containing the gC and gD genes was constructed. This was accomplished by cloning the 1,850 bp PstI fragment of pGC12, containing the H6-promoted gC gene, into the PstI site of pGD8. The plasmid generated by this manipulation was designated pGCD1.

A plasmid containing the gB, gC and gD genes was then constructed. This was accomplished by cloning the 2,800 bp BglII-BamHI fragment of pGB6, containing the H6-promoted gB gene, into the 6,800 bp BamHI (partial) fragment of pGCD1. The plasmid generated by this manipulation was designated pGBCD1.

Extraneous DNA was then eliminated. This was accomplished by cloning the E. coli DNA polymerase I (Klenow fragment) filled-in 6,000 bp HindIII-BamHI (partial) fragment of pGBCD1, containing the H6-promoted gB, gC and gD genes into the SmaI site of pMP831. The plasmid generated by this manipulation was designated pGBCDC1.

The H6-promoted gB, gC and gD genes were then cloned between vaccinia virus flanking arms. This was accomplished by cloning the oligonucleotides, HSVL1 (SEQ ID NO:79) 5'-TCGATCTAGA-3' and HSVL2 (SEQ ID NO:80) 5'-AGCTTCTAGA-3', and the 5,700 bp HindIII-BamHI (partial) fragment of pGBCDC1, containing the H6-promoted gB, gC and gD genes, into the 3,600 bp XhoI-BglII fragment of pSD541. This placed the H6-promoted gB, gC and gD genes between the vaccinia virus sequences flanking the ATI gene. The plasmid generated by this manipulation was designated pGBCD4.

Construction of vP914. A vaccinia virus recombinant, vP914, containing the HSV2 gB, gC and gD genes, was constructed. The procedures used to construct vaccinia virus recombinants have been described previously (Panicali et al., 1982; Guo et al., 1989; Guo et al., 1990). The vaccinia virus recombinant, vP914, was generated by transfecting pGBCD4 into vP866 (NYVAC) infected cells. The HSV2 genes in this recombinant are under the transcriptional control of the vaccinia virus H6 promoter.

Immunofluorescence and Immunoprecipitation of vP914 Infected Cells. Immunofluorescence and immunoprecipitations were performed as previously described (Guo et al., 1989). Rabbit antisera against HSV2 was obtained from DAKO Corp. (code no. B116). Monoclonal antibodies against HSV2 gB (H233) and HSV2 gD (HD1) (Meignier et al., 1987) were obtained from B. Meignier (Institut Merieux, Lyon, France).

In HSV2 infected cells, gB, gC and gD (as well as other HSV2 glycoproteins) are expressed on the cell surface. Immunofluorescence studies with vP914 infected cells, using monoclonal antibodies specific for HSV2 gB (H233) and HSV2 gD (HD1), indicated that the HSV2 gB and gD glycoproteins produced in these cells were also expressed on the cell surface.

In HSV2 infected cells, gB, gC and gD have molecular weights of approximately 117 kDa, 63 kDa and 51 kDa, respectively (Marsden et al., 1978; Marsden et al., 1984; Zweig et al., 1983). Immunoprecipitation of vP914 infected cells with a gB-specific monoclonal antibody (H233) precipitated three major proteins with molecular weights of approximately 117 kDa, 110 kDa and 100 kDa, as well as other minor proteins. Immunoprecipitation with a gD-specific monoclonal antibody (HD1) precipitated a major protein with a molecular weight of approximately 51 kDa and minor proteins with molecular weights of approximately 55 kDa and 46 kDa. Additionally, immunoprecipitation of vP914 infected cells with polyclonal antisera against HSV2 precipitated a protein with a molecular weight similar to gC, 63 kDa, (as well as an 85 kDa protein) and proteins corresponding in size to gB and gD. Therefore, cells infected with vP914 appeared to express HSV2 proteins with molecular weights similar to gB, gC and gD.

EXAMPLE 13

CONSTRUCTION OF NYVAC RECOMBINANTS EXPRESSING HEPATITIS B VIRUS GENES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories (Gaithersburg, Md.), New England Biolabs (Beverly, Mass.) and Boehringer Mannheim Biochemicals (Indianapolis, Ind.). T4 DNA ligase was obtained from New England Biolabs. T4 polynucleotide kinase was obtained from Bethesda Research Laboratories. Plasmid pGEM-3Z was obtained from Promega (Madison, Wis.). The origin of plasmid pTHBV containing the HBV genome cloned in pBR322 has been previously described (Paoletti et al., 1984).

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain terminating method (Sanger et al., 1977) using Sequenase (Tabor and Richardson, 1987) as previously described (Guo et al., 1989). DNA amplification by polymerase chain reaction (PCR) for cloning and sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler.

Virus and Transfection. The NYVAC strain of vaccinia virus and its intermediate ancestor, vP804 (FIG. 5), were used. Generation and processing of recombinant virus are as previously described (Panicali et al., 1982).

Immunoprecipitation. Vero cells were infected at an m.o.i. of 10 pfu per cell with recombinant vaccinia virus, with the NYVAC parent virus (vP866) or were mock infected. After a 1 hour adsorption period, the inoculum was removed and infected cells were overlayed with methionine-free media containing $^{35}$S-methionine (20 uCi/ml). All samples were harvested at 8 hours post infection. Samples were lysed in 3x buffer A containing triton and DOC (3% NP-40, 3% triton, 3% DOC, 30 mM Tris pH 7.4, 450 mM NaCl, 3 mM EDTA, 0.03% NaAzide, 0.6 mg/ml PMSF) containing 50 ul aprotinin (Sigma Chemical Co., St. Louis, Mo., #A6279). All lysates were precleared against normal rabbit sera linked to protein A-sepharose.

Rabbit antisera raised to HBV core antigen and to HBV S2 peptide (aa 120–153) were obtained from R. Neurath (The Lindsley F. Kimball Research Institute of the New York Blood Center). Anti-S2 antiserum was preadsorbed with vP866 infected Vero cells. HBV proteins were immunoprecipitated using anti-core or anti-S2 antiserum and resuspended in 2× Laemmli sample buffer (Laemmli, 1970) for electrophoresis and subsequent autoradiography.

Serology. Rabbits and guinea pigs were inoculated with $10^8$ pfu recombinant vaccinia virus vP919 in sets of two by intradermal, subcutaneous or intramuscular route. Six weeks after the primary inoculation, rabbits were boosted once by the same route and dose. Seven weeks after the primary inoculation, guinea pigs were boosted once by the same route and dose. Groups of 12 mice were inoculated with $10^7$ pfu recombinant vaccinia virus vP919 by intradermal, subcutaneous or intramuscular route. Seven weeks after the primary inoculation, mice were boosted once by the same route. Sera were collected at weekly intervals. Weekly bleedings from each group of mice were pooled. All sera were analyzed for antibody to HBV surface antigen using the AUSAB radioimmunoassay kit (Abbott, North Chicago, Ill.). All sera were analyzed for antibody to HBV core antigen using the CORAB competitive radioimmunoassay kit (Abbott) using standard techniques.

Construction of vP919. Vaccinia recombinant vP919 contains three genes from Hepatitis B Virus inserted into NYVAC vaccinia virus vector. The genes were inserted individually into three different sites of the virus. The three HBV genes encode the following protein products: (1) HBV M protein, (referred to here as small pre S antigen, or spsAg), (2) HBV L protein (referred to here as large pre S antigen, or lpsAg) and (3) a fusion protein, (referred to here as S12/core) composed of the entire pre-S region (S1+S2) linked onto the amino terminus of the core antigen.

Vaccinia virus does not maintain multiple copies of the same heterologous DNA sequences inserted contiguously into a single vaccinia genome (Panicali et al., 1982) Since coding sequences for the spsAg are contained within coding sequences for the lpsAg, insertion of both genes into a single vaccinia genome would be expected to lead to instability of the genome. Similarly, an S1+S2 DNA region present in a hybrid S12/core gene could undergo recombination with the equivalent S1+S2 region of lpsAg. These potential problems were prevented in two ways. (1) The three genes were inserted into three different loci in the vaccinia genome, separated from each other by large regions of vaccinia DNA containing essential genes. Thus, any recombination between the HBV genes would lead to incomplete vaccinia genomes which would not produce viable vaccinia progeny. (2) DNAs encoding the spsAg gene and the S1+S2 region of the S12/core hybrid gene were synthesized chemically with different codon usage to minimize DNA homology with the native HBV gene encoding the lpsAg and with each other. The native HBV gene encoding the lpsAg and the synthetic gene encoding the spsAg are of the ayw subtype; the S1+S2 region for the fusion S12/cure gene was synthesized to correspond to the adw2 subtype (Valenzuela et al., 1979).

Cassettes containing the three individual HBV genes under the control of poxvirus promoters were assembled in different vaccinia donor plasmids and inserted sequentially into vaccinia virus as detailed below.

The synthetic version of the gene encoding the HBV spsAg was synthesized using vaccinia favored codons with the following deviations. (1) The T5NT early transcription terminator TTTTTCT occurring in amino acids 19 through 21 of the sag (HBV S protein) was modified to TTCTTTC, and codon utilization was adjusted to prevent the generation of other T5NT termination signals (Yuen et al., 1987). (2) To avoid possible aberrant translation products, codon usage was adjusted to prevent the generation of any out of frame ATG initiation codons in either direction. The synthetic spsAg gene was linked precisely to the modified synthetic vaccinia virus H6 early/late promoter (Perkus et al., 1989). The complete sequence of promoter and gene is given in FIG. 9. Amino acid sequence is based on the sequence in plasmid. pTHBV, which differs from the published ayw sequence (Galibert et al., 1979) at two amino acid positions in the S2 region: Galibert, aa 31 thr; aa 36 leu; pTHBV, aa 31 ala; aa 36 pro.

Plasmid pGJ15 contains the H6 promoter/synthetic spsAg gene in the vaccinia ATI insertion locus (Perkus et al., 1990). pGJ15 was constructed by assembling portions of the synthetic spsAg gene in pGEM-3Z, then transferring the assembled gene to insertion plasmid pMP494H, a derivative of pSD492 which contains the synthetic H6 promoter in the ATI deletion locus.

Figure 10A:
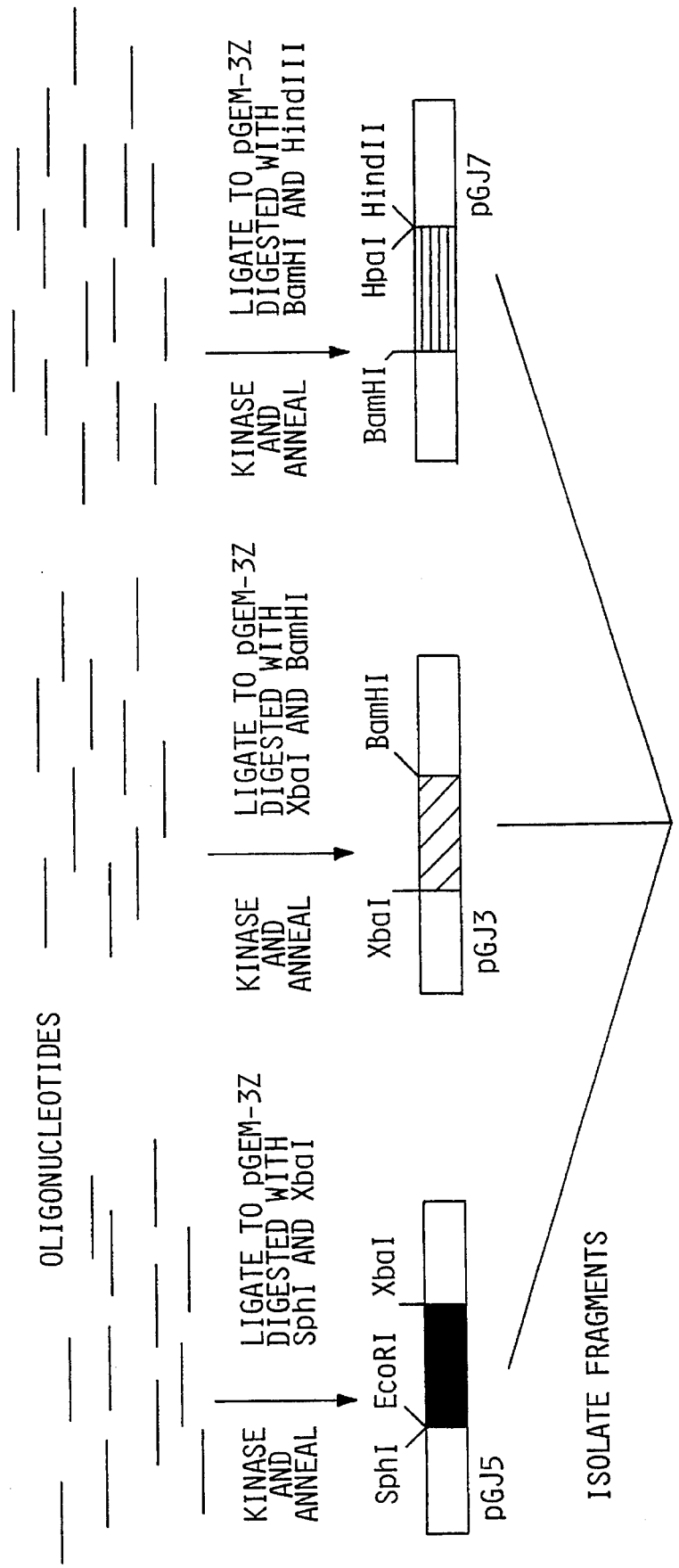
FIG. 10 (FIGS. 10A, 10B) schematically shows a method for the construction of recombinant vaccinia virus vP856.
Figure 10B:
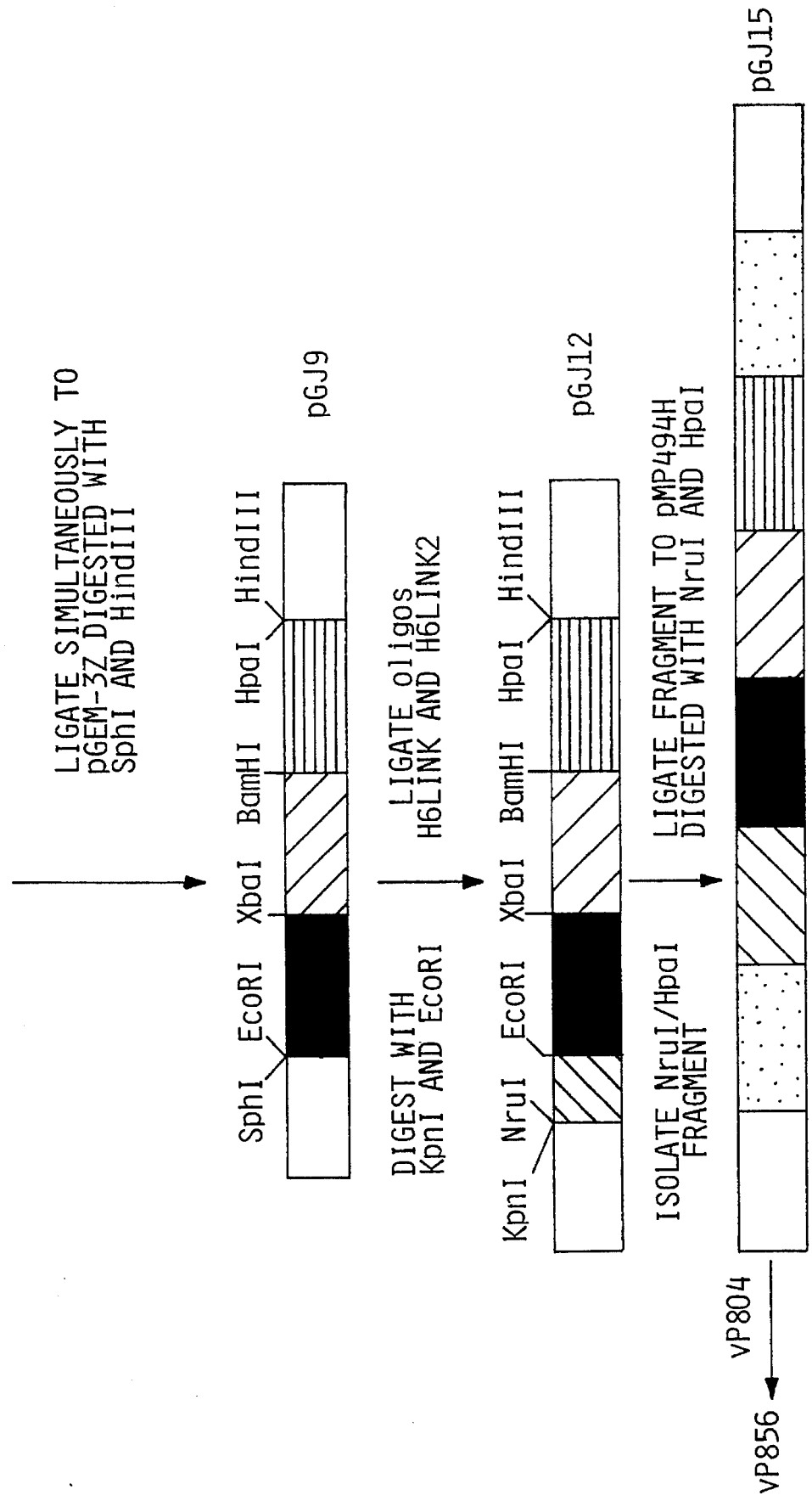

Referring now to FIG. 10, the synthetic HBV spsAg was assembled in three parts. Plasmids pGJ5, pGJ3, and pGJ7 were generated from 6, 5, and 8 pairs of complementary oligonucleotides respectively as follows. Complementary oligonucleotide pairs synthesized with standard chemistries were kinased under standard conditions followed by heating at 65° C. and allowed to cool slowly to room temperature to effect annealing. Aliquots of the annealed pairs comprising each fragment were combined with appropriately digested pGEM-3Z (Promega) and ligated under standard conditions. Fragment SX (indicated with a solid box), bounded by SphI and XbaI restriction sites, was ligated to pGEM-3Z vector plasmid digested with those enzymes creating plasmid pGJ5. Vector plasmid sequences are indicated with open regions. Similarly, fragments XB (diagonal cross-hatch) and BH (horizontal cross-hatch), were assembled in plasmid pGEM-3Z digested with either XbaI and BamHI, or BamHI and HindIII, respectively, generating plasmids pGJ3 and pGJ7. The integrity of the insert in each plasmid was verified by determination of the DNA sequence.

Synthetic HBV gene fragments were isolated by digestion of the plasmids pGJ5, pGJ3 and pGJ7 with the appropriate restriction enzymes flanking the SX, XB and BH gene segments and subsequently ligated to pGEM-3Z digested with SphI and HindIII generating plasmid pGJ9 which contains the contiguous HBV synthetic spsAg sequence. Oligonucleotides H6LINK (SEQ ID NO:81) (5'-CTCGC-GATATCCGTTAAGTTTGTATCGTAATGCAGTGG-3') and H6LINK2 (SEQ ID NO:82) (5'-AATTCCACTGCAT-TACGATACAAACTTAACGGATATCGCGAGGTAC-3') containing the 3' 28 bp of the H6 promoter (diagonal hatch) appended to the synthetic spsAg at the initiating methionine through the EcoRI site 9 bp downstream from the first codon, were ligated to pGJ9 digested with KpnI (5' to the SphI site within the multiple cloning region derived from pGEM-3Z) and with EcoRI, generating plasmid pGJ12. A NruI/HpaI fragment was isolated from pGJ12 and ligated to similarly digested pMP494H, generating plasmid pGJ15. pMP494H is an ATI insertion plasmid containing the vaccinia H6 promoter in the ATI deletion region. pGJ15 contains the H6 promoter-driven HBV synthetic spsAg gene flanked by vaccinia sequences (stippled) surrounding the ATI locus.

pGJ15 was used as donor plasmid for recombination with vaccinia recombinant vP804, generating recombinant vaccinia virus vP856. vP804 contains the NYVAC deletions for the TK, HA, u and [C7L–K1l]. Recombinant virus vP856 contains the above deletions with the insertion of the HBV synthetic spsAg gene replacing the ATI region. Progeny virus recombinant described below containing an insert in the I4L region will be equivalent to NYVAC in terms of deletions (TK, HA, ATI, I4L, u, [C7L–K1L]).

The gene encoding the HBV lpsAg was derived from plasmid pTHBV. In addition to the amino acid changes in the S2 region referred to above, pTHBV differs from the published ayw subtype at one amino acid position in the S1 region: Galibert et al., 1979, aa 90 ser; pTHBV aa 90 thr. The early translational termination signal in sag referred to above was modified from TTTTTCT to TTCTTCT. The entire lpsAg gene was placed under the control of the 105 bp cowpox u promoter (Pickup et al., 1986) The entire sequence of the u promoter/lpsAg gene cassette is given in FIG. 11.

Plasmid pMP550ulps contains the u promoter/lpsAg gene in the vaccinia I4L deletion locus. The construction of pMP550ulps is presented schematically in FIG. 12. The I4L deletion in pMP550ulps is equivalent to the I4L deletion in NYVAC.

Referring now to FIG. 12(A), by PCR using synthetic oligonucleotide primers MPSYN322 (SEQ ID NO:83), MPSYN323 (SEQ ID NO:84) and template plasmid pBScow, the 5' end of the HBV lpsAg gene was added to the cowpox u promoter (orientation indicated by an arrow) generating pMPuS1. (The dark box indicates the u promoter and the striped box indicates HBV sequences.) pSD550 is a vaccinia insertion plasmid for the I4L deletion region. (The triangle indicates the site of deletion and the open box indicates vaccinia sequences.) A SnaBI/BamHI fragment containing the u promoter/HBV junction was isolated and inserted into pSD550 cut with SmaI/BamHI, forming pMP550u.

Referring now to FIG. 12(B), a 1.1 kb DraI fragment containing the entire HBV lpsAg was isolated from pTHBV and inserted into pUC8, generating pMP8S. Translation initiating codon and stop codon are indicated. (*) indicates the site of T5NT transcriptional termination signal (Yuen et al., 1987). The transcriptional termination signal was removed from pMP8S by PCR mutagenesis as indicated, generating pMP8ST. A 1.1 kb BamHI (partial) fragment containing the bulk of the lpsAg gene was isolated from pMP8ST and inserted into plasmid pMP550u cut with BamHI, generating pMP550ulps. pMP550ulps was used for recombination with vaccinia recombinant vP856, generating vP896. Synthetic oligonucleotide sequences are as follows:

is underlined, the mutated base in MPSYN331 (SEQ ID NO:86) is underlined and restriction sites are indicated.

pMP550ulps was used as donor plasmid for recombination with rescuing virus vP856 described above to generate recombinant virus vP896. vP896 contains both the genes for HBV spsAg and HBV lpsAg in a NYVAC background (deletion of TK, HA, ATI, I4L, u, [C7L–K1L]). To generate a recombinant containing only the HBV lpsAg gene for purposes of comparison with multivalent HBV vaccinia recombinants, pMP550ulps was also used in recombination with vP866 (NYVAC), generating recombinant virus vP897.

The third HBV gene inserted into vaccinia virus encodes a fusion protein. Synthetic DNA specifying the HBV S1 and S2 regions was cloned onto the 5' end of the gene specifying the HBV core antigen. Synthetic DNA was designed to encode the S1+S2 regions of the adw subtype (Valenzuela et al., 1979), starting with the met at aa position 12 (equivalent to position 1 of the ayw subtype) (Galibert et al., 1979). Total translation region of S1+S2 is 163 codons. To prevent unwanted intramolecular recombination among HBV genes in a multivalent HBV vaccinia recombinant virus, codon utilization was adjusted to minimize DNA homology of the synthetic S1+S2 region with the native ayw S1+S2 region present in pTHBV and as well as the synthetic S2 region in pGJ15.

The entire gene encoding the core antigen was obtained from pTHBV. The amino acid sequence of the core antigen encoded by pTHBV agrees with the published ayw sequence (Galibert et al., 1979). The hepatitis fusion gene encoding S12/core was placed under the control of the vaccinia I3L early/intermediate promoter (Vos et al., 1988; Goebel et al., 1990b positions 64,973–65,074). The entire sequence of the I3L promoter/S12/core gene cassette is given in FIG. 13 (SEQ ID NO:87).

Plasmid pMP544I3S12C contains the I3L promoter/S1+S2/core gene in the HA deletion locus (Guo et al., 1989). The construction of pMP544I13S12C is presented schematically in FIG. 14.

Figure 14:
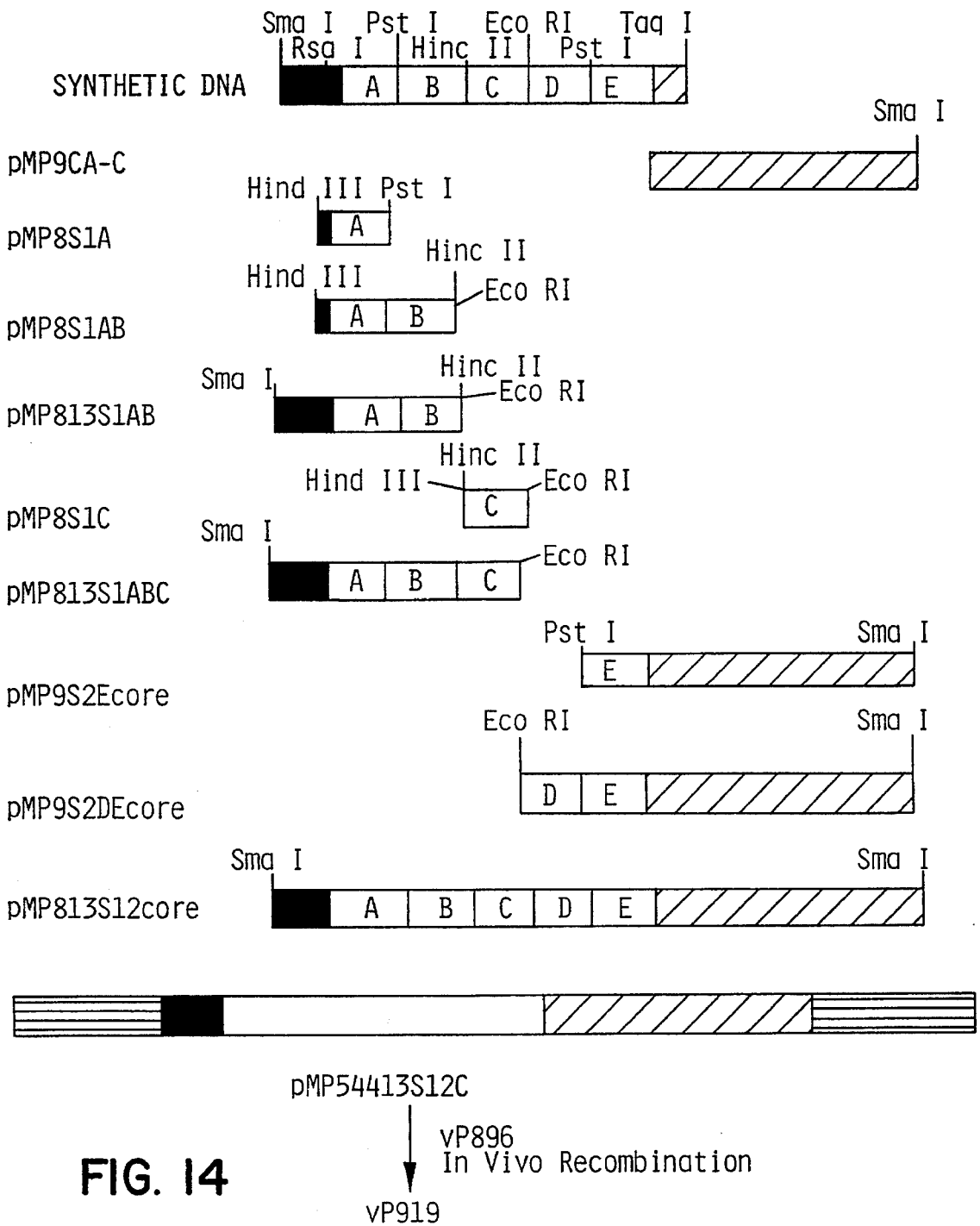
FIG. 14 schematically shows a method for the construction of recombinant vaccinia virus vP919.

Referring now to FIG. 14, plasmid pMPCA-B contains a 1 kb HhaI fragment from pTHBV inserted into the SmaI site of pUC9. pMP9CA-B contains the entire coding sequences for the HBV core antigen, as well as flanking HBV DNA upstream and downstream from the gene. pMP9CA-B was cut with BglII (partial) 30 bp upstream from the 3' end of the gene and with EcoRI in the polylinker region at the HBV/pUC junction. The 3.4 kb vector fragment containing the bulk of the HBV gene was isolated and ligated with annealed synthetic oligonucleotides MPSYN275/MPSYN276, (SEQ

```
                                    BglII  ClaI
MPSYN322  (SEQ ID NO:83)   5' CCCAGATCTATCGATTGCCATGGGGCAGA  3'

BamHI
MPSYN323  (SEQ ID NO:84)   5' TCTGAAGGCTGGATCCAACT  3'

XhoI
MPSYN330  (SEQ ID NO:85)   5' CAATCTTCTCGAGGATT  3'

HincII
MPSYN331  (SEQ ID NO:86)   5' AACAAGAAGAACCCCGCC  3'
```

The HBV initiation codon in MPSYN322 (SEQ ID NO:83)   ID NO:88/SEQ NO:89)

```
                             BglII
MPSYN275  (SEQ ID NO:88)  5'GATCTCAATCTCGGGAATCTCAATGTTAGAT—

SmaI
                         AACTAATTTTTATCCCGGGT  3'

MPSYN276  (SEQ ID NO:89)  3'    AGTTAGAGCCCTTAGAGTTACA—
                             ATCTATTGATTAAAAATAGGGCCCATTAA  5'
``` generating pMP9CA-C. Restriction sites are indicated, the translational stop codon is underlined and the early vaccinia transcriptional terminator is overlined.

pMP9CA-C contains the entire coding sequence for the HBV core antigen, and was used as the source for the bulk of the gene as indicated above.

The synthetic S1+S2 region was assembled in five double stranded sections A through E as indicated above using synthetic oligonucleotides, MPSYN290 through MPSYN308 (SEQ ID NO:90)–(SEQ ID NO:99), as set out below. Oligonucleotides ranged in size from 46mer through 71mer, with 4 to 8 bp sticky ends. 5' ends of oligonucleotides which were at internal positions within a section were kinased before annealing of the section. Sequence of synthetic oligonucleotides used to construct sections A through E are given below. Only the coding strand is shown. Relevant restriction sites are noted. Initiation codons for S1 (section A), S2 (section C) and core (section E) are underlined.

The vaccinia I3L promoter was synthesized using pMP1, a subclone of HindIII I, as template and synthetic oligonucleotides MPSYN310 (SEQ ID NO:100), MPSYN311 (SEQ ID NO:101) as PCR primers. Restriction sites are indicated. MPSYN310 (SEQ ID NO:100) 5'

```
Section A, MPSYN290-294 (SEQ ID NO:90)–(SEQ ID NO:92)
                    HindIII  RsaI    (I3L)          (S1)
MPSYN290 (SEQ ID NO:90) 5'AGCTTGTACAATTATTTAGGTTTAATCATGGGAA
                                       CGAACCTATCTGTT 3'

MPSYN292 (SEQ ID NO:91) 5'CCCAACCCACTTGGATTTTTTCCTGATCATCAGT
                                       TAGACCCTGCTTTC 3'

MPSYN294 (SEQ ID NO:92) 5'GGAGCCAACTCAAACAATCCTGACTGGGATTT
                                                             PstI
                       TAACCCCGTCAAAGACGATTGGCCTGCA 3'

Section B, MPSYN296-299
                      PstI
MPSYN296 (SEQ ID NO:93) 5'GCCAACCAAGTAGGTGTGGGAGCTTTCGGACC—
                              AAGGCTCACTCCTCCACACGGCGGT 3'

MPSYN298 (SEQ ID NO:94) 5'ATATTAGGTTGGTCTCCACAAGCTCAAGG—
                                                HincII EcoRI
                           CATATTGACCACAGTGTCAACCCG 3'

Section C, MPSYN300-303
                     HindIII HincII
MPSYN300 (SEQ ID NO:95) 5' AGCTTGTCAACAATTCCTCCACCAGCCTCT—
                              ACTAATCGGCAGTCTGGT 3'

MPSYN302 (SEQ ID NO:96) 5' AGACAGCCAACTCCCATCTCTCCTCCTCTA—
                                            (S2)      EcoRI
                        AGAGACAGTCACCCACAAGCTATGCAGTGG 3'

Section D, MPSYN304-305
                    HindIII    EcoRI
MPSYN304 (SEQ ID NO:97) 5' AGCTTGGGAATTCAACTGCTTTTCACCAG—

PstI
                ACACTTCAAGACCCTAGAGTCAGGGGTCTATATCTTCCTGCA 3'
Section E, MPSYN306-308

PstI
MPSYN306 (SEQ ID NO:98) 5'GGTGGATCTAGTTCTGGAACTGTAAACCCAGCT—
                              CCGAATATTGCCAGTCACATCTC 3'

MPSYN308 (SEQ ID NO:99) 5' GTCTATCTCCGCGAGGACTGGAGACCCAGTGAC (core) TaqI
GAACATGGACAT 3'
```

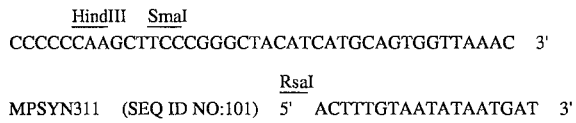

MPSYN311 (SEQ ID NO:101) 5' ACTTTGTAATATAATGAT 3'

The I3 promoter/HBV S1+S2/core expression cassette was assembled in pUC8 and pUC9 in steps, using the intermediate plasmid clones detailed above, resulting in pMP9I3S12core. Restriction sites are indicated only where relevant. Plasmid pMP9I3S12core was digested with SmaI and a 1.2 kb fragment containing the entire promoter/gene cassette was isolated. Vaccinia HA deletion plasmid pSD544 was cut with SmaI and ligated with the 1.2 kb fragment, producing plasmid pMP544I3S12C.

pMP544I3S12C was used as donor plasmid for recombination with vaccinia recombinant vP896 described above to generate recombinant vaccinia virus vP919. vP919 contains all three HBV inserts: spsAg, lpsAg and S12/core fusion in the NYVAC background. The sequence of all HBV insertions in vP919 was confirmed by polymerase chain reaction (PCR) using vP919 as template, followed by dideoxy sequencing of PCR generated material. In addition, pMP544I3S12C was used in recombination with vP804 described above to generate recombinant vaccinia virus vP858 containing only the HBV S12/core fusion. pMP544I3S12C was also used in recombination with recombinant vaccinia virus vP856 to generate recombinant vaccinia virus vP891. vP891 contains two HBV gene insertions, spsAg and S12/core.

Expression of HBV Proteins by vP919. To assay for the various HBV proteins synthesized by the triple HBV recombinant, metabolically labelled lysates from cells infected with vP919 and appropriate vaccinia recombinants containing single and double HBV gene insertions were subjected to immunoprecipitation and analyzed by SDS-polyacrylamide gel electrophoresis followed by radioautography. Proteins in uninfected cells and cells infected with vP866 (NYVAC), vP856 (spsAg), vP896 (spsAg+lpsAg) or vP919 (spsAg, lpsAg, S12/core) were immunoprecipitated using rabbit anti-S2 antiserum. Proteins in additional uninfected cells and additional cells infected with vP919 (spsAg, lpsAg, S12/core), vP858 (S12/core) or vP866 (NYVAC) were immunoprecipitated using rabbit anti-core antiserum. Anti-S2 serum precipitates a major protein of 33 kDa from vaccinia single recombinant vP856 containing the gene for spsAg. This corresponds to the expected size for the singly glycosylated form of HBV spsAg. A protein 36 kDa, corresponding to the expected size for the doubly glycosylated form of spsAg is precipitated in lesser amount. Anti-S2 serum precipitates the same proteins from vaccinia double recombinant vP896, containing the genes for spsAg and lpsAg. In addition, two larger proteins of 38 and 41 kDa are precipitated, which correspond well to the expected sizes of lpsAg (39 kDa unglycosylated and 42 kDa glycosylated). All proteins precipitated by anti-S2 serum from vP856 and vP896 are also precipitated from vaccinia HBV triple recombinant vP919.

The predicted size for the HBV S12/core fusion protein is 38 kDa. Rabbit anti-core antiserum precipitated a protein of the predicted size as well as a variety of smaller proteins from vP858, the vaccinia single recombinant containing the HBV fusion gene S12/core. The most abundant protein precipitated from vP858 by anti-core serum had a size of 27 kDa. This corresponds in size to the translation product which would be predicted if translation of the fusion protein gene began at the second (S2) ATG. The 29 kDa protein precipitated from vP858 may be the glycosylated form of the 27 kDa protein. A smaller protein of 20 kDa, corresponding in size to the translation product for core protein alone, was also precipitated from vP858 in lesser amounts. Vaccinia recombinant vP919, containing all three HBV genes (spsAg, lpsAg and S12/core fusion), gave an identical pattern to that observed with vP858 following immunoprecipitation with anti-core antiserum. The 27 kDa and 29 kDa proteins precipitated from vP858 and vP919 by anti-core antiserum were, as expected, also precipitated from vP919 by anti-S2 antiserum.

Antibody Response to vP919. To test for serological response to HBV proteins produced by vP919, the virus was inoculated into rabbits, guinea pigs and mice. Rabbits and guinea pigs were inoculated with $10^8$ pfu recombinant vaccinia virus vP919 in sets of two by intradermal, subcutaneous or intramuscular route. Six weeks after the primary inoculation, rabbits were boosted once by the same route and dose. Seven weeks after the primary inoculation, guinea pigs were boosted once by the same route and dose. Groups of 12 mice were inoculated with $10^7$ pfu recombinant vaccinia virus vP919 by intradermal, subcutaneous or intramuscular route. Seven weeks after the primary inoculation, mice were boosted once by the same route. Sera were collected at weekly intervals. Weekly bleedings from each group of mice were pooled. All sera were analyzed for antibody to HBV surface antigen using the AUSAB radioimmunoassay kit (Abbott). All sera were analyzed for antibody to HBV core antigen using the CORAB competitive radioimmunoassay kit (Abbott). Assays were performed using standard techniques. The results of these analyses are presented in Tables 2 (rabbits), 3 (guinea pigs) and 4 (mice).

Summarizing the results presented in Table 2, all six rabbits exhibited an anti-core antibody response following a single inoculation with vP919. In five of the six rabbits, the anti-core antibody response was boosted by a second inoculation of vP919. Four of six rabbits exhibited an anti sAg response following a single inoculation of vP919. These four rabbits, plus one additional rabbit, showed an increase in the anti sAg response following the second inoculation.

Summarizing the results presented in Table 3, one guinea pig exhibited an anti-core response following an initial inoculation with vP919; following the boost at 7 weeks, a total of three guinea pigs showed an anti-core response. One of these animals showed an anti-sAg antibody response in week eight only.

Summarizing the results presented in Table 4, all three groups of mice showed anti-core antibody responses at various times after inoculation with vP919; two of the three groups also showed anti-sAg responses.

AUSRIA Assay. Expression of particulate HBV surface antigen from cells infected with HBV-containing vaccinia recombinants was assayed using the commercially available AUSRIA II-125 kit (Abbott Laboratories, North Chicago, Ill.). Dishes containing $2 \times 10^6$ Vero cells were infected in triplicate with recombinant vaccinia virus at 2 pfu/cell. After 24 h, culture medium was removed, cells were washed with 2 ml PBS and the wash combined with the medium and centrifuged at 1000 rpm for 10 min. The supernatant wets designated the medium fraction. The cell fraction was prepared by adding 2 ml PBS to the dish, scraping off the cells and combining with the cell pellet from above. The final volume of both medium and cell fractions were adjusted to 4 ml with PBS. Cell fractions were sonicated for 2 min before assay. Cell fractions and medium fractions were assayed for the presence of HBV surface antigen at a 1:5 dilution using the AUSRIA kit. Samples below the cutoff value of 2.1×the negative control supplied in the kit were considered negative. Output virus of cell and medium fractions from all dishes were titered on Vero cells. Results are shown in Table 5.

Construction of Vaccinia Recombinants Expressing the HBV lpsAg under the Control of the EPV 42 kDa Promoter. Vaccinia recombinant vP919 contains three distinct HBV genes under the control of three different poxvirus promoters which function at early times post infection. To compare the relative strength of various poxvirus promoters expressing a foreign gene at early times post infection in the same vaccinia background, a sandwich ELISA assay was developed, utilizing the rabies glycoprotein G gene as the test gene. Using this test system, the vaccinia H6 promoter and the vaccinia I3L promoter were found to be stronger promoters than the cowpox u promoter. In vP919 the H6 promoter directs expression of the HBV spsAg, the I3L promoter directs expression of the HBV S12/core fusion, and the u promoter directs expression of the HBV lpsAg. The relatively weak u promoter was purposely selected for expression of HBV lpsAg, since it has been shown that coexpression of lpsAg interferes with particle formation and secretion of sAg or spsAg (Ou et al., 1987; Cheng et al., 1986; McLachlan et al., 1987; Chisari et al., 1986).

The AUSRIA radioimmunoassay kit was used to measure the in vitro production of particles containing sAg or spsAg by recombinant vaccinia virus expressing HBV genes. Preliminary investigation showed that AUSRIA-reactive particle formation and secretion occurred in vP856 (containing spsAg), vP896 (containing spsAg+lpsAg) and vP919 (containing spsAg+lpsAg+S12/core). In vP896 and vP919, the relative levels of secretion of AUSRIA-reactive particles were lower than that observed with vP856.

To determine whether formation and secretion of AUSRIA-reactive particles could be observed in the presence of higher levels of lpsAg expression, the lpsAg gene was placed under the control of the entomopox (EPV) 42 kDa promoter. By the comparative ELISA test described above, the EPV 42 kDa promoter in a vaccinia recombinant virus directed the expression of a foreign gene at a level equivalent to that observed with the vaccinia H6 promoter or the vaccinia I3L promoter.

Plasmid pMP550ulps contains the lpsAg gene under the control of the cowpox u promoter in the vaccinia I4L deletion locus (FIG. 12). The cowpox u promoter present in plasmid pMP550ulps was replaced by the EPV 42 kDa promoter as follows: Complementary oligonucleotides MPSYN371–374 were kinased at the internal 5' ends (MPSYN372; MPSYN373), annealed, and cloned into pUC8 cut with EcoRI/BamHI, forming plasmid pMP371/374. MPSYN371 (SEQ ID NO:102), MPSYN373 (SEQ ID NO:103) MPSYN372 (SEQ ID NO:104), and MPSYN374 (SEQ ID NO:105).

```
                 EcoRI      BglII
MPSYN371 5' AATTCAGATCTCAAAATTGAAAATATATAATTACAATA
                                                   TAAAATGGGGC 3'

MPSYN373 3'    GTCTAGAGTTTTAACTTTTATATATTAATGTTATAT
                                                   TTTACCCCGTCTT 5'

MPSYN372 5' AGAATCTTTCCACCAGCAATCCTCTGGGATTCTTTCCCGACC
                                                          BamHI
                                                      ACCAGTTG 3'

MPSYN374 3' AGAAAGGTGGTCGTTAGGAGACCCTAAGAAAGGGCTGGTGGTC
                                                      AACCTAG 5'
``` contain a 31 bp EPV 42 kDa promoter element, followed by HBV S1 region (ATG underlined) to the BamHI site. Following DNA sequence confirmation, the insert was isolated from pMP371/374 by digestion with BamHI/BglII, and used to replace the corresponding u promoter/HBV sequence in pMP550ulps as follows: pMP550ulps was digested with BamHI (partial)/BglII, and the appropriate 5 kb vector fragment isolated and ligated with the BamHI/BglII fragment from pMP371/374. In the resulting plasmid, pMP550E31lps, the HBV lpsAg is under the control of the EPV 42 kDa promoter. The entire sequence of the EPV 42 kDa promoter/lpsAg gene cassette is given in FIG. 15.

pMP550E31lps was used as donor plasmid with vaccinia recombinant vP856, containing the spsAg gene, to generate the double HBV recombinant vaccinia virus vP932. vP932 was used as rescuing virus with donor plasmid pMP544I3S12C containing the S12/core fusion to generate a triple HBV recombinant vaccinia virus vP975. To generate a vaccinia recombinant containing only the EPV 42 kDa promoter/lpsAg, pMP550E31lps was used as donor plasmid with vP866, generating recombinant vaccinia virus vP930.

Secretion of HBV Surface Antigen In Vitro by Recombinant Vaccinia Viruses. Dishes containing Vero cells were infected in triplicate with NYVAC (vP866) or recombinant vaccinia virus expressing HBV spsAg and/or HBV lpsAg. The relative amounts of HBV surface antigen particles associated with infected cells were compared with the amounts secreted into the medium using the AUSRIA II-125 kit (Table 5). The presence of HBV surface antigen in the medium was not due to lysis of infected cells because more than 99.8% of viral infectivity remained cell associated. Volumes of cell pellets and medium were equalized to allow for direct comparison. In cells infected with recombinant vaccinia virus vP856, expressing the spsAg, 42% of the AUSRIA reactive surface antigen was secreted into the medium. Coexpression of lpsAg under the control of the relatively weak u promoter (vP896) did not dramatically change the amount of cell associated AUSRIA reactive material, but decreased the relative amount of secreted material to 24% of the total. Coexpression of lpsAg under the control of the relatively strong EPV 42 kDa promoter (vP932) lowered the relative amount of secreted material to 6% of the total. As with vP896, coexpression of lpsAg with spsAg in vP932 did not lower the amount of AUSRIA reactive cell associated material. Interestingly, expression of lpsAg alone under the control of the EPV 42 kDa promoter (vP930) resulted in the production of a level of cell associated AUSRIA reactive material significantly above background for the assay, whereas expression of lpsAg under the control of the u promoter (vP897) did not. This is most likely due to the higher levels of spsAg or sAg produced in vP930 infected cells due to initiation at internal (S2 or S) initiation codons.

TABLE 2

Analysis of sera of rabbits inoculated with vP919[a]

| | | week | | | | | | | | | | |
|---|---|---|---|---|---|---|---|---|---|---|---|---|
| # | route | 0 | 1 | 2 | 3 | 4 | 5 | 6 | 7 | 8 | 9 | 10 |
| CORAB[b] | | | | | | | | | | | | |
| A074 | ID | – | 20 | 5 | 5 | 20 | 5 | 5 | 80 | 80 | 20 | 20 |
| A075 | ID | – | 20 | 5 | 5 | 5 | 5 | 5 | 80 | 20 | 20 | 20 |
| A076 | IM | – | 5 | 5 | 1 | 1 | 5 | 1 | 80 | 80 | 80 | 20 |
| A077 | IM | – | 1 | 1 | 1 | 1 | 5 | 1 | 80 | 80 | 80 | 20 |
| A078 | SC | – | 1 | 1 | – | 1 | 1 | 1 | 20 | 20 | 5 | 20 |
| A079 | SC | 1 | 5 | 5 | 1 | 5 | 5 | 5 | 5 | 5 | 5 | 5 |
| AUSAB[c] | | | | | | | | | | | | |
| A074 | ID | – | – | – | – | 51 | 157 | 145 | 9883 | 3083 | 3483 | 3783 |
| A075 | ID | – | 72 | 42 | 31 | 16 | 57 | 88 | 11192 | 4292 | 2792 | 1592 |
| A076 | IM | – | 3 | 7 | 23 | 23 | 15 | 7 | 1197 | 200 | 67 | 63 |
| A077 | IM | – | – | – | – | – | – | – | 332 | 127 | 20 | 20 |
| A078 | SC | – | – | – | 8 | – | – | – | 13 | – | – | – |
| A079 | SC | – | 24 | 32 | 50 | 80 | 76 | 540 | 4600 | 4300 | 4600 | 2800 |

[a]Sets of two rabbits were inoculated with $10^8$ pfu vaccinia recombinant vP919 at week 0 by intradermal (ID), intramuscular (IM) or subcutaneous (SC) route, and boosted by the same route and dose at week 6.
[b]Undiluted sera and sera diluted 1:5, 1:20, 1:80 and 1:320 with PBS were analyzed by CORAB competitive radioimmunoassay kit (Abbott). The reciprocal of the highest dilution giving a positive score is indicated. "–" indicates that undiluted serum gave a negative score.
[c]Sera were analyzed by AUSAB radioimmunoassay kit (Abbott). Titers are expressed in RIA units/ml. "–" indicates a negative test result.

TABLE 3

Analysis of sera of guinea pigs inoculated with vP919[a]

| | | week | | | | | | | | | | | |
|---|---|---|---|---|---|---|---|---|---|---|---|---|---|
| # | route | 0 | 1 | 2 | 3 | 4 | 5 | 6 | 7 | 8 | 9 | 10 | 11 |
| 047 | ID | – | – | – | – | – | – | – | – | – | 5 | 5 | 5 | 5 |
| 048 | ID | – | – | – | – | – | – | – | 5 | 5 | 5[c] | 5 | 5 | 5 |
| 049 | IM | – | – | – | – | – | – | – | – | – | – | – | – |
| 050 | IM | – | – | – | – | – | – | – | – | – | – | – | – |
| 051 | SC | – | – | – | – | – | – | – | – | – | 5 | 5 | 5 |
| 052 | SC | – | – | – | – | – | – | – | – | – | – | – | – |

[a]Sets of two guinea pigs were inoculated with $10^8$ pfu vaccinia recombinant vP919 at week 0 by intradermal (ID), intramuscular (IM) or subcutaneous (SC) route, and boosted by the same route and dose at week 7.
[b]Sera were diluted 1:5 with PBS and analyzed by CORAB competitive radioimmunoassay kit (Abbott). "5" indicates a positive score; "–" indicates a negative score.
[c]1:5 dilution of this serum tested borderline positive for antibody to HBV surface antigen using the AUSAB radioimmunoassay kit. All other sera were negative by AUSAB analysis.

TABLE 4

Analysis of sera of mice inoculated with vP919[a]

| | week | | | | | | | | | | |
|---|---|---|---|---|---|---|---|---|---|---|---|
| route | 0 | 1 | 2 | 3 | 4 | 5 | 6 | 7 | 8 | 9 | 10 |
| CORAB[b] | | | | | | | | | | | |
| ID | – | – | – | – | – | – | 5 | – | 5 | – | 5 |
| IM | – | – | – | – | – | – | – | – | 5 | 20 | 5 |
| SC | – | – | – | – | – | 5 | – | 5 | 5 | – | 5 |
| AUSAB[c] | | | | | | | | | | | |
| ID | – | – | – | – | – | – | – | – | + | – | 24 |
| IM | – | – | – | – | + | 10 | 10 | + | 54 | 13 | 50 |
| SC | – | – | – | – | – | – | – | – | – | – | – |

[a]Groups of 12 mice were inoculated with $10^7$ pfu vaccinia recombinant vP919 at week 0 by intradermal (ID), intramuscular (IM) or subcutaneous (SC) route, and boosted by the same route and dose at week 7. Sera from each group were pooled for analysis.
[b]Sera diluted 1:5, 1:20 and 1:80 with PBS were analyzed by CORAB competitive radioimmunoassay kit (Abbott). The reciprocal of the highest dilution giving a positive score is indicated. "–" indicates that serum diluted 1:5 gave a negative score.
[c]Sera were analyzed by AUSAB radioimmunoassay kit (Abbott). Titers are expressed in RIA units/ml. "+" indicates borderline positive titer; "–" indicates a negative test result.

TABLE 5

HBV surface antigen expression by recombinant vaccinia virus[a]

| Virus | HBV genes | AUSRIA[b] | | | | VIRUS TITER[c] | | |
|---|---|---|---|---|---|---|---|---|
| | | Cell | Medium | Total | % secreted | Cell | Medium | % released |
| vP866 | — | *[d] | * | | | $1.2 \times 10^{10}$ | $1.7 \times 10^7$ | 0.15% |
| vP856 | (H6) spsAg | 96645 | 69305 | 165950 | 42% | $1.1 \times 10^{10}$ | $1.5 \times 10^7$ | 0.14% |
| vP897b | (u) lpsAg | * | * | | | $8.4 \times 10^9$ | $6.8 \times 10^6$ | 0.08% |
| vP896 | (H6) spsAg (u) lpsAg | 94751 | 30020 | 124771 | 24% | $1.3 \times 10^{10}$ | $1.7 \times 10^7$ | 0.13% |
| vP930 | (42 kDa) lpsag | 5470 | * | | | $8.0 \times 10^9$ | $1.6 \times 10^7$ | 0.20% |
| vP932 | (H6) spsAg (42 kDa) lpsAg | 110808 | 6581 | 117389 | 6% | $1.3 \times 10^{10}$ | $1.6 \times 10^7$ | 0.13% |

[a]Dishes containing $2 \times 10^6$ Vero cells were infected in triplicate at 2 pfu/cell with recombinant vaccinia virus containing HBV genes as indicated or with control virus vP866. At 24 h pi, cell and medium fractions were harvested separately, and volumes equalized to 4 ml/fraction with PBS.
[b]Individual cell and medium fractions were assayed at a 1:5 dilution in PBS using the AUSRIA II-125 kit (Abbott Laboratories). Values for "Cell" and "Medium" represent the mean AUSRIA values in cpm for cell-associated and secreted HBV surface antigen, respectively, multiplied by the dilution factor. Appropriate background cpm corresponding to mean AUSRIA values for cell associated or medium fractions from vP866 infected samples were subtracted from mean AUSRIA values for the corresponding fractions from the recombinant HBV vaccinia virus infections. Values for "Total" represent the sum of the cell associated and secreted AUSRIA values multiplied by the dilution factor.
[c]Output virus was titered as pfu on Vero cells. Values for "Cell" and "Medium" represent total mean cell associated and released virus per dish, respectively.
*[d]AUSRIA values obtained were below the cutoff value of 2.1 × negative control as defined by the AUSRIA II-125 kit.

EXAMPLE 14

CONSTRUCTION OF NYVAC RECOMBINANTS EXPRESSING HEPATITIS B VIRUS AND EPSTEIN BARR VIRUS

Since Epstein Barr Virus (EBV) and Hepatitis B Virus (HBV) are endemic over similar geographical areas, including Africa, it would be advantageous to produce a recombinant vaccinia virus expressing immunogens for both pathogens. To this end, vP941, a recombinant vaccinia virus containing three EBV genes and three HBV genes in a NYVAC background was generated.

Immunoprecipitation of HBV Proteins. Metabolic labelling and immunoprecipitation of HBV proteins were as described for vP919 in Example 13 with the following modifications. Infections with recombinant vaccinia virus, parental NYVAC virus (vP866) and mock infections were performed on RK-13 cells, rather than Vero cells. Both anti-S2 and anti-core antisera were preadsorbed with vP866 infected RK-13 cells.

Generation of Recombinant Vaccinia Virus vP941. Plasmid EBV Triple.1, the donor plasmid containing three EBV genes which was used to generate the vaccinia virus recombinant EBV triplet vP944, was used in recombination with vP919, the vaccinia virus recombinant HBV triplet, as rescuing virus. The resulting virus, vP941, was identified by $^{32}$P-labelled EBV DNA. Like vP944, vP941 contained EBV genes gH under the control of the Entomopox virus 42 kDa promoter, gB under the control of the vaccinia H6 promoter and gp340 under the control of the vaccinia H6 promoter, all inserted in the vaccinia TK deletion locus. Like vP919, vP941 contained the synthetic HBV spsAg under the control of the vaccinia H6 promoter inserted into the ATI deletion locus, the HBV lpsAg under the control of the cowpox u promoter inserted into the I4L deletion locus, and the HBV S12/core fusion gene under the control of the I3L promoter inserted into the HA deletion locus. The integrity of the genome of recombinant vaccinia virus vP941 was confirmed by restriction analysis of the DNA.

Expression of HBV Proteins by vP941. To assay for the various HBV proteins synthesized by sextuplet HBV/EBV vaccinia recombinant vP941, metabolically labelled proteins synthesized in RK-13 cells infected with vP941 and appropriate single, double and triple HBV recombinants were subjected to immunoprecipitation. Proteins in uninfected cells and cells infected with vP866 (NYVAC), vP856 (spsAg), vP896 (spsAg+lpsAg), vP919 (spsAg+lpsAg+S12/core), or vP941 were immunoprecipitated using rabbit anti-S2 antiserum. Proteins in additional uninfected cells and additional cells infected with vP941, vP919, vP858 (S12/core), or vP866 were immunoprecipitated using anti-core antiserum.

Anti-S2 serum precipitates two proteins of 33 kDa and 36 kDa from vaccinia single recombinant vP856 containing the gene for spsAg. These correspond to the expected sizes for the singly and doubly glycosylated forms of HBV spsAg. Anti-S2 serum precipitates the same proteins from vaccinia double recombinant vP896, containing the genes for spsAg and lpsAg. In addition, a protein of 42 kDa, corresponding to the singly glycosylated form of lpsAg is precipitated, as well as larger proteins of 45 kDa and 48 kDa. The 39 kDa protein corresponding to the nonglycosylated form of lpsAg is precipitated in minor amounts compared to the glycosylated forms. All proteins precipitated by anti-S2 serum from vP856 and vP896 are also precipitated from HBV triple recombinant vP919 and the HBV/EBV sextuplet, vP941. In the radioautogram, HBV proteins are immunoprecipitated by anti-S2 serum from RK-13 cells infected with vaccinia recombinants. When HBV proteins were immunoprecipitated from Vero cells infected with the same vaccinia recombinants (vP856, vP896 and vP919) the same proteins were observed but in different relative amounts. In general, both spsAg and lpsAg expressed by these recombinant vaccinia virus seems to be more fully glycosylated in RK-13 cells than in Vero cells.

As was seen with Vero cells infected with vP858, the most abundant protein precipitated by anti-core serum from RK-13 cells infected with vP858 has a size of 27 kDa. This corresponds to the size of the translation product which would be predicted if translation of the S12/core fusion gene began at the second (S2) ATG. Unlike the situation observed following vP858 infection of Vero cells, vP858 infection of RK-13 cells followed by immunoprecipitation with anti-core serum does not result in a visible band corresponding in size to the 38 kDa expected for the complete S12/core translation product. All proteins precipitated by anti-core serum from HBV single recombinant vP858 are also precipitated from HBV triple recombinant vP919 and HBV/EBV sextuplet vP941.

EXAMPLE 15

CONSTRUCTION OF ALVAC RECOMBINANTS EXPRESSING RABIES VIRUS GLYCOPROTEIN G

This example describes the development of a canarypox-rabies recombinant designated as ALVAC-RG (vCP65) and its safety and efficacy.

RW146 (SEQ ID NO:108): GATCTTTATAAAAAC-TAGCTAGCTAGAATTCCCGG-GAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E (SEQ ID NO:109)–(SEQ ID NO. 113) are:

A (SEQ ID NO:109): CTGAAATTATTTCATTATCGCGATATCCGTTAA GTTTGTATCGTAATGGTTCCTCAGGCTCTCCTGTTTGT

B (SEQ ID NO: 110): CATTACGATACAAACTTAACGGATATCGCGATAA TGAAATAATTTCAG

C (SEQ ID NO: 111): ACCCCTTCTGGTTTTTCCGTTGTGTTTT GGGAAATTCCCTATTTACACGATCCCAGACA AGCTTAGATCTCAG

D (SEQ ID NO: 112): CTGAGATCTAAGCTTGTCTGGGATCGTGTAAATA GGGAATTTCCCAAAACA

E (SEQ ID NO: 113): CAACGGAAAAACCAGAAGGGGTACAAACAGGAGA GCCTGAGGAAC

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 16 between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:106) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:107): ACTCTCAAAAGCTTC-CCGGGAATTCTAGCTAGCTAGTTTTTATAAA

The diagram of annealed oligonucleotides A through E is as follows:

```
   A   |   C
-------+-------
       |
-------+---+-----
   B   | E |  D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is: GGATCCCCGGG (SEQ ID NO:380). pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC #CCL81) and MRC-5 cells (a fibroblast-like cell line derived from normal human fetal lung tissue ATCC #CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell lines:

(1) Primary chick embryo fibroblast (CEF) cells produced from 11 day old white leghorn embryos;

(2) Vero cells—a continuous line of African Green monkey kidney cells (ATCC #CCL81); and (3) MRC-5 cells—a diploid cell line derived from human fetal lung tissue (ATCC #CCL171). The initial inoculation was performed at an m.o.i. of 0.1 pfu per cell using three 60 mm dishes of each cell line containing 2×10$^6$ cells per dish. One dish was inoculated in the presence of 40 µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell line was inoculated undiluted onto three dishes of the same cell line (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 6 and 7.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 6 and 7 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell line was inoculated onto a permissive CEF monolayer and harvested at cytopathic effect (CPE) or at 7 days if no CPE was evident. The results of this experiment are shown in Table 8. Even after amplification through a permissive cell line, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 9. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with 1×10$^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 µl of a range of dilutions of different batches of vCP65. Mice were inoculated in the footpad. On day 14, mice were challenged by intracranial inoculation of from 15 to 43 mouse LD$_{50}$ of the virulent CVS strain of rabies virus. Survival of mice was monitored and a protective dose 50% (PD$_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 log$_{10}$ TCID$_{50}$ of ALVAC-RG. Four dogs and four cats were not inoculated. Animals were bled at 14 and 28 days post-inoculation and anti-rabies antibody assessed in an RFFI test. The animals receiving 6.7 log$_{10}$ TCID$_{50}$ of ALVAC-RG were challenged at 29 days post-vaccination with 3.7 log$_{10}$ mouse LD$_{50}$ (dogs) or 4.3 log$_{10}$ mouse LD$_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 µl instilled on the surface of the right eye without scarification; (2) 100 µl as several droplets in the mouth; (3) 100 µl in each of two intradermal injection sites in the shaven skin of the external face of the right arm; and (4) 100 µl in the anterior muscle of the right thigh.

Four monkeys were inoculated with each virus, two with a total of 5.0 log$_{10}$ pfu and two with a total of 7.0 log$_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 log$_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC #CCL81;

(b) MRC-5, human embryonic lung, ATCC #CCL 171;

(c) WISH human amnion, ATCC #CCL 25;

(d) Detroit-532, human foreskin, Downs's syndrome, ATCC #CCL 54; and (e) Primary CEF cells.

Chicken embryo fibroblast cells produced from 11 day old white leghorn embryos were included as a positive control. All inoculations were performed on preformed. monolayers of 2×10$^6$ cells as discussed below.

A. Methods for DNA analysis.

Three dishes of each cell line were inoculated at 5 pfu/cell of the virus under test, allowing one extra dish of each cell line un-inoculated. One dish was incubated in the presence of 40 µg/ml of cytosine arabinoside (Ara C). After an adsorption period of 60 minutes at 37° C. the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of 2×10$^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 µg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene.

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody. Results: Estimation of viral Yield. The results of titration for yield at 72 hours after inoculation at 0.1 pfu per cell are shown in Table 10. The results indicate that while a productive infection can be attained in the arian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 µl of dilutions inoculated into the footpad of four to six week old mice. Mice were challenged 14 days later by the intracranial route with 300 µl of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 11. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 µl of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 $\log_{10}$ mouse LD$_{50}$ (cats, in the neck) of the NYGS rabies virus challenge strain. The results of the experiment are shown in Table 12.

No adverse reactions to inoculation were seen in either cats or dogs with either dose of inoculum virus. Four of 5 dogs immunized with 6.7 $\log_{10}$ TCID$_{50}$ had antibody titers on day 14 post-vaccination and all dogs had titers at 29 days. All dogs were protected from a challenge which killed three out of four controls. In cats, three of five cats receiving 6.7 $\log_{10}$ TCID$_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ TCID$_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 13.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An amnanestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of antirabies serum neutralizing antibody assessed in an RFFI test. The results, shown in Table 14, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 15.

No adverse reactivity to inoculation was noted by either intramuscular or subcutaneous routes. Both chimpanzees responded to primary inoculation by 14 days and a strongly rising response was detected following revaccination.

TABLE 6

Sequential Passage of ALVAC in Avian and non-Avian Cells.

|  |  | CEF | Vero | MRC-5 |
|---|---|---|---|---|
| Pass 1 |  |  |  |  |
| Sample | t0[a] | 2.4 | 3.0 | 2.6 |
|  | t7[b] | 7.0 | 1.4 | 0.4 |
|  | t7A[c] | 1.2 | 1.2 | 0.4 |
| Pass 2 |  |  |  |  |
| Sample | t0 | 5.0 | 0.4 | N.D.[d] |
|  | t7 | 7.3 | 0.4 | N.D. |
|  | t7A | 3.9 | N.D. | N.D. |
| Pass 3 |  |  |  |  |
| Sample | t0 | 5.4 | 0.4 | N.D. |
|  | t7 | 7.4 | N.D. | N.D. |
|  | t7A | 3.8 | N.D. | N.D. |
| Pass 4 |  |  |  |  |
| Sample | t0 | 5.2 | N.D. | N.D. |
|  | t7 | 7.1 | N.D. | N.D. |
|  | t7A | 3.9 | N.D. | N.D. |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post infection.
[d]Not detectable

TABLE 7

Sequential Passage of ALVAC-RG in Avian and non-Avian Cells

|  |  | CEF | Vero | MRC-5 |
|---|---|---|---|---|
| Pass 1 |  |  |  |  |
| Sample | t0[a] | 3.0 | 2.9 | 2.9 |
|  | t7[b] | 7.1 | 1.0 | 1.4 |
|  | t7A[c] | 1.8 | 1.4 | 1.2 |
| Pass 2 |  |  |  |  |
| Sample | t0 | 5.1 | 0.4 | 0.4 |
|  | t7 | 7.1 | N.D.[d] | N.D. |
|  | t7A | 3.8 | N.D. | N.D. |
| Pass 3 |  |  |  |  |
| Sample | t0 | 5.1 | 0.4 | N.D. |

TABLE 7-continued

Sequential Passage of ALVAC-RG in Avian and non-Avian Cells

|  |  | CEF | Vero | MRC-5 |
|---|---|---|---|---|
|  | t7 | 7.2 | N.D. | N.D. |
|  | t7A | 3.6 | N.D. | N.D. |
| Pass 4 |  |  |  |  |
| Sample | t0 | 5.1 | N.D. | N.D. |
|  | t7 | 7.0 | N.D. | N.D. |
|  | t7A | 4.0 | N.D. | N.D |

[a]This sample was harvested at zero time and represents the residual input virus. The titer is expressed as $\log_{10}$ pfu per ml.
[b]This sample was harvested at 7 days post-infection.
[c]This sample was inoculated in the presence of 40 μg/ml of Cytosine arabinoside and harvested at 7 days post-infection.
[d]Not detectable.

TABLE 8

Amplification of residual virus by passage in CEF cells

|  |  | CEF | Vero | MRC-5 |
|---|---|---|---|---|
| a) ALVAC |  |  |  |  |
| Pass | 2[a] | 7.0[b] | 6.0 | 5.2 |
|  | 3 | 7.5 | 4.1 | 4.9 |
|  | 4 | 7.5 | N.D.[c] | N.D. |
|  | 5 | 7.1 | N.D. | N.D. |
| b) ALVAC-RG |  |  |  |  |
| Pass | 2[a] | 7.2 | 5.5 | 5.5 |
|  | 3 | 7.2 | 5.0 | 5.1 |
|  | 4 | 7.2 | N.D. | N.D. |
|  | 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 9

Schedule of inoculation of rhesus macaques with ALVAC-RG (vCP65)

| Animal |  | Inoculation |
|---|---|---|
| 176L | Primary: | 1 × 10⁸ pfu of vCP65 orally in TANG |
|  | Secondary: | 1 × 10⁷ pfu of vCP65 plus 1 × 10⁷ pfu of vCP82[a] by SC route |
| 185 L | Primary: | 1 × 10⁸ pfu of vCP65 orally in Tang |
|  | Secondary: | 1 × 10⁷ pfu of vCP65 plus 1 × 10⁷ pfu of vCP82 by SC route |
| 177 L | Primary: | 5 × 10⁷ pfu SC of vCP65 by SC route |
|  | Secondary: | 1 × 10⁷ pfu of vCP65 plus 1 × 10⁷ pfu of vCP82 by SC route |
| 186L | Primary: | 5 × 10⁷ pfu of vCP65 by SC route |
|  | Secondary: | 1 × 10⁷ pfu of vCP65 plus 1 × 10⁷ pfu of vCP82 by SC route |
| 178L | Primary: | 1 × 10⁷ pfu of vCP65 by SC route |
| 182L | Primary: | 1 × 10⁷ pfu of vCP65 by IM route |
| 179L | Primary: | 1 × 10⁶ pfu of vCP65 by SC route |
| 183L | Primary: | 1 × 10⁶ pfu of vCP65 by IM route |
| 180L | Primary: | 1 × 10⁶ pfu of vCP65 by SC route |
| 184L | Primary: | 1 × 10⁵ pfu of vCP65 by IM route |
| 187L | Primary | 1 × 10⁷ pfu of vCP65 orally |

[a]vCP82 is a canarypox virus recombinant expressing the measles virus fusion and hemagglutinin genes.

TABLE 10

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 11

Potency of ALVAC-RG as tested in mice

| Test | Challenge Dose[a] | PD$_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse LD$_{50}$
[b]Expressed as $\log_{10}$ TCID$_{50}$

TABLE 12

Efficacy of ALVAC-RG in dogs and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 13

Anti-rabies serological response of Squirrel monkeys inoculated with canarypox recombinants

| Monkey # | Previous Exposure | Rabies serum-neutralizing antibody[a] | | | | | | |
|---|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ TCID$_{50}$ of ALVAC
[d]Animals received 5.0 $\log_{10}$ TCID$_{50}$ of vCP37
[e]Animals received 5.0 $\log_{10}$ TCID$_{50}$ of ALVAC-RG
[f]Animals received 7.0 $\log_{10}$ TCID$_{50}$ of ALVAC-RG
[g]Not tested.

TABLE 14

Inoculation of rhesus macaques with ALVAC-RG[a]

| Days post-Inoculation | or/Tang | | SC | SC | SC | IM | SC | IM | SC | IM | OR |
|---|---|---|---|---|---|---|---|---|---|---|---|
| | 176L[b] | 185L | 177L | 186L | 178L | 182L | 179L | 183L | 180L | 184L | 187L[b] |
| −84 | − | − | | | | | | | | | |
| −9 | − | − | − | − | − | − | | | | | |
| 3 | − | − | − | − | | | | | | | |
| 6 | − | − | ± | ± | | | | | | | |
| 11 | — | — | 16[d] | 128 | | | | | | | |
| 19 | − | − | 32 | 128 | − | | − | | | | |
| 35 | − | − | 32 | 512 | | | | | | | |
| 59 | − | − | 64 | 256 | | | | | | | |
| 75 | − | − | 64 | 128 | − | | − | | | | |
| 99[c] | — | — | 64 | 256 | − | − | − | − | — | — | — |
| 2 | − | − | 32 | 256 | — | − | − | − | − | − | − |
| 6 | − | − | 512 | 512 | — | — | − | − | − | − | − |
| 15 | 16 | 16 | 512 | 512 | 64 | 32 | 64 | 128 | 32 | − | − |
| 29 | 16 | 32 | 256 | 256 | 64 | 64 | 32 | 128 | 32 | − | — |
| 55 | | 32 | | | | 32 | | 32 | 16 | − | |
| 57 | 16 | | 128 | 128 | 16 | | 16 | | | | — |

[a]See Table 9 for schedule of inoculations.
[b]Animals 176L and 185L received 8.0 log$_{10}$ pfu by the oral route in 5 ml Tang. Animal 187L received 7.0 log$_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 15

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation

EXAMPLE 16

CONSTRUCTION OF NYVAC RECOMBINANTS EXPRESSING FLAVIVIRUS PROTEINS

This example describes the construction of NYVAC donor plasmids containing genes from Japanese encephalitis virus (JEV), yellow fever virus (YF) and Dengue type 1, the isolation of the corresponding NYVAC Flavivirus recombinants and the ability of vaccinia recombinants expressing portions of the genomes of JEV or YF to protect mice against lethal challenge with the homologous virus.

Cell Lines and Virus Strains. A thymidine kinase mutant of the Copenhagen strain of vaccinia virus vP410 (Guo et al., 1989) was used to generate recombinants vP825, vP829, vP857 and vP864 (see below). The generation of vP555 has previously been described (Mason et al., 1991). Biosynthetic studies were performed using HeLa cells grown at 37° C. in Eagle's minimal essential medium supplemented with FBS and antibiotics. The JEV virus used in all in vitro experiments was a clarified culture fluid prepared from C6/36 cells infected with a passage 55 suckling mouse brain suspension of the Nakayama strain of JEV (Mason, 1989). Animal challenge experiments were performed using the highly pathogenic P3 strain of JEV (see below).

Cloning of JEV Genes Into a Vaccinia Virus Donor Plasmid. The JEV cDNAs used to construct the JEV-vaccinia recombinant viruses were derived from the Nakayama strain of JEV (McAda et al., 1987).

Plasmid pDr20 containing JEV cDNA (nucleotides −28 to 1000) in the SmaI and EcoRI sites of pUC18, was digested with BamHI and EcoRI and the JEV cDNA insert cloned into pIBI25 (International Biotechnologies, Inc., New Haven, Conn.) generating plasmid JEV18. JEV18 was digested with ApaI within the JE sequence (nucleotide 23) and XhoI within pIBI25 and ligated to annealed oligonucleotides J90 (SEQ ID NO:114) and J91 (SEQ ID NO:115) (containing an XhoI sticky end, SmaI site, and JE nucleotides 1 to 23) generating plasmid JEV19. JEV19 was digested with XhoI within pIBI25 and AccI within JE sequences (nucleotide 602) and the resulting 613 bp fragment was cloned into the XhoI and AccI fragment of JEV2 (Mason et al., 1991) containing the plasmid origin and JEV cDNA encoding the carboxy-terminal 40% prM and amino-terminal two thirds of E (nucleotides 602 to 2124), generating plasmid JEV20 containing JE sequences from the ATG of C through the SacI site (nucleotide 2124) found in the last third of E.

The SmaI-SacI fragment from JEV8 (a plasmid analogous to JEVL Mason et al., 1991) in which TTTTTGT nucleotides 1304 to 1310 were changed to TCTTTGT), containing JE sequences from the last third of E through the first two amino acids of NS2B (nucleotides 2124 to 4126), the plasmid origin and vaccinia sequences, was ligated to the purified SmaI-SacI insert from JEV20 yielding JEV22-1. The 6 bp corresponding to the unique SmaI site used to construct JEV22-1 were removed using oligonucleotide-directed double-strand break mutagenesis (Mandecki, 1986) creating JEV24 in which the H6 promoter immediately preceded the ATG start codon.

Plasmid JEV7 (Mason et al., 1991) was digested with SphI within JE sequences (nucleotide 2180) and HindIII within IBI24. Ligation to annealed oligonucleotides J94 and J95 [containing a SphI sticky end, translation stop, a vaccinia early transcription termination signal (TTTTTAT; Yuen et al., 1987) a translation stop, an EagI site and a HindIII sticky end] generated plasmid JEV25 which contains JE cDNA extending from the SacI site (nucleotide 2124) in the last third of E through the carboxy-terminus of E. The SacI-EagI fragment from JEV25 was ligated to the SacI-EagI fragment of JEV8 (containing JE cDNA encoding 15 aa C, prM and amino-terminal two thirds of E nucleotides 337 to 2124, the plasmid origin and vaccinia sequences) yielding plasmid JEV26. A unique SmaI site preceding the ATG start codon was removed as described above, creating JEV27 in which the H6 promoter immediately preceded the ATG start codon.

Oligonucleotides J96, J97, J98 and J99 (containing JE nucleotides 2243 to 2380 with an SphI sticky end) were kinased, annealed and ligated to SmaI-SphI digested and alkaline phosphatase treated pIBI25 generating plasmid JEV28. JEV28 was digested with HpaI within the JE sequence (nucleotide 2301) and with HindIII within the pIBI25 sequence and alkaline phosphatase treated. Ligation to the HpaI-HindIII fragment from JEV1 or HpaI-HindIII fragment from JEV7 (Mason et al., 1991) yielded JEV29 (containing a SmaI site followed by JE cDNA encoding 30 aa E, NS1, NS2A nucleotides 2293 to 4126) and JEV30 (containing a SmaI site followed by JE cDNA encoding 30 aa E, NS1, NS2A, NS2B nucleotides 2293 to 4512).

The SmaI-EagI fragment from JEV29 was ligated to SmaI-EagI digested pTP15 (Mason et al., 1991) yielding JEV31. The 6 bp corresponding to the unique SmaI site used to produce JEV31 were removed as described above creating JEV33 in which the H6 promoter immediately preceded the ATG start codon.

Figure 18:
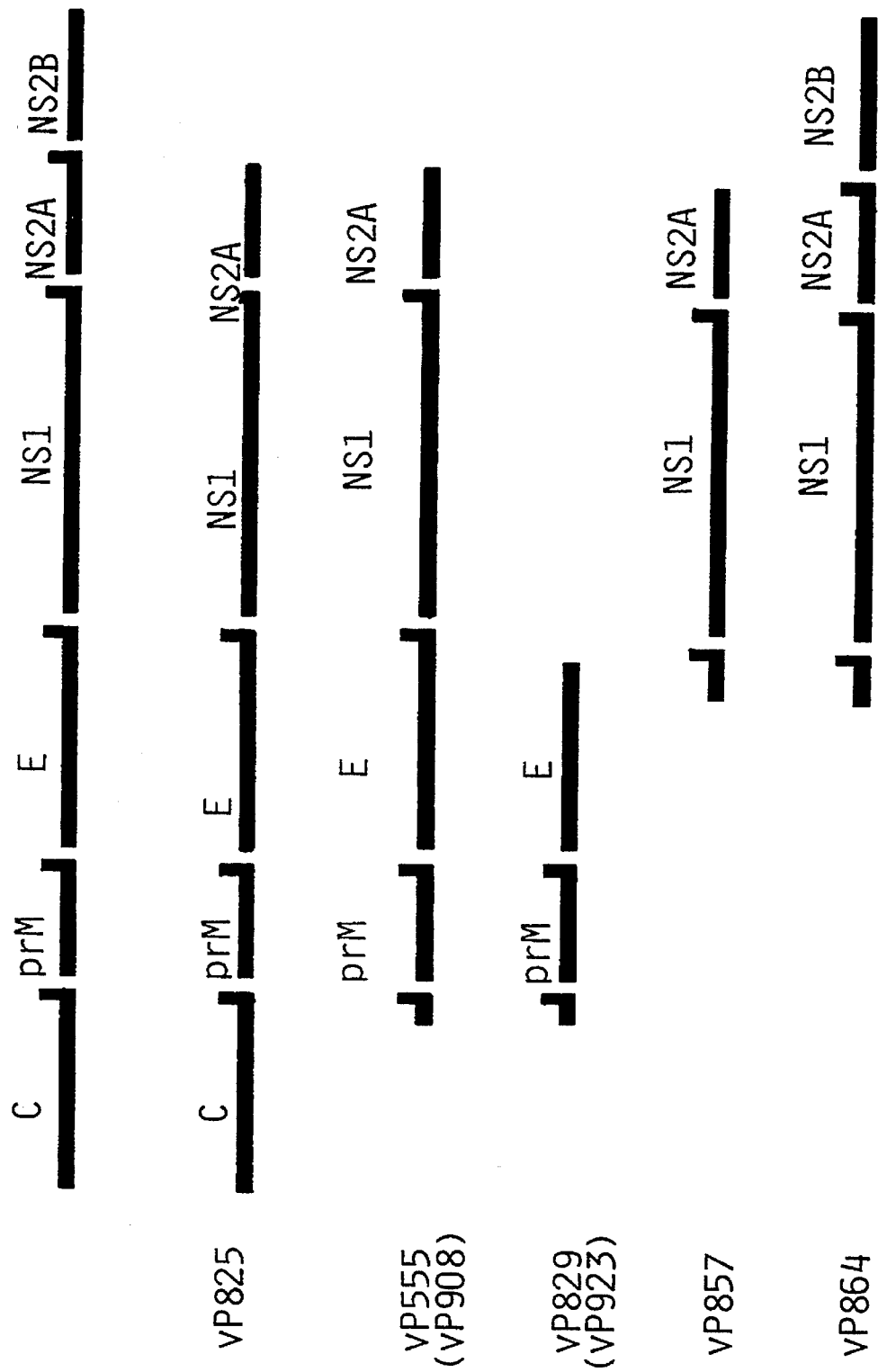
FIG. 18 is a schematic of the JEV coding regions inserted in the vaccinia viruses vP555, vP825, vP908, vP923, vP857 and vP864.

The SmaI-EagI fragment from JEV30 was ligated to SmaI-EagI digested pTP15 yielding JEV32. The 6 bp corresponding to the unique SmaI site used to produce JEV32 were removed as described above creating JEV34 in which the H6 promoter immediately preceded the ATG start codon. Oligonucleotides J90 (SEQ ID NO:114), J91 (SEQ ID NO:115), J94 (SEQ ID NO:116), J95 (SEQ ID NO:117), J96 and J97 (SEQ ID NO:118), and J99 and J98 (SEQ ID NO:119) are as follows:

nants vP825, vP829, vP857 and vP864 respectively (FIG. 18).

In Vitro Virus Infection and Radiolabeling. HeLa cell monolayers were prepared in 35 mm diameter dishes and infected with vaccinia viruses (m.o.i. of 2 pfu per cell) or JEV (m.o.i. of 5 pfu per cell) before radiolabeling. Cells were pulse labeled with medium containing $^{35}$S-Met and chased for 6 hr in the presence of excess unlabeled Met exactly as described by Mason et al. (1991).

Radioimmunoprecipitations, Polyacrylamide Gel Electrophoresis, and Endoglycosidase Treatment. Radiolabeled cell lysates and culture fluids were harvested and the viral proteins were immunoprecipitated, digested with endoglycosidases, and separated in SDS-containing polyacrylamide gels (SDS-PAGE) exactly as described by Mason (1989).

Animal Protection Experiments. Mouse protection experiments were performed exactly as described by Mason et al. (1991). Briefly, groups of 3-week-old mice were immunized by intraperitoneal (ip) injection with $10^7$ pfu of vaccinia virus recombinants, and 3 weeks later sera were collected from selected mice. Mice were then either re-inoculated with the recombinant virus or challenged with $1.3 \times 10^3$ LD$_{50}$ by intraperitoneal injection with a suspension of suckling mouse brain infected with the P3 strain of JEV. Three weeks later, the boosted animals were rebled and challenged with $4.9 \times 10^5$ LD$_{50}$ of the P3 strain of JEV. Following challenge, mice were observed at daily intervals for three weeks and lethal-dose titrations were performed in each challenge experiment using litter-mates of the experimental animals. In addition, sera were collected from all surviving animals 4 weeks after challenge.

Evaluation of Immune Response to the Recombinant Vaccinia Viruses. Sera were tested for their ability to precipitate JEV proteins from detergent-treated cell lysates or culture fluids obtained from $^{35}$S-Met-labeled JEV-infected cells exactly as described by Mason et al. (1991). Hemagglutination inhibition (HAI) and neutralization (NEUT) tests were performed as described by Mason et al. (1991) except carboxymethylcellulose was used in the overlay medium for the NEUT test.

Structure of Recombinant Vaccinia Viruses. Four different vaccinia recombinants (in the HA locus) were constructed that expressed portions of the JEV coding region extending from C through NS2B. The JEV cDNA sequences contained in these recombinant viruses are shown in FIG. 18. In all four recombinant viruses the sense strand of the JEV cDNA was positioned behind the vaccinia virus early/late H6 promoter, and translation was expected to be initiated from

```
J90  5'-TCGAG CCCGGG a t g ACT AAAAAACCAGGA GGGCC-3'
J91  3'-      C GGGCCC TAC TGATTTTTTGGTCCT C     -5'
     XhoI    SmaI                            ApaI

J94  5'-       CT t ga t t t t t at t g a CGGCCG A       -3'
J95  3'-GT ACG A ACT AAAAATA ACT GCCGGC TTCGA-5'
     SphI                          EagI    HindIII J96+J97  5'-GGG a t g  GGCGTT AACGCACGAGACCGATCAATTGCTTTGGCC
J99+J98  3'-CCC TAC    CCGCAATTGCGTGCTCTGGCTAGTTAACGAAACCGG TTCTTAGCCACAGGAGGTGTGCTCGTGTTCTTAGCGACCAATGT GCATG-3'
         AAGAATCGGTGTCCTCCACACGAGCACAAGAATCGCTGGTTACA C    -5'
                                                      SphI
```

Construction of Vaccinia Virus JEV Recombinants. Plasmids JEV24, JEV27, JEV33 and JEV34 were transfected into vP410 infected cells to generate the vaccinia recombinants naturally occuring JEV Met codons located at the 5' ends of the viral cDNA sequences.

Recombinant vP825 encoded the capsid protein, structural protein precursor prM, the structural glycoprotein E, the nonstructural glycoprotein NS1, and the nonstructural protein NS2A (McAda et al., 1987). Recombinant vP829 encoded the putative 15 aa signal sequence preceding the amino-terminus of prM, as well as prM, and E (McAda et al., 1987). Recombinant vP857 contained a cDNA encoding the 30 aa hydrophobic carboxy-terminus of E, followed by NS1 and NS2A. Recombinant vP864 contained a cDNA encoding the same proteins as vP857 with the addition of NS2B. In recombinants vP825 and vP829 a potential vaccinia virus early transcription termination signal in E (TTTTTGT; nucleotides 1304–1310) was modified to TCTTTGT without altering the aa sequence. This change was made in an attempt to increase the level of expression of E since this sequence has been shown to increase transcription termination in in vitro transcription assays (Yuen et al., 1987).

E and prM Are Correctly Processed When Expressed By Recombinant Vaccinia Viruses. Pulse-chase experiments demonstrate that proteins identical in size to E were synthesized in cells infected with all recombinant vaccinia viruses containing the E gene (Table 16). In the case of cells infected with JEV, vP555 and vP829, an E protein that migrated slower in SDS-PAGE was also detected in the culture fluid harvested from the infected cells (Table 16). This extracellular form of E produced by JEV- and vP555-infected cells contained mature N-linked glycans (Mason, 1989; Mason et al., 1991), as confirmed for the extracellular forms of E produced by vP829-infected cells. Interestingly, vP825, which contained the C coding region in addition to prM and E specified the synthesis of E in a form that is not released into the extracellular fluid (Table 16). Immunoprecipitations prepared from radiolabeled recombinant vaccinia-infected cells using a MAb specific for M (and prM) revealed that prM was synthesized in cells infected with vP555, vP825, and vP829, and M was detected in the culture fluid of cells infected with vP555 or vP829 (Table 16).

The extracellular fluid harvested from cells infected with vP555 and vP829 contained an HA activity that was not detected in the culture fluid of cells infected with vP410, vP825, vP857 or vP864. This HA appeared similar to the HA produced in JEV infected cells based on its inhibition by anti-JEV antibodies and its pH optimum (Mason et al., 1991). Sucrose density gradients were prepared with culture fluids from cells infected with vaccinia virus JEV recombinants vP829, vP825, vP857 and vP864. Analysis of the gradients identified a peak of HA activity in the vP829 infected sample that co-migrated with the peak of slowly-sedimenting hemagglutinin (SHA) found in the JEV culture fluids (data not shown). This result indicated that vP829 infected cells produce extracellular particles similar to the empty viral envelopes containing E and M observed in the culture fluids harvested from vP555 infected cells (Table 16 and Mason et al., 1991).

NS1 Is Correctly Processed and Secreted When Expressed By Recombinant Vaccinia Virus. The results of pulse-chase experiments demonstrated that proteins identical in size to authentic NS1 and NS1' were synthesized in cells infected with vP555, vP825, vP857 and vP864. NS1 produced by vP555-infected cells was released into the culture fluid of infected cells in a higher molecular weight form. NS1 was also released into the culture fluid of cells infected with vP857 and vP864, whereas NS1 was not released from cells infected with vP825 (Table 16). Comparison of the synthesis of NS1 from recombinant vaccinia viruses containing either the NS2A (vP857) or both the NS2A and NS2B coding regions showed that the presence or absence of the NS2B coding region had no affect on NS1 expression, consistent with previous data showing that only the NS2A gene is needed for the authentic processing of NS1 (Falgout et al., 1989; Mason et al., 1991).

Recombinant Vaccinia Viruses Induced Immune Responses To JEV Antigens. Pre-challenge sera pooled from selected animals in each group were tested for their ability to immunoprecipitate radiolabeled E and NS1. The results of these studies (Table 16) demonstrated that: (1) the magnitude of immune response induced to E was vP829>vP555>vP825, (2) all viruses encoding NS1 and NS2A induced antibodies to NS1, and (3) all immune responses were increased by a second inoculation with the recombinant viruses. Analysis of the neutralization and HAI data for the sera collected from these animals (Table 17) confirmed the results of the immunoprecipitation analyses, showing that the immune response to E as demonstrated by RIP correlated well with these other serological tests (Table 17).

Vaccination With the Recombinant Viruses Provided Protection From Lethal JEV Infection. All of the recombinant vaccinia viruses were able to provide mice with some protection from lethal infection by the peripherally pathogenic P3 strain of JEV (Huang, 1982) (Table 17). These studies confirmed the protective potential of vP555 (Mason et al., 1991) and demonstrated similar protection in animals inoculated with vP825 and vP829. Recombinant viruses vP857 and vP864 which induced strong immune responses to NS1 showed much lower levels of protection, but mice inoculated with these recombinants were still significantly protected when compared to mice inoculated with the control virus, vP410 (Table 17).

Post-Challenge Immune Responses Document the Level of JEV Replication. In order to obtain a better understanding of the mechanism of protection from lethal challenge in animals inoculated with these recombinant viruses, the ability of antibodies in post-challenge sera to recognize JEV antigens was evaluated. For these studies antigen present in lysates of radiolabeled JEV-infected cells was utilized, and the response to the NS3 protein which induces high levels of antibodies in hyperimmunized mice (Mason et al., 1987a) was examined. The results of these studies (Table 18) correlates with the survival data in that groups of animals vaccinated with recombinant viruses that induced high levels of protection (vP829, vP555, and vP825) showed low post-challenge responses to NS3, whereas the sera from survivors of groups vaccinated with recombinants that expressed NS1 alone (vP857 and vP864) showed much higher post-challenge responses to NS3.

TABLE 16

Characterization of proteins expressed by vaccinia recombinants expressing JEV proteins and their immune responses

| | vP555 | vP829 | vP825 | vP857 | vP864 |
|---|---|---|---|---|---|
| Proteins expressed[a] | | | | | |
| Intracellular | prM,E NS1 | prM,E | prM,E NS1 | NS1 | NS1 |
| secreted | M,E,NS1 | M,E | none | NS1 | NS1 |
| Particle formation[b] | + | + | − | − | − |
| Immune response[c] | | | | | |
| single | E | E | NS1 | NS1 | NS1 |
| double | E,NS1 | E | E,NS1 | NS1 | NS1 |

[a]Radiolabelled cell lysates and culture fluids from vaccinia virus JEV recombinant infected cells were harvested and JEV-specific proteins immunoprecipitated using mAbs to E, M and NS1 proteins.
[b]Formation of extracellular particles with HA activity as described in the text.

TABLE 16-continued

Characterization of proteins expressed by vaccinia
recombinants expressing JEV proteins and their immune
responses

| | vP555 | vP829 | vP825 | vP857 | vP864 |
|---|---|---|---|---|---|

[c]JEV proteins were immunoprecipitated from radiolabelled JEV-infected cells by sera from mice which had received one (single) or two (double) inoculations of the indicated vaccinia virus JEV recombinant.

TABLE 17

Protection of mice and immune response following
single or double inoculations with recombinant
vaccinia virus expressing JEV proteins

| | Immunize Virus[a] | | | | |
|---|---|---|---|---|---|
| Protection[b] | vP555 | vP829 | vP825 | vP857 | vP864 |
| single inoculation | 7/10 | 10/10 | 8/10 | 0/10 | 1/10 |
| double inoculation | 10/10 | 9/10 | 9/10 | 5/10 | 6/10 |
| Neut titer[c] | | | | | |
| single inoculation | 1:20 | 1:160 | 1:10 | <1:10 | <1:10 |
| double inoculation | 1:320 | 1:2560 | 1:320 | <1:10 | <1:10 |
| HAI titer[d] | | | | | |
| single inoculation | 1:20 | 1:40 | 1:10 | <1:10 | <1:10 |
| double inoculation | 1:80 | 1:160 | 1:40 | <1:10 | <1:10 |

[a]Groups of 20 mice were inoculated by ip route with $10^7$ pfu of the indicated vaccinia virus JEV recombinant. Sera were collected after three weeks. At this time, 10 mice per group were challenged with JEV as indicated in the text (single inoculation). The remaining 10 mice in each group were boosted with the same vaccinia virus JEV recombinant (double inoculation). After three weeks, sera were collected and the mice were challenged with JEV. All mice were challenged with JEV. All mice were observed for 21 days post challenge.
[b]Protection is expressed as number os mice surviving at 21 days post challenge/total.
[c]Neutralization titer is expressed as the reciprocal of the highest dilution that gives 90% JEV plaque reduction.
[d]HAI titer is expressed as the reciprocal of the highest dilution that gives measurable inhibition of hemagglutination of red blood cells.

TABLE 18

Post challenge immune response following single or
double inoculation with recombinant vaccinia virus
expressing JEV proteins.

| | Immunizing virus | | | | |
|---|---|---|---|---|---|
| | vP555 | vP829 | vP825 | vP857 | vP864 |
| single | ++ | + | ++ | –[a] | ++++ |
| double | +/–[b] | – | – | ++ | +++ |

+ NS3 antibodies present in post-challenge sera
[a]No surviving mice
[b]Very low level NS3 antibodies present in post-challenge sera 21 day post challenge sera from mice surviving JEV challenge following single or double inoculation with vaccinia virus JEV recombinants (Table 17) were analyzed for the presence of antibodies to JEV NS3.

Cloning of JEV Genes Into a Vaccinia (NYVAC) Donor Plasmid. Plasmid pMP2VCL (containing a polylinker region within vaccinia sequences upstream of the K1L host range gene) was digested within the polylinker with HindIII and XhoI and ligated to annealed oligonucleotides SPHPRHA A through D generating SP126 containing a HindIII site, H6 promoter −124 through −1 (Perkus et al., 1989) and XhoI, KpnI, SmaI, SacI and EcoRI sites.

Plasmid pSD544VC (containing vaccinia sequences surrounding the site of the HA gene which was replaced with a polylinker region and translation termination codons in six reading frames) was digested with XhoI within the polylinker, filled in with the Klenow fragment of DNA polymerase I and treated with alkaline phosphatase. SP126 was digested with HindIII, treated with Klenow and the H6 promoter isolated by digestion with SmaI. Ligation of the H6 promoter fragment to pSD544VC generated SPHA-H6 which contained the H6 promoter in the polylinker region (in the direction of HA transcription).

Plasmid JEVL14VC was digested with EcoRV in the H6 promoter and SacI in JEV sequences (nucleotide 2124) and a 1789 bp fragment isolated. JEVL14VC (Mason et al., 1991) was digested with EclXI at the EagI site following the T5NT, filled in with the Klenow fragment of DNA polymerase I and digested with SacI in JEV sequences (nucleotide 2124) generating a 2005 bp fragment. The 1789 bp EcoRV-SacI and 2005 bp (SacI-filled EclXI) fragments were ligated to EcoRV (within H6) and SmaI digested (within polylinker) and alkaline phosphatase treated SPHA-H6 generating JEV35. JEV35 was transfected into vP866 (NYVAC) infected cells to generate the vaccinia recombinant vP908 (FIG. 18).

JEV35 was digested with SacI (within JE sequences nucleotide 2124) and EclXI (after T5NT) a 5497 bp fragment isolated and ligated to a SacI (JEV nucleotide 2124) to EagI fragment of JEV25 (containing the remaining two thirds of E, translation stop and T5NT) generating JEV36. JEV36 was transfected into vP866 (NYVAC) infected cells to generate the vaccinia recombinant vP923 (FIG. 18). SPHPRHA A through D Oligonucleotides SPHPRHA:A+B (SEQ ID NO:120) and SPHPRHA:C+D (SEQ ID NO:121) are as follows

```
        HindIII
5'-   AGCTT CTTT ATT CT AT ACT T AAAAAGT GAAAAT AAAT ACAAAGGTT CTT GA
3'-         AGAAAT AAGAT AT GAATT TTT CACTTTT ATTT AT GTTT CCAAGAACT EcoRV
      GGGTT GT GTT AAATT GAAAGC GAGAAAT AAT CAT AAATT TATTT CATT AT CGC GAT ATCCG
      CCCAACACAATTT AACTTT CGCT CTTT ATT AGT ATTT AAT AAAGT AAT AGCGCT AT AGGC TT AAGTTT GT AT CGT AC    -3'
      AATT CAAACAT AGCAT GAGCT -5'
                        XhoI
```

Construction of Plasmids Containing YF Genes. The YF 17D cDNA clones used to construct the YF vaccinia recombinant viruses (clone 10III and clone 28III), were obtained from Charles Rice (Washington University School of Medicine, St. Louis, Mo.). All nucleotide coordinates are derived from the sequence data presented in Rice et al., 1985.

Plasmid YF0 containing YF cDNA encoding the carboxy-terminal 80% prM, E and amino-terminal 80% NS1 (nucleotides 537–3266) was derived by cloning an AvaI to NsiI fragment of YF cDNA (nucleotides 537–1659) and an NsiI to KpnI fragment of YF cDNA (nucleotides 1660–3266) into AvaI and KpnI digested IBI25 (International Biotechnologies, Inc., New Haven, Conn.). Plasmid YF1 containing YF cDNA encoding C and amino-terminal 20% prM (nucleotides 119–536) was derived by cloning a RsaI to AvaI fragment of YF cDNA (nucleotides 166–536) and annealed oligonucleotides SP46 and SP47 (containing a disabled HindIII sticky end, XhoI and ClaI sites and YF nucleotides 119–165) into AvaI and HindIII digested IBI25. Plasmid YF3 containing YF cDNA encoding the carboxy-terminal 60% of E and amino-terminal 25% of NS1 was generated by cloning an ApaI to BamHI fragment of YF cDNA (nucleotides 1604–2725) into ApaI and BamHI digested IBI25. Plasmid YF8 containing YF cDNA encoding the carboxy-terminal 20% NS1 NS2a, NS2B and amino-terminal 20% NS3 was derived by cloning a KpnI to XbaI fragment of YF cDNA (nucleotides 3267–4940) into KpnI and XbaI digested IBI25. Plasmid YF9 containing YF cDNA encoding the carboxy-terminal 60% NS2B and amino-terminal 20% NS3 was generated by cloning a SacI to XbaI fragment of YF cDNA (nucleotides 4339–4940) into SacI and XbaI digested IBI25. Plasmid YF13 containing YF cDNA encoding the carboxy-terminal 25% of C, prM and amino-terminal 40% of E was derived by cloning a BalI to ApaI fragment of YF cDNA (nucleotides 384–1603) into ApaI and SmaI digested IBI25.

Oligonucleotide-directed mutagenesis (Kunkel, 1985) was used to change the following potential vaccinia virus early transcription termination signals (Yuen et al., 1987) (1) 49 aa from the amino-terminus of the C gene in YF1 (TTTTTCT nucleotides 263–269 and TTTTTGT nucleotides 269–275) to (SEQ ID NO:122) TTCTTCTTCTTGT creating plasmid YF1B, (2) in the E gene in YF3 (nucleotides 1886–1893 TTTTTTGT to TTCTTTGT 189 aa from the carboxy-terminus and nucleotides 2429–2435 TTTTTGT to TTCTTGT 8 aa from the carboxy-terminus) creating plasmids YF3B and YF3C, respectively. A PstI to BamHI fragment from YF3C (nucleotides 1965–2725) was exchanged for the corresponding fragment of YF3B generating YF4 containing YF cDNA encoding the carboxy-terminal 60% E and amino-terminal 25% NS1 (nucleotides 1604–2725) with both mutagenized transcription termination signals. An ApaI to BamHI fragment from YF4 (nucleotides 1604–2725) was substituted for the equivalent region in YF0 creating plasmid YF6 containing YF cDNA encoding the carboxy-terminal 80% prM, E and amino-terminal 80% NS1 (nucleotides 537–3266) with both mutagenized transcription termination signals. Plasmid YF6 was digested with EcoRV within the IBI25 sequences and AvaI at nucleotide 537 and ligated to an EcoRV to AvaI fragment from YF1B (EcoRV within IBI25 to AvaI at nucleotide 536) generating YF2 containing YF cDNA encoding C through the amino-terminal 80% of NS1 (nucleotides 119–3266) with an XhoI and ClaI site at 119 and four mutagenized transcription termination signals.

Oligonucleotide-directed mutagenesis described above was used (1) to insert XhoI and ClaI sites preceding the ATG 17 aa from the carboxy-terminus of E (nucleotides 2402–2404) in plasmid YF3C creating YF5, (2) to insert XhoI and ClaI sites preceding the ATG 19 aa from the carboxy-terminus of prM (nucleotides 917–919) in plasmid YF13 creating YF14, (3) to insert an XhoI site preceding the ATG 23 aa from the carboxy-terminus of E (nucleotides 2384–2386) in plasmid YF3C creating plasmid YF25, (4) and to insert an XhoI site and ATG (nucleotide 419) in plasmid YF1 21 aa from the carboxy-terminus of C generating YF45.

An ApaI to BamHI fragment from YF5 (nucleotides 1604–2725) was exchanged for the corresponding region of YF0 creating YF7 containing YF cDNA encoding the carboxy-terminal 80% prM, E and amino-terminal 80% NS1 (nucleotides 537–3266) with XhoI and ClaI sites at 2402 (17 aa from the carboxy-terminus of E) and a mutagenized transcription termination signal at 2429–2435 (8 aa from the carboxy-terminus of E). The ApaI to BamHI fragment from YF25 (nucleotides 1604–2725) was exchanged for the corresponding region of YF0 generating YF26 containing YF cDNA encoding the carboxy-terminal 80% prM, E and amino-terminal 80% NS1 (nucleotides 537–3266) with an XhoI site at nucleotide 2384 (23 aa from the carboxy-terminus of E) and mutagenized transcription termination signal at 2428–2435 (8 aa from the carboxy-terminus of E).

An AvaI to ApaI fragment from YF14 (nucleotides 537–1603) was substituted for the corresponding region in YF6 generating YF15 containing YF cDNA encoding the carboxy-terminal 80% prM, E and amino-terminal 80% NS1 (nucleotides 537–3266) with XhoI and ClaI sites at nucleotide 917 (19 aa from the carboxy-terminus of prM) and two mutagenized transcription termination signals. YF6 was digested within IBI25 with EcoRV and within YF at nucleotide 537 with AvaI and ligated to an EcoRV (within IBI25) to AvaI fragment of YF45 generating YF46 containing YF cDNA encoding C through the amino-terminal 80% NS1 (nucleotides 119–3266) with an XhoI site at 419 (21 aa from the carboxy-terminus of C) and two transcription termination signals removed.

Oligonucleotide-directed mutagenesis described above was used to insert a SmaI site at the carboxy-terminus of NS2B (nucleotide 4569) in plasmid YF9 creating YF11, and to insert a SmaI site at the carboxy-terminus of NS2A (nucleotide 4180) in plasmid YF8 creating YF10. A SacI to XbaI fragment from YF11 (nucleotides 4339–4940) and Asp718 to SacI fragment from YF8 (nucleotides 3262–4338) were ligated to Asp718 and XbaI digested IBI25 creating YF12 containing YF cDNA encoding the carboxy-terminal 20% NS1, NS2A, NS2B and amino-terminal 20% NS2B (nucleotides 3262–4940) with a SmaI site after the carboxy-terminus of NS2B (nucleotide 4569).

Cloning of YF Genes into a pHES System Vaccinia Virus Donor Plasmid. Prior to insertion of YF cloning sequences into a NYVAC donor plasmid, YF coding sequences were inserted into vaccinia plasmid pHES4 (Perkus et al., 1989). A KpnI to SmaI fragment from YF12 encoding carboxy-terminal 20% NS1, NS2A and NS2B (nucleotides 3267–4569), XhoI to KpnI fragment from YF15 encoding 19 aa prM, E and amino-terminal 80% NS1 (nucleotides 917–3266) and XhoI-SmaI digested pHES4 were ligated generating YF23. An XhoI to BamHI fragment from YF26 encoding 23 aa E, amino-terminal 25% NS1 (nucleotides 2384–2725) was ligated to an XhoI to BamHI fragment from YF23 (containing the carboxy-terminal 75% NS1, NS2A and NS2B, the origin of replication and vaccinia sequences) generating YF28.

XhoI-SmaI digested pHES4 was ligated to a purified XhoI to KpnI fragment from YF7 encoding 17 aa E and amino-terminal 80% NS1 (nucleotides 2402–3266) plus a KpnI to SmaI fragment from YF10 encoding the carboxy-terminal 20% NS1 and NS2A (nucleotides 3267–4180) creating YF18. An XhoI to BamHI fragment from YF2 encoding C, prM, E and amino-terminal 25% NS1 (nucleotides 119–2725) was ligated to a XhoI to BamHI fragment of YF18 (containing the carboxy-terminal 75% NS1 and NS2A, the origin of replication and vaccinia sequences) generating YF19. The same XhoI to BamHI fragment from YF2 was ligated to a XhoI to BamHI fragment from YF28 (containing the carboxy-terminal 75% NS1 and NS2A, the origin of replication and vaccinia sequences) generating YF20. A XhoI to BamHI fragment from YF46 encoding 21 aa C, prM, E and amino-terminal 25% NS1 (nucleotides 419–2725) was ligated to the XhoI to BamHI fragment from YF18 generating YF47. Oligonucleotide SP46 (SEQ ID NO:123) AND SP47 (SEQ ID NO:124) are as follows:

```
        HindIII
SP46 5'- AGCTT CTCGAGCATCGATTACT a t g TCTGGTCGTAAAGCTCAGGG
SP47 3'-     A GAGCTCGTAGCTAATGA TAC AGACCAGCATTTCGAGTCCC

AAAAACCCTGGGCGTCAATATGGT  -3'
         TTTTTGGGACCCGCAGTTATACCA  -5'
```

Figure 19:
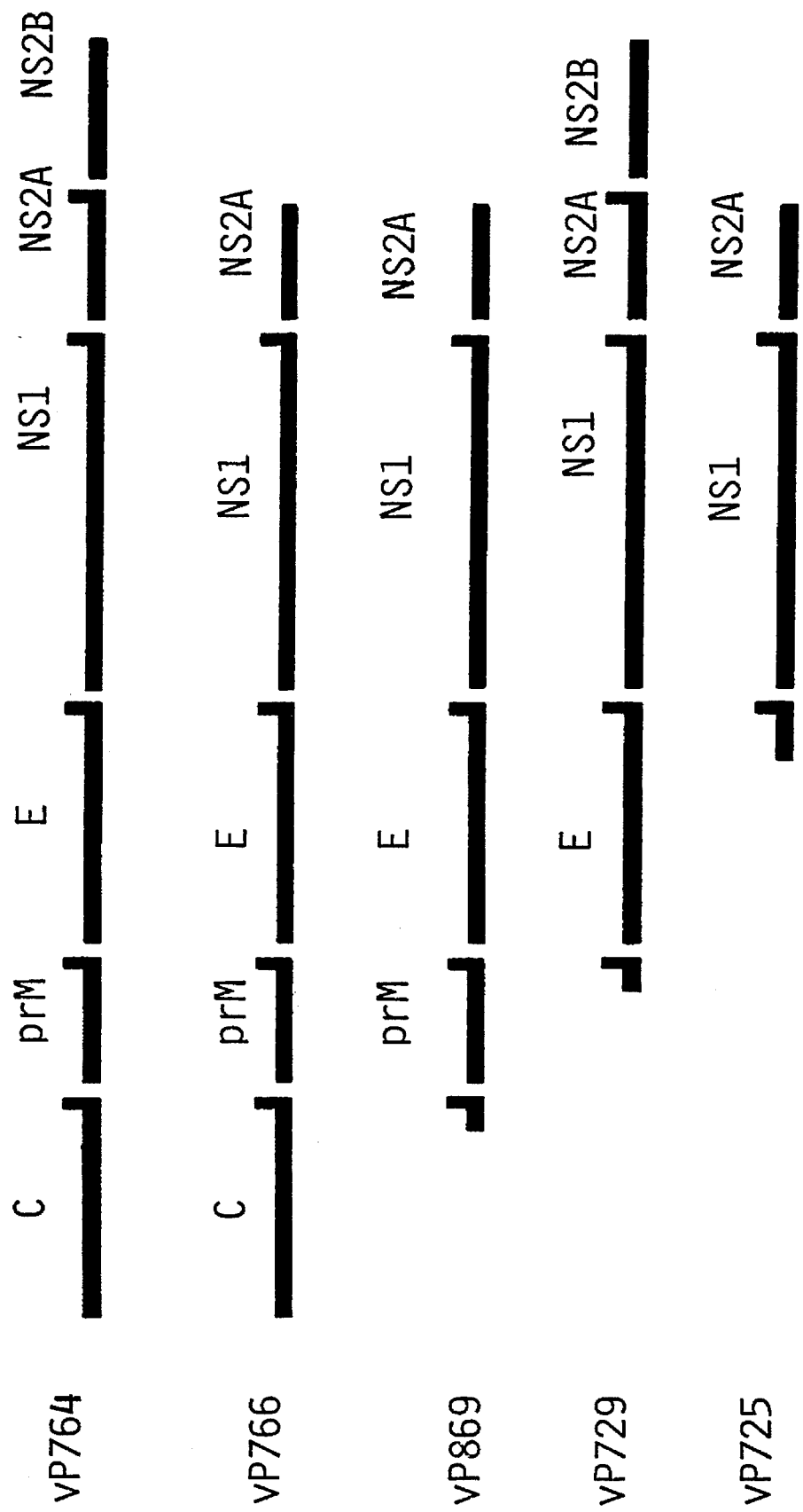
FIG. 19 is a schematic of the YF coding regions inserted in the vaccinia viruses vP766, vP764, vP869, vP729 and vP725.

Construction of Recombinant YF Vaccinia Viruses. Five different vaccinia virus recombinants that expressed portions of the YF coding region extending from C through NS2B were constructed utilizing a host range selection system (Perkus et al., 1989). Plasmids YF18, YF23, YF20, YF19 and YF47 were transfected into vP293 infected cells to generate the vaccinia recombinants vP725, vP729, vP764, vP766 and vP869. The YF cDNA sequences contained in these recombinants are shown in FIG. 19. In all five recombinant viruses the sense strand of YF cDNA was positioned behind the vaccinia virus early/late H6 promoter, and translation was expected to be initiated from Met codons located at the 5' ends of the viral cDNA sequences (FIG. 19).

Recombinant vP725 encoded the putative 17-aa signal sequence preceding the N terminus of the nonstructural protein NS1 and the nonstructural proteins NS1 and NS2A (Rice et al., 1985). Recombinant vP729 encoded the putative 19-aa signal sequence preceding the N terminus of E, E, NS1, NS2A and NS2B (Rice et al., 1985). Recombinant vP764 encoded C, prM, E, NS1, NS2A and NS2B (Rice et al., 1985). Recombinant vP766 encoded C, prM, E, NS1 and NS2A (Rice et al., 1985). Recombinant vP869 encoded the putative 21-aa signal sequence preceding the N terminus of the prM structural protein precursor as well as prM, E, NS1 and NS2A (Rice et al., 1985).

Protection From Lethal YF Challenge. vP869 secreted an HA activity not found in the culture fluid of cells infected with any of the other recombinants. This HA appeared similar to the HA produced in YF infected cells based on its inhibition by anti-YF antibodies and pH optimum.

Three-week-old mice were inoculated intraperitoneally with $10^7$ pfu vP869, vP764 or YF-17D and challenged three weeks later with 100 $LD_{50}$ of French neurotropic strain of YF. vP869 provided significant protection (Table 19) whereas vP764 offered no better protection than a control vaccinia virus lacking YF genes (vP457).

TABLE 19

Protection of mice by recombinant vaccinia viruses from YF challenge

| Immunizing Virus | Survival/total |
|---|---|
| vP457 | 2/10 |
| vP764 | 2/10 |
| vP869 | 9/10 |
| 17D | 5/10 |

Cloning of YF Genes Into a NYVAC Donor Plasmid. A XhoI to SmaI fragment from YF47 (nucleotides 419–4180) containing YF cDNA encoding 21 amino acids C, prM, E, NS1, NS2A (with nucleotide 2962 missing in NS1) was ligated to XhoI-SmaI digested SPHA-H6 (HA region donor plasmid) generating YF48. YF48 was digested with SacI (nucleotide 2490) and partially digested with Asp718 (nucleotide 3262) and a 6700 bp fragment isolated (containing the plasmid origin of replication, vaccinia sequences, 21 amino acids C, prM, E, amino-terminal 3.5% NS1, carboxy-terminal 23% NS1, NS2A) and ligated to a SacI-Asp718 fragment from YF18 (containing the remainder of NS1 with the base present at 2962) generating YF51. The 6 bp corresponding to the unique XhoI site in YF51 were removed using oligonucleotide-directed double-strand break mutagenesis (Mandecki, 1986) creating plasmid YF50 encoding YF21 amino acids C, prM, E, NS1, NS2A in the HA locus donor plasmid. Donor plasmid YF50 was transfected into vP866 (NYVAC) infected cells to generate vaccinia recombinant vP984.

The 6 bp corresponding to the unique XhoI site in YF48 were removed using oligonucleotide-directed double-strand break mutagenesis creating YF49. Oligonucleotide-directed mutagenesis (Kunkel, 1985) was used to insert a SmaI site at the carboxy-terminus of E (nucleotide 2452) in YF4 creating YF16. An ApaI-SmaI fragment of YF49 (containing the plasmid origin of replication, vaccinia sequences and YF cDNA encoding 21 amino acid C, prM, and amino-terminal 43% E) was ligated to an ApaI-SmaI fragment from YF16 (nucleotides 1604–2452 containing the carboxy-terminal 57% E) generating YF53 containing 21 amino acids of C, prM, E in the HA locus. Donor plasmid YF53 was transfected into vP913 (NYVAC-MV) infected cells to generate the vaccinia recombinant vP997.

Cloning of Dengue Type 1 Into a Vaccinia Virus Donor Plasmid. Plasmid DEN1 containing DEN cDNA encoding the carboxy-terminal 84% NS1 and amino-terminal 45% NS2A (nucleotides 2559–3745, Mason et al., 1987b) was derived by cloning an EcoRI-XbaI fragment of DEN cDNA (nucleotides 2559–3740) and annealed oligonucleotides DEN1 (SEQ ID NO:125) and DEN2 (SEQ ID NO:126) (containing a XbaI sticky end, translation termination codon, T5AT vaccinia virus early transcription termination signal (Yuen et al. 1987), EagI site and HindIII sticky end) into HindIII-EcoRI digested pUC8. An EcoRI-HindIII fragment from DEN1 (nucleotides 2559–3745) and SacI-EcoRI fragment of DEN cDNA encoding the carboxy-terminal 36% of E and amino-terminal 16% NS1 (nucleotides 1447–2559, Mason et al., 1987b) were ligated to HindIII -SacI digested IBI24 (International Biotechnologies, Inc., New Haven, Conn.) generating DEN3 encoding the carboxy-terminal 64% E through amino-terminal 45% NS2A with a base missing in NS1 (nucleotide 2467).

HindIII-XbaI digested IBI24 was ligated to annealed oligonucleotides DEN9 (SEQ ID NO:127) and DEN10 (SEQ ID NO:128) [containing a HindIII sticky end, SmaI site, DEN nucleotides 377–428 (Mason et al., 1987b) and XbaI sticky end] generating SPD910. SPD910 was digested with SacI (within IBI24) and AvaI (within DEN at nucleotide 423) and ligated to an AvaI-SacI fragment of DEN cDNA (nucleotides 424–1447 Mason et al., 1987) generating DEN4 encoding the carboxy-terminal 11 aa C, prM and amino-terminal 36% E.

Plasmid DEN6 containing DEN cDNA encoding the carboxy-terminal 64% E and amino-terminal 18% NS1 (nucleotides 1447–2579 with nucleotide 2467 present Mason et al., 1987b) was derived by cloning a SacI-XhoI fragment of DEN cDNA into IBI25 (International Biotechnologies, Inc., New Haven, Conn.). Plasmid DEN15 containing DEN cDNA encoding 51 bases of the DEN 5' untranslated region, C, prM and amino-terminal 36% E was derived by cloning a HindIII-SacI fragment of DEN cDNA (nucleotides 20–1447, Mason et al., 1987b) into HindIII-SacI digested IBI25. Plasmid DEN23 containing DEN cDNA encoding the carboxy-terminal 55% NS2A and amino-terminal 28% NS2B (nucleotides 3745–4213) was derived by cloning a XbaI-SphI fragment of DEN cDNA into XbaI-SphI digested IBI25. Plasmid DEN20 containing DEN cDNA encoding the carboxy-terminal 55% NS2A, NS2B and amino-terminal 24 amino acids NS3 (nucleotides 3745–4563) was derived by cloning a XbaI to EcoRI fragment of DEN cDNA into XbaI-EcoRI digested IBI25.

Oligonucleotide-directed mutagenesis (Kunkel, 1985) was used to change the following potential vaccinia virus early transcription termination signals (Yuen et al., 1987). The two T5NT sequences in the prM gene in DEN4 were mutagenized (1) 29 aa from the carboxy-terminus (nucleotides 822–828 TTTTTCT to TATTTCT) and (2) 13 aa from the carboxy-terminus (nucleotides 870–875 TTTTTAT to TATTTAT) creating plasmid DEN47. The single T5NT sequence in the NS1 gene in DEN6 17 aa from the amino-terminus was mutagenized (nucleotides 2448–2454 TTTTTGT to TATTTGT) creating plasmid DEN7.

Oligonucleotide-directed mutagenesis as described above was used (1) to insert an EagI and EcoRI site at the carboxy-terminus of NS2A (nucleotide 4102) in plasmid DEN23 creating DEN24, (2) to insert a SmaI site and ATG 15 aa from the carboxy-terminus of E in DEN7 (nucleotide 2348) creating DEN10, (3) to insert an EagI and HindIII site at the carboxy-terminus of NS2B (nucleotide 4492) in plasmid DEN20 creating plasmid DEN21, and (4) to replace nucleotides 63–67 in plasmid DEN15 with part of the vaccinia virus early/late H6 promoter (positions −1 to −21, Perkus et al., 1989) creating DEN16 (containing DEN nucleotides 20–59, EcoRV site to −1 of the H6 promoter and DEN nucleotides 68–1447).

A SacI-XhoI fragment from DEN7 (nucleotides 1447–2579) was substituted for the corresponding region in DEN3 generating DEN19 containing DEN cDNA encoding the carboxy-terminal 64% E and amino-terminal 45% NS2A (nucleotides 1447–3745) with nucleotide 2467 present and the modified transcription termination signal (nucleotides 2448–2454). A XhoI-XbaI fragment from DEN19 (nucleotides 2579–3745) and a XbaI-HindIII fragment from DEN24 (XbaI nucleotide 3745 DEN through HindIII in IBI25) were ligated to XhoI-HindIII digested IBI25 creating DEN25 containing DEN cDNA encoding the carboxy-terminal 82% NS1, NS2A and amino-terminal 28% NS2B (nucleotides 2579–4213) with a EagI site at 4102, nucleotide 2467 present and mutagenized transcription termination signal (nucleotides 2448–2454). The XhoI-XbaI fragment from DEN19 (nucleotides 2579–3745) was ligated to XhoI (within IBI25) and XbaI (DEN nucleotide 3745) digested DEN21 creating DEN22 encoding the carboxy-terminal 82% NS1, NS2A, NS2B and amino-terminal 24 aa NS3 (nucleotides 2579–4564) with nucleotide 2467 present, modified transcription termination signal (nucleotides 2448–2454) and EagI site at 4492.

A HindIII-PstI fragment of DEN16 (nucleotides 20–494) was ligated to a HindIII-PstI fragment from DEN47 (encoding the carboxy-terminal 83% prM and amino-terminal 36% of E nucleotides 494–1447 and plasmid origin of replication) generating DEN17 encoding C, prM and amino-terminal 36% E with part of the H6 promoter and EcoRV site preceding the amino-terminus of C. A HindIII-BglII fragment from DEN17 encoding the carboxy-terminal 13 aa C, prM and amino-terminal 36% E (nucleotides 370–1447) was ligated to annealed oligonucleotides SP111 and SP112 (containing a disabled HindIII sticky end, EcoRV site to −1 of the H6 promoter, and DEN nucleotides 350–369 with a BglII sticky end) creating DEN33 encoding the EcoRV site to −1 of the H6 promoter, carboxy-terminal 20 aa C, prM and amino-terminal 36% E.

SmaI-EagI digested pTP15 (Mason et al., 1991) was ligated to a SmaI-SacI fragment from DEN4 encoding the carboxy-terminal 11 aa C, prM and amino-terminal 36% E (nucleotides 377–1447) and SacI-EagI fragment from DEN3 encoding the carboxy-terminal 64% E, NS1 and amino-terminal 45% NS2A generating DENL. The SacI-XhoI fragment from DEN7 encoding the carboxy-terminal 64% E and amino-terminal 18% NS1 (nucleotides 1447–2579) was ligated to a BstEII-SacI fragment from DEN47 (encoding the carboxy-terminal 55% prM and amino-terminal 36% E nucleotides 631–1447) and a BstEII-XhoI fragment from DENL (containing the carboxy-terminal 11 aa C, amino-terminal 45% prM, carboxy-terminal 82% NS1, carboxy-terminal 45% NS2A, origin of replication and vaccinia sequences) generating DENS. A unique SmaI site (located between the H6 promoter and ATG) was removed using oligonucleotide-directed double-strand break mutagenesis (Mandecki, 1986) creating DEN8VC in which the H6 promoter immediately preceded the ATG start codon.

An EcoRV-SacI fragment from DEN17 (positions −21 to −1 H6 promoter DEN nucleotides 68–1447) was ligated to an EcoRV-SacI fragment of DEN8VC (containing vaccinia sequences, H6 promoter from −21 to −124, origin of replication and amino-terminal 64% E, NS1, amino-terminal 45% NS2A nucleotides 1447–3745) generating DEN18. A XhoI-EagI fragment from DEN25 (nucleotides 2579–4102) was ligated to an XhoI-EagI fragment of DEN18 (containing the origin of replication, vaccinia sequences and DEN C, prM, E and amino-terminal 18% NS1 nucleotides 68–2579) generating DEN26. An EcoRV-SacI fragment from DEN8VC (positions −21 to −1 H6 promoter DEN nucleotides 377–1447) was ligated to an EcoRV-SacI fragment of DEN26 (containing the origin of replication, vaccinia sequences and DEN region encoding the carboxy-terminal 64% E, NS1 and NS2A with a base missing in NS1 at nucleotide 2894) generating DEN32. DEN32 was transfected into vP410 infected cells to generate the recombinant vP867 (FIG. 20).

A SacI-XhoI fragment from DEN10 (nucleotides 1447–2579) was substituted for the corresponding region in DEN3 generating DEN11 containing DEN cDNA encoding the carboxy-terminal 64% E, NS1 and amino-terminal 45% NS2A with a SmaI site and ATG 15 aa from the carboxy-terminus of E. A SmaI-EagI fragment from DEN11 (encoding the carboxy-terminal 15 aa E, NS1 and amino-terminal 45% NS2A nucleotides 2348–3745) was ligated to SmaI-EagI digested pTP15 generating DEN12.

A XhoI-EagI fragment from DEN22 (nucleotides 2579–4492) was ligated to the XhoI-EagI fragment from DEN18 described above generating DEN27. An EcoRV-PstI fragment from DEN12 (positions −21 to −1 H6 promoter DEN nucleotides 2348–3447) was ligated to an EcoRV-PstI fragment from DEN27 (containing the origin of replication, vaccinia sequences, H6 promoter −21 to −124 and DEN cDNA encoding NS2A and NS2B) generating DEN31.

Figure 20:
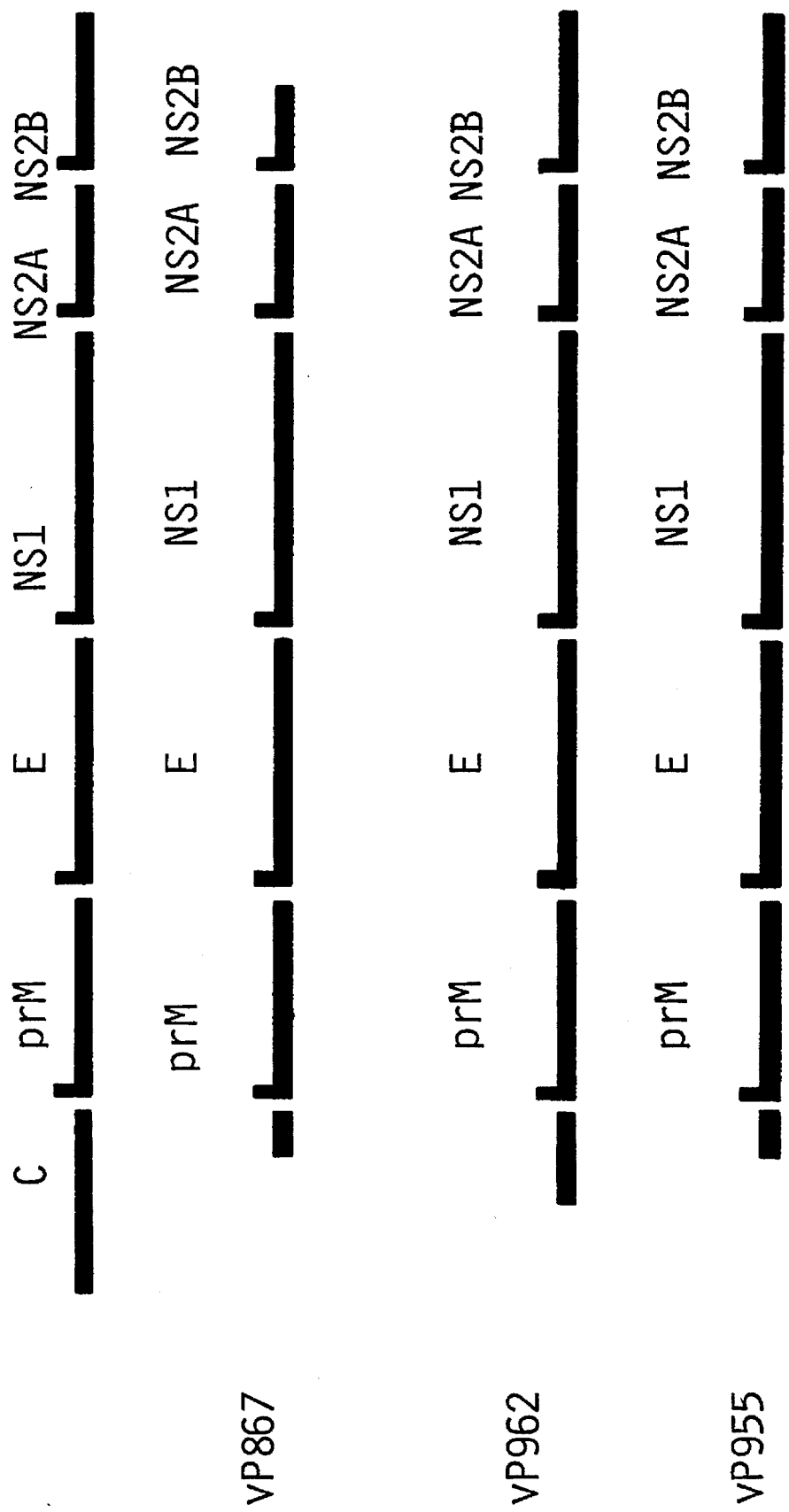
FIG. 20 is a schematic of the DEN coding regions inserted in the vaccinia viruses vP867, vP962 and vP955.

An EcoRV-XhoI fragment from DEN8VC (positions −21 to −1 H6 promoter DEN nucleotides 377–2579 encoding the carboxy-terminal 11 aa C, prM E, amino-terminal 18% NS1) was ligated to an EcoRV-XhoI fragment from DEN31 (containing the origin of replication, vaccinia sequences and DEN cDNA encoding the carboxy-terminal 82% NS1, NS2A, NS2B with the base present in NS1 at position 2894) generating DEN35. DEN35 was transfected into vP410 infected cells generating the recombinant vP955 (FIG. 20). An EcoRV-SacI fragment from DEN33 (positions −21 to −1 H6 promoter DEN nucleotides 350–1447 encoding the carboxy-terminal 20 aa C, prM and amino-terminal 36% E) and a SacI-XhoI fragment from DEN32 (encoding the carboxy-terminal 64% E and amino-terminal 18% NS1 nucleotides 1447–2579) were ligated to the EcoRV-SacI fragment from DEN31 described above generating DEN34. DEN34 was transfected into vP410 infected cells generating the recombinant vP962 (FIG. 20). Oligonucleotides DEN 1 (SEQ ID NO:125), DEN 2 (SEQ ID NO:126), DEN9 (SEQ ID NO:127), DEN10 (SEQ ID NO:128), SP111 (SEQ ID NO:129), and SP112 (SEQ ID NO:130) are as follows:

Transient Dominant Selection. Using circular donor plasmid, recombination with vaccinia virus was performed by the standard method of transfection of calcium phosphate precipitated plasmid DNA into vaccinia-infected Vero cells. After 24 h, the infected cells were harvested and the lysate plated in the presence of 1 microgram/ml mycophenolic acid (MPA). Individual plaques were picked and amplified on Vero cells in the presence of MPA. Virus was harvested and plaque purified by two rounds of plaque picking in the absence of MPA. Plaques picked from each round without MPA were plated on Vero cells and filters hybridized for the presence of pertinent genes.

NYVAC.1. The [C7L–K1L] deletion present in vP866 (NYVAC) was expanded to include the next two ORFs to the right, K2L and K3L. The putative translation product for the K2L ORF shows homology to the family of serine protease inhibitors (Boursnell et al., 1988). However, transcriptional mapping of this region of the vaccinia genome suggests that the K2L ORF is not expressed (Morgan et al., 1984).

The translation product for K3L shows 28% homology to eukaryotic initiation factor 2 alpha (eIF-2 alpha) over an 87 amino acid overlap spanning the serine (amino acid 51) phosphorylation site. Phosphorylation of eIF-2 alpha is a step in the antiviral state induced by interferon, suggesting that the vaccinia K3L gene product may be involved in the mechanism by which vaccinia evades the effects of interferon. The K3L gene from Copenhagen strain of vaccinia has been deleted (Beattie et al., 1991). The resulting virus exhibited heightened sensitivity to interferon in vitro as measured both by inhibition of vital induction of protein synthesis and inhibition of viral replication. This suggests that deletion of K3L from vaccinia virus could result in a

```
DEN 1   5'-    CT AGA t g a  TTTTTAT  CGGCCG  A             -3'
DEN2    3'-           T ACT  AAAAATA  GCCGGC  TTCGA  -5'
               XbaI                   EagI    HindIII DEN9    5'    AGCTT  CCCGGG  a t g  CT CCT CAT GCT GCT GCCC
DEN10   3'           A GGGCCC  TAC  GA GGA GTA CGA CGA CGGG
              HindIII     SmaI ACAGCCCT GGCGTT CCATCT GACCACCCGAG  T       -3'
              TGT CGGGA CCGCA AGGT AGACT GGT GGGCT C  AGATC-5'
                                                AvaI    XbaI SP111   5'   AGCT  GATATCCGTT AAGTTT GTATCGTA  a t g  AACAGGA
SP112   3'         A  CTATAGGCAATTCAAACATAGCAT  TAC  TTGTCCT
             HindIII   EcoRV
                                         GGAAA   A         -3'
                                         CCTTT   TCTAG-5'
                                                 BglII
```

EXAMPLE 17

CONSTRUCTION OF MODIFIED NYVAC VIRUSES

NYVAC was modified by increasing to different extents the size of the [C7L–K1L] deletion near the left terminus of vaccinia and by introducing a deletion near the right terminus. All deletions were accomplished using the E. coli guanine phosphoribosyl transferase gene and mycophenolic acid in a transient selection system.

safer vaccine strain which could be controlled by interferon treatment in the event of vaccination complications.

Construction of Plasmid pMPC7K3GPT for Deletion of C7L Through K3L. The left and right vaccinia arms flanking the [C7L–K3L] deletion were assembled separately. The left arm was derived from pSD420 (Perkus et al., 1990) and assembled in intermediate deletion plasmid pMP256/257 (Perkus et al., 1991). Synthetic oligonucleotides MPSYN379 (SEQ ID NO:131), MPSYN380 (SEQ ID NO:132)

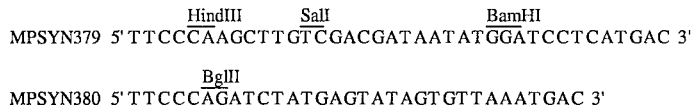
```
                   HindIII       SalI                      BamHI
MPSYN379 5' TTCCCAAGCTTGTCGACGATAATATGGATCCTCATGAC 3'

BglII
MPSYN380 5' TTCCCAGATCTATGAGTATAGTGTTAAATGAC 3'
``` were used as primers in a PCR reaction using plasmid pSD420 as template. The resulting 0.14 kb fragment was cut with HindIII/BglII and inserted into pMP256/257, replacing the left arm of the plasmid. The resulting plasmid was designated pMP379/380. A 0.7 kb SalI/BamHI fragment was isolated from pSD420 and ligated into pMP379/380 cut with SalI/BamHI, forming plasmid pMPC7F4.

To construct a right deletion junction containing sequences to the right of K3L, synthetic oligonucleotides MPSYN381/MPSYN382 (SEQ ID NO:133/SEQ ID NO:134)

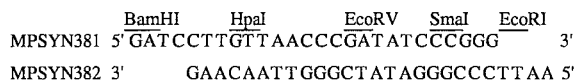
```
            BamHI      HpaI        EcoRV   SmaI   EcoRI
MPSYN381 5' GATCCTTGTTAACCCGATATCCCGGG          3'
MPSYN382 3'       GAACAATTGGGCTATAGGGCCCTTAA 5'
``` were annealed and ligated into pUC8 cut with BamHI/EcoRI, forming plasmid pMP381/382. A 1.0 kb HpaI (partial)/EcoRV fragment was isolated from cloned vaccinia HindIII K and ligated into pMP381/382, forming plasmid pMPK3R, which contains the entire right vaccinia flanking arm. The left vaccinia flanking arm was isolated from pMPC7F4 as a 0.8 kb BglII(partial)/HindIII fragment, and inserted into pMPK3R cut with BamHI/HindIII. The resulting plasmid, pMPC7K3, is deleted for 14 genes [C7L–K3L].

For use as a selectable marker, the *E. coli* gene encoding guanine phosphoribosyl transferase (Ecogpt) (Pratt et al., 1983) was placed under the control of a poxvirus promoter. A 31 bp promoter element immediately upstream from a gene encoding an entomopox 42 kDa protein can function as a strong promoter in recombinant vaccinia virus at early time post infection. Annealed synthetic oligonucleotides MPSYN369/370 (SEQ ID NO:135/SEQ ID NO:136)

```
             XhoI   EcoRI    SmaI
MPSYN369 5' TCGAGAATTCCCCGGGTCAAAATTGAAAATATATAATTACAA
                                                 BglII
                                            TATAAAATA 3'

MPSYN370 3'     CTTAAGGGCCCAGTTTTAACTTTTATATATTAATGTTA
                                            TATTTTATCTAG 5'
``` containing the 31 bp EPV 42 kDa promoter were ligated upstream from the Ecogpt gene in a pBS-SK background, resulting in plasmid pMP42GPT. A SmaI fragment containing the 42 kDa promoter/Ecogpt gene expression cassette was isolated from pMP42GPT and inserted into vaccinia deletion plasmid pMPC7K3 in the SmaI site at the pUC/vaccinia junction. The resulting plasmid, pMPC7K3GPT was transfected into vP866 (NYVAC). Mycophenolic acid was used in the culture medium for selection of intermediate products of recombination in a transient dominant selection system (Falkner et al., 1990). After removal of selective pressure, progeny virus were screened by plaque hybridization for loss of K2L DNA sequences and retention of K4L. The fidelity of the deletion junction was verified by PCR and DNA restriction and sequence analysis. Recombinant vaccinia virus vP954 (NYVAC.1) contains the [C7L–K3L] deletion, as well the other deletions present in NYVAC (TK, HA, ATI, I4L, [B13–B14]).

NYVAC.2. The [C7L–K1L] deletion present in NYVAC was expanded in both directions to include a total of 38 ORFs, [C23L–F4L]. This is the same deletion previously reported in vaccinia deletion mutant vP796 (Perkus et al., 1991), Noteworthy ORFs removed in the expanded deletion region include the vaccinia growth factor (VGF; C11R) located to the left of the NYVAC deletion. In contrast to WR strain of vaccinia which contains two copies of the VGF, C11R is the only ORF encoding the VGF in Copenhagen strain of vaccinia. Deletion of both copies of the vaccinia growth factor from WR has been shown to reduce the severity of skin lesions upon intradermal inoculation of rabbits and to reduce neurovirulence of the virus in mice (Buller et al., 1988). The rightmost ORF in the [C23L–F4L] deletion, F4L, encodes the gene for the small subunit of ribonucleotide reductase (Slabaugh et al., 1988). Also included in this deletion is ORF F2L, which shows homology to *E. coli* dUTPase, another enzyme involved in nucleotide metabolism (Goebel et al., 1990a,b). F2L also shows homology to retroviral protease (Slabaugh et al., 1989).

Construction of Plasmid pMPTRF4GPT for Deletion of C23L Through F4L. Plasmid pMPLENDΔ, which was used as an intermediate in the generation of vaccinia deletion mutant vP796 (Perkus et al., 1991) was modified by the addition of the SmaI expression cassette containing the EPV 42 kDa promoter/Ecogpt gene at the pUC/vaccinia junction. The resulting plasmid, pMPTRF4GPT, was transfected into NYVAC. Following selection using MPA, progeny virus were screened by plaque hybridization for loss of F4L DNA sequences and retention of F5L. Fidelity of the deletion junction was verified by PCR and DNA restriction analysis. Recombinant virus vP938 (NYVAC.2) contains the [C23L–F4L] deletion as well as the other deletions present in NYVAC.

Deletion of ORFs B13R–B29R. The u deletion [B13R–B14R] present in NYVAC was expanded to include all ORFs to the right, a total of 17 ORFs [B13R–B29R]. This is the same deletion previously reported in vaccinia deletion mutant vP759 (Perkus et al., 1991). The expanded deletion region includes two genes whose products show 20% amino acid identity with each other (Smith et al., 1991). The ORFs encoding these gene products are designated B16R and B19R in Copenhagen (Goebel et al., 1990a,b), which correspond to ORFs B15R and B18R, respectively, in the WR strain (Smith et al., 1991). Unlike the WR strain of vaccinia, in which both gene products contain typical signal sequences, the predicted translation product of Copenhagen ORF B16 is truncated at the amino terminus and does not contain a signal sequence. B19R encodes a vaccinia surface protein (S antigen) expressed at early times post infection (Ueda et al., 1990). Both B16R and B19R show homology to the immunoglobin superfamily, especially the IL-1 receptor. It has been suggested that one or both of the vaccinia gene products may help vaccinia evade the immune system by binding cytokines and thus diminishing the host inflammatory response (Smith et al., 1991).

Construction of Plasmid pMPTRB13GPT for Deletion of B13R Through B29R. Plasmid pMPRENDΔ, which was used as an intermediate in the generation of vaccinia deletion mutants vP759 and vP811 (Perkus et al., 1991) was modified by the addition of the SmaI expression cassette containing the EPV 42 kDa promoter/Ecogpt gene at the pUC/vaccinia junction. The resulting plasmid, pMPTRB13GPT, was transfected into NYVAC. Following selection using MPA, progeny virus were screened by plaque hybridization for loss of B15 DNA sequences and retention of B12. Fidelity of the deletion junction was verified by PCR and DNA restriction analysis. Recombinant virus vP953 contains the [B13R–B29R] deletion as well as the other deletions present in NYVAC.

Combining the Left [C23L–F4L] and Right [B13R–B29R] Deletions. The generation of vaccinia deletion mutant vP811, which contains deletions at both the left [C23L–F4L] and right [B13R–B29R] termini of vaccinia virus has been described (Perkus et al., 1991). vP811 contains both the vaccinia host range gene, C7L, and the selectable marker Ecogpt. To generate a virus containing the large terminal deletions without C7L or Ecogpt in a NYVAC background, pMPTRF4GPT was used as donor plasmid for recombination with vP953. Progeny virus is being selected by MPA in the transient dominant selection system described above and screened by plaque hybridization for loss of F4L DNA sequences and retention of F5L. Recombinant virus vP977 contains deletions for [B13R–B29R] and [C23L–F4L] as well as the other deletions present in NYVAC. Like vP811, vP977 is deleted for all genes from both copies of the vaccinia terminal repeats.

EXAMPLE 18

EXPRESSION OF HIV GENE PRODUCTS BY HOST-RESTRICTED POXVIRUSES

This Example describes the generation of host-restricted poxviruses that express HIV-1 gene products. The vectors employed are NYVAC and ALVAC.

Cells and Virus. NYVAC and ALVAC viral vectors and their derivatives were propagated as described previously (Piccini et al., 1989; Taylor et al., 1988a, b). Vero cells and primary chick embryo fibroblasts (CEF) were propagated as described previously (Taylor et al., 1988a, b). P815 murine mastocytoma cells (H-$2^d$) were obtained from ATCC (#TIB64) and maintained in Eagles MEM supplemented with 10% fetal bovine serum CFBS and 100 Iu/ml penicillin and 100 μg streptomycin per ml.

Mice. Female BALB/cJ (H-$2^d$) mice were purchased from Jackson Laboratories (Bar Harbor, Me.) and maintained on mouse chow and water ad libitum. All mice were used between the ages of 6 and 15 weeks of age.

Media. Assay Medium for immunological assays was comprised of RPMI 1640 medium supplemented with 10% FBS, 4 mM L-glutamine, 20 mM HEPES (N-2-hydroxyethylpiperazine-N'- 2-ethanesulfonate), $5\times10^{-5}$M 2-mercaptoethanol, 100 IU penicillin per ml, and 100 μg/ml streptomycin. Stim Medium was comprised of Eagle's Minimum Essential Medium supplemented with 10% FBS, 4 mM L-glutamine, $10^{-4}$M 2-mercaptoethanol, 100 IU penicillin per ml, and 100 μg streptomycin per ml.

ALVAC and NYVAC Recombinants Containing the V3 Loop and Epitope 88 of the HIV-1 (IIIB) Envelope. A 150 bp fragment encompassing the V3 loop (amino acids 299–344; Javeherian et al., 1989) of HIV-1 (IIIB) was derived by PCR using oligonucleotides HIV3BL5 (SEQ ID NO:137) (5'-ATGGTAGAAATTAATTGTAC-3') and HIV3BL3 (SEQ ID NO:138) (5'-ATCATCGAATTCAAGCTTATTATTTTTGCTCTACTAATGTTAC-3') with pHXB.2D (III) as template (provided by Dr. R. C. Gallo, NCI-NIH, Bethesda, Md.). Oligonucleotides HIV88A (SEQ ID NO:139) (5'-ATGAATGTGACAGAAAATTTTAACATGTGGAAAAATGTAGAAATTAATTGTACAAGACCC-3') and HIV88B (SEQ ID NO:140) (5'-GGGTCTTGTACAATTAATTTCTACATTTTTCCACATGTTAAAATTTTCTGTCACATTCAT-3') were annealed together to produce a double-stranded fragment containing the HIV-1 epitope 88 (amino acids 95–105, Shaffermann et al., 1989). The 150 bp V3-containing PCR fragment containing the epitope and the 42 bp fragment containing the 88 epitope sequences were fused together by PCR by virtue of the existence of complementary sequences. The reactions were performed using oligonucleotides HIV88C (SEQ ID NO:141) (5'-AGTAATGTGACAGAAAATTTTAAC-3') and HIV3BL3 (SEQ ID NO:138). The 192 bp PCR-derived fragment contains the epitope 88 sequences fused upstream to the V3 loop sequences. A termination codon (TAA) was incorporated into oligonucleotide HIV3BL3P to terminate translation of the open reading frame and an initiation codon was incorporated into oligonucleotide HIV88C to serve as the start of translation to express the epitope 88/V3 loop fusion protein. Additionally, oligonucleotide HIV3BL3 was synthesized so that an EcoRI site existed at the 3'-end of the 192 bp PCR fragment.

The entomopoxvirus 42 kDa (early) promoter was generated by PCR using oligonucleotides RG273 (SEQ ID NO:142) (5'-AGGCAAGCTTTCAAAAAAATATAAATGATTC-3') and RG274 (SEQ ID NO:143) (5'-TTTATATTGTAATTATATATTTTC-3') with plasmid, pAM12, as template. The 108 bp fragment containing the 42 kDa promoter was synthesized to contain a HindIII site at the 5'-end. The 42 kDa promoter containing segment was kinased and digested with HindIII prior to ligation to the epitope 88/V3 fragment digested with EcoRI and pRW831 digested with HindIII and EcoRI. The resultant plasmid was designated as pC5HIVL88. This plasmid was used in in vitro recombination assays with CPpp as rescue virus to generate vCP95. ALVAC recombinant, vCP95, contains the epitope 88/V3 loop in the de-ORFed C5 locus of CPpp.

The plasmid pC5HIVL88 was digested with HindIII and EcoRI to liberate a 300 bp fragment containing the epitope 88/V3 expression cassette described above. This fragment was excised from a LMP-agarose gel and isolated by phenol extraction (2×) and ether extraction (1×). The isolated fragment was blunt-ended using the Klenow fragment of the *E. coli* DNA polymerase in the presence of 2 mM dNTPs. The fragment was ligated to pSD550, a derivative of pSD548 (FIG. 6) digested with SmaI to yield plasmid pHIVL88VC. This plasmid was used with vP866 as the rescue virus to generate vP878. vP878 contains the epitope 88/V3 loop cassette in the de-ORFed I4L locus of NYVAC.

ALVAC- and NYVAC-Based Recombinants Expressing the HIV-1 (IIIB) Envelope Glycoproteins. An expression cassette composed of the HIV-1 (IIIB) u gene juxtaposed 3' to the vaccinia virus H6 promoter (Guo et al., 1989; Taylor et al., 1988a, b) was engineered for expression of gp160 from HIV-1 by the ALVAC and NYVAC vectors. A 1.4 kb fragment was amplified from pHXB.2D (III) (provided by Dr. R. C. Gallo, NCI-NIH, Bethesda, Md.) using oligonucleotides HIV3B1 (SEQ ID NO:144) (5'-GTTTTAATTGTGGAGGGGAATTCTTCTACTGTAATTC-3') and HIV3B5 (SEQ ID NO:145) (5'-ATCATCTCTAGAATAAAAATTATAGCAAAATCCTTTC-3'). This fragment contains the 3' portion of the env gene. PCR amplification with these primers placed a vaccinia virus early transcription termination T5NT sequence motif following the coding sequence and removed the T5NT motif situated at position 6146 to 6152 (Ratner et al., 1985) without altering the amino acid sequence. This change (T to C) creates an EcoRI (GAATTC) at this position. This 1.4 kb fragment was digested with EcoRI (5'- end) and XbaI (3'-end) and inserted into EcoRI and XbaI digested pBS-SK (Stratagene, La Jolla, Calif.). The resultant plasmid was designated as pBSHIVENV1,5. Nucleotide sequence analysis of this fragment demonstrated that the sequence was entirely correct except for a T to C transition at position 7848. This transition was corrected as follows: A 250 bp fragment was derived by PCR using oligonucleotides HIV3B1 (SEQ ID NO:144) (5'-GTTTTAATTGTGGAGGGGAATTCTTCTACTGTAATTC-3') and HIV3B17 (SEQ ID NO:146) (5'-TGCTACTCCTAATGGTTC-3') with pHXB.2D (III) as template. This fragment was digested with BglII and EcoRI. The fragment was inserted into pBSHIV3B1,5, digested with BglII and EcoRI and thus substituted for the region with the incorrect nucleotide to yield plasmid pBSHIV3BBP.

PCR was utilized to derive a 150 bp fragment containing the 5' portion of the env gene with oligonucleotides HIV3B9 (SEQ ID NO:147) (5'-CATATGCTTTAGCATCTGATG-3') and HIV3B10 (SEQ ID NO:148) (5'-ATGAAAGAGCAGAAGACAGTG-3') with pHXB.2D (III) as template. PCR was also used to generate a 128 bp fragment containing the vaccinia virus H6 promoter from pC3FGAG using oligonucleotides VVH65P (SEQ ID NO:149) (5'-ATCATCGGTACCGATTCTTTATTCTATAC-3') and VVH63P (SEQ ID NO:150) (5'-TACGATACAAACTTAACGG-3'). Both fragments were digested with KpnI and the 150 bp fragment was kinased prior to co-insertion of these fragments into pBS-SK digested with KpnI. The resultant plasmid was designated as pBSH6HIV3B5P.

PCR was used to generate a 600 bp fragment from pHXB.2D (III) with oligonucleotides HIV3B2 (SEQ ID NO:151) (5'-GAATTACAGTAGAAGAATTCCCCTCCACAATTAAAAC-3') and HIV3B7 (SEQ ID NO:152) (5'-CAATAGATAATGATACTAC-3'). This fragment was digested with EcoRI and kinased. PCR was also used to derive a 500 bp fragment with the same template but with oligonucleotides HIV3B6 (SEQ ID NO:153) (5'-GTATTATATCAAGTTTATATAATAATGCATATTC-3') and HIV3B8 (SEQ ID NO:154) (5'-GTTGATGATCTGTAGTGC-3'). This fragment was digested with KpnI. These fragments together correspond to nucleotide 5878 to 6368 (Ratner et al., 1985). The engineering of these fragments with these primers also removes a T5NT sequence positioned at nucleotide 6322 to 6328 without altering the amino acid sequence. These two fragments were inserted into pBSHIV3B3P digested with KpnI and EcoRI. This plasmid was designated as pBSHIV3BP2768.

Plasmid pBSH6HIV3B5P was digested with KpnI to liberate a 360 bp fragment containing the H6 promoter and the 5' portion (150 bp) of the HIV-1 env gene. This KpnI fragment was ligated into pBSHIV3B3P2768 digested with KpnI to yield plasmid pBSHIV3BEAII. A 2.8 kb fragment was derived from pBSHIV3BEAII by digestion with XbaI followed by a partial KpnI digestion. This fragment was blunt-ended and inserted into SmaI digested pSD550. The plasmid pI4LH6HIV3B was generated and used in in vitro recombination experiments with vP866 as the rescue virus. This generated vP911 which contains the HIV-1 env gene in the I4L locus of the NYVAC genome.

To insert the HIV-1 env gene into an ALVAC vector, pBSHIV3BEAII was digested with NruI and XbaI. The derived 2.7 kb fragment was blunt-ended with the Klenow fragment of the *E. coli* DNA polymerase in the presence of 2 mM dNTPs. This fragment contains the entire HIV-1 env gene juxtaposed 3' to the 3'-most 21 bp (to NruI site) of the vaccinia H6 promoter. This fragment was ligated to a 3.1 kb fragment derived by digestion of pRW838 with NruI and EcoRI with subsequent blunt-ending with Klenow. The pRW838 derived fragment contains the homologous arms derived from canarypox to direct the foreign gene to the C5 locus. It also contains the 5'-most 100 bp of the H6 promoter. Therefore, ligation of these fragments resulted in an insertion plasmid containing an expression cassette for the HIV-1 env gene and was designated pC5HIV3BE. This plasmid was used in in vitro recombination experiments with ALVAC as the rescue virus to generate vCP112.

NYVAC-Based Recombinants Expressing the HIV-1 (IIIB) gp120. The plasmid pBSHIV3BEAII was digested with EcORI and XbaI to liberate a 4.3 kb fragment. This fragment contains the vaccinia virus H6 promoter linked to the HIV-1 env gene to nucleotide 6946 (Ratner et al., 1985). The 4.3 kb fragment was ligated to 300 bp EcoRI/XbaI digested PCR-derived fragment corresponding to the 3' portion of the gp120 coding sequence. The 300 bp PCR fragment was derived using oligonucleotides HIV1-120A (SEQ ID NO:155) ( 5'-ATCATCTCTAGAATAAAAATTATGGTTCAATTTTTACTACTTTTATATTATATATTTC-3') and HIV1-120B (SEQ ID NO:156) (5'-CAATAATCTTTAAGCAAATCCTC-3') with pHXB.2D as template. The ligation of the 4.3 kb XbaI/EcoRI fragment and the 300 bp XbaI/EcoRI fragment yielded plasmid pBSHIVB120.

A 1.6 kb KpnI/XbaI fragment was derived from pBSHIVB120 by initially linearizing the plasmid with XbaI followed by a partial KpnI digestion. The 1.6 kb fragment was blunt-ended by treatment with the Klenow fragment of the *E. coli* DNA polymerase in the presence of 2 mM dNTPs. This fragment was inserted into pSD54IVC digested with SmaI to yield pATIHIVB120. This plasmid was used in in vitro recombination experiments to generate vP921. This recombinant contains the portion of the HIV-1 env gene encoding gp120 in the ATI locus of NYVAC.

Immunoprecipitation. To determine the authenticity of the HIV-1 gene products expressed by vP911, vP921 and vCP112, immunoprecipitation analyses were performed. Vero cells monolayers were either mock infected, infected with the parental virus vP866, or infected with recombinant virus at an m.o.i. of 10 PFU/cell. Following a 1 hr adsorption period, the inoculum was aspirated and the cells were overlayed with 2 mls of MEM (minus methionine containing 2% FBS and [$^{35}$S]-methionine (20 uCi/ml). Cells were harvested at 18 hr post infection by the addition of 1 ml of 3× Buffer A (3% NP-40, 30 mM Tris pH 7.4, 150 mM NaCl, 3 mM EDTA, 0.03% Na Azide, and 0.6 mg/ml PMSF) with subsequent scraping of the cell monolayers.

Lysates derived from the infected cells were analyzed for HIV-1 env gene expression using pooled serum from HIV-1 seropositive individuals (obtained from Dr. Genoveffa Franchini NCI-NIH, Bethesda Md.). The sera was preadsorbed with vP866-infected Vero cells. The preadsorbed human sera was bound to protein A-sepharose in an overnight incubation at 4° C. In some cases a monoclonal antiserum specific to gp120 (Dupont) was used as the primary serum and a rat anti-mouse as the second antibody. Following this incubation period, the material was washed 4 times with 1× Buffer A. Lysates precleared with normal human sera and protein A-Sepharose were then incubated overnight at 4° C. with the human sera from seropositive individuals bound to protein A-Sepharose. Following the overnight incubation period, the samples were washed four times with 1× Buffer A and 2× with $LiCl_2$/urea buffer. Precipitated proteins were dissociated from the immune complexes by the addition of 2× Laemmli's buffer (125 mM Tris (pH6.8), 4% SDS, 20% glycerol; 10% 2-mercaptoethanol) and boiling for 5 minutes. Proteins were fractionated on a 10% Dreyfuss gel system (Dreyfuss et al., 1984), fixed and treated with 1M Na-salicylate for fluorography.

The results of immunoprecipitation using sera pooled from HIV-1 seropositive individuals showed specific precipitation of the gp120 and gp41 mature forms of the gp160 envelope glycoprotein from vP911 infected cell lysates. No such specific gene products were detected in the parentally (NYVAC; vP866) infected cell lysates. Specific precipitation of gp120 was also found in vP921 infected cell lysates.

Immunofluorescence analysis with the same sera illustrated that the gp160 and gp120 species expressed by vP911 and vP921, respectively, were present on the surface of infected cells.

Immunoprecipitation was also performed with vCP112 infected CEF cells. No HIV-specific polypeptides were precipitated with a monoclonal antibody directed against the gp120 extracellular moiety from cells infected with the ALVAC parental virus and uninfected CEF cells. Two HIV-specific polypeptides species were, however, precipitated from vCP112 infected cells. These species migrated with apparent mobilities of 160 kDa and 120 kDa, corresponding to the precursor env gene product and the mature extracellular form, respectively.

Inoculations. Mice were intravenously inoculated with $5 \times 10^7$ plaque forming units (PFU) in 0.1 ml of phosphate-buffered saline via the lateral tail vein.

Spleen Cell Preparations. Following euthanasia by cervical dislocation, the spleens of mice were aseptically transferred to a sterile plastic bag containing Hank's Balanced Salt Solution. Individual spleens or pooled spleens from a single experimental group were processed to single cell suspensions by a 1 minute cycle in a Stomacher blender. The spleen cell suspensions were washed several times in either Assay Medium or Stim Medium, as appropriate. The spleen cells were enumerated by the use of a Coulter Counter or by trypan blue dye exclusion using a hemacytometer and microscope.

Sera. Mice were lightly anesthetized with ether and blood was collected from the retroorbital plexus. Blood from mice comprising an experimental group was pooled and allowed to clot. The serum was collected and stored at −70° C. until use.

In Vitro Stimulation for the Generation of Secondary Cytotoxic T Lyphocytes (CTL). The pooled spleen cells from the various experimental groups (responders) were diluted to $5 \times 10^6$ cells/ml in Stim Medium. The spleen cells from syngeneic, naive mice (stimulators) were diluted to $1 \times 10^7$ cells per ml and infected for 1 hour in tissue culture medium containing 2% FBS at 37° C. with the appropriate vaccinia virus at a m.o.i. of 25 pfu per cell. Following infection, the stimulator cells were washed several times in Stim Medium and diluted to $1 \times 10^6$ cells per ml with Stim Medium. Five mls of stimulator cells and 5 mls of responder cells were added to a 25 $cm^3$ tissue culture flask and incubated upright at 37° C., in 5% $CO_2$ for 5 days. On the day of the assay, the spleen cells were washed several times in Assay Medium and counted on a hemacytometer in trypan blue with the use of a microscope.

Target Cell Preparation. For vaccinia specific CTL activity, tissue culture cells were infected overnight by incubation at $1 \times 10^7$ cells per ml in tissue culture medium containing 2% FBS at a m.o.i. of 25 pfu per cell for 1 hour at 37° C. Following incubation, the cells were diluted to between $1-2 \times 10^6$ cells per ml with tissue culture medium containing 10% FBS and further incubated at 37° C., in 5% $CO_2$ until use. For HIV specific CTL activity, tissue culture cells were incubated overnight with 20 µg/ml of peptide HBX2 (American Biotechnologies, Cambridge, Mass.), SF2 (American Biotechnologies, Cambridge, Mass.) or MN (American Biotechnologies, Cambridge, Mass.) corresponding to the V3 loop region of gp120 of HIV-1 isolates $III_B$, SF2, and MN, respectively. On the day of the assay, the targets were washed several times by centrifugation in Assay Medium. After the final wash, the cells were resuspended in approximately 100 µCi of $Na_2^{51}CrO_4$ ($^{51}Cr$). Following incubation at 37° C. for 1 hr, the cells were washed at least 3 times in Assay Medium by centrifugation, counted on a hemacytometer, and diluted to $1 \times 10^5$/ml in Assay Medium.

Cytotoxicity Assays. For primary CTL assays, freshly prepared spleen cells were diluted with Assay Medium to $1 \times 10^7$ cells per ml. For secondary CTL assays (following either in vivo inoculation or in vitro stimulation), the spleen cells were diluted to $2 \times 10^6$/ml in Assay Medium. One tenth ml of spleen cell suspension was added to $^{51}Cr$ labelled target cells in the wells of a 96 well, round-bottom microtiter plate (EXP). In most cases, the spleen cells being assayed for primary CTL activity were further 2-fold diluted in the wells of the microtiter plate prior to the addition of the target cells. As a measure of spontaneous release of $^{51}Cr$ (SR), target cells were incubated in only Assay Medium. To determine the maximum release of $^{51}Cr$ (MAX), target cells were deliberately lysed at the beginning of the assay by adding 0.1 ml of 10% sodium dodecyl sulfate to the appropriate wells. To initiate the assay, the microtiter plates were centrifuged at 200×g for 2 min and incubated for 4 or 5 hrs at 37° C., in 5% $CO_2$. Following incubation, the culture supernatants of each well were collected using the Skatron Supernatant Collection System. Released $^{51}Cr$ was determined by a Beckman 5500B gamma counter. The percent specific cytotoxicity was determined from the counts by the following formula:

% CYTOTOXICITY=(EXP-SR)/(MAX-SR)×100

Depletion of T Helper Cells and Cytotoxic T Lymphocytes Using Monoclonal Anti-CD4 and Monoclonal Anti-CD8. Spleen cell suspensions were diluted to a density of $10^7$/ml in cytotoxicity medium (RPMI 1640 containing 0.2% BSA and 5 mM HEPES) containing a 1:5 dilution of anti-CD4 (monoclonal antibody 172.4) or a 1:200 dilution of anti-CD8 (monoclonal antibody anti-Lyt 2.2) and a 1:16 dilution of Cedar Lane Low-Tox rabbit complement. Appropriate controls for the single components (complement, anti-CD4, anti-CD8) were included.

Anti-HIV-1 gp160 ELISA. The wells of ELISA plates (Immulon II) were coated overnight at 4° C. with 100 ng of purified HIV-1 gp160 (provided by Dr. D. Bolognesi, Duke University, Durham N.C.) in carbonate buffer, pH 9.6. The plates were then washed with phosphate-buffered saline containing 0.05% Tween 20 (PBST). The plates were then blocked for 2 hrs at 37° C. with PBST containing 1% bovine serum albumin (BSA). After washing with PBST, sera were initially diluted 1:20 with PBST containing 0.1% BSA (dilution buffer). The sera were further 2-fold serially diluted in the wells of the ELISA plate. The plates were incubated at 37° C. for 2 hrs and washed with PBST. Horseradish peroxidase conjugated rabbit anti-mouse immunoglobulins (DAKO) was diluted 1:2000 in dilution buffer and added to the wells of the ELISA plate and incubated at 37° C. for 1 hour. After washing with PBST, OPD (o-phenylenediamine dihydrochloride) in substrate buffer was added and the color was allowed to develop at ambient temperature for about 20 minutes. The reaction was extinguished by the addition of 2.5M $H_2SO_4$. The absorbance at 490 nm was determined on a Bio-Tek EL-309 ELISA reader. The serum endpoint was defined as the reciprocal of the dilution giving an absorbance value of 1.0.

Lymphocyte Proliferation Assays. Single cell suspensions of the spleen cells of individual mice were diluted to $2\times10^6$/ml in Assay Medium and 0.1 ml was added to the wells of 96 well, flat-bottom microtiter plates containing Assay Medium alone, 1, 5, or 10 μg of HIV-1 peptide T1, 1, 5, or 10 μg of HIV-1 peptide T2, and 1 or 10 μg of purified HIV-1 gp160 (Immuno). The cells were incubated for 5 days at 37° C., in 5% $CO_2$. To each well was added 1.0 μCi of [$^3$H]-thymidine for the final 6 hrs of incubation and then harvested onto Beckman Ready Filters using a Cambridge PHD cell harvester. The filter disks were dry-counted in a liquid scintillation counter.

STIMULATION INDEX=$CPMs_{EXP}/CPMs_{MEDIUM}$

Results: A Recombinant Vaccinia Virus Expressing HIV gp120 Elicits Primary HIV-specific Cytotoxic T Lymphocyte Activity. Following iv administration with $5\times10^7$ PFUs of vaccinia virus recombinants vP878, vP911, or vP921, or, as a control, with NYVAC, the vector, splenic CTL activity of BALB/c mice was assessed against syngeneic P815 cells which had been incubated overnight with peptide HBX2 (Table 20). Modest, but significant (P<0.05) primary CTL activity was generated in the spleens of mice administered vP921, expressing HIV gp120. No other recombinant vaccinia virus nor the NYVAC parent vector was able to elicit primary HIV-specific CTL activity. This was not due to inadequate infection as each group of mice administered a vaccinia virus responded with primary vaccinia-specific CTL activity. Control, unimmunized mice responded to neither target.

Recombinant Poxviruses Expressing HIV env Peptides Generate HIV-Specific Memory Cytotoxic T Lymphocytes. At least one month following a single inoculation with one of the recombinant vaccinia viruses, mouse spleen cells were stimulated in vitro with syngeneic, naive spleen cells previously infected with NYVAC or with each of the HIV recombinant vaccinia viruses (Table 21). Strong HIV-specific CTL activity was detected only in the spleen cell cultures of mice immunized with vP878, vP911, and vP921 which were restimulated in vitro by cells infected with one of the same vaccinia virus HIV recombinants (vP878, vP911, or vP921). The vaccinia virus recombinants expressing HIV gp120 or gp160 were better able to generate memory CTLs than the vaccinia virus recombinant expressing only the V3 loop fused to the 88 epitope. HIV-specific memory CTL activity could not be elicited from unimmunized control or NYVAC immunized spleen cells. The absence of HIV-specific CTL activity from vector immunized mice could not be attributed to poor immunization since vaccinia-specific memory CTL activity was apparent after in vitro stimulation with spleen cells infected with any of the vaccinia viruses used.

In a similar study, the ability of a canarypox recombinant expressing the V3 loop region fused to the 88 epitope (vCP95) to generate HIV-specific memory CTLs was examined (Table 22). Three weeks following a single inoculation of $10^8$ PFUs of vCP95 or the ALVAC vector, CPpp, HIV-specific memory CTL responses were compared to that elicited by the recombinant vaccinia virus analog, vP878. Vaccinia and canarypox CTL responses were included as controls for proper immunization. Only spleen cells from vP878 and vCP95 immunized mice produced HIV-specific memory CTL activity which could be stimulated by vP878. The inability of vCP95 to stimulate existing memory CTLs to functional cytolytic CTLs may have been related to the in vitro conditions employed which were maximized based upon the use of vaccinia virus recombinants. Nonetheless, vCP95 was fully capable of generating significant HIV-specific memory CTLs in the spleens of immunized mice.

Characterization of the In Vitro Stimulated Cytotoxic Cells. It is conceivable that the cells mediating cytotoxicity against the HIV peptide-pulsed target cells represent a population of nonspecific effector cells unrelated to CTLs, such as natural killer cells. To test this, the spleen cells of mice immunized with vP921 and restimulated in vitro with vP921 infected spleen cells were depleted of T-lymphocytes bearing surface antigens characteristic of T helper lymphocytes (CD4) or of cytotoxic T lymphocytes (CD8) and assayed against V3 loop peptide pulsed target cells (Table 23). As before, only vP921 immunized mice generated memory HIV-specific CTL activity which could be stimulated in vitro with vP921 infected syngeneic spleen cells. Although the complement preparation (C') and the monoclonal anti-CD4 and anti-CD8 produced some toxic effects, only the cultures depleted of CD8-bearing cells (anti-CD8+ C') were also depleted of HIV-specific cytotoxic effector cells. Thus, the cells mediating cytolytic activity against the HIV peptide-pulsed target cells possessed CD8 antigens on their cell membranes, a characteristic of MHC class I restricted CTLs.

Specificity of CTL Antigen Receptor Recognition of the V3 Loop Region of HIV gp120. T lymphocyte antigen receptors are exquisitely sensitive to small alterations in the primary amino acid sequence of the epitope fragment. The V3 loop region of HIV gp120 is hypervariable and differs immunologically among HIV isolates. The hypervariability resides in substitutions and additions of only a few amino acids. To examine the specificity of cytotoxic cells generated by HIV vaccinia virus recombinants, susceptibility to CTL activity was compared among P815 target cells pulsed with peptides corresponding the V3 loop region of HIV isolates III$_B$, SF2, and MN. Only immunization with vP911 and vP921 induced HIV specific primary CTL activity (Table 24). Furthermore, HIV specific CTL activity was confined only to P815 target cells pulsed with peptide corresponding to the V3 loop of HIV isolate III$_B$. Similar results were obtained with in vitro stimulated, HIV specific secondary CTL activity induced by immunization with the vaccinia virus recombinants vP878, vP911, and vP921 (Table 25). Thus, HIV specific CTLs elicited by recombinant vaccinia viruses expressing various portions of the env gene of HIV isolate III_B recognize only target epitopes derived from the same antigenic isolate.

Lymphocyte Proliferation Responses to HIV Epitopes Following Immunization with Vaccinia Virus HIV Recombinants. Lymphocyte proliferation to antigens is an in vitro correlate of cell-mediated immunity. Presentation of the appropriate antigen induces cellular proliferation in the immune population of cells expressing receptors for the antigen. The initiation and continuation of proliferation requires the involvement of T helper lymphocytes via soluble mediators. To evaluate cell-mediated immunity to HIV antigens in mice immunized with recombinant vaccinia viruses expressing HIV antigens, spleen cells from mice immunized 27 days earlier were incubated for 5 days with peptides correlating to T helper lymphocyte epitopes designated $T_1$ and $T_2$, as well as with purified HIV gp160 (Table 26). No proliferative responses to the T helper cell epitopes $T_1$ and $T_2$ were observed in any of the spleen cell cultures. However, the spleen cells of mice previously immunized with vP921 vigorously responded to HIV gp160 as determined by the incorporation of [3H]-thymidine. A stimulation index (SI) of greater than 2.0 is considered indicative of immunity. Thus, inoculation of mice with vP921 elicited cell-mediated immunity to HIV gp160.

Antibody Responses of Mice Inoculated with Vaccinia Virus HIV Recombinants. To evaluate humoral responses to HIV, mice were immunized at day 0 with one of the vaccinia virus HIV recombinants and received a secondary immunization at week 5. The mice were bled at various intervals through 9 weeks after the initial immunization. Pooled sera from each treatment group were assayed for antibodies to HIV by ELISA employing purified gp160 as antigen (Table 27). Primary antibody responses were generally modest, but detectable with the highest levels induced by vP911. Following the secondary immunization, the antibody titers of mice immunized with vP911 and vP921 increased and peaked at week 7 with titers of over 4,600 and 3,200, respectively, before declining slightly by week 9. Thus, two vaccinia virus HIV recombinants, vP911 and vP921, were capable of inducing a significant antibody response.

TABLE 20

Primary CTL activity of spleen cells from mice immunized with vaccinia virus recombinants against vaccinia virus infected targets and targets pulsed with peptide corresponding to the V3 loop region of HIV-1 gp120.

| IMMUNIZATION | PERCENT CYTOTOXICITY TARGET | | |
|---|---|---|---|
| | P815 | VAC | HIV V3 |
| NONE | -3.5± 2.0 | -0.6 1.5 | -4.8 1.6 |
| NYVAC | -4.4± 1.9 | 9.5* 3.2 | -5.9 1.7 |
| vP878 | -4.9± 1.8 | 7.1* 2.2 | -4.0 1.2 |
| vP911 | -4.0± 2.5 | 4.6* 2.0 | 1.4 5.1 |
| vP921 | -3.4± 0.9 | 10.7* 1.5 | 15.5* 2.8 |

E:T = 100:1
*P < 0.05 vs appropriate controls, Student's t-test

TABLE 21

Secondary CTL activity of spleen cells following in vitro stimulation with vaccinia virus recombinants.

| IMMUNIZATION | | PERCENT CYTOTOXICITY TARGET | | |
|---|---|---|---|---|
| in vivo | in vitro | P815 | VAC | HIV V3 |
| NONE | NONE | -0.1 | 1.9 | 0.5 |
| | NYVAC | 3.7 | 8.9 | 3.8 |
| | vP878 | 4.6 | 9.0 | 5.5 |
| | vP911 | -1.7 | 2.9 | 4.8 |
| | vP921 | 2.9 | 2.9 | 1.5 |
| NYVAC | NONE | 0.0 | 4.4 | 1.1 |
| | NYVAC | 3.5 | 47.8* | 9.2 |
| | vP878 | 6.3 | 44.1* | 14.4 |
| | vP911 | 7.9 | 48.6* | 10.6 |
| | vP921 | 6.8 | 50.8* | 7.9 |
| vP878 | NONE | 0.1 | 1.7 | 1.3 |
| | NYVAC | 10.2 | 58.5* | 13.0 |
| | vP878 | 11.6 | 57.9* | 59.9* |
| | vP911 | 7.8 | 56.2* | 40.8* |
| | vP921 | 4.9 | 42.0* | 14.8 |
| vP911 | NONE | 0.3 | 2.9 | 4.0 |
| | NYVAC | 6.2 | 50.7* | 8.5 |
| | vP878 | 5.9 | 50.9* | 77.4* |
| | vP911 | 5.0 | 54.2* | 82.6* |
| | vP921 | 10.9 | 55.0* | 87.8* |
| vP921 | NONE | 2.9 | 5.0 | 9.4 |
| | NYVAC | 8.3 | 54.4* | 22.7 |
| | vP878 | 10.4 | 56.2* | 85.6* |
| | vP911 | 8.7 | 58.2* | 86.5* |
| | vP921 | 7.8 | 55.2* | 81.0* |

BALB/cJ spleen cells from mice immunized approximately 1 month earlier with the indicated vaccinia virus recombinants were incubated with infected syngeneic spleen cells for 5 days and assayed for cytotoxicity at an effector to target cell ratio of 20:1.
*P < 0.05 compared to controls, Student's t-test.

TABLE 22

Anamnestic CTL responses of the spleen cells of mice administered a single inoculation of recombinant vaccinia or canarypox virus expressing the V3 loop of HIV gp120.

| IMMUNIZATION | | PERCENT CYTOTOXICITY | | | |
|---|---|---|---|---|---|
| PRIMARY | BOOSTER | TARGET | | | |
| in vivo | in vitro | P815 | Vac | CP | HIV V3 |
| NONE | NONE | 0.4 | -2.5 | -2.3 | -1.5 |
| | vP804 | 0.5 | 8.8 | 0.7 | 0.8 |
| | vP878 | 1.8 | 6.1 | 0.4 | 1.6 |
| | CP | 5.8 | 4.2 | 4.9 | 0.4 |
| | vCP95 | 4.4 | 2.6 | 6.1 | 0.1 |
| | SB135 | -0.2 | -0.7 | -0.4 | 0.5 |
| vP804 | NONE | 0.7 | 1.7 | 0.1 | 1.3 |
| | vP804 | 5.5 | 43.5* | 5.8 | 3.5 |
| | vP878 | 3.6 | 42.5* | 1.6 | -0.3 |
| | CP | 8.5 | 7.0 | 5.6 | 3.9 |
| | vCP95 | 5.8 | 5.3 | 4.4 | 4.0 |
| | SB135 | 1.2 | -0.9 | -0.5 | -0.2 |
| vP878 | NONE | 0.2 | -2.9 | -0.8 | -0.2 |
| | vP804 | 5.3 | 56.4* | 7.5 | 4.1 |
| | vP878 | 6.7 | 60.2* | 7.7 | 41.7* |
| | CP | 8.7 | 13.4 | 9.4 | 4.7 |
| | vCP95 | 7.1 | 10.5 | 8.7 | 19.0 |
| | SB135 | 1.9 | -0.7 | -0.2 | -1.4 |
| CP | NONE | 4.6 | -0.6 | 2.3 | -0.0 |

TABLE 22-continued

Anamnestic CTL responses of the spleen cells of mice administered a single inoculation of recombinant vaccinia or canarypox virus expressing the V3 loop of HIV gp120.

| IMMUNIZATION | | PERCENT CYTOTOXICITY | | | |
|---|---|---|---|---|---|
| PRIMARY | BOOSTER | | TARGET | | |
| in vivo | in vitro | P815 | Vac | CP | HIV V3 |
| | vP804 | 11.0 | 17.7* | 5.7 | 6.1 |
| | vP878 | 7.1 | 14.6* | 12.3 | 5.5 |
| | CP | 7.4 | 5.9 | 19.3* | 3.1 |
| | vCP95 | 6.8 | 5.4 | 20.4* | 2.8 |
| | SB135 | 1.4 | −0.4 | 0.8 | −1.4 |
| vCP95 | NONE | −0.8 | −2.2 | −1.3 | 0.3 |
| | vP804 | 9.4 | 26.4* | 9.3 | 6.6 |
| | vP878 | 10.4 | 22.5* | 16.9 | 32.1* |
| | CP | 8.8 | 7.2 | 20.0* | 3.2 |
| | vCP95 | 5.1 | 4.2 | 19.6* | 7.8 |
| | SB135 | 1.9 | −1.5 | −0.3 | −1.2 |

Twenty-three days after immunization, the spleen cells were stimulated in vitro for 5 days with virus infected or peptide-pulsed syngeneic spleen cells and then assayed for specific cytotoxicity against virus infected or peptide-pulsed P815 target cells at an effector to target cell ratio of 20:1.
*P < 0.05 compared to appropriate controls, Student's t-test.

TABLE 23

Depletion of cytotoxic activity with monoclonal antibodies to CD8 plus complement.

| IMMUNIZATION | | | PERCENT CYTOTOXICITY TARGETS | | |
|---|---|---|---|---|---|
| in vivo | in vitro | TREATMENT | P815 | VAC | HIV V3 |
| NONE | NONE | NONE | 1.1 | 1.5 | −0.3 |
| NONE | NYVAC | NONE | −7.4 | 0.4 | −0.4 |
| NONE | vP921 | NONE | −0.2 | 1.1 | −0.7 |
| NYVAC | NONE | NONE | −3.1 | −0.3 | −1.4 |
| NYVAC | NYVAC | NONE | −2.6 | 40.5 | −0.3 |
| NYVAC | vP921 | NONE | 3.3 | 31.4 | −2.9 |
| vP921 | NONE | NONE | 3.0 | −1.3 | −0.1 |
| vP921 | NYVAC | NONE | −4.9 | 25.9 | 12.2 |
| vP921 | vP921 | NONE | −0.2 | 21.3 | 30.5 |
| vP921 | vP921 | C' | 4.6 | 20.1 | 22.9 |
| vP921 | vP921 | anti-CD4 | 4.2 | 22.6 | 23.2 |
| vP921 | vP921 | anti-CD8 | −5.0 | 22.5 | 26.9 |
| vP921 | vP921 | anti-CD4 + C' | 10.0 | 26.6 | 30.1 |
| vP921 | vP921 | anti-CD8 + C' | 9.2 | 7.1 | 2.3 |

TABLE 24

Specificity of primary CTL activity for the V3 loop of HIV-1 isolate III$_B$ following a single inoculation with HIV recombinant vaccinia viruses.

| IMMUNIZA-TION | PERCENT CYTOTOXICITY TARGET | | | |
|---|---|---|---|---|
| | P815 | V3 PEPTIDE | | |
| | | IIIB | SF2 | MN |
| NONE | −2.7± | −1.9 | −0.9 | −1.2 |
| NYVAC | 0.5 −1.6± | 0.5 −0.3 | 0.5 −0.6 | 0.5 −0.3 |
| vP878 | 0.5 −2.8± | 0.8 0.5 | 0.7 −0.5 | 0.2 −1.2 |
| vP911 | 0.8 −2.6± | 1.0 7.5* | 0.6 −0.5 | 0.5 −1.1 |
| vP921 | 0.2 −2.5± | 3.2 12.5* | 0.5 −0.1 | 0.4 −1.2 |
| | 0.7 | 3.6 | 0.5 | 0.5 |

Mice were administered a single iv inoculation with the indicated vaccinia virus recombinant and assayed for CTL activity 7 days later against P815 targets and P815 targets pulsed with one of three peptides corresponding to the V3 loop region of HIV-1 isolates III$_B$, SF2, and MN. Although assayed at effector to target cell ratios of 100:1, 50:1, and 25:1, only the 100:1 data are shown.
*P < 0.05 vs appropriate controls, Student's t-test?

TABLE 25

Specificity of secondary CTL activity for the V3 loop of HIV-1 isolate III$_B$ following a single inoculation with HIV recombinant vaccinia viruses.

| IMMUNIZATION | | PERCENT CYTOTOXICITY TARGET | | | |
|---|---|---|---|---|---|
| in vivo | in vitro | P815 | V3 PEPTIDE | | |
| | | | IIIB | SF2 | MN |
| NONE | NONE | 1.0 | 1.1 | 0.5 | −0.0 |
| | NYVAC | 0.4 | 0.5 | −0.6 | −0.3 |
| | vP878 | 0.2 | 0.2 | −0.5 | −1.0 |
| | vP911 | −1.5 | 0.3 | −0.5 | 0.2 |
| | vP921 | −0.6 | 1.4 | 0.1 | −0.5 |
| NYVAC | NONE | −2.2 | 0.2 | 0.5 | −1.0 |
| | NYVAC | 3.2 | 2.2 | 3.9 | 2.5 |
| | vP878 | 4.4 | 5.9 | 5.0 | 6.1 |
| | vP911 | 5.8 | 11.1 | 5.0 | 5.3 |
| | vP921 | 5.0 | 6.5 | 2.9 | 2.9 |
| vP878 | NONE | 0.1 | −0.2 | −0.9 | −1.0 |
| | NYVAC | 3.0 | 4.8 | 4.4 | 4.5 |
| | vP878 | 7.9 | 20.2 | 7.8 | 8.6 |
| | vP911 | 4.8 | 7.8 | 4.5 | 4.7 |
| | vP921 | 2.7 | 6.9 | 2.8 | 3.0 |
| vP911 | NONE | 0.9 | 1.8 | 1.4 | 0.5 |
| | NYVAC | 8.8 | 8.3 | 8.1 | 6.6 |
| | vP878 | 6.6 | 57.2 | 6.8 | 8.2 |
| | vP911 | 4.6 | 63.7 | 2.9 | 4.2 |
| | vP921 | 7.2 | 63.6 | 4.1 | 4.9 |
| vP921 | NONE | 0.5 | 0.8 | 1.2 | 0.6 |
| | NYVAC | 4.4 | 7.9 | 7.5 | 6.0 |
| | vP878 | 8.1 | 59.0 | 7.1 | 7.5 |
| | vP911 | 6.4 | 71.4 | 7.9 | 6.6 |
| | vP921 | 9.3 | 63.4 | 9.0 | 8.1 |

TABLE 26

Lymphocyte proliferative responses to HIV gp160 epitopes 27 days after a single immunization with HIV recombinant vaccinia viruses.

| | | COUNTS PER MINUTE | | | | | | | | |
|---|---|---|---|---|---|---|---|---|---|---|
| | | | HIV ANTIGEN | | | | | | | |
| | | | gp160 (µg) | | T1 (µg) | | | T2 (µg) | | |
| IMMUNIZATION | | RPMI | 1 | 10 | 1 | 5 | 10 | 1 | 5 | 10 |
| NONE | MEAN | 5,185 | 6,397 | 7,808 | 7,682 | 8,614 | 11,541 | 6,141 | 8,835 | 6,774 |
| | ±SD | 1,020 | 2,174 | 2,596 | 1,274 | 2,033 | 2,036 | 2,103 | 1,883 | 2,806 |
| | SI | 1.0 | 1.2 | 1.5 | 1.0 | 1.1 | 1.5 | 1.0 | 1.4 | 1.1 |
| NYVAC | MEAN | 10,327 | 13,589 | 15,969 | 11,360 | 12,654 | 15,369 | 10,339 | 9,834 | 8,868 |
| | ±SD | 1,543 | 3,323 | 4,583 | 1,352 | 2,272 | 1,821 | 762 | 1,731 | 502 |
| | SI | 1.0 | 1.3 | 1.5 | 1.0 | 1.1 | 1.4 | 1.0 | 1.0 | 0.9 |
| vP878 | MEAN | 10,126 | 13,150 | 18,329 | 11,114 | 11,956 | 13,754 | 10,415 | 11,442 | 9,147 |
| | ±SD | 1,269 | 1,103 | 4,245 | 1,217 | 1,106 | 1,568 | 335 | 1,288 | 1,033 |
| | SI | 1.0 | 1.3 | 1.8 | 1.0 | 1.1 | 1.2 | 1.0 | 1.1 | 0.9 |
| vP911 | MEAN | 12,155 | 15,564 | 26,083 | 12,417 | 15,380 | 17,007 | 10,681 | 11,412 | 10,702 |
| | ±SD | 1,307 | 9,707 | 16,327 | 873 | 1,847 | 6,266 | 2,428 | 3,201 | 1,468 |
| | SI | 1.0 | 1.3 | 2.1 | 1.0 | 1.2 | 1.4 | 1.0 | 1.1 | 1.0 |
| vP921 | MEAN | 9,701 | 49,256* | 61,036* | 10,550 | 15,367 | 15,816 | 8,818 | 9,232 | 8,803 |
| | ±SD | 2,601 | 23,673 | 25,866 | 3,447 | 3,481 | 7,176 | 954 | 2,265 | 2,860 |
| | SI | 1.0 | 5.1 | 6.3 | 1.0 | 1.5 | 1.5 | 1.0 | 1.0 | 1.0 |

SI - stimulation index.
*P < 0.05 compared to unstimulated control cultures Student's t-test

TABLE 27

HIV gp160 ELISA titers of mice immunized with HIV recombinant vaccinia viruses.

| | WEEKS AFTER IMMUNIZATION | | | | | |
|---|---|---|---|---|---|---|
| IMMUNIZATION | 0 | 1 | 2 | 4 | 7 | 9 |
| CONTROLS | 22 | 32 | 32 | 38 | 36 | 33 |
| NYVAC | 38 | 36 | 37 | 28 | 50 | 45 |
| vP878 | 20 | 43 | 27 | 46 | 65 | 63 |
| vP911 | 0 | 0 | 90 | 453 | 4,614 | 3,263 |
| vP921 | 0 | 26 | 25 | 77 | 2,614 | 1,689 |

EXAMPLE 19

EXPRESSION OF THE HIV-1 (ARV-2 OR SF-2 STRAIN) env GENE IN ALVAC, TROVAC AND NYVAC VECTORS Plasmid Constructions. The lambda clone containing the entire HIV-1 (ARV-2 or SF-2 strain) genome was provided by J. Levy and was described previously (Sanchez-Pescador et al., 1985). The env sequences were subcloned into pUC13, creating plasmid pMP7MX373, which contains the sequences from −1 relative to the initiation codon (ATG) of the env gene product to 715 bp downstream of the termination codon (TAA) of the env gene. These env sequences were excised from pMP7MX373 by digestion with EcoRI and HindIII and inserted into the plasmid vector, pIBI25 (International Biotechnologies, Inc., New Haven, Conn.), generating plasmid pIBI25env. Recombinant plasmid pIBI25env was used to transform competent E. coli CJ236 (dut- ung-) cells. Single-stranded DNA was isolated from phage derived by infection of the transformed E. coli CJ236 cells with the helper phage, MG408. This single-stranded template was used in vitro mutagenesis reactions (Kunkel et al., 1985) with oligonucleotide MUENVT12 (SEQ ID NO:157) (5'-AGAGGGGAATTCTTCTACTGCAATACA-3'). Mutagenesis with this oligonucleotide generates a T to C transition and disrupts the T5CT motif at nucleotide positions 6929–6935 of the ARV-2 genome (Sanchez-Pescador et al, 1985). This mutation does not alter the amino acid sequence of the env gene and creates an EcoRI site, which was used to screen for mutagenized plasmid clones. Sequence of confirmation was done by the dideoxynucleotide chain termination method (Sanger et al., 1977). The resultant mutagenized plasmid was designated as pIBI25mutenv11.

A 1.45 kb BglII fragment was derived from pIBI25mutenv11. This fragment contained the mutated env sequences. It was used to substitute for the corresponding unmutated fragment in pIBIenv. The resultant plasmid was designated as pIBI25mutenv8. Further modifications were made to pIBImutenv8. In vitro mutageneses were performed to remove the sequence coding for the rex protein and the LTR sequence (LTR region) from the 3'-end of the gene and to delete the putative immuno-suppressive (IS) region amino acids 583 through 599) (SEQ ID NO:158) Leu-Gln-Ala-Arg-Val-Leu-Ala-Val-Glu-Arg-Tyr-Leu-Arg-Asp-Gln-Gln-Leu) (Klasse et al., 1988). These reactions were done with the single-stranded template derived from pIBImutenv8 with oligonucleotides LTR2 (SEQ ID NO:159) (5'-TTG-GAAAGGCTTTTGGCATGCCACGCGTC-3') and MUENSVISR (SEQ ID NO:160) (5'-ACAGTCTGGGGCATCAAGCAGCTAGG-GATTTGGGGTTGCTCT-3'). Mutagenized clones were identified by hybridization and restriction analysis. A clone mutagenized such that it was deleted both of the IS and the LTR region and another deleted of the LTR was confirmed by nucleotide sequence analysis and designated pIBI25mut3env40 and pIBI25mut2env22, respectively.

A 3.4 kb SmaI/HindIII fragment containing the entire env gene was derived from pIBI25mut3env40 and from pIBImut2env22 and inserted into pCPCV1, digested with SmaI/HindIII. The plasmid pCPCV1 is an insertion plasmid which enables the generation of CP recombinants. The foreign genes were directed to the C3 insertion locus. Plasmids pCPCV1 and pFPCV2 have been described previously in PCT International Publication No. WO 89/03429 published Apr. 20, 1989, incorporated herein by reference.

Oligonucleotide PROVECNS (SEQ ID NO:161) (5'-CCGTTAAGTTTGTATCGTAATGAAAGT-GAAGGGGACCAGG-3') was used for in vitro mutagenesis reactions via the method of Mandecki (1986) to made a precise ATG:ATG construction with the VVH6 promoter and the env sequences. Potential mutants were screened for the loss of the SmaI site. Plasmid clones devoid of a SmaI site were identified and confirmed by nucleotide sequence analysis. Properly mutagenized plasmid clones were identified and designated as pCPenvIS+ or pCVenvIS− and pFPenvIS+ or pFPenvIS−.

The HIV-1 env genes were excised from pCPenvIS− by digestion with NruI and HindIII. The two env fragments of 2.5 kb (envIS+) and 2.4 kb (envIS−), respectively, were isolated and blunt-ended by reaction with the Klenow fragment of the E. coli DNA polymerase in the presence of 2 mMdNTPs. These fragments were ligated with the 3.5 kb fragment derived by digestion of pSIVenvVV with NruI and PstI with a subsequent blunting step with the Klenow fragment of the E. coli DNA polymerase in the presence of 2 mM dNTPs. The plasmid pSIVenvVV contains the SIV env gene expression cassette regulated by the vaccinia virus H6 promoter in the ATI insertion locus. Digestion of pSIV env VV with NruI and PstI excises the entire SIV env coding sequences and the 3'-most 20 bp of the promoter element. Ligation to the env IS− and env IS+ fragments restores the 20 bp of the H6 promoter and inserts the HIV-1 env gene into the ATI insertion plasmid. The resultant plasmids were designated as pAR5VV+ and pAR6VV− for env IS+ and env IS−, respectively.

In Vitro Recombination and Purification of Recombinants. Recombination was performed introducing plasmid DNA into infected cells by calcium phosphate precipitation both for CP (ALVAC) and for FP (TROVAC) recombinants, as previously described (Piccini et al., 1987). Plasmids pCPenvIS+ and pCPenvIS– (C5 locus, FIG. 16) were used to make recombinants vCP61 and vCP60 respectively. Plasmids pFPenvIS+ and pFPenvIS– (F7 locus, FIG. 22) were used to make recombinants vFP63 and vFP62, respectively. The plasmids pAR5VV+ and pAR6VV were used in in vitro recombination experiments with vP866 (NYVAC) as rescue to yield vP939 and vP940, respectively. Recombinant plaques were selected by autoradiography after hybridization with a $^{32}$P-labeled env specific probe and passaged serially three times to assure purity, as previously described (Piccini et al., 1987).

Radioimmunoprecipitation Analysis. Cell monolayers were infected at 10 pfu/cell in modified Eagle's methionine-free medium (MEM met–). At 2 hours post-infection, 20 uCi/ml of [$^{35}$S]-methionine were added in MEM (–met) containing 2% dialysed fetal bovine serum (Flow). Cells were harvested at 15 hrs post-infection by resuspending them in lysis buffer (150 mM NaCl, 1 mM EDTA pH 8, 10 mM Tris-HCl pH 7.4, 0.2 mg/ml PMSF, 1% NP40, 0.01% Na Azide) and 50 µl aprotinin, scraped into eppendorf tubes and the lysate was clarified by spinning 20 minutes at 4° C. One third of the supernatant of a 60 mm diameter Petri dish was incubated with 1 µl normal human serum and 100 µl of protein A-Sepharose CL-4B (SPA) (Pharmacia) for 2 hours at room temperature. After spinning for 1 minute, the supernatant was incubated for 1 h 30 minutes at 4° C. with 2 µl preadsorbed human serum from HIV seropositive individuals (heat-inactivated) and 100 µl SPA.

The pellet was washed four times with lysis buffer and two times with lithium chloride/urea buffer (0.2M LiCl, 2M urea, 10 mM Tris-HCl pH 8) and the precipitated proteins were dissolved in 60 µl Laemmli buffer (Laemmli, 1970). After heating for 5 minutes at 100° C. and spinning for 1 minute to remove Sepharose, proteins in the supernatant were resolved on an SDS 10% polyacrylamide gel and fluorographed.

Expression of the HIV-1 env Gene. Six different recombinant viruses were prepared where the HIV env gene of the ARV-2 or SF-2 strain was inserted downstream from a vaccinia early-late promoter, H6. For simplicity, the two ALVAC-based recombinant viruses, vCP61 and vCP60, will be referred to as CPIS+ and CPIS–, the two TROVAC-based recombinants, vFP63 and vFP62, as FPIS+ and FPIS–, and the two NYVAC-based recombinants vP939 and vp940 as VV– and VV+, respectively.

All the constructs were precise, in that, the ATG initiation codon of the HIV-1 env gene was superimposed on the ATG of the vaccinia H6 promoter. Moreover, all extraneous genetic information 3' to the termination codon was eliminated. CPIS–, FPIS–, and VV– were all obtained by deletion of a 51 bp region, corresponding to amino acids 583–599, located near the 5' portion of the gp41 gene product. This region shares homology with putative immunosuppressive regions (Klasse et al., 1988, Ruegg et al., 1989b) occurring in the transmembrane polypeptide of other retrovirus glycoproteins (Cianciolo et al., 1985; Ruegg et al., 1989a,b).

Expression analyses with all six recombinant viruses were performed in CEF, Vero, and MRC-5 cell monolayers. Immuno-precipitation experiments using sera pooled from HIV seropositive individuals were performed as described in Materials and Methods. All six recombinants directed the synthesis of the HIV-1 gp161 envelope precursor. The efficiency of processing of gp160 to gp120 and gp41, however, varied between cell types and was also affected by deletion of the immunosuppressive region. Recognition of gp41 by the pooled sera from HIV seropositive individuals also varied with the virus background and the cell type.

EXAMPLE 20

EXPRESSION OF THE HIV-2 (ISSY STRAIN) env GENE IN NYVAC

Expression of gp160. Oligonucleotides HIV25PA (SEQ ID NO. 162) (5'-ATGAGTGGTAAAATTCAGCTGCTTGTTGCCTTTCTGCTAACTAGTGCTTGCTTA-3') and HIV25PB (SEQ ID NO:163) (5'-TAAGCAAGCACTAGTTAGCAGAAAGGCAACAAGCAGCTGAATTTTACCACTCAT-3') were annealed to constitute the initial 54 bp of the HIV-2 SBL/ISY isolate (Franchini et al., 1989) env coding sequence. This fragment was fused 3' to a 129 bp fragment derived by PCR with oligonucleotides H65PH (SEQ ID NO:164) (5'-ATCATCAAGCTTGATTCTTTATTCTATAC-3') and H63PHIV2 (SEQ ID NO:165) (5'-CAGCTGAATTTTACCACTCATTACGATACAAACTTAACG-3') using pTP15 (Guo et al., 1989) as template. The fusion of these two fragments was done by PCR using oligonucleotides HIV25PC (SEQ ID NO:166) (5'-TAAGCAAGCACTAGTTAG-3') and H65PH (SEQ ID NO:164). The 174 bp PCR derived fragment was digested with HindIII and SacI and inserted into pBS-SK (Stratagene, La Jolla, Calif.) digested with HindIII and SacI. The resultant fragment was designated pBSH6HIV2. The insert was confirmed by nucleotide sequence analysis.

The 3' portion of the HIV-2 env gene was also derived by PCR. In this reaction a 270 bp fragment was amplified with oligonucleotides HIV2B1 (SEQ ID NO:167) (5'-CCGCCTCTTGACCAGAC-3') and HIV2B2 (SEQ ID NO:168)

(5'-ATCATCTCTAGAATAAAAATTACAG-
GAGGGCAATTTCTG-3') using pISSY-KPN (provided by Dr. Genoveffa Franchini, NCI-NIH, Bethesda, Md.) as template. This fragment was digested with BamHI and XbaI. The 150 bp fragment derived from this digestion contained a 5' BamHI and a 3' XbaI cohesive end. The fragment was engineered to contain a T5NT sequence motif known to be recognized as vaccinia virus early transcription termination signal (Yuen et al., 1987), following the termination codon (TAA).

The majority of the HIV-2 env gene was obtained from pISSY-KPN by digestion with SacI and BamHI. The 2.7 kb fragment generated by this digestion was coinserted into pBS-SK digested with SacI and XbaI with the 150 bp BamHI/XbaI fragment corresponding to the 3' end of the gene. The resultant plasmid was designated pBSHIV2ENV.

The 174 bp SpeI/HindIII fragment from pBSH6HIV2 and the 2.5 kb SpeI/XbaI fragment from pBSHIV2ENV were ligated into pBS-SK digested with HindIII and XbaI to yield pBSH6HIV2ENV. The 2.7 kb HindIII/XbaI insert from pBSH6HIV2ENV was isolated and blunt-ended with the Klenow fragment of the E. coli DNA polymerase in the presence of 2 mM dNTP. The blunt-ended fragment was inserted into a SmaI digested pSD5HIVC insertion vector. The resultant plasmid was designated as pATIHIV2ENV. This plasmid was used in vitro recombination experiments with vP866 (NYVAC) as the rescuing virus to yield vP920.

Immunoprecipitation analysis was performed to determine whether vP920 expresses authentic HIV-2 gp160. Vero cell monolayers were either mock infected, infected with the parental virus vP866, or infected with vP920 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 18 hrs post-infection by the addition of 1 ml 3× buffer A (3% NP-40, 30 mM Tris pH 7.4, 150 mM NaCl, 3 mM EDTA, 0.03% Na Azide and 0.6 mg/ml PMSF) with subsequent scraping of the cell monolayers.

Lysates from the infected cells were analyzed for HIV-2 env gene expression using pooled serum from HIV-2 seropositive individuals (obtained from Dr. Genoveffa Franchini). The sera was preadsorbed with vP866 infected Vero cells. The preadsorbed human sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the human sera from seropositive individuals bound to protein A-sepharose. After the overnight incubation period, the samples were washed 4× with 1× buffer A and 2× with a LiCl$_2$/urea buffer. Precipitated proteins were dissociated from the immune complexes by the addition of 2× Laemmlis buffer (125 mM Tris(pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-2 seropositive individuals specifically precipitated the HIV-2 gp160 envelope glycoprotein from vP920 infected cells. Furthermore, the authenticity of the expressed HIV-2 env gene product was confirmed, since the gp160 polyprotein is processed to the mature gp120 and gp41 protein species. No HIV-specific protein species were precipitated from mock-infected cells or cells infected with the NYVAC parental virus. Also, supportive of the proper expression of the HIV-2 env by vP920 was the observation that the gene product is expressed on the surface of vP920 infected cells.

Expression of gp120. The plasmid pBSH6HIV2 containing the vaccinia virus H6 promoter fused to the 5'-end of the HIV-2 env gene was digested with SpeI and HindIII to liberate the 180 bp fragment containing these sequences. This fragment was ligated into pBS-SK digested with HindIII and XbaI along with the 1.4 kb SpeI/XbaI fragment of pBSHIV2120A to yield pSHIV2120B.

The plasmid pBSHIV2120A was derived by initially deriving the 3' portion of the gp120 coding sequence by PCR. The PCR was performed using oligonucleotides HIV2120A (SEQ ID NO:169) (5'-ATCATCTCTA-GAATAAAAATTATCTCTTATGTCTCCCTGG-3') and HIV2120B (SEQ ID NO:170) (5'-AATTAACTTTACAG-CACC-3') with pISSY-KPN as template. The PCR-derived fragment was digested with EcoRI and XbaI to yield a 300 bp fragment which contained a 5'-EcoRI cohesive end and a 3'-XbaI cohesive end. The fragment was engineered with a translation termination sequence (TAA) and a T5NT sequence motif just 5' to the XbaI site. The 300 bp XbaI/EcoRI PCR fragment was ligated into pBS-SK digested with SacI/XbaI along with a 1.4 kb SacI/EcoRI fragment derived from pISSY-KPN to generate pBSHIV2120A.

The plasmid pBSHIV2120B was digested with HindIII and XbaI to generate a 1.8 kb fragment containing the HIV-2 gp120 coding sequence juxtaposed 3' to the vaccinia virus H6 promoter. This fragment was blunted with the Klenow fragment of the E. coli DNA polymerase in the presence of 2 mM dNTPs. The blunt-ended fragment was ligated to SmaI digested pSDSHIVC to generate pATI HIV 2120. This plasmid was used in in vitro recombination experiments to yield vP922.

Immunoprecipitation experiments with vP922 infected cells were performed as described above for the expression of the entire HIV-2 env gene. No HIV-specific species were precipitated from mock infected or vP866 infected Vero cells. A protein species of 120 kDa was, however, precipitated from lysates derived from cells infected with vP922. The HIV-2 gp120 expressed by vP920 was found to be present on the cell surface of vP920 infected Vero cells.

EXAMPLE 21

EXPRESSION OF SIV GENES IN NYVAC

Generation of NYVAC/SIV gp140 Recombinant. A plasmid pSSIIE containing the SIV (Mac142) env gene was obtained from Dr. Genoveffa Franchini (NCI-NIH, Bethesda, Md.). This plasmid was digested with HindIII and PstI to liberate a 2.2 kbp fragment containing from nucleotide 220 of the SIV env gene to a region 160 bp downstream from the translation termination codon. It should be noted that an expression cassette containing this fragment will result in the expression of a gp140 protein species rather that a gp160 species. This 40% deletion of the transmembrane region results from a premature termination at nucleotide 7,934 of the genome (Franchini et al., 1987). Such premature terminations of the env gene product are noted after propagation of SIV in culture (Kodama et al., 1989).

The amino portion of the gene was derived by PCR using pSSIIE as template and oligonucleotides SIVENV1 (SEQ ID NO:171) (5'-CGATATCCGTTAAGTTTGTATCG-TAATGGGATGTCTTGGGAATC-3') and SIVENV2 (SEQ ID NO:172) (5'-CAAGGCTTTATTGAGGTCTC-3'). The resultant 250 bp fragment contains the 5'-most 230 bp of the SIV env gene juxtaposed downstream from the 3'-most 20 bp of the vaccinia virus H6 promoter (3'-end of NruI site). A 170 bp fragment was obtained by digestion of the fragment with HindIII, which removes 80 bp of SIV env sequences.

The sequences containing the remainder of the SIV env gene following the premature termination signal were derived by PCR from pSS35E (obtained from Dr. Genoveffa Franchini). This plasmid contains sequences containing the C-terminal portion of the SIV env gene into the LTR region downstream from the env gene. The oligonucleotides used to derive the 360 bp fragment were SIVENV3 (SEQ ID NO:173) (5'-CCTGGCCTTGGCAGATAG-3') and SIVENV4A (SEQ ID NO:174) (5'-ATCATCGAAT-TCAAAAATATTACAAAGAGCGTGAGCT-CAAGTCCTTGCCTAATCCTCC3'). This fragment was digested with PstI and EcoRI to generate a 260 bp fragment having a 5' PstI cohesive end and a 3' EcoRI cohesive end.

The 2.2 kb HindIII/PstI fragment from pSSIIE, the 170 bp NruI/HindIII fragment containing the 5' end of the gene, and the 260 bp PstI/EcoRI containing the 3' end of the gene were ligated with a 3.1 kb NruI/EcoRI fragment derived from pRW838. pRW838 contains the vaccinia virus H6 promoter linked to the rabies G gene flanked by canarypox virus sequences which enable the insertion of genes into the C5 locus. Digestion with NruI and EcoRI liberates the rabies G gene and removes the 3'-most 20 bp of the H6 promoter. The resultant C5 insertion plasmid containing the SIV env gene linked to the vaccinia H6 promoter was designated as pC5SIVENV.

The plasmid, pC5SIVENV, was digested with HindIII and EcoRI to liberate a 2.2 kb fragment, containing from nucleotide 150 of the SIV env gene to the end of the entire gene. PCR was used to derive the vaccinia H6 promoter/SIV env linkage from pC5SIVENV with oligonucleotides MPSYN286 (SEQ ID NO:175) (5'-CCCCCCAAGCTTFTT-TATTCTATACTT-3') and SIVENV2 (SEQ ID NO:176) (5'-CAAGGCTTTATTGAGGTCTC-3'). The 320 bp fragment was digested with HindIII to derive a 240 bp fragment. The 2.2 kb HindIII/EcoRI and the 240 bp HindIII fragment were coligated into pC3I digested with HindIII and EcoRI. The resultant plasmid containing the HindIII fragment in the proper orientation relative to the SIVenv coding sequence was designated pC3SIVEM. The plasmid pC3I was derived as follows. The nucleotide sequence analysis of an 2.5 kb BglII canarypoxvirus genomic fragment revealed the entire C3 open reading frame and the 5' and 3' noncoding regions. In order to construct a donor plasmid for insertion of foreign genes into the C3 locus with the complete excision of the C3 open reading frame, PCR primers were used to amplify the 5' and 3' sequences relative to C3. Primers for the 5' sequences were RG277 (SEQ ID NO:177) (5'-CAGTTGG-TACCACTGGTATTTTATTTCAG-3') and RG278 (SEQ ID NO:178) (5'-TATCTGAATTCCTGCAGCCCGGGTTTT-TATAGCTAATTAGTCAAATGTGAGTTAATATTAG-3').

Primers for the 3' sequences were RG279 (SEQ ID NO:179) (5'-TCGCTGAATTCGATATCAAGCTTATC-GATTTTTATGACTAGTTAAT-CAAATAAAAAGCATACAAGC-3') and RG280 (SEQ ID NO:180) (5'-TTATCGAGCTCTGTAACATCAG-TATCTAAC-3'). The primers were designed to include a multiple cloning site flanked by vaccinia transcriptional and translation termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

The plasmid pC3SIVEM was linearized by digestion with EcoRI. Subsequent partial digestion with HindIII liberated a 2.7 kb HindIII/EcoRI fragment. This fragment was blunt-ended by treatment with Klenow fragment of the *E. coli* DNA polymerase in the presence of 2 mM dNTPs. The fragment was ligated into pSD550VC digested with SmaI. The resultant plasmid was designated as pSIVEMVC. This plasmid was used in in vitro recombination experiments with vP866 as rescue virus to generate vP873. vP873 contains the SIV env gene in the I4L locus.

Generation of a NYVAC/gag/pol and gag Recombinants. A plasmid, pSIVAGSSIIG, containing the SIV cDNA sequence encompassing the gag and pol genes was obtained from Dr. Genoveffa Franchini (NCI-NIH, Bethesda, Md.). The gag and pol genes from this plasmid were juxtaposed 3' to the vaccinia I3L promoter between vaccinia tk flanking arms. This was accomplished by cloning the 4,800 bp CfoI/TaqI fragment of pSIVGAGSSIIG, containing the gag and the oligonucleotides SIVL1 (SEQ ID NO:181) (5'-TCGAGTGAGATAAAGTGAAAATATATAT-CATTATATTACAAGTACAATTATTTAG-GTTTAATCATGGGCG- 3') and SIVL2 (SEQ ID NO:182) (5'-CCCATGATTAAACCTAAATAATTG-TACTTTGTAAATATAATGC-TATATATTTTCACTTTATCTCAC-3') corresponding to the I3L promoter into the 4,070 bp XhoI/AccI fragment of pSD542, a derivative of pSD460 (FIG. 1). The plasmid generated by this manipulation was designated pSIVG1.

To eliminate the pol gene, a 215 bp PCR fragment was derived from pSIVGAGSSIIG using oligonucleotides SIVP5 (SEQ ID NO:183) (5'-AATCAGAGAGCAGGCT-3') and SIVP6 (SEQ ID NO:184) (5'-TTGGATCCCTATGC-CACCTCTCT-3'). The PCR-derived fragment was digested with BamHI and StuI and ligated with the 5,370 bp partial BamHI/StuI fragment of SIVG1. This resulted in the generation of pSIVG2. pSIVG2 was used in in vitro recombination experiments with vP873 as rescue virus to yield vP948.

The plasmid to insert both gag and pol into NYVAC-based vectors was engineered in the following manner. pSIVG1, described above, contains extraneous 3'-noncoding sequences which were eliminated using a 1 kb PCR fragment. This fragment was generated from plasmid pSIV-GAGSSIIG with the oligonucleotides SIVP5 and SIVP6. This PCR derived fragment containing the 3' end of the pol gene was digested with BamHI and HpaI. The 1 kb BamHI/HpaI fragment was ligated to the 7,400 bp partial BamHI/HpaI fragment of pSIVG1 to yield pSIVG4.

Sequence analysis of pSIVG4 revealed a single base pair deletion within the pol gene. To correct this error the 2,300 bp BglII/StuI fragment from pSIVG1 was inserted into the 6,100 bp partial BglII/StuI fragment of pSIVG4 to yield pSIVG5. The plasmid, pSIVG5, was used in in vitro recombination experiments with vP873 as rescue to generate vP943.

Generation of NYVAC/SIV p16 and p28 Recombinants. The pol gene and the portion of the gag gene encoding p28, p2, p8, p1, and p6 were eliminated from pSIVG1. This was accomplished by cloning the oligonucleotides SIVL10 (SEQ ID NO:185) (5'-AGACCAACAGCACCATCTAGCGGCA-GAGGAGGAAATTACTAATTTTTATTCTAGAG-3') and SIVL11 (SEQ ID NO:186) (5'-GATCCTCTA-GAATAAAAATTAGTAATTTCCTCCTCT- GCCGCTAGATGGTGCTGTTGGT-3') into the 4,430 bp AccI/BamHI fragment of pSIVG1 to generate pSIVG1 to generate pSIVG3. This plasmid contains an expression cassette for the SIV p17 gene product expressed by the vaccinia I3L promoter.

The entomopoxvirus 42 kDa-promoted SIV p28 gene (5' end only) was inserted downstream from the I3L-promoted p17 gene. This was accomplished by cloning the 360 bp BspMI/BamHI fragment of pSIVGI, containing the 5' end of the p28 gene, the oligonucleotides pSIVL14 (SEQ ID NO:187) ( 5'-TAGACAAAATTGAAAATATATAATTA-CAATATAAAATGCCAGTACAACAAATAG-GTGGTAACTATGTCCACCTGCCATT-3') and SIVL15 (SEQ ID NO:188) ( 5'-GCTTAATGGCAGGTGGACAT-AGTTACCACCTATTTGTTGTACTG-GCATTTTATATTGTAATTATATATTTTCAATTTTGT-3'), containing the entomopox 42 kDa promoter into the 4,470 bp partial XbaI/BamHI fragment of pSIVG3. The resultant plasmid was designated as pSIVG6.

The 3' portion of the p28 gene was then inserted into pSIVG6. A 290 bp PCR fragment, containing the 3' end of the SIV p28 gene, was derived from pSIVGI using oligonucleotides SIVP12 (SEQ ID NO:189) (5'-TGGATGTACA-GACAAC-3') and SIVP13 (SEQ ID NO:190) (5'-AAG-GATCCGAATTCTTACATTAATCTAGCCTTC-3'). This fragment was digested with BamHI and ligated to the 4,830 bp BamHI fragment of pSIVG7, was used in in vitro recombination experiments with vP866 and vP873 as rescue experiments to generate vP942 and vP952, respectively.

Expression Analyses. The SIV gp140 env gene product is a typical glycoprotein associated with the plasma membrane of infected cells. It is expressed as a polyprotein of 140 kDa that is proteolytically cleaved to an extracellular species of 112 kDa and a transmembrane region of 28 kDa (Franchini et al., 1987). Immunofluorescence analysis using sera from rhesus macaques seropositive for SIV followed by fluorescein conjugated rabbit anti-monkey IgG demonstrated expression of the env gene product on the surface of recombinant infected Vero cells. Surface expression was not detectable on the surface of mock infected cells or cells infected with the NYVAC (vP866) parent virus. Furthermore, cells infected with recombinants containing only gag genes were not shown to express any SIV components on the surface. Surface expression in cells infected with vP873, vP943, vP948 and vP952 all demonstrated surface expression and significantly, all contain the SIV env gene.

The authenticity of the expressed SIV gene products (env and gag) in Vero cells infected with the NYVAC/HIV recombinants was analyzed by immunoprecipitation. Vero cells were infected at an m.o.i. of 10 with the individual recombinant viruses, with the NYVAC parent virus, or were mock infected. After a 1 hour adsorption period, the inoculum was removed and infected cells were overlayed with 2 ml methionine-free media containing [$^{35}$S]-methionine (20 µCi/ml). All samples were harvested at 17 hours post infection by the addition of 1 ml of 3× Buffer A. Lysates from the infected cells were analyzed with pooled sera from SIV seropositive rhesus macaques or a monoclonal antibody specific for gag p24 gene product (both obtained from Dr. Genoveffa Franchini, NCI-NIH, Bethesda Md.).

Immunoprecipitation with the SIV seropositive macaque sera was performed in the following manner. The macaque sera were incubated with protein A-sepharose at 4° C. for 16 hours. After washing with buffer A, the sera bound to protein A sepharose were added to lysates precleared with normal monkey sera and protein A sepharose. Following an overnight incubation at 4° C. the precipitates were washed 4× with buffer A and 2× with LiCl/urea buffer. To dissociate the precipitated protein from the antibody, the samples were boiled in 80 µl 2× Lammed buffer for 5 minutes. The samples were fractionated on a 12.5% gel using the Dreyfuss gel system (Dreyfuss et al., 1984). The gel was fixed and treated with 1M Na-salycate for fluorography. All the recombinants containing SIV genes were expressing the pertinent gene products. The NYVAC recombinants vP873, vP943, vP948 and vP952 which contain the SIV env gene all expressed the authentic gp140. However, it is difficult to assess the processing of the gp140 protein to the 112 kDa and 28 kDa mature forms. No species with an apparent molecular weight of 140 kDa was precipitated by macaque anti-SIV sera from mock infected Vero cells, vP866 infected Vero cells and Vero cells infected with a NYVAC/SIV recombinant not containing the SIV env gene. Expression of the SIV gag encoded gene products by vP942, vp943, vp948, and vP952 was demonstrated using the pooled sera from macaques infected with SIV and the monoclonal antibody specific to the p28 gag component. Expression of the entire p55 gag protein without the pol region, which contains the protease function, by NYVAC (vP948) in Vero cells is evident. These results demonstrate that lack of SIV protease expression prevents the complete proteolysis of p55 into its mature form. This is demonstrated much more clearly when a monoclonal antibody specific to p28 was used to precipitate gag specific gene products from vP948 infected Vero cells. Contrary to this result, expression of SIV gag with the pol gene (includes protease) in vP943 infected Vero cells enabled the expressed p55 gag precursor polypeptide to be proteolytically cleaved to its mature forms.

Expression of both the p16 and p28 SIV gene products in vP942 and vP952 infected Vero cells was demonstrated using the pooled sera from macaques infected with SIV. Using the monoclonal antibody specific to p28 obviously only recognized the p28 expressed component.

EXAMPLE 22

CONSTRUCTION OF TROVAC RECOMBINANTS EXPRESSING THE HEMAGGLUTININ GLYCOPROTEINS OF AVIAN INFLUENZA VIRUSES

This Example describes the development of fowlpox virus recombinants expressing the hemagglutinin genes of three serotypes of avian influenza virus.

Cells and Viruses. Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus. Plasmid pRW731.15 contains a 10 kbp PvuII-PvuII fragment cloned from TROVAC genomic DNA. The nucleotide sequence was determined on both strands for a 3661 bp PvuII-EcoRV fragment. This sequence is shown in FIG. 21. The limits of an open reading frame designated in this laboratory as F8 were determined within this sequence. The open reading frame is initiated at position 704 and terminates at position 1888. In order not to interfere with neighboring open reading frames, the deletion was made from position 781 to position 1928, as described below.

Plasmid pRW761 is a sub-clone of pRW731.15 containing a 2430 bp EcoRV-EcoRV fragment. The F8 ORF was entirely contained between an XbaI site and an SspI site in PRW761. In order to create an insertion plasmid which, on recombination with TROVAC genomic DNA would eliminate the F8 ORF, the following steps were followed. Plasmid pRW761 was completely digested with XbaI and partially digested with SspI. A 3700 bp XbaI-SspI band was isolated and ligated with the annealed double-stranded oligonucleotides JCA017 (SEQ ID NO:191) and JCA018 (SEQ ID NO:192).

JCA017 (SEQ ID NO:191)

5' CTAGACACTTTATGTTTTTTAATATCCGGTCTT
AAAAGCTTCCCGGGGATCCTTATACGGGGAATAAT 3'

JCA018 (SEQ NO:192)

5' ATTATTCCCCGTATAAGGATCCCCCGGGAA
GCTTTTAAGACCGGATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:193) and RW179 (SEQ ID NO:194) were cut with EcoRV and BamHI and inserted between the EcoRV and BamHI sites of JCA004 to form pRW846.

RW178 (SEQ ID NO:193):

5' TCATTATCGCGATATCCGTGTTAACTAGCTA
GCTAATTTTTATTCCCGGGATCCTTATCA 3'

RW179 (SEQ ID NO:194):

5' GTATAAGGATCCCGGGAATAAAAATTAGCT
AGCTAGTTAACACGGATATCGCGATAATGA 3'

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus. The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 22 was determined for a 2356 bp region encompassing the unique HincII site. Analysis of this sequence revealed that the unique HincII site (FIG. 22, underlined) was situated within an ORF encoding a polypeptide of 90 amino acids. The ORF begins with an ATG at position 1531 and terminates at position 898 (positions marked by arrows in FIG. 22).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:195) (5'-GACAATCTAAGTC-CTATATTAGAC-3') and F73PB (SEQ ID NO:196) (5'-GGATTTTTAGGTAGACAC-3'). A 270 bp arm (designated as EH) corresponding to the region downstream from the ORF was amplified using oligonucleotides F75PE (SEQ ID NO:197) (5'-TCATCGTCTTCATCATCG-3') and F73PH1 (SEQ ID NO:198) (5'-GTCTTAAACTTATTGTAAGGG-TATACCTG-3').

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La. Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the *E. coli* DNA polymerase in the presence of 2 mM dNTPs. This linearized plasmid was ligated with annealed oligonucleotides F7MCSB (SEQ ID NO:199) (5'-AACGATTAGTTAGT-TACTAAAAGCTTGCTGCAGC-CCGGGTTTTTTATTAGTTTAGTTAGTC-3') and F7MCSA (SEQ ID NO:200) (5'-GACTAACTAAC-TAATAAAAAACCCGGGCTGCAG-CAAGCTTTTTGTAACTAACTAATCGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus. A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:201) and RW153 (SEQ ID NO:202). These oligonucleotides represent the 3' portion of the H6 promoter from the EcoRV site and align the ATG of the promoter with the ATG of the H4 cDNA.

RW 152 (SEQ ID NO:201):

5' GCACGGAACAAAGCTTATCGCGATATCCGTTA
AGTTTGTATCGTAATGCTATCAATCACGATTCTGT
TCCTGCTCATAGCAGAGGGCTCATCTCAGAAT 3'

RW 153 (SEQ ID NO:202):

5' ATTCTGAGATGAGCCCTCTGCTATGAGCAGGA
ACAGAATCGTGATTGATAGCATTACGATACAAACT
TAACGGATATCGCGATAAGCTTTGTTCCGTGC 3'

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

Construction of Insertion Plasmid for H5 Hemagglutinin at the F8 Locus. A cDNA clone of avian influenza H5 derived from A/Turkey/Ireland/1378/83 was received in plasmid pTH29 from Dr. R. Webster. Synthetic oligonucleotides RW10 (SEQ ID NO:203) through RW13 (SEQ ID NO:206) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

RW10 (SEQ ID NO:203):

5' GAAAAATTTAAAGTCGACCTGTTTTGTTGAGT
TGTTTGCGTGGTAACCAATGCAAATCTGGTC
ACT 3'

RW11 (SEQ ID NO:204):

5' TCTAGCAAGACTGACTATTGCAAAAAGAAGCA
CTATTTCCTCCATTACGATACAAACTTAACG
GAT 3'

RW12 (SEQ ID NO:205):

5' ATCCGTTAAGTTTGTATCGTAATGGAGGAAA
TAGTGCTTCTTTTTGCAATAGTCAGTCTTGCTAGA
AGTGACCAGATTTGCATTGGT 3'

RW13 (SEQ ID NO:206):

5' TACCACGCAAACAACTCAACAAAACAGGTCG
ACTTTAAATTTTTCTGCA 3'

The oligonucleotides were annealed at 95° C. for three minutes followed by slow cooling at room temperature. This results in the following double strand structure with the indicated ends.

```
EcoRV                              PstI
|     RW12       |      RW13       |
      RW11       |      RW10
```

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5.

The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting pRW849 contains the H6 promoted avian influenza virus H5 gene in the de-ORFed F8 locus.

Construction of Insertion Vector for H7 Hemagglutinin at the F7 Locus. Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:207) and RW166 (SEQ ID NO:208) were annealed, cut with HincII and StyI and inserted between the EcoRV and StyI sites of pRW827 to generate pRW845.

RW165 (SEQ ID NO:207):

5' GTACAGGTCGACAAGCTTCCCGGGTATCGCG
ATATCCGTTAAGTTTGTATCGTAATGAATACTCAA
ATTCTAATACTCACTCTTGTGGCAGCCATTCACAC
AAATGCAGACAAAATCTGCCTTGGACATCAT 3'

RW166 (SEQ ID NO:208)

5' ATGATGTCCAAGGCAGATTTTGTCTGCATTTG
TGTGAATGGCTGCCACAAGAGTGAGTATTAGAATT
TGAGTATTCATTACGATACAAACTTAACGGATATC
GCGATACCCGGGAAGCTTGTCGACCTGTAC 3'

Oligonucleotides RW165 (SEQ ID NO:207) and RW166 (SEQ ID NO:208) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:209) and RW228 (SEQ ID NO:210). The resulting plasmid was pRW854.

RW227 (SEQ ID NO:209):

5' ATAACATGCGGTGCACCATTTGTATAT
AAGTTAACGAATTCCAAGTCAAGC 3'

RW228 (SEQ ID NO:210):

5' GCTTGACTTGGAATTCGTTAACTTATA
TACAAATGGTGCACCGCATGTTAT 3'

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the SmaI site of pF7DO described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the E. coli DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants. Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence. In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the $HA_2$ cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_0$. This is in agreement with the lack of cleavage of the hemagglutinins of avirulent subtypes in tissue culture. No H4 specific proteins were detected in uninfected CEF cells or cells infected with TROVAC.

EXAMPLE 23

DEVELOPMENT OF A TRIPLE RECOMBINANT EXPRESSING THREE AVIAN INFLUENZA GENES

Plasmid Construction. Plasmid pRW849 has been discussed previously and contains the H6 promoted avian influenza H5 gene. This plasmid was used for the development of vFP89. Plasmid pRW861 was an intermediate plasmid, described previously used in the development of vFP100. The plasmid contains the H6 promoted avian influenza H7 gene. Plasmid pRW849 was digested with SmaI and the resulting 1.9 kbp fragment from the 5' end of the H6 promoter through the H5 gene was inserted at the smaI site of pRW861 to produce pRW865. In order to insert the H4 coding sequence, plasmid pRW848 was utilized. Plasmid pRW848 was used in the development of vFP92 and contains the H6 promoted H4 gene (previously described). Plasmid pRW848 was digested with SmaI and a 1.9 kbp fragment containing the H6 promoted H4 coding sequence was then inserted into pRW865 at the SmaI site 5' of the H6 promoted H5 sequence. The resulting plasmid pRW872 therefore contains the H4, H5 and H7 coding sequences in the F7 de-ORFed insertion plasmid.

In order to direct insertion of the genes to the de-ORFed F8 locus, pRW872 was partially digested with SmaI, the linear fragment isolated and recut with HindIII. The 5.7 kbp SmaI to HindIII pRW872 fragment containing all three H6 promoted avian influenza genes was blunt-ended and inserted into pCEN100 which had been cut with HincII. Plasmid pCEN100 is a de-ORFed F8 insertion vector containing transcription and translation stop signals and multiple insertion sites. Plasmid pCEN100 was generated as described below. Synthetic oligonucleotides CE205 (SEQ ID NO:211) and CE206 (SEQ ID NO:212) were annealed, phosphorylated and inserted into the BamHI and HindIII sites of pJCA002 (previously described) to form pCE72. A BglII to EcoRI fragment from pCE72 was inserted into the BglII and EcoRI sites of pJCA021 to form pCEN100.

CE205 (SEQ ID NO:211):

5' GATCAGAAAAACTAGCTAGCTAGTACGTAGTT
AACGTCGACCTGCAGAAGCTTCTAGCTAGCTAGTT
TTTAT 3'

CE206 (SEQ ID NO:212):

5' AGCTATAAAAACTAGCTAGCTAGAAGCTTCTG
CAGGTCGACGTTAACTACGTACTAGCTAGCTAGTT
TTTCT 3'

Plasmid pJCA021 was obtained by inserting a 4900 bp PvuII-HindII fragment from pRW731-15 (previously described) into the SmaI and HindII sites of pBSSKT.

The final insertion plasmid pRW874 had the three arian influenza HA genes transcribed in the same direction as the deleted F8 ORF. The left flanking arm of the plasmid adjacent to the H4 gene consisted of 2350 bp of fowlpox sequence. The right flanking arm adjacent to the H7 gene consisted of 1700 bp of fowlpox sequence. A linear representation of the plasmid is shown below.

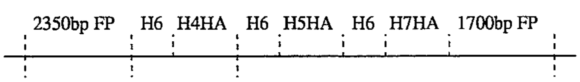

Development of Recombinant vFP122. Plasmid pRW874 was transfected into TROVAC infected primary CEF cells by using the calcium phosphate precipitation method previously described (Panicali et al., 1982; Piccini et al., 1987). Positive plaques were selected on the basis of hybridization to specific H4, H5 and H7 radiolabelled probes and subjected to 5 sequential rounds of plaque purification until a pure population was achieved. Surface expression of all three glycoproteins was confirmed by plaque immunoscreen using specific reagents previously described. Stability of inserted genes was confirmed after two rounds of amplification and the recombinant was designated as vFP122.

EXAMPLE 24

COMPARISON OF THE $LD_{50}$ OF ALVAC AND NYVAC WITH VARIOUS VACCINIA VIRUS STRAINS

Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population ($LD_{50}$) was determined by the proportional method of Reed and Muench.

Comparison of the $LD_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 28). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses ($3.85\times10^8$ PFUs, ALVAC and $3\times10^8$ PFUs, NYVAC) by an undetermined mechanism by this route of inoculation.

Comparison of the $LD_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 29). With mortality as the endpoint, $LD_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, $6.3\times10^7$ PFUs, 100% mortality resulted. Mortality rates of 33.3% were observed at $6.3\times10^6$ PFUs. The cause of death, while not actually determined, was not likely of toxicological or traumatic nature since the mean survival time (MST) of mice of the highest dosage group (approximately 6.3 $LD_{50}$) was 6.7±1.5 days. When compared to WR(L) at a challenge dose of 5 $LD_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, $6\times10^8$ and $6\times10^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 LD$_{50}$, survived to day 4.

TABLE 28

Calculated 50% Lethal Dose for mice by various vaccinia virus strains and for canarypox virus (ALVAC) by the ic route.

| POXVIRUS STRAIN | CALCULATED LD$_{50}$ (PFUs) |
|---|---|
| WR(L) | 2.5 |
| VC-2 | $1.26 \times 10^4$ |
| WYETH | $5.00 \times 10^4$ |
| NYVAC | $1.58 \times 10^8$ |
| ALVAC | $1.58 \times 10^8$ |

TABLE 29

Calculated 50% Lethal Dose for newborn mice by various vaccinia virus strains and for canarypox virus (ALVAC) by the ic route.

| POXVIRUS STRAIN | CALCULATED LD$_{50}$ (PFUs) |
|---|---|
| WR(L) | 0.4 |
| VC-2 | 0.1 |
| WYETH | 1.6 |
| NYVAC | $1.58 \times 10^6$ |
| ALVAC | $1.00 \times 10^7$ |

EXAMPLE 25

GENERATION OF NYVAC-BASED RECOMBINANTS EXPRESSING THE EHV-1 gB, gC AND gD GLYCOPROTEINS HOMOLOGS

Expression of the EHV-1 gB glycoprotein was accomplished by putting the EHV-1 gB homolog gene under the control of the vaccinia virus I3L promoter. Expression of the EHV-1 gC glycoprotein was accomplished by putting the EHV-1 gC homolog gene under the control of the vaccinia virus H6 promoter. Expression of the EHV-1 gD glycoprotein was accomplished by putting the EHV-1 gD homolog gene under the control of the entomopox virus 42K gene promoter.

Generation of vP1025 (gB and gC in ATI locus; gD in HA locus).

Generation of donor plasmid pJCA042. The 430 bp 5'-most region of the EHV-1 gB coding sequence was PCR-derived using the plasmid pJCA011 (cassette H6-EHV-1 gB in ATI locus) as template and oligonucleotides JCA156 (SEQ ID NO:223) (5'-ATGTCCTCTGGT-TGCCGTTCT-3') and JCA157 (SEQ ID NO:224) (5'-GACGGTGGATCCGGTAGGCGG-3'), digested with BamHI and kinased. This 430 bp fragment was fused to a 120 bp PCR-derived fragment containing the I3L promoter element obtained using plasmid pMP691 (I3L101RAB) as template and oligonucleotides JCA158 (SEQ ID NO:225) (5'-TTTTTCTAGACTGCAGCCCGGGACAT-CATGCAGTGGTTAAAC-3') and MP287 (SEQ ID NO:226)-(5'-GATTAAACCTAAATAATTGT-3'). This 120 bp fragment was digested with XbaI and kinased prior to be ligated with the 430 bp 5'-most region of EHV-1 gB fragment. The resulting plasmid was designated pJCA034. Sequences of the I3L promoter, of the junction I3L-ATG and of the EHV-1 5'-most region were confirmed by direct sequencing of pJCA034. Plasmid pJCA034 was digested with SmaI and BamHI to excise the 550 bp SmaI-I3L-EHV-1 gB 5'-BamHI fragment (A). Plasmid pMP665 (cassette H6-EHV-1 gB in COPCS systems) was digested with BamHI and XhoI to excise the 2530 bp BamHI-EHV-1 gB 3' fragment (B). Fragments A and B were then ligated together into vector pSD541VC (ATI deorfed locus) digested with SmaI and XhoI to produce pJCA037. Plasmid pJCA037 is the donor plasmid containing the cassette I3L-EHV-1 gB in the ATI deorfed locus. Plasmid pJCA037 was digested with SmaI and XhoI to isolate the 3050 bp SmaI-I3L-EHV-1 gB-XhoI fragment (C). The 225 bp KpnI-EHV-1 gC 3'end cleaned up-HindIII fragment was PCR-derived using plasmid pVHAH6g13 (cassette H6-EHV-1 gC in HA deorfed locus) and oligonucleotides JCA154 (SEQ ID NO:227) (5'-TATAGCTGCATAATAGAG-3') and JCA163 (SEQ ID NO:228) (5'-AATTAAGCTTGATATCA-CAAAAACTAAAAAGTCAGACTTCTTG-3'), digested with KpnI and HindIII, and ligated into vector pBS-SK$^+$ digested with KpnI and HindIII to produce pJCA033. Sequence of the cloned PCR fragment was confirmed by direct sequencing of pJCA033. Plasmid pJCA033 was digested with KpnI and EcoRV to isolate the 220 bp KpnI-EHV-1 gC 3'end-EcoRV fragment (D). Plasmid pVHAH6g13 was digested with BglII and KpnI to isolate the 1330 bp BglII-H6-EHV-1 gC 5'-KpnI fragment (E).

Fragments C, D and E were finally ligated together into vector pSD541VC digested with BglII and XhoI to produce plasmid pJCA042. Plasmid pJCA042 is the donor plasmid to insert the I3L-EHV-1 gB-H6-EHV-1 gC double construction in the NYVAC ATI deorfed locus. Plasmid pJCA042 was linearized using NotI prior to IVR.

In vitro recombination experiment was performed on Vero cells using pJCA042 as the donor plasmid and vP866 (NYVAC) as the rescue virus. Standard protocols were used to identify and purify the recombinant virus (Piccini et al., 1987). The NYVAC-based recombinant containing the EHV-1 gB and gC genes in the ATI deorfed locus was designated vP956.

Generation of Donor Plasmid pJCA064. Plasmid pEHV1BamHID (containing the EHV-1 BamHI D fragment) was digested with HindIII to excise the 1240 bp HindIII-HindIII containing the entire EHV-I gD coding sequence but the 15 5'-most bp. The 1240 bp HindIII-HindIII fragment was blunt-ended with Klenow polymerase and ligated into vector pCOPCS657 digested with SmaI and phosphatased. The resulting plasmid was designated pJCA006. Plasmid pJCA006 was digested with BglII and HindIII to excise the 1500 bp HindIII-H6-EHV-1 gD-BglII fragment. This fragment was ligated into vector pIBI24 digested with BamHI and HindIII to produce plasmid pEHV1gp50a. Plasmid pEHV1gp50a was digested with EcoRV and NcoI which are both unique sites to excise the 4100 bp fragment. This fragment was ligated with a synthetic double strand oligonucleotide obtained by hybridization between oligonucleotides JCA052 (SEQ ID NO:229) (5'-ATCCGTTAAGTTTGTATCGTAATGTC-TACCTTCAAGCTTATGATGGATG-GACGTTTGGTTTTTGC-3') and JCA053 (SEQ ID NO:230) (5'-CATGGCAAAAACCAAACGTCCATCCAT-CATAAGCTTGAAGGTAGACATTACGATA-CAAACTTAAGCGAT-3'). The resulting plasmid was designated pgp50a3-2. The 490 bp EcoRV-EHV-1 gD 3'end cleaned up -HpaI was PCR-derived using plasmid pJCA006 as template and oligonucleotides JCA041 (SEQ ID NO:231) (5'-TGTGTGATGAGAGATCAG-3') and JCA099 (SEQ ID NO:232) (5'-AACTCGAGTTAACAAAAATTACG- GAAGCTGGGTATATTTAACAT-3'). Plasmid pgp50a3-2 was digested with EcoRI and partially digested with HindIII to excise the 850 bp HindIII-H6-EHV-1 gD 5'-EcoRI fragment. This fragment was ligated with the 490 bp EcoRI-HpaI fragment into vector pBS-SK$^+$ digested with HindIII and SmaI to produce plasmid pJCA020. Plasmid pJCA020 contains the cassette H6-EHV-1 gD.

The 720 bp 5'-most region of the EHV-1 gD coding sequence was PCR-derived using plasmid pJCA020 as template and oligonucleotides JCA044 (SEQ ID NO:233) (5'-CTCTATGACCTCATCCAC-3') and JCA165 (SEQ ID NO:234) (5'-ATGTCTACCTTCAAGCTTATG-3'). This fragment was digested with EcoRI and kinased. The 107 bp 42K promoter element was PCR-derived using plasmid pAM12 as template and oligonucleotides RG286 (SEQ ID NO:235) (5'-TTTATATTGTAATTATA-3') and JCA164 (SEQ ID NO:236) (5'-TTTGGATCCGTTAACT-CAAAAAAATAAATG-3'). This fragment was digested with BamHI, kinased, and ligated with the 720 bp ATG-EHV-1 gD 5'-EcoRI fragment into vector pBS-SK$^+$ digested with BamHI and EcoRI to produce plasmid pJCA035. Sequences of the 42K promoter, of the junction 42K-EHV-1 gD and of the EHV-1 gD 5' portion were confirmed by direct sequencing of pJCA035.

Plasmid pJCA035 was digested with BamHI and EcoRI to isolate the 830 bp BamHI-42K-EHV-1 gD 5'portion-EcoRI fragment (F). Plasmid pJCA020 was digested with EcoRI and XbaI to isolate the 500 bp EcoRI-EHV-1 gD 3'end cleaned up-XbaI fragment (G). Fragments F and G were then ligated together into vector pBS-SK$^+$ digested with BamHI and XbaI to produce plasmid pJCA038. Plasmid pJCA038 is containing the cassette 42K-EHV-1 gD into vector pBS-SK$^+$. Plasmid pJCA038 was digested with BamHI and HpaI to isolate the 1340 bp HpaI-42K-EHV-1 gD-BamHI fragment. This fragment was ligated into plasmid pSD544 (PEA deorfed locus) digested with BamHI and SmaI to produce plasmid pJCA064. Plasmid pJCA064 is the donor plasmid to insert the cassette 42K-EHV-1 gD into the NYVAC HA deorfed locus. Plasmid pJCA064 was linearized using NotI prior to IVR.

In vitro experiment was performed on Vero cells using pJCA064 as the donor plasmid and recombinant vaccinia virus vP956 (NYVAC background) as the rescue virus. This was performed with standard procedures (Piccini et al., 1987). The NYVAC-based recombinant containing the EHV-1 gB and gC genes in the ATI deorfed locus and the EHV-1 gD gene in the HA deorfed locus was designated vP1025.

Generation of donor plasmid pJCA043. The 220 bp HindIII-EHV-1 gB 3'-most region was PCR-derived using plasmid pJCA011 and oligonucleotides JCA159 (SEQ ID NO:237) (5'-AGGCCAAGCTTGAAGAGGCTC-3') and JCA160 (SEQ ID NO:238) (5'-AAAGGATCCGTTAACA-CAAAAATTAAACCATTTTTTCATT-3'). This fragment was digested with BamHI and HindIII and ligated into vector pBS-SK$^+$ digested with BamHI and HindIII to produce plasmid pJCA036. Sequence of the EHV-1 gB 3'-most region PCR fragment was confirmed by direct sequencing pJCA036.

Plasmid pJCA033 was digested with EcoRV and KpnI to isolate the KpnI-EHV-1 gC 3'-most region-EcoRV fragment (H). Plasmid pJCA038 was digested with BamHI and HpaI to isolate the 1360 bp HpaI-42K-EHV-1 gD -BamHI fragment (I). Plasmid pVHAH6g13 was digested with KpnI and XhoI to isolate the 900 bp XhoI-EHV-1 gC central portion-KpnI fragment (J). Fragments H, I and J were then ligated together into vector pBS-SK$^+$ digested with BamHI and XhoI to produce plasmid pJCA041.

Plasmid pJCA034 was digested with HindIII and XhoI to isolate the 5900 bp linearized vector XhoI-pBS-SK$^+$-I3L-EHV-1 gB -HindIII fragment (K). Plasmid pJCA036 was digested with BamHI and HindIII to isolate the 220 bp HindIII-EHV-1 gB 3-most region-BamHI fragment (L). Plasmid pVHAH6g13 was digested with BglII and XhoI to isolate the 440 bp BglII-H6-EHV-1 gC 5'portion-XhoI fragment (M). Fragments K, L and M were then ligated together to produce plasmid pJCA040.

Plasmid pJCA040 was digested with SmaI and XhoI to isolate the 3550 bp SmaI-I3L-EHV-1 gB—H6-EHV-1 gC 5'portion-XhoI fragment (N). Plasmid pJCA041 was digested with BamHI and XhoI to isolate the 2460 bp XhoI-EHV-1 gC 3'portion—42K-EHV-1 gD -BamHI fragment (O). Fragments N and O were finally ligated together into plasmid pSD541VC (NYVAC ATI deorfed locus) digested with BglII and SmaI to produce plasmid pJCA043. Plasmid pJCA043 is the donor plasmid to insert the I3L-EHV-1 gB—H6-EHV-1 gC—42K-EHV-1 gD triple construction in the NYVAC ATI deorfed locus. Plasmid pJCA043 was linearized using NotI prior to IVR.

In vitro experiment was performed on primary chick embryo fibroblasts using pJCA043 as the donor plasmid and vP866 (NYVAC) as the rescue virus. Standard procedures were used to identify and purify the generated recombinant (Piccini et al., 1987). The NYVAC-based recombinant containing the EHV-1 gB, gC and gD genes in the ATI deorfed locus was designated vP1043.

EXAMPLE 26

GENERATION OF ALVAC-BASED RECOMBINANTS EXPRESSING THE EHV-1 gB, gC AND gD GLYCOPROTEINS HOMOLOGS

Generation of donor plasmid pJCA049. Plasmid pJCA040 was digested with SmaI and XhoI to isolate the 3550 bp SmaI-I3L-EHV-1 gB—H6-EHV-1 gC 5'portion-XhoI fragment (A). Plasmid pJCA041 was digested with BamHI and XhoI to isolate the 2460 bp XhoI-EHV-1 gC 3'portion—42K-EHV-1 gD -BamHI fragment (B). Fragments A and B were ligated together into plasmid pSPVQC3L digested with BamHI and SmaI to produce plasmid pJCA049. Plasmid pJCA049 is the donor plasmid to insert the I3L-EHV-1 gB—H6-EHV-1 gC —42K-EHV-1 gD triple construction in the ALVAC C3 deorfed locus. Plasmid pJCA049 was linearized using NotI prior to IVR.

In vitro experiment was performed on primary chick embryo fibroblasts using pJCA049 as the donor plasmid and CPpp (ALVAC) as the rescue virus. Standard procedures were followed to identify and purify the generated recombinant (Piccini et al., 1987). The ALVAC-based recombinant containing the EHV-1 gB, gC and gD genes in the C3 deorfed locus was designated vCP132.

EXAMPLE 27

EXPRESSION ANALYSIS OF THE NYVAC- AND ALVAC-BASED EQUINE HERPESVIRUS TYPE 1 TRIPLE RECOMBINANTS

Immunofluorescence assays were performed as described previously (Taylor et al., 1990) using monoclonal antibodies specific to EHV-1 gB (16G5 or 3F6), EHV-1 gC (14H7) and EHV-1 (20C4). All anti-EHV-1 monoclonals were obtained from George Allen (Department of Veterinary Science, University of Kentucky, Lexington, Ky., 40546-0076). Expression of all three EHV-1 specific products was detectable internally in cells infected with either vP1025, vP1043 vCP132. Only the EHV-1 gC glycoprotein was well expressed on the surface of infected cells. Surface expression for EHV-1 gB glycoprotein was much weaker and surface expression of EHV-1 gD glycoprotein was questionable.

Immunoprecipitations were done using the same monoclonal antibodies to determine the authenticity of the expressed EHV-1 gB, gC and gD gene products. Monoclonal 3F6 specific for EHV-1 gB glycoprotein precipitated proteins with apparent molecular masses on an SDS-PAGE gel system of 138 kDa, 70 kDa and 54 kDa from lysates derived from cells infected with the recombinant viruses vP956, vP1025, vP1043 or vCP132. No protein was precipitated from lysates derived from uninfected cells or from either parental virus (NYVAC and ALVAC) infected cells. Monoclonal 14H7 specific for EHV-1 gC glycoprotein precipitated a glycoprotein with an apparent molecular mass of 90 kDa from lysates derived from cells infected either with vP956, vP1025 or vP1043. The EHV-1 gC glycoprotein expressed by recombinant vCP132 has apparent molecular mass slightly smaller (about 2 kDa less) than that expressed by recombinants vP956, vP1025 or vP1043. Monoclonal antibody 20C4 specific for EHV-1 gD glycoprotein precipitated a glycoprotein with an apparent molecular of 55 kDa from lysates derived from cells infected with vP1025, vP1043 or vCP132.

Immunoprecipitations were also done using a rabbit anti-EHV-1 hyperimmune serum obtained from C. Allen. This serum precipitated all three EHV-1 products from lysates derived from cells infected either with vP1025, vP1043 or vCP132.

EXAMPLE 28

PROTECTION DATA OBTAINED USING THE HAMSTER CHALLENGE MODEL

Challenge experiments (hamster model) have been done at Rhone-Merieux (Lyon, France) to assess the relative level of vP1025 and vCP132. Hamsters were vaccinated on day 0 and boosted on day 14 with various dilutions of the EHV-1 recombinants. All immunized and control animals were challenged on day 28 with a hamster-adapted EHV-1 challenge strain. Final count of dead animals was made on day 35 (7 days post challenge). Results of the challenge experiment are shown below in Table 30:

TABLE 30

| Recombinant | EHV-1 genes | Dose TCID50 $log_{10}$/dead/total | | |
|---|---|---|---|---|
| vP956 | gB + gC | 7.6 | 5.6 | 3.6 |
| | | 0/4 | 3/4 | 2/4 |
| vP1025 | gB + gC + gD | 7.8 | 5.8 | 3.8 |
| | | 2/4 | 3/4 | 3/4 |
| vCP132 | gB + gC + gD | 8.8 | 6.8 | 4.8 |
| | | 0/4 | 0/4 | 2/4 |
| Control | none | 4/4 | | |

EXAMPLE 29

DURATION OF IMMUNITY STUDIES IN

The aim of this study was to determine how long a protective immune response would be maintained in dogs after a single inoculation with ALVAC-RG (vCP65). Forty-one beagle dogs of 8 months of age which were free of anti-rabies antibody were inoculated with one dose of 6.7 $log_{10}$ $TCID_{50}$ of ALVAC-RG by the subcutaneous route. Dogs were bled on day 0 and at 1, 2, 3, 6 and 12 months after vaccination and sera assayed for the presence of anti-rabies antibody using the RFFI test. All animals were monitored for side-effects of vaccination.

At 6 months post-vaccination, 5 dogs were challenged by intra-muscular inoculation of the virulent NYGS strain of rabies virus. Animals received $10^{3.4}$ 50% mouse lethal closes in the temporal muscle. Three uninoculated control animals received the same inoculation. A second group of 11 vaccinated dogs and 3 non-vaccinated control dogs were challenged in an identical manner at 12 months post-vaccination. The serological results and results of challenge at 6 and 12 months are shown below in Table 31.

None of the dogs vaccinated with ALVAC-RG (vCP65) exhibited adverse reaction to vaccination. All dogs vaccinated with ALVAC-RG (vCP65) demonstrated the induction of rabies virus neutralizing antibody by 7 days post-vaccination. Maximal titers were achieved between 14 and 28 days post-vaccination after which titers decreased. At the time of challenge at 6 or 12 months post-vaccination titers were low and in some animals, approaching zero. Despite the low titers, all animals survived a lethal rabies challenge in which unvaccinated control dogs succumbed. RFFI titers of animals that survived challenge at 6 months post-vaccination were assessed at 8 months (2 months post-challenge). The serum titers in these animals were 7.4, 7.4, 2.3, 1.8 and 7.4. International Units. These elevated and maintained levels of rabies neutralizing antibody indicate that animals were efficiently primed by the initial single inoculation. The experiment is on-going and the remaining animals will be challenged at 2 or 3 years following vaccination; however, to date, the experiment is successful and illustrates the utility of the present invention.

TABLE 31

Duration of immunity study in dogs vaccinated with ALVAC-RG: Results of challenge at 6 and 12 months RFFI Titer in International Units

| Treatment | Dog # | Maximum at day 28 | Day of Challenge | Survival or Day of Death |
|---|---|---|---|---|
| | SIX MONTH CHALLENGE[a] | | | |
| ALVAC-RG[b] | N2T90 | 7.45 | 0.23 | S |
| | N3V57 | 14.80 | 0.23 | S |
| | N4V49 | 7.45 | 0.29 | S |
| | N5W22 | 8.70 | 0.59 | S |
| | N7W22 | 7.45 | 0.18 | S |
| Non-vaccin-ated | 194 | 0.47 | 0.07 | D (16) |
| | 195 | 0.07 | 0.07 | D (24) |
| | 198 | 0.47 | 0.07 | D (17) |
| | TWELVE MONTH CHALLENGE | | | |
| ALVAC-RG | N1V9 | 7.45 | 0.09 | S |
| | N3V9 | 7.45 | 0.15 | S |
| | N2V9 | 3.73 | 0.07 | S |
| | N3W22 | 9.78 | 0.05 | S |
| | N4V9 | 7.45 | 0.15 | S |
| | N1W38 | 18.70 | 0.15 | S |
| | N8W22 | 2.35 | 0.15 | S |
| | N8V14 | 7.45 | 0.38 | S |
| | N7V14 | 3.73 | 0.15 | S |
| | N1R45 | 7.45 | 0.12 | S |
| | N9V14 | 0.94 | 0.15 | S |
| Non-vaccin- | N10V14 | 0.74 | 0.05 | D (14) |
| | N14V14 | 0.59 | 0.05 | D (13) |
| | N5R54 | 0.74 | 0.05 | D (14) |

[a]Animals were challenged at 6 and 12 months post-vaccination with a dose of $10^{3.4}$ 50% mouse lethal doses of NYGS strain of rabies virus in the temporal muscle.
[b]Dogs received one inoculation of 6.7 $log_{10}$ $TCID_{50}$ by the subcutaneous route.

TABLE 31-continued

Duration of immunity study in dogs vaccinated with ALVAC-RG:
Results of challenge at 6 and 12 months
RFFI Titer in International Units

| Treatment | Dog # | Maximum at day 28 | Day of Challenge | Survival or Day of Death |
|---|---|---|---|---|

S: Dog survived challenge.
D: Dog died on (day).

EXAMPLE 30

EXPRESSION OF BOVINE HERPESVIRUS TYPE 1 BHV1 GENES IN NYVAC

Generation of NYVAC/BHV1 gIV recombinant. A plasmid, pBHVgIV, was obtained from Rhone Merieux. This plasmid contains the BHV1 gIV gene (Straub strain), encoded on a 3.9 kb PstI fragment, cloned into the PstI site of pBS-SK$^+$. The gIV gene (Tikoo et al., J. Virol. (1990) 64:5132) from this plasmid was cloned between vaccinia virus flanking arms. This was accomplished by cloning the 2,000 bp PstI-XhoI fragment of pBHVgIV, containing the gIV gene, into the PstI-XhoI site of pSD542 (defined in Example 32). The generated by this manipulation is called pBHV1.

The 3'-end of the π promoter was then cloned upstream of the gIV gene. This was accomplished by cloning the oligonucleotides, BHVL7 (SEQ ID NO:239) (5'-TCGAGCT-TAAGTCTTATTAATATGCAAGGGCCGA-CATTGGCCGTGCTGGGCGCGCTGCTCGCCGTTGCG-GTGAGCTTGCCTACACCCGCGCCGC-3') and BHVL8 (SEQ ID NO:240) (5'-GGCGCGGGTGTAGGCAAGCT-CACCGCAACGGCGAGCAGCGCGCCCAG-CACGGCCAATGTCGGCCCTTGCATAT-TAATAAGACTTAAGC-3'), encoding the 3'-end of the π promoter and the 5'-end of the gIV gene, into the 5,500 bp partial SstII-XhoI fragment of pBHV1. The plasmid generated by this manipulation is called pBHV3.

Extraneous 3'-noncoding sequence was then eliminated. This was accomplished by cloning the oligonucleotides, BHVL5 (SEQ ID NO:241) (5'-GGGTGACTGCA-3') and BHVL6 (SEQ ID NO:242) (5'-GTCACCC-3'), into the 5,200 bp partial SmaI-PstI fragment of pBHV3. The plasmid generated by this manipulation is called pBHV4.

Extraneous linker sequence was then eliminated. This was accomplished by ligating the 5,200 bp PstI fragment of pBHV4. The plasmid generated by this manipulation is called pBHV5.

The 5'-end of the π promoter was then cloned into pBHV5. This was accomplished by cloning the 130 bp AflII-XhoI fragment of pPI4, containing the 5'-end of the π promoter, into the 5,200 bp AflII-XhoI fragment of pBHV5. The plasmid generated by this manipulation is called pBHV6.

pBHV6 was used in in vitro recombination experiments with vP866 (NYVAC) as the rescuing virus to yield vP1051.

Immunoprecipitation analysis was performed to determine whether vP1051 expresses an authentic BHV1 gIV glycoprotein. Vero cell monolayers were either mock infected, infected with NYVAC or infected with vP1051 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gIV expression using the BHV1 gIV-specific monoclonal antibody, 3402 (obtained from Dr. Geoffrey Letchworth, U. of Wisconsin, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gIV-specific monoclonal antibody, 3402. The lysates, meanwhile, were precleared by incubating normal mouse sera and the protein A-sepharose bound rat anti-mouse antibody overnight at 4° C. After washing this material 5× with 1× buffer A, the BHV1 gIV-specific monoclonal antibody, rat anti-mouse, protein A-sepharose conjugate was added to the lysate and incubated overnight at 4° C. After washing the samples 4× with 1× buffer A and 2× with a LiCl$_2$/urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gIV-specific monoclonal antibody, 3402, specifically precipitated the BHV1 gIV glycoprotein from vP1051 infected cells, but did not precipitate BHV1-specific proteins from NYVAC or mock infected cells.

Generation of NYVAC/BHV1 gI and gIV Recombinant. A plasmid, pBHVgIV, containing the BHV1 gIV gene, was obtained from Rhone Merieux. The gIV gene from this plasmid was cloned between vaccinia virus flanking arms. This was accomplished by cloning the 2,000 bp PstI-XhoI fragment of pBHVgIV, containing the gIV gene, into the PstI-XhoI site of pSD542. The plasmid generated by this manipulation is called pBHV1.

The 3'-end of the π promoter was then cloned upstream of the gIV gene. This was accomplished by cloning the oligonucleotides, BHVL7 (SEQ ID NO:239) and BHVL8 (SEQ ID NO:240), encoding the 3'-end of the π promoter and the 5'end of the gIV gene, into the 5,500 bp partial SstII-XhoI fragment of pBHV1. The plasmid generated by this manipulation is called pBHV3.

Extraneous 3'-noncoding sequence was then eliminated. This was accomplished by cloning the oligonucleotides, BHVL5 (SEQ ID NO:241) and BHVL6 (SEQ ID NO:242), into the 5,200 bp partial SmaI-PStI fragment of pBHV3. The plasmid generated by this manipulation is called pBHV4.

Extraneous linker sequence was then eliminated. This was accomplished by ligating the 5,200 bp PStI fragment of pBHV4. The plasmid generated by this manipulation is called pBHV5.

The 5'-end of the π promoter was then cloned into pBHV5. This was accomplished by cloning the 130 bp AflII-XhoI fragment of pPI4, containing the 5'-end of the π promoter, into the 5,200 bp AflII-XhoI fragment of pBHV5. The plasmid generated by this manipulation is called pBHV6.

The BHV1 gI gene was then cloned into pBHV6. This was accomplished by cloning the 2,900 bp BglII fragment of pBHV8, containing the H6-promoted gI gene, into the BglII site of pBHV6. The plasmid generated by this manipulation is called pBHV9.

pBHV8 was generated by the following procedure: a plasmid, pIBRS6, was received from Rhone Merieux. The plasmid contains a 6.6 kb SalI fragment, containing the BHV1 gI gene (Straub strain). The 5'-end of the gI gene (Whitbeck et al., J. Virol. (1988) 62:3319) was cloned downstream of the H6 promoter and between vaccinia virus HA flanking arms. This was accomplished by cloning the 540 bp SalI-PstI fragment of pIBRS6 into the 4,400 bp SalI-PstI fragment of pGD5. The plasmid generated by this manipulation is called pIBR2.

The initiation codon of the H6 promoter was then aligned with the initiation codon of the gI gene. This was accomplished by cloning the oligonucleotides, IBRL1 (SEQ ID NO:243) (5'-ATCCGTTAAGTTTGTATCGTAATGGC-CGCTCGCGGCGGTGCTGAACGCGCCGC-3') and IBRL2 (SEQ ID NO:244) (5'-GGCGCGTTCAGCACCGC-CGCGAGCGGCCATTACGATACAAACTTAACGGAT-3'), into the 3,800 bp NruI-SstII fragment of pIBR2. The plasmid generated by this manipulation is called pIBR4.

An NcoI site, necessary for future manipulations, was then generated downstream from the gI sequence. This was accomplished by cloning the oligonucleotides, IBRL3 (SEQ ID NO:245) (5'-CCATGGTTTAATGCA-3') and IBRL4 (SEQ ID NO:246) (5'-TTAAACCATGGTGCA-3'), into the PstI site of pIBR4. The plasmid generated by this manipulation is called pIBR5.

Additional gI sequence was then cloned into pIBR5. This was accomplished by cloning the 1,740 bp Tth111I-NcoI fragment of pIBRS6 into the 3,700 bp Tth111I-NcoI fragment of pIBR5. The plasmid generated by this manipulation is called pIBR7.

A BglII site, necessary for future manipulations, was then generated downstream from the gI sequence. This was accomplished by cloning the oligonucleotides, IBRL5 (SEQ ID NO:247) (5'-CATGGTTTAAGATCTC-3') and IBRL6 (SEQ ID NO:248) (5'-CATGGAGATCTTAAAC-3'), into the NcoI site of pIBR7. The plasmid generated by this manipulation is called pIBR8.

The 3'-end of the gI gene was then cloned into pIBR8. This was accomplished by cloning the 2,285 bp StuI fragment of pIBRS6 into the E. coli DNA polymerase I (Klenow fragment) filled-in 4,300 bp StuI-BglII (partial) fragment of pIBR8. The plasmid generated by this manipulation is called pIBR20.

The H6-promoted BHV1 gI gene was then moved to a vaccinia virus donor plasmid. This was accomplished by cloning the E. coli DNA polymerase I (Klenow fragment) filled-in 2,900 bp BglII-NCoI (partial) fragment of pIBR20 into the SmaI site of pSD542. This places the H6-promoted gI gene between tk flanking arms. The plasmid generated by this manipulation is called pIBR22.

A BglII site was then created upstream from the H6 promoter. This was accomplished by cloning the 2,800 bp HindIII-EcoRV fragment of pIBR22 into the 3,500 bp HindIII-EcoRV fragment of pGD3. (pGD3 is a plasmid that contains a BglII site upstream from an H6-promoted herpes simplex virus type 2 (HSV2) gD gene. This manipulation replaces the HSV2gD sequence with the BHVIgI gene, thereby creating a BglII site upstream from the H6-promoted gI gene). The plasmid generated by this manipulation is called pBHV8.

pBHV9 was used in in vitro recombination experiments with vP866 (NYVAC) as the rescuing virus to yield vP1074.

Immunoprecipitation analysis was performed to determine whether vP1074 expresses authentic BHV1 gI and gIV glycoproteins. Vero cell monolayers were either mock infected, infected with NYVAC or infected with vP1074 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gI and gIV expression using the BHV1 gI-specific monoclonal antibody, 5106, and the gIV-specific monoclonal antibody, 3402 (obtained from Dr. Geoffrey Letchworth, U. of Wisconsin,, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gI-specific monoclonal antibody and the gIV-specific monoclonal antibody. The lysates, meanwhile, were precleared by incubating normal mouse sera and the protein A-sepharose bound rat anti-mouse antibody overnight at 4° C. After washing this material 5× with 1× buffer A, the gI or gIV-specific monoclonal antibody, rat anti-mouse, protein A-sepharose conjugate was added to the lysate and incubated overnight at 4° C. After washing the samples 4× with 1× buffer A and 2× with a $LiCl_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gI and gIV-specific monoclonal antibodies, 5106 and 3402, specifically precipitated the BHV1 gI and gIV glycoproteins from vP1074 infected cells, but did not precipitate BHV1-specific proteins from mock or NYVAC infected cells.

Generation of NYVAC/BHV1 gIII recombinant. A plasmid, pBHVgIII, was obtained from Rhone Merieux. This plasmid contains the BHV1 gIII gene (Straub strain), encoded on a 3.4 kb BamHI/HindIII fragment cloned into the BamHI/HindIII site of pBSK$^+$. The gIII gene (Fitzpatrick et al., Virology (1989) 173:146) from this plasmid was cloned between vaccinia virus flanking arms. This was accomplished by cloning the 1,000 bp NcoI-XhoI fragment of pBHVgIII, containing the 5'-end of the gIII gene, and the oligonucleotides, BHVL1 (SEQ ID NO:249) (5'-GATCCT-GAGATAAAGTGAAAATATATATCAT-TATATTACAAAGTACAATTATTTAGGTTTAAT-3') and BHVL2 (SEQ ID NO:250) (5'-CATGATTAAAC-CTAAATAATTGTACTTTGTAATATAAT-GATATATATTTTCACTTTATCTCAG-3'), encoding the I3L promoter, into the BamHI-XhoI site of pSD544. The plasmid generated by this manipulation is called pBHV2.

The 3'-end of the gIII gene was then cloned into pBHV2. This was accomplished by cloning the oligonucleotides, BHVL15 (SEQ ID NO:251) (5'-TCGAGCCCGGGTAATC-CAACCCGGTCTTACTCGCGCTCGCGC-CCTCGGCTCCGCGCCCTAGG-3') and BHVL16 (SEQ ID NO:252) (5'-GTACCCTAGGGCGCGGAGC-CGAGGGCGCGAGCGCGAGTAAGAC-CGGGTTGGATTACCCGGGC-3'), encoding the 3'-end of the gIII gene, into the 4,700 bp XhoI-Asp718 fragment of pBHV2. The plasmid generated by this manipulation is called pBHV7.

The rest of the gIII gene was then cloned into pBHV7. This was accomplished by cloning the 500 bp partial SmaI-XhoI fragment of pBHVgIII, containing an interior portion of the gIII gene, into the 4,750 bp partial SmaI-XhoI fragment of pBHV7. The plasmid generated by this manipulation is called pBHV10.

pBHV10 was used in in vitro recombination experiments with vP866 (NYVAC) as the rescuing virus to yield vP1073.

Immunoprecipitation analysis was performed to determine whether vP1073 expresses an authentic BHV1 gIII glycoprotein. Vero cell monolayers were either mock infected, infected with NYVAC or infected with vP1073 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gIII expression using the BHV1 gIII-specific monoclonal antibody, 1507 (obtained from Dr. Geoffrey Letchworth, U. of Wisconsin, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gIII-specific monoclonal antibody, 1507. The lysates, meanwhile, were precleared by incubating normal mouse sera and the protein A-sepharose bound rat anti-mouse antibody overnight at 4° C. After washing this material 5× with 1× buffer A, the gIII-specific monoclonal antibody, rat anti-mouse, protein A-sepharose conjugate was added to the lysate and incubated overnight at 4° C. After washing the samples 4× with 1× buffer A and 2× with a LiCl$_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gIII-specific monoclonal antibody, 1507, specifically precipitated the BHV1 gIII glycoprotein from vP1073 infected cells, but did not precipitate BHV1-specific proteins from mock or NYVAC infected cells.

Generation of NYVAC/BHV1 gIII AND gIV recombinant. A plasmid, pBHVgIV, containing the BHV1 gIV gene, was obtained from Rhone Merieux. The gIV gene from this plasmid was cloned between vaccinia virus flanking arms. This was accomplished by cloning the 2,000 bp PstI-XhoI fragment of pBHVgIV, containing the gIV gene, into the PstI-XhoI site of pSD542. The plasmid generated by this manipulation is called pBHV1.

The 3'-end of the π promoter was then cloned upstream of the gIV gene. This was accomplished by cloning the oligonucleotides, BHVL7 (SEQ ID NO:239) and BHVL8 (SEQ ID NO:240), encoding the 3'-end of the π promoter and the 5'-end of the gIV gene, into the 5,500 bp partial SstII-XhoI fragment of pBHV1. The plasmid generated by this manipulation is called pBHV3.

Extraneous 3'-noncoding sequence was then eliminated. This was accomplished by cloning the oligonucleotides, BHVL5 (SEQ ID NO:241) and BHVL6 (SEQ ID NO:242), into the 5,200 bp partial SmaI-PstI fragment of pBHV3. The plasmid generated by this manipulation is called pBHV4.

Extraneous linker sequence was then eliminated. This was accomplished by ligating the 5,200 bp PstI fragment of pBHV4. The plasmid generated by this manipulation is called pBHV5.

The 5'-end of the π promoter was then cloned into pBHV5. This was accomplished by cloning the 130 bp AflII-XhoI fragment of pPI4, containing the 5'-end of the π promoter, into the 5,200 bp AflII-XhoI fragment of pBHV5. The plasmid generated by this manipulation is called pBHV6.

The BHV1 gIII gene was then cloned into pBHV6. This was accomplished by cloning the 1,600 bp Asp718-BamHI fragment of pBHV10, containing the I3L-promoted gIII gene, into the 5,300 bp partial BamHI-Asp718 fragment of pBHV6. The plasmid generated by this manipulation is called pBHV11.

pBHV11 was used in in vitro recombination experiments with vP866 (NYVAC) as the rescuing virus to yield vP1083.

Immunoprecipitation analysis was performed to determine whether vP1083 expresses authentic BHV1 gIII and gIV glycoproteins. Vero cell monolayers were either mock infected, infected with NYVAC or infected with vP1083 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gIII and gIV expression using the BHV1 gIII-specific monoclonal antibody, 1507, and the gIV-specific monoclonal antibody, 3402 (obtained from Dr. Geoffrey Letchworth, U. of Wisconsin, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gIII-specific monoclonal antibody and the gIV-specific monoclonal antibody. The lysates, meanwhile, were precleared by incubating normal mouse sera and the protein A-sepharose bound rat anti-mouse antibody overnight at 4° C. After washing this material 5× with 1× buffer A, the BHV1 gIII or gIV-specific monoclonal antibody, rat anti-mouse, protein A-sepharose conjugate was added to the lysate and incubated overnight at 4° C. After washing the samples 4× with 1× buffer A and 2× with a $LiCl_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gIII and gIV-specific monoclonal antibodies, 1507 and 3402, specifically precipitated the BHV1 gIII and gIV glycoproteins from vP1083 infected cells, but did not precipitate BHV1-specific proteins from mock or NYVAC infected cells.

Generation of NYVAC/BHV1 gI and gIII recombinant. A plasmid, pBHVgIII, containing the BHV1 gIII gene was obtained from Rhone Merieux. The gIII gene from this plasmid was cloned between vaccinia virus flanking arms. This was accomplished by cloning the 1,000 bp NcoI-XhoI fragment of pBHVgIII, containing the 5'-end of the gIII gene, and the oligonucleotides, BHVL1 (SEQ ID NO:249) and BHVL2 (SEQ ID NO:250), encoding the I3L promoter, into the BamHI-XhoI site of pSD544VC. The plasmid generated by this manipulation is called pBHV2.

The 3'-end of the gIII gene was then cloned into pBHV2. This was accomplished by cloning the oligonucleotides, BHVL15 (SEQ ID NO:251) and BHVL16 (SEQ ID NO:252), encoding the 3'-end of the gIII gene, into the 4,700 bp XhoI-Asp718 fragment of pBHV2. The plasmid generated by this manipulation is called pBHV7.

The rest of the gIII gene was then cloned into pBHV7. This was accomplished by cloning the 500 bp partial SmaI-XhoI fragment of pBHVgIII, containing an interior portion of the gIII gene, into the 4,750 bp partial SmaI-XhoI fragment of pBHV7. The plasmid generated by this manipulation is called pBHV10.

The BHV1 gI gene was then cloned into pBHV10. This was accomplished by cloning the 2,900 bp BglII fragment of pBHV8, containing the H6-promoted gI gene, into the BamHI site of pBHV10. The plasmid generated by this manipulation is called pBHV12.

pBHV12 was used in in vitro recombination experiments with vP866 (NYVAC) as the rescuing virus to yield vP1087.

Immunoprecipitation analysis was performed to determine whether vP1087 expresses authentic BHV1 gI and gIII glycoproteins. Vero cell monolayers were either mock infected, infected with NYVAC or infected with vP1087 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gI and gIII expression using the BHV1 gI-specific monoclonal antibody, 5106, and the gIII-specific monoclonal antibody, 1507 (obtained from Dr. Geoffrey Letchworth, U. of Wisconsin, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gI-specific monoclonal antibody and the gIII-specific monoclonal antibody. The lysates, meanwhile, were precleared by incubating normal mouse sera and the protein A-sepharose bound rat anti-mouse antibody overnight at 4° C. After washing this material 5× with 1× buffer A, the BHV1 gI or gIII-specific monoclonal antibody, rat anti-mouse, protein A-sepharose conjugate was added to the lysate and incubated overnight at 4° C. After washing the samples 4× with 1× buffer A and 2× with a $LiCl_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gI and gIII-specific monoclonal antibodies, 5106 and 1507, specifically precipitated the BHV1 gI and gIII glycoproteins from vP1087 infected cells, but did not precipitate BHV1-specific proteins from mock or NYVAC infected cells.

Generation of NYVAC/BHV1 gI, gIII and gIV recombinant. A plasmid, pBHVgIV, containing the BHV1 gIV gene, was obtained from Rhone Merieux. The gIV gene from this plasmid was cloned between vaccinia virus flanking arms. This was accomplished by cloning the 2,000 bp PStI-XhoI fragment of pBHVgIV, containing the gIV gene, into the PstI-XhoI site of pSD542VCVQ. The plasmid generated by this manipulation is called pBHV1.

The 3'-end of the π promoter was then cloned upstream of the gIV gene. This was accomplished by cloning the oligonucleotides, BHVL7 and BHVL8, encoding the 3'-end of the π promoter and the 5'-end of the gIV gene, into the 5,500 bp partial SstII-XhoI fragment of pBHV1. The plasmid generated by this manipulation is called pBHV3.

Extraneous 3'-noncoding sequence was then eliminated. This was accomplished by cloning the oligonucleotides, BHVL5 (SEQ ID NO:241) and BHVL6 (SEQ ID NO:242), into the 5,200 bp partial SmaI-PstI fragment of pBHV3. The plasmid generated by this manipulation is called pBHV4.

Extraneous linker sequences were then eliminated. This was accomplished by ligating the 5,200 bp PstI fragment of pBHV4. The plasmid generated by this manipulation is called pBHV5.

The 5'-end of the π promoter was then cloned into pBHV5. This was accomplished by cloning the 130 bp AflII-XhoI fragment of pPI4, containing the 5'-end of the π promoter, into the 5,200 bp AflII-XhoI fragment of pBHV5. The plasmid generated by this manipulation is called pBHV6.

The BHV1 gIII gene was then cloned into pBHV6. This was accomplished by cloning the 1,600 bp Asp718-BamHI fragment of pBHV10, containing the I3L-promoted gIII gene, into the 5,300 bp partial BamHI-Asp718 fragment of pBHV6. The plasmid generated by this manipulation is called pBHV11.

The BHV1 gI gene was then cloned into pBHV11. This was accomplished by cloning the 2,900 bp BglII fragment of pBHV8, containing the H6-promoted gI gene, into the BglII site of pBHV11. The plasmid generated by this manipulation is called pBHV13.

pBHV13 was used in in vitro recombination experiments with vP866 (NYVAC) as the rescuing virus to yield vP1079.

Immunoprecipitation analysis was performed to determine whether vP1079 expresses authentic BHV1 gI, gIII and gIV glycoproteins. Vero cell monolayers were either mock infected, infected with NYVAC or infected with vP1079 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 7 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BHV1 gI, gIII and gIV expression using the BHV1 gI-specific monoclonal antibody, 5106, the gIII-specific monoclonal antibody, 1507, and the gIV-specific monoclonal antibody, 3402 (obtained from Dr. Geoffrey Letchworth, U. of Wisconsin, Madison, Wis.). This was accomplished by the following procedure: rat anti-mouse sera was bound to protein-A sepharose at room temperature for 4 hours. After washing the material 5× with 1× buffer A, the protein A-sepharose bound rat anti-mouse antibody was bound to the gI, gIII and gIV-specific monoclonal antibodies. The lysates, meanwhile, were precleared by incubating normal mouse sera and the protein A-sepharose bound rat anti-mouse antibody overnight at 4°

C. After washing this material 5× with 1× buffer A, the BHV1 gI, gIII and gIV-specific monoclonal antibody, rat anti-mouse, protein A-sepharose conjugate was added to the lysate and incubated overnight at 4° C. After washing the samples 4× with 1× buffer A and 2× with a LiCl$_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BHV1 gI, gIII and gIV-specific monoclonal antibodies, 5106, 1507 and 3402, specifically precipitated the BHV1 gI, gIII and gIV glycoproteins from vP1079 infected cells, but did not precipitate BHV1-specific proteins from mock or NYVAC infected cells.

EXAMPLE 31

EXPRESSION OF BOVINE VIRAL DIARRHEA VIRUS (BVDV) GENES IN NYVAC

Generation of NYVAC/BVDV gE1/gE2 recombinant. The BVDV gel (gp48/gp25) "gene" (Osloss strain) was cloned into pIBI25. This was accomplished by blunt-ending the 1,370 bp EcoRI-BamHI fragment of pSP65-gE1 (obtained from Eurogentec, Liege, Belgium; Renard et al., European Patent Application No:86870095) with *E. coli* DNA polymerase I (Klenow fragment), ligating XhoI linkers onto the ends and cloning the resulting fragment into the XhoI site of pIBI25. The plasmid generated by this manipulation is called pBDV1.

The initiation codon of the H6 promoter was then aligned with the "initiation codon" of the gel "gene". This was accomplished by cloning the oligonucleotides, BDVM4 (SEQ ID NO:253) (5'-AGCTTGATATCCGTTAAGTTTG-TATCGTAATGGGCAAACTAGAGAAAGCCCTGT-3') and BDVM5 (SEQ ID NO:254) (5'-GGGCTTTCTCTAGTTTGCCCATTAC-GATACAAACTTAACGGATATCA-3'), encoding the 3'-end of the H6 promoter and the 5'-end of the gel "gene", into the 4,250 bp HindIII-BglI (partial) fragment of pBDV1. The plasmid generated by this manipulation is called pBDV6.

The gel "gene" was then cloned downstream of the H6+ATI+HA triple promoter (Portetelle et al., Vaccine (1991) 9:194) and between HA flanking arms. This was accomplished by cloning the 1,380 bp EcoRV-PstI (partial) fragment of pBDV6, containing the gel "gene" into the 3,700 bp EcoRV-PstI fragment of pATI25. The plasmid generated by this; manipulation is called pBDV7.

A BamHI site, necessary for future manipulations, was then generated downstream of the BVDV sequence. This was accomplished by cloning the oligonucleotide, BDVM6 (SEQ ID NO:255) (5'-TCGAGGATCC-3'), into the XhoI site of pBDV7. The plasmid generated by this manipulation is called pBDV8.

Approximately 830 bp of gE2 (gp53) sequence (Osloss strain) was then cloned downstream of the gel sequence. This was accomplished by cloning the 980 bp BglII-BamHI fragment of p7F2 (obtained from Eurogentec, Liege, Belgium; Renard et al , European Patent Application No:86870095) containing the gE2 sequence, into the 5,100 bp BamHI-BglII (partial) fragment of pBDV8. The plasmid generated by this manipulation is called pBDV9.

The H6 promoted-gE1/gE2 sequence was then cloned between ATI flanking arms. This was accomplished by cloning the 2,200 bp NruI-BamHI fragment of pBDV9, containing the gE1/gE2 sequence, into the 4,900 bp NruI-BamHI fragment of pPGI7. This places the gE1/gE2 sequence under the transcriptional control of the H6 promoter and into an insertion vector. The plasmid generated by this manipulation is called pBDV23.

Approximately 270 bp of additional gE2 sequence (Osloss strain) was then cloned downstream of the existing BVDV sequence. This was accomplished by cloning the 1,260 bp BglII-BamHI fragment of pSP65E1+E2-1 (obtained from Eurogentec, Liege, Belgium; Renard et al., European Patent Application No:86870095), containing the gE2 sequence, into the 6,100 bp fragment of pBDV23. The plasmid generated by this manipulation is called pBDV24.

pBDV24 was used in in vitro recombination experiments with vP866 (NYVAC) as the rescuing virus to yield vP972.

Immunoprecipitation analysis was performed to determine whether vP972 expresses authentic BVDV gel and gE2 glycoproteins. Vero cell monolayers were either mock infected, infected with NYVAC or infected with vP972 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) and 50 mls aprotinin, with subsequent scraping of the cell monolayers.

Lysates were then analyzed for BVDV gel and gE2 expression using the BVDV gp48-specific monoclonal antibodies, NYC16 and NY12B1, and the BVDV gp53-specific monoclonal antibody, 209D3 (obtained from Rhone Merieux, Lyon, France). This was accomplished by the following procedure: rat anti-mouse sera was bound to protein-A sepharose at room temperature for 4 hours. After washing the material 5× with 1× buffer A, protein A-sepharose bound rat anti-mouse antibody was bound to the gE1-specific monoclonal antibodies, NYC16 and NY12B1, and the gE2-specific monoclonal antibody, 209D3. The lysates, meanwhile, were precleared by incubating normal mouse sera and the protein A-sepharose bound rat anti-mouse antibody overnight at 4° C. After washing this material 5× with 1× buffer A, the BVDV gE1 or gE2-specific monoclonal antibody, rat anti-mouse, protein A-sepharose conjugate was added to the lysate and incubated overnight at 4° C. After washing the samples 4× with 1× buffer A and 2× with a LiCl$_2$urea buffer, the precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were then fractionated on a 10% Dreyfuss gel system (Dreyfuss et al., 1984), fixed and treated with 1M Na-salicylate for fluorography.

The BVDV gel or gE2-specific monoclonal antibodies precipitated BVDV-specific glycoproteins from vP972 infected cells, but did not precipitate BVDV-specific proteins from NYVAC or mock infected cells.

Generation of NYVAC/BVDV CAPSID/gE1/gE2 recombinant. The BVDV gel "gene" was cloned into pIBI25. This was accomplished by blunt-ending the 1,370 bp EcoRI-BamHI fragment of pSP65-gE1, containing the gel "gene", with *E. coli* DNA polymerase I (Klenow fragment), ligating XhoI linkers onto the ends and cloning the resulting fragment into the XhoI site of pIBI25. The plasmid generated by this manipulation is called pBDV1.

The gel "gene" was then cloned between u flanking arms. This was accomplished by cloning the 1,400 bp XhoI fragment of pBDV1, containing the gel sequence, into the XhoI site of pSD486. The plasmid generated by this manipulation is called pBDV11.

The "initiation codon" of the gel "gene" was then aligned with the initiation codon of π promoter. This was accomplished by cloning the oligonucleotides, BDVM7 (SEQ ID NO:256) (5'-CGATTACTATGGGCAAACTA-GAGAAAGCCCTGT-3') and BDVM8 (SEQ ID NO:257) (5'-GGGCTTTCTCTAGTTTGCCCATAGTAAT-3'), encoding the 3'-end of the π promoter and the 5'-end of the gel sequence, into the 4,800 bp partial BglI-ClaI fragment of pBDV11. The plasmid generated by this manipulation is called pBDV12.

Part of the BVDV gE2 "gene" was then cloned into pBDV12, downstream from the gel sequence. This was accomplished by cloning the 1,000 bp BglII-BamHI fragment of p7F2, containing the gE2 sequence, into the 4,650 bp BglII-BamHI fragment of pBDV12. The plasmid generated by this manipulation is called pBDV14.

The rest of the gE2 "gene" was then cloned into pBDV14. This was accomplished by cloning the 1,260 bp BglII-BamHI fragment of pSP65E1+E2-1, containing the gE2 "gene", into the 4,650 bp BglII-BamHI fragment of pBDV14. The plasmid generated by this manipulation is called pBDV17.

The capsid "gene" (Osloss strain) was then cloned into pBDV17, upstream from the gel sequence. This was accomplished in 2 steps. The first step aligned the initiation codon of the π promoter with the "initiation codon" of the capsid "gene". This was accomplished by cloning the oligonucleotides, BDVL12 (SEQ ID NO:258) (5'-CGATTACTATG-GAGTTGATTACAAATGAACTTTTATA-CAAAACATACAAACAAAAACCCGCTGGAGTGGAG-GAACCAGTATATAACCAAGCAGGTGACCCT-3') and BDVL13 (SEQ ID NO:259) (5'-CTAGAGGGTCACCT-GCTTGGTTATATACTGGTTCCTCCACTC-CAGCGGGTTTTTGTTTGTATGTTTTG-TATAAAAGTTCATTTGTAATCAACTCCATA- GTAAT-3'), encoding the 3'-end of the u promoter and the 5'-end of the capsid sequence, into the 5,200 bp ClaI-XbaI fragment of pBDV17. The plasmid generated by this manipulation is called pBDV25. The second step cloned the rest of the capsid "gene" into pBDV25. This was accomplished by cloning the 1,870 bp BstEII-BglII fragment of pSP65C-E1-E2 (obtained from Eurogentec, Liege, Belgium; Renard et al., European Patent Application No:86870095), containing the capsid "gene" into the 4,700 bp BstEII-BglII fragment of pBDV25. The plasmid generated by this manipulation is called pBDV26.

The u-promoted capsid/gE1/gE2 sequence was then cloned between tk flanking arms. This was accomplished by cloning the 3,200 bp SnaBI-BamHI fragment of pBDV26, containing the u-promoted capsid/gE1/gE2 sequence, into the 4,000 bp SmaI-BamHI fragment of pSD542. The plasmid generated by this manipulation is called pBDV27.

pBDV27 was used in in vitro recombination experiments with vP866 (NYVAC) as the rescuing virus to yield vP1017.

Immunoprecipitation experiments with vP1017 infected cells were performed as described above for the expression of vP972. No BVDV-specific proteins were precipitated from mock infected or NYVAC infected Vero cells. BVDV-specific proteins were precipitated, however, from lysates of vP1017.

Generation of NYVAC/BVDV gE2 recombinant. The BVDV gel "gene" was cloned into pIBI25. This was accomplished by blunt-ending the 1,370 bp EcoRI-BamHI fragment of pSP65-gE1, containing the gel "gene", with E. coli DNA polymerase I (Klenow fragment), ligating XhoI linkers onto the ends and cloning the resulting fragment into the XhoI site of pIBI25. The plasmid generated by this manipulation is called pBDV1.

The initiation codon of the H6 promoter was then aligned with the putative "initiation codon" of the gel "gene". This was accomplished by cloning the oligonucleotides, BDVM4 (SEQ ID NO:253) and BDVM5 (SEQ ID NO:254), encoding the 3'-end of the H6 promoter and the 5'-end of the gel "gene" into the 4,250 bp HindIII-BglI (partial) fragment of pBDV1. The plasmid generated by this manipulation is called pBDV6.

The gel "gene" was then cloned downstream of the H6+ATI+HA triple promoter and between HA flanking arms. This was accomplished by cloning the 1,380 bp EcoRV-PstI (partial) fragment of pBDV6, containing the gel "gene", into the 3,700 bp EcoRV-PstI fragment of pATI25. The plasmid generated by this manipulation is called pBDV7.

A BamHI site, necessary for future manipulations, was then generated downstream of the BVDV sequence. This was accomplished by cloning the oligonucleotide, BDVM6 (SEQ ID NO:255), into the XhoI site of pBDV7. The plasmid generated by this manipulation is called pBDV8.

Approximately 830 bp of BVDV gE2 sequence was then cloned downstream of the gel "gene". This was accomplished by cloning the 980 bp BglII-BamHI fragment of p7F2, containing the gE2 sequence, into the 5,100 bp BamHI-BglII (partial) fragment of pBDV8. The plasmid generated by this manipulation is called pBDV9.

The gE1/gE2 sequence was then cloned between ATI flanking arms. This was accomplished by cloning the 2,200 bp NruI-BamHI fragment of pBDV9, containing the H6-promoted gE1/gE2 "genes", into the 4,900 bp NruI-BamHI fragment of pPGI7. The plasmid generated by this manipulation is called pBDV23.

Approximately 270 bp of additional gE2 sequence was then cloned downstream of the existing BVDV sequence. This was accomplished by cloning the 1,260 bp BglII-BamHI fragment of pSP65E1+E2-1, containing the additional gE2 sequence, into the 6,100 bp BamHI-BglII (partial) fragment of pBDV23. The plasmid generated by this manipulation is called pBDV24.

The gE1 sequence was then deleted from BDV24. This was accomplished by cloning a 130 bp NruI-PstI PCR fragment, containing the 3'-end of the H6 promoter and the 5'-end of the gE2 "gene" into the 5,900 bp NruI-PstI fragment of pBDV24. This PCR fragment was generated from the plasmid, pBDV17, with the oligonucleotides, BDVP14 (SEQ ID NO:260) (5'-TTTCGCGATATCCGT-TAAGTTTGTATCGTAATGCTC-CCAGTTTGCAAACCC-3') and BDVP15 (SEQ ID NO:261) (5'-TCTCCACCTTTACACCACACT-3'). The plasmid generated by this manipulation is called pBDV28.

Sequence analysis revealed that the H6 promoter in pBDV28 contains a 2 bp insertion. To correct this error, the 130 bp NruI-PstI fragment of pBDV28, containing the 3'-end of the H6 promoter and the 5'-end of the gE2 "gene", was cloned into the 5,900 bp NruI-PstI fragment of pBDV24. The plasmid generated by this manipulation is called pBDV29.

pBDV29 was used in in vitro recombination experiments with vP866 (NYVAC) as the rescuing virus to yield vP1097.

Immunoprecipitation experiments with vP1097 infected cells are performed as described above to yield BVDV proteins from cells or lysates.

EXAMPLE 32

CLONING AND EXPRESSION OF HUMAN CYTOMEGALOVIRUS (HCMV) GLYCOPROTEIN ANTIGENS IN POXVIRUS VECTORS

Cloning f the HCMV gB gene into the NYVAC donor plasmid, pSD542. The 4800 bp HindIII-BamHI fragment of the HindIII D fragment of the HCMV DNA was cloned into the 2800 bp HindIII-BamHI fragment of the plasmid pIBI24. By in vitro mutagenesis (Kunkel, 1985; Russel et al., 1986) using the oligonucleotides CMVM5 (SEQ ID NO:262) (5'-GCCTCATCGCTGCTGGATATCCGT- TAAGTTTGTATC- 6'TAATGGAATCCAGGATCTG-3') and CMVM3 (SEQ ID NO:263) (5'-GACAGATTGT- GATTTTTATAAGCATCGTAAGCTGTCA-3'), the gB gene was modified to be expressed under the control of the vaccinia H6 promoter (Taylor et al., 1988a,b; Perkus et al., 1989). The plasmid containing the modified gB was designated 24CMVgB(5+3).

The 2900 bp EcoRV-BamHI fragment of 24CMVgB(5+3) was cloned into the 3100 bp EcoRV-BglII fragment of pSP131. This cloning step put the gB gene under the control of the H6 promoter. The resulting plasmid was designated SP131gB.

To modify the restriction sites flanking the H6 promoted gB in SP131gB the following steps were performed. Plasmid pMP22BHP contains a subclone of the HindIII F fragment of vaccinia (WR strain) containing a portion of the HBV sag in a polylinker region at the BamHI site. pMP22BHP was digested within the polylinker with HindIII and ligated to a HindIII fragment from SP131CMVgB (containing the H6 promoted gB gene) generating plasmid SAg22CMVgB. SAg22CMVgB was digested with BamHI and partially digested with HindIII and ligated to a polylinker derived from pIBI24 by BamHI and HindIII digestion creating plasmid 22CMVgB which contains the H6 promoted gB gene without the HBV sag.

Plasmid pSD542 (a NYVAC TK locus donor plasmid) was derived from plasmid pSD460 (Tartaglia et al., 1992) by forming vector plasmid pSD513 as described above in Example 7. The polylinker region in pSD513 was modified by cutting with PstI/BamHI and ligating to annealed synthetic oligonucleotides MPSYN288 (SEQ ID NO:264) (5' GGTCGACGGATCCT 3') and MPSYN289 (SEQ ID NO:265) (5' GATCAGGATCCGTCGACCTGCA 3') resulting in plasmid pSD542.

22CMVgB was digested with BamHI and NsiI to generate a fragment containing the H6 promoter and part of the gB gene, and with NsiI and PstI to generate a fragment containing the remainder of the gB gene. These two fragments were ligated to pSD542 that had been digested with BamHI and PstI within its' polylinker creating the NYVAC donor plasmid 542CMVgB.

Cloning of the HCMV gB size into the ALVAC donor plasmid CP3LVQH6. An 8.5 kb canarypox BglII fragment was cloned in the BamHI site of pBS-SK plasmid vector to form pWW5. Nucleotide sequence analysis revealed a reading frame designated C3. In order to construct a donor plasmid for insertion of foreign genes into the C3 locus with the complete excision of the C3 open reading frame, PCR primers were used to amplify the 5' and 3' sequences relative to C3. Primers for the 5' sequence were RG277 (SEQ ID NO:177) and RG278 (SEQ ID NO:178).

Primers for the 3' sequences were RG279 (SEQ ID NO:179) and RG280 (SEQ ID NO:180). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

A 908 bp fragment of canarypox DNA, immediately upstream of the C3 locus was obtained by digestion of plasmid pWW5 with NsiI and SspI. A 604 bp fragment of canarypox and DNA was derived by PCR (Engelke et al., 1988) using plasmid pWW5 as template and oligonucleotides CP16 (SEQ ID NO:266) (5'-TCCGGTACCGCGGC- CGCAGATATTTGTTAGCTTCTGC-3') and CP17 (SEQ ID NO:267) (5'-TCGCTCGAGTAGGATACCTACCTAC- TACCTACG-3'). The 604 bp fragment was digested with Asp718 and XhoI (sites present at the 5' ends of oligonucleotides CP16 and CP17, respectively) and cloned into Asp718-XhoI digested and alkaline phosphatase treated IBI25 (International Biotechnologies, Inc., New Haven, Conn.) generating plasmid SPC3LA. SPC3LA was digested within IBI25 with EcoRV and within canarypox DNA with NsiI and ligated to the 908 bp NsiI-SspI fragment generating SPCPLAX which contains 1444 bp of canarypox DNA upstream of the C3 locus.

A 2178 bp BglII-StyI fragment of canarypox DNA was isolated from plasmids pXX4 (which contains a 6.5 kb NsiI fragment of canarypox DNA cloned into the PStI site of pBS-SK. A 279 bp fragment of canarypox DNA was isolated by PCR (Engelke et al., 1988) using plasmid pXX4 as template and oligonucleotides CP19 (SEQ ID NO:268) (5'-TCGCTCGAGCTTTCTTGACAATAACATAG-3') and CP20 (SEQ ID NO:269) (5'-TAGGAGCTCTTTATAC- TACTGGGTTACAAC-3'). The 279 bp fragment was digested with XhoI and SacI (sites present at the 5' ends of oligonucleotides CP19 and CP20, respectively) and cloned into SacI-XhoI digested and alkaline phosphatase treated IBI25 generating plasmid SPC3RA.

To add additional unique sites to the polylinker, pC3I was digested within the polylinker region with EcoRI and ClaI, treated with alkaline phosphatase and ligated to kinased and annealed oligonucleotides CP12 (SEQ ID NO:272) and CP13 (SEQ ID NO:273) (containing an EcoRI sticky end, XhoI site, BamHI site and a sticky end compatible with ClaI) generating plasmid SPCP3S.

```
CP12 (SEQ ID NO:272) 5'-AATTCCTCGAGGGATCC    -3'
CP13 (SEQ ID NO:273) 3'-        GGAGCTCCCTAGGGC-5'
                        EcoRI  XhoI  BamHI
```

SPCP3S was digested within the canarypox sequences downstream of the C3 locus with StyI and SacI (pBS-SK) and ligated to a 261 bp BglII-SacI fragment from SPC3RA and the 2178 bp BglII-StyI fragment from pXX4 generating plasmid CPRAL containing 2572 bp of canarypox DNA downstream of the C3 locus. SPCP3S was digested within the canarypox sequences upstream of the C3 locus with Asp718 (in pBS-SK) and AccI and ligated to a 1436 bp Asp718-AccI fragment from SPCPLAX generating plasmid CPLAL containing 1457 bp of canarypox DNA upstream of the C3 locus. CPLAL was digested within the canarypox sequences downstream of the C3 locus with StyI and SacI (in pBS-SK) and ligated to a 2438 bp StyI-SacI fragment from CPRAL generating plasmid CP3L containing 1457 bp of canarypox DNA upstream of the C3 locus, stop codons in six reading frames, early transcription termination signal, a polylinker region, early transcription termination signal, stop codons in six reading frames, and 2572 bp of canarypox DNA downstream of the C3 locus. The resulting plasmid designated SPCP3L.

The early/late H6 vaccinia virus promoter (Guo et al., 1989; Perkus et al., 1989) was derived by PCR (Engelke et al., 1988) using pRW838 as template and oligonucleotides CP21 (SEQ ID NO:270) (5'-TCGGGATCCGGGTTAAT-TAATTAGTTATTAGACAAGGTG-3') and CP22 (SEQ ID NO:271) (5'-TAGGAATTCCTCGAGTACGATACAAACT-TAAGCGGATATCG-3'). The PCR product was digested with BamHI and EcoRV (sites present at the 5' ends of oligonucleotides CP21 and CP22, respectively) and ligated to CP3L that was digested with BamHI and EcoRI in the polylinker generating plasmid VQH6CP3L.

ALVAC donor plasmid VQH6CP3L was digested within the polylinker with XhoI and within the H6 promoter with NruI and ligated to a NruI/HindIII fragment from 22CMgB containing part of the H6 promoter and gB gene and a polylinker derived from pIBI24 by XhoI and HindIII digestion generating the ALVAC donor plasmid CP3LCMVgB.

EXAMPLE 33

CONSTRUCTION OF RECOMBINANT VIRUSES: CYTOMEGALOVIRUS

The CMW (cytomegalovirus) gB gene was inserted into the TK site of NYVAC. The recombinant virus was designated vP1001. The CMV gB gene was inserted into the C3 site ALVAC. The recombinant was designated vCP139.

EXAMPLE 34

IMMUNOFLUORESCENCE OF CMV GB PROTEIN IN RECOMBINANT VIRUS INFECTED CELLS

Immunofluorescence studies were performed as described previously (Taylor et al., 1990) using guinea pig polyclonal serum followed by fluorescein isothiocyanate goat anti-guinea pig. Cells infected with vP1001 showed gB expressed on the plasma membrane. Weak internal expression was detected within cells infected with vCP139.

EXAMPLE 35

IMMUNOPRECIPITATION OF CMV GB IN RECOMBINANT INFECTED CELLS

Immunoprecipitation experiments were performed as described previously (Taylor et al., 1990). The CMV gB glycoprotein produced in CMV infected cells has a molecular weight of 55 kDa with a precursor form of 130 kDa (Gretch et al., 1988). Cells infected with vP1001 and vCP139 produce two CMV gB coded proteins of approximately 116 kDa and 55 kDa.

EXAMPLE 36

NEUTRALIZING ANTIBODIES

Following immunization of CBA mice with vP1001 (NYVAC-HCMV gB), neutralizing antibody titers of the sera of inoculated mice were assessed (Gonczol et al., 1986). Antibodies capable of neutralizing human cytomegalovirus were detected in the sera of mice 14–21 days later (geometric mean titers of 1:16) and between 28 and 60 days post-immunization (gmt=1:26). Immunization of CBA mice with ALVAC-HCMV gB generated HCMV neutralizing antibody titers of 1:64 gmt (14–21 days pi, 1:91 gmt between 21 and 28 days pi), and 1:111 between 28 and 60 days pi. Thus, immunization of mice with vaccinia virus or canarypox virus recombinants expressing HCMV gB elicited antibodies able to neutralize the infectivity of HCMV.

EXAMPLE 37

CELL MEDIATED IMMUNITY

Besides HCMV neutralizing antibody titers, vCP139 is also capable of eliciting cytotoxic T lymphocytes capable of killing murine L929 cells infected with a recombinant vaccinia virus expressing HCMV gB (vaccinia WR-gB). CBA mice were immunized intraperitoneally with $2.5\times10^8$ pfu of vCP139. Sixteen to 30 days later, spleen cell suspensions of the mice were re-stimulated in vitro by co-incubation with syngeneic spleen cells previously infected with vP1001 at a ratio of 2:1. After 5 days, the spleen cells were counted and, using the $^{51}$Cr-release assay (Zinkernagel et al., 1984), assessed for cytotoxicity against uninfected L929 cells or L929 cells infected with adenovirus Ad5dlE3, recombinant adenovirus expressing HCMV gB (Ad-gB), vaccinia virus, and recombinant vaccinia virus expressing HCMV gB. Only background levels of reactivity were measured against the uninfected targets as well as the targets infected with Ad5dlE3. In contrast, the in vitro stimulated spleen cells readily killed L929 cells infected with Ad-gB expressing HCMV gB. Although some lytic reactivity was observed against targets infected with the vaccinia virus vector, much higher cytolysis was measured against targets infected with the recombinant vaccinia virus expressing gB. This clearly demonstrated that cytotoxic T lymphocytes specific for epitopes located within HCMV gB were generated by inoculation with the recombinant canarypox virus expressing HCMV gB (vCP139).

EXAMPLE 38

NYVAC AND ALVAC DONOR PLASMID CONSTRUCTION: CANINE PARVOVIRUS

In order to generate poxvirus recombinants expressing the canine parvovirus VP2 capsid gene, donor plasmids were constructed in which the VP2 gene was amplified from the genome of the CPV-d isolate (CPV-2 antigenic type), coupled to the vaccinia H6 promoter (Perkus et al., 1989) and inserted into NYVAC or ALVAC insertion vectors. The NYVAC insertion site is the deorfed ATI locus while the ALVAC insertion site is the deorfed C3 locus.

The VP2 gene sequences were obtained by PCR from the plasmid pBI265(1). This plasmid, obtained from Dr. Colin R. Parrish, James A. Baker Institute, Cornell University, Ithaca, N.Y., contains the genome of the CPV-d isolate (Cornell 790320)(antigenic type CPV-2). The DNA sequence of the VP2 gene from this isolate has been published (Parrish et al., 1988).

Using pBI265(1) as template and synthetic oligonucleotides RG451 (SEQ ID NO:274) (5'-TCGGGTACCTCGC-GATATCCGTTAAGTTTGTATCGTAAT-GAGTGATGGAGCAGT-3') anti RG452 (SEQ ID NO:275) (5'-TAGGAATTCCTCGAGT- TAATATAATTTTCTAGGTGC-3') as primers, the complete VP2 open reading frame (ORF) was amplified by PCR. The purified DNA fragment was cut with Asp718 and EcoRI and cloned into the Asp718 and EcoRI sites in pBluescript SK+, resulting in pDT4. The VP2 gene was confirmed by DNA sequence analysis.

The VP2 gene contains two TTTTTNT sequences within the ORF which could function as early transcriptional stop signals (Yuen et al., 1987). To eliminate these signals, PCR site-directed mutagenesis was used to change the nucleotide sequence while retaining the correct amino acid sequence. A 250 bp fragment was amplified from pBI265(1) using synthetic oligonucleotides RG453 (SEQ ID NO:276) (5'-ATCAGATCTGAGACATTGGGTTTCTATCCATG-3') and RG454 (SEQ ID NO:277) (5'-TTAGTCTACATGGTTTACAATCAAAGAAGAATGTTCCTG-3'). The purified fragment was digested with BglII and AccI, and used to replace the BglII/AccI VP2 fragment in pDT4. The resulting plasmid, pED3, contains the modified VP2 gene in which the TTTTTNT sequences have been changed to TTTCTAT and TTCTTCT.

A NYVAC donor plasmid containing the CPV VP2 capsid gene was constructed as follows. The modified VP2 gene was excised from pED3 with NruI and XhoI and cloned into pMPATIH6HSVTK cut with NruI/XhoI. pMPATIH6HSVTK is a derivative of pSD552 (described elsewhere in this disclosure) in which an expression cassette containing the coding sequences for the HSV-1 thymidine kinase gene under control of the H6 promoter is inserted between the HpaI and XhoI sites in the polylinker region. Cutting this plasmid with NruI and XhoI excises the tk gene, but retains the 5'end of the H6 promoter. Insertion of the modified VP2 gene into this vector as described above generates pATI-VP2. This NYVAC donor plasmid contains the H6 promoted VP2 gene flanked by the ATI insertion arms.

An ALVAC donor plasmid containing the CPV VP2 capsid gene was constructed as follows. The modified VP2 gene was excised from pED3 with NruI and XhoI and the purified fragment was cloned into pVQH6CP3L (plasmid described in Flavivirus section) cut with NruI and XhoI. The resulting plasmid, pC3-VP2, contains the H6 promoted VP2 gene flanked by the C3 insertion arms.

EXAMPLE 39

GENERATION OF NYVAC AND ALVAC RECOMBINANTS: CANINE PARVOVIRUS (CPV)

The donor plasmid pATI-VP2 was used in in vitro recombination experiments in VERO cells with NYVAC (vP866) and NYVAC-RG (vP879) as rescue viruses to yield vP998 and vP999 respectively (Tartaglia et al., 1992). Recombinant viruses were identified by in situ hybridization procedures (Piccini et al., 1987) using a radiolabelled VP2 specific DNA probe. Recombinant plaques were purified by three rounds of plaque purification and amplified for further analysis.

The donor plasmid pC3-VP2 was used in in vitro recombination experiments in CEF cells with ALVAC (CPpp) and ALVAC-RG (vCP65A) as rescue viruses to yield vCP123 and vCP136 respectively (Taylor et al., 1992). Recombinant viruses were identified by in situ hybridization procedures (Piccini et al., 1987) using a radiolabelled VP2 specific probe (positive signal) and C3 ORF specific probe (negative signal). Recombinant plaques were purified by three rounds of plaque purification and amplified for further analysis.

EXAMPLE 40

EXPRESSION ANALYSIS OF THE NYVAC- AND ALVAC-BASED CPV VP2 RECOMBINANTS

All the recombinants containing the CPV VP2 gene were tested for expression by immunofluorescence as previously described (Taylor et al., 1990) using monoclonal antibodies specific for VP2 epitopes or polyclonal CPV dog serum. All sera were obtained from Dr. Colin R. Parrish, James A. Baker Institute, Cornell University, Ithaca, N.Y. The NYVAC-based recombinants were tested on VERO cells while the ALVAC-based recombinants were tested on CEF cells. Recombinants vP998, vP999, vCP123, and vCP136 all displayed internal fluorescence, with localization in the nucleus. No surface fluorescence was detected. In addition, the two recombinants containing the rabies G gene (vP999 and vCP136) were screened with monoclonal antibodies specific for rabies G epitopes. Both displayed strong fluorescence on the surface of the cell.

To further characterize expression of an authenic VP2 gene product in the above recombinants, immunoprecipitation analysis was done using the same antisera (Taylor et al., 1990). The NYVAC-based recombinants were tested on VERO cells while the ALVAC-based recombinants were tested on CEF cells. In all recombinants (vP998, vP999, vCP123, and vCP136) the antisera precipitated a protein of 65 kDa, which is consistent with the size of the native VP2 gene. No protein of this size was detected from cell lysates or from either parental virus (NYVAC or ALVAC).

EXAMPLE 41

INSERTION OF EPSTEIN BARR VIRUS (EBV) GENES INTO ALVAC

Construction of donor plasmid EBV Triple.2. Plasmid EBV Triple.1 (Example 11) contains expression cassettes for EBV genes gH, gB and gp340 all inserted into a vaccinia TK locus insertion plasmid. Plasmid EBV Triple.1 was digested with SmaI/BamHI and a 0.3 kb fragment containing the 42 kDa Entomopox virus promoter and the 5' end of the EBV gH gene was isolated. EBV Triple.1 plasmid was also digested with BamHI and a 7.3 kb fragment containing the 3' end of the EBV gH gene, the EBV gB expression cassette, and the EBV gp340 expression cassette was isolated. These two fragments were then ligated into the ALVAC C5 locus insertion plasmid pNVQC5LSP7 (described herein, see Tetanus example) which had been cut with SmaI/BamHI. The resulting plasmid was designated EBV Triple.2.

Insertion of EBV genes into ALVAC. Plasmid EBV Triple.2, containing expression cassettes for the three EBV genes, gH, gB and gp340, in the C5 insertion locus, was used as donor plasmid for recombination with ALVAC, generating ALVAC recombinant vCP167.

Expression of EBV proteins by vP944 and vCP167. Metabolically labelled lysates from cells infected with ALVAC recombinant vCP167 and vP944, the NYVAC-based recombinant containing the same three genes (Example 11), were subjected to immunoprecipitation using human polyclonal serum to EBV as well as mouse monoclonal antibodies to EBV gB and gp340. Precipitates were analyzed by SDS-polyacrylamide gel electrophoresis followed by radioautography. Proteins of the correct molecular weights and specificities for EBV gB, gH and gp340 were observed for both NYVAC-based recombinant vP944 and ALVAC-based recombinant vCP167.

EXAMPLE 42

CONSTRUCTION OF AN EXPRESSION CASSETTE FOR INSERTION ON EQUINE INFLUENZA HA (A1/PRAGUE/56) INTO NYVAC AND ALVAC

Purified EIV (A1/Prague/56) genomic RNA was provided by Rhone-Merieux (Lyon, France). EIV-specific cDNA was prepared as described by Gubler and Hoffman (1983). Oligonucleotide EIVSIP (SEQ ID NO:278) (5'-ATCATC-CTGCAGAGCAAAAGCAGG-3') was used to synthesize first strand cDNA. This oligonucleotide (SEQ ID NO:278) is complementary to the 3'-end of each genomic RNA segment. As per Gubler and Hoffman (1983), the cDNA is dG-tailed and inserted into pMG5 digested with EcoRV and dC-tailed. Insertion of the cDNA in this manner in pMG5 creates a BamHI site on both plasmid/cDNA sequence borders.

Five hundred colonies from this EIV cDNA library were transferred in duplicate to LB-agar plates containing ampicillin (50 μg/ml). The colonies were transferred to nitrocellulose for hybridization with a radiolabeled EIV HA-specific probe. This probe was derived by using radiolabeled first strand cDNA synthesized with oligonucleotide EIVSIP (SEQ ID NO:278) and purified HA genomic RNA as template. The HA genomic segment was purified from a 1.2% low melting point agarose gel (Bethesda Research Laboratories, Gaithersburg, Md.). Total genomic RNA was fractionated in this gel system run at 2 volts/cm in 1× TBE. HA RNA was recovered by excising the HA band and melting the agarose at 75° C. followed by two cycles of phenol extraction, one ether extraction, and ETOH precipitation.

Colony hybridization was performed according to standard procedures (Maniatis et al., 1991) and a cDNA clone containing a 1.4 kb HA cDNA insert was identified. The clone was confirmed to be HA-specific by Northern blot analysis versus genomic RNA and nucleotide sequence analysis. This 1.4 kb fragment was used to generate a radiolabeled HA-specific DNA probe for subsequent cDNA library screenings.

Using the probe, other HA-specific cDNA clones were identified. The largest were of 1.0 kb, 1.2 kb, and 1.4 kb and they were designated as pEIVAIPHA-1, -10, and -8, respectively. Collectively, these clones contain an entire EIV HA coding sequence as determined by nucleotide sequence analysis. The entire sequence of the EIV HA (A1/Prague/56) determined from these analyses is provided in FIG. 23 (SEQ ID NO:279).

A full-length cDNA clone of the EIV HA was next generated by splicing segments from different cDNA clones. The 5'-most 1200 bp of the HA coding sequence was derived from pEIVAIPHA-8 by PCR using this plasmid as template and oligonucleotides EIVSIP (SEQ ID NO:278) and EIVAIP7A (SEQ ID NO:280) (5'-GTTGGTTTTTTC-TATTAG-3'). This 1200 bp fragment was digested with PstI creating PstI cohesive ends at both the 5' and 3' termini. The 3'-most 600 bp of the HA coding sequence was derived from pEIVAIPHA-10 by digestion with BamHI and PstI. These two fragments were inserted into pBS-SK (Stratagene, La Jolla, Calif.) digested with PstI and BamHI. The plasmid generated containing the entire EIV HA (A1/Prague/56) coding sequence was designated as pBSEIVAIPHA.

The EIV HA coding sequence (ATG to TAA) was derived by PCR from pBSEIVAIPHA using oligonucleotides EIVAIPHA5P ,(SEQ ID NO:281) (5'-CGATATCCGT-TAAGTTTGTATCGTAATGAAGACT-CAAATTCTAATATTAGCC-3') and EIVAIPHA3P (SEQ ID NO:282) (5'-ATCATCGGATCCATAAAAATTATATA-CAAATAGTGCACCG-3'). The oligonucleotide EIVAIPHA5P (SEQ ID NO:281) provides the 3'most 26 bp (from NruI site) of the vaccinia virus H6 promoter (Goebel et al., 1990a,b). The 1.7 kb PCR-derived fragment was inserted into NruI digested pCPCV1 to yield pC3EIVAIPHA. pCPCV1 is an insertion vector which contains the H6 promoter. Insertion of the 1.7 kb blunt-ended fragment in the proper orientation places the EIV HA 3' to the H6 promoter. The plasmid pCPCV1 was derived as follows. Plasmid pFeLV1A, which contains a 2.4 kb fragment containing the FeLV env gene (Guilhot et al., 1987) in the PstI site of pTP15 (Guo et al., 1989) was digested with PstI to excise the FeLV sequences and religated to yield plasmid pFeLVF4. The vaccinia virus H6 promoter element followed by a polylinker region were liberated from pFeLVF4 by digestion with KpnI and HpaI. The 150 bp fragment was blunt-ended using T4 DNA polymerase and inserted into pRW764.2, a plasmid containing a 3.3 kb PvuII genomic fragment of canarypox DNA. pRW764.2 was linearized with EcoRI, which recognizes a unique EcoRI site within the canarypox sequences, and blunt-ended using the Klenow fragment of the *E. coli* DNA polymerase. The resultant plasmid was designated as pCPCV1. This plasmid contains the vaccinia virus H6 promoter followed by a polylinker region and flanked by canarypoxvirus homologous sequences.

EXAMPLE 43

CONSTRUCTION OF AN EXPRESSION CASSETTE FOR INSERTION OF EIV HA (A2/FONTAINEBLEAU/79) INTO NYVAC AND ALVAC

Purified EIV (A2/Fontainebleau/79) genomic RNA was provided by Rhone-Merieux (Lyon, France). EIV-specific cDNA was prepared as described by Gubler and Hoffman (1983) and as described for the EIV (A1/Prague/56) cDNA preparation. The oligonucleotide EIVSIP (SEQ ID NO:278) was used for first-strand cDNA synthesis.

To screen bacterial colonies containing full-length cDNA clones of the HA gene, eight pools of transformed colonies were amplified in 500 ml cultures and plasmid DNA preparations obtained by standard procedures (Sambrook et al., 1989) Total plasmid DNA was used as template in standard PCR reactions with oligonucleotides EIVSIP (SEQ ID NO:278) and EIVS2H (SEQ ID NO:283) (5'-ATCAT-CAAGCTTAGTAGAAACAAGG-3'). Such a reaction would potentially amplify only full-length cDNA sequences of all eight EIV genomic segments, since these primers were complementary to conserved sequences at the 5' and 3' ends of these eight segments.

Plasmid preparation, pPEIVA2F-5, as template generated a 1.8 kb PCR-derived fragment consistent with the size of a full-length HA-specific fragment. This PCR-derived fragment was re-amplified by PCR for use as a probe against the remainder of the cDNA library. Using this probe, clones pEIVA2FHA-7 and -8 were identified and the cDNA insert analyzed by nucleotide sequence analysis using custom synthesized oligonucleotides (Goebel et al., 1990a).

Nucleotide sequence analysis demonstrated that clones #7 and #8 represented the 3'-most 1200 bp of the EIV (A2/Fontainebleau/79) HA coding sequence (FIG. 24) (SEQ ID NO:284).

The 1200 bp EIV sequence was amplified from clone #7 by PCR using oligonucleotides A2F3P (SEQ ID NO:285) (5'-ATCATCACTAGTATAAAAATCAAATG-CAAATGTTGCATCTGATGTTGCC-3') and A2FBAM2 (SEQ ID NO:286) (5'-ATCATCGGATCCATCACCCGAG-CACAAACAATGAGCAG-3'). The 5'-end of this 1200 bp fragment after digestion with BamHI corresponds to nucleotide 617 of the complete EIV (A2/Fontainebleau/79) HA coding sequence in FIG. 24 (SEQ ID NO:284). This fragment was also digested with SpeI which was engineered 3' to the coding sequence using oligonucleotide A2F3P (SEQ ID NO:285). This 1200 bp fragment was to be co-inserted into SmaI/SpeI digested pBS-SK (Stratagene, La Jolla, Calif.) with a fragment containing the 5'-most 616 bp (defined below). However, screening of potential transformants demonstrated that only the 1200 bp fragment was inserted. Numerous clones were chosen for nucleotide sequence analysis.

After nucleotide sequence analysis of numerous clones, pBSEIVA2FHA-19 was chosen for further manipulation. This clone contained errors near the BamHI site at nucleotide 617 (FIG. 24) (SEQ ID NO:284) and at nucleotide 1570 (FIG. 24) (SEQ ID NO:284). To correct these errors, the following manipulations were made. Plasmid pBSEIVA2FHA-19 was digested with BamHI and SphI and the excised 900 bp fragment was isolated. This fragment was co-inserted into pBS-SK digested with SpeI/BamHI with a 250 bp SphI/SpeI fragment encompassing the 3'-most region of the HA coding sequence. This 250 bp PCR fragment was derived using clone #7 (above) as template and oligonucleotides A2F3P (SEQ ID NO:285) and A2F6 (SEQ ID NO:287) (5'-TTGACTTAACAGATGCAG-3'). The resultant plasmid was designated as pEIVH33P.

The 5'-most 616 bp of the HA coding sequence for the EIV HA was generated in the following manner. First, first-stand cDNA was generated as above. This first-strand cDNA preparation was then used as template to amplify these sequences by PCR using oligonucleotides A2F5P (SEQ ID NO:288) (5'-ATGAAGACAACCATTATTTTG-3') and A2FBAM1 (SEQ ID NO:289) (5'-TGTTGAGACTGT-TACTCG-3'). This fragment was inserted into HincII digested pBS-SK (Stratagene, La Jolla, CA) and the resultant plasmid called pEIVH35P.

The vaccinia virus H6 promoter sequence (Goebel et al., 1990a,b) and the 5'-most region of the HA coding sequence were amplified and fused in the following manner. The H6 sequences were derived from a pBS-based plasmid containing the HIV-1 (IIIB) env gene linked precisely to the H6 promoter called pBSH6IIIBE. These sequences were amplified by PCR using oligonucleotides H65PH (SEQ ID NO:164) (5'-ATCATCAAGCTTGATTCTTTATTCTATAC-3') and H63P (SEQ ID NO:291) (5'-TACGATACAAACT-TAACGG-3'). The 120 bp H6 fragment was used as template with oligonucleotides H65PH (SEQ ID NO:164) and EIV5PACC (SEQ ID NO:292) (5'-GGTTGGGTTTTGACT-GTAGACCCAATGGGTCAGTAGTAT-CAAAATAATGGTTGTCTTCATTACGATA-CAAACTTAACGG-3') to yield a 161 bp fragment containing the H6 promoter and the initial 41 bp of the HA coding sequence to the AccI restriction site. This fragment was digested with HindIII and AccI and co-inserted into HindIII/BamHI digested pBS-SK with the 550 bp AccI/BamHI fragment from pEIVH35P. The resultant plasmid was designated as pH6EIVH35P.

The entire HA expression cassette was derived by co-insertion of the 710 bp HindIII/BamHI fragment from pH6EIVH35P and the 1200 bp BamHI/SpeI fragment from pEIVH33P into pBS-SK digested with HindIII and SpeI. The derived plasmid was designated as pBSA2FHAB.

To correct the base change noted above near the BamHI site at nucleotide position 617, the Mandecki procedure (Mandecki, 1986) was employed. pBSA2FHAB was linearized with BamHI and the mutagenesis procedure performed using oligonucleotide A2F7 (SEQ ID NO:293) (5'-CAATTTCGATAAACTATA-CATCTGGGGCATCCATCACCCGAGCA-CAAACAATGAGCAGACAAAATTG-3'). The plasmid containing the corrected version of the HA was designated pBSA2FHA.

EXAMPLE 44

CONSTRUCTION OF THE INSERTION PLASMIDS pEIVC5L AND pEIVHAVQVV USED TO GENERATE vCP128 and vP961, RESPECTIVELY Plasmid pC3EIVAIPHA was digested with NruI and HindIII to excise the 1.7kb fragment containing the 3'-most 26 bp of the H6 promoter and the entire EIV (A1/Prague/56) HA coding sequence. Following blunt-ending with Klenow, this fragment was inserted into plasmid pRW838 digested with NruI/EcoRI and blunt-ended with Klenow to provide plasmid pC5AIPHA. The plasmid pRW838 contains the rabies G gene (Kieny et al., 1984) fused to the vaccinia H6 promoter in a canarypox insertion plasmid (C5 locus). Digestion with NruI and EcoRI excises the rabies G gene leaving behind the 5'-most 100 bp of the H6 promoter and the C5 flanking arms.

The plasmid pC5AIPHA was digested with SmaI and SacI to excise an 820 bp fragment containing the H6 promoter and the 5'-most 645 bp of the EIV (A1/Prague/56) coding sequence. This fragment was co-inserted into pBS-SK digested with HindIII and SmaI with a 1.1 kb SacI/HindIII fragment from pC3EIVAIPHA containing the remainder of the HA coding sequence. The resultant plasmid was designated as pBSAIPHAVQ.

Plasmid pBSAIPHAVQ was then linearized with SpeI and SmaI. This 4.7 kb fragment was ligated to a 1.8 kb SpeI/partial HincII fragment derived from pBSA2FHA. The resultant pBS-based plasmid, containing the EIV (A1/Prague/56) and (A2/Fontainebleau/79) HA genes in a head to head configuration, was designated as pBSAIPA2FHAVQ.

A NotI/XhoI fragment (3.5 kb) derived from pBSAIP2FHAVQ containing the two HA genes was isolated and inserted into pSD542 (described below for EIV (A2/Suffolk/89) and pC5L to provide the insertion plasmids pEIVFAVQVV and pEIVC5L, respectively.

The C5L insertion plasmid was derived as follows. Using the cosmid vector pVK102 (Knauf and Nester, 1982), a genomic library for vCP65 (ALVAC-based rabies G recombinant with rabies in C5 locus) was constructed. This library was probed with the 0.9 kb PvuII canarypoxvirus genomic fragment contained within pRW764.5 (C5 locus). These canarypox DNA sequences contain the original insertion locus. A clone containing a 29 kb insert was grown up and designated pHCOS1. From this cosmid containing C5 sequences, a 3.3 kb Cla fragment was subcloned. Sequence analysis from this ClaI fragment was used to extend the map of the C5 locus from 1-1372.

The C5 insertion vector, pC5L, was constructed in two steps. The 1535 bp left arm was generated by PCR amplification using oligonucleotides C5A (SEQ ID NO:294) (5'-ATCATCGAATTCTGAATGTTAAATGT-TATACTTTG) and C5B (SEQ ID NO:295) (GGGGGTAC-CTTTGAGAGTACCACTTCAG-3'). The template DNA was vCP65 genomic DNA. This fragment was cloned into EcoRI/SmaI digested pUC8. The sequence was confirmed by standard sequencing protocols. The 404 bp right arm was generated by PCR amplification using oligonucleotides C5C (SEQ ID NO:296) (5'-ATCATCCTGCAGGTAT-TCTAAACTAGGAATAGATG-3') and C5DA (SEQ ID NO:297) (5'-ATCATCCTGCAGGTATTCTAAACTAG-GAATAGATG-3'). This fragment was then cloned into the vector previously generated containing the left arm digested with SmaI/PstI. The entire construct was confirmed by standard sequence analysis and designated pC5L. This insertion plasmid enables the insertion of foreign genes into the C5 locus.

EXAMPLE 45

CONSTRUCTION OF INSERTION PLASMIDS TO GENERATE ALVAC- AND NYVAC-BASED RECOMBINANTS EXPRESSING INFLUENZA VIRUS (A2/SUFFOLK/89) HEMAGGLUTININ GENE

An M13 clone containing the hemagglutinin (HA) gene from equine influenza virus (A2/Suffolk/89) was provided by Dr. M. Binns (Animal Health Trust, P.O. Box 5, Newmarket, Suffolk, CB8 7DW, United Kingdom). This clone contains a full-length 1.7 kb cDNA fragment containing this HA gene inserted into the M13 vector via the HindIII site.

Initially, the equine influenza virus (EIV) HA gene was amplified from the above M13 clone by PCR using oligonucleotides EIVS1 (SEQ ID NO:298) (5'-ATGAAGA-CAACCATTATTTTG-3') and EIVS2 (SEQ ID NO:299) (5'-TCAAATGCAAATGTTGCATCT-3'). This 1.7 kb fragment was ligated into pBS-SK (Stratagene, La Jolla, Calif.) digested with SmaI. Two positive clones were derived and analyzed by nucleotide sequence analysis (Goebel et al., 1990a). Clone A contained one non-conserved base change while clone B contained three such changes compared to the sequence provided in FIG. 25 (SEQ ID NO:300). To generate a full-length correct version of the EIVHA gene, clone B was digested with SacI and MscI to excise a 390 bp fragment. This fragment was ligated into a 4.3 kb MscI/partial SacI fragment derived from clone A. This provided a corrected EIVHA and was designated as pBSEIVHS.

The 5'-most 360 bp of the EIVHA coding sequence was derived from pBSEIVHS by PCR using oligonucleotides I3L5EIV (SEQ ID NO:301) (5'-GTTTAATCATGAAGA-CAACCATTATTTTGATAC-3') and EIVPVU (SEQ ID NO:302) (5'-AGCAATTGCTGAAAGCGC-3'). The entire I3L promoter region (Goebel et al., 1990a,b) was derived from pMPI3L101 by PCR using oligonucleotides I3L5B5 (SEQ ID NO:303) (5'-ATCATCGGATCCCGGGACAT-CATGCAGTGGTTAAAC-3') and EIV513L (SEQ ID NO:304) (5'-CAAAATAATGGTTGTCTTCATGAT-TAAACCTAAATAATTGTAC-3'). These fragments were fused due to the complementary conferred by the engineering of oligonucleotides I3L5EIV (SEQ ID NO:301) and EIV513L (SEQ ID NO:304) by PCR with oligonucleotides I3L5B5 (SEQ ID NO:303) and EIVPVU (SEQ ID NO:302) to yield a 480 bp fragment.

Plasmid pMPI3L101 contains an expression cassette consisting of the gene encoding the rabies glycoprotein under the control of the I3L promoter, all inserted into a vaccinia insertion plasmid deleted for ORFS C6L-K1L (Goebel et al., 1990a,b). The I3L promoter consists of 101 bases (nt 64,973–65,074 Goebel et al., 1990a,b) immediately upstream from the initiation codon of the ORF I3L.

The above derived fusion fragment linking the I3L promoter precisely to the 5' region of the EIVHA coding sequence was digested with BamHI (5'-end) and AccI (3'-end) and the 400 bp fragment isolated. This fragment was ligated to a 4.6 kb BamHI/partial AccI fragment derived from pBSEIVHS and the resultant plasmid designated as pBSEIVHSI3L.

A 1.8 kb SmaI/XhoI fragment containing the EIVHA expression cassette was derived from pBSEIVHSI3L. This fragment was inserted into a SmaI/XhoI digested pSD542 (described in Example 32) insertion vector to yield pTKEIVHSI3L.

The 1.8 kb SmaI/XhoI fragment from pBSEIVHEI3L (above) was inserted into the CPpp (ALVAC) insertion plasmid, VQCP3L, digested with SmaI/XhoI. The resultant plasmid was designated as pC3EIVHSI3L.

Insertion plasmid VQCP3L was derived as follows. VQCPCP3L was derived from pSPCP3L (defined in Example 32) by digestion with XmaI, phosphatase treating the linearized plasmid, and ligation to annealed, kinased oligonucleotides CP23 (SEQ ID NO:305) (5'-CCGGT-TAATTAATTAGTTATTAGACAAGGT-GAAAACGAAACTATTTGTAGCTTAAT-TAATTAGGTCACC-3') and CP24 (SEQ ID NO:306) (5'-CCGGGGTCGACCTAATTAATTAAGCTACAAATAGT-TTCGTTTTCACCTTGTCTAATAACTAATTAATTAA-3').

EXAMPLE 46

DEVELOPMENT OF ALVAC-EQUINE INFLUENZA VIRUS RECOMBINANTS

Plasmid pEIVC5L contains the hemagglutinin coding sequences for equine-1, A1/Prague/56 (H7) and equine-2, A2/Fontainebleau/79 (H3). Both genes are linked to the vaccinia virus H6 promoter and inserted at the de-orfed C5 locus. ALVAC virus was used as the rescuing virus in in vitro recombination to rescue the inserted DNA. Positive plaques were selected on the basis of hybridization to H7 and H3 coding sequences. Recombinant plaques were plaque purified until a pure population containing both foreign genes was achieved. At this time the recombinant was declared vCP128 and a stock virus was established. Immunofluorescence analysis was performed using a monoclonal antibody specific for the H3 hemagglutinin and a polyclonal anti-H7 serum from horse. Surface fluorescence was detected on vCP128 infected VERO cells using both reagents indicating that both antigens were appropriately presented on the infected cell surface.

Immunoprecipitation analysis using the H3 specific monoclonal antibodies demonstrated the presence of a protein of approximately 75 kd in vCP128 infected CEF cells. This potentially represents the $HA_o$ precursor glycoprotein. No cleavage products were detected. Immunoprecipitation analysis using the H7 specific polyclonal serum demonstrated the presence of a precursor glycoprotein of approximately 75 kd. The $HA_1$ and $HA_2$ cleavage products with molecular weights of approximately 45 and 30 kd respectively were also visualized.

Plasmid pC3EIVHSI3L contains the hemagglutinin coding sequence of the equine-2 A2/Suffolk/89 subtype. The gene is linked to the vaccinia virus I3L promoter and inserted at the de-orfed C3 insertion site. ALVAC virus was used as the rescuing virus in in vitro recombination to rescue the foreign gene. Recombinant plaques were selected on the basis of hybridization to a H3 specific radiolabelled probe. Positive plaques were plaque purified until a pure recombinant population was achieved. At this time the recombinant was declared vCP159 and a virus stock established. Immunofluorescence analysis on vCP159 infected CEF cells using an H3 specific serum polyclonal from chicken indicated that an immunologically recognized protein was expressed on the infected cell surface.

EXAMPLE 47

DEVELOPMENT OF NYVAC RECOMBINANTS CONTAINING THE HEMAGGLUTININ GLYCOPROTEINS OF EQUINE INFLUENZA VIRUS SUBTYPES

Plasmid pEIVHAVQVV contains the sequences encoding equine-1, A1/Prague/56 (H7) and equine-2 A2/Fontainebleau/79 (H3). Both genes are linked to the vaccinia virus H6 promoter and inserted at the TK site. NYVAC (vP866) was used as the rescuing virus in in vitro recombination to rescue the foreign genes. Recombinant plaques were selected on the basis of hybridization to radiolabelled H3 and H7 specific proteins. Recombinant progeny virus was plaque purified until a pure population was achieved. At this time the recombinant was declared vP961 and a virus stock established. Immunofluorescence analysis using a H3 specific monoclonal antibody and a polyclonal anti-H7 serum indicated that both glycoproteins were expressed on the infected cell surface. Immunoprecipitation analysis with the same reagents indicated that the H3 glycoprotein was expressed as a precursor glycoprotein with a molecular weight of approximately 75 kd. No cleavage products were evidenced. The H7 glycoprotein was evident as a precursor glycoprotein of approximately 75 kd and HA$_1$ and HA$_2$ cleavage products with molecular weights of approximately 45 and 30 kd, respectively.

Plasmid pTKEIVHSI3L contains the coding sequence of the equine-2 A2/Suffolk/89 hemagglutinin glycoprotein. The coding sequence is linked to the I3L promoter and inserted at the TK site. NYVAC (vP866) was used as the rescuing virus and recombinant plaques selected on the basis of hybridization to a H3 specific radiolabelled probe. Recombinant plaque progeny were plaque purified until a pure population was achieved. At this time the recombinant was declared vP1063 and a virus stock established. Immunofluorescence analysis using a polyclonal anti-H3 serum from chicken indicated that an immunologically recognized protein was expressed on the infected cell surface.

EXAMPLE 48

CONSTRUCTION OF VACCINIA VIRUS/FELV INSERTION PLASMIDS

FeLV (Feline Leukemia Virus) env DNA sequences were supplied by Dr. F. Galibert (Laboratories d'Hematologie Experimentale Hospital Saint-Luis, Paris, France) in the form of a 2.4 kbp FeSV-SM DNA (Guilhot et al., 1987) fragment inserted into an M13mp8 vector (Messing, 1983). This 2.4 bp PstI/KpnI fragment containing the entire open reading frame (FeLV p70+p13E) was isolated and inserted into pUC18 (Messing, 1983) for convenience. The KpnI site at the 3' end of the env sequences were converted to a PstI site and the 2.4 kbp PstI fragment was isolated and ligated into PstI digested pTp15 (Guo et al., 1989). The resultant plasmid was designated pFeLV1A.

In vitro mutagenesis (Mandecki, 1986) was used to convert pFeLV1A to pFeLV1B. This was done using oligonucleotide SPBGLD (SEQ ID NO:307) (5'-AATAAATCACTTTTTATACTAATTCTTTATTCTATACTTAAAAAGT-3'). Mutagenesis with this oligonucleotide enabled the removal of the BglII site at the border of the H6 promoter and HA sequences. This provides the actual sequences of these DNA segments as found in the virus.

Plasmid pFeLV1B was then mutagenized with oligonucleotide FeLV5P (SEQ ID NO:308) (5'-CGCTATAGGCAATTCAAACATAGCATGGAAGGTCCAAACGCACCCA-3') to create pFeLV1C. In vitro mutagenesis was done as described by Mandecki (1986) with the following modification. Following digestion of pFeLV1B at the unique SmaI site, the DNA was digested with Bal31. At times 5 sec., 10 sec., 20 sec., 40 sec., and 80 sec., aliquots were taken and the reaction terminated by adding EGTA to a final concentration of 20 mM. The aliquots were pooled and used in the mutagenesis reaction. Resultant plasmid, pFeLV1C, contained the FeLV env gene juxtaposed 3' to the vaccinia virus H6 promoter such that there exists and ATG to ATG substitution. The plasmid, pFeLV1C, was used in in vitro recombination tests with vP425 as the rescuing virus to construct a recombinant vaccinia virus (vP453) which expresses the entire FeLV envelope glycoprotein.

The plasmid pFeLV1C was used as a reagent to generate pFeLV1D. This recombinant plasmid contains the entire FeLV env gene except it lacks the putative immunosuppressive region (Cianciolo et al., 1985; Mathes et al., 1978). The sequence encoding the immunosuppressive region (nucleotide 2252–2332 of sequence in Guihot et al., 1987) was deleted by in vitro mutagenesis (Mandecki, 1986) in the following manner. The plasmid, pFeLV1C, was linearized with BsmI. The linearized plasmid was treated with Bal31 and aliquots were taken at 1 min., 2 min., 4 min., and 8 min. and pooled for use in the mutagenesis reaction. In vitro mutagenesis was done using oligonucleotide FeLV1SD (SEQ ID NO:309) (5'-ACCTCCCTCTCTGAGGTAGTCTATGCAGATCACACCGGACTCGTCCGAGACAATATGGCTAAATTAAGAGAAAGACTAAAACAGCGGCAGCAACTGTTTGACTCCCAACAG-3'). The resultant plasmid, pFeLV1D, was used in in vitro recombination tests with vP410 as the rescuing virus to generate vP456. This vaccinia virus recombinant was generated to express the entire envelope glycoprotein lacking the putative immunosuppressive region.

EXAMPLE 49

CONSTRUCTION OF AVIPOXVIRUS/FeLV INSERTION PLASMIDS

For construction of the FP-1 recombinants, the 2.4 kbp H6/FeLV env sequences were excised from pFELV1A (described above) with BglII and by partial digestion with PstI. The BglII site is at the 5' border of the H6 promoter sequence. The PstI site is located 420 bp downstream from the translation termination signal for the envelope glycoprotein open reading frame.

The 2.4 kbp H6/FeLV env sequence was inserted into pCE11 digested with BamH1 and PStI. The FP-1 insertion vector pCE11, was derived from pRW731.13 by insertion of a multiple cloning site into the nonessential HindII site., This insertion vector allows for the generation of FP-1 genome. The recombinant FP-1/FeLV insertion plasmid was then designated pFeLVF1. This FP-1/FeLV insertion plasmid was then designated pFeLVF1. This construction does not: provide a precise ATG for ATG substitution.

To achieve the precise ATG:ATG construction, a NruI/SstII fragment of approximately 1.4 kbp was derived from the vaccinia virus insertion vector pFeLV1C (described herein). The NruI site occurs within the H6 promoter at a positive 24 bp upstream from the ATG. The SstII site located 1.4 kbp downstream from the ATG and 1 kbp upstream from the translation termination codon. The NruI/SstII fragment was ligated to a 9.9 kbp fragment which was generated by digestion of pFeLVF1 with SstII and by partial digestion with NruI. This 9.9 kbp fragment contains the 5.5 kbp FP-1 flanking arms, the pUC vector sequences, 1.4 kbp of FeLV sequence corresponding to the downstream portions of the env gene, and the 5'-most portion (approximately 100 bp) of the H6 promoter. The resultant plasmid was designated pFeLVF2. The precise ATG:ATG construction was confirmed by nucleotide sequence analysis.

A further FP-1 insertion vector, pFeLVF3, was derived from FeLVF2 by removing the FeLV env sequences corresponding to the putative immunosuppressive region (described above). This was accomplished by isolating a PstI/SstII fragment of approximately 1 kbp obtained from the vaccinia virus insertion vector, pFeLV1D (described above), and inserting this fragment into a 10.4 kbp PstI/SstII fragment containing the remaining H6/FeLV env gene derived by digestion of pFeLVF2 with PstI and SstII.

The insertion plasmids, pFeLVF2 and pFeLVF3, were used in in vitro recombination tests with FP-1 as the rescuing virus. Progeny virus was plated on primary chick embryo fibroblast (CEF) monolayers obtained from 10 day old embryonated eggs (SPAFAS, Storrs, Conn.) and recombinant virus screened for by plaque hybridization on CEF monolayers. Recombinant progeny identified by hybridization analyses were selected and subjected to four round of plaque purification to achieve a homogeneous population. An FP-1 recombinant harboring the entire FeLV env gene has been designated vFP25 and an FP-1 recombinant containing the FeLV env gene except the putative immunosuppressive region has been designated vFP32.

For construction of the CP recombinants, a 2.2 bp fragment containing the H6/FeLV env sequences were excised from pFeLVF2 and pFeLVF3 by digestion with KpnI and HpaI. The KpnI site is at the 5' border of the H6 promoter sequence. The HpaI site is located 180 bp downstream from the translation termination signal for the envelope glycoprotein open reading frame. These isolated fragments were blunt-ended. These 2.2 kbp H6/FeLV env sequences were inserted into the nonessential EcoRI site of the insertion plasmid pRW764.2 following blunt-ending of the EcoRI site. This insertion vector enables the generation of CP recombinants harboring foreign genes in the C3 locus of the CP genome. The recombinant CP insertion plasmid was then designated pFeLVCP2 and pFeLVCP3, respectively.

The insertion plasmids, pFeLVCP2 and pFeLVCP3, were used in in vitro recombination tests with CP as the rescuing virus. Progeny of the recombination were plated on primary CEF monolayers obtained from 10 day old embryonated eggs (SPAFAS, Storrs, Conn.) and recombinant virus selected by hybridization using radiolabeled FeLV DNA as a probe. Positive hybridizing plaques were selected and subjected to four rounds of plaque purification to achieve a homogeneous population. A recombinant expressing the entire FeLV env gene has been designated vCP35 and a recombinant expressing the entire env gene lacking the immunosuppressive region was designated vCP37.

EXAMPLE 50

GENERATION OF AN ALVAC-BASED RECOMBINANT CONTAINING THE FeLV-B env GENE

Plasmid pFeLV env 24 was obtained from Rhone-Merieux (Lyon, France) and contains the FeLV-B env gene. The plasmid contains a 4.2 kb cDNA derived fragment derived from the NCE161 FeLV strain. Plasmid pFeLV env 34 contains the 4.2 kb FeLV-B-specific insert in the SmaI site of pBS-SK (Strategene, La Jolla, Calif.). The sequence of the FeLV-B env gene is presented in FIG. 26 (SEQ ID NO:310). In this sequence the initiation codon (ATG) and termination codon (TGA) are underlined.

The expression cassette for the FeLV-B env was constructed as follows. The vaccinia virus H6 promoter was derived from plasmid pI4LH6HIV3B (described herein with respect to HIV) by PCR using oligonucleotides H65PH (SEQ ID NO:164) (5'-ATCATCAAGCTTGATTCTTTATTCTATAC-3') and H63PFB (SEQ ID NO:311) (5'-GGGTGCGTTGGACCTTCCATTACGATAGAAACTTAACGG-3'). Amplification of these sequences with these oligonucleotides generated an H6 promoter with a 5' HindIII site and a 3'-end containing the initial 20 bp of the FeLV-B env coding sequence.

The 5'-portion of the FeLV-B env gene was derived by PCR from pFeLV-B env 34 using oligonucleotides FB5P (SEQ ID NO:312) (5'-CCGTTAAGTTTGTATCGTAATGGAAGGTCCAAGCG-3') and FB5PA (SEQ ID NO:313) (5'-GGGTAAATTGCAAGATCAAGG-3'). This PCR-derived fragment contains homology to the 3'-most 23 bp of the H6 promoter (5'-end) and a unique ApaI site at position 546. The H6 promoter was fused to the 5'-end of the FeLV-B env gene by PCR using the two PCR fragments defined above as template and oligonucleotides FB5PA (SEQ ID NO:313) and H65PH (SEQ ID NO:164). The PCR fusion fragment was digested with HindIII and ApaI to yield a 680 bp fragment.

Plasmid pFeLV-B env 34 was digested with ApaI and NcoI to liberate a 740 bp fragment containing the middle portion of the env gene (FIG. 26). The 3'-end of the gene was derived by PCR using pFeLV-b env 34 as template and oligonucleotides FBT5D (SEQ ID NO:314) (5'-CCCCATGCATTTCCATGGCAGTGCTCAATTGGACCTCTGATTTCTGTGTCTTAATAG-3') and FB3PX (SEQ ID NO:315) (5'-ATCATCTCTAGAATAAAAATCATGGTCGGTCCGGATC-3'). PCR amplification of the 3' portion of the env gene with these oligonucleotides eliminated a T5NT element at position 1326–1332. This sequence was altered by making a T to C substitution at position 1329 (FIG. 26). This change does not alter the amino acid sequence of the env gene product. The 3'-end of the gene was engineered with an XbaI site and a T5NT sequence. The 5'-end of this PCR-derived fragment also contains a unique NcoI site (corresponds with that at position 1298; FIG. 26). This fragment was digested with NcOI and XbaI to generate a 707 bp fragment.

The 740 bp NcoI/ApaI and 707 bp NcoI/XbaI fragments were co-inserted into pBS-SK digested with ApaI and XbaI. The resultant plasmid was designated as pBSFB3P. The 1.5 kb ApaI/XbaI fragment from pBSFB3P was then co-inserted into pBS-SK, digested with HindIII and XbaI, with the 680 bp PCR fragment containing the H6 promoted 5'-end of the FeLV-B env gene (above). The resultant plasmid was designated as pB5FEB.

The 2.2 kb HindIII/XbaI fragment from pB5FEB, containing the H6 promoted FeLV-B env gene, was isolated and blunt-ended with the Klenow fragment. This blunt-ended fragment was inserted into pC5L (see discussion regarding HIV herein) digested with SmaI to yield pC5LFEB.

Plasmid pC5LFEB was used in standard in vitro recombination assays with ALVAC(CPpp) as the rescue virus. Recombinant plaques were identified using FeLV-B env specific DNA probes. Following three round of plaque purification, the virus was propagated and designated as vCP177.

EXAMPLE 51

GENERATION OF AN ALVAC-FeLV-A ENV RECOMBINANT VIRUS

The plasmid pFGA-5 from which the FeLV-A env sequences were derived was provided by Dr. J. Nell (University of Glasgow) and described previously (Stewart et al., 1986). Initially, the 531 bp PstI/HindIII fragment corresponding to nucleotides 1 to 531 (Stewart et al., 1986) was excised and ligated into pCPCV1 digested with PstI and HindIII and designated as pC3FA-1. The plasmid pCPCV1 was derived as follows. Plasmid pFeLV1A was digested with PstI to excise the FeLV sequences and religated to yield plasmid pFeLVF4. The vaccinia virus H6 promoter element (Taylor et al., 1988) followed by a polylinker region were liberated from pFeLVF4 by digestion with KpnI and HpaI. The 150 bp fragment was blunt-ended using T4 DNA polymerase and inserted into pRW764.2, a plasmid containing a 3.3 kb PvuII genomic fragment of canarypox DNA. pRW764.2 was linearized with EcoRI, which recognizes a unique EcoRI site within the canarypox sequences, and blunt-ended using the Klenow fragment of the E. coli DNA polymerase. The resultant plasmid was designated as pCPCV1. This plasmid contains the vaccinia virus H6 promoter followed by a polylinker region and flanked by canarypoxvirus homologous sequences.

The plasmid pC3FA-1 was linearized with PstI and mutagenized in an in vitro reaction via the Mandecki procedure (1986) using oligonucleotide FENVAH6-1 (SEQ ID NO:316) (5'-CCGTTAAGTTTGTATCGTAATG-GAAAGTCCAACGCAC-3'). The in vitro mutagenesis procedure removed extraneous 5'-noncoding sequences resulting in a precise ATG:ATG configuration of the vaccinia H6 promoter element and the FeLV-A env sequences. The resultant plasmid was designated as pH6FA-1.

The remainder of the FeLV-A env gene was derived from pFGA-5 by standard PCR using custom synthesized oligonucleotides (Applied Biosystems, San Rafael, Calif.). An 836 bp PCR fragment was derived using pFGA-5 as template and the oligonucleotides FENVA-2 (SEQ ID NO:317) (5'-CCATAATTCGATTAAGACACAGAATTCA-GAGGTCCAATTGAGCACC-3') and FENVAH (SEQ ID NO:318) (5'-CAAGATGGGTTTTGTGCG-3'). This fragment corresponds to nucleotides 488 to 1327 of the FeLV-A env gene (Stewart et al., 1986). The use of oligonucleotide FENVA-2 (SEQ ID NO:317) alters the nucleotide sequence at positions 1301 to 1309 from $GAT_5GT$ to GAATTCTGT. This alteration eliminates the T5NT sequence motif known to be recognized as a poxvirus early transcription termination signal (Yuen and Moss, 1987) and introduces an EcoRI restriction site at this position. These nucleotide manipulations change amino acid 414 from glutamic acid to the conserved amino acid aspartic acid (Stewart et al., 1986). Amino acid 415 is not altered by these nucleotide changes. This 836 bp fragment was digested with HindIII and EcoRI to generate a 770 bp fragment corresponding to nucleotides 532 to 1302 of the FeLV-A env gene.

A 709 bp PCR fragment was derived using pFGA-5 as template and the oligonucleotides FENVA-3 (SEQ ID NO:319) (5'-GGTGCTCAATTGGACCTCTGAATTCTGT-GTCTTAATCGAATTATGG-3') and FENVA-4 (SEQ ID NO:320) (5'-ATCATCAAGCTTTCATGGTCGGTCCGG-3'). This fragment corresponds to nucleotides 1281 to 1990 of the FeLV-A env gene (Stewart et al., 1986). Using oligonucleotide FENVA-3 (SEQ ID NO:319) to amplify this fragment also alters the T5NT element and introduces an EcoRI site as above for the 836 bp PCR derived fragment. The 709 bp fragment was digested with EcoRI/HindIII and the resultant fragment was co-inserted with the 770 bp HindIII/EcoRI fragment, derived from the 836 bp fragment (above), into pBS-SK (Stratagene, La Jolla, Calif.) digested with HindIII. The resultant plasmid was designated as pF3BS1-B and the FeLV env sequences were confirmed by nucleotide sequence analysis.

To reconstruct the entire FeLV-A env gene linked precisely to the vaccinia virus H6 promoter, a 1.5 kb HindIII fragment was isolated from pF3BS1-B. This fragment corresponds to nucleotides 532 to 1990of the FeLV-A env (Stewart et al., 1986). The 1.5 kb HindIII fragment was ligated to pH6FA-1 digested with HindIII. Plasmid constructs containing the 1.5 kb HindIII fragment were screened for the proper orientation by restriction analysis and a plasmid clone containing the entire intact FeLV-A env gene linked to the H6 promoter was designated as pH6FA-3.

The 2.2 kb H6FeLV-A env expression cassette was excised from pH6FA-3 by partial digestion with EcoRI followed by a partial digestion with HindIII. The fragment was inserted into pRW831 digested with HindIII and EcoRI. The resultant plasmid was designated as pC5FA.

pRW831 refers to an ALVAC (CPpp) insertion plasmid which enables the insertion of foreign genes into the C5 open reading frame. In the process of insertion into this region, the use of pRW831 causes the deletion of most of the C5 open reading frame. To generate pRW831 the following manipulations were done. An 880 bp PvuII genomic fragment from the canarypoxvirus genome was inserted between the PvuII sites of pUC9. The canarypox sequences contained within the resultant plasmid, pRW764.5, was analyzed by nucleotide sequence analysis and the C5 open reading frame was defined. Previously, insertion between a pair of BglII sites situated within the C5 ORF was used to engineer recombinants at this locus (Taylor et al., 1992). The sequence of the entire region is provided in FIG. 16 (SEQ ID NO:220). The nucleotide sequence begins (SEQ ID NO:220) at the PvuII site. The C5 ORF initiates at position 166 and terminates at nucleotide 487. Precise manipulation of these sequences enabled the deletion of nucleotides 167 through 455. Such a deletion was made so as not to interrupt the expression of other viral genes.

The procedure to derive pRW831 is as follows. pRW764.5 was partially digested with RsaI and the linearized fragment was isolated. The RsaI linear fragment was redigested with BglII. The resultant 2.9 kb RsaI/BglII fragment (deleted of nucleotides 156 through 462) was isolated and ligated to annealed oligonucleotides RW145 (SEQ ID NO:107) and RW146 (SEQ ID NO:108). The resultant plasmid was designated as pRW831 and contains a sequence with unique HindIII, SmaI, and EcoRI sites in place of the C5 sequences.

Plasmid pC5FA was used in recombination experiments with ALVAC(CPpp) as the rescuing virus. Recombinant viruses were identified by in situ plague hybridization using a radiolabeled FeLV-A end-specific probe. Following three cycles of plaque purification with subsequent hybridization confirmation, the recombinant was designated as vCP83.

EXAMPLE 52

GENERATION OF AN ALVAC-FeLV-A ENV RECOMBINANT VIRUS LACKING THE PUTATIVE IMMUNOSUPPRESSIVE REGION OF p15E

The putative immunosuppressive region is situated within the p15E transmembrane region of the FeLV envelope glycoprotein (Cianciolo et al., 1986; Mathes et al., 1978). This region was deleted in the following manner. The FeLV-A env sequences from nucleotide 1282 to 1602 (Stewart et al., 1986) were amplified by PCR from pFGA-5 using oligonucleotides FENVA-3 (SEQ ID NO:320) and IS-A (SEQ ID NO:321) (5'-TAAGACTACTTCAGAAAG-3'). The env sequences from nucleotide 1684 to 1990(Stewart et al., 1986) were amplified by PCR from pFGA-5 using oligonucleotides FENVA-4 (SEQ ID NO:320) and IS-B (SEQ ID NO:323) (5'-GCGGATCACACCGGACTC-3'). The former PCR-derived fragment was digested with EcoRI and the latter with HindIII and was subsequently kinased with ATP and T4 kinase. These fragments were co-ligated into pBS-SK digested with HindIII and EcoRI. The resultant plasmid was confirmed by nucleotide sequence analysis and designated as pBSFAIS⁻. Ligation of the above fragments joins the sequences 5' and 3' to the 81 bp DNA segment encoding the putative immunosuppressive region and, therefore, deletes the sequences encoding the immunosuppressive peptide.

The FeLV-A sequences lacking the region encoding the immunosuppressive region were excised from pC5FA by digestion with SstII/ApaI. This 381 bp fragment was replaced by the 300 bp SstII/ApaI fragment from pBSFAIS⁻. The ligation that was done was with a 4.8 kb SstII/ApaI fragment from pC5FA and the 300 bp fragment described above. The resultant plasmid was designated pC5FAISD.

The plasmid pC5FAISD was employed in recombination experiments with ALVAC (CPpp) as the rescuing virus. Recombinant viruses were identified by in situ hybridization using a radiolabeled FeLV-A env specific probe. Following three cycles of plaque purification, the recombinant was designated as vCP87. This recombinant contains the FeLV-A env gene lacking the region encoding the putative 27 amino acid immunosuppressive region. The gene was inserted into the C5 locus.

EXAMPLE 53

GENERATION OF ALVAC-FeLV-A gag RECOMBINANT VIRUSES

The FeLV-A gag/pol sequences were derived from plasmid pFGA-2 gag. This plasmid was derived from the FeLV-A infectious clone pFGA-2 (Stewart et al., 1986) by subcloning the 3.5 kb PstI subfragment containing a portion of the LTR (651 bp) sequences, the entire gag gene, and 1272 bp of the pol gene. The 3.5 kb fragment was inserted into PstI digested pUC8 (Bethesda Research Laboratories, Gaithersburg, Md.). Initially, this 3.5 kb PstI FeLV-A DNA fragment was isolated and inserted into pBS-SK (Stratagene, La Jolla, Calif.). The resultant plasmid was designated as pBSGAG. The entire 3.5 kb insert was analyzed by nucleotide sequence (SEQ ID NO:324) (FIG. 27) analysis to confirm position of the initiation codon (nucleotide 652 to 654 underlined in FIG. 27) and pertinent restriction sites defined in the nucleotide sequence of the gag region previously reported for FeLV-B (Leprevotte et al., 1984).

The plasmid pFGA-2 gag was digested with BglII and PstI to liberate a 2.5 kb fragment. BglII recognizes a site at nucleotide position 1076 (SEQ ID NO:324) while PstI recognizes a site at the end of the FeLV-A insert. The 2.5 kb fragment was isolated and redigested with HindIII and PstI which recognize sites within the co-migrating plasmid sequences. This eliminated the ability of the plasmid sequences to compete in subsequent ligation reactions.

PCR was used to derive the 5' portion of the FeLV-A gag coding sequences. The plasmid pFGA2 gag was used as template with oligonucleotides FGAGBGL (SEQ ID NO:325) (5'-GATCTCCATGTAGTAATG-3') and FGAGATG (SEQ ID NO:326) (5'-CGATATCCGT-TAAGTTTGTATCGTAATGTCTGGAGCCTCTAGTG). Oligonucleotide FGAGATG (SEQ ID NO:326) contains the 3'-most 25 nucleotides of the vaccinia virus H6 promoter and includes the 3'-most 3 bp of the NruI site at its' 5'-end. These H6 sequences are precisely joined at the ATG (initiation codon) and the nucleotides corresponding to the initial 16 nucleotides of the gag coding sequence. Oligonucleotide FGAGBGL (SEQ ID NO:325) corresponds to the reverse complement of sequences 59 bp downstream from the unique BglII site in the gag sequences (Leprevotte et al., 1984). PCR using these reagents yielded a 500 bp fragment which was subsequently digested with BglII to generate a 450 bp fragment.

The 450 bp BglII digested PCR-derived fragment was coligated with the 2.5 kb BglII/PstI fragment, containing the remainder of the gag gene and a portion of the pol gene, and pCPCV1 (above in env construction) digested with NruI and PstI. pCPCV1 (NruI/PstI) contains the 5' portion of the vaccinia virus H6 promoter including the 5'-most 3 bp of the NruI recognition signal. The resultant plasmid was designated as pC3FGAG.

The plasmid pC3FGAG was linearized with PstI, blunt-ended with T4 DNA polymerase and ligated to a 100 bp SspI/SmaI fragment excised from pSD513 (defined in Example 7). The 100 bp SspI/SmaI fragment provides termination codons at the 3' end of the FeLV-A gag/pol sequences. The resultant plasmid was designated as pC3FGAGVQ.

The FeLV-A gag/pol expression cassette was excised from pC3FGAGVQ by digestion with EcoRI and HindIII. The resultant 3.4 kb fragment was isolated and ligated with pC3I (defined in Example 32) digested with EcoRI and HindIII to yield pC3D0FGAGVQ.

The plasmid pC3DOFGAGVQ was used in in vitro recombination experiments with vCP83 and vCP87 as rescue viruses. The recombinant containing the FeLV-A gag/pol sequences and the entire FeLV-A env gene was designated as vCP97 while the recombinant containing the same gag/pol sequences and the entire FeLV-A env lacking the immunosuppressive region was designated vCP93.

EXAMPLE 54

INSERTION OF FeLV-A gag INTO A VACCINIA VIRUS BACKGROUND

The insertion plasmid pCEN151 was generated by cloning a 3.3 kb EcoRI/HindIII fragment from pC3FGAG (above) into the SmaI site of pSD553. This insertion was performed following blunt-ending the fragment with the Klenow fragment of the *E. coli* DNA polymerase in the presence of 2 mM dNTPs.

Plasmid pSD553 is a vaccinia deletion/insertion plasmid of the COPAK series. It contains the vaccinia K1L host range gene (Gillard et al., 1986; Perkus et al., 1990) within flanking Copenhagen vaccinia arms, replacing the ATI region (ORFS A25L, A26L; Goebel et al., 1990a,b). pSD553 was constructed as follows. The polylinker region located at the vaccinia ATI deletion locus of plasmid pSD541 (defined in Example 10) was expanded as follows. pSD541 was cut with BglII/XhoI and ligated with annealed complementary synthetic deoxyoligonucleotides MPSYN333 (SEQ ID NO:329) (5'-GATCTTTTGTTAACAAAAACTAATCAGC-TATCGCGAATCGATTCCCGGGGGATCCGGTACCC-3') and MPSYN334 (SEQ ID NO:330) (5'-TCGAGGGTAC-CGGATCCCCCGGGAATCGATTCGCGAT-AGCTGATTAGTTTTTGTTAACAAAA-3') generating plasmid pSD552. The K1L host range gene was isolated as a 1 kb BalII(partial)/HpaI fragment from plasmid pSD452 (Perkus et al., 1990). pSD552 was cut with BglII/HpaI and ligated with the K1L containing fragment, generating pSD553.

Plasmid pCEN151 was used in in vitro recombination experiments with vP866 as rescue virus to generate Vp1011.

EXAMPLE 55

IMMUNOFLUORESCENCE AND IMMUNOPRECIPITATION ANALYSIS OF FeLV ENV AND gag GENES IN ALVAC RECOMBINANT VIRUSES Immunoprecipitation. Vero cell monolayers were infected at an m.o.i. equal to 10 pfu/cell with parental or recombinant viruses. At 1 hr post-infection, the inoculum was aspirated and methionine-free medium supplemented with ($^{35}$S)-methionine (DuPont, Boston, Mass.; 1000 Ci/mmol), 20 µCi/ml was added and further incubated till 18 hr post-infection. Immunoprecipitation and immunofluorescence analyses were performed as described previously (Taylor et al., 1990) using a bovine anti-FeLV serum (Antibodies, Inc., La Jolla, Calif.) or a monoclonal antibody specific for the p27 core protein (provided by Rhone-Merieux, Inc., Athens, Ga.).

FeLV Virus Isolation. On day one, $3 \times 10^4$ QN10 cells/well were plated in a 12-well plate in 1 ml of Dulbecco's MEM containing HEPES buffer (DFB), 10% FBS, and 4 µg/ml polybrene. The cells were incubated overnight at 37° C. Without removing the medium, 200 µl of sample (cat plasma) was added to each well. Following a 2 hr incubation at 37° C., the medium as replaced with 1.5 ml of fresh DFB and allowed to further incubate at 37° C. On day five, plates were examined for transformation. If negative, medium was replaced with 1.5 ml of fresh DFB and again allowed to further incubate at 37° C. On day eight, plates were re-examined for transformation. If negative, cells were subcultured in 5 cm plates by dispersing cells by two washes with trypsin-EDTA and placing in 4 ml DFB for inoculation into a 5 cm plate. Cells were allowed to incubate for four days at 37° C. prior to examination for transformation.

Detection of FeLV Antigen By Immunofluorescence. Blood smears were fixed for five min in MeOH at $-20°$ C., washed in dH$_2$O, and then air dried. A volume of 24 µl of rabbit anti-FeLV antibody was applied to the blood smear within a circle inscribed on the smear with a diamond pen. The smear was incubated in the presence of the antibody for 1 hr at 37° C. in a humidified chamber prior to washing three times with PBS and one time with dH$_2$O. The smear was then air dried. A volume of 25 µl of goat anti-cat IgG-FITC was applied to the circle and incubated as above with the primary antiserum. The sample was washed and dried as above for the primary antiserum prior to examination for immunofluorescence in a microscope with a ultra violet light source.

FeLV Antibody Neutralization Assay. On day one, $5 \times 10^4$ QN10 cells/well were plated in a 12-well plate in 1 ml DFB plus 4 µg/ml polybrene. The cells were inoculated at 37° C. Serum dilutions were prepared in round bottom 96 well plates from 1:2 to 1:256 using 50 µl volumes of Leibowitz medium. Added 50 µl FeLV-A at $4 \times 10^5$ focus forming units (ffu) per ml. Two wells were included with medium without serum as a virus control. Plates were incubated for 2 hr at 37° C. Following the 2 hrs adsorption period, 25 µl of each dilution was placed into a well of QN10 cells. Virus control was titrated by diluting 1:2, 1:4, 1:8, and 1:6 in 50 µl volumes of Leibowitz medium in the 96-well plate prior to inoculation of QN10 cells with 25 µl onto QN10 cells. Plates were inoculated at 37° C. for three days. On day day, medium was replaced with 1 ml of DFB/well. Two days later, foci were counted under a microscope. Neutralizing antibody titers were estimated as the dilution of serum producing 75% reduction in focus count compared to virus control.

In order to determine whether the env gene product expressed by vCP83 and vCP87 was transported to the plasma membrane of infected cells, immunofluorescence experiments were performed as described previously (Taylor et al., 1990). Primary CEF monolayers were infected with parental (ALVAC) or recombinant viruses, vCP83 and vCP87 and immunofluorescence was performed at 24 hr post-infection using a bovine anti-FeLV serum. The results demonstrate that cells infected with vCP83 showed strong surface fluorescent staining, whereas cells infected with vCP87 or parental ALVAC virus showed no significant surface staining.

Expression of the FeLV env gene product was also analyzed in immunoprecipitation assays using the bovine anti-FeLV serum. No FeLV-specific protein species were precipitated from lysates derived from uninfected CEFs or CEFs infected with the parental ALVAC virus. Three FeLV-specific proteins were precipitated from vCP83 infected cells with apparent molecular weights of 85 kDa, 70 kDa, and 15 kDa. This result is consistent with expression of the precursor env gene product (85 kDa) and the mature cleavage products p70 and p15E. Immunoprecipitation from lysates derived form vCP8 infected cells demonstrated a single FeLV-specific protein species with an apparent molecular weight of 83 kDa. This is consistent with expression of a non-proteolytically processed env gene product of the size expected following deletion of the putative immunosuppressive region. So, in short, expression of the env lacking the immunosuppressive region was apparently not properly transported to the surface of infected cells nor was it proteolytically cleaved to mature env specific protein forms.

Expression of the FeLV gag-specific gene products was analyzed by immunoprecipitation using monoclonal antibodies specific to an epitope within the p27 core protein (D5) and the bovine anti-FeLV serum. No FeLV-specific proteins were precipitated from lysates derived from uninfected cells or cells infected with parental viruses. Clearly, from vP1011, vCP93, and vCP97 infected cells, FeLV specific protein species of 55 kDa were precipitated with the D5 and bovine anti-FeLV serum. Protein species of these apparent molecular weights are consistent with gag-specific precursor forms. Low levels of a 27 kDa protein species consistent with the size of the mature p27 core protein were also apparent.

EXAMPLE 56

IN VIVO EVALUATION OF vCP93 AND vCP97

The protective efficacy of vCP93 and vCP97 were evaluated by a live FeLV challenge of cats following two inoculations of the recombinant viruses. The ALVAC-based FeLV recombinants were administered via the subcutaneous route with $10^8$ PFU on days 0 and 28. Cats were challenged by an oronasal administration of an homologous FeLV-A strain (Glasgow-1) at seven days following the booster inoculation. Blood samples were obtained pre- and post-challenge for evaluation of FeLV antigenemia (p27 detection), FeLV isolation, the presence FeLV antigen in white blood cell (WBC) smears by immunofluorescence, and the induction of FeLV neutralizing activity.

No adverse reactions were observed following vaccination with the ALVAC (canarypoxvirus)-based recombinant viruses, vCP93 and vCP97. All six non-vaccinated controls succumbed to the FeLV challenge and developed a persistent viremia by three weeks following the challenge exposure. This was evidenced by detection of p27 antigen in the blood, FeLV isolation and detection of FeLV antigen by immunofluorescent analysis of WBC smears (Table 32). The non-vaccinated controls remained persistently infected for the remainder of the study (until 12 weeks post-challenge).

A persistent viremia developed in three of six cats vaccinated with vCP93 at three weeks post-challenge. At this timepoint, blood samplings from these three cats were shown to contain p27 antigen and/or live FeLV (Table 32). One of these cats (No. 2) resolved this infection by six weeks post-infection and remained free of viremia through 12 weeks post-challenge. The other two cats (No. 1 and 5) remained persistently infected by the three criteria, p27 antigenemia, FeLV isolation, and FeLV antigen detection in WBCs. Three of six cats vaccinated with vCP93 (No. 3, 4, and 6) were free of persistent viremia through nine weeks post-challenge (Table 32). Two of these cats (No. 3 and 6) remained free of circulating virus through week 12 post-challenge, while one cat (No. 4) became suddenly infected at 12 weeks. So, partial protection (three of six cats) was afforded protection against persistent viremia by vaccination with vCP93.

Most impressively, all six cats vaccinated with vCP97 were fully protected against the homologous challenge with FeLV-A (Glasgow-1). Only one of these cats (No. 12) evidenced any suggestion of persistent viremia. This occurred at three weeks post-challenge when p27 antigen was detected in the blood sample (Table 32). No live FeLV was ever isolated from the blood of this cat following challenge. All other cats were free of p27 antigenemia, free of live FeLV, and never demonstrated any FeLV antigen in WBC smears for 12 weeks following challenge exposure (Table 32).

Evolution of FeLV Neutralizing Antibodies. Due to the potential role of neutralizing antibodies in protection against FeLV infection (Russell and Jarrett, 1978; Lutz et al., 1980), the generation of such a response was monitored pre- and post-challenge. None of the cats in the study, whether vaccinated with vCP93 or vCP97, demonstrated any neutralizing antibody titers prior to FeLV challenge (Table 33). Following challenge, none of the cats which developed a persistent viremia had any detectable neutralizing antibody titers. Significantly, cats protected against a persistent infection developed FeLV-specific serum neutralizing titers (Table 33). These titers increased in magnitude in all protected cats following challenge, with the highest level being observed at the terminal time point of the study, at 12 weeks post-challenge (Table 33).

TABLE 32

Response of cats to challenge with feline leukemia virus

| Group | Cat No. | Time (weeks) relative to challenge | | | | | | |
|---|---|---|---|---|---|---|---|---|
| | | −5 $E^1V^2$ | −2 EV | 0 EV | +3 EV | +6 $F^3EV$ | | +9 FEV | +12 FEV |
| 1. vCP 93: Felv-A env(IS−) +gag/pol | 1 | — | — | — | ++ | −++ | +++ | +++ | |
| | 2 | — | — | — | −+ | — | — | — | |
| | 3 | — | — | — | — | — | — | — | |
| | 4 | — | — | — | — | — | — | — | ++ |
| | 5 | — | — | — | ++ | −++ | +++ | +++ | |
| | 6 | — | — | — | — | — | | | |
| 2. vCP 97: Felv-A env(IS+) +gag/pol | 7 | — | — | — | — | — | — | — | |
| | 8 | — | — | — | — | — | — | — | |
| | 9 | — | — | — | — | — | — | — | |
| | 10 | — | — | — | — | — | — | — | |
| | 11 | — | — | — | — | — | — | — | |
| | 12 | — | — | — | +− | — | — | — | |
| 3. Unvaccinated Controls | 13 | — | — | — | ++ | −++ | +++ | +++ | |
| | 14 | — | — | — | ++ | −++ | +++ | +++ | |
| | 15 | — | — | — | ++ | +++ | +++ | +++ | |
| | 16 | — | — | — | ++ | −++ | +++ | +++ | |
| | 17 | — | — | — | ++ | −++ | +++ | +++ | |
| | 18 | — | — | — | ++ | −++ | +++ | +++ | |

TABLE 32-continued

Response of cats to challenge with feline leukemia virus

| | | Time (weeks) relative to challenge | | | | | | |
|---|---|---|---|---|---|---|---|---|
| Group | Cat No. | −5 E[1]V[2] | −2 EV | 0 EV | +3 EV | +6 F[3]EV | | +9 FEV | +12 FEV |

*E = FeLV p27 antigen in plasma (ELISA)
V = infectious virus in plasma (virus isolation)
F = FeLV antigen in blood smears (immunofluorescence)

TABLE 33

FeLV neutralizing antibody titers[1]

| | | Weeks Relative to Challenge | | | | | |
|---|---|---|---|---|---|---|---|
| Group | Cat. No. | −5 | −2 | 0 | +3 | +6 | +9 | +12 |
| vCP93 | 1 | 0 | 0 | 0 | 0 | 0 | 0 | 0 |
| | 2 | 0 | 0 | 0 | 0 | 0 | 4 | >32 |
| | 3 | 0 | 0 | 0 | 0 | 0 | 4 | 16 |
| | 4 | 0 | 0 | 0 | 0 | 0 | 0 | 0 |
| | 5 | 0 | 0 | 0 | 0 | 0 | 0 | 0 |
| | 6 | 0 | 0 | 0 | 0 | 0 | 4 | >32 |
| vCP97 | 7 | 0 | 0 | 0 | 0 | 0 | 4 | 16 |
| | 8 | 0 | 0 | 0 | 0 | 0 | 0 | >32 |
| | 9 | 0 | 0 | 0 | 0 | 0 | 4 | 8 |
| | 10 | 0 | 0 | 0 | 0 | 0 | 4 | 16 |
| | 11 | 0 | 0 | 0 | o | 0 | 4 | 8 |
| | 12 | 0 | 0 | 0 | 0 | 0 | 4 | >32 |
| Unvaccinated Controls | 13 | 0 | 0 | 0 | 0 | 0 | 0 | 0 |
| | 14 | 0 | 0 | 0 | 0 | 0 | 0 | 0 |
| | 15 | 0 | 0 | 0 | 0 | 0 | 0 | 0 |
| | 16 | 0 | 0 | 0 | 0 | 0 | 0 | 0 |
| | 17 | 0 | 0 | 0 | 0 | 0 | 0 | 0 |
| | 18 | 0 | 0 | 0 | 0 | 0 | 0 | 0 |

[1]expressed as dilution of serum producing 75% reduction in focus count.

EXAMPLE 57

GENERATION OF ALVAC-BASED RECOMBINANT EXPRESSING THE FHV-1 gD GLYCOPROTEIN

Expression of the feline herpesvirus type 1 (FHV-1) gD glycoprotein was accomplished by insertion of the FHV-1 gD homolog gene under the control of the vaccinia virus I3L promoter into the ALVAC vector. The donor plasmid required to insert the cassette I3L-FHV-1 gD into ALVAC was generated as follows.

The FHV-1 CO strain genomic DNA was completely digested with EcoRI and the fragment M (4470 bp) was excised from the agarose gel (Geneclean procedure) and cloned into vector pBS-SK+ digested with EcoRI and phosphatased. The resulting plasmid containing the FHV-1 EcoRI M fragment was designated pHFeM2. The FHV-1 EcoRI M fragment complete nucleotide sequence for both strands was obtained from several subclones of the FHV-1 EcoRI M fragment inserted into vector pBS-SK+, using the modified T7 enzyme Sequenase (U.S. Biochemical Corp.) (Tabor and Richardson, 1987). Standard dideoxynucleotide chain termination reactions (Sanger et al., 1977) were performed using double-stranded templates that had been denatured in 0.4 M-NaOH (Hattori and Sakaki, 1986). The M13 forward and reverse primers were used to obtain the initial sequence of each clone. Custom primers (18 mer), synthesized by using standard chemistries (Biosearch 8700 and Applied Biosystems 380B) were used for subsequent sequence reactions. Sequences of the junctions between consecutive fragments were confirmed on the initial clone, pHFeM2. The PC\GENE (Intelligenetics) and IBI Pustell software packages were used in all sequence data analyses. Homology searches were done with the FASTP program (Lipman and Pearson, 1985) against Swissprot release 18.0 (Intelligenetics). The full sequence of the FHV-1 CO strain gD homolog gene is shown in FIG. 28 (SEQ ID NO:290).

The 185 bp 5'-most region of the FHV-1 gD coding sequence was derived using the plasmid pHFeM2 as template and oligonucleotides JCA234 (SEQ ID NO:331) (5'-ATGATGACACGTCTACATTTT-3') and JCA235 (SEQ ID NO:332) (5'-TGTTACATAACGTACTTCAGC-3') and digested with BamHI. This 185 bp fragment was fused to a 120 bp PCR-derived fragment containing the I3L promoter element obtained using plasmid pMP691 (I3L101RAB) and oligonucleotides MP287 (SEQ ID NO:226) (5'-GAT-TAAACCTAAATAATTGT-3') and JCA158 (SEQ ID NO:225) (5'-TTTTTCTAGACTGCAGCCCGGGACAT-CATGCAGTGGTTAAAC-3') and digested with XbaI. The 185 bp and 120 bp fragments were ligated together into vector pBS-SK+ digested with XbaI and BamHI to produce plasmid pJCA071. Sequences of the I3L promoter, of the junction I3L-ATG and of the FHV-1 gD 5'-most region were confirmed by direct sequencing of pJCA071. Plasmid pJCA067 is a subclone of FHV-1 EcoRI M fragment. It has been generated as follows. Plasmid pHFeM2 was digested with BamHI and the 1850 bp BamHI-BamHI fragment was excised from the agarose gel and ligated into pBS-SK+ digested with BamHI. This clone contains the 3'-region of FHV-1 gD and sequences further downstream. Plasmid pJCA067 was digested with BamHI and XhoI to excise the 1270 bp BamHI-FHV-1 gD 3'-region-gI 5'-region-XhoI fragment. This fragment was ligated into vector pBS-SK+ digested with BamHI and XhoI to produce pJCA072. The 3'-most 290 bp of the FHV-1 gD coding sequence was derived by PCR using plasmid pHFeM2 as template and oligonucleotides JCA237 (SEQ ID NO:333) (5'-AATTTTCTCGAGAAGCTTGTTAA-CAAAAATCATTAAGGATGGTAGATTGCATG-3') and JCA242 (SEQ ID NO:334) (5'-GAGGATTCGAAACG-GTCC-3'). Synthesis of this fragment with these custom synthesized oligonucleotides 1) contains the 3' most sequences of FHV-1 gD and XbaI site at the 5'end, and 2) adds a T5NT element and unique HpaI, HindIII and XhoI sites at the 3'end of the FHV-1 gD coding sequence. This fragment was digested with XbaI and XhoI and ligated with the 3575 bp XbaI-XhoI fragment obtained from plasmid pJCA072 digested with XbaI and XhoI. The resulting plasmid was designated pJCA073.

Sequence of the 290 bp XbaI→XhoI portion of FHV-1 gD was confirmed by direct sequencing of pJCA073. Plasmid pJCA071 was digested with SmaI and BamHI to excise the 305 bp SmaI-I3L-FHV-1 gD 5'-most region-BamHI fragment. Plasmid pJCA073 was digested with BamHI and XhoI to excise the 970 bp BamHI-FHV-1 gD 3'region-XhoI fragment. The SmaI-BamHI 305 bp and the BamHI-XhoI 970 bp fragments were finally ligated together into vector pCPC6L (C6 deorfed locus; see other ALVAC C6 donor plasmids for the generation of pCPC6L) digested with SamI and XhoI. The plasmid resulting from this ligation was designated pJCA084.

The plasmid pJCA084 was used in in vitro recombination experiment in primary chick embryo fibroblasts with CPpp as rescue virus to yield vCP162. Recombinant virus was identified by in situ hybridization according to standard procedures (Piccini et al., 1987) using a radiolabeled FHV-1 gD specific probe. Recombinant plaques were purified by three rounds of plaque purification and amplified for further analysis. Recombinant virus vCP162 contains the FHV-1 gD coding sequence in the C6 locus of canarypox virus.

EXAMPLE 58

EXPRESSION ANALYSIS OF vCP162

Immunofluorescence assays were performed as described previously (Taylor et al., 1990) using a sheep anti-FHV-1 gD polyclonal serum obtained from D. Fargeaud, Rhone-Merieux, France. Recombinant vCP162 displayed intense internal as well surface fluorescence, indicating expression of FHV-1 gD glycoprotein on the surface of the infected cells.

Immunoprecipitation was done using the same antiserum to determine the authenticity of the expressed FHV-1 gD product. This procedure was done according to that previously described (Taylor et al., 1990). The sheep anti-FHV-1 gD serum precipitated a product with an apparent molecular mass on an SDS-PAGE gel system (Dreyfuss et al., 1984) of 60 kDa from lysates derived from cells infected with the recombinant virus vCP162. No protein was precipitated from uninfected cells or lysates derived from parental canarypox virus (CPpp) infected cells.

EXAMPLE 59

GENERATION OF NYVAC- AND ALVAC-BASED RECOMBINANTS EXPRESSING THE HANTAAN VIRUS G1 AND G2 GLYCOPROTEINS

Expression of the Hantaan virus G1 and G2 glycoproteins was accomplished by insertion of the M segment into the NYVAC and ALVAC vectors under the control of the entomopoxvirus 42 kDa promoter. The poxvirus expression cassette inserted into these viral vectors was constructed as follows.

A cDNA clone of the Hantaan virus M segment was derived as described by Schmaljohn et al. (1987) and provided by Dr. J. Dalrymple (Virology Division, U.S. Army Medical Research Institute of Infectious Disease, Frederick, Md.) inserted in the plasmid vector pTZ19R (Pharmacia, Piscataway, N.J.). The full sequence of the cDNA was presented previously by Schmaljohn et al. (1987). The 326 bp 5'-most region of the M segment coding sequence was derived using the plasmid pTZ19R containing the M segment cDNA as template and oligonucleotides HM5P (SEQ ID NO:335) (5'-ATGGGGATATGGAAGTGG-3') and HM3P (SEQ ID NO:336) (5'-CATGTTCCTTTCAAGT-CAAC-3'). This 326 bp fragment was fused to a 107 bp PCR-derived fragment containing the 42 kDa promoter element obtained using pAM12 as template and oligonucleotides RG273 (SEQ ID NO:142) (5'-AG-GCAAGCTTTCAAAAAAATATAAATGATTC-3') and RG274 (SEQ ID NO:143) (5'-TTTATATTGTAAT-TATATATTTTC-3'). The PCR fusion was performed using an equimolar mixture of the 107 bp and 326 bp fragments as template and oligonucleotides RG273(SEQ ID NO:142) and HM3P(SEQ ID NO:336). The fused fragment was digested with HindIII (5' end) and BclI (3' end) to yield a 343 bp fragment.

The plasmid pAM12 was derived as follows. Genomic DNA isolated from *Amsacta moorei* entomopoxvirus (AmEPV) was digested with ClaI and the fragments separated by agarose gel electrophoresis. A 2.6 kb fragment, previously identified as containing a highly transcribed AmEPV gene, was purified from the gel and cloned into the ClaI site of pBS-SK+ yielding pAM12. DNA sequence analysis of this fragment revealed a complete ORF of 42 kDa. The 5' untranslated sequence from this gene (AmEPV 42K promoter) was subsequently shown to function as a strong, early promoter in both vaccinia and avipox viruses.

The 3'-most 748 bp of the M segment coding sequence was derived by PCR using the cDNA clone contained in pTZ19R as template and oligonucleotides HMTS-5 (SEQ ID NO:337) (5'-ATCATGAGTCCAAGAGACAAAG-GTTTCTTATGCCCTGAG-3') and HMTS-3 (SEQ ID NO:338) (5'-ATCATCGAATTCATAAAAACTAT-GATTTTTTATGCTTCCTTACGGGAC-3'). Synthesis of this fragment with these custom synthesized oligonucleotides 1) contains the 3' most sequences of and EcoRV site at the 5' end, 2) disrupts the $T_5NT$ sequence motif (Yuen and Moss, 1987) at nucleotide positions 2687 to 2693 (Schmaljohn et al., 1987), and 3) adds a $T_5NT$ element and a unique EcoRI site at the 3' end of the coding sequence. This fragment was digested with and EcoRI to yield a 741 bp EcoRV/EcoRI fragment. The 741 bp EcoRV/EcoRI fragment was inserted into pBS-SK (Stratagene, La Jolla, Calif.) to yield plasmid pBSHVM3P.

The plasmid containing the M-specific cDNA clone in pTZ19R was used to transform GM48 (Dam⁻) bacterial cells (BRL, Gaithersburg, Md.). Plasmid DNA derived from this bacterial strain was digested with BclI and EcoRV to generate a 2362 bp fragment. This 2362 bp fragment was co-inserted into pBSHVM3P digested with HindIII and EcoRV with the 343 bp HindIII/BclI fragment containing the 42 kDa promoter fused to the 5' most region of the coding sequence. The resultant plasmid containing the entire M segment expression cassette was designated as pBSHVM. The entire M segment cassette was excised from pBSHVM using restriction endonucleases HindIII and EcoRI. The 3508 bp derived fragment was blunt-end using the Klenow fragment of the *E. coli* in the presence of 2 mM dNTPs. The blunt ended fragment was inserted into pSD550to yield pHVMVC.

Plasmid pSD550was derived from pSD548 as follows. Plasmid pSD548 (Tartaglia et al., 1992) is a vaccinia vector plasmid in which the I4L ORF (Goebel et al., 1990a, b) is replaced by a cloning region consisting of BglII and SmaI sites. To expand the multicloning region, pSD548 was cut with BglII and SmaI and ligated with annealed complementary synthetic oligonucleotides 539A (SEQ ID NO:339) (5'-AGAAAAATCAGTTAGCTAAGATCTC-CCGGGCTCGAGGGTACCGGATCCTGATT-AGTTAATTTTTGT-3') and 539B (SEQ ID NO:340) (5'-GATCACAAAAATTAACTAATCAGGATCCGGTACCC-TCGAGCCCGGGAGATCTTAGCTAACTGATTTTTCT- 3'). In the resulting plasmid, pSD550, the multicloning region contains BglII, SmaI, XhoI, KpnI and BamHI restriction sites.

The plasmid pHVMVC was used in in vitro recombination experiments in Vero cells with vP804 (Tartaglia et al., 1992) as rescue virus to yield vP882. Recombinant virus was identified by in situ hybridization according to standard procedures (Piccini et al., 1987) using a radiolabeled M-specific DNA probe. Recombinant plaques were purified by 3 rounds of plaque purification and amplified for further analysis. Recombinant virus, vP882, contains the Hantaan M segment in the I4L locus of vaccinia virus. Replacement of the I4L open reading frame with the M segment cassette in the vP804 background creates a NYVAC- equivalent virus background (Tartaglia et al., 1992).

The 3508 bp HindIII/EcoRI fragment derived from pBSHVM, containing the M segment cassette (above), was inserted into pC4I digested with HindIII and EcoRI. The plasmid pC4I was derived as follows. A 6.5 kb NsiI fragment from CPpp was cloned into the BamHI site of pBS-SK+ yielding pXX-4. DNA sequence analysis identified the complete open reading frame (ORF) which contained the C4 insert in locus. In order to construct a donor plasmid in which the C4 ORF is deleted, oligonucleotides RG287 (SEQ ID NO:341) (5'-CAGTTGGTACCTATGTTAAGGAG-GACGA-3'), RG293 (SEQ ID NO:342) (5'-TATCTGAAT-TCCTGCAGCCCGGGTTTTTAT-AGCTAATTAGTCATATGATATTATCTCTAT-3'), RG289 (SEQ ID NO:343) (5'-TCGATGAATTCGATATCAAGCT-TATCGATTTTTATGATTAACTAGT-CAAGTGATTTTATTCAATTACG-3'), and RG290 (SEQ ID NO:344) (5'-TTATCGAGCTCATTTA-CATTTCTAAACTC-3') were used as primers to amplify the 5' and 3' untranslated regions of the C4 ORF from pXX4. The purified PCR fragments were cloned into pBS-SK+ at the KpnI-SacI sites. The resulting plasmid, pC4I, contains the 5' and 3' untranslated regions of C4 (201 bp each) in which the complete ORF has been replaced with a multiple cloning site flanked by translational and vaccinia early transcriptional stop signals (Yuen and Moss, 1987).

Insertion of the M segment cassette into pC4I yielded plasmid pC4HVM. The plasmid pC4HVM was linearized with SmaI for insertion of a 100 bp SspI/SmaI fragment derived from pSD513 (defined in Example 7). The resultant plasmid was designated as pC4HVMVQ. Plasmid pC4HVMVQ was digested with SmaI followed by a subsequent partial HindIII digestion to recover a 3.6 kb fragment containing the M segment cassette. This fragment was blunt-ended using the klenow fragment of the *E. coli* DNA polymerase in the presence of 2 mM dNTPs. This blunt-ended fragment was inserted into SmaI digested pSPCPC3L to generated pC3HVMVQ (defined in Example 32).

In vitro recombination experiment were performed on primary chick embryo fibroblasts using pC3HVMVQ as the donor plasmid and CPpp (ALVAC) as the rescue virus. Standard protocols were used to identify and to purify the recombinant virus (as above; Piccini et al., 1987). The ALVAC-based recombinant containing the Hantaan virus M segment was designated as vCP114.

EXAMPLE 60

GENERATION OF NYVAC- AND ALVAC-BASED RECOMBINANTS CONTAINING THE HANTAAN VIRUS S CODING SEQUENCE

Expression of the Hantaan virus nucleoprotein was accomplished by insertion of the S segment into the NYVAC and ALVAC vectors under the control of the vaccinia virus H6 promoter (Goebel et al., 1990a,b). The poxvirus expression cassette inserted into these viral vectors was constructed as follows.

A cDNA clone of the Hantaan virus S segment was derived as described by Schmaljohn et al. (1986) and provided by Dr. Joel Dalrymple (Virology Division, U.S. Army Medical Research Institute of Infectious Disease, Ft. Detrick, Frederick, Md.) inserted into the plasmid vector pGEM-1 (Promega Biotech, Madison, Wis.). The entire sequence of the S segment has been described previously (Schmaljohn et al., 1986).

The H6 promoter element was amplified by PCR using plasmid pI4LH6HIV3B as template and oligonucleotides H65PH(SEQ ID NO:164) (5'-ATCATCAAGCTTGAT-TCTTTATTCTATAC- and HTH63P (SEQ ID NO:346) (5'-CCCTCTGTAATTCCTCCATAGTTGCCAT-TACGATACAAACTTAACGG-3'). This 150 bp PCR-derived fragment contains a HindIII site at the 5'-end and has a 28 bp extension at the 3' end containing the 5'-most region of the S segment coding sequence.

The 5' end of the S segment coding sequence was synthesized by PCR with oligonucleotides HTS5P (SEQ ID NO:347) (5'-CCGTTAAGTTTGTATCGTAATGGCAAC-TATGGAGG-3') and HTS5PNCI (SEQ ID NO:348) (5'-GGACACGTAAAGATGTTTTGG-3') and the S-specific cDNA clone as template. The 560 bp PCR-derived fragment was fused by PCR using oligonucleotides H65PH (SEQ ID NO:164) and HTS5PNCI (SEQ ID NO:348). The PCR-derived fusion product was digested with HindIII and NciI.

The central region of the Hantaan virus S segment was generated by PCR using oligonucleotides T5HT3PPS (SEQ ID NO:349) (5'-GTCCTGCAGGATGGAAAAGAATGC-CCCAAGC-3') and HTS55PN (SEQ ID NO:350) (5'-GGGGGAGGCAAACTACCAAGG-3') and the S-specific cDNA clone as template. The 581 bp fragment contains a PstI site at its 3' end and the 5' end includes the NciI site of position 499 of the S segment (Schmaljohn et al., 1986). Furthermore, using the oligonucleotide T5HT3PPS (SEQ ID NO:349) eliminates the $T_5NT$ element at position 1029 to 1035 without altering the amino acid sequence. This fragment was then digested with NciI and PstI. The PCR fragment containing the 5' end of the coding sequence fused to the H6 promoter (HindIII/NCiI digested above) was ligated into pBS-SK digested with HindIII and PstI along with the 581 bp NCiI/PstI fragment containing the central region of the S segment. The resultant plasmid was designated pBSHTSH65P.

The 3' most 438 bp of the S segment was derived by PCR using oligonucleotides HTS3PXBA (SEQ ID NO:351) (5'-ATCATCTCTAGAATAAAAATTAGAGTTTCAAAGGC-3') and T5HT5PSP (SEQ ID NO:352) (5'-CGCCAGCATG-CAGAAGCAGC-3') and the S-specific cDNA clone as template. The 5' end of this fragment contains the PstI site situated at position 1039 of the S segment coding sequence (Schmaljohn et al., 1986) and the 3' end contains a $T_5NT$ sequence motif and a unique Xba I site. This fragment was digested with PstI and XbaI prior to insertion into PstI/XbaI digested pBS-SK to yield pBSHTS3P.

To generate the entire S segment expression cassette, a 1122 bp PstI/partial HindIII fragment was derived from pBSHTSH65P. This fragment was co-inserted into HindIII/ XbaI digested pBS-SK with a 290 bp PstI/XbaI fragment from pBSHTS3P. The resultant plasmid was designated pBSHVS by linearization with XbaI followed by a partial HindIII digestion. This fragment was blunt-ended using the klenow fragment of the *E. coli* DNA polymerase in the presence of 2 mM dNTPs and then inserted into the SmaI site of pSD541L (defined in Example 10) to generate pATIHVS.

The plasmid pATIHVS was used in in vitro recombination experiments in Vero cells with vP866 (NYVAC) and vP882 as rescue virus. This was performed with standard protocols (Piccini et al., 1987). Plaques derived from recombinant virus were identified by a plaque hybridization procedure defined previously (Piccini et al., 1987) using a radiolabeled S segment-specific DNA probe. The generated recombinants were designated as vP950 and vP951 for virus recovered using the rescue virus vP866 and vP882, respectively. Recombinant virus, vP950, contains the S segment expression cassette in the ATI site and vP951 contains this cassette at the same locus, but by virtue of rescue with the M segment containing vP882, also contains the M segment in the I4L locus.

The plasmid pBSHVM was linearized with SalI and blunt-ended using the Klenow fragment of the *E. coli* DNA polymerase in the presence of 2 mM dNTPs. This was ligated to the 1.4 kb XbaI/partial HindIII (Blunt-ended with Klenow as above) fragment derived from pBSHVS containing the Hantaan S segment expression cassette. The derived plasmid was designated as pBSHVMS. This plasmid contained the M and S cassettes in a head to head configuration. Plasmid pBSHVMS was linearized with XhoI, blunted with Klenow (as above), and ligated to a 100 bp SspI/SmaI fragment from pSD513 (defined in Example 7) to yield pBSHVMSVQ.

The plasmid pBSHVMSVQ was digested with ClaI/Asp718 to liberate a 1.5 kb fragment containing the S segment expression cassette. This fragment was blunt-ended using the Klenow fragment of the *E. coli* DNA polymerase in the presence of 2 mM dNTPs and inserted into the SmaI site of pSPCP3L (defined in Example 32) to yield pC3HVSVQ.

Plasmid pC3HVSVQ was used in in vitro recombination experiments in primary chick embryo fibroblasts with CPpp (ALVAC) as the rescuing virus. This was performed using standard procedures, as were the plaque identification, plaque purification, and virus amplification (Piccini et al., 1987). The recombinant generated was designated as vCP119. This recombinant contains the S segment in the C3 locus of ALVAC.

EXAMPLE 61

EXPRESSION/ANALYSIS OF THE NYVAC- AND ALVAC-BASED VIRUSES AS SEGMENT RECOMBINANTS

Immunofluorescence assays were performed as described previously (Taylor et al., 1990) using either a pool or monoclonal antibodies specific to G1, G2, or a rabbit Hantaan polyclonal serum. All sera were obtained from Dr. C. Schmalcohn (Vicology Division, U.S. Army Medical Research Institute of Infectious Diseases, Ft. Derrick, Frederick, MD). The recombinant viruses containing the segment alone (vP55, and vCP114) or in combination with the S segment (vP951) displayed intense surface fluorescence using any the above antiserum, indicating expression of both the and G1 glycoproteins on the surface of the infected cells. Surface fluorescence was not observed using the recombinants containing the S segment alone (vP950 and vCP119), since the nucleoprotein is not displayed on the surface of infected cells. Internal fluorescence was observed, however, with the recombinants, vP950 and vCP119, using the rabbit anti-Hantaan Immunoprecipitations were done using the same antigene to determine the authenticity of the expressed G1, G2, and gene products. This procedure was done according to that previously described (Taylor et al., 1990). Monoclonal antibody pools specific for C1 precipitated a protein with an apparent molecular mass on an SDS-PAGE gel (Dreyfuss et al., 1984) of 64 kDa from lysates derived from cells infected with the recombinant viruses vP882, vP951, and vCP114. No protein was precipitated from uninfected cells or lMsates derived from either parental (NYVAC and ALVAC) infected cells or cells infected with the recombinant viruses containing only the S segment (vP950 and vCP119). Equivalent results were obtained using the monoclonal antibody pool specific for G2, except that the polypeptide precipitated had u molecular mass of approximately kDa. These size proteins (64 kDa and 50–55 kDa ) are consistent with the size of the G1 and G2 respectively (Schmalgohn et al., 1990).

The rabbit anti-Hantaan precipitated three protein species with apparent molecular weights of 64 kDa 50–55 kDa, and 48 kDa from lysates derived from cells infected with vP951, consistent with expression of G1, G2 and the nucleoprotein. The same serum specifically precipitated the G1 and G2 (64 kDa, 50–55 kDa) species from vP882 and vCP114 and the nucleoprotein (48 kDa) from vP950 and vCP119 infected cell lysates. No such proteins were precipitated from lysates derived form uninfected cells or cells infected with the NYVAC or ALVAC parent viruses.

EXAMPLE 62

INSERTION OF HEPATITIS B VIRUS (HBV) GENES INTO AN ALVAC INSERTION PLASMID

ALVAC C5 insertion plasmid pNVQH6C5LSP18 (defined in Example 44) was cut with BamHI and ligated with kinased, annealed synthetic oligonucleotides MPSYN438/MPSYN439 (SEQ ID NOS:353/354).
MPSYN438 5' GATCCCCGGGA 3'
MPSYN439 5' GATCTCCCGGG 3'
The resulting plasmid, pMPC5Sma, contains a SmaI site next to the BamHI site in the linker region.

pMP550E31lps (defined in other HBV example herein) was cut with BglII/BamHI (partial) and a 1.2 kb fragment containing the HBV lpsAg gene under the control of the EPV 42 kDa promoter was isolated and ligated with pMPC5Sma cut with BamHI, resulting in plasmid pMPC5L. pMPC5L was cut with SmaI (partial) and the unit length (4 kb) fragment was isolated. This fragment was cut with NruI and the largest band (4 kb) isolated.

pGJ15 (defined in Example 13) was digested with SmaI (partial) and NruI and a 0.9 kb fragment, containing the HBV spsAg and 24 bp of the H6 promoter, was isolated and ligated to the 4 kb SmaI/NruI vector fragment from pMPC5L, generating plasmid pMPC5LS.

pMPI3S12C (defined in Example 13) was cut with SmaI, and a 1.2 kb fragment containing the S12/core fusion gene under the control of the I3L promoter was isolated. This fragment was ligated into plasmid pMPC5LS which had been cut with SmaI, resulting in plasmid pMPC5LSC.

EXAMPLE 63

INSERTION OF HBV GENES ENCODING SPSAG AND LPSAG INTO ALVAC pMPC5LS, containing both the HBV lpsAg and spsAg in the C5 insertion locus, was used as donor plasmid for recombination with ALVAC, generating ALVAC recombinant vCP157.

Expression of HBV proteins by vCP157. Metabolically labelled lysates from cells infected with ALVAC-HBV double recombinant vCP157 were subjected to immunoprecipitation using rabbit anti-S2 serum, and analyzed by SDS-polyacrylamide gel electrophoresis followed by radioautography. Proteins of the correct size for lpsAg (41 kDa, 38 kDa) and spsAg (36 kDa, 33 kDa), were observed. These proteins co-migrated with the same proteins produced by NYVAC single HBV recombinants expressing spsAg or lpsAg which were used as controls.

EXAMPLE 64

INSERTION OF HBV GENES ENCODING SPSAG, LPSAG AND THE S12/CORE FUSION INTO ALVAC pMPC5LSC, containing both the HBV lpsAg and spsAg genes as well as the gene specifying the S12/core fusion in the C5 insertion locus, was used as donor plasmid for recombination with ALVAC, generating ALVAC recombinant vCP169.

EXAMPLE 65

NYVAC-BASED RECOMBINANTS EXPRESSING THE HBV GENES: SEROLOGICAL DATA FROM RABBITS, MICE AND GUINEA PIGS

Rabbits, mice and guinea pigs were inoculated with NYVAC-based Hepatitis B virus (HBV) recombinants vP856, vP930, vP932 and vP975 (Example 13). vP856 expresses spsAg, the middle (M) form of the surface antigen. vP930 expresses lpsAg, the large (L) form of the surface antigen. vP932 expresses both spsAg and lpsAg. vP975 expresses spsAg, lpsAg and a fusion protein composed of the surface antigen preS1+preS2 regions fused to the core antigen. Sera were analyzed for antibody to HBV surface antigen using the AUSAB test (Abbott), and for antibody to HBV core antigen using the CORAB competitive radioimmunoassay kit (Abbott). Antibody to HBV preS1 and preS2 regions were assayed by ELISA. Results are presented in Tables 34–40.

TABLE 34

AUSAB and CORAB
Rabbits
Analysis of sera of rabbits inoculated with NYVAC-based HBV recombinants
expressing the middle (M) form of the surface antigen
(small pre S antigen), the large (L) form
of the surface antigen (large pre S antigen) and a fusion protein (S/C) consisting of
the pre S 1 + 2 regions fused to the core antigen.

| | | | week | | | | | | | |
|---|---|---|---|---|---|---|---|---|---|---|
| # | vP | HBV genes | 1 | 2 | 3 | 4 | 5 | 6 | 7 | 8 |
| | | | AUSAB[a] | | | | | | | |
| A133 | 932 | M + L | >512 | >512 | 262 | 352 | 13000 | 6500 | 3600 | 5400 |
| A134 | 932 | M + L | 250 | 235 | 72 | 80 | 3900 | 561 | 800 | 218 |
| A135 | 975 | M + L + S/C | 36 | 58 | 274 | 406 | 1300 | 646 | 436 | 268 |
| A136 | 975 | M + L + S/C | 103 | >512 | 127 | 136 | 13468 | 4968 | 3168 | 2768 |
| | | | CORAB[b] | | | | | | | |
| A135 | 975 | M + L + S/C | 80 | 20 | 20 | 80 | 320 | 80 | 320 | 80 |
| A136 | 975 | M + L + S/C | 20 | 5 | 5 | 5 | 80 | 80 | 320 | 80 |

Rabbits were inoculated with $10^8$ pfu of the indicated vaccinia recombinant at week 0 by the IM route, and boosted by the same route and dose at week 4.
[a]Sera were analyzed by AUSAB radioimmunoassay kit (Abbott). Titers are expressed in RIA units.
Note: Three sera (indicated ">512") scored above the sensitivity of the AUSAB test for undiluted sera (512 RIA units) and below the sensitivity of the test for sera diluted 1:100 (800 RIA units).

TABLE 35

Pre-S2 ELISA
Rabbits
Analysis by ELISA of sera from rabbits inoculated with NYVAC-based HBV
recombinants expressing the middle (M) form of the surface antigen, the
large (L) form of the surface antigen and a fusion protein (S/C)
consisting of the pre S 1 + 2 regions fused to the core antigen.

| | | | week | | | | | | | |
|---|---|---|---|---|---|---|---|---|---|---|
| # | vP | HBV genes | 1 | 2 | 3 | 4 | 5 | 6 | 7 | 8 |
| A133 | 932 | M + L | 0 | 0 | 29 | 35 | 474 | 602 | 358 | 419 |
| A134 | 932 | M + L | 0 | 0 | 0 | 277 | 2017 | 3099 | 847 | 500 |
| A135 | 975 | M + L + S/C | 0 | 0 | 0 | 0 | 175 | 105 | 94 | 48 |
| A136 | 975 | M + L + S/C | 0 | 0 | 0 | 0 | 2440 | 763 | 672 | 355 |

TABLE 35-continued

Pre-S2 ELISA
Rabbits
Analysis by ELISA of sera from rabbits inoculated with NYVAC-based HBV recombinants expressing the middle (M) form of the surface antigen, the large (L) form of the surface antigen and a fusion protein (S/C) consisting of the pre S 1 + 2 regions fused to the core antigen.

| # | vP | HBV genes | week 1 | 2 | 3 | 4 | 5 | 6 | 7 | 8 |
|---|----|-----------|---|---|---|---|---|---|---|---|

Rabbits were inoculated by the intramuscular (IM) route with $10^8$ pfu of the indicated vaccinia recombinant at week 0 and boosted by the same route and dose at week 4.
Sera were analyzed by indirect ELISA for the detection of antibodies to HBV pre-S2 region (aa 120–145). Microtiter plates were coated with HBV pre-S2 region peptide (adw 120–145) at a concentration of 50 ng/well. Each serum sample was assayed in duplicate, with initial dilution of 1:10 followed by two-fold serial dilutions. Numbers, based on a standard curve, reflect the dilution factor giving an optical density of 0.25 (compared to 0.14 for prebleed).

TABLE 36

Pre-S1 ELISA
Rabbits
Analysis by ELISA test of sera from rabbits inoculated with NYVAC-based HBV recombinants expressing the middle (M) form and the large (L) form of the surface antigen and the preS 1 + 2/core fusion protein (S/C).

| # | vP | HBV genes | 0 | 2 | 4 | 5 | 6 | 8 |
|---|-----|-----------|-----|-----|-----|-----|-----|-----|
| A133 | 932 | M + L | <10 | <10 | <10 | <10 | <10 | <10 |
| A134 | 932 | M + L | <10 | <10 | <10 | <10 | 17 | <10 |
| A135 | 975 | M + L + S/C | <10 | <10 | 15 | 40 | <10 | 24 |
| A136 | 975 | M + L + S/C | 15 | 16 | 17 | 117 | 52 | 49 |

Rabbits were inoculated by the intradermal (ID) route with $10^8$ pfu of the indicated vaccinia recombinant at week 0 and boosted by the same route and dose at week 4.
Sera were analyzed by indirect ELISA for the detection of antibodies to HBV pre-S1 region. Microtiter plates were coated with HBV pre-S1 peptide (subtype adw aa 20–54, obtained from Dr. Colin Howard, The Royal Veterinary College, London) at a concentration of 500 ng/well. Each serum sample was assayed in duplicate, with initial dilution of 1:10 followed by two-fold serial dilutions. Numbers, based on a standard curve, reflect the dilution factor giving an optical density of 0.20.

TABLE 37

Pre-S2 ELISA
Guinea Pigs
Analysis by ELISA of sera from guinea pigs inoculated with NYVAC-based HBV recombinants expressing the middle (M) form of the surface antigen, the large (L) form of the surface antigen and the preS 1 + 2/core fusion protein (S/C).

| # | vP | HBV genes | 0 | 5 | 6 |
|---|-----|-----------|-----|-----|-----|
| 85 | 856 | M | <10 | <10 | <10 |
| 86 | 856 | M | <10 | <10 | <10 |
| 87 | 930 | L | <10 | 46 | 35 |
| 88 | 930 | L | <10 | 30 | 93 |
| 89 | 932 | M + L | <10 | 39 | <10 |
| 90 | 932 | M + L | <10 | 33 | 19 |
| 91 | 975 | M + L + S/C | <10 | 22 | 84 |
| 92 | 975 | M + L + S/C | <10 | 53 | 269 |

Guinea pigs were inoculated by the SC route with $10^8$ of the indicated HBV recombinant vaccinia virus. Animals were boosted at 4 weeks with the same dose and route. Sera were analyzed by indirect ELISA for the detection of antibodies to HBV preS2 region. Microtiter plates were coated with synthetic S2 peptide (subtype adw, aa 120–145, Bachem Bioscience) at a concentration of 50 ng/well. Each serum sample was assayed in duplicate, with initial dilution of 1:10 followed by two-fold serial dilutions. Titers, based on a standard curve, represent the dilution factor giving an optical density of 0.45 (compared to a mean prebleed value of 0.26).

TABLE 38

CORAB
Mice
Analysis of sera by CORAB test of mice inoculated with vaccinia recombinant vP975 expressing the HBV middle (M) form of the surface antigen, the large (L) form of the surface antigen and a fusion protein (S/C) consisting of the pre S 1 + 2 regions fused to the core antigen

| Group | vP | HBV genes | Week |||||||| 
|---|---|---|---|---|---|---|---|---|---|---|
| | | | 1 | 2 | 3 | 4 | 5 | 6 | 7 | 8 |
| D | 975 | M + L + S/C | -a | - | - | - | 5 | 5 | 5 | 5 |

Mice were inoculated by the IM route with $10^7$ pfu of vP975 and boosted at 4 weeks with the same dose and route. A total of 12 mice were inoculated. Sera from each weekly bleeding were pooled. Sera diluted 1:5, 1:20, 1:80 or 1:320 with bovine serum were analyzed by CORAB competitive radioimmunoassay kit (Abbott). The reciprocal of the highest dilution giving a positive score is indicated. In all cases, the sample was tested at least one further dilution beyond the value indicated.
a"—" indicates that mouse sera diluted 1:5 with bovine serum gave a negative score.

TABLE 39

Pre-S2 ELISA
Mice
Analysis by ELISA of sera from mice inoculated with NYVAC-based HBV recombinants expressing the middle (M) form of the surface antigen, the large (L) form of the surface antigen and the preS 1 + 2/core fusion protein (S/C).

| | vP | HBV genes | week |||
|---|---|---|---|---|---|
| | | | 0 | 5 | 6 |
| Group A | 856 | M | <10 | 73 | 70 |
| Group B | 930 | L | <10 | 93 | 112 |
| Group C | 932 | M + L | <10 | 970 | 1146 |
| Group D | 975 | M + L + S/C | <10 | 1054 | 1062 |

Groups of eight or twelve mice were inoculated by the IM route with 107 of the indicated HBV recombinant vaccinia virus. Animals were boosted at four weeks with the same dose and route. Sera from each group for each bleeding were pooled.
Sera were analyzed by indirect ELISA for the detection of antibodies to HBV preS2 region. Microtiter plates were coated with synthetic S2 peptide (subtype adw, aa 120–145, Bachem Bioscience) at a concentration of 50 ng/well. Each serum sample was assayed in duplicate, with initial dilution of 1:10 followed by two-fold serial dilutions. Titers, based on a standard curve, represent the dilution factor giving an optical density of 0.25 (compared to a mean prebleed value of 0.11).

TABLE 40

Pre-S1 ELISA
Mice
Analysis by ELISA of sera from mice inoculated with NYVAC-based HBV recombinants expressing the middle (M) form of the surface antigen, the large (L) form of the surface antigen and the preS 1 + 2/core fusion protein (S/C).

| | vP | HBV genes | week ||
|---|---|---|---|---|
| | | | 0 | 5 |
| Group B | 930 | L | 60 | 244 |
| Group C | 932 | M + L | 66 | 125 |
| Group D | 975 | M + L + S/C | 63 | 1554 |

Groups of eight or twelve mice were inoculated by the IM route with $10^7$ of the indicated HBV recombinant vaccinia virus. Animals were boosted at 4 weeks with the same dose and route. Sera from each group for each bleeding were pooled.
Sera were analyzed by indirect ELISA for the detection of antibodies to HBV preS1 region. Microtiter plates were coated with synthetic S1 peptide (subtype adw, aa 20–54, obtained from Dr. Colin Howard, The Royal Veterinary College, London) at a concentration of 500 ng/well. Each serum sample was assayed in duplicate, with initial dilution of 1:10 followed by two-fold serial dilutions. Titers, based on a standard curve, represent the dilution factor giving an optical density of 0.2.

EXAMPLE 66

EXPRESSION OF BACTERIAL GENES IN POXVIRUS: TETANUS TOXIN FRAGMENT C (*C. TETANI*) IN POXVIRUSES

*C. tetani* is bacteria of the genus clostridium, spore forming anaerobes; included in the genus is also *C. botulinum*. *C. Tetani* produces a toxin, tetanospasmin (TT) which is primarily responsible for the paralytic effects observed upon infection. TT is a single 150 kDa light chain and 100 kDa heavy chain upon release from the bacteria. The heavy chain yields two fragments, B and C (45 kDa and 55 kDa) upon mild proteolytic treatment. This Example demonstrates that viruses of the invention can be used to express immunogenic bacterial gene products such as fragment C of *C. tetani*.

The expression cassette was generated by a series of polymerase chain reactions. This approach was necessary to remove a TTTTTAT early transcription termination signal (Yuen and Moss, 1987) present in the native tetanus toxin sequence (Eisel et al. ,1986; Fairweather and Lyness, 1986).

The H6 promoter-linked fragment C was derived by PCR from plasmid pSS1261 (Halpern et al., 1990) using primers H6TETC (SEQ ID NO:355) (5'- ATCATCGCGATATCCGT-TAAGTTTGTATCGTAATGAAAAATCTG-GATTGTTGGG -3') and TETFIX2 (SEQ ID NO:356) (5'-GTAATAGTTATGAAAACCC-3'). The remainder of the coding region for the construct was generated by PCR amplification of plasmid pSS1261 using primers TETFIX1 (SEQ ID NO:357) (5'-GGGTTTTCATAACTATTAC-3') and TETEND (SEQ ID NO:358) (5'-GGATGGACAAATGAT-TAATTTTTATCTCGAGCCCGGGATGAT-3'). Fusion of these coding regions was accomplished by PCR amplification of these 553 bp and 881 bp PCR-derived products using primers H6TETC (SEQ ID NO:355) and TETEND (SEQ ID NO:358). The resulting 1.4 kb PCR-derived product was digested with EcoRV and XhoI. A fragment of 1.4 kb was isolated from an agarose gel and ligated to similarly digested pBS-SK+ (Stratagene, La Jolla, Calif.). Nucleotide sequence analysis was used to verify the insert in the resulting plasmid pBSTETC. A T to C silent substitution was found in this plasmid, corresponding to position 3535 in the sequence of Eisel et al. (1986).

pC5L (defined in Example 44) was digested within the polylinker with Asp718 and NotI, treated with alkaline phosphatase and ligated to kinased and annealed oligonucleotides CP26 (SEQ ID NO:359) (5'-GTACGTGACTAATT-AGCTATAAAAAGGATCCGGTACCCTC-GAGTCTAGAATCGATCCCGGGTTTTTATGACTAGT-TAATCAC-3') and CP27 (SEQ ID NO:360) (5'-GGCCGT- GATTAACTAGTCATAAAAACCCGGGATC-
GATTCTAGACTCGAGGGTACCGGATC-
CTTTTTATAGCTAATTAGTCAC-3') (containing a disabled Asp718 site, translation stop codons in six reading frames, vaccinia early transcription termination signal (Yuen and Moss, 1987), BamHI, KpnI, XhoI, XbaI, ClaI, and SmaI restriction sites, vaccinia early transcription termination signal, translation stop codons in six reading frames, and a disabled NotI site) generating plasmid pC5LSP. The early/late H6 vaccinia virus promoter (Perkus et al., 1989) was derived by PCR from a plasmid containing the promoter using oligonucleotides CP30 (SEQ ID NO:361) (5'-TCGG-GATCCGGGTTAATTAATTAGTCATCAGGCAGGGCG-3') and CP31 (SEQ ID NO:362) (5'-TAGCTCGAGGGTAC-CTACGATACAAACTTAACGGATATCG-3'). The PCR product was digested with BamHI and XhoI (sites created at the 5' and 3' termini by the PCR) and ligated to similarly digested pC5LSP generating pVQH6C5LSP. pVQH6C5LSP was digested with EcoRI, treated with alkaline phosphatase, ligated to self-annealed oligonucleotide CP29 (SEQ ID NO:363) (5'-AATTGCGGCCGC-3'), digested with NotI and linear purified followed by self-ligation. This procedure introduced a NotI site to pVQH6C5LSP, generating pNVQH6C5LSP18. The 1.4 kb EcoRV/XhoI fragment from pBSTETC was isolated and ligated to similarly digested pNVQH6C5LSP18 creating pC5TETC.

The H6 promoter through the EcoRV site was derived from a plasmid containing the synthetic H6 promoter (Perkus et al., 1989), using PCR and primers H6PCR1 (SEQ ID NO:364) (5'-ACTACTAAGCTTCTTTATTCTATACT-TAAAAAGTG-3') and H6PCR2 (SEQ ID NO:365) (5'-TTAACGGATATCGCGATAATG-3'), creating a 5' HindIII site. This 122 bp PCR-derived fragment was digested with HindIII and EcoRV followed by ligation to similarly digested pBS-SK+ (Stratagene, La Jolla, Calif.), generating plasmid pBSH6. The insert was confirmed by nucleotide sequence analysis. The 1.4 kb EcoRV/XbaI fragment from pC5TETC was excised and ligated to similarly digested pBSH6, creating pH6TETC.

A 1.5 kb XhoI fragment from pH6TETC containing the entire H6-Fragment C cassette was then ligated to pSD542 (defined in Example 32) creating pTKTETC.

pC5TETC and pTKTETC were employed in in vitro recombination experiments with ALVAC and NYVAC creating recombinants vCP161 and vP1075, respectively.

Immunoprecipitation analysis was performed to determine whether vCP161 and vP1075 express authentic fragment C. Vero cell monolayers were either infected with parental virus, CPpp (ALVAC) or vP866 (NYVAC), or infected with vCP161 or vP1075 at an m.o.i. of 10 pfu/cell. Cells were infected, incubated in modified Eagle's medium (minus methionine) containing [$^{35}$S]-methionine (20 µCi/ml), lysed and precipitated as described by Taylor et al. (1990) using a mouse monoclonal antibody (clone 49.4, Boehringer Mannheim, Indianapolis, Ind.) and goat anti-mouse antisera as secondary antibody. Lysates were pre-cleared with normal mouse sera and protein A-sepharose.

The monoclonal antibody specifically precipitated 4 species corresponding to approximately 47 kDa from vCP161 and vP1075 infected cells. No similar protein species were precipitated from either CPpp (ALVAC) or vP866 (NYVAC) infected cells. The 47 kDa size is in agreement with observations by Makoff et al., 1989) for fragment C produced by papain digestion of native tetanus toxin as well as an E. coli produced recombinant fragment C which is identical to that encoded by vCP161 and vP1075.

EXAMPLE 67

EFFICACY OF NYVAC-BASED PSEUDORA-BIES VIRUS (PRV) RECOMBINANTS IN SWINE

Six groups of four piglets were inoculated with either the NYVAC-based gII recombinant (vP881), gIII recombinant (vP883), gp50 recombinant (vP900), the NYVAC parental virus (vP866), a commercially available inactivated pseudorabies virus vaccine, or Eagle's MEM containing fetal bovine serum as a sham vaccine. All pigs received two inoculations 28 days apart via the intramuscular route. The pigs receiving parental or recombinant NYVAC viruses were inoculated with approximately $10^6$ TCID$_{50}$ per inoculation. All pigs were monitored for body temperature and clinical signs for 12 days post-inoculation. No local or systemic adverse reactions were observed to vaccination with recombinant or parental NYVAC viruses.

Serum neutralizing antibody titers against pseudorabies virus were monitored for 1, 2, and 4 weeks following each inoculation. As is evident from Table 41, only the inactivated vaccine preparation was able to elicit significant pseudorabies virus serum neutralizing titers following a single inoculation. However, following a second inoculation all three NYVAC-based recombinants were able to elicit observable pseudorabies virus serum neutralizing titers (Table 42). The titers were most significant with the NYVAC recombinant expressing the pseudorabies virus gp50 glycoprotein. In fact, the titers elicited by the gp50 expressing NYVAC recombinant were comparable to levels attained with two inoculations of the commercially available inactivated vaccine (Table 42).

Four weeks following the second immunization all pigs were challenged with approximately $10^5$ PFU of a virulent pseudorabies virus strain via intranasal instillation. Expectedly, the sham and parental NYVAC vaccinated controls all demonstrated the most severe clinical symptoms and the highest levels of pseudorabies virus isolated via nasal and oropharyngeal swabs up to 14 days post-challenge. NYVAC-based pseudorabies virus recombinant viruses were all shown to reduce the effects of the virulent pseudorabies virus challenge (i.e. clinical signs and virus isolation) compared to the controls, with the gp50 expressing recombinant virus being the most efficacious. In fact, this recombinant was as effective as the commercially available inactivated pseudorabies virus vaccine.

Since PRV, like other herpesviruses, has the potential of developing a latent infection that can be reactivated by stress or corticosteroid administration (Whittmann and Rziha, 1989), experiments were performed with two pigs were group to evaluate protective efficacy of the NYVAC recombinants against such infections. The protocol involved administering dexamethasone to the pigs in the following schedule: 1.25 mg/pound via the intravenous route and 0.25 mg/pound via the intravenous route on day one. This was followed by subsequent dexamethasone administration (0.5 mg/pound) approximately every 12 hr for four days. Virus shedding was evaluated from day 0 to day 10 post-dexamethasone treatment using nasal (N) and throat (T) swabs. The results are shown in Table 43. These results clearly demonstrate the efficacy of the NYVAC-based PRV recombinant viruses in protecting against the establishment of latent PRV infections. The NYVAC-gII (vP881) was indeed the most efficacious by this criterion.

TABLE 41

PRV SN Titers Following First Immunization

| Pig weeks | Group | Day 0 | 1 week | 2 weeks | 4 |
|---|---|---|---|---|---|
| 1 |  | <2 | <2 | <2 | <2 |
| 2 | NYVAC/gII | <2 | <2 | <2 | <2 |
| 3 |  | <2 | <2 | <2 | <2 |
| 4 |  | <2 | <2 | <2 | <2 |
| 5 |  | <2 | <2 | <2 | 2 |
| 6 | NYVAC/gIII | <2 | <2 | <2 | 2 |
| 7 |  | <2 | <2 | <2 | 2 |
| 8 |  | <2 | <2 | <2 | 2 |
| 9 |  | <2 | <2 | 8 | <2 |
| 10 | NYVAC/gp50 | <2 | <2 | 4 | 8 |
| 11 |  | <2 | 2 | 2 | 4 |
| 12 |  | <2 | 2 | 2 | 8 |
| 13 |  | <2 | <2 | <2 | <2 |
| 14 | NYVAC | <2 | <2 | <2 | <2 |
| 15 |  | <2 | <2 | <2 | <2 |
| 16 |  | <2 | <2 | <2 | <2 |
| 17 |  | <2 | 8 | 128 | 64 |
| 18 | Inact. vaccine | <2 | 16 | 512 | 256 |
| 19 |  | <2 | 16 | 128 | 128 |
| 20 |  | <2 | 2 | 16 | 8 |
| 21 |  | <2 | <2 | <2 | <2 |
| 22 | Control | <2 | <2 | <2 | <2 |
| 23 |  | <2 | <2 | <2 | <2 |
| 24 |  | <2 | <2 | <2 | <2 |

TABLE 42

PRV SN Titers Following Second Immunization

| Pig | Group | 1 week | 2 weeks | 4 weeks* |
|---|---|---|---|---|
| 1 |  | 16 | 32 | 16 |
| 2 | NYVAC/gII | 32 | 16 | 8 |
| 3 |  | 64 | 64 | 8 |
| 4 |  | 128 | 64 | 64 |
| 5 |  | 16 | 32 | 8 |
| 6 | NYVAC/gIII | 8 | 8 | 8 |
| 7 |  | 8 | 8 | 4 |
| 8 |  | 16 | 64 | 16 |
| 9 |  | 2048 | >4096 | 1024 |
| 10 | NYVAC/gp50 | >4096 | 4096 | 2048 |
| 11 |  | 1024 | 1024 | 512 |
| 12 |  | 4096 | 2048 | 1024 |
| 13 |  | <2 | <2 | <2 |
| 14 | NYVAC | <2 | <2 | <2 |
| 15 |  | <2 | <2 | <2 |
| 16 |  | <2 | <2 | <2 |
| 17 |  | >4096 | >4096 | 2048 |
| 18 | Inact. vaccine | >4096 | >4096 | 4096 |
| 19 |  | 2048 | 2048 | 256 |
| 20 |  | >4096 | >4096 | 2048 |
| 21 |  | <2 | <2 | <2 |
| 22 | Control | <2 | <2 | <2 |
| 23 |  | <2 | <2 | <2 |
| 24 |  | <2 | <2 | <2 |

TABLE 43

VIRUS ISOLATION POST DEXAMETHASONE

| Const | Pig | Site | d-0 | d-1 | d-2 | d-3 | d-4 | d-5 | d-6 | d-7 | d-8 | d-9 | d-10 |
|---|---|---|---|---|---|---|---|---|---|---|---|---|---|
| gII | 3 | N | – | – | – | – | – | – | – | – | – | – | – |
|  |  | T | – | – | – | – | – | – | – | – | – | – | – |
|  | 4 | N | – | – | – | – | – | – | – | – | – | – | – |
|  |  | T | – | – | – | – | 1+ | – | – | – | – | – | – |
| gIII | 6 | N | – | – | – | (+) | 1+ | 3+ | (+) | – | – | – | – |
|  |  | T | – | – | (+) | 1+ | 1+ | – | – | – | – | – | – |
|  | 7 | N | – | – | 1+ | (+) | – | – | – | – | – | – | – |
|  |  | T | – | – | 1+ | 2+ | 3+ | 1+ | – | – | – | – | – |
| gp50 | 9 | N | – | – | – | – | – | – | – | – | – | – | – |
|  |  | T | – | – | – | – | – | – | – | – | – | – | – |
|  | 11 | N | – | – | – | – | – | 1+ | – | – | (+) | – | – |
|  |  | T | – | – | (+) | (+) | – | (+) | (+) | 1+ | 1+ | (+) | (+) |
| parent vac | 14 | N | – | – | 2+ | 4+ | 4+ | 4+ | 3+ | (+) | (+) | – | – |
|  |  | T | – | – | (+) | 2+ | 2+ | 3+ | 1+ | 1+ | – | – | – |
|  | 16 | N | – | – | 1+ | 2+ | – | – | – | – | – | – | – |
|  |  | T | – | – | – | 1+ | – | (+) | – | – | – | – | – |
| inact PRV | 17 | N | – | – | 1+ | (+) | 1+ | – | – | – | – | – | – |
|  |  | T | – | – | – | – | – | – | – | – | – | – | – |
|  | 19 | N | – | – | – | – | – | – | – | – | – | – | – |
|  |  | T | – | – | 1+ | 1+ | 1+ | (+) | – | (+) | – | – | – |
| cont | 22 | N | – | – | – | – | – | – | – | – | – | – | – |
|  |  | T | – | – | 1+ | – | – | – | – | – | – | – | – |
|  | 24 | N | – | – | 3+ | 2+ | 2+ | 3+ | 1+ | – | – | – | – |
|  |  | T | – | – | 2+ | 2+ | 1+ | 2+ | 2+ | 1+ | – | – | – |

1+ = 1–10 plaques @ 24 hr;
2+ = 11–100 plaques @ 24 hr;
3+ = 101–1000 plaques @ 24 hr;
4+ = complete CPE @ 24 hr;
(+) = plaques after 24 hr.

EXAMPLE 68

USE OF NYVAC.1 (vP954) AS A VECTOR

In NYVAC.1 (vP954) (Example 17) the [C7L-K1L] deletion in NYVAC (vP866) is expanded to the right, through K3L, a gene whose deletion confers heightened sensitivity to interferon (Beattie et al., 1991). NYVAC.1 was tested as an immunization vector for the rabies glycoprotein and for the measles HA and F genes as detailed below.

Insertion of the Rabies Glycoprotein Gene Into vP954; Generation of Vaccinia Recombinant. vP1006. Donor plasmid pRW842 (Example 7), which contains an expression cassette for the rabies glycoprotein inserted in the TK deletion locus, was used in recombination with vP954 rescuing virus. Recombinant vaccinia virus vP1006 was identified by plaque hybridization using $^{32}P$-labelled DNA probe to rabies glycoprotein G coding sequences.

Insertion of Genes Encoding Measles HA, F Into vP954; Generation of Vaccinia Recombinant vP1015. pRW857 (Example 9), which contains expression cassettes for both the measles F and measles HA in the TK insertion locus, was used as donor plasmid for recombination with vP954 rescuing virus. Recombinant virus vP1015 was identified by plaque hybridization using $^{32}P$-labelled probe to both the measles HA and the measles F coding sequences.

Efficacy of K3L-MINUS NYVAC. 1 Based Vector As An Immunization Vehicle; Rabies G recombinant vP1006. Four to six week old mice (10 per dilution per virus) were inoculated with either undiluted $10^{-2}$, $10^{-4}$, or $10^{-6}$dilutions of vP1006, vP954 (parent of vP1006), vP879 (NYVAC-based rabies G, Example 7), or vaccinia rabies 187 XP1[2]. The inoculations were performed in 50–100 µl per mouse via the footpad. Fourteen days post-inoculation all mice were challenged with an intercerebral inoculation of 20 $LD_{50}$ of the CVS strain (in 0.03 ml). Surviving mice were counted and protective dose 50% ($PD_{50}$) was calculated.

As shown in Table 44, the parent virus of vP1006, vP954, did not protect any mice from live rabies challenge even at the highest inoculum. Recombinant viruses 187 XP12 (Kieny et al., 1984), vP879, and vP1006 all demonstrated the ability to protect mice from live rabies challenge. The relative efficacy of these viruses in this capacity did however vary as illustrated by the $PD_{50}$ values (Table 44).

Measles Virus Recombinant vP1015. Two rabbits (A168 and A169) were inoculated with 8.0 $log_{10}$ PFU of vP1015 via the subcutaneous route on days 0 and 28. Serial bleeds were taken on days 0, 14, 21, 28, 35, 42 and 49. Sera were analyzed for the presence of virus neutralizing antibody using the plaque reduction neutralization method described by Albrecht et al. (1981).

Results from this analysis are shown in Table 45. Both animals seroconverted after a single inoculation of vP1015 with animal A169 exhibiting protective levels of antibody by two weeks post-inoculation. A significant boost in antibody levels was observed following a second inoculation. The results of inoculation of two rabbits with NYVAC-MV (vP913; Example 9) in an equivalent protocol are included in Table 45. The results indicate that deletion of K2L and K3L did not affect the ability of the virus to function as an effective immunization vehicle.

TABLE 44

Efficacy of vP1006 in mice.

| Virus | 187 XP12 | | vP879 | | vP1006 | | vP954 | |
|---|---|---|---|---|---|---|---|---|
| | (1) | (2) | (1) | (2) | (1) | (2) | (1) | (2) |
| | 6.7 | 8/10 | 6.7 | 7/10 | 6.1 | 6/10 | 6.25 | 0/10 |
| | 4.7 | 9/10 | 4.7 | 7/10 | 4.1 | 6/10 | 4.25 | 0/10 |
| | 2.7 | 3/10 | 2.7 | 1/10 | 2.1 | 0/10 | 2.25 | 0/10 |
| | 0.7 | 3/10 | 0.7 | 0/10 | 0.1 | 0/10 | 0.25 | 0/10 |
| $PD_{50}$ | 2.60 | | 4.12 | | 5.25 | | ND | |

[1]dose $TCID_{50}$ log 10/ml
[2]surviving mice/total mice challenged
[3]Kieny et al. (1984)
ND- not detected

TABLE 45

Comparison of levels of measles virus neutralizing antibody in sera of rabbits inoculated with vP1015 and vP913.

| Animal | Titer at Days Post-inoculation 0[a] | 14 | 21 | 28[b] | 35 | 42 | 49 |
|---|---|---|---|---|---|---|---|
| Animals receiving vP1015 | | | | | | | |
| A168 | <1.3[d] | <1.3 | <1.3 | 1.3[c] | 2.2 | 2.2 | 2.2 |
| A169 | <1.3 | 1.6 | 1.6 | 1.6 | 3.1 | 3.1 | 2.5 |
| Animals receiving vP913 | | | | | | | |
| A116 | <1.3 | <1.3 | N.D[e] | <1.3 | 2.8 | 2.2 | 2.2 |
| A117 | <1.3 | <1.3 | N.D. | <1.3 | 1.9 | 1.9 | 1.9 |

[a]Day of inoculation with 8.0 $log_{10}$ pfu of vP1015 or vP913 by the sc route
[b]Day of re-inoculation
[c]Titer expressed as $log_{10}$ of reciprocal of highest dilution showing a 50% reduction in plaque number as compared to pre-inoculation serum.
[d]Lowest dilution tested was 1:20
[e]Not done

EXAMPLE 69

USE OF NYVAC.2 (vP938) AS A VECTOR; GENERATION OF VACCINIA RECOMBINANT VP996 CONTAINING THE RABIES GLYCOPROTEIN G

In NYVAC.2 (vP938) (Example 17) the [C7L-K1L] deletion in NYVAC (vP866) is expanded in both directions to include a total of 38 ORFs [C23L-F4L]. Donor plasmid pRW842 (Example 7), which contains an expression cassette for the rabies glycoprotein inserted in the TK deletion locus, was used in recombination with vP938 rescuing virus. Recombinant vaccinia virus vP996 was identified by plaque hybridization using $^{32}P$-labelled DNA probe to rabies glycoprotein G coding sequences.

Growth of Modified NYVAC Viruses on vero and MRC-5 Cells. To examine the effect of the large deletions near the left [C23L-F4L] and right [B13R-B29R] termini of vaccinia on growth in tissue culture, NYVAC (vP866), vP938, vP996 and the following additional NYVAC-based viruses were tested for replication on MRC-5 and Vero cells.

vP879 (Example 7) contains the rabies glycoprotein gene inserted into the TK locus of NYVAC.

vP953 (Example 17) contains the NYVAC deletions and an additional deletion [B13R-B29R] near the right terminus of the genome.

vP977 (Example 17) contains the NYVAC deletions plus the additional deletions near both the left and right termini of the genome.

Vero cells (African Green Monkey kidney cell line,. ATCC CCL 81) and MRC-5 cells (Human embryonic lung, ATCC CCL 171) were seeded 2 days before infection in 60 mm dishes at $1.5\times10^{6}$. At the time of infection all cells were confluent, the dishes containing $2\times10^{6}$ cells. The cells were infected with virus (Table 46) at a multiplicity of 0.1 pfu per cell, diluted in MEM+2% newborn calf serum (NCS) with or without ara C (final concentration 40 µg/ml). The infected monolayers were incubated for 60 min at 37° C. with occasional rocking. After the one hour adsorption period, cells were washed twice with MEM+2% NCS and then overlayed with 3 ml of MEM+2% NCS with or without ara C, and incubated at 37° C. The infected cells were harvested at 1 or 72 hours post-infection by three cycles of freezing and thawing. Each sample was titered in duplicate on Vero cells.

As indicated in Table 46, NYVAC (vP866) is capable of limited growth on human MRC-5 cells. Under the conditions tested here (moi of 0.1 pfu/cell, 72 hr incubation) NYVAC showed an increase in titer of approximately two logs. Under these same conditions, modified NYVAC virus containing the deletion near the left (vP938) or right (vP953) terminus of the genome showed an increase in titer of approximately one log. Yield from the modified NYVAC virus (vP977) containing deletions near both termini was decreased relative to input virus, indicating no amplification on MRC5 cells. In contrast, under these conditions, all viruses tested amplified to approximately the same extent on Vero cells. As indicated in Table 46, the percentage of vaccinia virus yield on MRC-5 cells compared to yield on Vero cells for the various modified NYVAC virus deletion mutants is as follows: vP866 (NYVAC) 3.5%; vP938 (NYVAC.2, left end deletion) 1.42%; vP953 (right end deletion) 0.5%; vP977 (left and right end deletions) 0.06%. Yields of NYVAC-based rabies recombinant vP879 and NYVAC.2-based rabies recombinant vP996 on MRC-5 cells are essentially the same as for their respective parental viruses, indicating that expression of the foreign gene does not affect growth of the recombinant virus in tissue culture.

Urabe AM-9 F and HN genes from the first strand cDNA using polymerase chain reaction (PCR). The F gene was amplified using synthetic oligonucleotides RG503 (SEQ ID NO:366) (5'-TCTGAGCTCGAAAATAGAATTGATCAG-3') and RG494 (SEQ ID NO:367) (5'-TCTGGTACCTTTCT-GAATGCAGGATG-3'). The HN gene was amplified using RG500 (SEQ ID NO:368) (5'-TCTGAGCTCCAATACAA-CACAGAACC-3') and RG501 (SEQ ID NO:369) (5'-TCTGGTACCGCATTCACTATTACTCA-3'). The 5' primers (RG503 and RG500) were designed with SacI sites and the 3' primers (RG494 and RG501) with Asp718 sites. The amplified F and HN fragments were digested with SacI and Asp718 and cloned into pBluescript SK+ at the SacI and Asp718 sites in the multiple cloning site. Six F gene clones and five HN gene clones were DNA sequenced to eliminate any reverse transcriptase or PCR errors. FIG. 29 provides the consensus F sequence is represented by pURF3 (SEQ ID NO:370) and FIG. 30 provides the consensus HN sequence represented by pURHN5 (SEQ ID NO:371).

EXAMPLE 71

ALVAC DONOR PLASMID CONSTRUCTION: MUMPS F AND HN GENES

The overall design of an ALVAC donor plasmid for the generation of ALVAC recombinants expressing the mumps F and HN genes is as follows. The mumps F gene was coupled to the entomopox 42K promoter (described in Example 59) and the mumps HN gene was coupled to the vaccinia H6 promoter (Perkus et al., 1989). The two promoted genes were configured in a 5' to 5' orientation and inserted into an ALVAC C3 locus insertion plasmid. Specific details of the construction are presented in the following paragraphs.

The multiple cloning region of pSPCP3L (described in Example 32) was changed by adding a 31 bp linker fragment containing EcoRV, RsrII, SmaI and PstI restriction sites. The linker was generated by annealing synthetic oligonucleotides RG560 (SEQ ID NO:372) (5'-TTAGATATCCGGAC-CGCCCGGGCTGCAGAAT-3') and RG561 (SEQ ID NO:373) (5'-ATTCTGCAGCCCGGGCGGTCCG-GATATCTAA-3'), then digesting with EcoRV and PstI. The linker was cloned into the EcoRV and PstI sites of pSPCP3L to generate pC3LR.

TABLE 46

| VIRUS | DELETIONS | INSERT | HPI | VERO TITER (pfu/ml) | MRC TITER (pfu/ml) | MRC YIELD (% of VERO) |
|---|---|---|---|---|---|---|
| vP866 | NYVAC | | 1 | $2.9 \times 10^3$ | $4.4 \times 10^3$ | 3.5% |
| | | | 72 | $3.7 \times 10^6$ | $1.3 \times 10^5$ | |
| | | | 72A | $3.8 \times 10^2$ | $1.1 \times 10^3$ | |
| vP879 | NYVAC | RABIES | 1 | $2.7 \times 10^3$ | $6.1 \times 10^3$ | 3.4% |
| | | | 72 | $4.3 \times 10^6$ | $1.5 \times 10^5$ | |
| | | | 72A | $6.5 \times 10^2$ | $2.1 \times 10^2$ | |
| vP938 | NYVAC, | | 1 | $7.9 \times 10^3$ | $8.8 \times 10^3$ | 1.42% |
| | C23-F4L | | 72 | $3.8 \times 10^6$ | $5.4 \times 10^4$ | |
| | | | 72A | $4.7 \times 10^2$ | 0 | |
| vP996 | NYVAC, | RABIES | 1 | $6.6 \times 10^3$ | $7.3 \times 10^3$ | 1.05% |
| | C23-F4L | | 72 | $4.0 \times 10^6$ | $4.2 \times 10^4$ | |
| | | | 72A | $6.2 \times 10^2$ | 0 | |
| vP953 | NYVAC, | | 1 | $4.0 \times 10^3$ | $5.1 \times 10^3$ | 0.5% |
| | B13-B29 | | 72 | $6.7 \times 10^6$ | $3.1 \times 10^4$ | |
| | | | 72A | $5.2 \times 10^2$ | $7.5 \times 10^1$ | |
| vP977 | NYVAC, | | 1 | $2.4 \times 10^3$ | $5.3 \times 10^3$ | 0.06% |
| | C23-F4L, | | 72 | $1.5 \times 10^6$ | $1.0 \times 10^3$ | |
| | B13-B29 | | 72A | $1.0 \times 10^2$ | 0 | |

EXAMPLE 70 cDNA CLONING OF MUMPS F AND HN GENES

The Urabe AM-9 strain of mumps virus is a live, attenuated virus which is licensed for use as a vaccine in Europe and Japan. This virus was obtained as a vaccine preparation (Imovax Oreillons) from Institut Merieux, Marcy l'Etoile, France. The virus was amplified on VERO cells (two passages) and total RNA was isolated and purified from the infected cells (Chirgwin et al., 1979). First strand cDNA was prepared from this RNA using AMV reverse transcriptase and random primers (Watson and Jackson, 1985). Using the published sequence from the RW mumps strain (Waxham et al., 1987; Waxham et al., 1988), sets of specific primers were synthesized from the 5' and 3' untranslated regions of the F and HN genes. These primers were used to amplify the The H6 promoter was amplified by PCR from pRW823 using synthetic oligonucleotides RG562 (SEQ ID NO:374) (5'-TATGAATTCCCATGGTTAATTAATTAGTCATC-3') and RG563 (SEQ ID NO:375) (5'-TCTCCCGGGCG-GATATCGCGATAATG-3'). pRW823 contains the H6 promoter sequences as described by Perkus et al., 1989. The purified fragment was digested with EcoRI and SmaI and ligated into the EcoRI and SmaI sites in pC3LR, resulting in pC3LRVQH6.

The mumps F gene was excised from pURF3 as a HindIII/Asp718 fragment (F gene ORF minus about 50 codons from the N-terminus). The ends of this fragment were repaired using Klenow polymerase, and ligated into pC3LRVQH6 which had been digested with EcoRI and repaired with Klenow polymerase. Screening for correct orientation yielded pC3LRFVQH6.

A fragment containing the 42K promoter sequences and the N-terminal portion of the F gene were amplified by PCR from pURF3 using synthetic oligonucleotides RG564 (SEQ ID NO:376) (5'-TAACCATGGTTTATTGGGAAGAATAT-GATAATATTTTGGGATTTCAAAAT-TGAAAATATATAATTACAATATAAAAT-GAAGGCTTTTTTAGTTAC-3') and RG565 (SEQ ID NO:377) (5'-CCACTGCAGGCGTCATAC-3'). The purified fragment was digested with NcoI and PstI and ligated into pC3LRFJQH6 cut with NcoI and PstI. The resulting plasmid, pC3LRF42KVQH6, was confirmed by DNA sequence analysis of the inserted fragment.

The mumps HN gene was excised from pURHN5 as a SspI/Asp718 fragment (HN gene ORF minus about 35 codons from the N-terminus). The ends of this fragment were repaired using Klenow polmerase, and ligated into pC3LRF42KVQH6 cut with SmaI. Screening for the correct orientation yielded pFR2A-30.

A fragment containing the 3' portion of the H6 promoter and the N-terminal sequence of the HN gene were amplified by PCR from pURHN5 using synthetic oligonucleotides RG566 (SEQ ID NO:378) (5'-TTATCGCGATATCCGT-TAAGTTTGTATCGTAATGGAGCCCTCAAAACTC-3') RG567 (SEQ ID NO:379) (5'-AAACCTAAGGTCAT-TAAC-3'). The purified fragment was cut with NruI and Bsu36I and ligated into pFR2A-30 cut with NruI and BSu36I. The resulting ALVAC donor plasmid, pC3URFHN, was confirmed by DNA sequence analysis of the inserted fragment.

EXAMPLE 72

GENERATION OF ALVAC RECOMBINANTS

The donor plasmid pC3URFHN was used in in vitro recombination experiments in CEF cells with ALVAC (CPpp) to yield vCP171 (Taylor et al., 1992). Recombinant viruses were identified by in situ hybridization procedures (Piccini et al., 1987) using radiolabelled F and HN specific probes. Recombinant plaques were purified by three rounds of plaque purification and amplified for expression analysis. By expression analysis F and HN are expressed.

EXAMPLE 73

CONSTRUCTION OF INSERTION VECTOR CONTAINING JAPANESE ENCEPHALITIS VIRUS (JEV) 15aaC, prM, E, NS21, NS2A

Construction of pRW838 is as described above (see Example 15).

pRW838 was digested at the 3' end of the rabies glycoprotein gene with EcoRI filled in with the Klenow fragment of DNA polymerase I digested within the H6 promoter with EcoRV, and treated with alkaline phosphatase and a 3202 bp fragment containing the 5' 103 bp of the H6 promoter, plasmid origin of replication and C5 flanking arms isolated. Plasmid JEVL14VC containing JEV cDNA encoding 15 amino acids C, prM, E, NS1, NS2A in a vaccinia virus donor plasmid (Mason et al., 1991) (nucleotides 337–4125, Konishi et al., 1991) was digested with EcoRV in the H6 promoter and SacI in JEV sequences (nucleotide 2124) and a 1809 bp fragment isolated. JEVL14VC was digested with EclXI at the EagI site following the T5AT, filled in with the Klenow fragment of DNA polymerase I and digested with SacI in JEV sequences (nucleotide 2124) generating a 2011 bp fragment. The 1809 bp EcoRV-SacI, 2011 bp SacI-filled EclXI and 3202 bp EcpRV filled EcoRI fragments were ligated generating JEVCP1.

EXAMPLE 74

CONSTRUCTION OF C5 INSERTION VECTOR CONTAINING JEV 15aaC, prM, E

Plasmid JEV36 was digested within the H6 promoter with EcoRV and within JEV sequences with SphI (nucleotide 2380) and a 2065 bp fragment isolated. Plasmid VQH6C5LSP (defined in Example 44) was digested within the H6 promoter with EcoRV and within the polylinker with XbaI and ligated to the 2065 bp fragment plus annealed oligonucleotides SP131 (SEQ ID NO:382) and SP132 (SEQ ID NO:383) (containing a SphI sticky end, T nucleotide completing the E coding region, translation stop, a vaccinia early transcription termination signal (AT5AT; Yuen and Moss, 1987), a second translation stop, and XbaI sticky end) generating plasmid JEVCP5 which encodes 15 amino acids C, prM and E under the control of the H6 promoter between C5 flanking arms.

EXAMPLE 75

CONSTRUCTION OF ALVAC-BASED JEV RECOMBINANTS

JEVCP1 was transfected into ALVAC infected primary CEF cells to generate the canarypox recombinant vCP107 encoding 15 amino acids C, prM, E, NS1, NS2A. JEVCP5 was transfected into ALVAC infected primary CEF cells to generate the canarypox recombinant vCP140 encoding JEV 15 aa C, prM and E.

```
SP131 (SEQ ID NO:382) 5'-        C T tga tttttat tgaT       -3'
SP132 (SEQ ID NO:383) 3'-GTACG A ACT AAAAATA ACT AGATC-5'
                         SphI                       XbaI
```

EXAMPLE 76

IMMUNOPRECIPITATION OF JEV PROTEINS IN RECOMBINANT INFECTED CELLS

Immunoprecipitation experiments were performed as described previously (Konishi et al., 1991). The E protein produced in vCP107 and vCP140 infected cells comigrates with the E protein produced by JEV-vaccinia recombinants which have been shown to produce an authentic E protein (Konishi et al., 1991). vCP107 produces an NS1 protein that comigrates with the NS1 protein produced by JEV-vaccinia recombinants which have been shown to produce an authentic NS1 protein (Konishi et al., 1991).

EXAMPLE 77

IMMUNIZATION OF MICE WITH vCP107

Three-week-old Swiss mice were immunized by intraperitoneal injection with $10^7$ PFU of vCP107 and 3 weeks later sera were collected from selected mice. One half of the mice were reinoculated with vCP107 and sera were collected 3 weeks later. Sera were assayed for neutralizing (Neut) and hemagglutination inhibiting antibodies (HAI) as previously described (Konishi et al., 1991). Mice immunized once or twice with vCP107 developed high titers of Neut and HAI antibodies, both titers were increased by the second immunization. Mice receiving parental ALVAC did not demonstrate antibody titers. The levels of antibodies obtained in vCP107 immunized mice were comparable to those achieved by immunization with JEV-vaccinia recombinants (Konishi et al., 1991).

EXAMPLE 78

EFFICACY STUDIES ON TROVAC-NDV (vFP96)

A number of studies have been performed to determine the protective efficacy against NDV (Newcastle Disease virus) of TROVAC-NDV (vFP96) (Example 8) in specific pathogen free (SPF) chickens and in commercial broiler chickens.

Study A- Four groups of one day old SPF chickens were inoculated by the intramuscular route in the leg with a range of doses from 0.3 to 6.3 $\log_{10}$ $TCID_{50}$ of TROVAC-NDV (vFP96) or the parental TROVAC virus. Birds were monitored for reaction at the site of inoculation and serum samples were collected at 14 days post-inoculation for analysis; of the presence of anti-NDV serum neutralizing antibody and hemagglutinin-inhibiting antibody. At 21 days post-inoculation, birds were challenged by intramuscular inoculation of 5.0 $\log_{10}$ 50% egg infectious doses of the velogenic NDV strain Texas GB. Birds were maintained for 14 days post-challenge at which time healthy birds were considered protected.

It was determined that intramuscular inoculation of 6.3 or 2.6 $\log_{10}$ $TCID_{50}$ of TROVAC-NDV (vFP96) or TROVAC parental virus led to a cutaneous lesion at the point of inoculation which in some cases led to death. There was a specific dose effect on the severity of the lesion, which, at a dose of 1.1 to 1.4 $\log_{10}$ $TCID_{50}$, was limited to slight inflammatory reaction at the point of inoculation. In all cases the lesion was limited to the point of inoculation and did not spread to other parts of the chicken. The effect was not due to expression of the NDV F and HN genes in TROVAC-NDV as the same effect was noted with the parental virus. The response is specific to this route of inoculation as no detrimental side effects of inoculation of high doses of TROVAC or TROVAC based recombinants have been seen when other routes of inoculation are utilized.

The results of serological analysis and protective efficacy are shown in Table 47. All birds inoculated with TROVAC parental virus succumbed to the lethal challenge. All birds vaccinated with 1.1 and 2.6 $\log_{10}$ $TCID_{50}$ of TROVAC-NDV (vFP96) survived challenge while 82% of birds receiving 0.3 $\log_{10}$ $TCID_{50}$ survived. This indicates that the 50% protective dose ($PD_{50}$) for this recombinant by this route is less than 0.3 TCID50.

TABLE 47

Safety studies and protective efficacy of TROVAC-NDV in specific pathogen free day old chickens.

| Virus | Dose[a] | Antibody[b] SN | Antibody[b] HI | Safety[c] post-vaccination | Protection[d] post-challenge |
|---|---|---|---|---|---|
| TROVAC | 0.3 | ND | ND | 0/17 | 17/17 |
|  | 1.4 | ND | ND | 0/7 | 7/7 |
|  | 2.7 | ND | ND | 1/17 | 16/16 |
|  | 6.2 | ND | ND | 5/7 | 2/2 |
| TROVAC-NDV | 0.3 | NT | NT | 0/17 | 3/17 |
|  | 1.1 | NT | NT | 0/17 | 0/7 |
|  | 2.6 | 0.8 | 4.5 | 0/17 | 0/17 |
|  | 6.3 | 1.1 | 6.0 | 3/14 | 2/11 |
| CONTROLS | None | NT | NT |  | 10/10 |

[a]Birds received one inoculation of either TROVAC or TROVAC-NDV by the intramuscular route at one day of age. Dose expressed as $\log_{10}$ $TCID_{50}$.
[b]Serum neutralizing (SN) titers and hemagglutination-inhibition (HI) titers are expressed as mean of birds tested. SN titer expressed as $\log_{10}$ of reciprocal of highest antibody dilution showing complete neutralization of cytopathic effect. HI titer expressed as $\log_2$ of reciprocal of last antibody dilution showing inhibition of agglutination.
[c]Ratio of number of birds dying to number of birds vaccinated
[d]Ratio of number of birds dying to number of birds challenged. Birds were challenged by intramuscular inoculation of 5.0 $\log_{10}$ $EID_{50}$ of NDV Texas strain GB.
ND: Not detectable
NT: Not tested Study B. Protective efficacy of TROVAC-NDV (vFP96) in two sources of commercial broiler chickens and in SPF chickens was assessed. Three groups of one day old birds were studied. Group 1: Chickens were hatched from eggs, obtained from a hatchery in which there was no prior history of vaccination with fowlpox virus. Group 2: Chickens were hatched from eggs obtained from a hatchery in which there was a prior history of vaccination with fowlpox virus. Group 3: Specific pathogen free chickens were obtained.

Birds were vaccinated subcutaneously with either 2.0 or 4.0 $\log_{10}$ $EID_{50}$ of TROVAC-NDV. Birds of each group were kept as un-vaccinated contact controls. Birds were bled at 21 and 28 days post-vaccination and the presence of NDV HI antibody assessed. Sera were also assessed for the presence of fowlpox antibody post-vaccination using the agar gel precipitin test. At 28 days post-vaccination, 10 birds of each group and 10 controls were challenged by intramuscular inoculation of 4.2 $\log_{10}$ $EID_{50}$ of the velogenic NDV strain Texas GB and survivors were assessed. Ten birds of each group and 10 controls were also challenged by wing stab inoculation of the NVSL strain of fowlpox virus. Protection from fowlpox challenge was assessed on the basis of lack of a take or lesion at the site of inoculation. Results of this experiment are shown in Table 48.

The results indicate that the commercial broiler chickens did not develop a detectable immune response to NDV antigens expressed by TROVAC-NDV while SPF chickens did show an immune response. Despite the lack of specific anti-NDV antibody in commercial birds, there was no difference in the level of protection seen after a velogenic NDV challenge. None of the birds showed an immune response to fowlpox vaccination detectable by the agar gel precipitin test. Despite this lack of detectable anti-fowlpox antibody all vaccinated birds were protected from fowlpox challenge while non-vaccinated birds succumbed. These results indicate that prior exposure of the hen to fowlpox virus does not prohibit the induction of protective immunity against NDV or fowlpox in chickens vaccinated with a fowlpox based NDV recombinant.

TABLE 48

Protective efficacy of TROVAC-NDV (vFP96) in SPF and commercial broiler chickens.

| Bird Group | Dose | NDV HI GMT[d] Week 3 | NDV HI GMT[d] Week 4 | Percent Protection[e] NDV | Percent Protection[e] FP |
|---|---|---|---|---|---|
| Group 1[a] | 2.0 | <5 | <5 | 70 | 100 |
|  | 4.0 | <5 | <5 | 70 | 100 |
|  | None | <5 | <5 | 0 | 0 |
| Group 2[b] | 2.0 | <5 | <5 | 40 | 100 |
|  | 4.0 | <5 | <5 | 70 | 100 |
|  | None | <5 | <5 | 0 | 0 |
| Group 3[c] | 2.0 | 17 | 13 | 80 | 100 |
|  | 4.0 | 20 | 11 | 80 | 100 |
|  | None | <5 | <5 | 0 | 0 |

[a]Birds from a hatchery with no prior history of vaccination with fowlpox virus.
[b]Birds from a hatchery with prior history of vaccination with fowlpox virus
[c]Specific pathogen free birds
[d]Geometric mean titer of HI antibody
[e]Percent protection of birds after NDV or Fowpox challenge Certain Materials and Methods for Following Examples 79 to 81, Which Relate to Human Recombinant Immunodeficiency Virus-NYVAC or -ALVAC Virus; Cell Lines. P815 murine mastocytoma cells (H-2$^d$) were obtained from the American Type Culture Collection and maintained in Eagle's Minimum Essential Medium supplemented with 10% fetal bovine serum (FBS) and 100 IU/ml penicillin and 100 µg/ml streptomycin.

Mice. Female BALB/cJ (H-2$^d$) mice were purchased from Jackson Laboratories (Bar Harbor, Me.) and maintained on mouse chow and water ad libitum. All mice were used between the ages of six and fifteen weeks of age.

Inoculations. Mice were intravenously inoculated with 5×10$^7$ plaque forming units (pfu) in 0.1 ml of phosphate-buffered saline via the lateral tail vein.

Sera. Mice were lightly anesthetized with ether and blood was collected from the retroorbital plexus. Blood from mice comprising an experimental group was pooled and allowed to clot. The serum was collected and stored at −70° C. until use.

Assay for Cytotoxic T Lymphocytes and In Vitro Stimulation of Memory Precursors of Cytotoxic T Lymphocytes. Six week old female BALB/c mice were inoculated intravenously with 5×10$^7$ pfu of vaccinia virus (NYVAC), recombinant vaccinia virus expressing HIV-1 (IIIB) env (vP911), canarypoxvirus (ALVAC), or with recombinant canarypoxvirus expressing HIV-1 (IIIB) env (vCP112). Seven days later, the spleen cells were assayed for primary CTL activity against unmodified P815 cells or P815 cells that had been incubated overnight with a peptide corresponding to the hypervariable V3 loop region of HIV-1 (IIIB) gp120. Twenty-two days after the initial immunization, the spleen cells of the experimental mice were incubated with poxvirus infected stimulator spleen cells and assayed for memory CTL activity against peptide pulsed targets as before. To determine secondary CTL activity, 29 days after the primary immunization mice received a second inoculation of identical dosage and content as the first. Five days later, the spleen cells were assayed for cytolytic activity against peptide pulsed targets. For cytotoxicity assays, H-2$^d$ P815 murine mastocytoma cells were incubated overnight in medium (Minimum Essential Medium containing Earle's salts and supplemented with 10% fetal bovine serum, 2 mM L-glutamine, 100 U/ml penicillin, and 100 µg/ml streptomycin) with or without 20 µg/ml V3 peptide (CNTRKR-IRIQRGPGRAFVTGK, American Bio-Technologies, Inc.) (SEQ ID NO:457). The following morning, the P815 cells were washed by centrifugation and labeled for 1 hr at 37° C. in 100 µCi of Na$_2$$^{51}$CrO$_4$ per 2×10$^6$ cells. Intact spleens were aseptically removed from euthanized mice, bathed in ice cold Hank's Balanced Salt Solution, and disrupted into single cell suspensions using a Stomacher blender. The spleen cell suspensions were washed several times by low speed centrifugation and resuspended in Assay Medium (RPMI 1640 containing 10% fetal bovine serum, 20 mM HEPES, 2 mM L-glutamine, 5×10$^{-5}$M 2-mercaptoethanol, 100 U/ml penicillin, and 100 µg/ml streptomycin). For memory CTL activity, the spleen cells from immunized mice were resuspended in Stimulation Medium (Minimum Essential Medium with Earle's salts containing 10% fetal bovine serum, 2 mM L-glutamine, 10$^{-4}$M 2-mercaptoethanol, 100 U/ml penicillin, and 100 µg/ml streptomycin) and stimulated in vitro in upright 25 cm$^2$ tissue culture flasks with naive syngeneic stimulator spleen cells that had been infected with one of the poxviruses or poxvirus recombinants. After five days at 37° C., the cells were washed, counted, and resuspended in Assay Medium. $^{51}$Chromium labelled target cells were added to titrated effector cells in 96-well microtiter plates for a 4 hr $^{51}$Cr release assay. Effector to target cell ratios (E:T) shown for the three assays were 100:1 (primary), 20:1 (memory), and 50:1 (secondary). Percent cytotoxicity was calculated as (experimental $^{51}$Cr release−spontaneous $^{51}$Cr release)/(maximum $^{51}$Cr release−spontaneous $^{51}$Cr release)×100. Maximum release was determined by the addition of 5% sodium dodecyl sulfate to target cells while spontaneous release was determined by incubating target cells in the absence of effector cells. In none of the experiments presented did spontaneous release of $^{51}$Cr from target cells exceed 20% of maximum $^{51}$Cr release. Error bars represent 1 standard deviation from the mean. (*) $P<0.05$, Student's t-test compared to appropriate vaccinia or canarypoxvirus immunized mice.

Cell Surface Phenotype of Cytotoxic Effector Cells Methods were essentially mice spleen cells immunized with vaccinia virus a canarypox virus vectors (NYVAC, ALVAC) or with vaccinia virus or canarypox virus recombinants expressing HIV IIIB env (vP911, vCP112). A second inoculation was administered 30 days after the first. Prior to addition to V3 peptide pulsed targets, the spleen cells were treated with monoclonal antibodies or alloantiserum to murine T-lymphocyte surface antigens in a two-stage protocol. Briefly, the spleen cells were resuspended at 10$^7$ viable cells per ml of Cytotoxicity Medium (RPMI 1640 containing 0.2% BSA and 5 mM HEPES) to which was added alloanti-Thy 1.2 (Cedarlane), monoclonal anti-CD4 (172.4, the generous gift of K. J. Weinhold, Duke University Medical Center), or monoclonal anti-Lyt 2.2 (Cedarlane). After 30 min at 5° C., the cells were washed and resuspended in the original volume of Cytotoxicity Medium, divided into two equal portions with or without complement (Rabbit Lo-Tox M, Cedarlane) and incubated at 37° C. for 45 min. The cells were then washed in Assay Medium and, based on the pre-treatment cell densities, resuspended in volumes of Assay Medium approximating effector to target cell ratios of 100:1 (primary), 10:1 (memory), or 80:1 (secondary) before addition to a 5 hr $^{51}$Cr release assay. Error bars represent 1 standard deviation from the means.

Specificity of CTL Antigen Receptor Recognition of the V3 Loop Region of HIV IIIB gp120. Cytotoxic T lymphocytes and memory precusors of cytotoxic T lymphocytes were generated by inoculation of mice with vCP112 as described above. Assays for cytotoxic T lymphocytes were performed as described above except that P815 target cells were pulsed overnight with V3 peptide from HIV-1 IIIB (CNTRKRIRIQRGPGRAFVTGK) (SEQ ID NO:384), MN (CNKRKRIHIGPGRAFYTTKN) (SEQ ID NO:385), or SF2 (CNTRKSIYIGPGRAFHTTGR) (SEQ ID NO:386). Effector to target cell ratios were 100:1 (primary), 20:1 (memory), and 50:1 (secondary).

Antibody Responses to HIV-1 (IIIB) gp120. The wells of ELISA plates (Immulon II) were coated overnight at 4° C. with 0.5 µg of partially purified HIV-1 (IIIB) gp120 (Dr. G. Franchini, NCI-NIH) in carbonate buffer, pH 9.6. The plates were then washed with phosphate-buffered saline containing 0.05% Tween 20 (PBST). The plates were then blocked for 2 hr at 37° C. with PBST containing 1% bovine serum albumin (BSA). After washing with PBST, sera were initially diluted 1:20 with PBST containing 0.1% BSA (dilution buffer). The sera were further 2-fold serially diluted in the wells of the ELISA plate. The plates were incubated at 37° C. for 2 hr and washed with PBST. Horseradish peroxidase conjugated rabbit anti-mouse immunoglobulins (DAKO) was diluted 1:2000 in dilution buffer and added to the wells of the ELISA plated and incubated at 37° C. for 1 hour. After washing with PBST, OPD (o-phenylenediamine dihydrochloride) in substrate buffer was added and the color was allowed to develop at ambient temperature for about 20 min. The reaction was extinguished by the addition of 2.5M $H_2SO_4$. The absorbance at 490 nm was determined on a Bio-Tek EL-309 ELISA reader. The serum endpoint was defined as the reciprocal of the dilution giving an absorbance value of 0.4.

EXAMPLE 79

Figure 31:
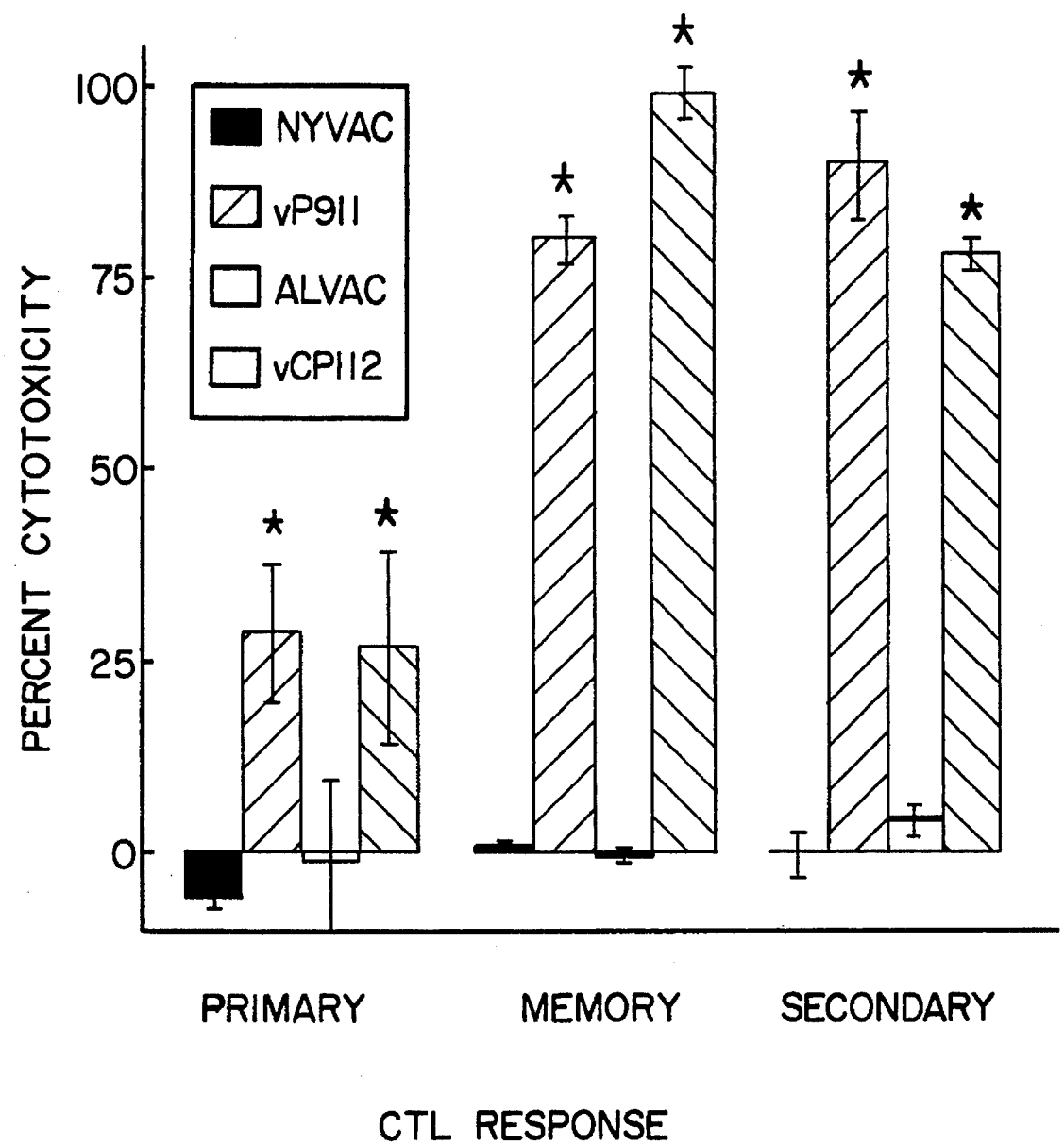
FIG. 31 shows the cytotoxic responses of spleen cells of mice and immunized with vaccinia virus or canarypox virus vectors (NYVAC, ALVAC) or with vaccinia virus or canarypox virus recombinants expressing HIV III B env (vP911, vCP112)

A RECOMBINANT CANARYPOXVIRUS EXPRESSING HIV env ELICITS HIV-SPECIFIC CYTOTOXIC T LYMPHOCYTE ACTIVITY Seven days after the initial inoculation with the HIV canarypoxvirus recombinant (vCP112; defined in Example 18), cytotoxic responses of spleen cells against HIV V3 peptide pulsed target cells were roughly equivalent to the cytotoxic responses elicited by the same dose, 5×10$^7$ pfu, of a vaccinia virus recombinant (vP911) (Example 18) expressing the same HIV env gene (FIG. 31). Following appropriate in vitro stimulation or a second inoculation, the levels of cytotoxicity of the spleen cells of mice given the canarypoxvirus recombinant increased and were comparable to spleen cells from mice similarly administered the vaccinia virus recombinant. No such cytotoxic responses were detected from spleen cells of mice inoculated with the non-recombinant vaccinia virus or canarypoxvirus vectors, NYVAC and ALVAC, respectively, confirming the requirement for immunization with a poxvirus recombinant expressing the HIV env gene. Furthermore, no cytotoxic reactivity was detected against unmodified P815 cells from the spleen cells of any of the mice regardless of the inoculation regimen. Thus, only mice inoculated with recombinant vaccinia virus or, more significantly, recombinant canarypoxvirus expressing the env coding sequence from HIV-1 demonstrated V3-specific cytotoxic responses.

EXAMPLE 80

CHARACTERIZATION OF CYTOTOXIC EFFECTOR CELLS

Figure 32:
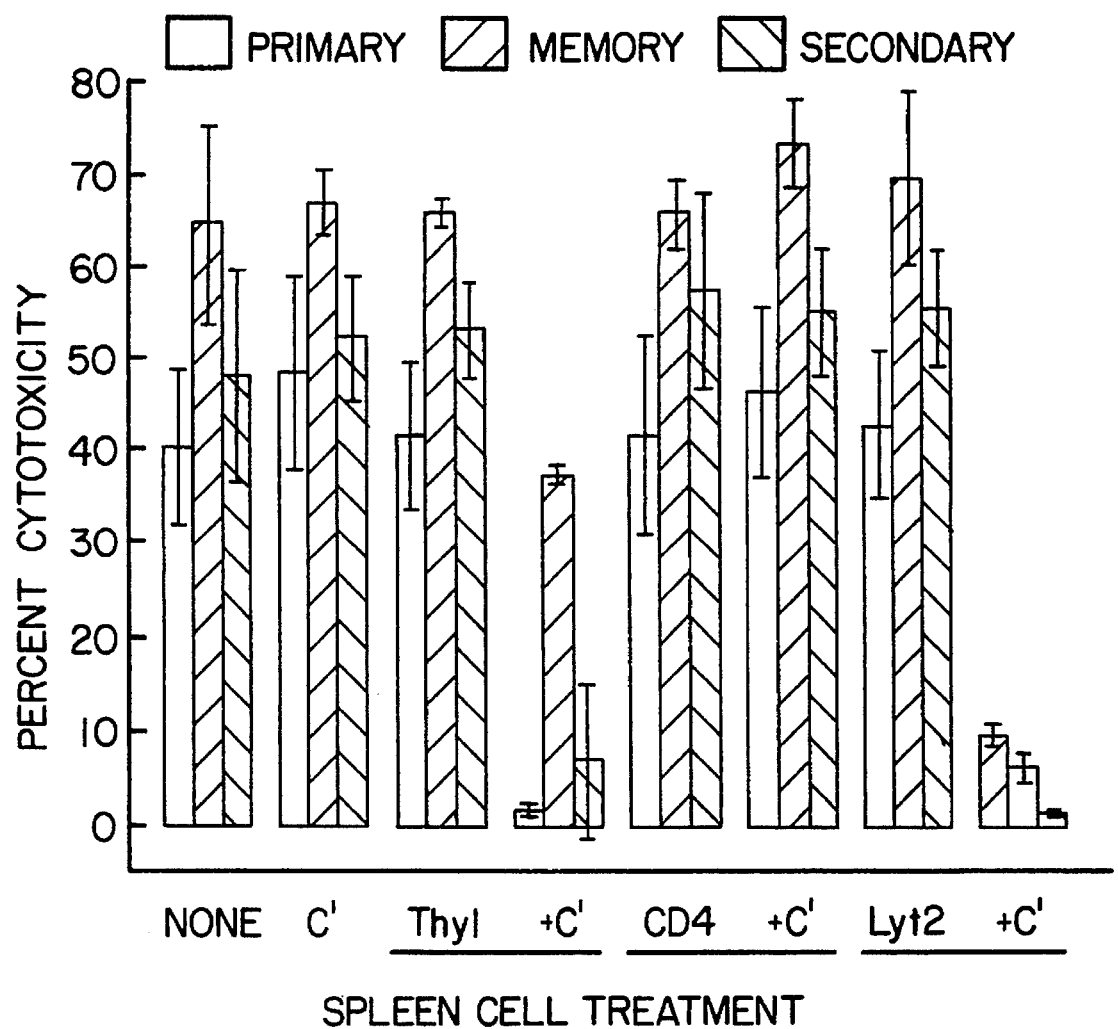
FIG. 32 shows the sensitivity of the cytotoxic effector cells from the spleens of mice immunized with vCP112 to antibodies against cytotoxic T lymphocyte cell surface antigens Thy 1.2 and Lyt 2.2.

To determine the identity of the spleen cells associated with the lysis of HIV-1 V3 peptide pulsed target cells, mice were immunized with vCP112. After each immunization, or in vitro stimulation 21 days after the first inoculation, a two-step depletion procedure was performed, and the spleen cells were assessed for cytotoxicity against V3 peptide pulsed P815 cells. Mice inoculated with the canarypox vector ALVAC did not generate spleen cells capable of killing peptide pulsed targets and are not shown. Following a single immunization, vCP112 induced spleen cells able to kill V3 peptide pulsed targets. The lytic effector cells were sensitive to treatment with anti-murine Thy 1.2 or Lyt 2.2 plus complement and were resistant to anti-CD4 as shown in FIG. 32 which shows the sensitivity of the cytotoxic effector cells from spleen cells of immunized with vCP112 to antibodies against cytotoxic T lymphocyte cell surface antigens Thy 1.2 and Lyt 2.2. Neither complement nor any of the monoclonal antibodies or alloantisera alone affected the cytolytic action of these cells. Similar results were obtained five days after a second immunization administered on day 30. Twenty-one days after a single inoculation, in vitro stimulation with vCP112 infected syngeneic spleen cells gave rise to lytic effector cells only partially sensitive to anti-Thy 1.2 although completely sensitive to anti-Lyt 2.2 and resistant to anti-CD4. These Thy 1.2–, CD4–, Lyt 2.2+ effector cells are not seen following in vitro stimulation with vP911 of spleen cells from vCP112 inoculated mice. Nonetheless, it is clear that HIV V3 loop specific cytotoxicity was mediated by a population of T lymphocytes expressing Thy 1.2 and Lyt 2.2, but not CD4. This cell surface phenotype is characteristic of classical cytotoxic T lymphocytes.

EXAMPLE 81

SPECIFICITY OF CTL ANTIGEN RECEPTOR RECOGNITION OF THE V3 LOOP REGION OF HIV gp120

Figure 33:
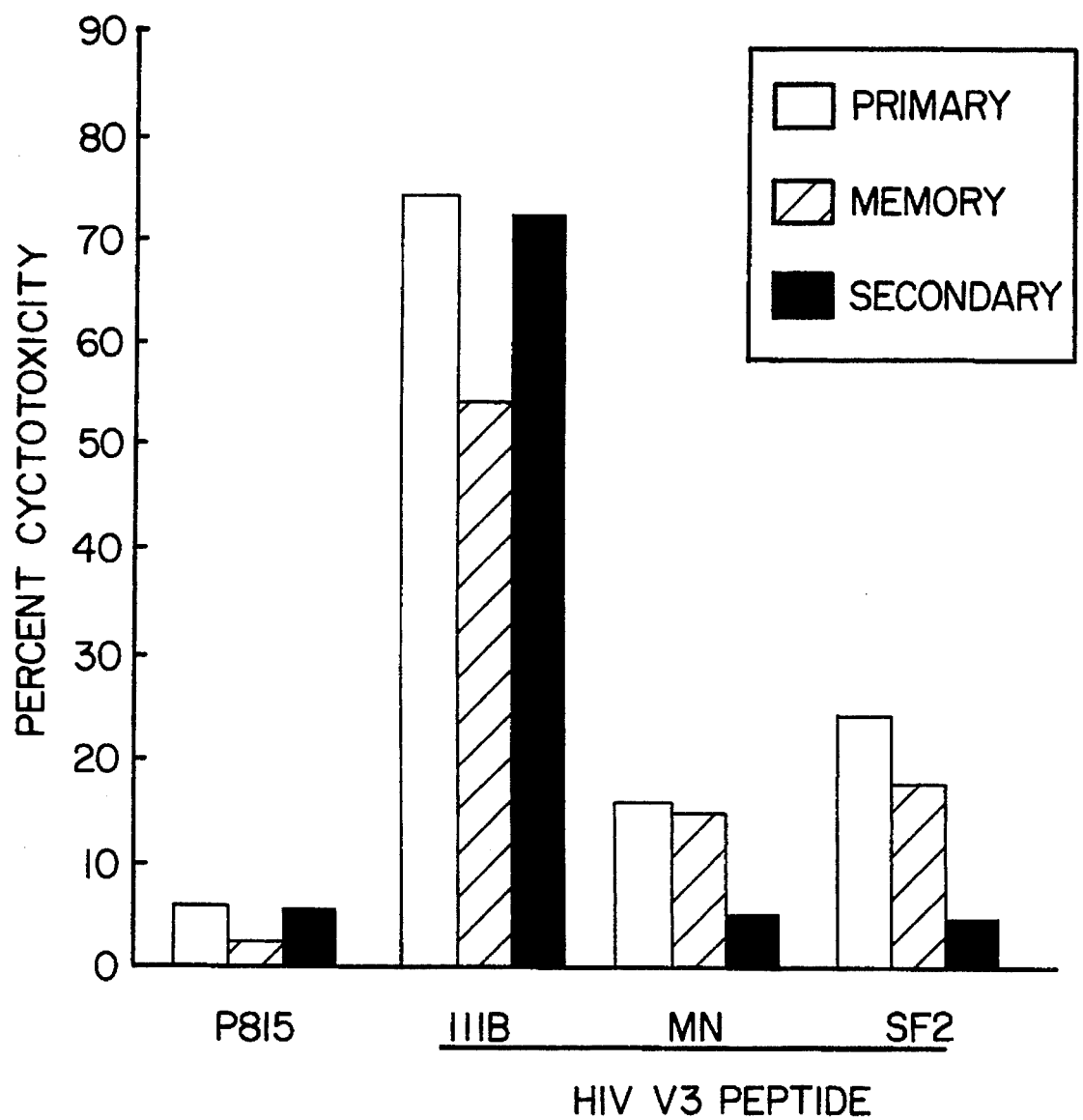
FIG. 33 shows the specificity of cytotoxic T lymphocyte antigen receptor for the HIV III B hypervariable V3 loop of gp120, but not for the V3 loop of HIV MN or SF2.
Figure 34:
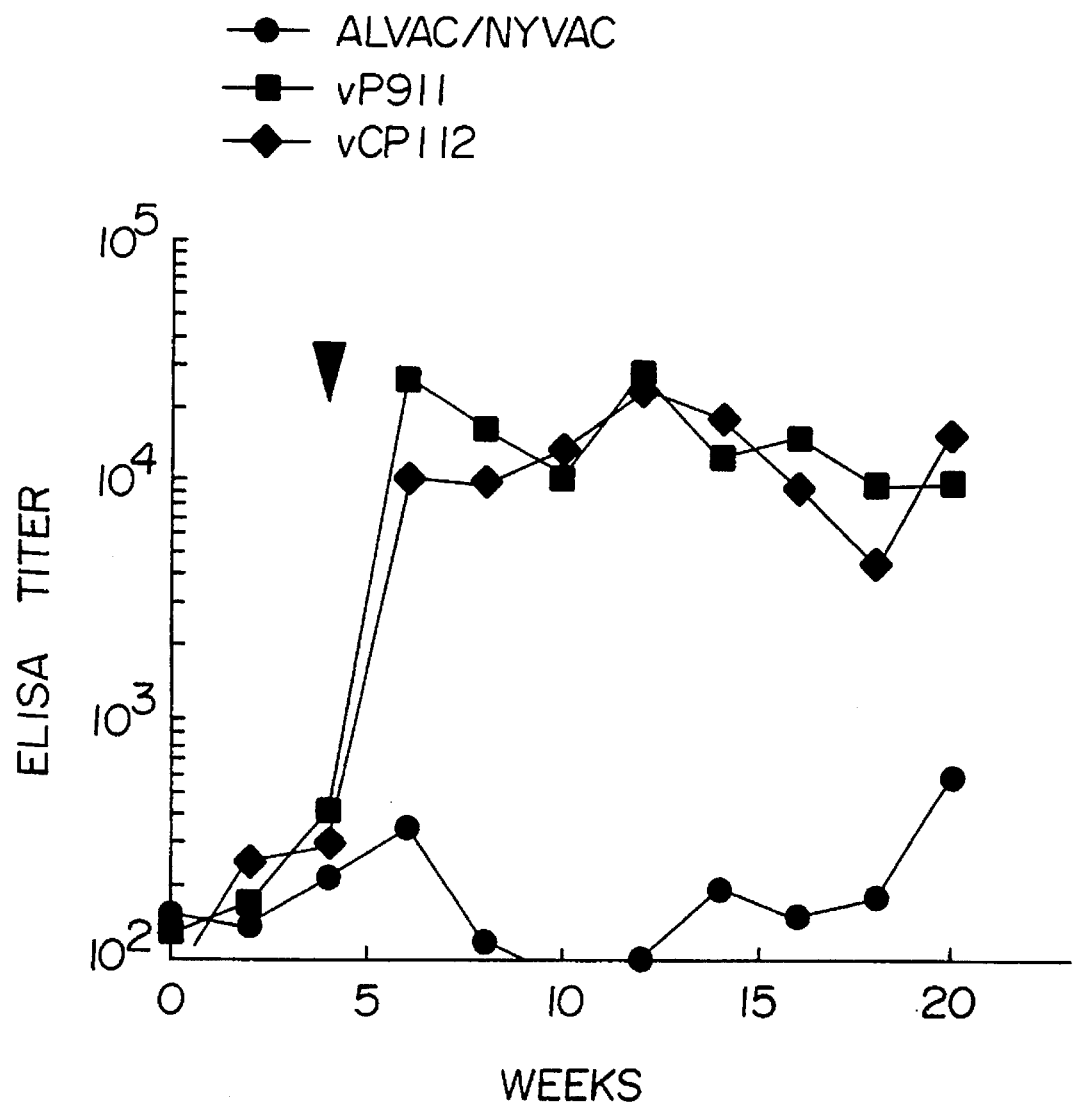
FIG. 34 shows the antibody responses to HIV III B gp120 of mice immunized with vectors (NYVAC, ALVAC) or with vaccinia virus recombinant vP911 or canarypox recombinant vCP112 expressing HIV-1 env (inverted triangle indicates time of administration of second inoculation)
Figure 35A:
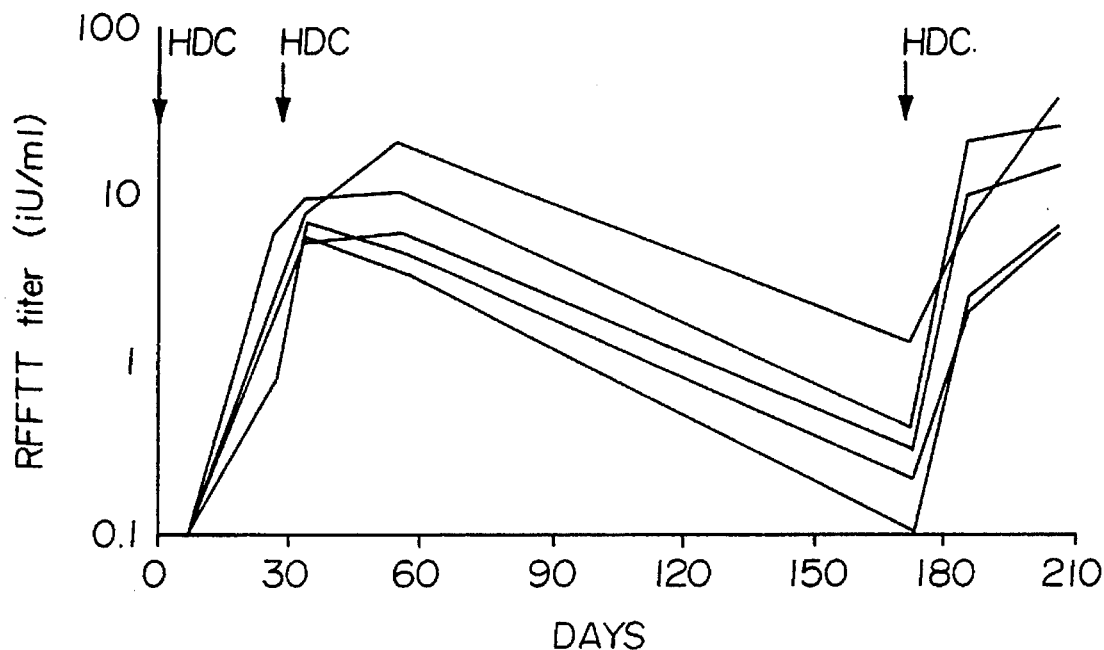
FIG. 35 (FIGS. 35A, 35B, 35C, 35D) shows graph of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208)
Figure 35C:
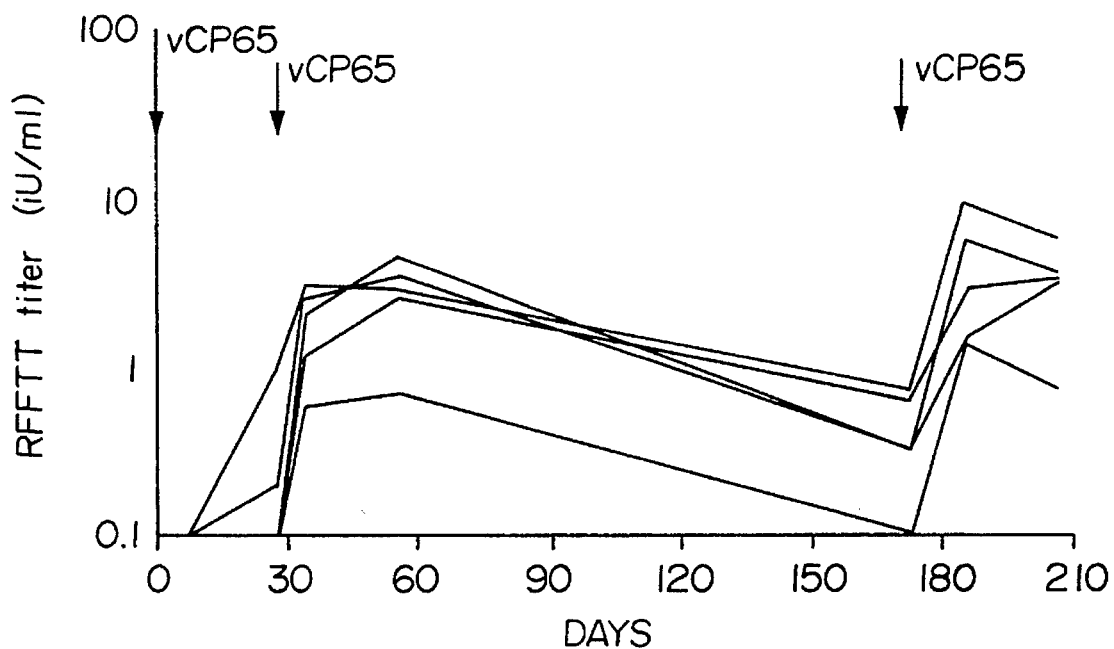
Figure 35B:
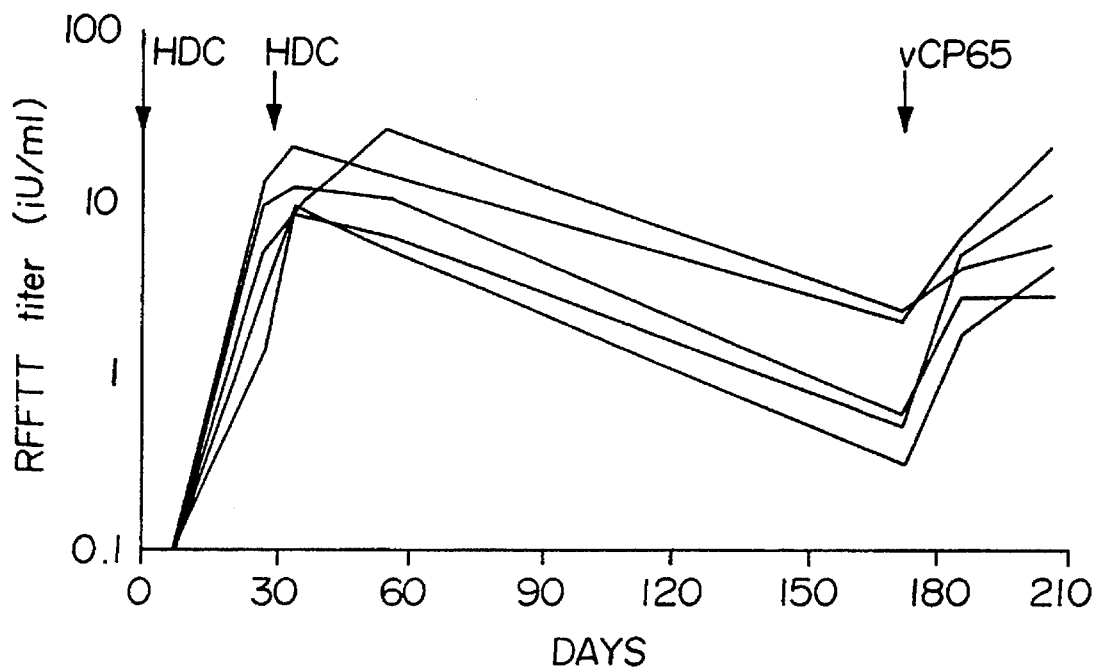
Figure 35D:
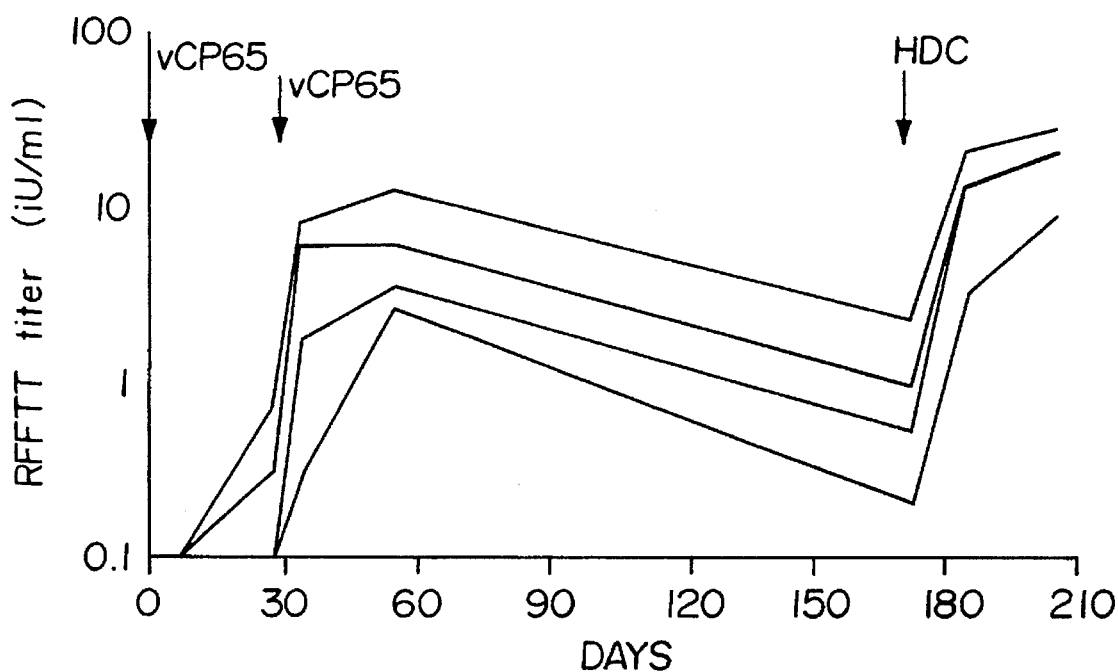
Figure 37A:
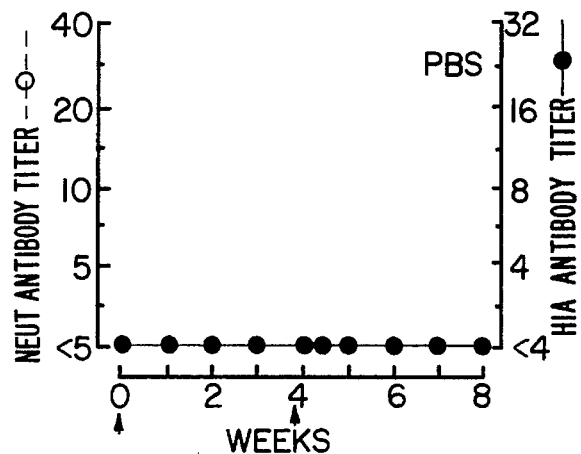
FIG. 37 (FIGS. 37A, 37B, 37C, 37D) shows NEUT and HAI activities observed in swine immunized on days 0 and 28 with vP908, vP923, vP866 and PBS (arrows indicated days of inoculation)
Figure 37B:
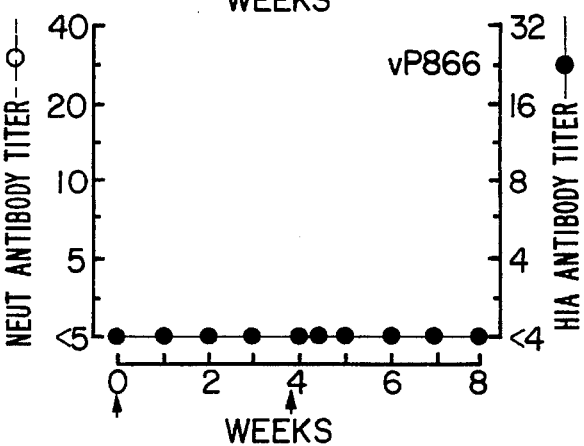
Figure 37C:
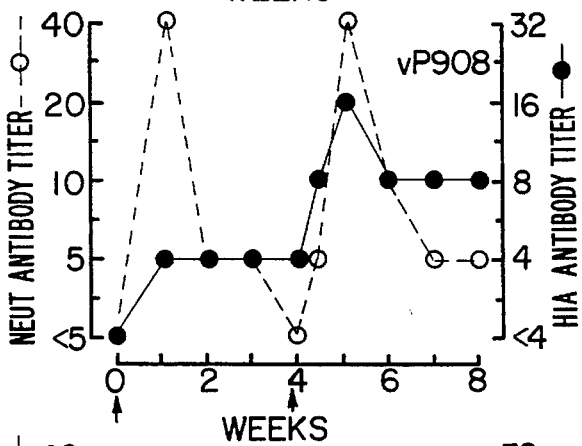
Figure 37D:
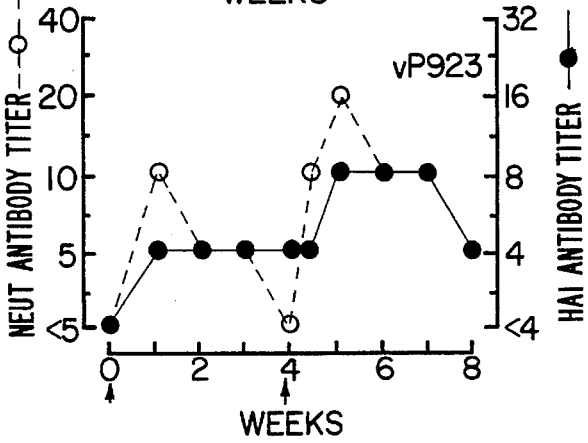
Figure 38A:
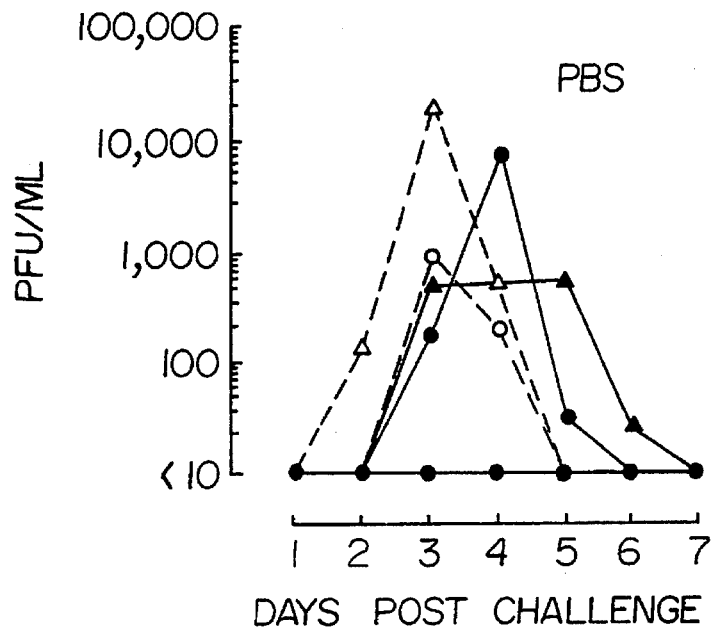
FIG. 38 (FIGS. 38A, 38B, 38C, 38D) shows time course of viremia detected in individual pigs of each group immunized with PBS, vP866, vP908 or vP923 and then challenged with the B-2358/84 strain of JEV.
Figure 38B:
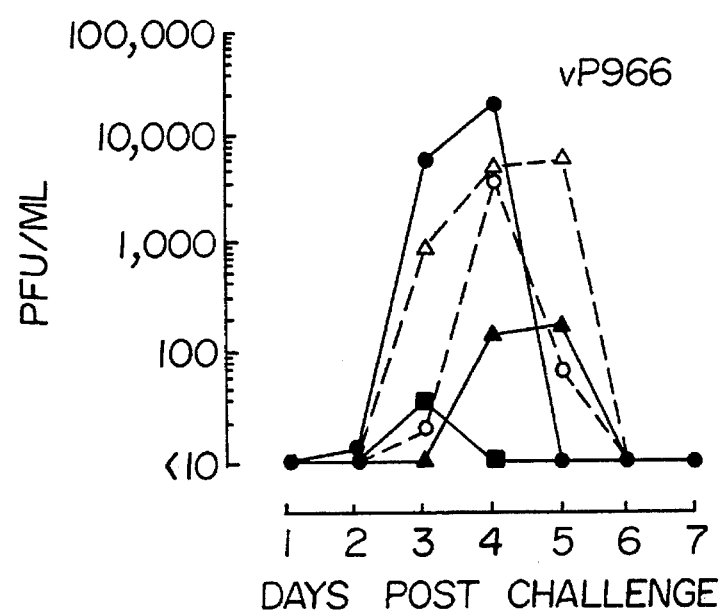
Figure 38C:
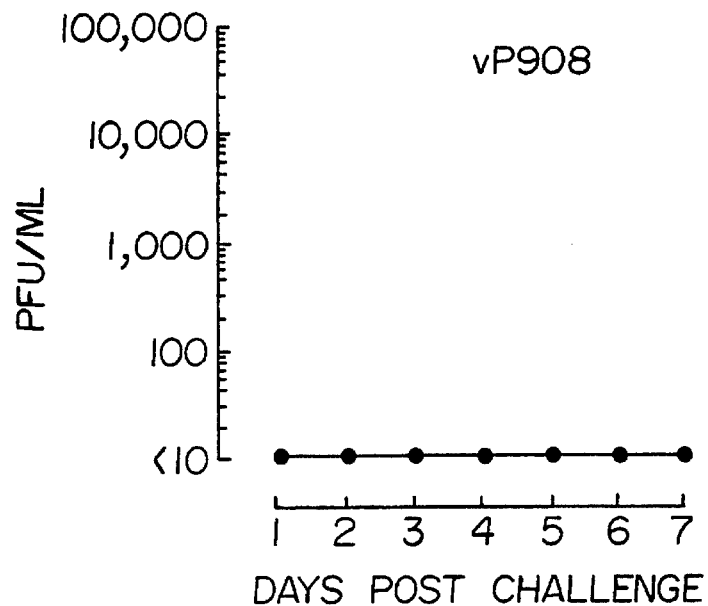
Figure 38D:
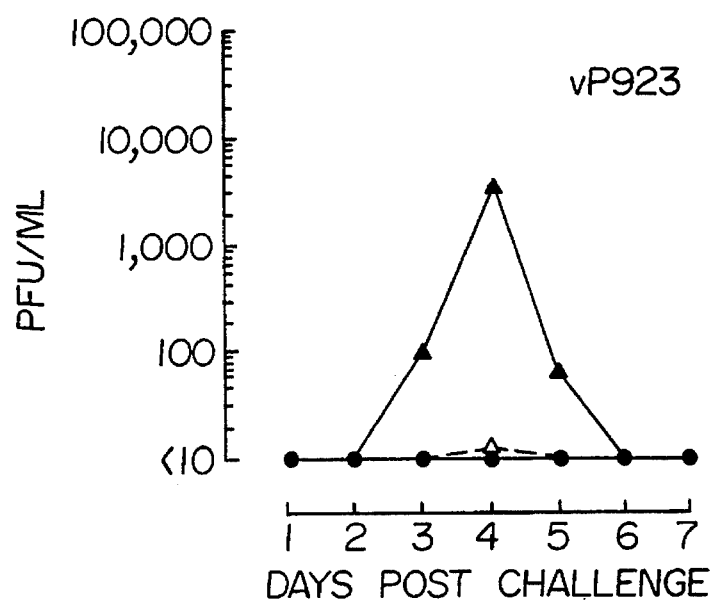

T lymphocyte antigen receptors are exquisitely sensitive to small alterations in the primary amino acid sequence of the epitope fragment. The V3 loop region of HIV gp120 is hypervariable and differs immunologically among HIV isolates. The hypervariability resides in substitutions and additions of only a few amino acids. To examine the specificity of cytotoxic cells generated by the HIV canarypox virus recombinant, susceptibility to CTL activity was compared among P815 target cells pulsed with peptides corresponding the V3 loop region of gp120 of HIV isolates IIIB, MN, or SF2. HIV specific primary CTL activity was confined only to P815 target cells pulsed with peptide corresponding to the V3 loop of HIV isolate IIIB, but not target cells pulsed with peptides corresponding to the V3 loop region of gp120 of HIV isolates MN or SF2, as shown in FIG. 33 which illustrates the specificity of cytotoxic T lymphocyte antigen receptor for the HIV III B hypervariable V3 loop of gp120, but not for the V3 loop of HIV MN or SF2. Similar results were obtained with in vitro stimulated, HIV specific memory CTL activity and secondary CTL activity induced by immunization with the canarypox virus recombinant vCP112. Thus, HIV specific CTLs elicited by a recombinant canarypox virus expressing the env gene of HIV isolate IIIB recognize only target epitopes derived from the same antigenic isolate. These results clearly indicate the exquisite specificity of the lymphocyte effector cells generated by immunization with the HIV canarypox virus recombinant and eliminate such nonspecific effector mechanisms as natural killer (NK) cell activity. These results are in complete agreement with other reports characterizing the precision of epitope recognition by HIV V3-specific murine cytotoxic T lymphocytes.

EXAMPLE 82

ANTIBODY RESPONSES OF MICE INOCULATED WITH NYVAC- and ALVAC-BASED HIV RECOMBINANTS To evaluate humoral responses to HIV, mice were immunized at day 0 with a vaccinia virus HIV recombinant or canarypoxvirus recombinant and received a secondary immunization at week four. The mice were bled at various intervals through 20 weeks after the initial immunization. Pooled sera from each treatment group were assayed for antibodies to HIV by ELISA employing purified gp120 as antigen; the results are shown in FIG. 34 which provides the antibody responses to HIV III B gp120 of mice immunized with vectors (NYVAC, ALVAC) or with vaccinia virus recombinant vP911 or canarypox recombinant (vCP112) expressing HIV-1 env, wherein the inverted triangle indicates the time of administration of the second inoculation. Primary antibody responses were generally modest, but detectable. Following the secondary immunization, the antibody titers of mice immunized with both vP911 and vCP112 increased and peaked at week six with titers of over 10,000. These antibody titers remained at approximately the same levels throughout the duration of the study. Thus, a canarypoxvirus HIV recombinant, vCP112, was capable of inducing a significant antibody response.

Inoculation of mice with a canarypoxvirus expressing the env gene of HIV-1 elicits spleen cell reactivity with characteristics of cytotoxic T lymphocytes: the requirement for immunization, cell surface phenotype, memory, and elegant epitope specificity. Furthermore, antibody responses to HIV-1 gp120 are induced by inoculation with this recombinant canarypoxvirus.

EXAMPLE 83

DERIVATION OF NYVAC- ALVAC-BASED HIV-1 RECOMBINANTS EXPRESSION OF HIV-1(MN) env BY ALVAC AND NYVAC HIV-1(MN) env sequences were derived from plasmid pMN1.8-9 and pMN1.8-10 which contain a 1774 bp and 1803 bp subfragment from a genomic cDNA clone of HIV-1(MN), respectively. These plasmids were provided by the laboratory of Dr. R. C. Gallo (NCI-NIH). A 1,026 bp KpnI/EcoRI fragment was derived by amplifying these sequences from pMN1.8-9 by PCR using oligonucleotides HIV MN6 (SEQ ID NO:387) (5'-GGGTTATTAATGATCTGTAG-3') and HIV3B2 (SEQ ID NO:151) followed by digestion with KpnI/EcoRI. This fragment was inserted into pBS-SK digested with KpnI and EcoRI to yield pBSMIDMN.

A 1,028 bp SalI/XbaI fragment was derived from pMN1.810 by PCR using oligonucleotides HIVMN5 (SEQ ID NO:388) (5'-ATCATCGAGCTCTGTTCCTTGGGTTCTTAG-3') and HIVMN3P (SEQ ID NO:389) (5'-ATCATCTCTAGAATAAAAAATTATAGCAAAGCCCTTTCCAAGCC-3') followed by digestion with SacI and XbaI. This fragment was co-ligated into pBS-SK digested with EcoRI and XbaI with a 404 bp EcoRI/SacI fragment. The 404 bp fragment was derived by PCR with pMN1.8–9 as template and oligonucleotides HIV3B1 (SEQ ID NO:144) and HIVMN4 (SEQ ID NO:390) (5'-ATCATCGAGCTCCTATCGCTGCTC-3'). The resultant plasmid was designated as pBS3MN.

The 1.026 bp EcoRI/KpnI fragment from pBSMIDMN was inserted into the 4,315 bp pBS3MN digested with EcoRI/KpnI to generate pBSMID3MN. This plasmid contains most of the env gene except the 5'-most region. The vaccinia virus H6 promoter (Goebel et al., 1990a,b) and the 5'-most region of the env gene were obtained by isolating a 318 bp KpnI fragment from pH6HIIIBE (defined in Example 18). This fragment was ligated into KpnI/XbaI digested pBS-SK along with the 2.9 bp KpnI/XbaI fragment from pBSMID3MN. The resultant plasmid was designated as pH6HMNE.

The 2.7 kb NruI/XbaI fragment from pH6HMNE, containing the entire HIV-1(MN) env gene juxtaposed 3' to the 3'-most 26 bp of the H6 promoter, was blunt-ended and inserted into NruI/SmaI digested pSPHAH6. This generated plasmid pHAHIVMNE. Plasmid pSPHAH6 was derived as follows.

Plasmid pMP2VCL (containing a polylinker region within vaccinia sequences upstream of the K1L host range gene) was digested within the polylinker with HindIII and XhoI and ligated to annealed oligonucleotides SPHPRHA A through D (SPHPRHA A (SEQ ID NO:391) 5'-AGCTTCTTTATTCTATACTTAAAAAGTGAAAATAAATACAAAGGTTCTTGAGGGT-3' SPHPRHA B (SEQ ID NO:392) 5'-TGTGTTAAATTGAAAGCGAGAAATAATCATAAATTATTTCATTATCGCGATATCCGTTAAGTTTGTATCGTAC-3' SPHPRHA C (SEQ ID NO:393) 3'-TTATTAGTATTTAATAAAGTAATAGCGCTATAGGCAATTCAAACATAGCATGAGCT-5' SPHPRHA D (SEQ ID NO:394) 3'-AGAAATAAGATATGAATTTTTCACTTTTATTTATGTTTCCAAGAACTCCCAACACAATTTAACTTTCGCTCT-5') generating pSP126 containing a HindIII site, H6 promoter −124 through —1 (Perkus et al., 1989) and XhoI, KpnI, SmaI, SacI and EcoRI sites.

Plasmid pSD544 (containing vaccinia sequences surrounding the site of the HA gene replaced with a polylinker region and translation termination codons in six reading frames) was digested with XhoI within the polylinker, filled in with the Klenow fragment of DNA polymerase I and treated with alkaline phosphatase. SP126 was digested with HindIII, treated with Klenow and the H6 promoter isolated by digestion with SmaI. Ligation of the H6 promoter fragment to pSD544 generated pSPHAH6 which contained the H6 promoter in the polylinker region (in the direction of HA transcription). This insertion plasmid enables the replacement of the vaccinia HA gene (A56; Goebel et al., 1990a,b) with foreign genetic material.

The 2.8 kb XbaI/partial KpnI fragment from pH6HMNE was isolated and inserted into pC5L (defined in Example 44) digested with XbaI and KpnI. The resultant plasmid was designated as pC5HIVMNE.

Plasmids pHAHIVMNE and pC5HIVMNE were used in vitro recombination experiments with NYVAC (vP866) and ALVAC(CPpp), respectively, as the rescue virus. These were done by standard procedures (Piccini et al., 1987). Plaques derived from recombinant virus were identified by plaque hybridization using a radiolabeled env-specific DNA probe (Piccini et al., 1987). After three rounds of plaque purification, the recombinant viruses were amplified. The NYVAC-based HIV-I(MN) env recombinant was designated vP1008 and the ALVAC-based recombinant vCP125.

Recombinant viruses, vCP125 and vP1008, were analyzed for expression of the HIV-1(MN) env gene by immunofluorescence and immunoprecipitation using previously reported procedures (Taylor et al., 1990). Pooled human sera from HIV-seropositive individuals (obtained from Dr. K. Steimer, Chiron Corp., Emeryville, Calif.) was used in these assays. Results from immunofluorescence revealed that cells infected with either vCP125 or vP1008 express the HIV-1(MN) gene product on their surface. Immunoprecipitation from lysates prepared from vP1008 and vCP125 infected cells demonstrated the presence of three predominant HIV-1-specific proteins with apparent molecular masses of 160 kDa, 120 kDa, and 41 kDa, respectively. These are consistent with expression of the precursor envelope glycoprotein (160 kDa) and the proteolytically derived mature forms (120 kDa and 41 kDa).

EXAMPLE 84

EXPRESSION OF THE HIV-1(MN) gp120 BY NYVAC AND ALVAC

A 391 bp EcoRI/XbaI fragment was amplified from pBS3MN using oligonucleotides T7 (SEQ ID NO:395) (5'-AATACGACTCACTATAG-3') and HIVMN120 (SEQ ID NO:396) (5'-ATCATCTCTAGAATAAAAAT-TATCTTTTTTCTCTCTGCACCACTC-3') followed by digestion with EcoRI and XbaI. This fragment was ligated to the 4.2 kb EcoRI/XbaI fragment derived from pH6HMNE (defined in Example 83). The resultant plasmid contains a poxvirus expression cassette for HIV-1(MN) gp120 in pBS-SK and was designated pBSHIVMN120.

A 1.7 kb XbaI/partial KpnI fragment was isolated and inserted into pC5L digested with KpnI/XbaI. The resultant plasmid was designated as pC5HIVMN120. The insertion plasmid for integrating the HIV-1(MN) gp120 gene into NYVAC was obtained by first isolating the 1.6 kb NruI/SmaI fragment from pBSHIVMN120. This fragment was inserted into pSPHAH6 digested with NruI and SmaI to provide pHAHIVMN120.

Insertion plasmids, pC5HIVMN120 and pHA-HIVMN120, were used in recombination experiments with ALVAC(CPpp) and NYVAC (vP866) as the rescuing virus. These assays and plaque identification and purification were performed by standard procedures (Piccini et al., 1987). Hybridization analyses were performed with a radiolabeled HIV-1(MN) gp120-specific probe. Purified recombinants were amplified. The ALVAC-based HIV-1(MN) gp120 recombinant was designated as vCP124 and the NYVAC-based HIV-1(MN) gp120 recombinant as vP1004.

Cells infected with vCP124 and vP1004 were analyzed for the presence of the recombinant expressed HIV-1(MN) gp120 by immunofluorescence and immunoprecipitation. These assays were performed as previously described (Taylor et al., 1990) using a pooled human sera from HIV-seropositive individuals (obtained from K. Steimer, Chiron Corporation, Emeryville, Calif.). Results from these studies clearly indicated that cells infected with either vCP124 and vP1004 contained HIV-1(MN) gp120, whereas gp120 was not observed in uninfected cells and cells infected with parental viruses, ALVAC and NYVAC.

EXAMPLE 85

EXPRESSION OF A NON-CLEAVABLE FORM OF HIV-1 gp160 BY ALVAC AND NYVAC

In order to express a non-cleavable form of the HIV-1 (IIIB) gp160 an arginine to threonine mutation was engineered at amino acid 511 (Ratner et al., 1985) as was demonstrated by Guo et al. (1990). These modifications were made to decrease the shedding of gp120 from the surface of infected cells. These manipulations were performed as follows. A 376 bp PstI/XbaI fragment was obtained by first amplifying the sequences from pH6HIIIBE using oligonucleotides HIV3B2A (SEQ ID NO:397) (5'-GAAATAATAAAACAATAATC-3') and HIVECB (SEQ ID NO:398) (5'-GCTCCTATTCCCACTG-CAGTTTTTTCTCTCTGCAC-3') followed by digestion with PstI and XbaI. This fragment was ligated with a 1,061 bp PstI/XbaI fragment and a 4.5 kb EcoRI/XbaI fragment from pH6HIIIBE to yield pBSHIV3BEEC.

The 2.6 kb NruI/XbaI fragment from pBSHIV3BEEC, containing the 3'-most 26 bp of the H6 promoter linked to the gp160 cassette, was isolated and ligated to a 3.0 kb NruI/XbaI fragment of pBSHVS (defined in Example 60) to yield pBSHIV3BEECM. Digestion with NruI and XbaI excises the 3'-most 26 bp of the H6 promoter and the Hantaan virus S sequence. The 3.0 kb NruI/XbaI fragment contains the 5'-most 100 bp of the H6 promoter in a pBS-SK plasmid.

The 2.8 kb XbaI/partial KpnI fragment from pBSHIV3BEECM was ligated to XbaI/KpnI digested pC5L to yield pC5HIV3BEEC. A 2.7 kb NruI/XbaI fragment from pBSHIV3BEECM was blunt-ended with the Klenow fragment of the *E. coli* DNA polymerase and inserted into NruI/SmaI digested pSPHAH6 to yield pHAHIV3BEEC.

The insertion plasmids, pC5HIV3BEEC and pHAHIV3BEEC, were used in in vitro recombination experiments by standard procedures (Piccini et al., 1987) using ALVAC(CPpp) and NYVAC (vP866), respectively, as rescue virus. Recombinant plaques were identified by standard plaque hybridization analysis (Piccini et al., 1987) using a radiolabeled probe specific for the HIV-1 env gene. Recombinant viruses were amplified following three rounds of purification. The ALVAC-based HIV-1(IIIB) gp160 (non-cleavable) was designated as vCP126 and the NYVAC-based equivalent as vP1020.

Immunofluorescence and immunoprecipitation analyses were performed by previously described procedures (Taylor et al., 1990) on vP1020 and vCP126 infected cells using pooled human serum from HIV-seropositive individuals (obtained from K. Steimer, Chiron Corp., Emeryville, Calif.). Immunofluorescence results clearly demonstrated the surface expression of the HIV-1(IIIB) gp160 (non-cleavable form) on the surface of cells infected with either vCP126 or vP1020. Furthermore, immunoprecipitation results demonstrated the presence of a HIV-1(IIIB) gp160 in these infected cells that was not proteolytically cleaved into the mature gp120 and gp41 frames.

A non-cleavable form of the HIV-1(MN) gp160 was also pursued and the recombinant viruses obtained as follows.

A PstI/XbaI fragment was obtained by PCR amplification from pH6HMNE using oligonucleotides HIVMN3P (SEQ ID NO:389) (5'-ATCATCTCTAGAATAAAAATTATAG- GAAAGCCCTTTCCAAGCC-3') and HIVECA (SEQ ID NO:399) (5'-GTGCAGAGAAAAAACTGCAGTGG-GAATAGGAGC-3') followed by digestion with PstI and XbaI. This 1061 bp fragment was ligated with the 391 bp EcoRI/PstI from pBSHIVMNT (below) and the 4.2 kb EcoRI/XbaI fragment from pH6HMNE (defined in Example 83). The resultant plasmid was designated as pBSHIVM-NEEC1. Sequence analysis of the HIV env insert demonstrated that a single nucleotide was missing. To correct this, the following manipulations were performed. The 4.6 kb SacI/XbaI from pH6HMNE resulting in the formation of pBSHIVMNEEC.

The 2.6 NruI/XbaI fragment from pBSHIVMNEEC was isolated, blunt-ended with Klenow, and inserted into NruI/SmaI digested pSPHAH6 (defined in Example 83). The resultant plasmid was designated pHAHIVMNEEC. The 2.6 kb NruI/XbaI fragment from pBSHIVMNEEC was also inserted into NruI/XbaI digested pVQH6C5LSP6 (below) to yield pC5HIVMNEEC.

Insertion plasmids, pHAHIVMNEEC and pC5HIVMNEEC, were used in standard recombination experiments (Piccini et al., 1987) with NYVAC (vP866) and ALVAC(CPpp), respectively, as rescue virus. Recombinant virus was identified and plaque purified by standard plaque hybridization (Piccini et al., 1987) using a radiolabeled HIV env-specific DNA probe. Purified rcombinant virus were then amplified. The NYVAC-based recombinant containing the HIV-1 (MN) non-cleavable gp160 was designated as vP1078 and the ALVAC equivalent vCP144.

Expression analysis of vCP144 and vP1078 was performed as described above. These results demonstrated that expression was qualitatively equivalent to the HIV-1 (IIIB) counterparts, vP1020 and vCP126.

EXAMPLE 86

EXPRESSION OF A NON-CLEAVABLE, SECRETED FORM OF HIV-1 env BY ALVAC AND NYVAC

ALVAC- and NYVAC-based recombinant viruses were generated which express an HIV-1(MN) env that is not proteolytically cleaved and is secreted by virtue of the elimination of the transmembrane sequence near the carboxy terminus of the gene product. A 502 bp PstI/XbaI fragment was obtained by first amplifying these sequences from pH6HMNE (defined in Example 83) using oligonucleotides HIVECA (SEQ ID NO:399) and HIVMNT1 (SEQ ID NO:400) (5'-ATCATCTCTAGAATAAAAATTACAAACT-TGCCCATTTATCCAATTCC-3') followed by digestion with PstI (5'-end) and XbaI (3'-end). This fragment corresponds to nucleotides 7219 to 7808 (Ratner et al., 1985). This fragment will serve as the 3'-end of the env expression cassette. As such, the env gene product will lack the transmembrane region, will be terminated by a termination codon provided by oligonucleotide HIVMNT1 (SEQ ID NO:400), and will not be cleaved due to an amino change at 511 (above) provided using oligonucleotide HIVECA (SEQ ID NO:399). This 502 bp fragment was ligated to the 391 bp EcoRI/PstI fragment derived by PCR from pH6HMNE using oligonucleotides HIV3B1 (SEQ ID NO:144) and HIVECB (SEQ ID NO:398), and the 4.2 kb EcoRI/XbaI fragment to pH6MNE. The resultant plasmid was designated pBSHIVMNT.

The 2.2 kb XbaI/partial KpnI fragment from pBSHIVMNT was isolated and inserted into pC5L digested with XbaI and KpnI. The resultant plasmid was designated as pC5HIVMNT. The NYVAC insertion plasmid was derived by isolating the 2.1 kb NruI/XbaI fragment from pBSHIVMNT. This fragment was then blunt-ended with the Klenow fragment of the E. coli DNA polymerase in the presence of 2 mM dNTPs and inserted into pSPHAH6 digested with NruI and SmaI to yield pHAHIVMNT.

The insertion plasmids, pC5HIVMNT and pHA-HIVMNT, were used in standard recombination experiments (Piccini et al., 1987) with ALVAC(CPpp) and NYVAC (vP866), respectively, as the rescue virus. Recombinant virus was identified by standard plaque hybridization assays (Piccini et al., 1987) using a radiolabeled HIV env-specific probe. Recombinant virus was subjected to three rounds of purification prior to amplification. The ALVAC-based HIV-1(MN) env (non-cleavable; secreted) was designated as vCP120 and the NYVAC equivalent as vP994.

Immunoprecipitation analyses were performed as previously described (Taylor et al., 1990) for vCP120 and vP994 infected cells using pooled human sera from HIV-seropositive individuals. Both vCP120 and vP994 expressed an HIV-1(MN) env-specific gene product with a molecular weight consistent with a non-cleavable, truncated gene product. Furthermore, immunoprecipitation of the cell-free medium from vCP120 and vP994 infected cell cultures indicated the secretion of this env gene product.

A similar construction was engineered for the HIV-1(IIIB) env. The following manipulations were performed to accomplish this. A 487 bp PstI/XbaI fragment was obtained by first amplifying these sequences from pH6HIIIBE (defined in Example 18) using oligonucleotides HIVECA (SEQ ID NO:399) and HIV3BT (SEQ ID NO:401) (5'-ATCATCTCTAGAATAAAAATTACAAACT-TGCCCATTTATCTAATTCC-3') followed by digestion with PstI and XbaI. A 397 bp EcoRI/PstI fragment was isolated from pBSHIV3BEEC and a 4.2 kb EcoRI/XbaI fragment was isolated from pH6HIIIBEM. These three fragments were ligated together to yield pBSHIV3BT1.

The 2.1 kb and 2.9 kb fragments derived by HindIII/XbaI digestion of pBSHIV3BEECM were ligated to the 105 bp HindIII/XbaI fragment from pBSHIV3BT1 to yield pBSHIV3BT. This plasmid was digested with NruI and XbaI to excise a 2.1 kb fragment. This fragment was blunt-ended and inserted into pSPHAH6 digested with NruI and smaI to generate pHAHIV3BT.

The plasmid pHAHIV3BT was used in recombination experiments, as above, with NYVAC (vP866) as the rescue virus. Recombinant virus was identified and purified as above and the resultant recombinant was designated as vP1036. This recombinant had all the expression characteristics noted above for vCP120 and vP994.

EXAMPLE 87

EXPRESSION OF HIV-1(MN) gp120 ANCHORED WITH A TRANSMEMBRANE SEQUENCE BY NYVAC AND ALVAC

To fuse the env region encoding the gp120 to the region encoding the hydrophobic transmembrane sequence, the following manipulations were performed. A 200 bp fragment corresponding to the 3'-most region of the gp120 coding sequence was derived by PCR from pH6HMNE (defined in Example 83) using oligonucleotides HIV3B1 (SEQ ID NO:144) and HIVMN18 (SEQ ID NO:402) (5'-GCCTCCTACTATCATTAT-GAATAATCTTTTTCTCTCTG-3'). This fragment was fused by PCR to annealed oligonucleotides HIVTM1 (SEQ ID NO:403) (5'-TTATTCATAATGATAGTAGGAGGCT-TGGTAGGTTTAAGAATAGTTTTTGCTG-TACTCTCTGTAGTGAATAGAGTTAGGCAGGGATAA-3') and HIVTM2 (SEQ ID NO:404) (5'-TTATCCCTGCCTAACTCTATTCACTACAGAGAGTA-CAGCAAAAACTATTCTTAAACCTAC-CAAGCCTCCTACTATCATTATGAATAA-3') using oligonucleotides HIV3B1 (SEQ ID NO:144) and HIVTM3 (SEQ ID NO:405) (5'-ATCATCTCTAGAATAAAAATTATCCCT-GCCTAACTCTATTCAC-3'). Oligonucleotides HIVTM1 (SEQ ID NO:403) and HIVTM2 (SEQ ID NO:404) correspond to nucleotides 7850 to 7934 (Ratner et al., 1985) and represent the region encoding the HIV env hydrophobic anchor sequence. Fusion with HIVTM3 (SEQ ID NO:405) engineers the 3'-end of the eventual cassette with a termination codon and a 3' XbaI site. The derived fragment was digested with EcoRI/XbaI and ligated to pH6HMNE digested with EcoRI and XbaI to yield pBSHIVMN120T.

The 1.7 bk NruI/XbaI fragment from pBSHIVMN120T, containing the 3'-most 26 bp of the H6 promoter and the entire HIV-1 cassette, was isolated and inserted into the 5.1 kb NruI/XbaI fragment from pVQH6C5LSP6 to derive pC5HIVMN120T. The plasmid pVQH6C5LSP6 was derived as follows.

pC5LSP (defined in Example 66) was digested with BamHI and ligated to annealed oligonucleotides CP32 (SEQ ID NO:406) (5'-GATCTTAATTAATTAGTCATCAG-GCAGGGCGAGAACGAGACTATCT-GCTCGTTAATTAATTAGGTCGACG-3') and CP33 (SEQ ID NO:407) (5'-GATCCGTCGACCTAATTAATTAAC-GAGCACATAGTCTCGTTCTCGCCCTGC-CTGATGACTAATTAATTAA-3') to generate pVQC5LSP6.

The 1.7 kb NruI/XbaI fragment from pBSHIVMN120T was also blunt-ended and inserted into pSPHAH6 digested with NruI and SmaI. The resultant plasmid was designated as pHAHIVMN120T.

Insertion plasmids, pC5HIVMN120T and pHAHIVMN120T, were used in standard recombination experiments (Piccini et al., 1987) with ALVAC and NYVAC, respectively, as the rescue virus. Recombinant virus was identified and purified by standard plaque hybridization (Piccini et al., 1987) using a radiolabeled HIV-1 gp120-specific DNA probe. The pure populations were amplified and the ALVAC-based anchored HIV-1(MN) gp120 recombinant was designated vCP138. The NYVAC-based equivalent was designated vP1035.

Immunofluorescence and immunoprecipitation analyses were performed by standard procedures (Taylor et al., 1990) to evaluate expression of the HIV-1(MN) anchored gp120 in vP138 and vP1035 infected cells. The assays were performed using pooled human sera from HIV-seropositive individuals (obtained from Dr. K. Steimer, Chiron Corp., Emeryville, Calif.). Investigation of surface immunofluorescence indicated that vCP138 and vP1035 infected cells contained HIV-1(MN) gp120 in the plasma membrane. Significantly, the surface staining of vCP138 and vP1035 infected cells was greatly enhanced compared to cells infected with recombinant viruses (i.e. vCP125, vCP124, vP1004, and vP1008) expressing gp160 or a non-anchored gp120. Results from immunoprecipitation analyses confirmed the expression of gp120 in vCP138 and vP1035 infected cells and that the expressed product was of the expected molecular mass.

EXAMPLE 88

GENERATION OF NYVAC/HIV-1 GAG (PROTEASE⁻) RECOMBINANT

A plasmid, pHXB2D, containing human immunodeficiency virus type 1 (HIV-1) cDNA sequence was obtained from Dr. R. C. Gallo (NCI-NIH) (NCI-NIH). The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542 (defined in Example 32). The plasmid generated by this manipulation is called pHIVG2.

The 3'-end of the gag gene was then cloned downstream from the rest of the gag gene. This was accomplished by cloning a 280 bp ApaI-BamHI PCR fragment, containing the 3'-end of the gag gene, into the 5,620 bp ApaI-BamHI fragment of pHIVG2. This PCR fragment was generated from the plasmid, pHXB2D, with the oligonucleotides, HIVP5 (SEQ ID NO:408) (5'-TGTGGCAAAGAAGGGC-3') and HIVP6 (SEQ ID NO:409) (5'-TTGGATCCTTAT-TGTGACGAGGGTC-3')- The plasmid generated by this manipulation is called pHIVG3.

The I3L promoter was then cloned upstream of the gag gene. This was accomplished by cloning the oligonucleotides, HIVL17 (SEQ ID NO:410) (5'-GATCT-TGAGATAAAGTGAAAATATATATCAT-TATATTACAAAGTACAATTATTTAGGTTTAATCATGG-GTGCGAGAGCGTCAGTATTAAGCGGGG-GAGAATTAGAT-3') and HIVL18 (SEQ ID NO:411) (5'-CGATCTAATTCTCCCCCGCTTAATACT-GACGCTCTCGCACCCATGATTAAACCTAAATAATT-GTACTTTGTAATATAAT-GATATATATTTTCACTTTATCTCAA-3'), encoding the vaccinia virus I3L promoter and the 5'-end of the gag gene, into the 5,540 bp partial BglII-ClaI fragment of pHIVG3. The plasmid generated by this manipulation is called pHIVG4.

pHIVG4 was used in recombination experiments with vP866 (NYVAC) as the rescuing virus to yield vP969.

Immunoprecipitation analysis was performed to determine whether vP969 expresses authentic HIV-1 gag precursor protein. Vero cell monolayers were either mock infected, infected with the parental virus or infected with vP969 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for HIV-1 gag precursor expression using pooled serum from HIV-1 seropositive individuals (obtained from Chiron, Emeryville, Calif.). The sera was preadsorbed with vP866 infected Vero cells. The preadsorbed sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the HIV-1 seropositive human sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-1 seropositive individuals specifically precipitated the HIV-1 gag precursor protein from vP969 infected cells, but did not precipitate HIV-1-specific proteins from mock infected or NYVAC infected cells.

EXAMPLE 89

GENERATION OF NYVAC/HIV-1 gag/pol RECOMBINANT

The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542 (defined in Example 32). The plasmid generated by this manipulation is called pHIVG2.

The 3'-end of the gag gene was then cloned into pHIVG2. This was accomplished by cloning a 280 bp ApaI-BamHI PCR fragment, containing the 3'-end of the gag gene, into the 5,620 bp ApaI-BamHI fragment of pHIVG2. This PCR fragment was generated from the plasmid, pHXB2D, with the oligonucleotides, HIVP5 (SEQ ID NO:408) and HIVP6 (SEQ ID NO:409). The plasmid generated by this manipulation is called pHIVG3.

The I3L promoter was then cloned upstream of the gag gene. This was accomplished by cloning the oligonucleotides, HIVL17 (SEQ ID NO:410) and HIVL18 (SEQ ID NO:411), encoding the vaccinia virus I3L promoter and the 5'-end of the gag gene, into the 5,540 bp partial BglII-ClaI fragment of pHIVG3. The plasmid generated by this manipulation is called pHIVG4.

The portion of the gag gene encoding p24, p2, p7 and p6 was then eliminated. This was accomplished by cloning the oligonucleotides, HIVL19 (SEQ ID NO:412) (5'-CTGACA-CAGGACACAGCAATCAGGTCAGC-CAAAATTACTAATTTTTATCTCGAGGTC-GACAGGACCCG-3') and HIVL20 (SEQ ID NO:413) (5'-GATCCGGGTCCTGTCGACCTCGAGATAAAAATTA-GTAATTTTGGCTGACCTGATTGCTGT-GTCCTGTGTCAG-3'), into the 4,450 bp partial PvuII-BamHI fragment of pHIVG4. The plasmid generated by this manipulation is called pHIVG5.

The remainder of the gag gene, as well as the pol gene, was then cloned downstream of the p17 "gene". This was accomplished by cloning the 4,955 bp ClaI-SalI fragment of pHXB2D, containing most of the gag gene and all of the pol gene, into the 4,150 bp ClaI-SalI fragment of pHIVG5. The plasmid generated by this manipulation is called pHIVG6.

Extraneous 3'-noncoding sequence was then eliminated. This was accomplished by cloning a 360 bp AflII-BamHI PCR fragment, containing the 3'-end of the pol gene, into the 8,030 bp AflII-BamHI fragment of pHIVG6. This PCR fragment was generated from the plasmid, pHXB2D, with the oligonucleotides, HIVP7 (SEQ ID NO:414) (5'-AA-GAAAATTATAGGAC-3') and HIVP8 (SEQ ID NO:415) (5'-TTGGATCCCTAATCCTCATCCTGT-3'). The plasmid generated by this manipulation is called pHIVG7.

pHIVG7 was used in recombination experiments with vP866 (NYVAC) as the rescuing virus to yield vP989.

Immunoprecipitation experiments with vP989 infected cells were performed as described above for the expression of the HIV-1 gag precursor protein. No HIV-1-specific species were precipitated from mock infected or NYVAC infected Vero cells. Protein species corresponding to the gag precursor protein, as well as various intermediate and mature gag cleavage products, were precipitated, however, from lysates of vP989 infected cells.

EXAMPLE 90

GENERATION OF NYVAC/HIV-1 gag/pol AND env (gp120) RECOMBINANT

The sequence encoding the 5'-end of the gag gene was cloned between vaccinia virus tk flanking arms. This was accomplished by initially preparing plasmid pHIVG7, as described above (see Example 89).

pHIVG7 was used in recombination experiments with vP921 as the rescuing virus to yield vP991.

Immunoprecipitation experiments with vP991 infected cells were performed as described above for the expression of the HIV gag precursor protein. No HIV-specific species were precipitated from mock infected Vero cells. Protein species corresponding to the env and gag precursor proteins, as well as various intermediate and mature gag cleavage products, were precipitated, however, from lysates of vP991 infected cells.

EXAMPLE 91

GENERATION OF NYVAC/HIV-1 gag/pol AND env (gp160) RECOMBINANT.

The sequence encoding the 5'-end of the gag gene was cloned between vaccinia virus tk flanking arms. This was accomplished by initially preparing plasmid pHIVG7, as described above (see Example 89).

pHIVG7 was used in recombination experiments with vP911 (above) as the rescuing virus to yield vP990.

Immunoprecipitation experiments with vP990 infected cells were performed as described above for the expression of the HIV-1 gag precursor protein. No HIV-1-specific species were precipitated from mock infected Vero cells. Protein species corresponding to the env and gag precursor proteins, as well as various intermediate and mature gag cleavage products, were precipitated, however, from lysates of vP990 infected cells.

EXAMPLE 92

GENERATION OF NYVAC/HIV-1 p17, p24 RECOMBINANT

A plasmid, pHXB2D, containing HIV-1 cDNA sequence, was obtained from Dr. R. C. Gallo (NCI-NIH). The sequence encoding the 5'-end of the gag gene was cloned between vaccinia virus tk flanking arms. This was accomplished by initially preparing pHIVG5, as described above (see Example 89).

The 3'-end of the p24 "gene" was then cloned into pHIVG5. This was accomplished by cloning a 660 bp SalI-BamHI PCR fragment, containing the 3'-end of the p24 "gene", into the 4,450 bp SalI-BamHI fragment of pHIVG5. This PCR fragment was generated from the plasmid, pHXB2D, with the oligonucleotides, HIVP25 (SEQ ID NO:416) (5'-AAAGTCGACCCATATCACCTAGAAC-3')

and HIVP26 (SEQ ID NO:417) (5'-TTTGGATCCTTA-CAAAACTCTTGCCTTAT-3'). The plasmid generated by this manipulation is called pHIVG8.

The entomopox 42 kd promoter was then cloned upstream of the p24 "gene". This was accomplished by cloning the oligonucleotides, HIVL21 (SEQ ID NO:418) (5'-TCGAG-CAAATTGAAAATATATAATTA-CAATATAAAATGCCTATAGTGCAGAA-CATCCAGGGGCAAATGGTACATCAGGCCATATCAC-CTAGAACTTTAAATGCA-3') and HIVL22 (SEQ ID NO:419) (5'-TTTAAAGTTCTAGGTGATATGGCCTGAT-GTACCATTTGCCCCTGGATGTTCTGCAC-TATAGGCATTTTATATTGTAAT-TATATATTTTCAATTTTGC-3'), encoding the entomopox 42 kd promoter and the 5'-end of the p24 "gene" into the 5,070 bp XhoI-NsiI fragment of pHIVG8 The plasmid generated by this manipulation is called pHIVG9.

pHIVG9 was used in recombination experiments with vP866 (NYVAC) as the rescuing virus to yield vP970.

Immunoprecipitation experiments with vP970 infected cells were performed as described above for the expression of the HIV-1 gag precursor protein. No HIV-1-specific species were precipitated from mock infected or NYVAC infected Vero cells. A protein species corresponding to p24 was precipitated, however, from lysates of vP970 infected cells.

EXAMPLE 93

GENERATION OF NYVAC/HIV-1 p17, p24 AND env (gp120) RECOMBINANT

A plasmid, pHXB2D, containing HIV-1 cDNA sequence, was obtained from Dr. R. C. Gallo (NCI-NIH). The sequence encoding the 5'-end of the gag gene was cloned between vaccinia virus tk flanking arms. This was accomplished by initially preparing plasmid pHIVG9 as described above (see Example 92).

pHIVG9 was used in recombination experiments with vP921 as the rescuing virus to yield vP973.

Immunoprecipitation experiments with vP973 infected cells were performed as described above for the expression of the HIV-1 gag precursor protein. No HIV-1-specific species were precipitated from mock infected Vero cells. Protein species corresponding to env and p24 were precipitated, however, from lysates of vP973 infected cells.

EXAMPLE 94

GENERATION OF NYVAC/HIV-1 p17, p24 AND env (gp160) RECOMBINANT

A plasmid, pHXB2D, containing HIV-1 cDNA sequence, was obtained from Dr. R. C. Gallo (NCI-NIH). The sequence encoding the 5'-end of the gag gene was cloned between vaccinia virus tk flanking arms. This was accomplished by initially preparing plasmid pHIVG9, as described above (see Example 92).

pHIVG9 was used in recombination experiments with vP911 as the rescuing virus to yield vP971.

Immunoprecipitation experiments with vP971 infected cells were performed as described above for the expression of the HIV-1 gag precursor protein. No HIV-1-specific species were precipitated from mock infected Vero cells. Protein species corresponding to env and p24 were precipitated, however, from lysates of vP971 infected cells.

EXAMPLE 95

GENERATION OF NYVAC/HIV-1 gag (PROTEASE⁻) AND env (TRUNCATED) RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG-9 as described above (see Example 89).

An H6-promoted truncated HIV-1 envelope gene was then inserted into pHIVG4. This was accomplished by cloning the *E. coli* DNA polymerase I (Klenow fragment) filled-in 1,600 bp XhoI-NotI fragment of pHIVE10, containing an H6-promoted truncated HIV-1 envelope gene, into the filled-in BamHI site of pHIVG4. The plasmid generated by this manipulation is called pHIVGE11.

The plasmid pHIVE10 was derived by inserting a SacI/partial KpnI fragment from pBSHIV3BCDT1 into the multiple cloning region of pIBI25 (IBI, New Haven, Conn.). The plasmid pBSHIV3BCDT1 contains an H6 promoted cassette to express a severely truncated form of the HIV-1(IIIB) envelope (amino acid 1 to 447; Ratner et al., 1985). Expression of this cassette was evaluated to eliminate CD4 binding while retaining the V3 loop region and the T1 epitope.

To construct pBSHIV3BCDT1 the following manipulations were performed. A PCR-derived fragment of 200 bp was amplified from pH6HIIIBE (defined in Example 18) using oligonucleotides HIV3B2A (SEQ ID NO:397) and HIVCD4A (SEQ ID NO:420) (5'-GCCTCCTACTATCAT-TATGAATAAACTGATGGGAGGGGCATAC-3'). This fragment was fused by PCR to annealed oligonucleotides HIVTM1 (SEQ ID NO:403) and HIVTM2 (SEQ ID NO:404) using oligonucleotides HIV3B2A (SEQ ID NO:397) and HIVTM3 (SEQ ID NO:405). These manipulations create the 3'-end of the truncated env cassette by placing sequences encoding the HIV-1 env transmembrane anchor (amino acids 691 to 718; Ratner et al., 1985), a translation termination codon (TAA), and a 3' XbaI site. This PCR-fusion product was digested with EcoRI and XbaI to yield a 243 bp fragment. The fragment was ligated to the 4.5 bp EcoRI/XbaI fragment of pH6HIIIBE to generate pBSHIV3BCDT1.

pHIVGE11 was used in recombination experiments with vP866 (NYVAC) as the rescuing virus to yield vP979.

Immunoprecipitation experiments with vP979 infected cells were performed as described above for the expression of the HIV-1 gag precursor protein. No HIV-1-specific species were precipitated from mock infected of NYVAC infected Vero cells. Protein species corresponding to env and the gag precursor proteins were precipitated, however, from lysates of vP979 infected cells.

EXAMPLE 96

GENERATION OF NYVAC/HIV-1 gag/pol AND env (TRUNCATED) RECOMBINANT

The sequence encoding the 5'-end of the gag gene was cloned between vaccinia virus tk flanking arms. This was accomplished by initially preparing plasmid pHIVG7 as described above (see Example 89).

An H6-promoted truncated HIV-1 envelope gene was then inserted into pHIVG7. This was accomplished by cloning the E. coli DNA polymerase I (Klenow fragment) filled-in 1,600 bp XhoI-NotI fragment of pHIVE10 (defined in Example 95), containing an H6-promoted truncated HIV-1 envelope gene, into the filled-in BamHI site of pHIVG7. The plasmid generated by this manipulation is called pHIVGE12.

pHIVGE12 was used in recombination experiments with vP866 (NYVAC) as the rescuing virus to yield vP978.

Immunoprecipitation experiments with vP978 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP978 infected cells.

EXAMPLE 97

GENERATION OF NYVAC/HIV-1 gag/pol AND env (gp120) RECOMBINANT

The sequence encoding the gag gene was cloned between vaccinia virus tk flanking arms. This was accomplished by initially preparing plasmid pHIVG7, as described above (see Example 89).

The I3L-promoted gag and pol genes were then inserted into a canary pox insertion vector. This was accomplished by cloning the 4,360 bp partial BglII-BamHI fragment of pHIVG7, containing the I3L-promoted gag and pol genes, into the BamHI site of pVQH6CP3L. The plasmid generated by this manipulation is called pHIVGE14.

The H6-promoted HIV-1(MN) envelope (gp120) gene was then inserted into pHIVGE14. This was accomplished by cloning the oligonucleotides, HIVL29 (SEQ ID NO:421) (5'-GGCCGCAAC-3') and HIVL30 (SEQ ID NO:422) (5'-TCGAGTTGC-3'), and the 1,600 bp NruI-NotI fragment of pBSHIVMN120, containing the H6-promoted gp120 gene, into the 11,500 bp NruI-XhoI fragment of pHIVGE14. The plasmid generated by this manipulation is called pHIVGE15.

The H6-promoted envelope (gp120) gene and the I3L-promoted gag and pol genes were then inserted into a vaccinia virus insertion vector. This was accomplished by cloning the 6,400 bp NotI-BamHI fragment of pHIVGE15, containing the H6-promoted gp120 gene and the I3L-promoted gag and pol genes, into the 4,000 bp NotI-BglII fragment of pSD542VCVQ. The plasmid generated by this manipulation is called pHIVGE16.

pHIVGE16 was used in in vitro recombination experiments with vP866 (NYVAC) as the rescuing virus to yield vP988.

Immunoprecipitation experiments with vP988 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP988 infected cells.

EXAMPLE 98

GENERATION OF NYVAC/HIV-1 gag/pol AND env (gp160) RECOMBINANT

The sequence encoding the 5'-end of the gag gene was cloned between vaccinia virus tk flanking arms. This was accomplished by initially preparing plasmid pHIVGE16 as described above (see Example 97).

The gp120 gene was then replaced by the gp160 gene. This was accomplished by cloning the 2,600 bp NruI-NotI fragment of pH6HMNE, containing the entire HIV-1(MN) envelope (gp160) gene, into the 8,000 bp partial NruI-NotI fragment of pHIVGE16. The plasmid generated by this manipulation is called pHIVGE19.

pHIVGE19 was used in in vitro recombination experiments with vP866 (NYVAC) as the rescuing virus to yield vP1009.

Immunoprecipitation experiments with vP1009 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP1009 infected cells.

EXAMPLE 99

GENERATION OF ALVAC/HIV-1 gag/pol AND env (GP120) RECOMBINANT

The sequence encoding the 5'-end of the gag gene was cloned between vaccinia virus tk flanking arms. This was accomplished by intially preparing plasmid pHIVGE15, as described above (see Example 97).

pHIVGE15 was used in recombination experiments with CPpp (ALVAC) as the rescuing virus to yield vCP117.

Immunoprecipitation analysis was performed to determine whether vCP117 expresses authentic HIV-1 gag and env gene products. CEF cell monolayers were either mock infected, infected with the parental virus or infected with vCP117 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for HIV gag and env gene expression using serum from HIV-1 seropositive individuals (obtained from New York State Department of Health). The sera was preadsorbed with CPpp infected CEF cells. The preadsorbed sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the HIV-1 seropositive human sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-1 seropositive individuals specifically precipitated the HIV-1 gag and env proteins from vCP117 infected cells, but did not precipitate HIV-1-specific proteins from mock infected or CPpp infected cells.

EXAMPLE 100

GENERATION OF ALVAC/HIV-1 gag/pol AND env (gp160) RECOMBINANT

The sequence encoding the 5'-end of the gag gene was cloned between vaccinia virus tk flanking arms. This was accomplished by initially preparing plasmid pHIVGE15 as described above (see Example 97).

The gp120 gene was then replaced by the gp160 gene. This was accomplished by cloning the 2,600 bp NruI-NotI fragment of pH6HMNE, containing the entire HIV-1(MN) envelope (gp160) gene, into the 9,800 bp NruI-NotI fragment of pHIVGE15. The plasmid generated by this manipulation is called pHIVGE18.

The canary pox flanking arm deleted in the previous step was then cloned into pHIVGE18. This was accomplished by cloning the 1,500 bp NotI fragment of pHIVGE15, containing the C3 flanking arm, into the 12,400 bp NotI fragment of pHIVGE18. The plasmid generated by this manipulation is called pHIVGE20.

pHIVGE20 was used in recombination experiments with CPpp (ALVAC) as the rescuing virus to yield vCP130.

Immunoprecipitation analysis was performed to determine whether vCP130 expresses authentic HIV-1 gag and env gene products. CEF cell monolayers were either mock infected, infected with the parental virus or infected with vCP130 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for HIV-1 gag and env gene expression using pooled serum from HIV-1 seropositive individuals (obtained from Chiron, Emeryville, Calif.). The sera was preadsorbed with CPpp infected CEF cells. The preadsorbed sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the HIV-1 seropositive human sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography. Human sera from HIV-1 seropositive individuals specifically precipitated the HIV-1 gag and env proteins from vCP130 infected cells, but did not precipitate HIV-1-specific proteins from mock infected or CPpp infected cells.

EXAMPLE 101

GENERATION OF ALVAC/HIV-1 gag/pol RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by intially preparing plasmid pHIVG7 as described above (see Example 89).

The gag and pol genes were then cloned between canary pox flanking arms. This was accomplished by cloning the 4,400 bp SmaI-NotI fragment of pHIVG7, containing the I3L-promoted gag and pol genes, and the oligonucleotides, HIV2L6 (SEQ ID NO:423) (5'-GGCCAAAC-3') and HIV2L7 (SEQ ID NO:424) (5'-TCGAGTTT-3'), into the SmaI-XhoI site of pSPCP3L. The plasmid generated by this manipulation is called pHIVG24.

pHIVG24 was used in recombination experiments with CPpp (ALVAC) as the rescuing virus to yield vCP152.

Immunoprecipitation experiments with vCP152 infected cells were performed as described above for the expression of the HIV-1 env and gag proteins. No HIV-1-specific species were precipitated from mock infected or ALVAC infected cells. Protein species corresponding to the gag precursor protein, as well as various intermediate and mature gag cleavage products, were precipitated, however, from lysates of vCP152 infected cells.

EXAMPLE 102

GENERATION OF ALVAC/HIV-1 gag/pol AND env (TRUNCATED) RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG24 as described above (see example 101).

pHIVG24 was used in recombination experiments with vCP120 as the rescuing virus to yield vCP155.

Immunoprecipitation experiments with vCP155 infected cells were performed as described above for the expression of the HIV-1 env and gag proteins. No HIV-1-specific species were precipitated from mock infected cells. Protein species corresponding to the env and gag precursor proteins, as well as various intermediate and mature gag cleavage products, were precipitated, however, from lysates of vCP155 infected cells.

EXAMPLE 103

GENERATION OF ALVAC/HIV-1 gag/pol AND env (gp120 WITH TRANSMEMBRANE ANCHOR) RECOMBINANT A plasmid, pHXB2D, containing HIV-1 cDNA sequence was obtained from Dr. R. C. Gallo (NCI-NIH). The sequence encoding the 5'-end of the gag gone was cloned between vaccinia virus tk flanking arms. This was accomplished by intially preparing plasmid pHIVG24 as described above (see Example 101).

pHIVG24 was used in recombination experiments with vCP138 as the rescuing virus to yield vCP156.

Immunoprecipitation experiments with vCP156 infected cells were performed as described above for the expression of the HIV-1 env and gag proteins. No HIV-1-specific species were precipitated from mock infected cells. Protein species corresponding to the env and gag precursor proteins, as well as various intermediate and mature cleavage products, were precipitated, however, from lysates of vCP156 infected cells.

Expression of HIV-1 gag-specific gene products either alone or in combination with env by vaccinia virus has been shown to lead to the production of non-infectious virus-like particles (Haffar et al., 1990; Hu et al., 1990). With this background we sought to investigate whether cells infected ALVAC-based recombinant expressing HIV-1 gag-pol and env genes would also produce such particles. Furthermore, if these ALVAC-based recombinants were used to infect non-avian cells (i.e. Vero, MRC-5, etc.) then HIV-1 virus-like particles could be purified without any poxvirus virion contaminants.

To evaluate particle formation using Vero cells infected with vCP156, the following experiment was performed. Vero cells were infected at an m.o.i. of approximately 5 pfu/cell. After a 24 hr infection period, the supernatant was harvested and clarified by centrifugation at 2000 rpm for 10 min. The supernatant was then spun through filters which have a molecular weight cutoff of 30,000 kDa. Thus, any molecules smaller would pass through these filters. The material retained by the filters was then analyzed by standard Western blot analysis (Maniatis et al., 1990) using pooled human serum from HIV-seropositive individuals (obtained from Dr. J. Conroy, New York State Department of Health). The results from the Western blot analysis demonstrated the presence of the major core protein p24 and the HIV-1(MN) anchored gp120 in the material retained by the filters. With the size exclusion noted above, the p24 would have passed through unless it was in a higher structural configuration (i.e. virus-like particles). Therefore, these results strongly suggest that HIV-1 virus-like particles containing the gp120 envelope component are produced in vCP156 infected cells.

EXAMPLE 104

EXPRESSION OF THE T1, T2, AND TH4.1 EPITOPES OF THE HIV-1 env GENE IN ALVAC AND NYVAC Recombinant poxviruses vP1062 and vCP146 were generated to express the T1, T2, and TH4.1 epitopes of HIV-1 env (Hosmalin et al., 1991) as individual peptides.

Construction of plasmid p731T1. Plasmid pMPI3H contains the vaccinia I3L early/intermediate promoter element (Schmitt and Stunnenberg, 1988; Vos and Stunnenberg, 1988) in a pUC8 background. The promoter element was synthesized by polymerase chain reaction (PCR) using pMPVC1, a subclone of vaccinia HindIII I, as template and synthetic oligonucleotides MPSYN283 (SEQ ID NO:425) (5'-CCCCCCAAGCTTACATCATGCAGTGGTTAAAC-3') and MPSYN287 (SEQ ID NO:426) (5'-GATTAAACCTAAATAATTGT-3') as primers. DNA from this reaction was cut with HindIII and RsaI and a 0.1 kb fragment containing the promoter element was purified. A linker region was assembled by annealing complementary synthetic oligonucleotides MPSYN398 (SEQ ID NO:427) (5'-ACAATTATTTAGGTTAACTGCA-3') and MPSYN399 (SEQ ID NO:428) (5'-GTTAACCTAAATAATTGT-3'). The PCR-derived promoter element and the polylinker region were ligated with vector plasmid pUC8 which had been cut with HindIII and PstI. The resulting plasmid, pMPI3H, contains the I3L promoter region from positions −100 through −6 relative to the initiation codon, followed by a polylinker region containing HpaI, PstI, SalI, BamHI, SmaI and EcoRI sites. Cleavage with HpaI produces blunt ended DNA linearized at position −6 in the promoter.

A cassette containing the T1 peptide driven by the vaccinia I3L promoter was generated by ligating complementary oligonucleotides T1C (SEQ ID NO:429) (5'-TAATCATGAAACAAATTATTAATATGTGGCAAGAAGAGGAAAAGCTATGTACGCTTGACTAGTTAATCACTCGAG-3') and T1N (SEQ ID NO:430) (5'-GATCCTCGAGTGATTAACTAGTCAAGCGTACATAGCTTTTCCTACTTCTTGCCACATATTAATAATTTGTTTCATGATTA-3') to plasmid pMPI3H digested with HpaI and BamHI. This ligation reconstitutes the last 5 base pairs of the promoter, provides the complete coding sequence of the T1 peptide, and creates a XhoI site between the stop codon and BamHI site. This is plasmid p731T1. The sequence of the fragment was confirmed by nucleotide sequence analysis.

Construction of plasmid pH6T2. A cassette containing the T2 peptide driven by the vaccinia H6 promoter was generated in two steps: The H6 promoter through the EcoRV site was derived from a plasmid containing the synthetic H6 promoter (Perkus et al., 1989), using PCR and primers H6PCR1 (SEQ ID NO:364) and H6PCR2 (SEQ ID NO:365), creating a 5' HindIII site. This 122 bp PCR-derived fragment was digested with HindIII and EcoRV followed by ligation to similarly digested pBS-SK+ (Stratagene, La Jolla, Calif.), generating plasmid pBSH6. Complementary oligonucleotides T2C (SEQ ID NO:431) (5'-ATCCGTTAAGTTTGTATCGTAATGCACGAAGATATTATTTCTTTGTGGGATCAATCTTTAAAATGACTAGTTAATCAG-3') and T2N (SEQ ID NO:432) (5'-GATCCTGATTAACTAGTCATTTTAAAGATTGATCCCACAAAGAAATAATATCTTCGTGCATTACGATACAAACTTAACGGAT-3') which complete the 3' end of the H6 promoter from the EcoRV site, encode the T2 peptide and create a BamHI site at the 3' end of the gene were annealed then ligated to pBSH6 that was digested with EcoRV and BamHI. This plasmid was designated pH6T2 following confirmation of the fragment by nucleotide sequence analysis.

Construction of plasmid pVQ42KTH4.1. A cassette containing the TH4.1 peptide driven by the AmEPV 42K promoter was generated by sequential PCR reactions: the 107 bp 42K promoter with 5' PstI and SmaI sites was derived by PCR from plasmid p42KRABI, a plasmid containing the gene for the rabies glycoprotein under control of the 42K promoter, using primers 42KVQ1 (SEQ ID NO:433) (5'-AATTAATTAGCTGCAGCCCCGGGTCAAAAAAATATAAATG-3') and 42KVQ2 (SEQ ID NO:434) (5'-CCTTGTACTACTTCAATTACTCTATCCATTTTTATATTGTAATTATATATTTTC). The sequence of the 107 bp promoter region of this PCR-derived fragment is (SEQ ID NO:435) 5'-TCAAAAAAATATAAATGATTCACCATCTGATAGAAAAAAAATTTATTGGGAAGAATATGATAATATTTTGGGATTTCAAAATTGAAAATATATAATTACAATATAAA-3'. The 159 bp PCR-derived fragment was fused to the coding sequences of TH4.1 with a second PCR using this fragment and synthetic oligonucleotides encoding the TH4.1 peptide TH41C (SEQ ID NO:436) (5'-ATGGATAGAGTAATTGAAGTAGTACAAGGAGCTTATAGAGCTATTAGATGACTAGTTAATCACTCGAGGATCC-3') and TH41N (SEQ ID NO:437) (5'-GGATCCTCGAGTGATTAACTAGTCATCTAATAGCTCTATAAGCTCCTTGTACTACTTCAATTACTCTATCCAT-3') as template and primers 42KTH41 (SEQ ID NO:438) (5'-ATCATCGGATCCTCGAGTGATTAAACTAGTCATCTAATAGCTC-3') and 42KVQ1 (SEQ ID NO:433). This 210 bp PCR-derived fragment was extended in the 5' direction, incorporating a BamHI site at the 5' end using the fragment and synthetic oligonucleotides VQC (SEQ ID NO:439) (5'-TTAATCAGGATCCTTAATTAATT-AGTTATTAGACAAGGTGAAAACGAAAC-TATTTGTAGCTTAATTAATTAGCTGCAGCCCGGG-3') and VQN (SEQ ID NO:440) (5'-CCCGGGCTG-CAGCTAATTAATTAAGCTACAAAT-AGTTTCGTTTTCACCTTGTCTAATAAC-TAATTAATTAAGGATCCTGATTAA-3') as template for a third PCR using primers 42KTH41 (SEQ ID NO:438) and BAMVQ (SEQ ID NO:441) (5'-TTAATCAGGATCCT-TAATTAATTAGTTATTAGAC-3'). Subsequent nucleotide sequence analysis revealed an error in the sequence of oligonucleotide 42KTH41 (SEQ ID NO:438) such that an extra base (an A) was inserted after position 24 as indicated by the underline in the above sequence for 42KTH41. This was corrected with a final PCR employing the 272 bp fragment derived from the third PCR as template with primers BAMVQ (SEQ ID NO:441) and 42KTH41A (SEQ ID NO:442) (5'-ATCATCGGATCCTCGAGTGATTAAC-TAGTCATCTAATAGCTC-3'). After the final PCR, the cassette was to contain BamHI, PstI, and SmaI sites 5' to 42K-TH4.1 with XhoI and BamHI sites 3'. This 271 bp PCR-derived fragment was digested with BamHI and cloned into the BamHI site of pBS-SK+ (Stratagene, La Jolla, Calif.) generating plasmid pVQ42KTH4.1. Nucleotide sequence analysis of this plasmid confirmed that the sequence of the promoter and coding region was correct. However, a 3 bp deletion was revealed resulting in loss of the 3' BamHI site.

Construction of plasmid pT1T2TH4.1. These three cassettes were combined into a singular plasmid pT1T2TH4.1 such that I3L-T1 is opposite in orientation to the other two genes in the following manner: A 170 bp HindIII/XhoI fragment was isolated from p731T1 and ligated to similarly digested pH6T2 generating pT1T2. A 290 bp BamHI/SacI fragment from pVQ42KTH4.1 was ligated to similarly digested pT1T2, creating pT1T2TH4.1. The sequence of the insert was confirmed by nucleotide sequence analysis.

pC5LSP (defined in Example 66) was digested with EcoRI, treated with alkaline phosphatase and ligated to self-annealed oligonucleotide CP29 (SEQ ID NO:363) (5'-AATTGCGGCCGC-3'), digested with NotI and linear purified followed by self-ligation. This procedure introduced a NotI site to pC5LSP, generating pNC5LSP5.

The 602 bp XhoI fragment from pT1T2TH4.1 containing the genes for the epitopes driven by their respective promoters was cloned into donor plasmids pNC5LSP5 and pSD550 (defined in Example 59) in their XhoI sites. Nucleotide sequence analysis was used to confirm the sequence and the orientation of the insert. The resulting plasmids pC5T1T2TH4.1 and pI4T1T2TH4.1 were used in in vitro recombination experiments with ALVAC and NYVAC to generate recombinant viruses vCP146 and vP1062, respectively. These recombinant viruses were demonstrated to contain the desired genes by hybridization of a specific DNA probe to viral plaques.

EXAMPLE 105

EXPRESSION OF TWO FUSION PEPTIDES CONTAINING THE T1, T2, AND TH4.1 EPITOPES OF HIV-1 env WITH AND WITHOUT A TRANSMEMBRANE ANCHOR DOMAIN FROM HIV-1 env Recombinant poxviruses vP1060, vP1061, vCP154 and vCP148 were created to express a fusion peptide consisting of the signal sequences from HIV-1 env coupled to sequences corresponding to the T1, T2, and TH4.1 epitopes of HIV-1 env by cleavable linker regions. vP1060 and vCP154 differ from vP1061 and vCP148 in that the former recombinant viruses express the fusion peptide along with sequences corresponding to the transmembrane region of HIV-1 env.

Both fusion peptides include the 51 amino acid N-terminal portion of HIV-1 (IIIB) env, residues 1–50 (plus initiating Met) based on Ratner et al. (1985). The amino acid sequence of this signal region (SEQ ID NO:443) is MKEQKTVAMRVKEKYQHLWRWGWRWGTMLLGMLMICSATEKLWVTVYYGVP. This is followed by the T1, T2, and TH4.1 epitopes (Hosmalin et al., 1991) separated from the signal, each other, and anchor sequence where present, by a cleavable linker region up to 5 amino acids in length. The amino acid sequence of this region of the peptide (SEQ ID NO:444) is [signal]-PFR-KQIINMWQEVGKAMYA-PPFRK-HEDIISLWDQSLK-PPFRK-DRVIEVVQGAYRAIR-[PPFRK-anchor]. The anchor domain is a 28 amino acid transmembrane region of HIV-1 (IIIB) env, residues 691–718. The amino acid sequence of this region (SEQ ID NO:445) is LFIMIVGGLVGLRIVFAVLSVVNRVRQG-[stop].

For both versions of the fusion peptide, the H6 promoter and HIV-1 env signal sequences were derived by PCR from plasmid pH6HIIIBEM (defined in Example 18) using primers H6PCR1 (SEQ ID NO:364) and PCRSIGT1 (SEQ ID NO:446) (5'-CATATTAATTTGTTTTCTAAAAGGAGGTACCCCATAATAGACTGTG-3'). This 314 bp PCR-derived fragment consists of a 5' HindIII site followed by the H6 promoter and coding sequences for the signal, linker, and the first 6 amino acids of the T1 peptide.

The remainder of the coding region for the construct without the transmembrane region was generated by PCR amplification of oligonucleotides T2T4A (SEQ ID NO:447) (5'-GCTCCTCCTTTTAGAAAACACGAAGATATTATTTCTTTGTGGGATCAATCTTTAAAACCTCCTTTTAGAAAAGATAGAGTAATTGAAGTAGTAC-3') and T2T4B (SEQ ID NO:448) (5'-GTACTACTTCAATTACTCTATCTTTTCTAAAAGGAGGTTTTAAAGATTGATCCCACAAAGAAATAATATCTTCGTGTTTTCTAAAAGGAGGAGC-3') using primers PCRT1T2 (SEQ ID NO:449) (5'-AAACAAATTATTAATATGTGGCAAGAAGTAGGAAAAGCTATGTACGCTCCTCCTTTTAGAAAACACGAAG-3') and PCRT4END (SEQ ID NO:450) (5'-ACTACTTCTAGATTATCTAATAGCTCTATAAGCTCCTTGTACTACTTCAATTACTC-3'). This 177 bp PCR-derived fragment encodes the T1 peptide, a linker region, the T2 peptide, another linker region, and the TH4.1 peptide, followed by a 3' XbaI site. This fragment was fused with the 314 bp PCR-derived fragment containing the promoter and signal sequences by PCR with primers H6PCR1 (SEQ ID NO:364) and PCRT4END (SEQ ID NO:450). Following digestion of this 473 bp PCR-derived fragment with HindIII and XbaI a fragment of 455 bp was isolated from an agarose gel, ligated to similarly digested pBS-SK, and the sequence of the insert verified by nucleotide sequence analysis. The resulting plasmid was designated pBST1T2TH4.1.

The remainder of the coding region of the version with the transmembrane anchor was generated by PCR amplification of oligonucleotides, T2T4A (SEQ ID NO:447) and T2T4B (SEQ ID NO:448), using primers PCRT1T2 (SEQ ID NO:449) and PCRT4TM (SEQ ID NO:451) (5'-TACTATCATTATGAATAATTTTCTAAAAGGAG- GTCTAATAGCTCTATAAGCTCCTTGTAC-TACTTCAATTACTC-3'), altering the 3' end to accommodate the transmembrane region. This 195 bp PCR-derived fragment was fused by PCR with oligonucleotides comprising the anchor, HIVTM1 (SEQ ID NO:403) and HIVTM2 (SEQ ID NO:404) using primers PCRT1T2 (SEQ ID NO:449) and PCRTMEND (SEQ ID NO:450). This 276 bp PCR-derived fragment was fused with the 314 bp PCR-derived fragment containing the promoter and signal sequences by PCR with primers H6PCR1 (SEQ ID NO:364) and PCRTMEND (SEQ ID NO:450). Following digestion of this 572 bp PCR-derived fragment with HindIII and XbaI a fragment of 554 bp was isolated from an agarose gel, ligated to similarly digested pBS, and the sequence of the insert verified by nucleotide sequence analysis. The resulting plasmid was designated pBST1T2TH4.1A.

pC5LSP (defined in Example 66) was digested with BamHI and ligated to annealed oligonucleotides CP32 (SEQ ID NO:406) and CP33 (SEQ ID NO:407) to generate pVQC5LSP6. pVQC5LSP6 was digested with EcoRI, treated with alkaline phosphatase and ligated to self-annealed oligonucleotide CP29 (SEQ ID NO:363), digested with NotI and linear purified followed by self-ligation. This procedure introduced a NotI site to pVQC5LSP6, generating pNVQC5LSP7.

Both cassettes were placed individually between the XhoI and XbaI sites of insertion plasmid pNVQC5LSP7. These plasmids pC5ST1T1TH4.1 and pC5ST1T2TH4.1A were used to generate canarypoxviruses recombinant in the C5 locus, vCP148 and vCP154 respectively. BamHI-SmaI fragments were excised from pC5ST1T1TH4.1 and pC5ST1T2TH4.1A and ligated to similarly digested pSD550 (defined in Example 59) generating plasmids pI4ST1T2TH4.1 and pI4ST1T1TH4.1A, respectively. These plasmids were used in IVR with the I4 locus of NYVAC, resulting in recombinants vP1061 and vP1060, respectively. These recombinant viruses were demonstrated to contain the desired genes by hybridization of a specific DNA probe to viral plaques.

EXAMPLE 106

EXPRESSION OF THE HIV-1 nef GENE IN ALVAC, TROVAC, AND NYVAC

Recombinant poxviruses vP1084, vFP174, and vCP168 were generated expressing HIV-1 nef (MN) as follows:

The I3L promoter was derived by PCR from plasmid pMPI3H using primers I3PCR1 (SEQ ID NO:452) (5'-ATCATCGGATCCAAGCTTACATCATGCAGTGG-3') and PI3NEF2 (SEQ ID NO:453) (5'-CGTTTTGAC-CATTTGCCACCCATGATTAAAC-CTAAATAATTGTACTTTG-3'). The coding region of nef was generated by PCR amplification of pMN1.8–10 (a clone of that portion of the MN genome between SstI sites at 7792 and 9595) using primers PI3NEF1 (SEQ ID NO:454) (5'-AGTACAATTATTTAGGTTTAAT-CATGGGTGGCAAATGGTCAAAACG-3') and PNEF-BAM (SEQ ID NO:455) (5'-ATCATCGGATCCTAACACTTCTCTCTCCGG-3'). Fusion of the coding region with the promoter was accomplished by amplification of the previous PCR products using primers I3PCR1 (SEQ ID NO:452) and PNEFBAM (SEQ ID NO:455). Following digestion of this product with BamHI a fragment of 0.7 kb was isolated from an agarose gel and ligated to similarly digested pBS-SK+ (Stratagene, La Jolla, Calif.), generating plasmid pI3NEF. It was at this point that sequence deviations were first observed. The sequence of the cassette was determined to differ from the published sequence (Gurgo et al., 1988, GenBank Accession Number M17449) due to deviations in plasmid pMN1.8–10. These differences are summarized below relative to the published sequence.

| Base # | Gurgo et al. | pMN1.8–10 | Result | Cassette |
|---|---|---|---|---|
| 8834 | T | T | silent | C (aa = Arg) |
| 8863 | G | A | Lys→Arg | A (aa = Lys) |
| 8890 | T | C | Pro→Leu | C (aa = Pro) |
| 9028 | A | G | Arg→Lys | G (aa = Arg) |
| 9127 | A | A | silent | G (aa = Gln) |
| 9330–9331 | GG | GGG | frameshift | GG |

The two silent mutations in the cassette (at positions 8834 and 9127) were apparently errors in PCR. Since there is no effect on the encoded protein, these were allowed to persist. The frameshift at 9930 results in a lengthened open reading frame more closely resembling other HIV-1 isolates. In keeping with the published size of nef from the MN isolate, this cassette required a fourth PCR to generate the truncated 3' end of the coding region.

Removal of the extra base at position 9930 was accomplished by PCR amplification of the insert in pI3NEF with primers I3PCR1 (SEQ ID NO:452) and PNEFFIX1 (SEQ ID NO:456) (5'-ATCATCGGATCCTAACACTTCTCTCTC-CGGGTCATCCATCCATGCTGGCTCATAG-3'). Following digestion of this 678 bp PCR-derived fragment with BamHI a fragment of 660 bp was isolated from an agarose gel and ligated to similarly digested pBS, generating plasmid pBSI3NEF. The insert was verified by nucleotide sequence analysis.

The 660 bp BamHI fragment from pBSI3NEF containing the nef gene was placed in the BamHI site of insertion plasmid pNVQC5LSP7 (defined in Example 105). The resulting plasmid pC513NEF was employed in an IVR into the C5 locus of ALVAC, generating the recombinant vCP168. The same 660 bp BamHI fragment was also placed in the BamHI site of insertion plasmid pSD550VC (defined in Example 59) creating plasmid pI4I3NEF. An IVR with this plasmid with NYVAC generated recombinant vP1084.

An insertion plasmid for the F16 locos of TROVAC was derived in the following manner. A 7.3 kb NaeI/NdeI fragment was isolated from a plasmid containing the 10.5 kb HindIII fragment of fowlpox virus described by Tartaglia et al. (1990) and ligated to similarly digested pUC9 creating plasmid pRW866.

pUC9 was digested with PvuII and an EcoRI linker ligated between the PvuII sites creating plasmid pRW715. A cloning site flanked by fowlpox sequences was generated by PCR amplification of a portion of the 10.5 kb fragment with primers RW264 (SEQ ID NO:457) (5'-AATTAACCCGG-GATCCAAGCTTCTAGCTAGCTAATTTT-TATAGCGGCCGCTATAATCGTTAACTTATTAG-3') and RW267 (SEQ ID NO:458) (5'-GCTAGAAATCTCT-TAGTTTTTATAGTTG-3'). An adjacent region was also amplified by PCR using primers RW266 (SEQ ID NO:459) (5'-GTTACATATGTACAGAATCTGATCATAG-3') and RW265 (SEQ ID NO:460) (5'-CTAGCTAGAAGCTTG-GATCCCGGGTTAATTAAT-TAATAAAAAGCGGCCGCGTTAAAGTAGAAAAATG-3'). These PCR-derived fragments were fused by a third PCR using primers RW266 (SEQ ID NO:459) and RW267 (SEQ ID NO:458). The resulting PCR-derived fragment consisted of fowlpox sequences flanked by a 5' EcoRI site and a 3'

NdeI site. Central in the fragment is a polycloning region containing SmaI, BamHI, and HindIII sites, flanked by NotI sites and translation stop codons in six reading frames. An early transcription termination signal (Yuen and Moss, 1987) is adjacent to the 3' NotI site. This PCR-derived fragment, digested with EcoRI and NdeI, was ligated to similarly digested pRW715 creating plasmid pRW864. An 11K promoted lac Z gene was excised from pAM1 by partial BamHI, total PstI digestion. This fragment was made blunt ended with Klenow polymerase and ligated to SmaI digested pRW864, creating pRW867A. The NotI fragment from pRW867A was made blunt ended with Klenow polymerase in the presence of dNTPs so that the NotI sites would be regenerated when ligated into an FspI site, and ligated to pRW866 which was partially digested with FspI such that the insertion was made corresponding to position 1955 described by Tartaglia et al. (1990). The resulting plasmid, pRW868, was then digested with NotI to remove the lac Z cassette, and ligated to the 66 bp polylinker from pRW864 which was excised by NotI digestion. The resulting plasmid was designated pRW673. An 81 bp SmaI fragment was derived from pVQ42KTH4.1 (defined in Example 104) and inserted into SmaI digested pRW873 generating plasmid pVQ873.

The nef cassette was excised from pBSI3NEF as a 684 bp HindIII fragment for insertion into pVQ873 followed by IVR into the F16 locus of TROVAC to generate vFP174.

EXAMPLE 107

EXPRESSION OF HIV-2 GENES IN NYVAC

Generation of NYVAC/HIV2 gag/pol recombinant. A plasmid, pISSYEGP, containing the human immunodeficiency virus type 2 (HIV2) gag and pol genes was obtained from Dr. G. Franchini (NCI-NIH). The gag and pol genes from this plasmid were cloned downstream of the I3L promoter and between vaccinia virus tk flanking arms. This was accomplished by cloning the 4,400 bp BstUI-BglII fragment of pISSYEGP, containing the HIV2 gag and pol genes, and the oligonucleotides, SIVL1 (SEQ ID NO:181) and HIV2L1 (SEQ ID NO:461) (5'-CGCCCATGAT-TAAACCTAAATAATTGTACTTTG-TAATATAATGATATATATTTTCACTTTATCTCAC-3'), containing the I3L promoter, into the 4,070 bp XhoI-BglII fragment of pSD542 (defined in Example 32). The plasmid generated by this manipulation is called pHIV21.

Extraneous 3'-noncoding sequence was then eliminated. This was accomplished by cloning a 280 bp BclI-SmaI PCR fragment, containing the 3'-end of the pol gene, into the 8,100 bp BclI-SmaI fragment of pHIV21. This PCR fragment was generated from the plasmid, pISSYEGP, with the oligonucleotides, HIV2P2 (SEQ ID NO:462) (5'-ATG-GCAGTTCATTGCAT-3') and HIV2P3 (SEQ ID NO:380) (5'-TTCCCGGGAGATCTCTATGCCATTTCTCCAT-3'). The plasmid generated by this manipulation is called pHIV22.

pHIV22 was used in recombination experiments with vP866 (NYVAC) as the rescuing virus to yield vP1045.

Immunoprecipitation analysis was performed to determine whether vP1045 expresses authentic HIV2 gag gene products. Vero cell monolayers were either mock infected, infected with the parental virus or infected with vP1045 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 μCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for HIV2 gag expression using pooled serum from HIV2 seropositive individuals (obtained from Dr. G. Franchini (NCI-NIH), NCI-NIH, Bethesda, Md.). The sera was preadsorbed with vP866 infected Vero cells. The preadsorbed sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the HIV2 seropositive human sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV2 seropositive individuals specifically precipitated the HIV2 gag precursor protein, as well as various intermediate and mature gag cleavage protein products, from vP1045 infected cells, but did not precipitate HIV2-specific proteins from mock infected or NYVAC infected cells.

EXAMPLE 108

GENERATION OF NYVAC/HIV2 gag/pol AND env (gp160) RECOMBINANT

A plasmid, pISSYEGP, containing the HIV2 gag and genes was obtained from Dr. G. Franchini (NCI-NIH). The gag and pol genes from this plasmid were cloned downstream of the I3L promoter and between vaccinia virus tk flanking arms. This was accomplished by initially preparing plasmid pHIV22 as described above (see Example 107).

pHIV22 was used in recombination experiments with vP920 as the rescuing virus to yield vP1047.

Immunoprecipitation experiments with vP1047 infected cells were performed as described above for the expression of the HIV2 gag proteins. No HIV2-specific species were precipitated from mock infected cells. Protein species corresponding to the HIV2 env and gag precursor proteins, as well as various intermediate and mature gag cleavage products, were precipitated, however, from lysates of vP1047 infected cells.

EXAMPLE 109

GENERATION OF NYVAC/HIV2 gag/pol AND env (gp120) RECOMBINANT

A plasmid, pISSYEGP, containing the HIV2 gag and pol genes was obtained from Dr. G. Franchini (NCI-NIH). The gag and pol genes from this plasmid were cloned downstream of the I3L promoter and between vaccinia virus tk flanking arms. This was accomplished by initially preparing plasmid pHIV22 as described above (see Example 107).

pHIV22 was used in recombination experiments with vP922 as the rescuing virus to yield vP1044.

Immunoprecipitation experiments with vP1044 infected cells were performed as described above for the expression of the HIV2 gag proteins. No HIV2-specific species were precipitated from mock infected cells. Protein species corresponding to the HIV2 env and gag precursor proteins, as well as various intermediate and mature gag cleavage products, were precipitated, however, from lysates of vP1044 infected cells.

EXAMPLE 110

EXPRESSION OF HIV2 GENES IN ALVAC

Generation of ALVAC/HIV2 gag/pol and env (gp160) recombinant. The plasmid, pBSH6HIV2ENV, contains the H6-promoted HIV2 env (gp160) gene. The H6-promoted env gene from this plasmid was cloned between canary pox flanking arms. This was accomplished by cloning the 2,700 bp XhoI-SacII fragment of pBSH6HIV2ENV, containing the H6-promoted env gene, and the oligonucleotides, HIV2L4 (SEQ ID NO:345) (5'-GGTTG-3') and HIV2L5 (SEQ ID NO:328) (5'-AATTCAACCGC-3'), into the XhoI-EcoRI site of pC6L. The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:423) and HIV2L7 (SEQ ID NO:424), into the 7,000 bp XmaI-XhoI fragment of pHIV23. The plasmid generated by this manipulation is called pHIV25.

pHIV25 was used in recombination experiments with CPpp (ALVAC) as the rescuing virus to yield vCP153.

Immunoprecipitation analysis was performed to determine whether vCP153 expresses authentic HIV2 gag and env gene products. CEF cell monolayers were either mock infected, infected with the parental virus or infected with vCP153 at an m.o.i. of 10 PFU/cell. Following an hour adsorption period, the inoculum was aspirated and the cells were overlayed with 2 mls of modified Eagle's medium (minus methionine) containing 2% fetal bovine serum and [$^{35}$S]-methionine (20 µCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for HIV2 gag and env gene expression using pooled serum from HIV2 seropositive individuals (obtained from Dr. G. Franchini (NCI-NIH), NCI-NIH, Bethesda, Md.). The sera was preadsorbed with CPpp infected CEF cells. The preadsorbed sera was bound to Protein A-sepharose in an overnight incubation at 4° C. Following this incubation period, the material was washed 4× with 1× buffer A. Lysates precleared with normal human sera and protein A-sepharose were then incubated overnight at 4° C. with the HIV2 seropositive human sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV2 seropositive individuals specifically precipitated the HIV2 env and gag precursor proteins, as well as various intermediate and mature cleavage products, from vCP153 infected cells, but did not precipitate HIV2-specific proteins from mock infected or CPpp infected cells.

EXAMPLE 111-EXPRESSION OF SIV GENES IN NYVAC GENERATION OF NYVAC/SIV env (gp120-gp28) AND gag (PROTEASE$^-$) RECOMBINANT Immunoprecipitation analysis was performed to determine whether vP948 (defined in Example 21) expresses authentic SIV env and gag precursor proteins. Vero cell monolayers were either mock infected, infected with the parental virus or infected with vP948 at an m.o.i. of 10 PFU/cell. Following an hour adsorption period, the inoculum was aspirated and the cells were overlayed with 2 mls of modified Eagle's medium (minus methionine) containing fetal bovine serum and [$^{35}$S]-methionine (20 µCi/ml). Cells were harvested at 18 hrs post-infection by the addition of 1 ml 3× buffer A (3% NP-40, 30 mM Tris (pH7.4), 3 mM EDTA, 0.03% Na Azide and 0.6 mg/ml PMSF) with subsequent scraping of the cell monolayers.

Lysates from the infected cells were analyzed for SIV env and gag precursor expression using serum from SIV seropositive macaques (obtained from Dr. G. Franchini (NCI-NIH), NCI-NIH, Bethesda, Md.). The sera was preadsorbed with vP866 (NYVAC) infected Vero cells. The preadsorbed sera was bound to Protein A-sepharose in an overnight incubation at 4° C. Following this incubation period, the material was washed 4× with 1× buffer A. Lysates precleared with normal macaque sera and protein A-sepharose were then incubated overnight at 4° C. with the SIV seropositive macaque sera bound to protein A-sepharose. After the overnight incubation period, the samples were washed 4× with 1× buffer A and 2× with a LiCl$_2$urea buffer. Precipitated proteins were dissociated from the immune complexes by the addition of 2× Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Macaque sera from SIV seropositive individuals specifically precipitated the SIV gag precursor protein and the envelope glycoprotein from vP948 infected cells, but did not precipitate SIV-specific proteins from mock infected cells.

EXAMPLE 112

GENERATION OF NYVAC/SIV gag/pol RECOMBINANT

A plasmid, pSIVGAGSS11G, containing SIV$_{MAC142}$ cDNA sequence was obtained from Dr. G. Franchini (NCI-NIH). The gag and pol genes from this plasmid were cloned downstream of the I3L promoter and between vaccinia virus tk flanking arms. This was accomplished by preparing plasmid pSIVG5 as described above (see Example 21).

Extraneous 3'-noncoding sequence was then eliminated. This was accomplished by cloning a 1,000 bp BamH1-HpaI PCR fragment, containing the 3'-end of the pol gene into the 7,400 bp partial BamH1-HpaI fragment of pSIVG1. This PCR fragment was generated from the plasmid, pSIVGAGSS11G, with the oligonucleotides, SIVP5 (SEQ ID NO:183) and SIVP6 (SEQ ID NO:184). The plasmid generated by this manipulation is called pSIVG4.

Sequence analysis revealed that pSIVG4 contains a single base pair deletion within the pol gene. To correct this error the 2,320 bp BglII-StuI fragment of pSIVG1 was cloned into the 6,100 bp partial BglII-StuI fragment of pSIVG4. The plasmid generated by this manipulation is called pSIVG5.

pSIVG5 was used in recombination experiments with vP866 (NYVAC) as the rescuing virus to yield vP1042.

Immunoprecipitation experiments with vP1042 infected cells were performed as described above for the expression of the SIV env and gag precursor proteins. No SIV-specific species were precipitated from mock infected or NYVAC infected Vero cells. Protein species corresponding to the gag precursor protein, as well as various intermediate and mature gag cleavage products, were precipitated, however, from lysates of vP1042 infected cells.

EXAMPLE 113

GENERATION OF NYVAC/SIV gag/pol AND env (gp120-gp41) RECOMBINANT pSIVG5 (Example 21) was used in recombination experiments with vP1050 as the rescuing virus to yield vP1071.

Immunoprecipitation experiments with vP1071 infected cells show expression of SIV genes.

EXAMPLE 114

GENERATION OF NYVAC/SIV gag/pol AND env (gp120-gp28) RECOMBINANT pSIVG5 (Example 21) was used in recombination experiments with vP874 as the rescuing virus to yield vP943.

Immunoprecipitation experiments with vP943 infected cells were performed as described above for the expression of the SIV env and gag precursor proteins. No SIV-specific species were precipitated from mock infected Vero cells. Protein species corresponding to the env and gag precursor proteins, as well as various intermediate and mature gag cleavage products, were precipitated, however, from lysates of vP943 infected cells.

EXAMPLE 115

GENERATION OF NYVAC/SIV p16, p28 RECOMBINANT

Immunoprecipitation experiments with vP942 (Example 21) infected cells were performed as described above for the expression of the SIV env and gag precursor proteins. No SIV-specific species were precipitated from mock infected Vero cells. Protein species corresponding to p16 and p28 were precipitated, however, from lysates of vP942 infected cells.

EXAMPLE 116

GENERATION OF NYVAC/SIV p16, p28 AND env (gp120-gp28) RECOMBINANT

Immunoprecipitation experiments with vP952 (Example 21) infected cells were performed as described above for the expression of the SIV env and gag precursor proteins. No SIV-specific species were precipitated from mock infected Vero cells. Protein species corresponding to env and p16 and p28 were precipitated, however, from lysates of vP952 infected cells.

EXAMPLE 117

GENERATION OF NYVAC/SIV env (gp120-gp41) RECOMBINANT

The plasmid, pSIVEMVC, contains the H6-promoted $SIV_{MAC142}$ envelope gene (in vitro selected truncated version). The region of the envelope gene containing the premature termination codon was cloned into pBSK+. This was accomplished by cloning the 1,120 bp ClaI-BamHI fragment of pSIVEMVC into the ClaI-BamHI site of pBSK+. The plasmid generated by this manipulation is called pSIV10.

The upstream termination codon, TAG, was then changed to the original CAG codon. This was accomplished by cloning the oligonucleotides, SIVL20 (SEQ ID NO:327) (5'-CTAGCTAAGTTAAGGCAGGGGTATAGGC-CAGTGTTCTCTTCCCCACCCTCT-TATTTCCAGCAGACTCATACCCAACAG-3') and SIVL21 (SEQ ID NO:322) (5'-GTCCTGTTGGGTAT-GAGTCTGCTGGAAATAAGAGGGTGGG-GAAGAGAACACTGGCCTATACCCCTGC-CTTAACTTAG-3'), into the 4,000 bp NheI-PpuMI fragment of pSIV10. The plasmid generated by this manipulation is called pSIV11.

The region containing the modified codon was then cloned back into pSIVEMVC. This was accomplished by cloning the 380 bp BglII-NheI fragment of pSIV11, containing the modified codon, into the 5,600 bp partial BglII-NheI fragment of pSIVEMVC. The plasmid generated by this manipulation is called pSIV12.

pSIV12 was used in in vitro recombination experiments with vP866 (NYVAC) as the rescuing virus to yield vP1050.

Immunoprecipitation experiments with vP1050 infected cells were performed as described above for the expression of the SIV env and gag precursor proteins. No SIV-specific species were precipitated from mock infected or NYVAC infected Vero cells. A protein species corresponding to env was precipitated, however, from lysates of vP1050 infected cells.

EXAMPLE 118

EXPRESSION OF SIV GENES IN ALVAC

Generation of ALVAC/SIV gag/pol recombinant. A plasmid, pSIVGAGSS11G, containing $SIV_{MAC142}$ cDNA sequence was obtained from Dr. G. Franchini (NCI-NIH). The gag and pol genes from this plasmid were cloned downstream of the I3L promoter and between vaccinia virus flanking arms. This was accomplished by initially preparing plasmid pSIVG5 as described above (see Example 21).

The gag/pol genes were then cloned between canary pox flanking arms. This was accomplished by cloning the 4,500 bp SmaI-NotI fragment of pSIVG5, containing the I3L-promoted gag/pol genes, into the SmaI-NotI site of pC5L (defined in Example 44). The plasmid generated by this manipulation is called pSIVGC13.

pSIVGC13 was used in recombination experiments with CPpp (ALVAC as the rescuing virus to yield vCP172.

Immunoprecipitation experiments with vCP172 infected cells show expression of SIV genes.

EXAMPLE 119

IMMUNIZATION OF HUMANS USING CANARYPOX EXPRESSING RABIES GLYCOPROTEIN (ALVAC-RG; vCP65)

Figure 17A:
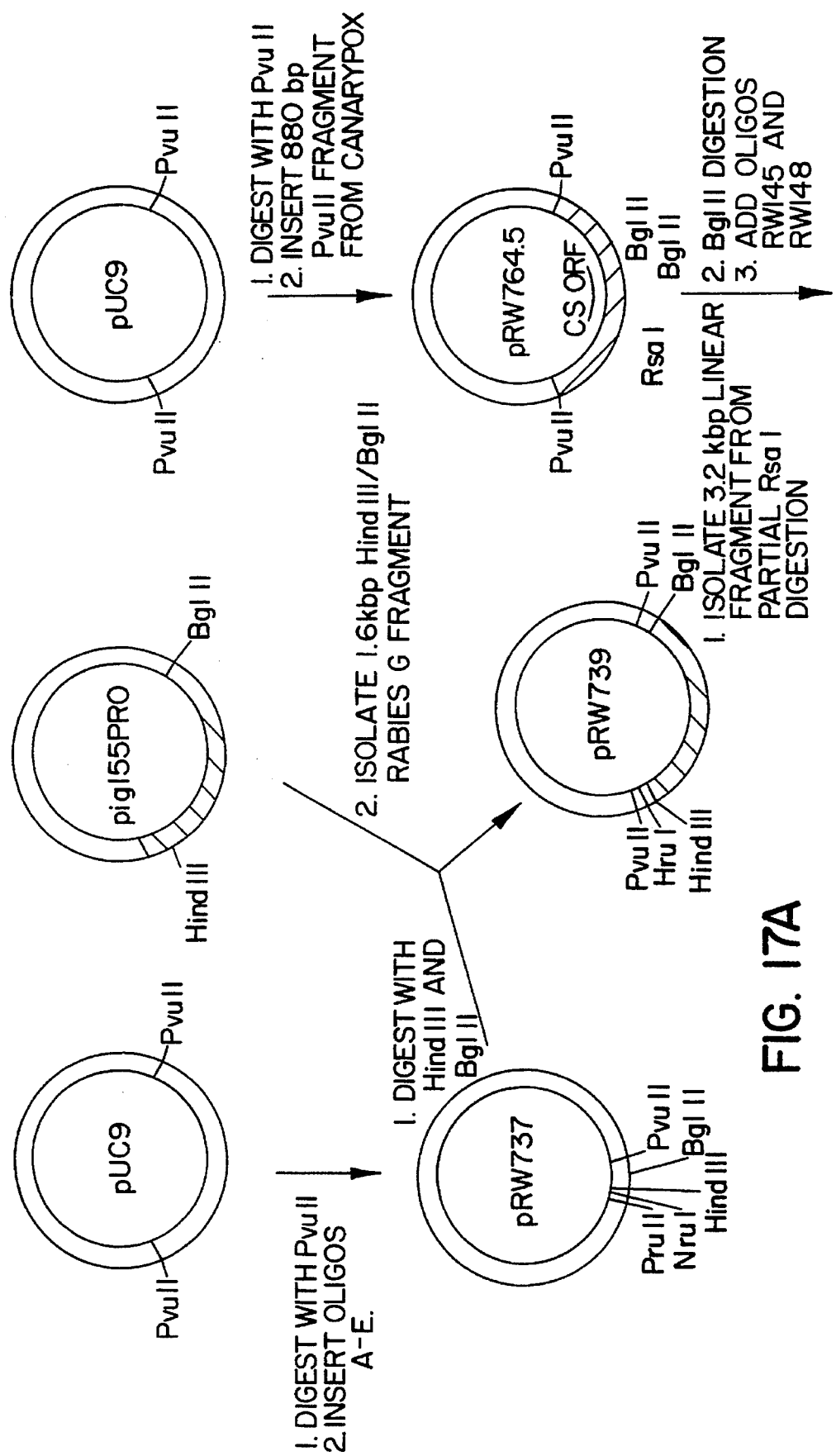
FIG. 17 (FIGS. 17A, 17B) schematically shows a method for the construction of recombinant canarypox virus vCP65 (ALVAC-RG)
Figure 17B:
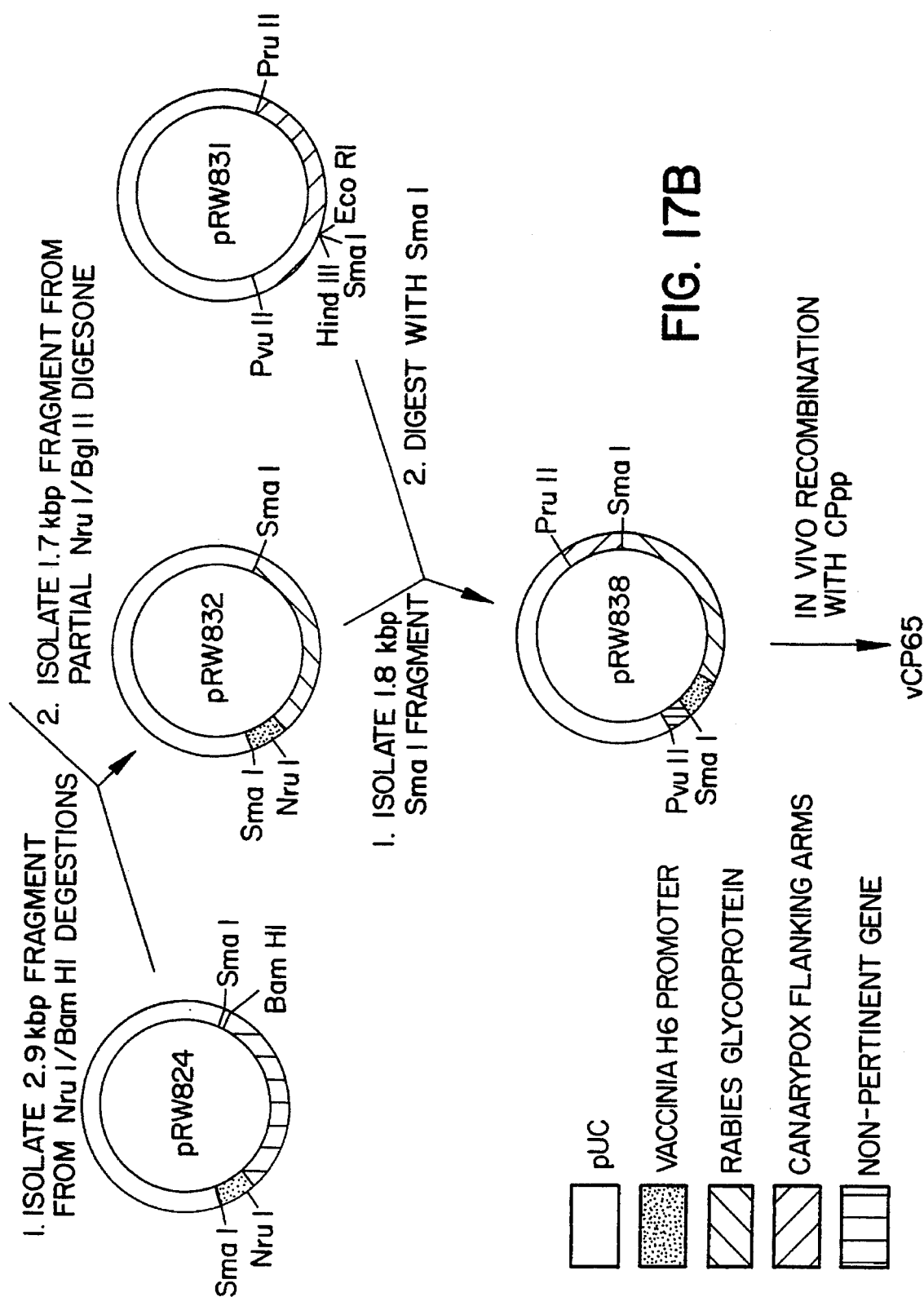

ALVAC-RG (vCP65) was generated as described in Example 15 and FIG. 17. For scaling-up and vaccine manufacturing ALVAC-RG (vCP65) was grown in primary CEF derived from specified pathogen free eggs. Cells were infected at a multiplicity of 0.01 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No desirable trait was found.

Preclinical data. Studies in vitro indicated that VERO or MRC-5 cells do not support the growth of ALVAC-RG (vCP65); a series of eight (VERO) and 10 (MRC) blind seria passages caused no detectable adaptation of the virus to grow in these non avian lines. Analyses of human cell lines (MRC-5, WISH Detroit 532, HEL, HNK or EBC transformed lymphoblastoid ALVAC-RG (vCP65)) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose (TCID$_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC-HDC; 2. HDC, HDC-ALVAC-RG (vCP65); 3. ALVAC-RG (vCP65), ALVAC-RG (vCP65) - HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith & Yaeger, In Laboratory Techniques on Rabies). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ TCID$_{50}$), nine subjects received $10^{5.5}$ TCID$_{50}$ and ten received the HDC vaccine.

Safety (Table 49). During the primary series of immunization, fever greater than 37.7° C. was noted within 24 hours after injection in one HDC recipient (37.8° C.) and in one vCP65 $10^{5.5}$ TCID$_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ TCID$_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 50). Twenty eight days after the first injection all the HDC recipients had protective titers ($\geq$0.5 IU/ml). By contrast none in groups A and B ($10^{3.5}$ and $10^{4.5}$ TCID$_{50}$) and only 2/9 in group C ($10^{5.5}$ TCID$_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 51). The preimmune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Infection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIG. 35 shows graphs of rabies neutralizing antibody titers (Rapid Fluorescent Focus Inhibition Test or RFFIT, IU/ml): Booster effect of HDC and vCP65 ($10^{5.5}$ TCID$_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIG. 35 the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)-ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of Vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al, Lancet 1991, 337:567–72; Etlinger et al, Vaccine 1991, 9:470–72).

Thus, this Example clearly demonstrates that a non-replicating poxvirus can serve as an immunizing vector in humans, with all of the advantages that replicating agents confer on the immune response, but without the safety problem created by a fully permissive virus.

TABLE 49

| Reactions in the 5 days following vaccination | | | | | | | | |
|---|---|---|---|---|---|---|---|---|
| vCP65 dosage (TCID50) | $10^{3.5}$ | | $10^{4.5}$ | | $10^{5.5}$ | | HDC control | |
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 50

Rabies neutralizing antibodies (REFIT; IU/ml)
Individual titers and geometric mean titers (GMT)

| no. | TCID50/ dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| | G.M.T. | <0.1 | <0.1 | 2.96 | 9.0 | 11.5* |

*p = 0.007 student t test

TABLE 51

Canarypox antibodies: ELISA Geometric Mean Titers*

| vCP65 dosage | Days | | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

EXAMPLE 120

PROTECTION AGAINST JAPANESE ENCEPHALITIS VIRUS BY NYVAC-JEV RECOMBINANTS (vP908, vP923)

Using NYVAC-JEV recombinants, protection against Japanese Encephalitis virus was provided. NYVAC vP866, NYVAC recombinants vP908 and vP923, and vaccinia recombinants vP555 and vP829 were produced as described herein.

Mouse Protection Experiments. Mouse protection experiments were performed as previously described (Mason et al., 1991). Briefly, groups of 10 to 12 4-week-old outbred Swiss mice were immunized by intraperitoneal (i.p.) injection with $10^7$ PFU of vP829, vP866, vP908 or vP923, and sera were collected three weeks alter. Mice were challenged by i.p. injection with the Beijing P3 strain of JEV. Following challenge, mice were observed at daily intervals until the experiment was concluded three weeks later. Lethal dose titrations were performed using litter mates of the experimental animals.

Swine protection experiments. Landrace cross castrated swine of about 25 kg body weight were used. Groups of five pigs were immunized by subcutaneous (s.c.) injection with phosphate buffered saline (PBS), or $1\times10^8$ PFU of vP866, vP908 or vP923 diluted in 2 ml of PBS. Twenty-eight days after inoculation, the pigs were boosted by injection in the same manner as shown above, and 56 days after the first inoculation they were challenged by s.c. injection with $2\times10^5$ PFU of the B-2358/84 strain of JEV. Sera were collected from the animals in all groups on days 0 (before immunization), 7, 14, 21, 28 (before boosting), 31, 35, 42, 56 (before challenge), 57, 58, 59, 60, 61, 62, 63, 64 and 76 (after challenge).

Evaluation of Immune Responses. Swine sera were tested for their ability to precipitate JEV proteins from detergent treated cell lysates or culture fluids obtained from [$^{35}$S]Met-labeled JEV infected cells as described in Bonishi et al. (1991), except for the use of fixed *Staphylococcus aureus* bacteria coated with anti-swine immunoglobulin (Ig) G (DAKO Corp., Carpinteria, Calif.). The HAI test for swine and mouse pre-challenge sera was performed by a modification of the method of Clarke and Casals (1958). The NEUT test was performed essentially as described by Mason et al. (1991), except that freshly thawed human serum was not used for testing pig sera.

Viremia. Freshly thawed aliquots of spine sera collected for eight days after JEV challenge were plaque titrated for infectious JEV on VERO monolayer cells in 6-well microplates. Following virus adsorption, the cell monolayers were overlayed with medium containing 1% carboxymethylcellulose, and plaques were visualized at five days post-infection by staining with 0.1% crystal violet dissolved in 20% ethanol. If three or fewer plaques were observed in the wells incubated with 300 μl of serum, the titer was recorded as <10 PFU/ml.

Structures of the Recombinant Vaccinia Viruses. The JEV cDNA sequences contained in vaccinia recombinants constructed in this study are shown in FIG. 36. In these recombinant viruses the sera strand of the JEV cDNA was positioned behind the early/late H6 promoter. Recombinant vP908 (and vP555; Mason et al., 1991) includes the putative 15 amino acid signal sequence preceding the N-terminus of prM, prM, E, NS1 and NS2A. Recombinant vP923 (and vP828; Konishi et al., 1991) encodes the putative signal sequence of prM, prM, and E.

Synthesis of E and NS1 by Recombinant Vaccinia Viruses. Immunoprecipitation of the E or NS1 gene was performed using a monoclonal antibody specific for E or NS1. Proteins reactive with the E MAb were synthesized in cells infected with vP555, vP908 and vP923, and proteins reactive with NS1 MAb were synthesized in cells infected with vP555 and vP908 but not in cells infected with vP923. vP555 infected cells produced correct forms of E and NS1 inside and outside of the cell. The proteins produced by vP908 and vP923 were identical in size to those produced by vP555. For both E and NS1, the extracellular forms migrated slower than the intracellular forms in SDS-PAGE, consistent with maturation of the N-linked glycans immediately preceding release from the cells. In addition, vP908 infected cells produced a higher molecular weight form of NS1, NS1', which is derived by alternative processing of the sequences encoded by the NS2A region of the JEV genome (Mason et al., 1987). Immunoprecipitates prepared from radiolabeled vaccinia recombinant infected cells using a MAb specific for M (and prM) revealed that prM was synthesized in cells infected with vP908 and vP923.

The extracellular fluid of vP908 or vP923 infected HeLa cells showed an HA activity that was undetectable in the culture fluid of vP866 infected cells. Data had indicated that vP829 induced the synthesis of approximately eight times more extracellular hemagglutinin than vP555 (Konishi et al., 1991). In parallel to this difference, cells infected with vP923 produced approximately 8 times more HA activity than cells infected with vP908. These results indicated that the recombinant form of JEV proteins produced by vP980 and vP923 are equivalent to those produced by vP555 and vP829, respectively.

Immunization and Challenge of Mice. The ability of the NYVAC based recombinant viruses to induce protective immunity was examined in mice. The NEUT and HAI data for the pre-challenge sera indicated that vP908 and vP923 produced the same levels of antibody as vP829 (Table 52) and Konishi et al, 1991) (Table 52). Consistent with these serological data, vP908 and vP923 were able to provide mice with protection from lethal JEV infection by the pathogenic P3 strain of JEV (Table 52). The levels of protection were similar to that achieved by immunization with vP829 (Table 52) and Konishi et al., 1991). These studies confirmed that vP908 and vP923, the two NYVAC based recombinants, were immunogenic in mice at a level similar to those previously described (Konishi et al., 1991).

Introduction of Immune Responses to JEV Antigens in Swine by Recombinant Vaccinia Viruses. Pre-challenge sera pooled from all swine in each group collected every seven days were tested for anti-JEV NEUT and HAI activity. As shown in FIG. 37, both NEUT and HAI activities were observed in swine immunized with vP908 and vP923, but not in swine inoculated with PBS or vP866. Relatively high levels of NEUT antibodies were observed seven days after the first and second inoculation in both vP908 and vP923 immunized swine, and decreased to barely detectable levels 21 days alter. For both the primary inoculation and boost, HAI decreased more slowly than NEUT antibodies (FIG. 37). vP908 provided slightly higher levels of HAI and NEUT antibodies than vP923. The HAI titers with both recombinants were greater after the second inoculation than that achieved after a single inoculation. vP923 provided a higher NEUT titer after the second inoculation that upon a single inoculation, whereas vP908 induced equivalent NEUT titers after a single or double inoculation.

Swine were immunized on days 0 and 28, and sera collected on day 56 from swine immunized with PBS or vP866 and on days 0, 7, 28, 35 and 56 from swine immunized with vP908 or vP923. Sera pooled from all animals in each group of 5 were tested for their ability to immunoprecipitate radiolabeled proteins harvested from the culture fluid of JEV-infected cells.

The immune response to E correlated well with the results of the NEUT and HAI tests. The RIP response to E observed in swine immunized with vP923 on day 35 was higher than the RIP response to E in swine immunized with vP908, whereas the HAI titers on day 35 were equivalent in the two groups. However, NEUT titers on day 35 were higher in the swine immunized with vP923 than in swine immunized with vP908. Antibodies other than those involved in NEUT or HAI may be induced but the quantitative aspects of the RIP analysis was not further validated. Weak RIP responses of sera to E on day seven in spite of relatively high NEUT antibody titers could be explained by IgM antibody early after immunization. Levels of JEV-specific IgM was not further analyzed. None of the pooled sera showed an immune response to NS1.

Viremia in Swine Immunized With Recombinant Vaccinia Viruses. JE virus titers of >10 PFU/ml were detected in post-challenge sera from the control swine [PBS (4/5) or vP866 (5/5)], whereas only 2 of 5 swine inoculated with vP923 exhibited viremias of >10 PFU/ml (FIG. 38). Significantly, none of the five swine immunized with vP908 had measurable viremia >10 PFU/ml. The geometric mean of the maximum virus titers in individual swine in groups immunized with PBS and vP866 ($1.2 \times 10^3$ PFU/ml) was significantly higher than the mean in groups immunized with vP908 and vP923 ($1.9 \times 10^1$ PFU/ml; $P<0.001$ by the student t-test; assuming a titer of 10 PFU/ml for all swine with viremias of <10 PFU/ml). Moreover, the average period of viremia for swine showing >10 PFU per ml of virus was 2.7 days for PBS and vP866, and 2.0 days for the two vP923 immunized swine which had titers of >10 PFU/ml. These results indicate that immunization of vP908 and vP923 considerably reduced JEV viremia following challenge.

In order to evaluate the immune response to JEV challenge, we tested individual sera collected 20 days post-challenge for antibodies against JEV. The swine vaccinated with vP908 or vP923 had higher responses to E than those inoculated with PBS or vP866, indicating that the antibody reactivity to E that was present before challenge was boosted by JEV infection. Reactions to NS3 and NS5, JEV proteins which were not expressed in the recombinant vaccinia viruses were detected in all post-challenge sera suggesting that some level of JEV replication occurred even in pigs which had viremias of <10 PFU/ml. Thus, the expected reciprocal relationship between reactivity of post-challenge sera to NS3 and absence of infection as measured by serum JEV titers was not observed. This is in contrast to previous data obtained with mice in which lack of reactivity of pooled mouse sera to NS3 post-challenge correlated with protection (Konishi et al., 1991)

During the protection experiment, one pig in the parental vaccinia (vP866) group died 12 days after the challenge. This animal showed a higher body temperature than any other swine during the post-challenge period and was the only animal with JEV serum titers of >1,000 PFU for three days (FIG. 38). Although JEV was not detected from the brain specimen sampled at necropsy, the animal may have died from the disease caused by JEV infection.

Observations. The Example demonstrates that NYVAC-JEV provides effective protection against JEV viremia; and thus, NYVAC-JEV is useful and safe for veterinary applications.

TABLE 52

Immunization and JEV challenge in mice

| Immunizing Virus[a] | JEV Genes Expressed | Antibody titer | | Survival[d] |
|---|---|---|---|---|
| | | NEUT[b] | HAI[c] | |
| vP829 | prM, E | 1:320 | 1:80 | 10/10 (100%) |
| vP866 | None | <1:10 | <1:10 | 0/12 (0%) |
| vP908 | prM, E, NS | 1:320 | 1:80 | 11/12 (92%) |
| vP923 | prM, E | 1:320 | 1:80 | 12/12 (100%) |

[a]Vaccinia recombinant virus used for immunizing groups of 4-week old mice.
[b]Serum dilution yielding 90% reduction in plaque number (Mason et al., 1991)
[c]Serum dilution.
[d]Number survival/number challenged (% survival). Mice of each group were challenged with the Beijing P3 strain three weeks after immunization. The challenge doze was $3.8 \times 10^5$ LD$_{50}$ as determined by a lethal-dose titration using litter-mates of the mice.

EXAMPLE 121

EVALUATION OF NYVAC (vP866) AND NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, New Jersey). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$ or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 24.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per µl for untreated mice (n=4) and 4,220 cells per µl for CY-treated control mice (n=5).

Calculation of LD$_{50}$. The lethal dose required to produce 50% mortality (LD$_{50}$) was determined by the proportional method of Reed and Muench (Reed and Muench 1938).

Potency Testing of NYVAC-RG in Mice- Four to six week old mice were inoculated in the footpad with 50 to 100 µl of a range of dilutions (2.0–8.0 log$_{10}$ tissue culture infective dose 50% (TCID$_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 LD$_{50}$ of the rabies virus CVS strain (0.03 ml). On day 28, surviving mice were counted and protective does 50% (PD$_{50}$) calculated.

Figure 39:
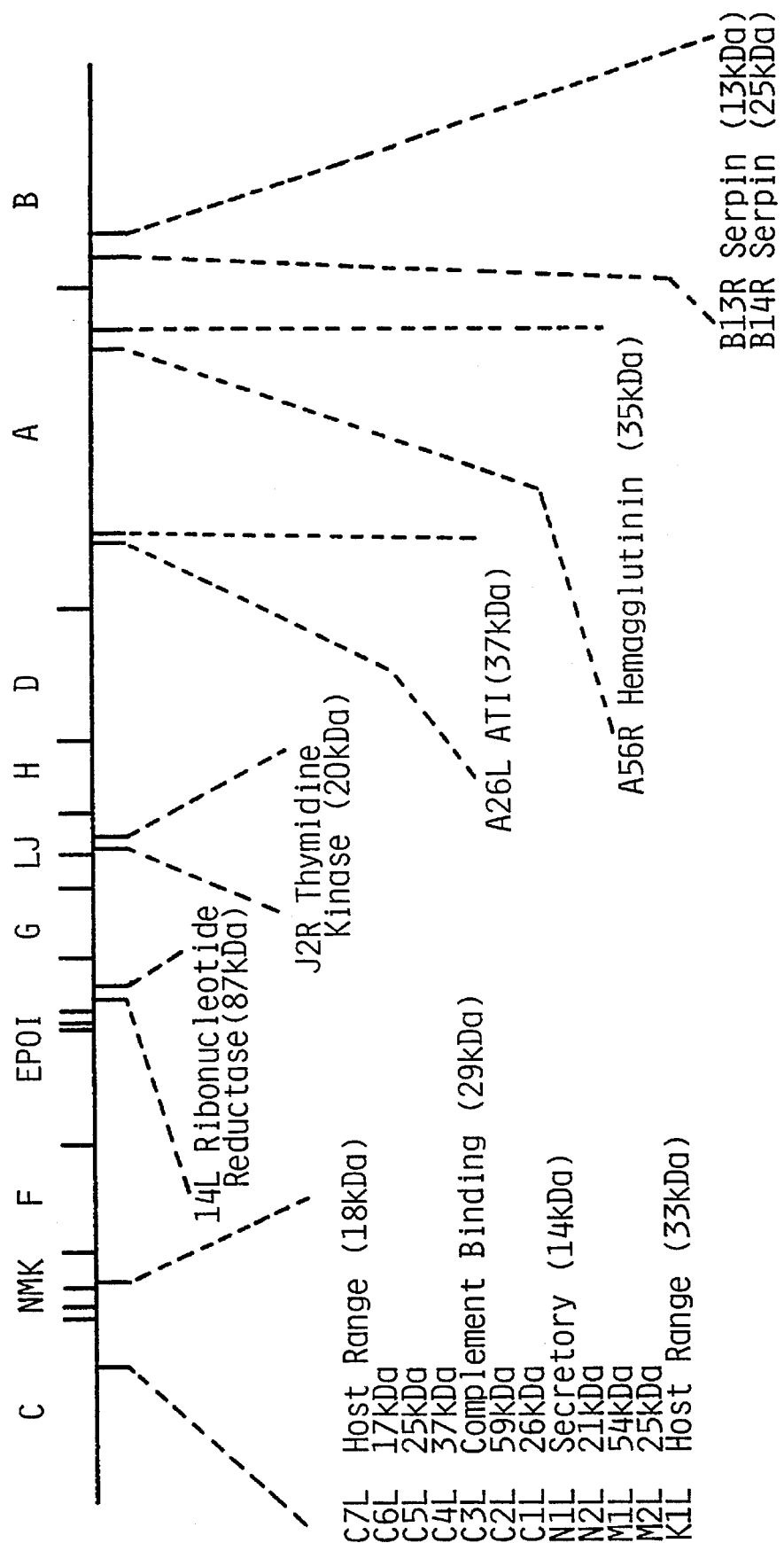
FIG. 39 shows schematically the ORFs deleted to generate NYVAC.

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 39 schematically depicts the ORFs deleted to generate NYVAC. At the top of FIG. 39 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 53. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contract, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70–151) cells. Replication on these cell lines was significantly reduced when compared to virus yields obtained from NYVAC-infected CEF cells or with parental VC-2 (Table 53). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 53. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 54). No local reactions were observed from sites injected with the control PBS. Ulcerative lesions were observed at sites injected with WR, VC-2 and WYETH vaccinia virus strains. Significantly, no induration or ulcerative lesions were observed at sites; of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$, $10^8$ or pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 55). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 55. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5 \times 10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5 \times 10^7$ or $5 \times 10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 56.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 56, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5\times10^4$ to $9.5\times10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65\times10^5$ to $1.65\times10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 57 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 24). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 28–29, 53–57). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 24, Tables 28, 29, 56). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 54 and 55). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 54 and 55). Considering the results with ALVAC, a virus unable to replicate in nonavian species, the ability to replicate at the site of inoculation is not the sole correlate with reactivity, since intradermal inoculation of ALVAC caused areas of induration in a dose dependent manner (unpublished observations). Therefore, it is likely that factors other than the replicative capacity of the virus contribute to the formation of the lesions. Deletion of genes in NYVAC prevents lesion occurrence.

Together, the results in this Example and in foregoing Examples, including Example 24, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 53) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 57). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1990). Furthermore, the use of NYVAC as a general laboratory expression vector system may greatly reduce the biological hazards associated with using vaccinia virus.

By the following criteria, the results of this Example and the foregoing Examples, including Example 24, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 53

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |

TABLE 53-continued

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 μg/ml of cytosine arabinoside.
[d]Not determined.
*ATCC #CCL25 Human amnionic cells.

TABLE 54

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one site.
[b]mean maximum size of lesions (mm²)
[c]mean time after inoculation for complete healing of lesion.
[d]no lesions discernable.

TABLE 55

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |

TABLE 55-continued

Persistence of poxviruses at the site of intradermal inoculation

| Virus | Inoculum Dose | Total Virus Recovered |
|---|---|---|
| NYVAC | 6.0 | 3.97 |
|  | 8.0 | 0 |
|  | 7.0 | 0 |
|  | 6.0 | 0 |

[a]expressed as $\log_{10}$ pfu.

TABLE 56

Virulence studies in immunocompromised mice

| Poxvirus Strain | $LD_{50}$[a] | |
|---|---|---|
|  | Nude mice | Cyclophosphamide treated mice |
| WR | 422 | 42 |
| VC-2 | >10$^9$ | <1.65 × 10$^5$ |
| WYETH | 1.58 × 10$^7$ | 1.83 × 10$^6$ |
| NYVAC | >5.50 × 10$^8$ | 7.23 × 10$^8$ |
| ALVAC | >10$^9$ | ≧5.00 × 10$^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of 5 × 10$^8$ pfu.

TABLE 57

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $\log_{10}$ tissue culture infection dose 50% (TCID$_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% (LD$_{50}$) per mouse. At day 28, surviving mice were counted and a protective dose 50% (PD$_{50}$) was calculated.

Having thus described in detail preferred embodiments of the present invention, it is to be understood that the invention defined by the appended claims is not to be limited to particular details set forth in the above description as many apparent variations thereof are possible without departing from the spirit or scope of the present invention.

REFERENCES

1. Adamowicz, Ph., F. Tron, R. Vinas, M. N. Mevelec, I. Diaz, A. M. Courouce, M. C. Mazert, D. Lagarde and M. Girard, In Viral Hepatitis and Liver Disease, pp. 1087–1090 (1988).
2. Alexander, D. J. In Diseases of Poultry, 9th edition, eds. B. W. Calnek, H. J. Barnes, C. W. Beard, W. M. Reid and H. W. Yoder, Jr., (Iowa State University Press, Ames, Iowa, USA) pp. 496–519 (1991).
3. Alkhatib, G. and D. Briedis, Virology 150, 479–490 (1986).
4. Alkhatib, G., C. Richardson, and S-H. Shen, Virology 175, 262–270 (1990).
5. Allen, P. and Rapp, F., J. Infect. Dis. 145, 413–421 (1982).
6. Alp, N. J., T. D. Allport, J. Van Zanken, B. Rodgers, J. G. P. Sissons, and L. K. Borysiewicz, J. Virol. 65, 4812–4820.
7. Altenburger, W., C-P. Suter and J. Altenburger, Archives Virol. 105, 15–27 (1989).
8. Arikawa, J., Schmaljohn, A. L., Dalrymple, J. M., and Schmaljohn, C. S., J. Gen. Virology 70, 615–624 (1989).
9. Asada, H., Tamura, M., Kondo, K., Dohi, Y, Yamanishi, K., J. Gen Virology 69, 2179–2188 (1988).
10. Asada, H. M., Tamura, K., Kondo, Y., Okano, Y., Takahashi, Y., Dohi, T., Nagai, T., Kurata, T., and Yamanishi, K., J. Gen. Virology 68, 1961–1969 (1987).
11. Avery, R. J., and J. Niven., Infect. and Immun. 26, 795–801 (1979).
12. Baer. R., Bankie, A. T., Biggin. M. D., Deiniger. P. L., Farrel. P. J., Gibson. T. J., Hatfull. G., Hudsson. G. S., Satchwell. S. C., Seguin. C., Tuffnell. P. S., Barrell. B. G., Nature 310, 207–211 (1984).
13. Balachandran, N., Bacchetti, S. and Rawls, W., Infec. Immun. 37, 1132–1137 (1982).
14. Baxby, D. In Jenner's Smallpox Vaccine, (Heinemann Educational Books, Ltd., London) pp 214 (1981).
15. Baxby D., Paoletti, E., Vaccine 9, 8–9 (1992).
16. Beard, C. W., Avian Diseases 23, 327–334 (1979).
17. Beard, C. W., and R. P. Hanson, In Disease of poultry, 8th edition, ed. M. S. Hofstad, (Iowa State University Press, Ames, Iowa) pp. 452–470 (1984).
18. Beattie, E., Tartaglia, J., and Paoletti, E., Virology 183, 419–422 (1991).
19. Behbehani, A. M., Microbiological Reviews 47, 455–509 (1983).
20. Ben-Porat, T. and A. S. Kaplan, Virology 41, 265–273 (1970).
21. Ben-Porat, T. and A. S. Kaplan, In The Herpesviruses, vol. 3, ed. B. Roizman, (Plenum Publishing Corp., New York) pp. 105–173 (1985).
22. Ben-Porat, T., J. DeMarchi, J. Pendrys, R. A. Veach, and A. S. Kaplan, J. Virol. 57, 191–196 (1986).
23. Ben-Porat, T., F. J. Rixon, and M. L. Blankenship, Virology 95, 285–294 (1979).
24. Ben-Porat, T. In Organization and replication of viral DNA, ed. A. S. Kaplan, (CRC Press, Inc., Boca Raton, Fla.) pp. 147–172 (1982).
25. Bergoin, M., and Dales, S., In Comparative Virology, eds. K. Maramorosch and E. Kurstak, (Academic Press, NY) pp. 169–205 (1971).
26. Berns, K. I., In: Fields Virology, eds. B. N. Fields and D. M. Knipe, (Raven Press, New York) pp. 1743–1763 (1990).
27. Bertholet, C., Drillien, R., and Wittek, R., Proc. Natl. Acad. Sci. USA 82, 2096–2100 (1985).
28. Bishop, D. H. L., In: Bunyaviridae and Their Replication in Virology: 2nd Edition, pp. 1155–1173 (1990).
29. Borysiewicz, L. K., J. K. Hickling, S. Graham, J. Sinclair, M. P. Crange, G. L. Smith, and J. G. Sissons, J. Exp. Med. 168, 919–931 (1988).
30. Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).
31. Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).
32. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297-300. (1990c).
33. Boursnell, M. E. G., I. J. Foulds, J. I. Campbell and M. M. Binns, J. Gen. Virol. 69, 2995–3003 (1988).

34. Brandt, W. E., J Infect Dis. 157, 1105–1111 (1988).
35. Brochier B., Kieny M. P., Costy F., et al., Nature, 354 520–522 (1991).
36. Bryson, Y., Dillon, M., Lovett, M., Acuna, G., Taylor, S., Cherry, J., Johnson, B., Wiesmeier, E., Growdon, W., Creagh-Kirk, T. and Keeney, R., N. Engl. J. Med. 308, 916–921 (1983).
37. Bucher, D., Popplo, S., Baer, M., Mikhail, A., Gong, Y-F., Whitaker, C., Paoletti, E., and Judd, A., J. Virol. 63, 3622–3633 (1989).
38. Buller, R. M. L., and Palumbo, G. J., Microbiol. Rev. 55, 80–122 (1991).
39. Buller, R. M. L., Chakrabarti, S., Cooper, J. A., Twardzik, D. R., and Moss, B., J.Virol. 62, 866–874 (1988).
40. Buller, R. M. L., G. L. Smith, Cremer, K., Notkins, A. L., and Moss, B., Nature 317, 813–815 (1985).
41. Bunn, T. O., In: Rabies, eds. Campbell, J. B. and Charlton K. M. (Kluwer Academy Press, Boston) pp. 474–491 (1988).
42. Cantin, E., Eberle, R., Baldrick, J., Moss, B., Willey, D., Notkins, A. and Openshaw, H., Proc. Natl. Acad. Sci. USA, 84, 5908–5912 (1987).
43. Chakrabarti, S., Brechling, K., and Moss, B., Mol. Cell. Biol. 5, 3403–3409 (1985).
44. Chakrabarti, S., Robert-Guroff, M., Wong-Staal, F., Gallo, R. C., and Moss, B. Nature 320, 535–537 (1986)
45. Chambers, T. M., Y. Kawaoka, and R. G. Webster, Virology 167, 414–421 (1988).
46. Chambers, P., N. S. Millar, and P. T. Emmerson, J. Gen. Virol. 67, 2685–2694 (1986).
47. Chambers, T. J., Hahn, C. S., Galler, R., and Rice, C. M., Ann. Rev. Microbiol. 44, 649–688 (1990)
48. Chan, W., Immunol. 49, 343–352 (1983).
49. Charles, I. G., Rodgers, B. C., Makoff, A. J., Chatfield, S. N., Slater, D. E., and Fairweather, N. F., Infect. Immun. 59, 1627–1632 (1991).
50. Chen, C., R. W. Coupans, and P. W. Choppin, J. Gen. Virol. 11, 53–58 (1971).
51. Cheng, K-C, G. L. Smith and B. Moss, J. Virol. 60, 337–344 (1986).
52. Child, S. J., Palumbo, G. J., Buller, R. M. L., and Hruby, D. E. Virology 174, 625–629 (1990).
53. Chirgwin, J. M., Przybyla, A. E., MacDonald, R. J., and Rutter, W. J., Biochemistry 18, 5294–5299 (1979).
54. Chisari, F. V., P. Filippi, A. McLachlan, D. R. Milich, M. Riggs, S. Lee, R. R. Palmiter, C. A. Pinkert and R. L. Brinster, J. Virol. 60, 880–887 (1986).
55. Cianciolo, G. J., Copeland, T. D., Oroszlan, S., and Snyderman, R. Science 230, 453–455 (1985).
56. Clark, N., Kushner, B. S., Barrett, M. S., Kensil, C. R., Salsbury, D., and Cotter, S., JAVMA 199, 1433–1442 (1991).
57. Clarke, B. E., S. E. Newton, A. R. Carroll, M. J. Francis, G. Appleyard, A. D. Syred, P. E. Highfield, D. J. Rowlands and F. Brown, Nature 330, 381–384 (1987).
58. Clarke D. H., and Casals J. Am., J. Trop. Med. Hyg. 7, 561–573 (1958).
59. Clewell, D. B., J. Bacteriol 110, 667–676 (1972).
60. Clewell, D. B. and D. R. Helinski, Proc. Natl. Acad. Sci. USA 62, 1159–1166 (1969).
61. Colinas, R. J., R. C. Condit and E. Paoletti, Virus Research 18, 49–70 (1990).
62. Collett, M. S., Keegan, K., Hu, S.-L, Sridhar, P., Purchio, A. F., Ennis, W. H., and Dalrymple, J. M., The Biology of Negative Strand Viruses, pp. 321–329 (1987).
63. Collins P. L., Purcell R. H., London W. T. et al., Vaccine 8, 154–168 (1990).
64. Cooney E. L., Corrier A. C., Greenberg P. D., et al., Lancet 337, 567–572 (1991).
65. Cox, J. H., B. Dietzschold, and L. G. Schneider, Infect. Immun. 16, 754–759 (1977).
66. Dales, S., Ann. Rev. Microbiol. 44, 173–192 (1990).
67. Daniels, R. S., Skehel, J. J., and Wiley, D. C., J. Gen. Virol. 66, 457–464 (1985).
68. Dantas, J. R., Ft., Okuno, Y., Asada, H., Tamura, M., Takahashi, M., Tanishita, O., Takahashi, Y. Kurata, T., and Yamanishi, K., Virology 151, 379–384 (1986).
69. Davis, W., Taylor, J. and Oakes, J., J. Infect. Dis. 140, 534–540 (1979).
70. De, B. K., M. W. Shaw, P. A. Rota, M. W. Harmon, J. J. Esposito, R. Rott, N. J. Cox and A. P. Kendal, Vaccine 257–261 (1988).
71. Delpeyroux, F., N. Peillon, B. Blondel, R. Crainic and R. E. Streeck, J. Virol., 62, 1836–1839 (1988).
72. DeNoronha, F., Schafer, W., and Essex, M., Virology 85, 617–621 (1978).
73. Derosiers, R. C., M. S. Wyand, T. Kodama, T. J. Ringler, L. O. Arthur, P. K. Sehgal, N. L. Letvin, N. W. King and M. D. Daniel, Proc. Natl. Acad. Sci. USA 86, 6353–6357 (1989).
74. Diallo, A., Vet. Micro. 23, 155–163 (1990).
75. Douglas, J., Critchlow, C., Benedetti, J., Mertz, G., Connor, J., Hintz, M., Fahnlander, A., Remington, M., Winter, C. and Corey, L., N. Engl. J. Med. 310, 1551–1556 (1984).
76. Dowbenko, D. and Lasky, L., J. Virol. 52, 154–163 (1984).
77. Dowling, P. C., B. M. Blumberg, J. Menonna, J. E. Adamus, P. Cook, J. C. Crowley, D. Kolakofsky, and S. D. Cook, J. Gen. Virol. 67, 1987–1992 (1986).
78. Dreyfuss, G., Adam, S. A., and Choi, Y. D., Mol. Cell. Biol. 4, 415–423 (1984).
79. Drillien, R., F. Koehren and A. Kirn, Virology 111, 488–499 (1981).
80. Drillien, R., D. Spehner, A. Kirn, P. Giraudon, R. Buckland, F. Wild, and J. P. Lecocq, Proc. Natl. Acad. Sci. USA 85, 1252–1256 (1988).
81. Easterday, B. C. and V. S. Hinshaw, In Diseases of Poultry, Ninth edition, eds. B. W. Calnek, H. J. Barnes, et al., (Iowa State University Press, Ames, Iowa) pp. 531–551 (1991).
82. Eble, B. E., V. R. Lingappa and D. Ganem, Mol. Cell. Biol. 6, 1454–1463 (1986).
83. Edbauer, C., R. Weinberg, J. Taylor, A. Rey-Senelonge, J. F. Bouquet, P. Desmettre, and E. Paoletti, Virology 179, 901–904 (1990).
84. Eisel, U., Jarausch, W., Goretzki, K., Henschen, A., Engels, J., Weller, U., Hudel, M., Habermann, E., and Niemann, H. EMBO J. 5, 2495–2502 (1986).
85. Elder, J. H., McGee, J. S., Munson, M., Houghton, R. A., Kloetzer, W., Bittle, J. L., and Grant, C. K., J. Virol. 61, 8–15 (1987).
86. Elder, J. H., and Mullins, J. V., J. Virol. 46, 871–880 (1983).
87. Engelke, D. R., Hoener, P. A., and Collins, F. S., Proc. Natl. Acad. Sci. USA 85, 544–548 (1988).
88. Espion, D., S. de Henau, C. Letellier, C.-D. Wemers, R. Brasseur, J. F. Young, M. Gross, M. Rosenberg, G. Meulemans and A. Burny. Arch. Virol. 95, 79–95 (1987).
89. Esposito, J. J., K. Brechling, G. Baer and B. Moss, Virus Genes 1, 7–21 (1987).
90. Esposito, J. J., J. C. Knight, J. H. Schaddock, F. J. Novembre and G. Baer, Virology 165, 313–316 (1988).
91. Etinger H. M., Altenburger W., Vaccine 1991, 9, 470–472.

92. Fairweather, N. F., and Lyness, V. A. Nucleic Acids Res. 14, 7809–7812 (1986).
93. Falgout, B., Chanock, R. and Lai, C.-J, J. Virology 63, 1852–1860 (1989).
94. Falkner, F. G. and B. Moss, J. Virol. 64, 3108–3111. (1990).
95. Fenner, F., Wittek, R., and Dumbell, K. R., (Academic Press, Inc., San Diego, Calif.) p. 432 (1989).
96. Fenner, F., Virology 5, 502–529 (1958).
97. Flexner, C., Hugen, A., and Moss, B., Nature 330, 259–262 (1987).
98. Franchini, G., Gurgo, C., Guo, H.-G., Gallo, R. C., Collati, E., Fargnoli, K. A., Hall, L. F., Wong-Staal, F., and Reitz, Jr., M. S., Nature (London) 328, 539–543 (1987).
99. Franchini, G., Fargnoli, K. A., Giomnini, F., Jagodzinski, L., DeRossi, A., Bosch, M., Biberfield, G., Fenyo, E. M., Albert, J., Gallo, R. C., and Wong-Staal, F., Proc. Natl. Acad. Sci. USA 86, 2433–2437 (1989).
100. Fujisaki Y., Sugimori T., Morimoto T., Muira Y., Kawakani Y. and Nakano K., Natl. Inst. Anim. Health Q. 15, 55–60 (1975b).
101. Funahashi, S., T. Sato and H. Shida, J. Gen. Virol. 69, 35–47 (1988).
102. Galibert, F., E. Mandart, F, Fitoussi, P. Tiollais and P. Charnay, Nature 281, 646–650 (1979).
103. Garten, W., Kohama, T., and H-D. Klenk. J. Gen. Virol. 51, 207–211 (1980).
104. Ghendon, Y. Z., and Chernos, V. I., Acta Virol. 8, 359–368 (1964).
105. Giavedoni, L., Jones, L., Mebus, C., and Yilma, T. A, Proc. Natl. Acad. Sci. USA 88, 8011–8015 (1991).
106. Gibson, C. A., Schlesinger, J. J., and Barrett, A. D. T., Vaccine 6, 7–9 (1988).
107. Gillard, S., Spehner, D., Drillien, R., and Kirn, A., Proc. Natl. Acad. Sci. USA 83, 5573–5577 (1986).
108. Glosser, J. W., Environmental assessment and preliminary finding of NO significant impact. Veterinary biologics authorized field trial of an experimental biologic: The Wistar Institute of Anatomy and Biology proposed field trial of a live experimental vaccinia vectored rabies vaccine. United States Department of Agriculture, Animal, and Plant Health Inspection Services (1989).
109. Goebel S. J., Johnson G. P., Perkus M. E., Davis S. W., Winslow J. P. and E. Paoletti, Virology 179, 247–266 (1990).
110. Goebel, S. J., G. P. Johnson, M. E. Perkus, S. W. Davis, J. P. Winslow and E. Paoletti, Virology 179, 517–563 (1990b).
111. Goldstein, D. J. and S. K. Weller, Virology 166, 41–51 (1988).
112. Gonczol, E., Furlini, G., Ianacone, J, and Plotkin, S. A., J. Virol. 14, 37–41 (1986).
113. Gonczol, E., C. de Taisne, G. Hirka, K. Berensci, W. Lin, E. Paoletti, and S. Plotkin, Vaccine 9, 631–637 (1991).
114. Gonzolez-Scarano, F., Shope, R. E., Calisher, C. H., and Nathanson, N, Virology, 120, 42–53 (1982).
115. Gould, E. A., Buckley, A., Barrett, A. D. T., and Cammack, N., J. Gen. Virol. 67, 591–595 (1986).
116. Graves, M. C., J. M. Silver, and P. W. Choppin, Virology 86, 254–263 (1978).
117. Gretch, D. R., B. Kari, L. Rasmussen, R. C. Gehrz, and M. F. Stinski, J. Virol. 62, 875–881 (1988).
118. Gubler, U., and Hoffman, B. J., Gene 25, 263–269 (1983).
119. Guilhot, S., Hampe, A., D'Auriol, L., and Galibert, F. Virology 161, 252–258 (1987).
120. Guo, P., Goebel, S., Perkus, M. E., Taylor, J., Norton, E., Allen, G., Languet, B., Desmettre, P., and Paoletti, E., J. Virol. 64, 2399–2406 (1990).
121. Guo, P., Goebel, S., Davis, S., Perkus, M. E., Languet, B., Desmettre, P., Allen, G., and Paoletti, E., J. Virol. 63, 4189–4198 (1989)
122. Guo, H-G., diMarzo Veronese, F., Tschachler, E., Pal, R., Kalyanaraman, V. S., Gallo, R. C., and Reitz, Jr., M. S., Virology 174, 217–224 (1990).
123. R. K., Misra, C. N., Gupta, V. K., and Saxena, S. N., Vaccine 9, 865–867 (1991).
124. Gurgo, C., Guo, H.-G., Franchini, G., Aldovini, A., Collalti, E., Farrell, K., Wong-Staal, F., Gallo, R. C., and Reitz, M. S., Jr., Virology 164, 531 (1988).
125. Haffar, O., Garrigues, J., Travis, B., Moran, P., Zarling, J., and Hu, S.-L. J. Virol. 64, 2653–2659. (1990).
126. Halpern, J. L., Habig, W. H., Neale, E. A., and Stibitz, S. Infect. Immun. 58, 1004–1009 (1990).
127. Hampl, H., Ben-Porat, T., Ehrlicher, L., Habermehl, K.,-O., and Kaplan, A. S., J, Virol. 52, 583–590 (1984).
128. Hardy, Jr., W. D., Hess, P. W., MacEven, E. G., McClelland, A. J., Zuckerman, E. E., Essex, M., Cotter, S.M., and Jarrett, O., Cancer Res. 36 582–588 (1976).
129. Hardy, Jr., W. D., Adv. Viral Oncology 5, 1–34 (1985).
130. Hashimura K., Kaminiyada M., Akazaki M., Yonemaru K., Okuzono Y., Hukomoto M., Miura Y., and Hayashi S., J. Vet. Med. Sci. 34, 314–319 (in Japanese with English summary) (1981).
131. Heermann, K. H., U. Goldmann, W. Schwartz, T. Seyffarth, H. Baumgarten and W. H. Gerlich, J. Virol. 52, 396–402 (1984).
132. Henchal, E. A., Henchal, L. S., and Schlesinger, J. J., J. Gen. Virol. 69, 2101–2107 (1988).
133. Hinshaw, V. S., R. G. Webster, W. J. Bean, G. Sriram, Comp. Immunol. Microbiol. Infect. Dis. 3, 155–164 (1981).
134. Hinshaw, V. S., Naeve, C. W., Webster, R. G., Douglas, A., Dkehel, J. J., and Bryans, J. T., Bull. World Health Organization 61, 153–158 (1983).
135. Hoffar, O., Garrigues, J., Travis, B., Moran, P., (1990).
136. Homma, M., and M. Ohuchi, J. Virol. 12, 1457–1465 (1973).
137. Hoshikawa, N., Kojima, A., Yasuda, A., Takayashiki, E., Masuko, S., Chiba, J., Sata, T., and Kurata, T., J. Gen. Virol. 72, 2509–2517 (1991).
138. Hosmalin, A., Nara, P. L., Zweig, M., Lerche, N. W., Cease, K. B., Gard, E. A., Markham, P. D., Putney, S. D., Daniel, M. D., Desrosiers, R. C., and Berzofsky, J. A. J. Immunol. 146, 1667–1673 (1991).
139. Hruby, D. E., R. A. Maki, D. B. Miller and L. A. Ball, Proc. Natl. Acad. Sci. USA 80, 3411–3415 (1983).
140. Hruby, D. E. and L. A. Ball, J. Virol. 43, 403–409 (1982).
141. Hu, S.-L., Kosowski, S. and Dalrymple, J., Nature 320, 535–537, (1986).
142. Hu, S.-L. Travis, B. M., Garrigues, J., Zarling, J. M., Sridhar, P., Dykers, T., Eichberg, J. W., and Alpers, C. Virology 179, 321–329 (1990).
143. Hu, S. -L., Fultz, P., McClure, H., Eichberg, J., Thomas, E., Zarling, J., Singhal, M., Kosowski, S., Swenson, R., Anderson, D. and Todaro, G., Nature 328, 721–723 (1987).
144. Hu S. L., Kosowski S. G., Dallyrmple J. M., Nature 320, 537–540 (1986).
145. Hu, S.-L., Travis, B. M., Garrigues, J., Zarling, J. M., Eichberg, J. W. and Alpers, C. E., In Vaccine 90, eds. Chanock, R. M., Lerner, R. A., Brown, F., and Ginsberg, H., (Cold Spring Harbor Press, Cold Spring Harbor, N.Y.) pp. 231–236 (1990).

146. Huang, C. H., Advances in Virus Research 27, 71–101 (1982)
147. Hunt, L. A., D. W., Brown, H. L. Robinson, C. W. Naeve, and R. G. Webster, J. Virol. 62, 3014–3019 (1988).
148. Ichihashi, Y. and Dales, S., Virology 46, 533–543 (1971).
149. Igarashi A., J. Gen. Virol. 40, 531–544 (1978).
150. Inoue Y. K., Bull. WHO 30, 181–185 (1964).
151. Itamura, S., H. Iinuma, H. Shida, Y. Morikawa, K. Nerome and A. Oya, J. Gen. Virol. 71, 2859–2865 (1990).
152. Ito H., Maruyama N., Maruyama S., Yamashita T., Tserumizu T., Ogonuki M., Matsui S., Fuse Y., Araki H., Nishi Y., Yamashita M., Takabata S., Sakurai Y., and Otake S., J. Vet. Med. Sci., 27, 331–334 (in Japanese with English summary) (1974).
153. Itoh, Y., E. Takai, H. Ohnuma, K. Kitajima, F. Tsuda, A. Machida, S. Mishiro, T. Nakamura, Y. Miyakawa and M. Mayumi, Proc. Natl. Acad. Sci. USA 83, 9174–9178 (1986).
154. Jacobson, J. G., D. A. Leib, D. J. Goldstein, C. L. Bogard, P. A. Schaffer, S. K. Weller and D. M. Coen, Virology 173, 276–283 (1989).
155. Jahn, G., B-C. Scholl, B. Troupe, and B. Fleckenstein. J. Gen Virol. 68, 1327–1337 (1987).
156. Jamieson, A. T., G. A. Gentry and J. H. Subak-Sharpe, J. Gen. Virol. 24, 465–480 (1974).
157. Jarrett, O., and Russell, P. H., Int. J. Cancer 27, 466–472 (1978).
158. Jarrett, O., Hardy, Jr., W. D., Golder, M. C., and Hay, D., Int. J. Cancer 21, 334–337 (1978).
159. Jarrett, O., Laird, H. M., and Hay, D., J. Gen. Virol. 20, 169–175 (1973).
160. Javeherian, K., Langlois, A. J., McDanal. C., Ross;, K. L., Eckler, L. I., Jellib, C. L., Profy, A. T., Rusche, J. R., Bolognesi, D. P., Putney, S. D., and Mathews, T. J., Proc. Natl. Acad. Sci. USA 86, 6768–6772 (1989).
161. Jilg, W., C. Delhoune, F. Deinhardt, A. J. Roumeliotou-Karayannis, G. J. Papaevangelou, I. K. Mushahwar and L. R. Overby, J. Med. Virol. 13, 171–178 (1984).
162. Jin, H. and Elliot, R. M., J. Virology 65, 4182–4189 (1991).
163. Joklik, W. K., Pickup, D. J., Patel, D. D., and Moody, M. D., Vaccine 6, 123–128 (1988).
164. Karacostas, V., Nagashima, K., Gonda, M. A., and Moss, B., Proc. Natl. Adad. Sci, USA 86, 8964–8968 (1989).
165. Kari, B., N. Lussenhop, R. Goertz, M. Wabuke-Bunoti, R. Radeke, and R. Gehrz, J. Virol. 60, 345–352 (1986).
166. Kato, S., M. Takahashi, S. Kameyama and J. Kamahora, Biken's 2, 353–363 (1959).
167. Kaufman, B. M., Summers, P. L., Dubois, D. R., and Eckels, K. H., Am. J Trop. Med. Hyg. 36, 427–434 (1987).
168. Kaufman, B. M., Summers, P. L., Dubois, D. R., Cohen, W. H., Gentry, M. I., Timchak, R. L., Burke, D. S. and Eckels, K. H., Am. J. Trop. Med. Hyg. 41, 576–580 (1989).
169. Kawaoka, Y., Bean, W. J., Webster, R. G., Virology 169, 83–292 (1989).
170. Keegan, K. and Collett, M. S., J. Virology 58, 263–270 (1986).
171. Kensil, C. R., Barrett, M. S., Kushner, B. S., Beltz, G., Storey, J., patel, U., Recchia, J., Aubert, A., and Marciaini, D., JAVMA 199, 1402–1405 (1991).
172. Kieff, E., and Liebowitz, D., In Virology, Second Edition, eds. B. N. Fields, D. M. Knipe et al., (Raven Press) (1990).
173. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
174. Killington, R. A., J. Yeo, R. W. Honess, D. H. Watson, B. E. Duncan, I. W. Halliburton, and J. Mumford, J. gen. Virol. 37, 297–310 (1977).
175. Kimura-Kuroda, J., and Yasui, K., Immunol. 141, 3606–3610 (1988).
176. Kingsbury, D. W., In Virology, Second Edition, eds. B. N Fields, D. M. Knipe et al., (Raven press, Ltd. New York) pp. 1075–1089 (1990).
177. Kingsbury, D. W., M. A. Bratt, P. W. Choppin, R. P. Hanson, T. Hosaka, Y. ter Meulen, E. Norrby, W. Plowright, R. Rott and W. H. Wunner, Intervirology 10, 137–152 (1978).
178. Kingsford, L., Ishizawa, L. D., and Hill, D. W., Virology 129, 443–455 (1983).
179. Klasse, P. J., Pipkorn, R., and Blomberg, J., Proc. Natl. Acad. Sci. USA 85, 5225–5229 (1988).
180. Kleitmann W., Schottle A., Kleitmann B., et al., In Cell Culture Rabies Vaccines and Their protective Effect in Man. ed. Kuwert/Wiktor/Koprowski, (International Green Cross-Geneva) pp. 330–337 (1981).
181. Knauf, V. C., and Nester, E. W., Plasmid 8, 45–54 (1982).
182. Kodama K., Sasaki N., and Kanda Inoue Y., J. Immunol. 100, 194–200 (1967).
183. Kodama, T., Wooley, D. P., Naidu, Y. M., Kestler III, H. W., Daniel, M. D., Li, Y. and Derosiers, R. C. J. Virol. 63, 4709–4714 (1989).
184. Koff, W. C. and Fauci, A. S., AIDS 1, 5125–5129 (1989).
185. Konishi, E., Pincus, S., Fonseca, B. A. L., Shope, R. E., Paoletti, E., and Mason, P. W., Virology 185, 401–410 (1991).
186. Konno J., Endo K., Agatsuma H., and Ishida N. Cyclic, Am. J. Epidemiol. 84, 292–300 (1966).
187. Kost, T. A., E. V. Jones, K. M. Smith, A. P Reed, A. L. Brown, and T. J. Miller, Virology 171, 365–376 (1989).
188. Kotwal, G. J. and Moss, B., Nature (Lond.) 335, 176–178 (1988).
189. Kotwal, G. J. and B. Moss, J. Virol. 63, 600–606 (1989b).
190. Kotwal, G J and B Moss, Virology 167, 524–537 (1988b).
191. Kotwal, G. J., S. N. Isaacs, R. McKenzie, M. M. Frank and B. Moss, Science 250, 827–830 (1990).
192. Kotwal, G. J., A. W. Hugin and B. Moss, Virology 171, 579–587 (1989a).
193. Koup, R. A., Sullivan, J. L., Levine, P. H., Brettler, D., Mahr, A., Mazzara, G., McKenzie, S., and Panicali, D. Blood 73, 1909–1919 (1989).
194. Kunkel, T. A., Proc. Natl. Acad. Sci. USA 82, 488–492 (1985).
195. Kunkel, T. A., Roberts, J. D., and Zakour, R. A., Method in Enzym. 154, 367–382 (1987).
196. Kurata K., J. Vet. Med. Sci. 33, 85–87 (in Japanese)(1980).
197. Kuroda, K., C. Hauser, R. Rott, H.-D. Klenk, and W. Doerfler, EMBO 5, 1359–1365 (1986).
198. Kuroki, K., R. Russnak and D. Ganem, Mol. Cell. Biol. 9, 4459–4466 (1989).
199. Kuwert E. K., Barsenbach C., Werner J., et al., In Cell Culture Rabies Vaccines and Their Protection Effect in Man, eds. Kuwert/Wiktor/Koprowski (International Green Cross—Geneva) pp. 160–167 (1981).
200. Laemmli, U. K., Nature (London) 227, 680–685 (1970).

201. Lai, A. C.-K. and B. G.-T. Pogo, Virus Res. 12, 239–250 (1989).
202. Lane, J. M., Ruben, F. L., Neff, J. M., and Millar, J. D., New Eng. J. Med. 281, 1201–1208 (1969).
203. Lathe, R., M. P. Kieny, D. Schmitt, P. Curtis and J. P. Lecocq, J. Mol. Appl. Gen. 2, 331–342 (1984).
204. Le, L., R. Brasseur, C. Werners, G. Meulemans, and A. Burny, Virus Genes 1, 333–350 (1988).
205. Lecocq, J. P., M. P. Kieny, Y. Lemoine, R. Drillien, T. Wiktor, H. Koprowski and R. Lathe, In World's Debt to Pasteur, eds. Koprowski, H. and Plotkin, S. A., (Alan R. Liss, New York), 259–271 (1985).
206. Lecocq, J. P., M. Zukowski and R. Lathe, In Methods in Virology, eds. Maramorosch, K. and Koprowski, H., (Academic Press, New York) Vol. VII, 124–172 (1984).
207. Leprevotte, I., Hampe, A., SHerr, C., and Galivert, F., J. Virol. 50, 884–894 (1984).
208. Liu, Y-N. C., A. Klaus, B. Kari, M. F. Stinski, J. Exhkardt, and R. C. Gehrz, J. Virol. 65, 1644–1648 (1991).
209. Lukacs, N., Theil, H.,-J., Mettenleiter, T. C., and Rziha, H.,-J., J. Virol. 53, 166-172 (1985).
210. Lutz, H., Pedersen, N. C., and Higgens, J., Cancer Res. 40, 3642–3651 (1980).
211. Macfarlan, R. I., B. Dietzschold, and H. Koprowski, J. Mol Immunol. 23, 733–741 (1986).
212. Mackett M., Smith G. L., Moss B., Proc. Natl. Acad. Sci. 79, 7415–7419 (1982).
213. Makoff, A. J., Ballantine, S. P., Smallwood, A. E., and Fairweather, N. F. *Bio/Technology* 7, 1043–1046 (1989).
214. Mandecki, W., Proc. Natl. Acad. Sci. USA 83, 7177–7181 (1986).
215. Maniatis, T., Fritsch, E. F., and Sambrook, J. In Molecular cloning: a laboratory manual, (Cold Spring Harbor Laboratory, Cold Spring Harbor, NY) (1982).
216. Marsden, H., Buckmaster, A., Palfreyman, J., Hope, R. and Minson, A., J. Virol. 50, 547–554 (1984).
217. Marsden, H., Stow, N., Preston, V., Timbury, M. and Wilkie, N., J. Virol. 28, 624–642 (1978).
218. Marshall, G. S., G. P. Rabalais, G. G. Stuart, and S. L. Waldeyer, J. Infect. Dis. 165, 381–384 (1992).
219. Mason P. W., Virology 169, 354–364 (1989).
220. Mason P. W., Dalrymple J. M., Gentry M. K., McCown J. M., Hoke C. H., Burke D. S., Fournier M. J. and Mason T. L., J. Gen. Virol. 70, 2037–2049 (1989).
221. Mason, P. W., Pincus, S., Fournier, M. J., Mason, T. L., Shope, R. E., and Paoletti, E., Virol. 180, 294–305 (1991).
222. Mason, P. W., McAda, P. C., Dalrymple, J. M., Fournier, M. J., and Mason, T. L., Virology 158, 361–372 (1987a).
223. Mason, P. W., McAda, P. W., Mason, T. L., and Fournier, M. J., Virol. 161, 262–267 (1987b).
224. Mathes, L. E., Olsen, R. D., Hebebrand, L. C., Hoover, E. A., and Schaller, J. P., Nature 274, 687–691 (1978).
225. Matthews, R. E. F., Intervirology 17, 104–105 (1982a).
226. Matthews, R. E. F., Intervirology 17, 42–44 (1982b).
227. Mazzara, G. P, Destree, A. T., Williams, H. W., Sue. J. M., Belanger, L. M. and Panicali, D., Vaccines 87, 419–424 (1987).
228. McAda, P. C., Mason, P. W., Schmaljohn, C. S., Dalrymple, J. M., Mason, T. L. and Fournier, M. J. Virology 158, 348–360 (1987).
229. McGinnes, L. W., and T. G. Morrison, Virus Research 5, 343–356 (1986).
230. McLachlan, A., D. R. Milich, A. K. Raney, M. G. Riggs, J. L. Hughes, J. Sorge and F. V. Chisari, J. Virol. 61, 683–692 (1987).
231. McLaughlin-Taylor, E., Willey, D., Cantin, E., Eberle, R., Moss, B. and Openshaw H., J. Gen. Virol. 69, 1731–1734 (1988).
232. McGeoch, D., Moss, H., McNab, D. and Frame, M., J. Gen. Virol. 68, 19–38 (1987).
233. Meignier, B., Jourdier, T., Norrild, B., Pereira, L. and Roizman, B., J. Infect. Dis. 155, 921–930 (1987).
234. Merz, D. C., A. Scheid, and P. Choppin, J. Exper. Med. 151, 275–288 (1980).
235. Messing, J., Vol 101, eds. R. Wu, L. Grossman, and K. Moldave, (Academic Press, New York) pp. 20–78 (1983).
236. Mettenleiter, T. C., N. Lukacs, H.-J. Thiel, C. Schreurs, and H.-J. Rziha, Virology 152, 66–75 (1986).
237. Mettenleiter, T. C., N. Lukacs, and H.-J. Rziha, J. Virol. 53, 52–57 (1985).
238. Meulemans, G., C. Letellier, M. Gonze, M. C. Carlief, and A. Burny, Avian Pathol. 17, 821–827 (1988).
239. Michel, F., Hoffenbach, A., Langlade-Demoyen, P., Guy, B., Lecocq, J.-P., Wain-Hobson, S., Kieny, M.-P. and Plata, F., Eur. J. Immunology 18, 1917 (1988).
240. Milich, D. R. and A. McLachlan, In Viral Hepatitis and Liver Disease, pp. 645–649 (1988).
241. Milich, D. R., A. McLachlan, A. Moriarty and G. B. Thornton, J. Immun. 138, 4457–4465 (1987a).
242. Milich, D. R., A. McLachlan, G. B. Thornton and J. L. Hughes, Nature 329, 547–549 (1987b).
243. Milich, D. R., G. B. Thornton, A. R. Neurath, S. B. Kent, M-L. Michel, P. Tiollais and F. V. Chisari, Science 228, 1195–1199 (1985).
244. Milich, D. R., A. McLachlan, F. V. Chisari, S. B. H. Kent and G. B. Thornton, J. Immun. 137, 315–322 (1986).
245. Miller, G., In Virology, Second Edition, eds. B. N. Fields, D. M. Knipe et al., (Raven Press) (1990).
246. Monath, T. P., In The Togaviridae and Flaviviridae, eds. S. Schlesinger and M. J. Schlesinger, (Plenum Press, New York/London) pp. 375–440 (1986).
247. Morgan, A. J., M. Mackett, S. Finerty, J. R. Arrand, F. T. Scullion and M. A. Epstein, J. Med. Virol. 25, 189–195 (1988).
248. Morgan, J. R. and B. E. Roberts, J. Virol. 51, 283–297 (1984).
249. Moss B., Smith G. L., Gerin, J. L. et al., Nature 67–69 (1984).
250. Moss, B., E. Winters and J. A. Cooper, J. Virol. 40, 387–395 (1981).
251. Mullins, J. I., and Hoover, E. A., In: Retrovirus Biology and Human Disease, (eds. Gallo, R. C., Wong-Staal, F.) Marcel Dekker, Inc., New York, pp. 87–116 (1990).
252. Murphy, B. R., and R. G. Webster, In: Virology, eds. Fields, B. N, Knope, D. M. et al., Raven Press, NY, 1091–1151 (1990).
253. Murphy-Corb, M., Martin, L. N., Davison-Fairburn, B., Montelaro, R. C., Miller, M., West, M., Ohkawa, S., Baskin, G. B., Zhang, J.-Y., Putney, S. D., Allison, A. C. and Eppstein, D. A., Science 246, 1293–1297 (1989).
254. Murray, K., S. A. Bruce, A. Hinnen, P. Wingfield, P. M. C. A. van Erd, A. de Reus and H. Schellekens, EMBO 3, 645–650 (1984).
255. Nagai, Y., H. D. Klenk, and R. Rott, Virology 72, 494–508 (1976).
256. Nagai, Y., T. Yoshida, M. Hamaguchi, H. Naruse, M. Iinuma, K. Maeno, and T. Matsumoto, Microbiol. Immunol. 24, 173–177 (1980).
257. Neurath, A. R., S. B. H. Kent and N. Strick, Science 392–395 (1984).
258. Neurath, A. R, S. B. H. Kent, N. Strick and K. Parker, Cell 46, 429–436 (1986).

259. Neurath, A. R., B. A. Jameson and T. Huima, Microbiological Sciences 4, 45–51 (1987).
260. Neurath, A. R. and S. B. H. Kent, Adv. Vir. Res. 34, 65–142 (1988).
261. Neurath, A. R., N. Strick and M. Girard, Mol. Immun. 26, 53–62 (1989).
262. Nixon, D. F., Townsend, A. R. M., Elvin, J. G., Rizza, C. R., Gallwey, J. and McMichael, A. J., Nature 326, 484–487 (1988).
263. Norrby, E., and Y. Gollmar, Infect. and Immun. 11, 231–239 (1975).
264. Norrby, E., and M. N. Oxman, u Fields Virology, 2nd Edition, eds. B. N. Fields and D. M. Knipe, (Raven Press, NY) pp. 1013–1044 (1990).
265. Norrby, E., S. N. Chen, T. Togashi, H. Shesberadaran, and K. P. Johnson, Archives of Virology 71, 1–11 (1982).
266. Nunberg, J. H., Williams, M. E., and Innis, M. A., J. Virol., 49, 629–632 (1984b).
267. Nunberg, J. H., Rodgers, J., GIlbert, J., and Snead, R. M., Proc. Natl. Acad. Sci. USA 81, 3675–3679 (1984a).
268. Oakes, J., Davis, W., Taylor, J. and Weppner, W., Infect. Immun. 29, 642–649 (1980).
269. Oakes, J. and Rosemond-Hornbeak, H., Infect. Immun. 21, 489–495 (1978).
270. Ogasa A., Yokoki Y., Fujisaki U., and Habu A., Jpn. J. Anim. Reprod. 23, 171–175 (1977).
271. Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).
272. Oie, M., Shida, H., and Ichihashi, Y., Virology 176, 494–504 (1990).
273. Ono, Y., H. Onda, R. Sasada, K. Igarashi, Y. Sugino and K. Nishioka, Nuc. Acids Res. 11, 1747–1757 (1983).
274. Osterhaus, A., Weijer, K., and UytdeHaag, F., Vaccine 7, 137–140 (1989)
275. Ou, J-H. and W. J. Rutter, J. Virol. 61, 782–786 (1987).
276. Oya A., Jpn. J. Med. Sci. Biol., Suppl. 20, 26–30 (1967).
277. Pachl, C., W. S. Probert, K. M. Hermsen, F. R. Masiarz, L. Rasmussen, T. C. Merigan, and R. R. Spaete, Virology 169, 418–426 (1989).
278. Paez, E., S. Dallo and M. Esteban, Proc. Natl. Acad. Sci. USA 82, 3365–3369 (1985).
279. Palumbo, G. J., D. J. Pickup, T. N. Fredrickson, L. J. Mcintyre and R. M. L. Buller, Virology 172, 262–273 (1989).
280. Palumbo, G. J., Pickup, D. J., Fredrickson, T. N., Mcintyre, L. J., and Buller, R. M. L., Virology 172, 262–273 (1989).
281. Pande, H., K. Campo, B. tanamuchi, and J. A. Zaia, Virology 182, 220–228 (1991).
282. Panicali, D. and E. Paoletti, Proc. Natl. Acad. Sci. USA 79, 4927–4931 (1982).
283. Panicali, D., Grezlecki, A., and Huang, C., gene 47, 193–199 (1986).
284. Panicali, D., Davis, S. W., Mercer, S. R., and Paoletti, E., J. Virol. 37, 1000–1010 (1981).
285. Paoletti, E., B. Lipinskas, C. Samsonoff, S. Mercer and D. Panicali, Proc. Natl. Acad. Sci. USA 81, 193–197 (1984).
286. Parker, R. F., Bronson, L. H., and Green, R. H., J. Exp. Med. 74, 263–281 (1941).
287. Parrish, C. R., Aquadro, C. F., and Carmichael, L. E., Virology 166, 293–307 (1988).
288. Parrish, C. R., Aquadro, C. F., Strassheim, M. L., Evermann, J. F., Sgro, J-Y., and Mohammed, H. O., J. Virology 65, 6544–6552.
289. Parrish, C. R., Adv. Virus Res. 38, 403–450 (1990).
290. Patel, D. D., Ray, C. A., Drucker, R. P., and Pickup, D. J., Proc. Natl. Acad. Sci. USA 85, 9431–9435 (1988).
291. Patel, D. D. and Pickup, D. J., EMBO 6, 3787–3794 (1987).
292. Pedersen, N. C., and Johnson, L. JAVMA 199, 1453–1455 (1991).
293. Pedersen, N. C., Johnson, L., and Oh, R. L., Feline Pract. 15, 7–20 (1985).
294. Perkus M. E., Piccini A., Lipinskas B. R., et al., Science 229, 981–984 (1985).
295. Perkus, M. E., Limbach, K., and Paoletti, E., J. Virol. 63, 3829–3836 (1989).
296. Perkus, M. E., D. Panicali, S. Mercer and E. Paoletti, Virology 152, 285–297 (1986).
297. Perkus, M. E., S. J. Goebel, S. W. Davis, G. P. Johnson, E. K. Norton and E. Paoletti, Virology 180, 406–410 (1991).
298. Perkus, M. E., Goebel, S. J., Davis, S. W., Johnson, G. P., Limbach, K., Norton, E. K., and Paoletti, E., Virology 179, 276–286 (1990).
299. Petrovskis, E. A., Timmins, J. G., Armentrout, M. A., Marchioli, C. C., Yancey, Jr., R. J., Post, L. E., J. Virol. 59, 216–223 (1986b).
300. Petrovskis, E. A., J. G. Timmins, and L. E. Post, J. Virol. 60, 185–193 (1986a).
301. Piccini, A., M. E. Perkus, and E. Paoletti, Methods in Enzymology 153, 545–563 (1987).
302. Pickup, D. J., B. S. Ink, B. L. Parsons, W. Hu and W. K. Joklik, Proc. Natl. Acad. Sci. USA 83, 6817–6821 (1984).
303. Pickup, D. J., B. S. Ink, W. Hu, C. A. Ray and W. K. Joklik, Proc. Natl. Acad. Sci. USA 83, 7698–7702 (1986).
304. Plata, F., Autran, B., Martins, L. P., Wain-Hobson, S., Raphael, M., Mayaud, C., Denis, M., Guillon, J.-M., Debre, P., Nature 328, 348–351 (1987).
305. Plotkin, S. A., S. E. Starr, H. M. Friedman, E. Gonczol, and R. E. Weibel, J. Inf. Dis. 159, 860–865 (1989b),
306. Plotkin, S. A., H. M. Friedman, S. E. Starr, and E. Gonczol, In Contemporary Issues in Infectious Diseases, Vol. 8, eds. Root et al. (Churchill Livingstone, New York) pp. 65–92 (1989a).
307. Pontisso, P, M-A. Petit, M. J. Bankowski and M. E. Peeples, J. Virol. 63, 1981–1988 (1989).
308. Portetelle, D., Limbach, K., Burny, A., Mammerickx,. M., Desmetttre, P., Riviere, M., Zavada, J. and Paoletti, E. Vaccine 9, 194–200 (1991).
309. Powell, K. and Watson, D. J., Gen. Virol. 29, 167–178 (1975).
310. Pratt, D. and S. Subramani, Nuc. Acids Res. 11, 8817–8823 (1983).
311. Prevec, L., J. B. Campbell, B. S. Christie, L. Belbek, and F. L. Graham, J. Infect. Dis. 161, 27–30 (1990).
312. Pujisaki Y., Sugimori T., Morimoto T., and Miura U., Natl. Inst. Anim. Health Q. 15, 15–23 (1975a).
313. Rasmussen, L., M. Nelson, M. Neff, and T. C. Merigan, Jr., Virology 163, 308–318 (1988).
314. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, S. R. Jr., Pearson, M. L., Lautenberger, J. A., Papas, T. S., Ghrayeb, J., Chang, N. T., Gallo, R. C., and Wong-Staal, F., Nature 313, 277 (1985).
315. Rautmann, G., Kieny, M. P., Brandely, R., Dott, K., Girard, M., Montagnier, L., and Lecocq, J.-P., AIDS Research and Human Retroviruses 5, 147–157 (1989).
316. Rea, T. J., J. G. Timmins, G. W. Long, and L. E. Post, J. Virol. 54, 21–29 (1985).

317. Reed, L. J. and Muench, H., Am. J. Hyg. 27, 493–497 (1938).
318. Research Committee for Prevention of Stillbirth in Sows due to Japanese Encephalitis Prevention of stillbirth in sows by inoculation with killed Japanese encephalitis vaccine, Bull. Natl. Inst. Anim. Health 57, 1–8 (in Japanese with English summary).(1968).
319. Rice, C. M., Strauss, E. G., and Strauss, J. H., In The Togaviridae and Flaviviridae, eds. S. Schlesinger and M. J. Schlesinger, (Plenum Press, New York/London) pp. 279–326 (1986).
320. Rice, C. M., Lenches, E. M., Eddy, S. R., Shin, S. J., Sheets, R. L., and Strauss, J. H., Science 229, 726–733 (1985).
321. Richardson, C., D. Hull, P. Greer, K. Hasel, A. Berkovich, G. Englund, W. Bellini, B. Rima, and R. Lazzarini, Virology 155, 508–523 (1986).
322. Richardson, C. D., A. Berkovich, S. Rozenblatt, and W. Bellini, J. Virol. 54, 186–193 (1985).
323. Rickinson, A. B., Rowe, M., Hart, I. J., Yao, Q. Y., Henderson, L. E., Rabin, H., and Epstein, M. A., Cell. Immunol. 87, 646–658 (1984).
324. Riviere Y., Tanneau-Salvadori, F., Regnault, A., Lopez, O., Sansonetti, P., Guy, B., Kieny, M.-P., Fournel, J. J. and Montagnier, L., J. Virol. 63, 2270–2277 (1989).
325. Robbins, A. K., Dorney, D. J., Wathen, M. W., Whealy, M. E., Gold, C., Watson, R. J., Holland, L. E., Weed, S. D., Levine, M., Gloricso, J. C., and Enquist, L. W., J. Virol. 63, 2691–2701 (1987).
326. Robbins, A. K., Watson, R. J., Whealy, M. A., Harp, W W., and Enquist, L. W., J. Virol. 60, 436–449 (1986b).
327. Robbins, A. K., J. H. Weis, L. W. Enquist, and R. J. Watson, J. Mol. Appl. Genet. 2, 485–496 (1984).
328. Robbins, A. K., R. J. Watson, M. E. Whealy, W. W. Hays, and L. W. Enquist, J. Virol. 58, 339–347 (1986a).
329. Roizman, B. and Sears, A., In Virology, eds. Fields, B. and Knipe, D., (Raven press, Ltd.) pp. 1795–1841 (1990).
330. Rojko, J. L., and Olsen, R. G. (1984) Vet. Imm. Immunopath. 6, 107–165 (1984).
331. Rojko, J. L., Hoover, E. A., Quackenbush, S. L., and Olsen, R. G., Nature 298, 385–388 (1982).
332. Romanos, M. A., Makoff, A. J., Fairweather, N. F., Beesley, K. M., Slater, D. E., Rayment, F. B., Payne, M. M., and Clare, J. J. *Nucleic Acids Res.* 19, 1461–1467 (1991).
333. Rooney F. F., Wohlenberg C., Cramer E. J. et al., J. Virol. 62, 1530–1534 (1988).
334. Rosenthal K., Smiley, S., South, S. and Johnson, D., J. Virol. 61, 2438–2447 (1987).
335. Rubenstein, A. S. and A. S. Kaplan, Virology 66, 385–392 (1975).
336. Ruegg, C. L., Monell, C. R., and Strand, M., J. Virol. 63, 3250–3256 (1989a).
337. Russell, P. H., and Jarrett, O., Int. J. Cancer 21, 768–778 (1978).
338. Russell, M., S. Kidd, and M. R. Kelley, Gene 45, 333–338 (1986).
339. Saiki, R. K., Gelfand, D. H., Stoffel, S. Scharf, S. J., Higuihi, R., Horn, G. T., Mullis, K. B., Erlich, Science 239,487–491 (1988).
340. Saliki, J. T., Mizak, B., Flore, H. P., Gettig, R. R.,. Burand, J. P., Carmichael, L. E., Wood, H. A., and Parrish, C. R., J. Gen. Virol. (accepted) (1992).
341. Sambrook, J., Fritsch, E. F., and Maniatis, T., In Molecular Cloning: A Laboratory Manual, 2nd Edition, (Cold Spring Harbor Laboratory, Cold Spring Harbor, N.Y.).
342. Sanchez-Pescador, R., Power, M. D., Bart, P. J., Steimer, K. S., Stempien, M. M., Brown-Shimer, S. L., Gee, W., Renard, A., Randolph, A., Levy, J. A., Dina, D., and Luciw, P. A., Science 227, 484–492 (1985).
343. Sanger, F., Nickeln, S. Coulson, A. R., Proc. Natl. Acad. Sci. 74, 5463–5467 (1977).
344. Sarma, P. S., and Log, T., Virology 54:160–169 (1973).
345. Sazawa H., Sugimori T., Morimoto T., Miura Y. and Watanabe M., Natl. Inst. Anim. Health Q. 9, 74–82 (1969).
346. Scheid, A., L. A. Caliguiri, R. W. Compans, and P. W. Choppin, Virology 50, 640–652 (1972).
347. Scheid, A., and P. W. Choppin, Virology 57,475–490 (1974).
348. Scherer W. F. , Moyer J. T., Izumi T., Gresser I., and McCown J., Am. J. Trop. Med. Hyg. 8, 698–706 (1959]).
349. Schlesinger, J. J., Brandriss, M. W., and Walsh, E. E., J. Immunol. 135, 2805–2809 (1985).
350. Schlesinger, J. J., Brandriss, M. W., Cropp, C. B., and Monath, T. P., J. Virol. 60, 1153–1155 (1986).
351. Schlicht, H-J. and H. Schaller, J. Virol. 63, 5399–5404 (1989).
352. Schmaljohn, C. S., Jennings, G. B., Hay, J., Dalrymple, J. M., Virology 155, 633–643 (1986).
353. Schmaljohn, C. S., and Dalrymple, J. M., Virology 131, 482–491 (1983).
354. Schmaljohn, C. S., Schmaljohn, A. L., and Dalrymple, J. M., Virology 157, 31–39 (1987).
355. Schmaljohn, C. S., Sugiyama, K., Schmaljohn, A. L., and Bishop, D. H. L., J. Gen. Virology 69, 777–786 (1988).
356. Schmaljohn, C. S., Chu, Y. K., Schmaljohn, A. L., and Dalrymple, J. M., J. Virology 64, 3162–3170 (1990).
357. Schmidt, D. M., Sidhu, N. K., Cianciolo, G. J., and Snyderman, R. (1987) Proc. Natl. Acad. Sci. USA 84, 7290–7294.
358. Schmitt, J. F. C. and H. G. Stunnenberg, J. Virol. 62, 1889–1897 (1988).
359. Sebring, R. W., Chu, H.-J., Chavez, L. G., Sandblom, D. S., Hustead, D. R., Dale, B., Wolf, D., Acree, W. M. (1991) JAVMA 199, 1413–1418.
360. Seligmann, E. B., In Laboratory Techniques in Rabies, eds. M. M. Kaplan and H. Koprowski, (World Health Organization, Geneva) pp. 279–285 (1973).
361. Shafferman, A., Lennox, J., Grosfeld, H., Sadoff, J., Redfield, R. R., and Burke, D. S., AIDS Research and Human Retroviruses 5, 33–39 (1989).
362. Shapira, S. K., Chou, J., Richaud, F. V. and Casadaban, M. J., Gene 25, 71–82 (1983).
363. Shibley, G. P., Tanner, J. E., and Hanna, S. A., JAVMAk 199, 1402–1405 (1991).
364. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
365. Shida, H., Virology 150, 451–462 (1986).
366. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
367. Shimizu T. and Kawakami Y., Bull. Natl. Inst. Anim. Health, 23, 117–127 (1949).
368. Shioda, T. and H. Shibuta, Virology 175, 139–148 (1990).
369. Shope, R. E., In The Togaviruses, ed. R. W. Schlesinger, (Academic Press, New York) pp. 47–82 (1980).

370. Slabaugh, M. B. and N. A. Roseman, Proc. Natl. Acad. Sci. USA 86, 4152–4155 (1989).
371. Slabaugh, M., N. Roseman, R. Davis and C. Mathews, J. Virol. 62, 519–527 (1988).
372. Smith J. S. and Yager P. A. A rapid tissue culture test for determining rabies neutralization antibody. In: Laboratory Techniques on Rabies. Eds. M. M. Kaplan and H. Koprowski.
373. Smith, G. L., M. Mackett and B. Moss, Nature 302, 490–495 (1983).
374. Smith, G. L. and Y. Sang Chan, J. Gen. Virol. 72, 511–518 (1991).
375. Smith, J. S., P. A. Yager and G. M. Baer, In Laboratory Techniques in Rabies, eds. M. M. Kaplan and H. Koprowski (WHO Geneva) pp. 354–357 (1973).
376. Sovinova, D., Tumova, B., Pouska, F., and Nemec, J., (1958).
377. Spear, P., In Herpesviruses, Vol. 3, ed. Roizman, B. (Plenum, NY) pp. 315–356 (1984).
378. Spehner, D., R. Drillien, and J. P. Lecocq, J. Virol. 64, 527–533 (1990).
379. Spehner, D., Gillard, S., Drillien, R., and Kirn, A., J. Virol. 62, 1297–1304 (1988).
380. Stahl, S. J. and K. Murray, Proc. Natl. Acad. Sci. USA 86, 6283–6287 (1989).
381. Stanberry, L. R., S. Kit and M. G. Myers, J. Virol. 25 322–328 (1985).
382. Starcich et al., Cell 45, 637–648 (1986).
383. Stevely, W. S., J. Virol. 22, 232–234 (1977).
384. Stewart, M. A., Warnock, M., Wheeler, A., Wiklie, N., Mullins, J. I., Onions, D. E., and Neil, J. C. J. Virol. 58, 825–834 (1986).
385. Stuve, L., Brown-Shimer, S., Pachl, C., Najarian, R., Dina, D. and Burke, R., J. Virol. 61, 326–335 (1987).
386. Tabor, S. and C. C. Richardson, Proc. Natl. Acad. Sci. USA 84, 4767–4771 (1987).
387. Takahashi M., JK. Med. Entomol. 13, 275–284 (1976).
388. Takehara K., Mitsui T., Nakamura H., Fukusho K., Kuramasu S., and Nakamura L., Nibs Bul. Biol. Res. 23–37 (1969).
389. Tartaglia, J., Pincus, S., and Paoletti, E., Crit. Rev. Immunol. 10, 13–30 (1990).
390. Tartaglia, J., M. E. Perkus, J. Taylor, E. K. Norton, J. C. Audonnet, W. I. Cox, S. W. Davis, J. VanderHoeven, B. Meignier, M. Riviere, B. Languet, and E. Paoletti, Virology bee (1992).
391. Tartaglia, J. and Paoletti, E., In Immunochemistry of viruses, II, eds. van Regenmortel, M. H. V. and Neurath, A. R., (Elsevier Science Publishers B. V., Amsterdam) pp. 125 (1990b).
392. Taylor, J., Weinberg, R., Tartaglia, J., Richardson, C., Alkhatib, G., Briedis, D., Appel, M., Norton, E., and Poaletti, E., Virology 187, 321–328 (1992).
393. Taylor, J., Weinberg, R., Kawaoka, Y., Webster, R. G., and Paoletti, E., Vaccine 6, 504–508 (1988a).
394. Taylor, J., C. Trimarchi, R. Weinberg, B. Languet, F. Guillemin, P. Desmettre and E. Paoletti, Vaccine 9, 190–193 (1991b).
395. Taylor, J., S. Pincus, J. Tartaglia, C. Richardson,. G. Alkhatib, D. Briedis, M. Appel, E. Norton and E. Paoletti, J. Virol. 65, 4263–4274 (1991c).
396. Taylor, J., Edbauer, C., Rey-Senelonge, A., Bouquet, J.-F., Norton, E., Goebel, S., Desmettre, P., and Paoletti, E. J. Virol. 64, 1441–1450 (1990).
397. Taylor, J., R. Weinberg, B. Languet, P. Desmettre, and E. Paoletti, Vaccine 6, 497–503 (1988).
398. Taylor, G., E. J. Stott, G. Wertz and A. Ball, J. ,Sen. Virol. 72, 125–130 (1991a).
399. Thomson, G. R., Spooner, P. R., and Powell, D. G., Vet. Res. 100, 465–468 (1977).
400. Thornton, G. B., D. Milich, F. Chisari, K. Mitamura, S. B. Kent, R. Neurath, R. Purcell and J. Gerin, In Vaccines 87, (Cold Spring Harbor Laboratory, Cold Spring Harbor, N.Y.) (1987).
401. Tomley, F., Vaccine 9, 4–5 (1991).
402. Toyoda, T., T. Sakaguchi, K. Imai, N. M. Inocencio, B. Gotoh, M. Hamaguchi, and Y. Nagai, Virology 158, 242–247 (1987).
403. Tsubaki S., Masu S., Obata Y., and Shimada F., Kitasato Arch. Exp. Med., 23, 71–77 (1950).
404. Tsuchiya N., Karaki T., Kuroda A., Karoji Y., and Sasaki O., Virus, 20, 290–300 (1970).
405. Turner, P. C. and Moyer, R. W., In Poxvirus, eds. R. W. Moyer and P. C. Turner, (Springer Verlag, NY.) pp. 125–152 (1990).
406. Ueda, Y., S. Morikawa and Y. Matsuura, Virology 177, 588–594 (1990).
407. Valenzuela, P., A. Medina, W. J. Rutter, G. Ammerer and B. D. Hall, Nature 298, 347–350 (1982).
408. Valenzuela, P., D. Coit, M. A. Medina-Selby, C. H. Kuo, G. V. Nest, R. L. Burke, P. Bull, M. S. Urdea and P. V. Graves, Bio/Technology 3, 323–326 (1985).
409. Valenzuela, P., P. Gray, M. Quiroga, J. Zaldivar, H. M. Goodman and W. J. Rutter, Nature 280, 815–819 (1979).
410. Varma M. G., Pudney M., and Leeke C. J., Trans. R. Soc. Trop. Med. Hyg., 68, 374–382 (1974).
411. Vialard, J., M. Lalumiere, T. Vernet, D. Briedis, G. Alkhatib, D. Henning, D. Levin, and C. Richardson, J. Virol. 64, 37–50 (1990).
412. Vos, J. C. and Stunnenberg, H. G., EMBO J. 7, 3487–3492 (1988).
413. Wachsman, M., Aurelian, L., Smith, C., Lipinskas, B., perkus, M. and paoletti, E., J. Infect. Dis. 155, 1188–1197 (1987).
414. Waddell, G. H., Teigland, M. B., and Sigel, M. M., JAVMA 142, 587–590 (1963).
415. Walker, B. D., Flexner, C., Birch-Limberger, K., Fisher, L., Paradis, T. J., Aldovini, A., Young, R., Moss, B., and Schooley, R. T., Proc. Natl. Acad. Sci. 86, 9514–9519 (1989).
416. Walker, B. D., Flexner, C., Paradis, T. J., Fuller, T. C., Hirsch, M. S., Schooley, R. T. and Moss, B., Science 240, 64–66 (1988).
417. Walker, B. D., Chakrabarti, S., Moss, B., Paradi, T. J., Flynn, T., Durno, A. G., Blumberg, R. S., Kaplan, J. C., Hirsch, M. S., and Schooley, R. T., Nature 328, 345–348 (1987).
418. Wathen, M. W. and Wathen, L. M. K., J. Virol. 51, 57–62 (1984).
419. Watson, R., Gene 26, 307–312 (1983).
420. Watson, C. J., and Jackson, J. F., In: DNA Cloning, Vol. I., ed., Glover, D. M., (IRL Press, Washington, D.C.), pp. 79–88 (1985).
421. Waxham, M. N., Aronowski, J., Server, A. C., Walinsky, J. S., Smith, J. A., and Goodman, H. M., Virology 164 318–325 (1988).
422. Waxham, M. N., Server, A. C., Goodman, H. M., and Walinsky, J. S., Virology 159, 381–388 (1987).
423. Weibel, R. E., In: Vaccines, eds. Plotkin, S. A., and Mortimer, E. A., (W. B. Saunders), pp. 223–234 (1988).
424. Weir, J., Bennett, M., Allen, E., Elkins, K., Martin, S. and Rouse, B., J. Gen. Virol. 70, 2587–2594 (1989).
425. Weir, J. P. and B. Moss, J. Virol. 46, 530–537 (1989).
426. Weiss, R. A., Clapham, P. R., Cheingsong-Popov, R., Dalgleish, G., Carne, C. A. Weller, I. V., and Tedder, R. S. Nature 316, 69–72 (1985).

427. Wengler, G., and Wengler, G., J. Virol. 63, 2521–2526 (1989).
428. Wengler, G., and Wengler, G., J. Gen. Virol. 70, 987–992 (1989b).
429. Weston, K., and B. G. Barrell, J. Mol. Biol. 192, 177–208 (1986).
430. WHO Meeting, Geneva, June 19–22, Vaccine 8, 425–437 (1990).
431. Wiktor T. J., Macfarlan R. I., Reagan K. J. et al., Proc. Natl. Acad. Sci. USA, 81, 7194–7198 (1984).
432. Wiktor, T. J., S. A. Plotkin and H. Koprowski, In Vaccines, eds. Plotkin, S. A. and E. A. Mortimer (W. B. Saunders, Philadelphia), 474–491 (1988).
433. Wiktor, T. J., E. Gyorgy, H. D. Schlumberger, F. Sokol and H. Koprowski, J. Immunol. 110, 269–276 (1973).
434. Wiktor, T. J., R. I. Macfarlan, K. J. Reagan, B. Dietzschold, P. J. Curtis, W. H. Wunner, M. P. Kieny, R. Lathe, J. P. Lecocq, M. Mackett, B. Moss and H. Koprowski, Proc. Natl. Acad. Sci. USA 81, 7194–7198 (1984).
435. Wiktor, T. J., Dev. Biol. Stand 40, 255–264 (1977).
436. Wild F., Giraudon P., Spenner D., et al., Vaccine 8, 441–442 (1990)
437. Wild, T. F., E. Malvoisin, and R. Buckland, J. Gen. Virol. 72, 439–447 (1991).
438. Winkler, G., Randolph, V. B., Cleaves, G. R., Ryan, T. E., and Stollar, V., Virol 162, 187–196 (1988).
439. Wittmann, G. and Rziha, H.-J. Aujeszky's disease (pseudorabies) in pigs, In Herpesvirus Diseases of Cattle, Horses and Pigs, ed Wittmann, G., (Kluwer Academic Publishers), 230–325 (1989).
440. Wolff, L. H., Mathes, L. E., and Osone, R. G., J. Immunol. Meth. 26, 151–156 (1979).
441. Wolinsky, J. S., and Waxham, M. N., In: Virology, eds. Fields, B. N., and Knipe, D. M., (Raven Press), pp. 989–1011 (1990).
442. Wunner, W. H., B. Dietzschold, P. J. Curtis and T. J. Wiktor, J. Gen. Virol. 64, 1649–1650 (1983).
443. Wunsch, M., Schultz, A. S., Koch, W., Friedrich, R., and Hunsmann, G., EMBO J. 2, 2239–2246 (1983).
444. Yamagishi A., J. Vet. Med. 820, 14–18 (1989).
445. Yamanishi, K., Dantas, J. R, Jr., Takahashi, M., Yamanouchi, T., Damae, K., Takahoashi, Y., Tanishita, O., J. Virology 52, 231–237 (1984).
446. Yasuda, A., Kimura-Kuroda, J., Ogimoto, M., Miyamoto, M., Sata, T., Sato, T., Takamura, C., Kurata, T., Kojima, A., and Yasui, K., J. Virol. 64, 2788–2795 (1990).
447. Yelverton, E., S. Norton, J. F. Obijeski and D. V. Goeddel, Science 219, 614–620 (1983).
448. Yoshida I., Takagi M., Inokuma E., Goda H., Ono K., Takaku K., and Oku J., Biken J. 24, 47–67 (1981).
449. Yoshinaka, Y., Katch, I., Copeland, T. D. and Oroszlan, S. J. Virol. 55, 870–873 (1985).
450. Yuen, L., and Moss, B., Proc. Natl. Acad. Sci. USA 84, 6417–6421 (1987).
451. Zagury, D., Bernard, J., Cheynier, R., Desportes, I., Leonard, R., Fouchard, I., Reveil, B., Ittele, D., Lurhuma, Z., Mbayo, K., Wane, J., Salaun, J.-J., Goussard, B., Dechazal, L., Burny, A., Nara, P. and Gallo, R. C., Nature 332, 728–731 (1988).
452. Zanetti, A. R., E. Tanzi, L. Romano, P. Vigano, A. Cargnel, S. Hojvat and A. J. Zuckerman, J. Med. Virol. 32, 219–224 (1990).
453. Zarling, J. M., Morton, W., Moran, P. A., McClure, J., Kosowski, S. G. and Hu, S.-L., Nature 323, 344–346 (1986).
454. Zhang, X.-K., Takashima, I., and Hashimoto, N., Arch. Virol., 105, 235–246 (1989).
455. Zhou, J., L. Crawford, L. McLean, X. Sun, M. Stanley, N. Almond and G. L. Smith, J. Gen. Virol. 71, 2185–2190 (1990).
456. Zingernagel, R. M., Sato, T., Althage, A., and Kamisaku, H., Eur. J. Immunol. 14, 14–23 (1984).
457. Zweig, M., Showalter, S., Bladen, S., Heilman, C. and Hampar, B., J. Virol. 47, 185–192 (1983).

What is claimed is:

1. A recombinant vaccinia virus wherein regions C7L.-K1L, J2R, B13R+B14R, A26L, A56R and I4L have been deleted therefrom, and further comprising exogenous coding DNA from a non-vaccinia source in a nonessential region of the vaccinia genome.

2. A recombinant vaccinia virus wherein the open reading frames for the thymidine kinase gene, the hemorrhagic region, the A type inclusion body region, the hemagglutinin gene, the host range gene region, and, the large subunit, ribonucleotide reductase have been deleted therefrom, and further comprising exogenous coding DNA from a non-vaccinia source in a nonessential region of the vaccinia genome.

3. A recombinant vaccinia virus as claimed in claim 2 wherein the non-vaccinia source is selected from the group consisting of rabies virus, Hepatitis B virus, yellow fever virus, Dengue virus, pseudorabies virus, Epstein-Barr virus, herpes simplex virus, simian immunodeficiency virus, equine herpes virus, bovine herpes virus, bovine viral diarrhea virus, human cytomegalovirus, canine parvovirus, equine influenza virus, feline leukemia virus, feline herpes virus, Hantaan virus, *C. tetani*, avian influenza virus, mumps virus and Newcastle Disease virus.

4. A recombinant vaccinia virus as claimed in claim 3, wherein the non-vaccinia source is rabies virus and the recombinant vaccinia virus is vP879 or vP999.

5. A recombinant vaccinia virus as claimed in claim 3, wherein the non-vaccinia source is Hepatitis B virus and the recombinant vaccinia virus is vP856, vP896, vP897, vP858, vP891, vP932, vP975, vP930, vP919, vP941 or vP944.

6. A recombinant vaccinia virus as claimed in claim 3, wherein the non-vaccinia source is yellow fever virus and the recombinant vaccinia virus is vP766, vP764, vP869, vP729, vP725, vP997, or vP984.

7. A recombinant vaccinia virus as claimed in claim 3, wherein the non-vaccinia source is Dengue virus and the recombinant vaccinia virus is vP867, vP962 or vP955.

8. A recombinant vaccinia virus as claimed in claim 3, wherein the non-vaccinia source is pseudorabies virus and the recombinant vaccinia virus is vP881, vP883, vP900, vP912, vP925, vP915 or vP916.

9. A recombinant vaccinia virus as claimed in claim 3, wherein the non-vaccinia source is Epstein-Barr virus and the recombinant vaccinia virus is vP941 or vP944.

10. A recombinant vaccinia virus as claimed in claim 3, wherein the non-vaccinia source is herpes simplex virus and the recombinant vaccinia virus is vP914.

11. A recombinant vaccinia virus as claimed in claim 3, wherein the non-vaccinia source is simian immunodeficiency virus and the recombinant vaccinia virus is vP873, vP948, vP943, vP942, vP952, vP948, vP1042, vP1071, vP943, vP942, vP952 or vP1050.

12. A recombinant vaccinia virus as claimed in claim 3 wherein the non-vaccinia source is equine herpes virus and the recombinant vaccinia virus is vP1043, vP1025 or vP956.

13. A recombinant vaccinia virus as claimed in claim 3 wherein the non-vaccinia source is bovine herpes virus and the recombinant vaccinia virus is vP1051, vP1074, vP1073, vP1083, vP1087 or vP1079.

14. A recombinant vaccinia virus as claimed in claim 3 wherein the non-vaccinia source is bovine viral diarrhea virus and the recombinant vaccinia virus is vP972, vP1017 or vP1097.

15. A recombinant vaccinia virus as claimed in claim 3 wherein the non-vaccinia source is human cytomegalovirus and the recombinant vaccinia virus is vP1001.

16. A recombinant vaccinia virus as claimed in claim 3 wherein the non-vaccinia source is canine parvovirus and the recombinant vaccinia virus is vP998 or vP999.

17. A recombinant vaccinia virus as claimed in claim 3 wherein the non-vaccinia source is equine influenza virus and the recombinant vaccinia virus is vP961 or vP1063.

18. A recombinant vaccinia virus as claimed in claim 3 wherein the non-vaccinia source is feline leukemia virus and the recombinant vaccinia virus is vP1011.

19. A recombinant vaccinia virus as claimed in claim 3 wherein the non-vaccinia source is Hantaan virus and the recombinant vaccinia virus is vp882, vP950 or vP951.

20. A recombinant vaccinia virus as claimed in claim 3 wherein the non-vaccinia source is *C. tetani* and the recombinant vaccinia virus is vp1075.

21. An immunological composition for inducing an immunological response in a host inoculated with the composition, said composition comprising a carrier and a recombinant virus as claimed in any one of claims 2, 33, 44, 5, 6, 8, 9, 10, 11, 12, 13, 14, 15, 16, 17, 18, 19 or 20.

22. A method for expressing a gene product in a cell cultured in vitro, which method comprises introducing into the cell a modified recombinant virus as claimed in claim 2.

* * * * *

UNITED STATES PATENT AND TRADEMARK OFFICE
CERTIFICATE OF CORRECTION

PATENT NO. : 5,494,807
DATED : Feb. 27, 1996
INVENTOR(S) : Paoletti et al.

It is certified that error appears in the above-indentified patent and that said Letters Patent is hereby corrected as shown below:

```
Claim 1, line 2 (column 431, line 43), delete
   the period (".") following "C7L".

Claim 11, line 5 (column 432, line 66), delete
   "vP943, vP942, vP952".

Claim 19, line 3 (column 434, line 6), change
   "vp882" to --vP882--.

Claim 20, line 3 (column 434, line 9), change
   "vp1075" to --vP1075--.

Claim 21, line 4 (column 434, line 13), change
   "33, 44" to --3, 4--.
```

Signed and Sealed this

Eighteenth Day of June, 1996

Attest:

BRUCE LEHMAN

Attesting Officer          Commissioner of Patents and Trademarks